United States Patent
Schwark et al.

(10) Patent No.: US 12,428,636 B1
(45) Date of Patent: Sep. 30, 2025

(54) METHODS AND COMPOSITIONS FOR MODIFICATION OF PROTOSPACER ADJACENT MOTIF SPECIFICITY OF CAS12A

(71) Applicant: Pairwise Plants Services, Inc., Durham, NC (US)

(72) Inventors: David Gerhard Schwark, New Hill, NC (US); Joanne Hunt, Wake Forest, NC (US); Joseph Matthew Watts, Cary, NC (US)

(73) Assignee: Pairwise Plants Services, Inc., Durham, NC (US)

( * ) Notice: Subject to any disclaimer, the term of this patent is extended or adjusted under 35 U.S.C. 154(b) by 0 days.

(21) Appl. No.: 18/765,699

(22) Filed: Jul. 8, 2024

(51) Int. Cl.
*C12N 15/10* (2006.01)
*C07K 19/00* (2006.01)
*C12N 9/22* (2006.01)
*C12N 9/78* (2006.01)
*C12N 15/11* (2006.01)

(52) U.S. Cl.
CPC ............ *C12N 15/102* (2013.01); *C07K 19/00* (2013.01); *C12N 9/22* (2013.01); *C12N 9/78* (2013.01); *C12N 15/111* (2013.01); *C07K 2319/70* (2013.01); *C12N 2310/20* (2017.05); *C12Y 305/04001* (2013.01); *C12Y 305/04002* (2013.01)

(58) Field of Classification Search
CPC .......... C12N 15/102; C12N 9/22; C12N 9/78; C12N 15/111; C12N 2310/20; C07K 19/00; C07K 2319/70; C12Y 305/04001; C12Y 305/04002
See application file for complete search history.

(56) References Cited

U.S. PATENT DOCUMENTS

| | | | |
|---|---|---|---|
| 5,459,252 A | 10/1995 | Conkling et al. | |
| 5,604,121 A | 2/1997 | Hilder et al. | |
| 5,625,136 A | 4/1997 | Koziel et al. | |
| 5,641,876 A | 6/1997 | Mcelroy et al. | |
| 6,040,504 A | 3/2000 | Rice et al. | |
| 7,141,424 B2 | 11/2006 | Shin et al. | |
| 7,166,770 B2 | 1/2007 | Hohn et al. | |
| 7,579,516 B2 | 8/2009 | Boudreau | |
| 9,790,490 B2 | 10/2017 | Zhang et al. | |
| 9,982,053 B2 | 5/2018 | Pantaleo et al. | |
| 10,113,163 B2 | 10/2018 | Liu et al. | |
| 10,167,457 B2 | 1/2019 | Liu et al. | |
| 10,421,972 B2 | 9/2019 | Lira et al. | |
| 2017/0219596 A1 | 8/2017 | Tanenbaum et al. | |
| 2018/0155716 A1 | 6/2018 | Zhang et al. | |
| 2019/0010441 A1 | 1/2019 | Kindaichi | |
| 2019/0010481 A1 | 1/2019 | Joung et al. | |
| 2021/0115421 A1 | 4/2021 | Watts et al. | |
| 2021/0155911 A1* | 5/2021 | Zhang | C12N 15/11 |
| 2022/0112473 A1 | 4/2022 | Guffy et al. | |
| 2022/0145305 A1 | 5/2022 | Petris et al. | |
| 2023/0383271 A1 | 11/2023 | Guffy et al. | |
| 2024/0076639 A1 | 3/2024 | Watts | |
| 2024/0076640 A1 | 3/2024 | Jali | |
| 2024/0141382 A1* | 5/2024 | Gasiunas | A61K 48/005 |
| 2024/0229063 A1* | 7/2024 | Bauer | C12N 15/111 |

FOREIGN PATENT DOCUMENTS

| | | | |
|---|---|---|---|
| CN | 112725487 A * | 4/2021 | ........... C12Q 1/6844 |
| EP | 0255378 A2 | 2/1988 | |
| EP | 0342926 A2 | 11/1989 | |
| EP | 0452269 A2 | 10/1991 | |
| WO | 9307278 A1 | 4/1993 | |
| WO | 9942587 A1 | 8/1999 | |
| WO | 0173087 A1 | 10/2001 | |
| WO | 2017184768 A1 | 10/2017 | |
| WO | 2018136783 A1 | 7/2018 | |
| WO | 2018176009 A1 | 9/2018 | |
| WO | 2018213708 A1 | 11/2018 | |
| WO | 2018213726 A1 | 11/2018 | |
| WO | 2019126716 A1 | 6/2019 | |
| WO | 2019126762 A2 | 6/2019 | |
| WO | 2019138052 A1 | 7/2019 | |
| WO | 2021016086 A1 | 1/2021 | |
| WO | 2021076682 A1 | 4/2021 | |
| WO | 2021087182 A1 | 5/2021 | |
| WO | 2021222703 A2 | 11/2021 | |
| WO | 2022047135 A1 | 3/2022 | |
| WO | 2022174108 A1 | 8/2022 | |

OTHER PUBLICATIONS

International Search Report and Written Opinion corresponding to PCT/US2019/055659; dated Mar. 9, 2021 (12 pages).

Gaj, Thomas, et al., "Genome-Editing Technologies: Principles and Applications", Cold Spring Harbor Perspectives in Biology, 8:a023754, 2016.

(Continued)

*Primary Examiner* — Jennifer Dunston
*Assistant Examiner* — Tiffany Nicole Grooms
(74) *Attorney, Agent, or Firm* — Myers Bigel, P.A.

(57) ABSTRACT

This invention relates to variants of Cas12a nucleases having altered protospacer adjacent motif recognition specificity. The invention further relates to methods of making CRISPR-CAS nuclease variants and methods of modifying nucleic acids using the variants.

13 Claims, 22 Drawing Sheets

Specification includes a Sequence Listing.

(56) References Cited

OTHER PUBLICATIONS

Gao, Linyi, et al., "Engineered Cpf1 variants with altered PAM specificities", Nat Biotechnol 35(8): 789-792, 2017.
Hu, Jonny H., et al., "Evolved Cas9 variants with broad PAM compatibility and high DNA specificity", Nature 556: 57-63, 2018.
Jinek, Martin, et al., "A Programmable Dual-RNA-Guided DNA Endonuclease in Adaptive Bacterial Immunity", Science, 337(6096): 816-821, 2012.
Kleinstiver, Benjamin P., et al., "Broadening the targeting range of Staphylococcus aureus CRISPR-Cas9 by modifying PAM recognition", Nat Biotechnol 33(12): 1293-1298, 2015.
Kleinstiver, Benjamin P., et al., "Engineered CRISPR-Cas12a variants with increased activities and improved targeting ranges for gene, epigenetic and base editing", Nat Biotechnol 37: 276-282, 2019.
Kleinstiver, Benjamin P., et al., "Engineered CRISPR-Cas9 nucleases with altered PAM specificities", Nature 523: 481-485, 2015.
Leenay, Ryan T., et al., "Identifying and Visualizing Functional PAM Diversity across CRISPR-Cas Systems", Molecular Cell. 62: 137-147, 2016.
Nihongaki, et al., "A split CRISPR-Cpf1 platform for inducible genome editing and gene activation", Nature Chemical Biology, 15: 882-888, 2019.
Nishimasu, Hiroshi, et al., "Engineered CRISPR-Cas9 nuclease with expanded targeting space", Science 361 (6408): 1259-1262, 2018.
Tang, Xu, et al., "A CRISPR-Cpf1 system for efficient genome editing and transcriptional repression in plants", Nat Plants 3, Article No. 17018, 2017.
Yamano, Takashi, et al., "Structural Basis for the Canonical and Non-canonical PAM Recognition by CRISPR-Cpf1", Molecular Cell, 67(4): 633-645.e3, 2017.
Zetsche, Bernd, et al., "Cpf1 is a single RNA-guided endonuclease of a Class 2 CRISPR-Cas system", Cell. vol. 163(3): 759-771, 2015.
GenBank Accession No. 6KLB_D "Chain D, LbCas12a" (5 pages) (Sep. 17, 2019).
International Search Report and the Written Opinion of the International Searching Authority corresponding to International Patent Application No. PCT/US2021/047913 (25 pages) (mailed Jan. 27, 2022).
International Search Report and the Written Opinion of the International Searching Authority corresponding to International Patent Application No. PCT/US2023/063398 (21 pages) (mailed Jun. 29, 2023).
Notification of Transmittal of the International Search Report and the Written Opinion of the International Searching Authority, or the Declaration, in corresponding PCT Application No. PCT/US2024/018165 (Jun. 24, 2024).
Barrangou, Rodolphe, "Diversity of CRISPR-Cas immune systems and molecular machines", Genome Biology, 16(247), 2015, 1-11.
Chen, et al., "Engineered DNase-inactive Cpf1 variants to improve targeting scope for base editing in *E. coli*", Synthetic and Systems Biotechnology, 6:326-334 (2021).
Deveau, Hélène, et al., "Phage Response to CRISPR-Encoded Resistance in Streptococcus thermophilus", Journal of Bacteriology, 190(4), 2008, 1390-1400.
Esvelt, Kevin M., et al., "Orthogonal Cas9 proteins for RNA-guided gene regulation and editing", Nature Methods, 10(11), 2013, 1116-1121.
Gaudelli, Nicole M., et al., "Programmable base editing of A.T to G.C in genomic DNA without DNA cleavage", Nature. 551(7681), 2017, pp. 464-471.
Gilbreth, Ryan N., et al., "Structural insights for engineering binding proteins based on nonantibody scaffolds", Current Opinion in Structural Biology, 22, 2012, 413-420.

Grissa, et al., "CRISPRFinder: a web tool to identify clustered regularly interspaced short palindromic repeats", Nucleic Acids Research, 35:W52-W57 (2007).
Hou, et al., "Efficient genome engineering in human pluripotent stem cells using Cas9 from Neisseria meningitidis", Proceedings of the National Academy of Sciences, 110(39):15644-15649 (2013).
Huang, et al., "RosettaRemodel: A Generalized Framework for Flexible Backbone Protein Design", PLoS ONE, 6(8):e24109 (2011).
Jablonska, et al., "Systematic classification of the His-Me finger superfamily", Nucleic Acids Research, 45(20):11479-11494 (2017).
Jiang, et al., "CRISPR-assisted editing of bacterial genomes", Nature Biotechnology, 31(3), 2013, 233-239.
Li, X., et al., "Base editing with a Cpf1-cytidine deaminase fusion", Nature Biotechnology, 36:324-327 2018.
Majorek, et al., "The RNase H-like superfamily: new members, comparative structural analysis and evolutionary classification", Nucleic Acids Research, 42(7):4160-4179 (2014).
Mali, et al., "Cas9 as a versatile tool for engineering biology", Nature Methods, 10(10), 2013, 957-963.
Mali, Prashant, et al., "RNA-Guided Human Genome Engineering via Cas9", Science, 339(6121), 2013, 823-826.
Pediaditakis, et al., "*Bacillus subtilis* hlpB Encodes a Conserved Stand-Alone HNH Nuclease-Like Protein That Is Essential for Viability Unless the hlpB Deletion Is Accompanied by the Deletion of Genes Encoding the AddAB DNA Repair Complex", Journal of Bacteriology, 194(22):6184-6194 (2012).
Peng, et al., "Structural insight into multistage inhibition of CRISPR-Cas12a by AcrVA4", Proceedings of the National Academy of Sciences, 116(38):18928-18936 (2019).
Ran, et al., "Genome engineering using the CRISPR-Cas9 system", Nature Protocols, 8(11):2281-2308 (2013).
Sadowski, M I, et al., "The sequence-structure relationship and protein function prediction", Current Opinion in Structural Biology 19:357-362 (May 2009).
Schindele, et al., "Engineering CRISPR/LbCas12a for highly efficient, temperature-tolerant plant gene editing". Plant Biotechnology Journal, 18:1118-1120 (2020).
Seffernick, Jennifer L., et al., "Melamine Deaminase and Atrazine Chlorohydrolase: 98 Percent Identical but Functionally Different", Journal of Bacteriology, 183(8), 2001, 2405-2410.
Sha, et al., "Monobodies and other synthetic binding proteins for expanding protein science", Protein Science, 26:910-924 (2017).
Singh, et al., "Protein Engineering Approaches in the Post-Genomic Era", Current Protein & Peptide Science, 19:5-15 (2018).
Stella, et al., "Structure of the Cpf1 endonuclease R-loop complex after target DNA cleavage", Nature, 546:559-563 (2017).
Swarts, et al., "Cas9 versus Cas12a/Cpf1: Structure-function comparisons and implications for genome editing", WIREs RNA, 9(5):e1481 (2018).
Tak, et al., "Inducible and multiplex gene regulation using CRISPR-Cpf1-based transcription factors", Nature Methods, 14(12):1163-1166 (2017).
Tang, et al., "Identification of Dehalobacter reductive dehalogenases that catalyse dechlorination of chloroform, 1, 1, 1-trichloroethane and 1,1-dichloroethane", Philosophical Transactions of the Royal Society of London, Series B, 368:20120318 (2013).
Thuronyi, et al., "Continuous evolution of base editors with expanded target compatibility and improved activity", Nature Biotechnology, 37(9):1070-1079 (2019).
Vob, et al., "Chemically induced dimerization: reversible and spatiotemporal control of protein function in cells", Current Opinion in Chemical Biology, 28:194-201 (2015).
Witowski, et al., "Conversion of a B-Ketoacyl Synthase to a Malonyl Decarboxylase by Replacement of the Active-Site Cysteine with Glutamine", Biochemistry, 38:11643-11650 (1999).
Yamano, Takashi, et al., "Crystal structure of Cpf1 in complex with guide RNA and target DNA", Cell, 165(4):949-962 (May 5, 2016).
U.S. Appl. No. 18/593,590, filed Mar. 1, 2024, Guffy et al.

\* cited by examiner

1. WEDGE DOMAIN
2. PAM-INTERACTING
3. REC1
4. REC2
5. RUVC
6. NUC
7. NUCLEIC ACID

- NICKED PLASMID
- LINEARIZED PLASMID
- SUPERCOILED PLASMID

METHODS AND COMPOSITIONS FOR MODIFICATION OF PROTOSPACER ADJACENT MOTIF SPECIFICITY OF CAS12A

STATEMENT REGARDING ELECTRONIC FILING OF A SEQUENCE LISTING

A Sequence Listing in XML format, entitled 1499-145_ST26.xml, 444,520 bytes in size, generated on Jul. 3, 2024 and filed herewith, is hereby incorporated by reference into the specification for its disclosures.

FIELD OF THE INVENTION

This invention relates to variants of CRISPR-Cas nucleases having altered protospacer adjacent motif recognition specificity. The invention further relates to methods of making the CRISPR-CAS nuclease variants and methods of modifying nucleic acids using the variants.

BACKGROUND OF THE INVENTION

Genome editing/modifying is a process that utilizes site-directed nucleases, for example, CRISPR-Cas nucleases, to introduce variation at a targeted genomic location. The most widely utilized nuclease for genome modification, Cas9, can introduce mutations at a genomic region upstream of an NGG motif (e.g., a protospacer adjacent motif (PAM)). Other Cas nucleases have different PAM recognition specificities. When the PAM specificities of these nucleases are particularly stringent, they can reduce the usefulness of the nuclease for genome modification by limiting the number of genomic target sites available for modification by that nuclease.

To address the shortcomings in the art, the present invention provides modified CRISPR-Cas nucleases having improved PAM specificity and methods for designing, identifying and selecting such CRISPR-Cas nucleases.

SUMMARY OF THE INVENTION

One aspect of the invention provides method of modifying a target nucleic acid, comprising contacting the target nucleic acid with (a) a Cas12a polypeptide having a mutation, wherein the mutation is an arginine at position 532 and at 595, or (b) a Cas12a polypeptide having a mutation, wherein the mutation is an arginine at position 532 and 542 and a valine at position 538, each of which position in the Cas12a polypeptide of (a) and/or (b) is in reference to position numbering of the amino acid sequence of SEQ ID NO:180, wherein the Cas12a polypeptide of (a) recognizes a PAM sequence in the target nucleic acid of

TTAA, TTAC, ACCA, ACCC, ACCG, ATCA, ATCC, ATCG,

CCCA, CCCG, CTCA, CTCC, CTCG, GCCA, GCCC, GCCG,

GTCA, GTCC, GTCG, GTCT, TCCT, TTCT, ACTA, ACTC,

ACTG, ATTA, ATTC, ATTG, CCTA, CCTC, CCTG, CTTA,

CTTC, CTTG, GCTA, GCTC, GCTG, GTTA, GTTC, GTTG,

TCTA, TCTC, TCTG, TCTT, TTTT, CCCC, TCCA, TCCC,

TCCG, TTCA, TTCC, and/or TTCG, and the Cas12a polypeptide of (b) recognizes a PAM sequence in the target nucleic acid of

AACC, TACC, AATC, GATA, AATA, AATG, GATG, GATC,

TATA, TATC, and/or TATG, and/or (c) an engineered protein comprising: a first polypeptide that is a first portion of a modified protein, wherein the modified protein comprises an amino acid sequence having at least 80%, 85%, 90%, or 95% identity to the amino acid sequence of SEQ ID NO:180 (LbCas12a) and a second polypeptide that is heterologous to the first polypeptide and is not a Type V CRISPR-Cas effector polypeptide, wherein the first polypeptide and second polypeptide are different from each other, and wherein the engineered protein comprises a mutation, and (i) the mutation is an arginine at position 680 and at 743 with reference to position numbering of the amino acid sequence of SEQ ID NO:184 (RR), or (ii) the mutation is an arginine at position 680 and 690 and a valine at position 686 with reference to position numbering of the amino acid sequence of SEQ ID NO:185 (RVR), wherein the engineered protein of (c)(i) recognizes a PAM sequence in the target nucleic acid of

TTAA, TTAC, ACCA, ACCC, ACCG, ATCA, ATCC, ATCG,

CCCA, CCCG, CTCA, CTCC, CTCG, GCCA, GCCC, GCCG,

GTCA, GTCC, GTCG, GTCT, TCCT, TTCT, ACTA, ACTC,

ACTG, ATTA, ATTC, ATTG, CCTA, CCTC, CCTG, CTTA,

CTTC, CTTG, GCTA, GCTC, GCTG, GTTA, GTTC, GTTG,

TCTA, TCTC, TCTG, TCTT, TTTT, CCCC, TCCA, TCCC,

TCCG, TTCA, TTCC, and/or TTCG, and the engineered protein of (c)(ii) recognizes a PAM sequence in the target nucleic acid of

AACC, TACC, AATC, GATA, AATA, AATG, GATG, GATC,

TATA, TATC, and/or TATG, (d) a fusion protein comprising the Cas12a polypeptide of (a) and/or (b) and a guide nucleic acid (e.g., CRISPR RNA, CRISPR DNA, crRNA, crDNA) or a fusion protein comprising the engineered protein of (c) and a guide nucleic acid; (e) a complex comprising the Cas12a polypeptide of (a) and/or (b) and a guide nucleic acid, or comprising the fusion protein of (d), or a complex comprising the engineered protein of (c) and a guide nucleic acid, or comprising the fusion protein of (d); and/or (f) a composition comprising the Cas12a polypeptide of (a) and/or (b) and a guide nucleic acid or comprising the fusion protein of (d), or a composition comprising the engineered protein of (c) and a guide nucleic acid or comprising the fusion protein of (d), thereby modifying the target nucleic acid.

A second aspect of the invention provides a method of editing a target nucleic acid, comprising contacting the target nucleic acid with: (a) a Cas12a polypeptide having a mutation, wherein the mutation is an arginine at position 532 and at 595, or (b) a Cas12a polypeptide having a mutation, wherein the mutation is an arginine at position 532 and 542 and a valine at position 538, each of which position in the Cas12a polypeptide of (a) and/or (b) is in reference to position numbering of the amino acid sequence of SEQ ID NO:180, wherein the Cas12a polypeptide of (a) recognizes a PAM sequence in the target nucleic acid of TTAA, TTAC, ACCA, ACCC, ACCG, ATCA, ATCC, ATCG,
CCCA, CCCG, CTCA, CTCC, CTCG, GCCA, GCCC, GCCG,
GTCA, GTCC, GTCG, GTCT, TCCT, TTCT, ACTA, ACTC,
ACTG, ATTA, ATTC, ATTG, CCTA, CCTC, CCTG, CTTA,
CTTC, CTTG, GCTA, GCTC, GCTG, GTTA, GTTC, GTTG,
TCTA, TCTC, TCTG, TCTT, TTTT, CCCC, TCCA, TCCC,
TCCG, TTCA, TTCC, and/or TTCG, and the Cas12a polypeptide of (b) recognizes a PAM sequence in the target nucleic acid of AACC, TACC, AATC, GATA, AATA, AATG, GATG, GATC,
TATA, TATC, and/or TATG;

and/or (c) an engineered protein comprising: a first polypeptide that is a first portion of a modified protein, wherein the modified protein comprises an amino acid sequence having at least 80%, 85%, 90%, or 95% identity to the amino acid sequence of SEQ ID NO:180 (LbCas12a) and a second polypeptide that is heterologous to the first polypeptide and is not a Type V CRISPR-Cas effector polypeptide, wherein the first polypeptide and second polypeptide are different from each other, and wherein the engineered protein comprises a mutation, and (i) the mutation is an arginine at position 680 and at 743 with reference to position numbering of the amino acid sequence of SEQ ID NO:184 (RR), or (ii) the mutation is an arginine at position 680 and 690 and a valine at position 686 with reference to position numbering of the amino acid sequence of SEQ ID NO:185 (RVR), wherein the engineered protein of (c)(i) recognizes a PAM sequence in the target nucleic acid of TTAA, TTAC, ACCA, ACCC, ACCG, ATCA, ATCC, ATCG,
CCCA, CCCG, CTCA, CTCC, CTCG, GCCA, GCCC, GCCG,
GTCA, GTCC, GTCG, GTCT, TCCT, TTCT, ACTA, ACTC,
ACTG, ATTA, ATTC, ATTG, CCTA, CCTC, CCTG, CTTA,
CTTC, CTTG, GCTA, GCTC, GCTG, GTTA, GTTC, GTTG,
TCTA, TCTC, TCTG, TCTT, TTTT, CCCC, TCCA, TCCC,
TCCG, TTCA, TTCC, and/or TTCG, and the engineered protein of (c)(ii) recognizes a PAM sequence in the target nucleic acid of AACC, TACC, AATC, GATA, AATA, AATG, GATG, GATC,
TATA, TATC, and/or TATG, (d) a fusion protein comprising the Cas12a polypeptide of (a) and/or (b) and a guide nucleic acid (e.g., CRISPR RNA, CRISPR DNA, crRNA, crDNA) or a fusion protein comprising the engineered protein of (c) and a guide nucleic acid; (e) a complex comprising the Cas12a polypeptide of (a) and/or (b) and a guide nucleic acid, or comprising the fusion protein of (d), or a complex comprising the engineered protein of (c) and a guide nucleic acid, or comprising the fusion protein of (d); and/or (f) a composition comprising the Cas12a polypeptide of (a) and/or (b) and a guide nucleic acid or comprising the fusion protein of (d), or a composition comprising the engineered protein of (c) and a guide nucleic acid or comprising the fusion protein of (d) thereby editing the target nucleic acid.

A third aspect of the invention provides a method of editing a target nucleic acid, comprising contacting a cell or a cell free system comprising the target nucleic acid with: (a) a Cas12a polypeptide having a mutation, wherein the mutation is an arginine at position 532 and at 595, (b) a Cas12a polypeptide having a mutation, wherein the mutation is an arginine at position 532 and 542 and a valine at position 538, each of which position in the Cas12a polypeptide of (a) and/or (b) is in reference to position numbering of the amino acid sequence of SEQ ID NO:180, wherein the Cas12a polypeptide of (a) recognizes a PAM sequence in the target nucleic acid of TTAA, TTAC, ACCA, ACCC, ACCG, ATCA, ATCC, ATCG,
CCCA, CCCG, CTCA, CTCC, CTCG, GCCA, GCCC, GCCG,
GTCA, GTCC, GTCG, GTCT, TCCT, TTCT, ACTA, ACTC,
ACTG, ATTA, ATTC, ATTG, CCTA, CCTC, CCTG, CTTA,
CTTC, CTTG, GCTA, GCTC, GCTG, GTTA, GTTC, GTTG,
TCTA, TCTC, TCTG, TCTT, TTTT, CCCC, TCCA, TCCC,
TCCG, TTCA, TTCC, and/or TTCG, and the Cas12a polypeptide of (b) recognizes a PAM sequence in the target nucleic acid of AACC, TACC, AATC, GATA, AATA, AATG, GATG, GATC,
TATA, TATC, and/or TATG, or an expression cassette or vector comprising the same and a guide nucleic acid, or an expression cassette or vector comprising the same; and/or (c) an engineered protein comprising: a first polypeptide that is a first portion of a modified protein, wherein the modified protein comprises an amino acid sequence having at least 80%, 85%, 90%, or 95% identity to the amino acid sequence of SEQ ID NO:180 (LbCas12a) and a second polypeptide that is heterologous to the first polypeptide and is not a Type V CRISPR-Cas effector polypeptide, wherein the first polypeptide and second polypeptide are different from each other, and wherein the engineered protein comprises a mutation, and (i) the mutation is an arginine at position 680 and at 743 with reference to position numbering of the amino acid sequence of SEQ ID NO:184 (RR), or (ii) the mutation is an arginine at position 680 and 690 and a valine at position 686 with reference to position numbering of the amino acid sequence of SEQ ID NO:185 (RVR), wherein the engineered protein of (c)(i) recognizes a PAM sequence in the target nucleic acid of TTAA, TTAC, ACCA, ACCC, ACCG, ATCA, ATCC, ATCG,
CCCA, CCCG, CTCA, CTCC, CTCG, GCCA, GCCC, GCCG,
GTCA, GTCC, GTCG, GTCT, TCCT, TTCT, ACTA, ACTC,
ACTG, ATTA, ATTC, ATTG, CCTA, CCTC, CCTG, CTTA, -continued

CTTC, CTTG, GCTA, GCTC, GCTG, GTTA, GTTC, GTTG,

TCTA, TCTC, TCTG, TCTT, TTTT, CCCC, TCCA, TCCC,

TCCG, TTCA, TTCC, and/or TTCG, and the engineered protein of (c)(ii) recognizes a PAM sequence in the target nucleic acid of

AACC, TACC, AATC, GATA, AATA, AATG, GATG, GATC,

TATA, TATC, and/or TATG;

and/or (d) a nucleic acid construct encoding a complex comprising a fusion protein that comprises (i) the Cas12a polypeptide of (a) and/or (b) and a guide nucleic acid, or an expression cassette or vector comprising the same; or (ii) the engineered protein of (c) and a guide nucleic acid, or an expression cassette or vector comprising the same, thereby editing the target nucleic acid.

The invention further provides expression cassettes and/or vectors comprising polynucleotides encoding CRISPR-Cas nucleases, engineered proteins and/or fusion proteins and/or cells comprising polynucleotides, polypeptides and/or fusion proteins of the invention and/or kits comprising the same for carrying out the methods of the invention.

These and other aspects of the invention are set forth in more detail in the description of the invention below.

BRIEF DESCRIPTION OF THE SEQUENCES

SEQ ID NO:1 and 169-174 are exemplary HNH domain polypeptide sequences useful with this invention.

SEQ ID NOs:2-17, 105-107, 125-132, 157-168, and 181-193 are exemplary engineered protein polypeptide sequences useful with this invention.

SEQ ID NOs:18-47, 153-154, and 175-179 are exemplary linker amino acid sequences useful with this invention.

SEQ ID NO:48-49 are exemplary regulatory sequences encoding a promoter and intron.

SEQ ID NOs:50-66 and 180 are exemplary Cas12a polypeptide sequences useful with this invention.

SEQ ID NOs:67-69 are exemplary Cas12a polynucleotide sequences useful with this invention.

SEQ ID NOs:70-80 and 140-143 are exemplary Cas9 polynucleotide sequences useful with this invention.

SEQ ID NOs:81-82 are exemplary Cas9 polypeptide sequences useful with this invention.

SEQ ID NOs:83-84, 86-92, 152 and 156 are exemplary cytosine deaminase polypeptide sequences useful with this invention.

SEQ ID NO:85 is an exemplary cytosine deaminase polynucleotide sequence useful with this invention.

SEQ ID NOs:93-103 and 155 are exemplary adenine deaminase polypeptide sequences useful with this invention.

SEQ ID NO:104 is an exemplary uracil-DNA glycosylase inhibitor (UGI) sequence useful with this invention.

SEQ ID NOs:108-118 provide example RNA recruiting motifs and corresponding affinity polypeptides useful with this invention.

SEQ ID NOs:119-121 provide example peptide tags and an affinity polypeptide useful with this invention.

SEQ ID NO:122 is an exemplary RuvC domain sequence useful with this invention.

SEQ ID NOs:123 and 133-135 are exemplary target sites and substrates useful with this invention.

SEQ ID NOs:124, 136-139, 144-150, and 196-271 are example CRISPR RNA and spacer sequences for nucleic acid guides useful with this invention.

SEQ ID NO:151 is an exemplary Cas12b polypeptide sequences useful with this invention.

SEQ ID NO:194-195 are exemplary expression vector polynucleotide sequences useful with this invention.

BRIEF DESCRIPTION OF THE DRAWINGS

FIG. 4 is a diagram of Cas12a domains viewed facing the REC lobe. From this view, a portion of the crRNA/target DNA duplex is visibly exposed to the surface of Cas12a.

FIG. 5 is an overlay of the HNH domain from SpCas9 onto the candidate insertion site in LbCas12a.

DETAILED DESCRIPTION

Figure 1:
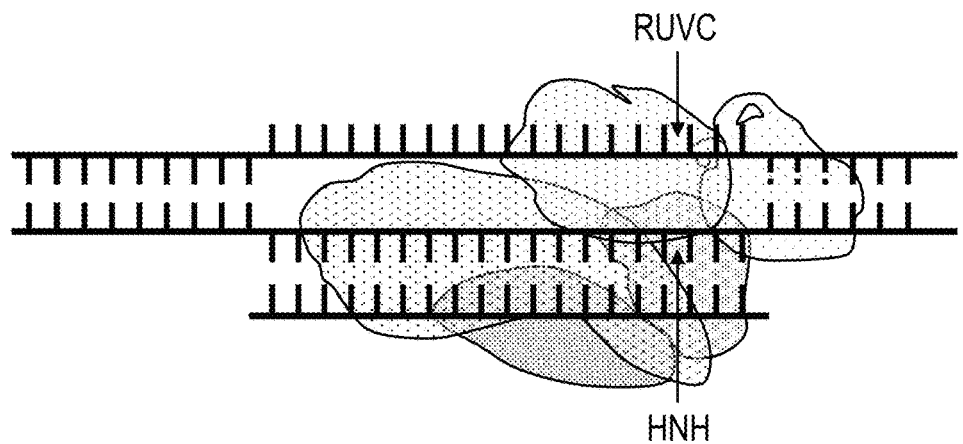
FIG. 1 is an illustration depicting the mechanism of action for Type II CRISPR endonucleases.
Figure 2:
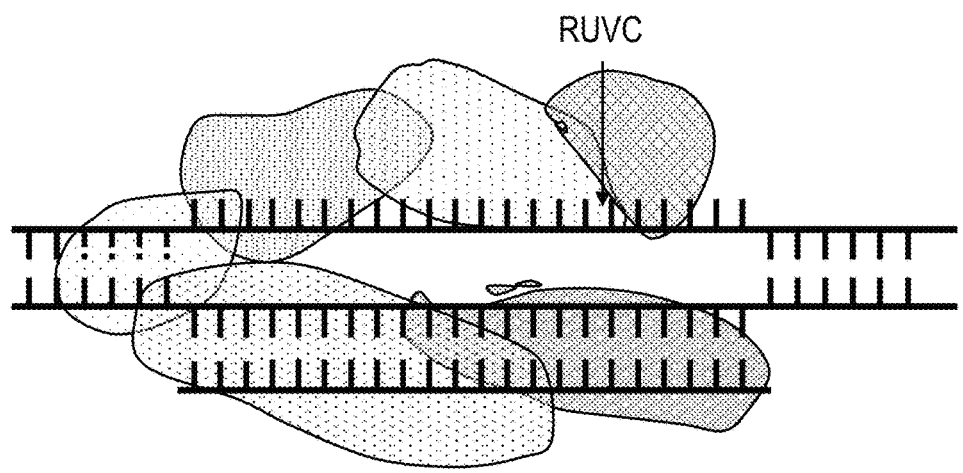
FIG. 2 is an illustration depicting the mechanism of action for Type V CRISPR endonucleases.
Figure 2:
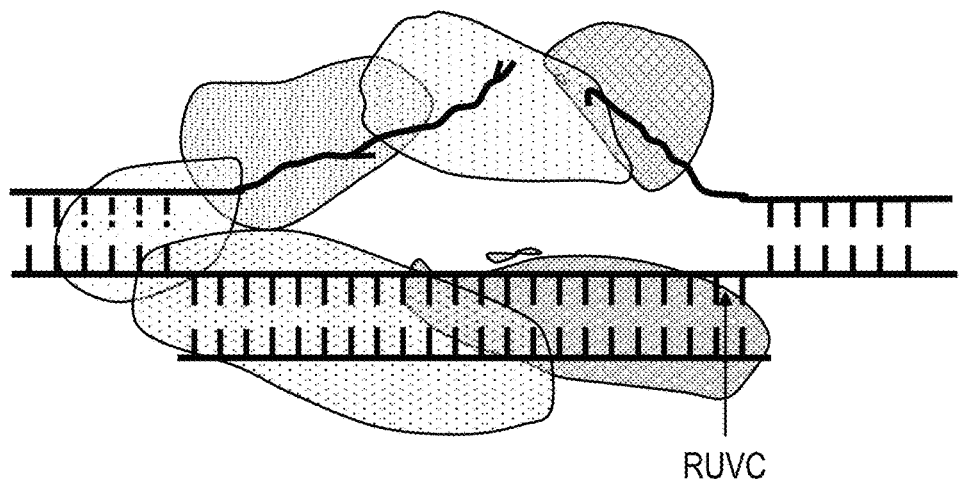

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

Except where defined differently for a specific aspect, the term "about," as used herein when referring to a measurable value such as an amount or concentration and the like, is meant to encompass variations of ±10%, ±5%, ±1%, ±0.5%, or even ±0.1% of the specified value as well as the specified value. For example, "about X" where X is the measurable value, is meant to include X as well as variations of ±10%, ±5%, ±1%, ±0.5%, or even ±0.1% of X. A range provided herein for a measurable value may include any other range and/or individual value therein.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

Recitation of ranges of values herein are merely intended to serve as a shorthand method of referring individually to each separate value falling within the range, unless otherwise indicated herein, and each separate value is incorporated into the specification as if it were individually recited herein. For example, if the range 10 to 15 is disclosed, then 11, 12, 13, and 14 are also disclosed.

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the terms "increase," "increasing," "enhance," "enhancing," "improve" and "improving" (and grammatical variations thereof) describe an elevation of at least about 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500% or more as compared to a control.

or more as compared to a control.

As used herein, the terms "reduce," "reduced," "reducing," "reduction," "diminish," and "decrease" (and grammatical variations thereof), describe, for example, a decrease of at least about 5%, 10%, 15%, 20%, 25%, 35%, 50%, 75%, 80%, 85%, 90%, 95%, 96%, 97%, 98%, 99%, 99.5%, 99.6%, 99.7%, 99.8%, 99.9%, or 100% as compared to a control. In particular embodiments, the reduction can result in no or essentially no (i.e., an insignificant amount, e.g., less than about 10% or even 5%) detectable activity or amount.

A control plant is typically the same plant as the edited plant, but the control plant has not been similarly edited and therefore is devoid of the mutation. A control plant maybe an isogenic plant and/or a wild type plant. Thus, a control plant can be the same breeding line, variety, or cultivar as the subject plant into which a mutation as described herein is introgressed, but the control breeding line, variety, or cultivar is free of the mutation. In some embodiments, a comparison between a plant of the invention and a control plant is made under the same growth conditions, e.g., the same environmental conditions (soil, hydration, light, heat, nutrients, and the like).

As used herein, the terms "express," "expresses," "expressed" or "expression," and the like, with respect to a nucleic acid molecule and/or a nucleotide sequence (e.g., RNA or DNA) indicates that the nucleic acid molecule and/or a nucleotide sequence is transcribed and, optionally, translated. Thus, a nucleic acid molecule and/or a nucleotide sequence may express a polypeptide of interest or, for example, a functional untranslated RNA.

As used herein, the term "heterologous" refers to a nucleotide/polypeptide that originates from a foreign species, or, if from the same species, is substantially modified from its native form in composition and/or genomic locus by deliberate human intervention. A "heterologous" or a "recombinant" nucleotide sequence is a nucleotide sequence not naturally associated with a host cell into which it is introduced, including non-naturally occurring multiple copies of a naturally occurring nucleotide sequence.

A "native" or "wild type" nucleic acid, nucleotide sequence, polypeptide or amino acid sequence refers to a naturally occurring or endogenous nucleic acid, nucleotide sequence, polypeptide or amino acid sequence. Thus, for example, a "native nucleic acid" is a nucleic acid that is naturally occurring in or endogenous to a reference organism. A "homologous" nucleic acid sequence is a nucleotide sequence naturally associated with a host cell into which it is introduced.

As used herein, the term "heterozygous" refers to a genetic status wherein different alleles reside at corresponding loci on homologous chromosomes.

As used herein, the term "homozygous" refers to a genetic status wherein identical alleles reside at corresponding loci on homologous chromosomes.

As used herein, the term "allele" refers to one of two or more different nucleotides or nucleotide sequences that occur at a specific locus.

The term "mutation" refers to point mutations (e.g., missense, or nonsense, or insertions or deletions of single base pairs that result in frame shifts), insertions, deletions, and/or truncations. When the mutation is a substitution of a residue within an amino acid sequence with another residue, or a deletion or insertion of one or more residues within a sequence, the mutations are typically described by identifying the original residue followed by the position of the residue within the sequence and by the identity of the newly substituted residue. A truncation can include a truncation at the C-terminal end of a polypeptide or at the N-terminal end of a polypeptide. A truncation of a polypeptide can be the result of a deletion of the corresponding 5' end or 3' end of the gene encoding the polypeptide. A frameshift mutation can occur when deletions or insertions of one or more base pairs are introduced into a gene, optionally resulting in an out-of-frame mutation or an in-frame mutation. Frameshift mutations in a gene can result in the production of a polypeptide that is longer, shorter or the same length as the wild type polypeptide depending on when the first stop codon occurs following the mutated region of the gene. As an example, an out-of-frame mutation that produces a premature stop codon can produce a polypeptide that is shorter that the wild type polypeptide, or, in some embodiments, the polypeptide may be absent/undetectable. A DNA inversion is the result of a rotation of a genetic fragment within a region of a chromosome.

A "null allele" is a nonfunctional allele caused by a genetic mutation that results in a complete lack of production of the corresponding protein or produces a protein that is non-functional.

A "knock-out mutation" is a mutation that results in a non-functional protein, but which may have a detectable transcript or protein.

A "recessive mutation" is a mutation in a gene that produces a phenotype when homozygous but the phenotype is not observable when the locus is heterozygous.

A "dominant mutation" is a mutation in a gene that produces a mutant phenotype in the presence of a non-mutated copy of the gene. A dominant mutation may be a loss or a gain of function mutation, a hypomorphic mutation, a hypermorphic mutation or a weak loss of function or a weak gain of function.

A "dominant negative mutation" is a mutation that produces an altered gene product (e.g., having an aberrant function relative to wild type), which gene product adversely affects the function of the wild-type allele or gene product. For example, a "dominant negative mutation" may block a function of the wild type gene product. A dominant negative mutation may also be referred to as an "antimorphic mutation."

A "semi-dominant mutation" refers to a mutation in which the penetrance of the phenotype in a heterozygous organism is less than that observed for a homozygous organism.

A "weak loss-of-function mutation" is a mutation that results in a gene product having partial function or reduced function (partially inactivated) as compared to the wild type gene product.

A "hypomorphic mutation" is a mutation that results in a partial loss of gene function, which may occur through reduced expression (e.g., reduced protein and/or reduced RNA) or reduced functional performance (e.g., reduced activity), but not a complete loss of function/activity. A "hypomorphic" allele is a semi-functional allele caused by a genetic mutation that results in production of the corresponding protein that functions at anywhere between 1% and 99% of normal efficiency.

A "hypermorphic mutation" is a mutation that results in increased expression of the gene product and/or increased activity of the gene product.

A "gain-of-function" allele or mutation is a mutation that confers a new function on the encoded gene product and/or confers a new gene expression pattern. In some embodiments, a gain-of-function mutation may be dominant or semi-dominant.

As used herein, a "non-natural mutation" refers to a mutation that is generated through human intervention and differs from mutations found in the same gene that have occurred in nature (e.g., occurred naturally and not as a result of a modification made by a human).

A "locus" is a position on a chromosome where a gene or marker or allele is located. In some embodiments, a locus may encompass one or more nucleotides.

As used herein, the terms "desired allele," "target allele" and/or "allele of interest" are used interchangeably to refer to an allele associated with a desired trait. In some embodiments, a desired allele may be associated with either an increase or a decrease (relative to a control) of or in a given trait, depending on the nature of the desired phenotype. In some embodiments of this invention, the phrase "desired allele," "target allele" or "allele of interest" refers to an allele(s) that is associated with increased yield under non-water stress conditions in a plant relative to a control plant not having the target allele or alleles.

A marker is "associated with" a trait when said trait is linked to it and when the presence of the marker is an indicator of whether and/or to what extent the desired trait or trait form will occur in a plant/germplasm comprising the marker. Similarly, a marker is "associated with" an allele or chromosome interval when it is linked to it and when the presence of the marker is an indicator of whether the allele or chromosome interval is present in a plant/germplasm comprising the marker.

As used herein, the terms "nucleic acid," "nucleic acid molecule," "nucleotide sequence" and "polynucleotide" refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made.

As used herein, the term "nucleotide sequence" refers to a heteropolymer of nucleotides or the sequence of these nucleotides from the 5' to 3' end of a nucleic acid molecule and includes DNA or RNA molecules, including cDNA, a DNA fragment or portion, genomic DNA, synthetic (e.g., chemically synthesized) DNA, plasmid DNA, mRNA, and anti-sense RNA, any of which can be single stranded or double stranded. The terms "nucleotide sequence" "nucleic acid," "nucleic acid molecule," "nucleic acid construct," "oligonucleotide" and "polynucleotide" are also used interchangeably herein to refer to a heteropolymer of nucleotides. Nucleic acid molecules and/or nucleotide sequences provided herein are presented herein in the 5' to 3' direction, from left to right and are represented using the standard code for representing the nucleotide characters as set forth in the U.S. sequence rules, 37 CFR §§ 1.831-1.835 and the World Intellectual Property Organization (WIPO) Standard ST.26. A "5 region" as used herein can mean the region of a polynucleotide that is nearest the 5' end of the polynucleotide. Thus, for example, an element in the 5' region of a polynucleotide can be located anywhere from the first nucleotide located at the 5' end of the polynucleotide to the nucleotide located halfway through the polynucleotide. A "3' region" as used herein can mean the region of a polynucleotide that is nearest the 3' end of the polynucleotide. Thus, for example, an element in the 3' region of a polynucleotide can be located anywhere from the first nucleotide located at the 3' end of the polynucleotide to the nucleotide located halfway through the polynucleotide.

As used herein, the term "gene" refers to a nucleic acid molecule capable of being used to produce mRNA, anti-sense RNA, miRNA, anti-microRNA antisense oligodeoxyribonucleotide (AMO) and the like. Genes may or may not be capable of being used to produce a functional protein or gene product. Genes can include both coding and non-coding regions (e.g., introns, regulatory elements, promoters, enhancers, termination sequences and/or 5 and 3' untranslated regions). A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

The terms "complementary" or "complementarity," as used herein, refer to the natural binding of polynucleotides under permissive salt and temperature conditions by base-pairing. For example, the sequence "A-G-T" (5 to 3') binds to the complementary sequence "T-C-A" (3' to 5). Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

"Complement," as used herein, can mean 100% complementarity with the comparator nucleotide sequence or it can mean less than 100% complementarity (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like, complementarity; e.g., substantial complementarity) to the comparator nucleotide sequence.

A "portion" or "fragment" of a nucleotide sequence of the invention will be understood to mean a nucleotide sequence of reduced length relative (e.g., reduced by 1, 2, 3, 4, 5, 6, 7, 8, 9, 10, 11, 12, 13, 14, 15, 16, 17, 18, 19, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 400, 450, 500, 550, 600, 650, 700, 750, 800, 850, 900, 950 or 1000 or more nucleotides or any range or value therein) to a reference nucleic acid and that comprises, consists essentially of and/or consists of a nucleotide sequence of contiguous nucleotides identical or almost identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical) to a corresponding portion of the reference nucleic acid. Such a nucleic acid fragment may be, where appropriate, included in a larger polynucleotide of which it is a constituent. As an example, a repeat sequence of guide nucleic acid of this invention may comprise a portion of a wild type CRISPR-Cas repeat sequence (e.g., a wild-type Type V CRISPR Cas repeat, e.g., a repeat from the CRISPR Cas system that includes, but is not limited to, Cas12a (Cpf1), Cas12b, Cas12c (C2c3), Cas12d (CasY), Cas12e (CasX), Cas12g, Cas12h, Cas12i, C2c1, C2c4, C2c5, C2c8, C2c9, C2c10, Cas14a, Cas14b, and/or Cas14c, and the like). Similarly, a portion of a polypeptide may be included in a larger polypeptide of which it is a constituent.

As used herein with respect to polypeptides, the term "fragment" or "portion" may refer to a polypeptide that is reduced in length relative to a reference polypeptide and that comprises, consists essentially of and/or consists of an amino acid sequence of contiguous amino acids identical or almost identical (e.g., 90%, 91%, 92%, 93%, 94%, 95%, 96%, 97%, 98%, 99% identical) to a corresponding portion of the reference polypeptide. Such a polypeptide fragment may be, where appropriate, included in a larger polypeptide of which it is a constituent. In some embodiments, a "portion" may be related to the number of amino acids that are deleted from a polypeptide. In some embodiments, a polypeptide fragment comprises, consists essentially of or consists of at least about 5, 6, 7, 8, 9, 10, 11, 12, 13, 14, 15, 20, 21, 22, 23, 24, 25, 26, 27, 28, 29, 30, 35, 40, 45, 46, 47, 48, 49, 50, 55, 60, 65, 70, 75, 80, 85, 90, 95, 100, 125, 150, 175, 200, 225, 250, 300, 350, 400 or more consecutive amino acids of a reference polypeptide. A "region" of a polynucleotide or a polypeptide refers to a portion of consecutive nucleotides or consecutive amino acid residues of that polynucleotide or a polypeptide, respectively.

As used herein with respect to nucleic acids, the term "functional fragment" refers to nucleic acid that encodes a functional fragment of a polypeptide. A "functional fragment" with respect to a polypeptide is a fragment of a polypeptide that retains one or more of the activities of the native reference polypeptide.

Different nucleic acids or proteins having homology are referred to herein as "homologues." The term homologue includes homologous sequences from the same and other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the invention further comprise homologues to the nucleotide sequences and polypeptide sequences of this invention. "Orthologous," as used herein, refers to homologous nucleotide sequences and/or amino acid sequences in different species that arose from a common ancestral gene during speciation. A homologue of a nucleotide sequence of this invention has a substantial sequence identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100%) to said nucleotide sequence of the invention.

As used herein "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence as compared to a reference polypeptide.

As used herein, the phrase "substantially identical," or "substantial identity" in the context of two nucleic acid molecules, nucleotide sequences or protein sequences, refers to two or more sequences or subsequences that have at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% nucleotide or amino acid residue identity, when compared and aligned for maximum correspondence, as measured using one of the following sequence comparison algorithms or by visual inspection. In some embodiments of the invention, the substantial identity exists over a region of consecutive nucleotides of a nucleotide sequence of the invention that is about 10 nucleotides to about 20 nucleotides, about 10 nucleotides to about 25 nucleotides, about 10 nucleotides to about 30 nucleotides, about 15 nucleotides to about 25 nucleotides, about 30 nucleotides to about 40 nucleotides, about 50 nucleotides to about 60 nucleotides, about 70 nucleotides to about 80 nucleotides, about 90 nucleotides to about 100 nucleotides, or more nucleotides in length, and any range therein, up to the full length of the sequence. In some embodiments, the nucleotide sequences can be substantially identical over at least about 20 nucleotides (e.g., about 20, 21, 22, 23, 24, 25, 26, 27, 28, 29, 30, 31, 32, 33, 34, 35, 36, 37, 38, 39, 40 nucleotides). In some embodiments, a substantially identical nucleotide or protein sequence performs substantially the same function as the nucleotide (or encoded protein sequence) to which it is substantially identical.

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Methods of alignment of sequences for comparison are well known in the art and can be accomplished using mathematical algorithms such as the algorithm of Myers and Miller (1988) CABIOS 4:11-17; the local alignment algorithm of Smith et al. (1981) Adv. Appl. Math. 2:482; the global alignment algorithm of Needleman and Wunsch (1970) J. Mol. Biol. 48:443-453; and the algorithm of Karlin and Altschul (1990) Proc. Natl. Acad. Sci. USA 872264, modified as in Karlin and Altschul (1993) Proc. Natl. Acad. Sci. USA 90:5873-5877. Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA).

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., San Diego, CA) as well as web-based alignment programs such as Clustal Omega, EMBOSS Needle, EMBOSS Stretcher, EMBOSS Water, LALIGN, GGSEARCH2SEQ, EMBOS Cons, Kalign, MAFFT, MUSCLE, and T-Coffee. In some embodiments, an "optimal alignment" of two sequences (e.g., two polypeptide sequences) is the highest scoring alignment, optionally from an alignment conducted by a tool such as the local homology algorithm of Smith and Waterman, the homology alignment algorithm of Needleman and Wunsch, the search for similarity method of Pearson and Lipman, GAP, BESTFIT, FASTA, and TFASTA available as part of the GCG® Wisconsin Package® (Accelrys Inc., San Diego, CA), Clustal Omega, EMBOSS Needle, EMBOSS Stretcher, EMBOSS Water, LALIGN, GGSEARCH2SEQ, EMBOS Cons, Kalign, MAFFT, MUSCLE, and/or T-Coffee. In some embodiments, an "optimal alignment" of two sequences (e.g., two polypeptide sequences) is the alignment that provides the highest percent sequence identity, optionally allowing for one or more gap(s) to be introduced into one or both sequences. An "identity fraction" for aligned segments of a test sequence and a reference sequence is the number of identical components which are shared by the two aligned sequences divided by the total number of components in the reference sequence segment, e.g., the entire reference sequence or a smaller defined part of the reference sequence. Percent sequence identity is represented as the identity fraction multiplied by 100. The comparison of one or more sequences may be to a full-length sequence or a portion thereof, or to a longer sequence. For purposes of this invention "percent identity" and/or optimal alignment may be determined using Basic Local Alignment Search Tool (BLAST) provided by the National Center for Biotechnology Information such as BLASTX, for translated nucleotide sequences, BLASTN for polynucleotide sequences, and BLASTP for polypeptide sequences.

Two nucleotide sequences may also be considered substantially complementary when the two sequences hybridize to each other under stringent conditions. In some representative embodiments, two nucleotide sequences considered to be substantially complementary hybridize to each other under highly stringent conditions.

"Stringent hybridization conditions" and "stringent hybridization wash conditions" in the context of nucleic acid hybridization experiments such as Southern and Northern hybridizations are sequence dependent, and are different under different environmental parameters. An extensive guide to the hybridization of nucleic acids is found in Tijssen *Laboratory Techniques in Biochemistry and Molecular Biology-Hybridization with Nucleic Acid Probes* part I chapter 2 "Overview of principles of hybridization and the strategy of nucleic acid probe assays" Elsevier, New York (1993). Generally, highly stringent hybridization and wash conditions are selected to be about 5° C. lower than the thermal melting point ($T_m$) for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleotide sequences which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleotide sequences that do not hybridize to each other under stringent conditions are still substantially identical if the proteins that they encode are substantially identical. This can occur, for example, when a copy of a nucleotide sequence is created using the maximum codon degeneracy permitted by the genetic code.

Any nucleotide sequence, polynucleotide and/or recombinant nucleic acid construct of this invention can be optimized for expression in any organism of interest. Optimization for expression is well known in the art and involves, for example, modification of a nucleotide sequence for codon usage bias using species specific codon usage tables. Also relevant for optimization of expression is the editing efficiency of the target gene. Thus, the ability to generate a specific edit with a frequency that produces a sufficient number of edited alleles to enable selection of a commercially relevant edited allele of a target gene is a factor to be considered when optimizing for expression. In some embodiments, a polynucleotide, nucleic acid construct, expression cassette, and/or vector of the present invention (e.g., that comprises/encodes a polypeptide of the present invention (e.g., an engineered protein), a nucleic acid binding polypeptide (e.g., a DNA binding polypeptide such as a sequence-specific DNA binding domain from a polynucleotide-guided endonuclease, a zinc finger nuclease, a transcription activator-like effector nuclease (TALEN), an Argonaute protein, and/or a CRISPR-Cas effector protein), a guide nucleic acid, a cytosine deaminase and/or adenine deaminase) may be optimized for expression in an organism (e.g., an animal such as a human, a plant, a fungus, an archaeon, or a bacterium). In some embodiments, the optimized nucleic acid constructs, polynucleotides, expression cassettes, and/or vectors of the invention have about 70% to about 99.9% (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.9% or 100%) identity or more to the reference nucleic acid constructs, polynucleotides, expression cassettes, and/or vectors but which have not been optimized for expression.

To modify a nucleotide sequence for codon usage, codon usage tables are generated based on a sequence analysis of the most highly expressed genes for a organism/species of interest. When the nucleotide sequences are to be expressed in the nucleus, the codon usage tables are generated based on a sequence analysis of highly expressed nuclear genes for the species of interest. The modifications of the nucleotide sequences are determined by comparing the species specific codon usage table with the codons present in the native polynucleotide sequences. As is understood in the art, codon optimization of a nucleotide sequence results in a nucleotide sequence having less than 100% identity (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, or 99.9%, and any range or value therein) to the native nucleotide sequence but which still encodes a polypeptide having the same function as that encoded by the original, native nucleotide sequence. Thus, in some embodiments of the invention, the polynucleotides, nucleic acid constructs, expression cassettes, and/or vectors of the invention (e.g., comprising/encoding a polypeptide, fusion protein, complex of the invention, e.g., a modified CRISPR-Cas nuclease) are codon optimized for expression in a particular species of interest, e.g., a particular plant species, a particular bacterial species, a particular animal species, and the like. In some embodiments, the codon optimized nucleic acid constructs, polynucleotides, expression cassettes, and/or vectors of the invention have about 70% to about 99.9% (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.9% or 100%) identity or more to the polynucleotides, nucleic acid constructs, expression cassettes, and/or vectors of the invention that have not been codon optimized In some embodiments, a polynucleotide or nucleic acid construct of the invention may be operatively associated with a variety of promoters and/or other regulatory elements for expression in a plant and/or a cell of a plant. Thus, in some embodiments, a polynucleotide or nucleic acid construct of this invention may further comprise one or more promoters, introns, enhancers, and/or terminators operably linked to one or more nucleotide sequences. In some embodiments, a promoter may be operably associated with an intron (e.g., Ubi1 promoter and intron). In some embodiments, a promoter associated with an intron maybe referred to as a "promoter region" (e.g., Ubi1 promoter and intron).

By "operably linked" or "operably associated" as used herein in reference to polynucleotides, it is meant that the indicated elements are functionally related to each other, and are also generally physically related. Thus, the term "operably linked" or "operably associated" as used herein, refers to nucleotide sequences on a single nucleic acid molecule that are functionally associated. Thus, a first nucleotide sequence that is operably linked to a second nucleotide sequence means a situation when the first nucleotide sequence is placed in a functional relationship with the second nucleotide sequence. For instance, a promoter is operably associated with a nucleotide sequence if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, nucleic acid sequences can be present between a promoter and the nucleotide sequence, and the promoter can still be considered "operably linked" to the nucleotide sequence.

As used herein, the term "linked," in reference to polypeptides, refers to the attachment of one polypeptide to another. A polypeptide may be linked to another polypeptide (at the N-terminus or the C-terminus) directly (e.g., via a peptide bond) or through a linker.

The term "linker" in reference to polypeptides is art-recognized and refers to a chemical group, or a molecule linking two molecules or moieties, e.g., two polypeptides or domains of a fusion protein, such as, for example, a CRISPR-Cas effector protein and a peptide tag and/or a polypeptide of interest. A linker may be comprised of a single linking molecule (e.g., a single amino acid) or may comprise more than one linking molecule. In some embodiments, the linker can be an organic molecule, group, polymer, or chemical moiety such as a bivalent organic moiety. In some embodiments, the linker may be an amino acid or it may be a peptide. In some embodiments, the linker is a peptide (e.g., a peptide linker).

In some embodiments, a peptide linker useful with this invention may be about 2, to about 100 or more amino acids in length, for example, about 2, 3, 4, 6, 7, 8, 9, 10, 11, 12, 13, 14, 15, 16, 17, 18, 19, 20, 21, 22, 23, 24, 25, 26, 27, 28, 29, 30, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length (e.g., about 2 to about 40, about 2 to about 50, about 2 to about 60, about 4 to about 40, about 4 to about 50, about 4 to about 60, about 5 to about 40, about 5 to about 50, about 5 to about 60, about 9 to about 40, about 9 to about 50, about 9 to about 60, about 10 to about 40, about 10 to about 50, about 10 to about 60, or about 2, 3, 4, 5, 6, 7, 8, 9, 10, 11, 12, 13, 14, 15, 16, 17, 18, 19, 20, 21, 22, 23, 24, 25 amino acids to about 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length (e.g., about 105, 110, 115, 120, 130, 140, 150 or more amino acids in length) In some embodiments, a peptide linker may be a GS linker. In some embodiments, the peptide linker is a GS linker having 1, 2, 3, or 4 amino acid residues, optionally 2 or 4 amino acid residues. In some embodiments, the peptide linker has one of the amino acid sequences of SEQ ID NOs:18-47 or 175-179. In some embodiments, the peptide linker may comprise an amino acid sequence of $(GGS)_n$, GS, SG, GSSG (SEQ ID NO:175), GSSGSS (SEQ ID NO:176), GSSGSSGS (SEQ ID NO:177), $(GSS)_n$ (SEQ ID NO:178), $(GSS)_nGS$ (SEQ ID NO:179), $S(GGS)_n$ (SEQ ID NO:42), SGGS (SEQ ID NO:43), or (GGGGS)n (SEQ ID NO:44), wherein n is an integer of 1-20 (e.g., 1, 2, 3, 4, 5, 6, 7, 8, 9, 10, 11, 12, 13, 14, 15, 16, 17, 18, 19, or 20). In some embodiments, the peptide linker may comprise the amino acid sequence: SGGSGGSGGS (SEQ ID NO:45). In some embodiments, the peptide linker may comprise the amino acid sequence: SGSETPGTSESATPES (SEQ ID NO:46), also referred to as the XTEN linker. In some embodiments, the peptide linker may comprise the amino acid sequence: SGGSSGGSSGSETPGTSESATPESSGGSSGGS (SEQ ID NO:47), also referred to as the GS-XTEN-GS linker.

As used herein, the term "linked," or "fused" in reference to polynucleotides, refers to the attachment of one polynucleotide to another polynucleotide. In some embodiments, two or more polynucleotide molecules may be linked by a linker that can be an organic molecule, group, polymer, or chemical moiety such as a bivalent organic moiety. A polynucleotide may be linked or fused to another polynucleotide (at the 5' end or the 3' end) via a covalent or non-covanent linkage or binding, including e.g., Watson-Crick base-pairing, or through one or more linking nucleotides. In some embodiments, a polynucleotide motif of a certain structure may be inserted within another polynucleotide sequence (e.g., extension of the hairpin structure in guide RNA). In some embodiments, the linking nucleotides may be naturally occurring nucleotides. In some embodiments, the linking nucleotides may be non-naturally occurring nucleotides.

A "promoter" is a nucleotide sequence that controls or regulates the transcription of a nucleotide sequence (e.g., a coding sequence) that is operably associated with the promoter. The coding sequence controlled or regulated by a promoter may encode a polypeptide and/or a functional RNA. Typically, a "promoter" refers to a nucleotide sequence that contains a binding site for RNA polymerase II and directs the initiation of transcription. In general, promoters are found 5', or upstream, relative to the start of the coding region of the corresponding coding sequence. A promoter may comprise other elements that act as regulators of gene expression; e.g., a promoter region. These include a TATA box consensus sequence, and often a CAAT box consensus sequence (Breathnach and Chambon, (1981) *Annu. Rev. Biochem.* 50:349). In plants, the CAAT box may be substituted by the AGGA box (Messing et al., (1983) in Genetic Engineering of Plants, T. Kosuge, C. Meredith and A. Hollaender (eds.), Plenum Press, pp. 211-227). In some embodiments, a promoter region may comprise at least one intron (e.g., SEQ ID NO:48 or SEQ ID NO:49).

Promoters useful with this invention can include, for example, constitutive, inducible, temporally regulated, developmentally regulated, chemically regulated, tissue-preferred and/or tissue-specific promoters for use in the preparation of recombinant nucleic acid molecules, e.g., "synthetic nucleic acid constructs" or "protein-RNA complex." These various types of promoters are known in the art.

The choice of promoter may vary depending on the temporal and spatial requirements for expression, and also may vary based on the host cell to be transformed. Promoters for many different organisms are well known in the art. Based on the extensive knowledge present in the art, the appropriate promoter can be selected for the particular host organism of interest. Thus, for example, much is known about promoters upstream of highly constitutively expressed genes in model organisms and such knowledge can be readily accessed and implemented in other systems as appropriate.

In some embodiments, a promoter functional in a plant may be used with the constructs of this invention. Non-limiting examples of a promoter useful for driving expression in a plant include the promoter of the RubisCo small subunit gene 1 (PrbcS1), the promoter of the actin gene (Pactin), the promoter of the nitrate reductase gene (Pnr) and the promoter of duplicated carbonic anhydrase gene 1 (Pdca1) (See, Walker et al. *Plant Cell Rep.* 23:727-735 (2005); Li et al. *Gene* 403:132-142 (2007); Li et al. *Mol Biol. Rep.* 37:1143-1154 (2010)). PrbcS1 and Pactin are constitutive promoters and Pnr and Pdca1 are inducible promoters. Pnr is induced by nitrate and repressed by ammonium (Li et al. *Gene* 403:132-142 (2007)) and Pdca1 is induced by salt (Li et al. *Mol Biol. Rep.* 37:1143-1154 (2010)).

Examples of constitutive promoters useful for plants include, but are not limited to, cestrum virus promoter (cmp) (U.S. Pat. No. 7,166,770), the rice actin 1 promoter (Wang et al. (1992) *Mol. Cell. Biol.* 12:3399-3406; as well as U.S. Pat. No. 5,641,876), CaMV 35S promoter (Odell et al. (1985) *Nature* 313:810-812), CaMV 19S promoter (Lawton et al. (1987) *Plant Mol. Biol.* 9:315-324), nos promoter (Ebert et al. (1987) *Proc. Natl. Acad. Sci USA* 84:5745-5749), Adh promoter (Walker et al. (1987) *Proc. Natl. Acad. Sci. USA* 84:6624-6629), sucrose synthase promoter (Yang & Russell (1990) *Proc. Natl. Acad. Sci. USA* 87:4144-4148), and the ubiquitin promoter. The constitutive promoter derived from ubiquitin accumulates in many cell types. Ubiquitin promoters have been cloned from several plant species for use in transgenic plants, for example, sunflower (Binet et al., 1991. *Plant Science* 79: 87-94), maize (Christensen et al., 1989. *Plant Molec. Biol.* 12: 619-632), and *Arabidopsis* (Norris et al. 1993. *Plant Molec. Biol.* 21:895-906). The maize ubiquitin promoter (UbiP) has been developed in transgenic monocot systems and its sequence and vectors constructed for monocot transformation are disclosed in the patent publication EP 0 342 926. The ubiquitin promoter is suitable for the expression of the nucleotide sequences of the invention in transgenic plants, especially monocotyledons. Further, the promoter expression cassettes described by McElroy et al. (*Mol. Gen. Genet.* 231: 150-160 (1991)) can be easily modified for the expression of the nucleotide sequences of the invention and are particularly suitable for use in monocotyledonous hosts.

In some embodiments, tissue specific/tissue preferred promoters can be used for expression of a heterologous polynucleotide in a plant cell. Tissue specific or preferred expression patterns include, but are not limited to, green tissue specific or preferred, root specific or preferred, stem specific or preferred, flower specific or preferred or pollen specific or preferred. Promoters suitable for expression in green tissue include many that regulate genes involved in photosynthesis and many of these have been cloned from both monocotyledons and dicotyledons. In one embodiment, a promoter useful with the invention is the maize PEPC promoter from the phosphoenol carboxylase gene (Hudspeth & Grula, *Plant Molec. Biol.* 12:579-589 (1989)). Non-limiting examples of tissue-specific promoters include those associated with genes encoding the seed storage proteins (such as β-conglycinin, cruciferin, napin and phaseolin), zein or oil body proteins (such as oleosin), or proteins involved in fatty acid biosynthesis (including acyl carrier protein, stearoyl-ACP desaturase and fatty acid desaturases (fad 2-1)), and other nucleic acids expressed during embryo development (such as Bce4, see, e.g., Kridl et al. (1991) *Seed Sci. Res.* 1:209-219; as well as EP Patent No. 255378). Tissue-specific or tissue-preferential promoters useful for the expression of the nucleotide sequences of the invention in plants, particularly maize, include but are not limited to those that direct expression in root, pith, leaf or pollen. Such promoters are disclosed, for example, in WO 93/07278, herein incorporated by reference in its entirety. Other non-limiting examples of tissue specific or tissue preferred promoters useful with the invention the cotton rubisco promoter disclosed in U.S. Pat. No. 6,040,504; the rice sucrose synthase promoter disclosed in U.S. Pat. No. 5,604,121; the root specific promoter described by de Framond (FEBS 290:103-106 (1991); EP 0 452 269 to Ciba-Geigy); the stem specific promoter described in U.S. Pat. No. 5,625,136 (to Ciba-Geigy) and which drives expression of the maize trpA gene; the cestrum yellow leaf curling virus promoter disclosed in WO 01/73087; and pollen specific or preferred promoters including, but not limited to, ProOsLPS10 and ProOsLPS11 from rice (Nguyen et al. *Plant Biotechnol. Reports* 9(5):297-306 (2015)), ZmSTK2_USP from maize (Wang et al. *Genome* 60(6):485-495 (2017)), LAT52 and LAT59 from tomato (Twell et al. *Development* 109(3):705-713 (1990)), Zm13 (U.S. Pat. No. 10,421,972), PLA$_2$-δ promoter from *Arabidopsis* (U.S. Pat. No. 7,141,424), and/or the ZmC5 promoter from maize (International PCT Publication No. WO1999/042587.

Additional examples of plant tissue-specific/tissue preferred promoters include, but are not limited to, the root hair-specific cis-elements (RHEs) (Kim et al. *The Plant Cell*

18:2958-2970 (2006)), the root-specific promoters RCc3 (Jeong et al. *Plant Physiol.* 153:185-197 (2010)) and RB7 (U.S. Pat. No. 5,459,252), the lectin promoter (Lindstrom et al. (1990) *Der. Genet.* 11:160-167; and Vodkin (1983) *Prog. Clin. Biol. Res.* 138:87-98), corn alcohol dehydrogenase 1 promoter (Dennis et al. (1984) *Nucleic Acids Res.* 12:3983-4000), S-adenosyl-L-methionine synthetase (SAMS) (Vander Mijnsbrugge et al. (1996) *Plant and Cell Physiology*, 37(8):1108-1115), corn light harvesting complex promoter (Bansal et al. (1992) *Proc. Natl. Acad. Sci. USA* 89:3654-3658), corn heat shock protein promoter (O'Dell et al. (1985) *EMBO J.* 5:451-458; and Rochester et al. (1986) *EMBO J.* 5:451-458), pea small subunit RuBP carboxylase promoter (Cashmore, "Nuclear genes encoding the small subunit of ribulose-I,5-bisphosphate carboxylase" pp. 29-39 In: Genetic Engineering of Plants (Hollaender ed., Plenum Press 1983; and Poulsen et al. (1986) *Mol. Gen. Genet.* 205:193-200), Ti plasmid mannopine synthase promoter (Langridge et al. (1989) *Proc. Natl. Acad. Sci. USA* 86:3219-3223), Ti plasmid nopaline synthase promoter (Langridge et al. (1989), supra), *Petunia chalcone* isomerase promoter (van Tunen et al. (1988) *EMBO J.* 7:1257-1263), bean glycine rich protein 1 promoter (Keller et al. (1989) *Genes Dev.* 3:1639-1646), truncated CaMV 35S promoter (O'Dell et al. (1985) *Nature* 313:810-812), potato patatin promoter (Wenzler et al. (1989) *Plant Mol. Biol.* 13:347-354), root cell promoter (Yamamoto et al. (1990) *Nucleic Acids Res.* 18:7449), maize zein promoter (Kriz et al. (1987) *Mol. Gen. Genet.* 207:90-98; Langridge et al. (1983) *Cell* 34:1015-1022; Reina et al. (1990) *Nucleic Acids Res.* 18:6425; Reina et al. (1990) *Nucleic Acids Res.* 18:7449; and Wandelt et al. (1989) *Nucleic Acids Res.* 17:2354), globulin-1 promoter (Belanger et al. (1991) *Genetics* 129:863-872), α-tubulin cab promoter (Sullivan et al. (1989) *Mol. Gen. Genet.* 215:431-440), PEPCase promoter (Hudspeth & Grula (1989) *Plant Mol. Biol.* 12:579-589), R gene complex-associated promoters (Chandler et al. (1989) *Plant Cell* 1:1175-1183), and chalcone synthase promoters (Franken et al. (1991) *EMBO J.* 10:2605-2612).

Useful for seed-specific expression is the pea vicilin promoter (Czako et al. (1992) *Mol. Gen. Genet.* 235:33-40; as well as the seed-specific promoters disclosed in U.S. Pat. No. 5,625,136. Useful promoters for expression in mature leaves are those that are switched at the onset of senescence, such as the SAG promoter from *Arabidopsis* (Gan et al. (1995) *Science* 270:1986-1988).

In addition, promoters functional in chloroplasts can be used. Non-limiting examples of such promoters include the bacteriophage T3 gene 9 5' UTR and other promoters disclosed in U.S. Pat. No. 7,579,516. Other promoters useful with the invention include but are not limited to the S-E9 small subunit RuBP carboxylase promoter and the Kunitz trypsin inhibitor gene promoter (Kti3).

Additional regulatory elements useful with this invention include, but are not limited to, introns, enhancers, termination sequences and/or 5' and 3' untranslated regions.

An intron useful with this invention can be an intron identified in and isolated from a plant and then inserted into an expression cassette to be used in transformation of a plant. As would be understood by those of skill in the art, introns can comprise the sequences required for self-excision and are incorporated into nucleic acid constructs/expression cassettes in frame. An intron can be used either as a spacer to separate multiple protein-coding sequences in one nucleic acid construct, or an intron can be used inside one protein-coding sequence to, for example, stabilize the mRNA. If they are used within a protein-coding sequence, they are inserted "in-frame" with the excision sites included. Introns may also be associated with promoters to improve or modify expression. As an example, a promoter/intron combination useful with this invention includes but is not limited to that of the maize Ubi1 promoter and intron.

Non-limiting examples of introns useful with the present invention include introns from the ADHI gene (e.g., Adh1-S introns 1, 2 and 6), the ubiquitin gene (Ubi1), the RuBisCO small subunit (rbcS) gene, the RuBisCO large subunit (rbcL) gene, the actin gene (e.g., actin-1 intron), the pyruvate dehydrogenase kinase gene (pdk), the nitrate reductase gene (nr), the duplicated carbonic anhydrase gene 1 (Tdca1), the psbA gene, the atpA gene, or any combination thereof. As a non-limiting example, a nucleic acid construct of the present invention may encode a base editor comprising a CRISPR-Cas nuclease (e.g., SEQ ID NOs:180 and/or 51-66, or 193 (amino acid sequences) or SEQ ID NOs:67-69 (nucleotide sequences), and a deaminase, optionally SEQ ID NO:180, SEQ ID NO:51, SEQ ID NO:55, SEQ ID NO:194 or SEQ ID NO:195, wherein the nucleic acid construct further comprises a promoter comprising/associated with an intron. As a further non-limiting example, a nucleic acid construct of the present invention may encode a base editor comprising a CRISPR-Cas nuclease (e.g., SEQ ID NOs:180 and/or 51-66, or 193 or SEQ ID NOs:67-69, optionally SEQ ID NO:180, SEQ ID NO:51, SEQ ID NO:55, SEQ ID NO:194 or SEQ ID NO:195) which has been modified as described herein and a deaminase, wherein the nuclease and/or the deaminase comprises one or more introns and optionally, the nucleic acid construct further comprises a promoter comprising/associated with an intron.

An "editing system" as used herein refers to any site-specific (e.g., sequence-specific) nucleic acid editing system now known or later developed, which system can introduce a modification (e.g., a mutation) in a nucleic acid in target specific manner. For example, an editing system (e.g., a site- and/or sequence-specific editing system) can include, but is not limited to, a CRISPR-Cas editing system, a meganuclease editing system, a zinc finger nuclease (ZFN) editing system, a transcription activator-like effector nuclease (TALEN) editing system, a base editing system and/or a prime editing system, each of which may comprise one or more polypeptide(s) and/or one or more polynucleotide(s) that when present and/or expressed together (e.g., as a system) in a composition and/or cell can modify (e.g., mutate) a target nucleic acid in a sequence specific manner. In some embodiments, an editing system (e.g., a site- and/or sequence-specific editing system) can comprise one or more polynucleotide(s) and/or one or more polypeptide(s), including but not limited to a nucleic acid binding polypeptide (e.g., a DNA binding domain), a nuclease, another polypeptide, and/or a polynucleotide. In some embodiments, a CRISPR-Cas editing system is provided and/or is used that comprises an engineered protein of the present invention.

In some embodiments, an editing system comprises one or more sequence-specific nucleic acid binding polypeptide(s) (e.g., a DNA binding domain) that can be from, for example, a polynucleotide-guided endonuclease, a CRISPR-Cas endonuclease (e.g., CRISPR-Cas effector protein), a zinc finger nuclease, a transcription activator-like effector nuclease (TALEN) and/or an Argonaute protein. In some embodiments, an editing system comprises one or more cleavage polypeptide(s) (e.g., nucleases) including, but not limited to, an endonuclease (e.g., Fok1), a polynucleotide-guided endonuclease, a CRISPR-Cas endonuclease (e.g., CRISPR-Cas effector protein), a zinc finger nuclease, and/or a transcription activator-like effector nuclease (TALEN).

A "nucleic acid binding polypeptide" as used herein refers to a polypeptide or domain that binds and/or is capable of binding a nucleic acid (e.g., a target nucleic acid). A DNA binding domain is an exemplary nucleic acid binding polypeptide and may be a site- and/or sequence-specific nucleic acid binding domain. In some embodiments, a nucleic acid binding polypeptide may be a sequence-specific nucleic acid binding polypeptide such as, but not limited to, a sequence-specific binding domain from, for example, a polynucleotide-guided endonuclease, a CRISPR-Cas effector protein (e.g., a CRISPR-Cas endonuclease), a zinc finger nuclease, a transcription activator-like effector nuclease (TALEN) and/or an Argonaute protein. In some embodiments, a nucleic acid binding polypeptide comprises a cleavage domain (e.g., a nuclease domain) such as, but not limited to, an endonuclease (e.g., Fok1), a polynucleotide-guided endonuclease, a CRISPR-Cas endonuclease, a zinc finger nuclease, and/or a transcription activator-like effector nuclease (TALEN). In some embodiments, the nucleic acid binding polypeptide is a polypeptide associates with and/or is capable of associating with (e.g., forms a complex with) one or more nucleic acid molecule(s) (e.g., forms a complex with a guide nucleic acid as described herein), which may direct and/or guide the nucleic acid binding polypeptide to a specific target nucleotide sequence (e.g., a gene locus of a genome) that is complementary to the one or more nucleic acid molecule(s) (or a portion or region thereof), thereby causing the nucleic acid binding polypeptide to bind to the nucleotide sequence at the specific target site. In some embodiments, the nucleic acid binding polypeptide is a CRISPR-Cas effector protein as described herein.

In some embodiments, an editing system comprises or is a ribonucleoprotein such as an assembled ribonucleoprotein complex (e.g., a ribonucleoprotein that comprises a CRISPR-Cas effector protein, a guide nucleic acid, and optionally a deaminase). In some embodiments, a ribonucleoprotein of an editing system may be assembled together (e.g., a pre-assembled ribonucleoprotein including a CRISPR-Cas effector protein, a guide nucleic acid, and optionally a deaminase) such as when contacted to a target nucleic acid or when introduced into a cell (e.g., a mammalian cell or a plant cell). In some embodiments, a ribonucleoprotein of an editing system may assemble into a complex (e.g., a covalently and/or non-covalently bound complex) while a portion of the ribonucleoprotein is contacting a target nucleic acid and/or may assemble after and/or during introduction into a plant cell. In some embodiments, an editing system may be assembled (e.g., into a covalently and/or non-covalently bound complex) when introduced into a plant cell. In some embodiments, a ribonucleoprotein may comprise an engineered protein of the present invention, a guide nucleic acid, and optionally a deaminase.

The terms "transgene" or "transgenic" as used herein refer to at least one nucleic acid sequence that is taken from the genome of one organism or produced synthetically, and which is then introduced into a host cell (e.g., a plant cell) or organism or tissue of interest and which is subsequently integrated into the host's genome by means of "stable" transformation or transfection approaches. In contrast, the term "transient" transformation or transfection or introduction refers to a way of introducing molecular tools including at least one nucleic acid (DNA, RNA, single-stranded or double-stranded or a mixture thereof) and/or at least one amino acid sequence, optionally comprising suitable chemical or biological agents, to achieve a transfer into at least one compartment of interest of a cell, including, but not restricted to, the cytoplasm, an organelle, including the nucleus, a mitochondrion, a vacuole, a chloroplast, or into a membrane, resulting in transcription and/or translation and/or association and/or activity of the at least one molecule introduced without achieving a stable integration or incorporation into the genome and thus without inheritance of the respective at least one molecule introduced into the genome of a cell. The term "transgene-free" refers to a condition in which a transgene is not present or found in the genome of a host cell or tissue or organism of interest.

In some embodiments, a polynucleotide and/or a nucleic acid construct of the invention can be an "expression cassette" or can be comprised within an expression cassette. As used herein, "expression cassette" means a recombinant nucleic acid molecule comprising, for example, a nucleic acid construct of the invention (e.g., encoding a Cas12a of the invention, a polynucleotide encoding an engineered protein of the present invention, a polynucleotide encoding a nuclease, a polynucleotide encoding a cytosine deaminase, a polynucleotide encoding an adenine deaminase, a polynucleotide encoding a deaminase fusion protein, a polynucleotide encoding a peptide tag, a polynucleotide encoding an affinity polypeptide, a polynucleotide encoding a glycosylase, and/or a polynucleotide comprising a guide nucleic acid), wherein the nucleic acid construct is operably associated with at least a control sequence (e.g., a promoter). Thus, some embodiments of the invention provide expression cassettes designed to express, for example, a nucleic acid construct of the invention. When an expression cassette comprises more than one polynucleotide, the polynucleotides may be operably linked to a single promoter that drives expression of all of the polynucleotides or the polynucleotides may be operably linked to one or more separate promoters (e.g., three polynucleotides may be driven by one, two or three promoters in any combination). When two or more separate promoters are used, the promoters may be the same promoter, or they may be different promoters. Thus, a polynucleotide encoding a sequence specific nucleic acid binding domain, a polynucleotide encoding a nuclease protein/domain, a polynucleotide encoding a CRISPR-Cas effector protein/domain, a polynucleotide encoding an deaminase protein/domain, a polynucleotide encoding a reverse transcriptase polypeptide/domain (e.g., RNA-dependent DNA polymerase), and/or a polynucleotide encoding a 5'-3' exonuclease polypeptide/domain, a guide nucleic acid, an extended guide nucleic acid and/or RT template when comprised in a single expression cassette may each be operably linked to a single promoter, or separate promoters in any combination. As a further example, a polynucleotide encoding an engineered protein, a polynucleotide encoding a deaminase (e.g., an adenine deaminase), and a polynucleotide comprising a guide nucleic acid comprised in an expression cassette may each be operably associated with a single promoter or one or more of the polynucleotide(s) may be operably associated with separate promoters (e.g., two or three promoters) in any combination, which may be the same or different from each other.

In some embodiments, an expression cassette comprising the polynucleotides/nucleic acid constructs of the invention may be optimized for expression in an organism (e.g., an animal, a plant, a bacterium and the like).

An expression cassette comprising a nucleic acid construct of the invention may be chimeric, meaning that at least one of its components is heterologous with respect to at least one of its other components (e.g., a promoter from the host organism operably linked to a polynucleotide of interest to be expressed in the host organism, wherein the polynucleotide of interest is from a different organism than the host or is not normally found in association with that promoter). An expression cassette may also be one that is naturally occurring but has been obtained in a recombinant form useful for heterologous expression.

An expression cassette can optionally include a transcriptional and/or translational termination region (i.e., termination region) and/or an enhancer region that is functional in the selected host cell. A variety of transcriptional terminators and enhancers are known in the art and are available for use in expression cassettes. Transcriptional terminators are responsible for the termination of transcription and correct mRNA polyadenylation. The termination region and/or the enhancer region may be native to the transcriptional initiation region, may be native to a gene encoded by a nucleic acid construct of the invention, e.g., a CRISPR-Cas effector protein or a gene encoding a deaminase, may be native to a gene encoding a polypeptide of the present invention, may be native to a host cell, or may be native to another source (e.g., foreign or heterologous to the promoter, to a gene encoding the CRISPR-Cas effector protein or a gene encoding the deaminase, to a host cell, or any combination thereof). The enhancer region may be native to a gene encoded by a nucleic acid construct of the invention, e.g., a CRISPR-Cas effector protein or a gene encoding a deaminase, may be native to a gene encoding a polypeptide of the present invention, may be native to a host cell, or may be native to another source (e.g., foreign or heterologous to the promoter, to a gene encoding the CRISPR-Cas effector protein or a gene encoding the deaminase, to a host cell, or any combination thereof).

An expression cassette of the invention also can include a nucleotide sequence encoding a selectable marker, which can be used to select a transformed host cell. As used herein, "selectable marker" means a nucleotide sequence that when expressed imparts a distinct phenotype to the host cell expressing the marker and thus allows such transformed cells to be distinguished from those that do not have the marker. Such a nucleotide sequence may encode either a selectable or screenable marker, depending on whether the marker confers a trait that can be selected for by chemical means, such as by using a selective agent (e.g., an antibiotic and the like), or whether the marker is simply a trait that one can identify through observation or testing, such as by screening (e.g., fluorescence). Many examples of suitable selectable markers are known in the art and can be used in the expression cassettes described herein.

The expression cassettes, the nucleic acid molecules/constructs and polynucleotide sequences described herein can be used in connection with vectors. The term "vector" refers to a composition for transferring, delivering or introducing a nucleic acid (or nucleic acids) into a cell. A vector comprises a nucleic acid construct comprising the nucleotide sequence(s) to be transferred, delivered or introduced. Vectors for use in transformation of host organisms are well known in the art. Non-limiting examples of general classes of vectors include viral vectors, plasmid vectors, phage vectors, phagemid vectors, cosmid vectors, fosmid vectors, bacteriophages, artificial chromosomes, minicircles, or *Agrobacterium* binary vectors in double or single stranded linear or circular form which may or may not be self-transmissible or mobilizable. In some embodiments, a viral vector can include, but is not limited to, a retroviral, lentiviral, adenoviral, adeno-associated, or herpes simplex viral vector. A vector as defined herein can transform a prokaryotic or eukaryotic host either by integration into the cellular genome or exist extrachromosomally (e.g. autonomous replicating plasmid with an origin of replication). Additionally included are shuttle vectors by which is meant a DNA vehicle capable, naturally or by design, of replication in two different host organisms, which may be selected from actinomycetes and related species, bacteria and eukaryotic (e.g. higher plant, mammalian, yeast or fungal cells). In some embodiments, the nucleic acid in the vector is under the control of, and operably linked to, an appropriate promoter or other regulatory elements for transcription in a host cell. The vector may be a bi-functional expression vector which functions in multiple hosts. In the case of genomic DNA, this may contain its own promoter and/or other regulatory elements and in the case of cDNA this may be under the control of an appropriate promoter and/or other regulatory elements for expression in the host cell. Accordingly, a nucleic acid construct of this invention and/or expression cassettes comprising the same may be comprised in vectors as described herein and as known in the art. In some embodiments, the vector may be a high copy number vector (e.g., a high copy number *E. coli* vector; e.g., pUC, pBluescript, pGEM and the like). Thus, for example, a library of the present invention may be constructed using a high copy number vector.

As used herein, "contact", "contacting", "contacted," and grammatical variations thereof, refers to placing the components of a desired reaction together under conditions suitable for carrying out the desired reaction (e.g., transformation, transcriptional control, genome editing, nicking, and/or cleavage). Thus, for example, a target nucleic acid may be contacted with (a) a Cas12a polypeptide having a mutation, wherein the mutation is an arginine at position 532 and at 595, or (b) a Cas12a polypeptide having a mutation, wherein the mutation is an arginine at position 532 and 542 and a valine at position 538, each of which position in the Cas12a polypeptide of (a) and/or (b) is in reference to position numbering of the amino acid sequence of SEQ ID NO:180, wherein the Cas12a polypeptide of (a) recognizes a PAM sequence in the target nucleic acid of

TTAA, TTAC, ACCA, ACCC, ACCG, ATCA, ATCC, ATCG,

CCCA, CCCG, CTCA, CTCC, CTCG, GCCA, GCCC, GCCG,

GTCA, GTCC, GTCG, GTCT, TCCT, TTCT, ACTA, ACTC,

ACTG, ATTA, ATTC, ATTG, CCTA, CCTC, CCTG, CTTA,

CTTC, CTTG, GCTA, GCTC, GCTG, GTTA, GTTC, GTTG,

TCTA, TCTC, TCTG, TCTT, TTTT, CCCC, TCCA, TCCC,

TCCG, TTCA, TTCC, and/or TTCG, and the Cas12a polypeptide of (b) recognizes a PAM sequence in the target nucleic acid of

AACC, TACC, AATC, GATA, AATA, AATG, GATG, GATC,

TATA, TATC, and/or TATG, (b) a fusion protein comprising the Cas12a polypeptide of (a) and/or (b) and a guide nucleic acid (e.g., CRISPR RNA, CRISPR DNA, crRNA, crDNA); (c) a complex comprising the Cas12a polypeptide of (a) and/or (b) and a guide nucleic acid, or comprising the fusion protein of (b); and/or (d) a composition comprising the Cas12a polypeptide of (a) and/or (b) and a guide nucleic acid or comprising the fusion protein of (b), thereby modifying the target nucleic acid. In some embodiments, a target nucleic acid may be contacted with a Cas12a polypeptide of (a) or (b) and/or a fusion protein comprising the same (e.g., Cas12a polypeptide of (a) or (b) and a polypeptide of interest (e.g., a deaminase)) and (b) a guide nucleic acid, wherein the Cas12a polypeptide of (a) or (b) forms a complex with the guide nucleic acid and the complex hybridizes to the target nucleic acid, thereby modifying the target nucleic acid. In some embodiments, the PAM sequence that is recognized is not ACCA, ACCC, ACCG, ATCA, ATCC, ATCG, CCCA, CCCC, CCCG, CTCA, CTCC, CTCG, GCCC, GCCA, and/or GCCG.

In some embodiments, the PAM sequence that is recognized is not AATA, AATG, GATA, and/or GATG.

As described herein, a target nucleic acid may be contacted with the polynucleotides/nucleic acid constructs/polypeptides of the invention prior to, concurrently with, or after contact with the guide nucleic acid. In some embodiments, a target nucleic acid may be contacted with a nucleic acid construct of the invention encoding, for example, a nucleic acid binding polypeptide (e.g., a DNA binding domain such as a sequence-specific DNA binding protein (e.g., a polynucleotide-guided endonuclease, a CRISPR-Cas effector protein (e.g., a CRISPR-Cas endonuclease), a zinc finger nuclease, a transcription activator-like effector nuclease (TALEN) and/or an Argonaute protein)), a guide nucleic acid, a polynucleotide encoding a polypeptide of the present invention, and optionally a cytosine deaminase and/or adenine deaminase under conditions whereby the nucleic acid binding polypeptide (e.g., a CRISPR-Cas effector protein) is expressed, and the nucleic acid binding polypeptide forms a complex with the guide nucleic acid, the complex hybridizes to the target nucleic acid, and optionally the polypeptide of the present invention, cytosine deaminase, and/or adenine deaminase is/are recruited to the nucleic acid binding polypeptide (and thus, to the target nucleic acid) or is/are fused to the nucleic acid binding polypeptide, thereby modifying the target nucleic acid. In some embodiments, the polypeptide of the present invention, cytosine deaminase, and/or adenine deaminase and the nucleic acid binding polypeptide localize at the target nucleic acid, optionally through covalent and/or non-covalent interactions.

In some embodiments, a target nucleic acid may be contacted with a nucleic acid construct of the invention encoding an engineered protein of the present invention, a guide nucleic acid, and optionally a cytosine deaminase and/or adenine deaminase under conditions whereby the engineered protein is expressed, or a target nucleic acid may be contacted with an engineered protein of the present invention, a guide nucleic acid, and optionally a cytosine deaminase and/or adenine deaminase. The engineered protein can form a complex with the guide nucleic acid, and the complex can hybridize to the target nucleic acid, and optionally the cytosine deaminase and/or adenine deaminase is/are recruited to the engineered protein (and thus, to the target nucleic acid) or the cytosine deaminase and/or adenine deaminase are fused to the engineered protein, thereby modifying the target nucleic acid. The cytosine deaminase and/or adenine deaminase and the engineered protein may localize at the target nucleic acid, optionally through covalent and/or non-covalent interactions.

As used herein, "modifying" or "modification" in reference to a target nucleic acid includes editing (e.g., mutating), covalent modification, exchanging/substituting nucleic acids/nucleotide bases, deleting, cleaving, nicking, and/or transcriptional control of a target nucleic acid. In some embodiments, a modification may include one or more single base changes (SNPs) of any type. In some embodiments, a modification comprises a SNP. In some embodiments, a modification comprises exchanging and/or substituting one or more (e.g., 1, 2, 3, 4, 5, or more) nucleotides. In some embodiments, an insertion or deletion may be about 1 base to about 30,000 bases or more in length (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1200, 1300, 1400, 1500, 1600, 1700, 1800, 1900, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 20,500, 21,000, 21,500, 22,000, 22,500, 23,000, 23,500, 24,000, 24,500, 25,000, 25,500, 26,000, 26,500, 27,000, 27,500, 28,000, 28,500, 29,000, 29,500, 30,000 bases in length or more, or any value or range therein). Thus, in some embodiments, an insertion or deletion may be about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300 to about 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 bases in length, or any range or value therein; about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300 bases to about 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1200, 1300, 1400, 1500, 1600, 1700, 1800, 1900, 2000 bases or more in length, or any value or range therein; about 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1200, 1300, 1400, 1500, 1600, 1700, 1800, 1900, 2000 bases to about 2500, 3000, 3500, 4000, 4500, 5000, 5500, 6000, 6500, 7000, 7500, 8000, 8500, 9000, 9500, or 10,000 bases or more in length, or any value or range therein; or about 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, or 700 bases to about 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1200, 1300, 1400, 1500, 1600, 1700, 1800, 1900, 2000, 2500, 3000, 3500, 4000, 4500, or 5000 bases or more in length, or any value or range therein. In some embodiments, an insertion or deletion may be about 1000, 1100, 1200, 1300, 1400, 1500, 1600, 1700, 1800, 1900, 2000, 2500, 3000, 3500, 4000, 4500, 5000, 5500, 6000, 6500, 7000, 7500, 8000, 8500, 9000, 9500, or 10,000 bases to about 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 20,500, 21,000, 21,500, 22,000, 22,500, 23,000, 23,500, 24,000, 24,500, 25,000, 25,500, 26,000, 26,500, 27,000, 27,500, 28,000, 28,500, 29,000, 29,500, or 30,000 bases or more in length, or any value or range therein.

"Recruit," "recruiting" or "recruitment" as used herein refer to attracting one or more polypeptide(s) or polynucleotide(s) to another polypeptide or polynucleotide (e.g., to a particular location in a genome) using protein-protein interactions, nucleic acid protein interactions (e.g., RNA-protein interactions), and/or chemical interactions. Protein-protein interactions can include, but are not limited to, peptide tags (epitopes, multimerized epitopes) and corresponding affinity polypeptides, RNA recruiting motifs and corresponding affinity polypeptides, and/or chemical interactions. Example chemical interactions that may be useful with polypeptides and polynucleotides for the purpose of recruitment can include, but are not limited to, rapamycin-inducible dimerization of FRB-FKBP; Biotin-streptavidin interaction; SNAP tag (Hussain et al. *Curr Pharm Des.* 19(30):5437-42 (2013)); Halo tag (Los et al. ACS *Chem Biol.* 3(6):373-82 (2008)); CLIP tag (Gautier et al. *Chemistry & Biology* 15:128-136 (2008)); DmrA-DmrC heterodimer induced by a compound (Tak et al. *Nat Methods* 14(12):1163-1166 (2017)); Bifunctional ligand approaches (fuse two protein-binding chemicals together) (Voß et al. *Curr Opin Chemical Biology* 28:194-201 (2015)) (e.g. dihyrofolate reductase (DHFR) (Kopyteck et al. *Cell Chem Biol* 7(5):313-321 (2000)).

"Introducing," "introduce," "introduced" (and grammatical variations thereof) in the context of a polynucleotide of interest or editing system means presenting a nucleotide sequence of interest (e.g., polynucleotide, a nucleic acid construct, and/or a guide nucleic acid) and/or editing system (e.g., a polynucleotide, polypeptide, and/or ribonucleoprotein) to a host organism or cell of said organism (e.g., host cell; e.g., a plant cell) in such a manner that the nucleotide sequence or editing system gains access to the interior of a cell. Thus, for example, a polynucleotide of the invention encoding a Cas12a nuclease as described herein and guide nucleic acid or a nucleic acid construct of the invention encoding an engineered protein of the present invention, a guide nucleic acid, and a cytosine deaminase and/or adenine deaminase may be introduced into a cell of an organism, thereby transforming the cell with the Cas12a nuclease and guide nucleic acid or transforming the cell with the engineered protein, a guide nucleic acid, and a cytosine deaminase and/or adenine deaminase. In some embodiments, an engineered protein and/or a guide nucleic acid may be introduced into a cell of an organism, optionally wherein the engineered protein and guide nucleic acid may be comprised in a complex (e.g., a ribonucleoprotein). In some embodiments, the organism is a eukaryote (e.g., a mammal such as a human).

The term "transformation" or "transfection" may be used interchangeably and as used herein refer to the introduction of a heterologous nucleic acid into a cell. Transformation of a cell may be stable or transient. Thus, in some embodiments, a host cell or host organism may be stably transformed with a polynucleotide/nucleic acid molecule of the invention. In some embodiments, a host cell or host organism may be transiently transformed with a polynucleotide/nucleic acid construct of the invention.

"Transient transformation" in the context of a polynucleotide means that a polynucleotide is introduced into the cell and does not integrate into the genome of the cell.

By "stably introducing" or "stably introduced" in the context of a polynucleotide introduced into a cell is intended that the introduced polynucleotide is stably incorporated into the genome of the cell, and thus the cell is stably transformed with the polynucleotide. "Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. "Genome" as used herein includes the nuclear and the plastid genome, and therefore includes integration of the nucleic acid into, for example, the chloroplast or mitochondrial genome. Stable transformation as used herein can also refer to a transgene that is maintained extrachromasomally, for example, as a minichromosome or a plasmid.

Transient transformation may be detected by, for example, an enzyme-linked immunosorbent assay (ELISA) or Western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant). Stable transformation of a cell can be detected by, for example, a Northern blot hybridization assay of RNA of the cell with nucleic acid sequences which specifically hybridize with a nucleotide sequence of a transgene introduced into a host organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods Transformation can also be detected by direct sequencing and/or hybridization protocols well known in the art.

Accordingly, in some embodiments, nucleotide sequences, polynucleotides, and/or nucleic acid constructs of the invention and/or expression cassettes and/or vectors comprising the same may be expressed transiently and/or they can be stably incorporated into the genome of the host organism. Thus, in some embodiments, a nucleic acid construct of the invention (e.g., encoding a Cas12a polypeptide of the invention (e.g., (a) a Cas12a polypeptide having a mutation, wherein the mutation is an arginine at position 532 and at 595, or (b) a Cas12a polypeptide having a mutation, wherein the mutation is an arginine at position 532 and 542 and a valine at position 538, each of which position in the Cas12a polypeptide of (a) and/or (b) is in reference to position numbering of the amino acid sequence of SEQ ID NO:180), or a fusion protein thereof; e.g., a fusion protein comprising the Cas12a polypeptide linked to e.g., a polynucleotide of interest, e.g., a deaminase domain), optionally wherein the nucleic acid construct encoding the Cas12a polypeptide may be optimized for expression in an organism (e.g., a plant, a mammal, a fungus, a bacterium, and the like) and may be transiently introduced into a cell of the organism along with a guide nucleic acid and as such no DNA (none of the nucleic acid construct) is maintained in the cell.

A polynucleotide/nucleic acid construct, polypeptide, and/or ribonucleoprotein of the invention can be introduced into a cell by any method known to those of skill in the art. In some embodiments, transformation methods include, but are not limited to, transformation via bacterial-mediated nucleic acid delivery (e.g., via Agrobacteria), viral-mediated nucleic acid delivery, silicon carbide and/or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) and/or biological mechanism that results in the introduction of nucleic acid into the cell (e.g., a plant cell or an animal cell), including any combination thereof. In some embodiments of the invention, transformation of a cell comprises nuclear transformation. In some embodiments, transformation of a cell comprises plastid transformation (e.g., chloroplast transformation). In some embodiments, a recombinant nucleic acid construct of the invention can be introduced into a cell via conventional breeding techniques.

Procedures for transforming both eukaryotic and prokaryotic organisms are well known and routine in the art and are described throughout the literature (See, for example, Jiang et al. 2013. *Nat. Biotechnol.* 31:233-239; Ran et al. *Nature Protocols* 8:2281-2308 (2013)). General guides to various plant transformation methods known in the art include Miki et al. ("Procedures for Introducing Foreign DNA into Plants" in Methods in Plant Molecular Biology and Biotechnology, Glick, B. R. and Thompson, J. E., Eds. (CRC Press, Inc., Boca Raton, 1993), pages 67-88) and Rakowoczy-Trojanowska (Cell. Mol. Biol. Lett. 7:849-858 (2002)).

A nucleotide sequence therefore can be introduced into a host organism or its cell in any number of ways that are well known in the art. The methods of the invention do not depend on a particular method for introducing one or more nucleotide sequences into the organism, only that they gain access to the interior of at least one cell of the organism. Where more than one nucleotide sequence is to be introduced, they can be assembled as part of a single nucleic acid construct, or as separate nucleic acid constructs, and can be located on the same or different nucleic acid constructs. Accordingly, the nucleotide sequences can be introduced into the cell of interest in a single transformation event, and/or in separate transformation events, or, alternatively, where relevant, a nucleotide sequence may be incorporated into a plant, for example, as part of a breeding protocol. In some embodiments, the cell is a eukaryotic cell (e.g., a plant cell or a mammalian such as a human cell). In some embodiments, the cell is not a mammalian cell. In some embodiments, the cell is not a human cell.

In some embodiments, a nucleic acid construct of the invention (e.g., a polynucleotide encoding a Cas12a polypeptide of the invention, a polynucleotide encoding an engineered protein of the present invention, a polynucleotide encoding a deaminase, and/or a guide nucleic acid and/or expression cassettes and/or vectors comprising the same) may be operably linked to at least one regulatory sequence, optionally, wherein the at least one regulatory sequence may be optimized for expression in a plant. In some embodiments, the at least one regulatory sequence may be, for example, a promoter, an operon, a terminator, or an enhancer. In some embodiments, the at least one regulatory sequence may be a promoter. In some embodiments, the regulatory sequence may be an intron. In some embodiments, the at least one regulatory sequence may be, for example, a promoter operably associated with an intron or a promoter region comprising an intron. In some embodiments, the at least one regulatory sequence may be, for example a ubiquitin promoter and its associated intron (e.g., *Medicago truncatula* and/or *Zea mays* and their associated introns). In some embodiments, the at least one regulatory sequence may be a terminator nucleotide sequence and/or an enhancer nucleotide sequence.

In some embodiments, a nucleic acid construct of the invention may be operably associated with a promoter region, wherein the promoter region comprises an intron, optionally wherein the promoter region may be a ubiquitin promoter and intron (e.g., a *Medicago* or a maize ubiquitin promoter and intron, e.g., SEQ ID NO:48 or SEQ ID NO:49). In some embodiments, the nucleic acid construct of the invention that is operably associated with a promoter region comprising an intron may be optimized for expression in a plant.

In some embodiments, a nucleic acid construct of the invention may encode one or more (e.g., 1, 2, 3, 4, or more) polypeptide(s) of interest. The one or more polypeptides of interest may be optimized for expression in a eukaryote (e.g., a human or a plant). In some embodiments, an engineered protein may comprise one or more (e.g., 1, 2, 3, 4, or more) polypeptide(s) of interest. For example, the heterologous polypeptide of an engineered protein may comprise or be a polypeptide of interest.

A polypeptide of interest useful with this invention can include, but is not limited to, a polypeptide or protein domain having deaminase activity, nickase activity, recombinase activity, transposase activity, methylase activity, glycosylase (DNA glycosylase) activity, glycosylase inhibitor activity (e.g., uracil-DNA glycosylase inhibitor (UGI)), a reverse transcriptase, a peptide tag (e.g., a GCN4 peptide tag), demethylase activity, transcription activation activity, transcription repression activity, transcription release factor activity, histone modification activity, nuclease activity, single-strand RNA cleavage activity, double-strand RNA cleavage activity, restriction endonuclease activity (e.g., Fok1), nucleic acid binding activity, methyltransferase activity, DNA repair activity, DNA damage activity, dismutase activity, alkylation activity, depurination activity, oxidation activity, pyrimidine dimer forming activity, integrase activity, transposase activity, polymerase activity, ligase activity, helicase activity, a nuclear localization sequence or activity, an affinity polypeptide, a peptide tag, and/or photolyase activity. In some embodiments, the polypeptide of interest is a Fok1 nuclease, or a uracil-DNA glycosylase inhibitor. When encoded in a nucleic acid (polynucleotide, expression cassette, and/or vector) the encoded polypeptide or protein domain may be optimized for expression in an organism. In some embodiments, a polypeptide of interest may be linked to an engineered protein of the present invention or CRISPR-Cas effector protein domain to provide a CRISPR-Cas fusion protein. In some embodiments, a CRISPR-Cas fusion protein that comprises a CRISPR-Cas effector protein domain linked to a peptide tag may also be linked to a polypeptide of interest (e.g., a CRISPR-Cas effector protein domain may be, for example, linked to both a peptide tag (or an affinity polypeptide) and, for example, a polypeptide of interest.

In some embodiments, an editing system of the present invention comprises a CRISPR-Cas effector protein. As used herein, a "CRISPR-Cas effector protein" is a protein or polypeptide that cleaves, cuts, or nicks a nucleic acid; binds a nucleic acid (e.g., a target nucleic acid and/or a guide nucleic acid); and/or that identifies, recognizes, or binds a guide nucleic acid as defined herein. In some embodiments, a CRISPR-Cas effector protein may be an enzyme (e.g., a nuclease, endonuclease, nickase, etc.) and/or may function as an enzyme. In some embodiments, a CRISPR-Cas effector protein refers to a CRISPR-Cas nuclease. In some embodiments, a CRISPR-Cas effector protein comprises nuclease activity and/or nickase activity, comprises a nuclease domain whose nuclease activity and/or nickase activity has been reduced or eliminated, comprises single stranded DNA cleavage activity (ss DNAse activity) or which has ss DNAse activity that has been reduced or eliminated, and/or comprises self-processing RNAse activity or which has self-processing RNAse activity that has been reduced or eliminated. A CRISPR-Cas effector protein may bind to a target nucleic acid. A CRISPR-Cas effector protein may be a Type I, II, III, IV, V, or VI CRISPR-Cas effector protein. In some embodiments, a CRISPR-Cas effector protein may be from a Type I CRISPR-Cas system, a Type II CRISPR-Cas system, a Type III CRISPR-Cas system, a Type IV CRISPR-Cas system, Type V CRISPR-Cas system, or a Type VI CRISPR-Cas system. In some embodiments, a CRISPR-Cas effector protein of the invention may be from a Type II CRISPR-Cas system or a Type V CRISPR-Cas system. In some embodiments, a CRISPR-Cas effector protein may be a Type II CRISPR-Cas effector protein, for example, a Cas9 effector protein. In some embodiments, a CRISPR-Cas effector protein may be Type V CRISPR-Cas effector protein, for example, a Cas12 effector protein. In some embodiments, a CRISPR-Cas effector protein may be Cas12a and optionally may have an amino acid sequence of any one of SEQ ID NOs:50-66 or 180 and/or a nucleotide sequence of any one of SEQ ID NOs:67-69. In some embodiments, a CRISPR-Cas effector protein may be an active Cas12a and optionally may have an amino acid sequence of SEQ ID NO:58 or 180. In some embodiments, a CRISPR-Cas effector protein may be an inactive (i.e., dead) Cas12a and optionally may have an amino acid sequence of SEQ ID NO:50. In some embodiments, a CRISPR-Cas effector protein may be Cas12b and optionally may have an amino acid sequence of SEQ ID NO:151.

Exemplary CRISPR-Cas effector proteins include, but are not limited to, a Cas9, C2c1, C2c3, Cas12a (also referred to as Cpf1), Cas12b, Cas12c, Cas12d, Cas12e, Cas13a, Cas13b, Cas13c, Cas13d, Casl, CaslB, Cas2, Cas3, Cas3', Cas3", Cas4, Cas5, Cas6, Cas7, Cas8, Cas9 (also known as Csnl and Csx12), Cas10, Csyl, Csy2, Csy3, Csel, Cse2, Cscl, Csc2, Csa5, Csn2, Csm2, Csm3, Csm4, Csm5, Csm6, Cmrl, Cmr3, Cmr4, Cmr5, Cmr6, Csbl, Csb2, Csb3, Csx17, Csx14, Csx10, Csx16, CsaX, Csx3, Csxl, Csx15, Csfl, Csf2, Csf3, Csf4 (dinG), and/or Csf5 nuclease, optionally wherein the CRISPR-Cas effector protein may be a Cas9, Cas12a (Cpf1), Cas12b, Cas12c (C2c3), Cas12d (CasY), Cas12e (CasX), Cas12g, Cas12h, Cas12i, C2c4, C2c5, C2c8, C2c9, C2c10, Cas14a, Cas14b, and/or Cas14c effector protein.

In some embodiments, a CRISPR-Cas effector protein useful with the invention may comprise a mutation in its nuclease active site and/or nuclease domain (e.g., RuvC, HNH, e.g., a RuvC site of a Cas12a nuclease domain; e.g., a RuvC site and/or HNH site of a Cas9 nuclease domain). A CRISPR-Cas effector protein having a mutation in its nuclease active site and/or nuclease domain, and therefore, no longer comprising nuclease activity, is commonly referred to as "inactive" or "dead," e.g., dCas9. In some embodiments, a CRISPR-Cas effector protein having a mutation in its nuclease active site and/or nuclease domain may have impaired activity or reduced activity (e.g., nickase activity) as compared to the same CRISPR-Cas effector protein without the mutation.

A CRISPR Cas9 effector protein or Cas9 useful with this invention may be any known or later identified Cas9 nuclease. In some embodiments, a Cas9 of the present invention may be a protein from, for example, *Streptococcus* spp. (e.g., *S. pyogenes, S. thermophilus*), *Lactobacillus* spp., *Bifidobacterium* spp., *Kandleria* spp., *Leuconostoc* spp., *Oenococcus* spp., *Pediococcus* spp., *Weissella* spp., and/or *Olsenella* spp. In some embodiments, a CRISPR-Cas effector protein may be a Cas9 and optionally may have a nucleotide sequence of any one of SEQ ID NOs:70-80 or 140-143 and/or an amino acid sequence of any one of SEQ ID NOs:81-82.

In some embodiments, the CRISPR-Cas effector protein may be a Cas9 derived from *Streptococcus pyogenes* and/or may recognize the PAM sequence motif NGG, NAG, NGA (Mali et al, Science 2013; 339(6121): 823-826). In some embodiments, the CRISPR-Cas effector protein may be a Cas9 derived from *Streptococcus thermophiles* and/or may recognize the PAM sequence motif NGGNG and/or NNAGAAW (W=A or T) (See, e.g., Horvath et al, Science, 2010; 327(5962): 167-170, and Deveau et al, J Bacteriol 2008; 190(4): 1390-1400). In some embodiments, the CRISPR-Cas effector protein may be a Cas9 derived from *Streptococcus mutans* and/or may recognize the PAM sequence motif NGG and/or NAAR (R=A or G) (See, e.g., Deveau et al, J Bacteriol 2008; 190(4): 1390-1400). In some embodiments, the CRISPR-Cas effector protein may be a Cas9 derived from *Streptococcus aureus* and/or may recognize the PAM sequence motif NNGRR (R=A or G). In some embodiments, the CRISPR-Cas effector protein may be a Cas9 derived from *S. aureus* and/or may recognize the PAM sequence motif NGRRT (R=A or G). In some embodiments, the CRISPR-Cas effector protein may be a Cas9 derived from *S. aureus* and/or may recognize the PAM sequence motif NGRRV (R=A or G). In some embodiments, the CRISPR-Cas effector protein may be a Cas9 that is derived from *Neisseria meningitidis* and/or may recognize the PAM sequence motif NGATT or NGCTT (R=A or G, V=A, G or C) (See, e.g., Hou et ah, PNAS 2013, 1-6). In the aforementioned embodiments in this paragraph, N in the PAM sequence motif can be any nucleotide residue, e.g., any of A, G, C or T. In some embodiments, the CRISPR-Cas effector protein may be a Cas13a derived from Leptotrichia shahii and/or may recognize a protospacer flanking sequence (PFS) (or RNA PAM (rPAM)) sequence motif of a single 3' A, U, or C, which may be located within the target nucleic acid.

A Type V CRISPR-Cas effector protein useful with embodiments of the invention may be any Type V CRISPR-Cas nuclease. Exemplary Type V CRISPR-Cas effector proteins include, but are not limited to, Cas12a (Cpf1), Cas12b, Cas12c (C2c3), Cas12d (CasY), Cas12e (CasX), Cas12g, Cas12h, Cas12i, C2c1, C2c4, C2c5, C2c8, C2c9, C2c10, Cas14a, Cas14b, and/or Cas14c nuclease. In some embodiments, a Type V CRISPR-Cas effector protein may be a Cas12a. In some embodiments, a Type V CRISPR-Cas effector protein may be a nickase, optionally, a Cas12a nickase. In some embodiments, a Type V CRISPR-Cas effector protein may be a Cas12b (e.g., SEQ ID NO:151).

In some embodiments, the CRISPR-Cas effector protein may be a Type V Clustered Regularly Interspaced Short Palindromic Repeats (CRISPR)-Cas nuclease. Cas12a, originally identified in *Prevotella* spp. and *Francisella* spp., differs in several respects from the more well-known Type II CRISPR Cas9 nuclease. For example, Cas9 recognizes a G-rich protospacer-adjacent motif (PAM) that is 3' to its guide RNA (gRNA, sgRNA, crRNA, crDNA, CRISPR array) binding site (protospacer, target nucleic acid, target DNA) (3'-NGG), while Cas12a recognizes a T-rich PAM that is located 5' to the target nucleic acid (5'-TTN, 5'-TTTN. In fact, the orientations in which Cas9 and Cas12a bind their guide RNAs are very nearly reversed in relation to their N and C termini. Furthermore, Cas12a enzymes use a single guide RNA (gRNA, CRISPR array, crRNA) rather than the dual guide RNA (sgRNA (e.g., crRNA and tracrRNA)) found in natural Cas9 systems, and Cas12a processes its own gRNAs. Additionally, Cas12a nuclease activity produces staggered DNA double stranded breaks instead of blunt ends produced by Cas9 nuclease activity, and Cas12a relies on a single RuvC domain to cleave both DNA strands, whereas Cas9 utilizes an HNH domain and a RuvC domain for cleavage.

A CRISPR Cas12a effector protein useful with this invention may be any known or later identified Cas12a (previously known as Cpf1) (see, e.g., U.S. Pat. No. 9,790,490, which is incorporated by reference for its disclosures of Cpf1 (Cas12a) sequences). The term "Cas12a" refers to an RNA-guided protein that can have nuclease activity, the protein comprising a guide nucleic acid binding domain and an active, inactive, or partially active DNA cleavage domain, thereby the RNA-guided nuclease activity of the Cas12a may be active, inactive or partially active, respectively. In some embodiments, a Cas12a useful with the invention may comprise a mutation in the nuclease active site (e.g., a RuvC site of the Cas12a domain). A Cas12a having a mutation in its nuclease domain and/or nuclease active site, and therefore, no longer comprising nuclease activity, is commonly referred to as deadCas12a (e.g., dCas12a). In some embodiments, a Cas12a having a mutation in its nuclease domain and/or nuclease active site may have impaired activity, e.g., may have reduced nickase activity.

In some embodiments, a Cas12a domain that may be modified to alter PAM specificity as described herein can include, but is not limited to, the amino acid sequence of any one of SEQ ID NO:180, SEQ ID NOs:51-66 or SEQ ID NO:193 (e.g., SEQ ID NOs:180, 51, 52, 53, 54, 55, 56, 57, 58, 59, 60, 61, 62, 63, 64, 65 and/or 66 and/or 193) or a polynucleotide encoding the same (e.g., SEQ ID NOs:27-29). In some embodiments, a Cas12a domain that may be modified to alter PAM specificity as described herein can include, but is not limited to, the amino acid sequence of any one of SEQ ID NO:180, SEQ ID NO:51 and/or SEQ ID NO:55.

In some embodiments, a CRISPR-Cas effector protein may be optimized for expression in an organism, for example, in an animal (e.g., a mammal such as a human), a plant, a fungus, an archaeon, or a bacterium. In some embodiments, a CRISPR-Cas effector protein (e.g., Cas12a polypeptide/domain or a Cas9 polypeptide/domain) may be optimized for expression in a plant.

Any deaminase domain/polypeptide useful for base editing may be used with this invention. A "cytosine deaminase" and "cytidine deaminase" as used herein refer to a polypeptide or domain thereof that catalyzes or is capable of catalyzing cytosine deamination in that the polypeptide or domain catalyzes or is capable of catalyzing the removal of an amine group from a cytosine base. Thus, a cytosine deaminase may result in conversion of cytosine to a thymidine (through a uracil intermediate), causing a C to T conversion, or a G to A conversion in the complementary strand in the genome. Thus, in some embodiments, the cytosine deaminase encoded by the polynucleotide of the invention generates a C→T conversion in the sense (e.g., "+"; template) strand of the target nucleic acid or a G→A conversion in antisense (e.g., "−", complementary) strand of the target nucleic acid. In some embodiments, a cytosine deaminase encoded by a polynucleotide of the invention generates a C to T, G, or A conversion in the complementary strand in the genome.

A cytosine deaminase useful with this invention may be any known or later identified cytosine deaminase from any organism (see, e.g., U.S. Pat. No. 10,167,457 and Thuronyi et al. *Nat. Biotechnol.* 37:1070-1079 (2019), each of which is incorporated by reference herein for its disclosure of cytosine deaminases). Cytosine deaminases can catalyze the hydrolytic deamination of cytidine or deoxycytidine to uridine or deoxyuridine, respectively. Thus, in some embodiments, a deaminase or deaminase domain useful with this invention may be a cytidine deaminase domain, catalyzing the hydrolytic deamination of cytosine to uracil. In some embodiments, a cytosine deaminase may be a variant of a naturally-occurring cytosine deaminase, including, but not limited to, a primate (e.g., a human, monkey, chimpanzee, gorilla), a dog, a cow, a rat or a mouse. Thus, in some embodiments, an cytosine deaminase useful with the invention may be about 70% to about 100% identical to a wild-type cytosine deaminase (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical, and any range or value therein, to a naturally occurring cytosine deaminase).

In some embodiments, a cytosine deaminase useful with the invention may be an apolipoprotein B mRNA-editing complex (APOBEC) family deaminase. In some embodiments, the cytosine deaminase may be an APOBEC1 deaminase, an APOBEC2 deaminase, an APOBEC3A deaminase, an APOBEC3B deaminase, an APOBEC3C deaminase, an APOBEC3D deaminase, an APOBEC3F deaminase, an APOBEC3G deaminase, an APOBEC3H deaminase, an APOBEC4 deaminase, a human activation induced deaminase (hAID), an rAPOBEC1, FERNY, and/or a CDA1, optionally a pmCDA1, an atCDA1 (e.g., At2g19570), and evolved versions of the same. Evolved deaminases are disclosed in, for example, U.S. Pat. No. 10,113,163, Gaudelli et al. Nature 551(7681):464-471 (2017)) and Thuronyi et al. (Nature Biotechnology 37: 1070-1079 (2019)), each of which are incorporated by reference herein for their disclosure of deaminases and evolved deaminases. In some embodiments, the cytosine deaminase may be an APOBEC1 deaminase having the amino acid sequence of SEQ ID NO:83. In some embodiments, the cytosine deaminase may be an APOBEC3A deaminase having the amino acid sequence of SEQ ID NO:84. In some embodiments, the cytosine deaminase may be an CDA1 deaminase, optionally a CDA1 having the nucleotide sequence of SEQ ID NO:85. In some embodiments, the cytosine deaminase may be a FERNY deaminase, optionally a FERNY having the amino acid sequence of SEQ ID NO:86. In some embodiments, the cytosine deaminase may be a rAPOBEC1 deaminase, optionally a rAPOBEC1 deaminase having the amino acid sequence of SEQ ID NO:87. In some embodiments, the cytosine deaminase may be a hAID deaminase, optionally a hAID having the amino acid sequence of SEQ ID NO:88 or SEQ ID NO:89. In some embodiments, a cytosine deaminase useful with the invention may be about 70% to about 100% identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% identical) to the amino acid sequence of a naturally occurring cytosine deaminase (e.g., "evolved deaminases") (see, e.g., SEQ ID NO:90, SEQ ID NO:91, SEQ ID NO:92). In some embodiments, a cytosine deaminase useful with the invention may be about 70% to about 99.5% identical (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical) to the amino acid sequence of any one of SEQ ID NOs:83, 84, or 86-92 or to the nucleotide sequence of SEQ ID NO:85 (e.g., at least 80%, at least 85%, at least 90%, at least 92%, at least 95%, at least 96%, at least 97%, at least 98%, at least 99%, or at least 99.5% identical to the amino acid sequence of any one of SEQ ID NOs:83, 84, or 86-92 or to the nucleotide sequence of SEQ ID NO:85). In some embodiments, a polynucleotide encoding a cytosine deaminase may be codon optimized for expression in a plant and the codon optimized polypeptide may be about 70% to 99.5% identical to the reference polynucleotide.

An "adenine deaminase" and "adenosine deaminase" as used herein refer to a polypeptide or domain thereof that catalyzes or is capable of catalyzing the hydrolytic deamination (e.g., removal of an amine group from adenine) of adenine or adenosine. In some embodiments, an adenine deaminase may catalyze the hydrolytic deamination of adenosine or deoxyadenosine to inosine or deoxyinosine, respectively. In some embodiments, the adenosine deaminase may catalyze the hydrolytic deamination of adenine or adenosine in DNA. In some embodiments, an adenine deaminase encoded by a nucleic acid construct of the invention may generate an A→G conversion in the sense (e.g., "+"; template) strand of the target nucleic acid or a T→C conversion in the antisense (e.g., "−", complementary) strand of the target nucleic acid. An adenine deaminase useful with this invention may be any known or later identified adenine deaminase from any organism (see, e.g., U.S. Pat. No. 10,113,163, which is incorporated by reference herein for its disclosure of adenine deaminases).

In some embodiments, an adenosine deaminase may be a variant of a naturally-occurring adenine deaminase. Thus, in some embodiments, an adenosine deaminase may be about 70% to 100% identical to a wild-type adenine deaminase (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical, and any range or value therein, to a naturally occurring adenine deaminase). In some embodiments, the deaminase or deaminases does not occur in nature and may be referred to as an engineered, mutated or evolved adenosine deaminase. Thus, for example, an engineered, mutated or evolved adenine deami- nase polypeptide or an adenine deaminase domain may be about 70% to 99.9% identical to a naturally occurring adenine deaminase polypeptide/domain (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8% or 99.9% identical, and any range or value therein, to a naturally occurring adenine deaminase polypeptide or adenine deaminase domain). In some embodiments, the adenosine deaminase may be from a bacterium, (e.g., *Escherichia coli, Staphylococcus aureus, Haemophilus influenzae, Caulobacter crescentus,* and the like). In some embodiments, a polynucleotide encoding an adenine deaminase polypeptide/domain may be codon optimized for expression in a plant.

In some embodiments, an adenine deaminase domain may be a wild-type tRNA-specific adenosine deaminase domain, e.g., a tRNA-specific adenosine deaminase (TadA) and/or a mutated/evolved adenosine deaminase domain, e.g., mutated/evolved tRNA-specific adenosine deaminase domain (TadA*). In some embodiments, a TadA domain may be from *E. coli*. In some embodiments, the TadA may be modified, e.g., truncated, missing one or more N-terminal and/or C-terminal amino acids relative to a full-length TadA (e.g., 1, 2, 3, 4, 5, 6, 7, 8, 9, 10, 11, 12, 13, 14, 15, 16, 17, 18, 19, or 20 N-terminal and/or C terminal amino acid residues may be missing relative to a full length TadA). In some embodiments, a TadA polypeptide or TadA domain does not comprise an N-terminal methionine. In some embodiments, a wild-type *E. coli* TadA comprises the amino acid sequence of SEQ ID NO:93. In some embodiments, a mutated/evolved *E. coli* TadA* comprises the amino acid sequence of any one of SEQ ID NOs:94-97. In some embodiments, a polynucleotide encoding a TadA/TadA* may be codon optimized for expression in a plant. In some embodiments, an adenine deaminase may comprise all or a portion of an amino acid sequence of any one of SEQ ID NOs:98-103. In some embodiments, an adenine deaminase may comprise all or a portion of an amino acid sequence of any one of SEQ ID NOs:93-103.

In some embodiments, a nucleic acid construct of this invention may further encode a glycosylase inhibitor (e.g., a uracil glycosylase inhibitor (UGI) such as uracil-DNA glycosylase inhibitor). In some embodiments, the invention provides fusion proteins comprising an engineered protein and a UGI and/or one or more polynucleotides encoding the same, optionally wherein the one or more polynucleotides may be codon optimized for expression in a plant.

A "uracil glycosylase inhibitor" useful with the invention may be any protein or polypeptide that is capable of inhibiting a uracil-DNA glycosylase base-excision repair enzyme. In some embodiments, a UGI domain comprises a wild-type UGI or a fragment thereof. In some embodiments, a UGI domain useful with the invention may be about 70% to about 100% identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% identical and any range or value therein) to the amino acid sequence of a naturally occurring UGI domain. In some embodiments, a UGI domain may comprise the amino acid sequence of SEQ ID NO:104 or a polypeptide having about 70% to about 99.5% identity to the amino acid sequence of SEQ ID NO:104 (e.g., at least 80%, at least 85%, at least 90%, at least 92%, at least 95%, at least 96%, at least 97%, at least 98%, at least 99%, or at least 99.5% identical to the amino acid sequence of SEQ ID NO:104). For example, in some embodiments, a UGI domain may comprise a fragment of the amino acid sequence of SEQ ID NO:104 that is 100% identical to a portion of consecutive nucleotides (e.g., 10, 15, 20, 25, 30, 35, 40, 45, 50, 55, 60, 65, 70, 75, 80 consecutive nucleotides; e.g., about 10, 15, 20, 25, 30, 35, 40, 45 to about 50, 55, 60, 65, 70, 75, 80 consecutive nucleotides) of the amino acid sequence of SEQ ID NO:104. In some embodiments, a UGI domain may be a variant of a known UGI (e.g., SEQ ID NO:104) having about 70% to about 99.5% identity (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% identity, and any range or value therein) to the known UGI. In some embodiments, a polynucleotide encoding a UGI may be optimized for expression in a plant (e.g., a plant) and the codon optimized polypeptide may be about 70% to about 99.5% identical to the reference polynucleotide.

In some embodiments, a polypeptide of interest for use with this invention may comprise at least one polypeptide or protein domain having glycosylase inhibitor activity. In some embodiments, the polypeptide of interest may be a uracil-DNA glycosylase inhibitor (UGI) polypeptide/domain. In some embodiments, a nucleic acid construct encoding a Cas12a nuclease of this invention and a cytosine deaminase domain (e.g., encoding a fusion protein comprising a Cas12a nuclease of the invention and a cytosine deaminase domain) may further encode a uracil-DNA glycosylase inhibitor (UGI), wherein the UGI is optimized for expression in an organism. In some embodiments, the invention provides a fusion protein comprising a Cas12a nuclease modified as described herein, a cytosine deaminase domain, and a UGI and/or one or more polynucleotides encoding the same, optionally wherein the one or more polynucleotides may be optimized for expression in an organism.

In some embodiments, the present invention is directed to methods of using (e.g., modifying and/or editing target nucleic acids) Cas12a polypeptides and/or engineered proteins that recognize non-natural PAM sites/sequences in the target nucleic acids (e.g., a Cas12a polypeptide and/or engineered protein that comprises non-natural PAM recognition specificity in addition to or instead of the natural PAM recognition specificity for that particular Cas12 or Cas12a nuclease). For example, an engineered protein useful with the methods of the invention may be a nuclease that comprises non-natural PAM recognition specificity (e.g., altered binding affinity, altered PAM recognition) in addition to or instead of the natural PAM recognition specificity (e.g., wild-type binding affinity) for a Cas12a. In addition, the present invention is directed to methods for designing, identifying and selecting Cas12a polypeptides and/or engineered proteins having desirable characteristics including improved PAM recognition specificity. As used herein, a "non-natural PAM recognition site, a "non-native PAM recognition site," "non-natural PAM sequence," and/or "non-native PAM sequence," refer to PAM sequences that are recognized by a modified Cas nuclease or engineered protein as described herein, but which are not recognized by the corresponding wild type Cas nuclease.

As used herein in reference to a modified protein, a modified Cas12a polypeptide, engineered protein, and/or nuclease, "altered PAM specificity" means that the PAM specificity of the modified protein, modified Cas12a polypeptide, engineered protein, and/or nuclease is altered from that of the wild-type nuclease (e.g., non-native PAM sequences are recognized in addition to and/or instead of the native PAM sequence(s)). For example, a modified Cas12a nuclease (e.g., a modified protein) would be altered in its PAM specificity if it recognizes a PAM sequence other than and/or in addition to the native Cas12a PAM sequence of TTTV, wherein V is A, C or G (natural or wild type PAM recognition sequence for Cas12a). In some embodiments, an engineered protein of the present invention comprises a polypeptide that is a portion of Cas12a and the engineered protein has altered PAM specificity in that it recognizes a PAM sequence other than and/or in addition to the native Cas12a PAM sequence of TTTV, wherein V is A, C or G. In some embodiments, a modified protein of the present invention may be as described in U.S. Patent Application Publication No. 2021/0115421 and/or a nuclease or portion thereof (e.g., polypeptide thereof) may be modified and/or altered as described in U.S. Patent Application Publication No. 2021/0115421, which is incorporated herein by reference in its entirety. In some embodiments, an engineered protein of the present invention recognizes a native PAM sequence (e.g., a PAM sequence of TTTV, wherein V is A, C or G) and/or recognizes a non-native PAM sequence.

In some embodiments, a non-native PAM sequence may be a PAM sequence of any one or more of

CCCC, TCCA, TCCC, TCCG, TTCA, TTCC, TATA, TATC, and TATG.

In some embodiments, a non-native PAM sequence may be a PAM sequence of any one or more of

TTAA, TTAC, ACCA, ACCC, ACCG, ATCA, ATCC, ATCG,

CCCA, CCCG, CTCA, CTCC, CTCG, GCCA, GCCC, GCCG,

GTCA, GTCC, GTCG, GTCT, TCCT, TTCT, ACTA, ACTC,

ACTG, ATTA, ATTC, ATTG, CCTA, CCTC, CCTG, CTTA,

CTTC, CTTG, GCTA, GCTC, GCTG, GTTA, GTTC, GTTG,

TCTA, TCTC, TCTG, TCTT, TTTT, CCCC, TCCA, TCCC,

TCCG, TTCA, TTCC, and/or TTCG.

In some embodiments, a non-native PAM sequence may be a PAM sequence of any one or more of

AACC, TACC, AATC, GATA, AATA, AATG, GATG, GATC,

TATA, TATC, and/or TATG.

In some embodiments, a non-native PAM sequence does not include the PAM sequence of

ACCA, ACCC, ACCG, ATCA, ATCC, ATCG, CCCA, CCCC,

CCCG, CTCA, CTCC, CTCG, GCCC, GCCA, and/or GCCG.

In some embodiments, a non-native PAM sequence does not include the PAM sequence of AATA, AATG, GATA, and/or GATG.

Accordingly, the present invention is directed to methods of using Cas12a polypeptides having modified PAM recognition specificities. In some embodiments, a *Lachnospiraceae bacterium* CRISPR (Clustered Regularly Interspaced Short Palindromic Repeats) Cas12a polypeptide is provided having at least 80% identity (e.g., about 80, 81, 82, 83, 84, 85, 86, 87, 88, 89, 90, 91, 92, 93, 94, 95, 96, 97, 98, 99, 100% identity; e.g., about 80% to about 100%, about 85% to about 100%, about 90% to about 100% about 95% to about 100%, optionally at least 95% identity) to the amino acid sequence of SEQ ID NO:180 and (a) a mutation that is an arginine at position 532 and at 595, or (b) a mutation that is an arginine at position 532 and 542 and a valine at position 538, each of which position in the Cas12a polypeptide of (a) and/or (b) is in reference to position numbering of the amino acid sequence of SEQ ID NO:180, wherein the Cas12a polypeptide of (a) recognizes a PAM sequence in the target nucleic acid of

TTAA, TTAC, ACCA, ACCC, ACCG, ATCA, ATCC, ATCG,

CCCA, CCCG, CTCA, CTCC, CTCG, GCCA, GCCC, GCCG,

GTCA, GTCC, GTCG, GTCT, TCCT, TTCT, ACTA, ACTC,

ACTG, ATTA, ATTC, ATTG, CCTA, CCTC, CCTG, CTTA,

CTTC, CTTG, GCTA, GCTC, GCTG, GTTA, GTTC, GTTG,

TCTA, TCTC, TCTG, TCTT, TTTT, CCCC, TCCA, TCCC,

TCCG, TTCA, TTCC, and/or TTCG, and the Cas12a polypeptide of (b) recognizes a PAM sequence in the target nucleic acid of

AACC, TACC, AATC, GATA, AATA, AATG, GATG, GATC,

TATA, TATC, and/or TATG.

In some embodiments, a Cas12a polypeptide of (a) may comprise an arginine at position G532 and at K595 and recognize a PAM sequence in the target nucleic acid of

TTAA, TTAC, ACCA, ACCC, ACCG, ATCA, ATCC, ATCG,

CCCA, CCCG, CTCA, CTCC, CTCG, GCCA, GCCC, GCCG,

GTCA, GTCC, GTCG, GTCT, TCCT, TTCT, ACTA, ACTC,

ACTG, ATTA, ATTC, ATTG, CCTA, CCTC, CCTG, CTTA,

CTTC, CTTG, GCTA, GCTC, GCTG, GTTA, GTTC, GTTG,

TCTA, TCTC, TCTG, TCTT, TTTT, CCCC, TCCA, TCCC,

TCCG, TTCA, TTCC, and/or TTCG, or a Cas12a polypeptide of (b) may comprise an arginine at position G532 and Y542 and a valine at position K538 and recognize a PAM sequence in the target nucleic acid of TACC, AATC, GATA, AATA, AATG, GATG, GATC, TATA, TATC, and/or TATG, wherein each of which position in the Cas12a polypeptide of (a) and/or (b) is in reference to position numbering of the amino acid sequence of SEQ ID NO:180. In some embodiments, a Cas12a polypeptide may comprise the mutation of G532R and K595R with reference to position numbering of SEQ ID NO:180 and may recognize a PAM sequence in the target nucleic acid of

TTAA, TTAC, ACCA, ACCC, ACCG, ATCA, ATCC, ATCG,

CCCA, CCCG, CTCA, CTCC, CTCG, GCCA, GCCC, GCCG,

GTCA, GTCC, GTCG, GTCT, TCCT, TTCT, ACTA, ACTC,

ACTG, ATTA, ATTC, ATTG, CCTA, CCTC, CCTG, CTTA,

CTTC, CTTG, GCTA, GCTC, GCTG, GTTA, GTTC, GTTG,

TCTA, TCTC, TCTG, TCTT, TTTT, CCCC, TCCA, TCCC,

TCCG, TTCA, TTCC, and/or TTCG, or a Cas12a polypeptide may comprise the mutations of G532R, K538V and Y542R with reference to position numbering of SEQ ID NO:180 and may recognize a PAM sequence in the target nucleic acid of

TACC, AATC, GATA, AATA, AATG, GATG, GATC, TATA,

TATC, and/or TATG.

In some embodiments, a Cas12a polypeptide of (a) may comprise an amino acid sequence having at least 90% sequence identity to SEQ ID NO:181 (LbCas12aRR) and/or may be encoded by a nucleic acid sequence encoding an amino acid sequence having at least 90% sequence identity to SEQ ID NO:181 (LbCas12aRR), and/or a Cas12a polypeptide of (b) may comprise an amino acid sequence having at least 90% sequence identity to SEQ ID NO:182 (LbCAs12aRVR) and/or is encoded by a nucleic acid sequence encoding an amino acid sequence having at least 90% sequence identity to SEQ ID NO:181 (LbCAs12aRVR).

In some embodiments, a Cas12a polypeptide of (a) may comprise a mutation of arginine at position 542 and at position 607 with reference to position numbering of SEQ ID NO:51, which may recognize a PAM sequence in the target nucleic acid of

TTAA, TTAC, ACCA, ACCC, ACCG, ATCA, ATCC, ATCG,

CCCA, CCCG, CTCA, CTCC, CTCG, GCCA, GCCC, GCCG,

GTCA, GTCC, GTCG, GTCT, TCCT, TTCT, ACTA, ACTC,

ACTG, ATTA, ATTC, ATTG, CCTA, CCTC, CCTG, CTTA,

CTTC, CTTG, GCTA, GCTC, GCTG, GTTA, GTTC, GTTG,

TCTA, TCTC, TCTG, TCTT, TTTT, CCCC, TCCA, TCCC,

TCCG, TTCA, TTCC, and/or TTCG;

or a Cas12a polypeptide of (b) having mutations of arginine at position 542 and 552 and valine at position 548 with reference to position numbering of SEQ ID NO:51, which may recognize a PAM sequence in the target nucleic acid of TACC, AATC, GATA, AATA, AATG, GATG, GATC, TATA, TATC, and/or TATG. In some embodiments, a Cas12a polypeptide of (a) may comprise a mutation of arginine at position 607 and at position 671 with reference to position numbering of SEQ ID NO:55, which may recognize a PAM sequence in the target nucleic acid of

TTAA, TTAC, ACCA, ACCC, ACCG, ATCA, ATCC, ATCG,

CCCA, CCCG, CTCA, CTCC, CTCG, GCCA, GCCC, GCCG,

GTCA, GTCC, GTCG, GTCT, TCCT, TTCT, ACTA, ACTC,

ACTG, ATTA, ATTC, ATTG, CCTA, CCTC, CCTG, CTTA,

CTTC, CTTG, GCTA, GCTC, GCTG, GTTA, GTTC, GTTG,

TCTA, TCTC, TCTG, TCTT, TTTT, CCCC, TCCA, TCCC,

TCCG, TTCA, TTCC, and/or TTCG;

or a Cas12a polypeptide of (b) having mutations of arginine at position 607 and 671 and valine at position 613 with reference to position numbering of SEQ ID NO:55 which may recognize a PAM sequence in the target nucleic acid of

TACC, AATC, GATA, AATA, AATG, GATG, GATC, TATA,

TATC, and/or TATG.

In some embodiments, a Cas12a polypeptide of (a) may comprise a mutation of arginine at position S542 and at position K607 with reference to position numbering of SEQ ID NO:51, which may recognize a PAM sequence in the target nucleic acid of

TTAA, TTAC, ACCA, ACCC, ACCG, ATCA, ATCC, ATCG,

CCCA, CCCG, CTCA, CTCC, CTCG, GCCA, GCCC, GCCG,

GTCA, GTCC, GTCG, GTCT, TCCT, TTCT, ACTA, ACTC,

ACTG, ATTA, ATTC, ATTG, CCTA, CCTC, CCTG, CTTA,

CTTC, CTTG, GCTA, GCTC, GCTG, GTTA, GTTC, GTTG,

TCTA, TCTC, TCTG, TCTT, TTTT, CCCC, TCCA, TCCC,

TCCG, TTCA, TTCC, and/or TTCG;

or a Cas12a polypeptide of (b) may comprise mutations of arginine at position S542 and N552 and valine at position K548 with reference to position numbering of SEQ ID NO:51, which may recognize a PAM sequence in the target nucleic acid of

AATC, GATA, AATA, AATG, GATG, GATC, TATA, TATC, and/or TATG. TACC,

In some embodiments, a Cas12a polypeptide of (a) may comprise a mutation of arginine at position N607 and at position K671 with reference to position numbering of SEQ ID NO:55, which may recognize a PAM sequence in the target nucleic acid of

ACCG, ATCA, ATCC, ATCG, CCCA, CCCG, CTCA, CTCC,

CTCG, GCCA, GCCC, GCCG, GTCA, GTCC, GTCG, GTCT,

TCCT, TTCT, ACTA, ACTC, ACTG, ATTA, ATTC, ATTG,

CCTA, CCTC, CCTG, CTTA, CTTC, CTTG, GCTA, GCTC,

GCTG, GTTA, GTTC, GTTG, TCTA, TCTC, TCTG, TCTT,

TTTT, CCCC, TCCA, TCCC, TCCG, TTCA, TTCC, and/or

TTAA, TTAC, ACCA, ACCC, TTCGor a Cas12a polypeptide of (b) may comprise mutations of arginine at position N607 and N617 and valine at position K613 with reference to position numbering of SEQ ID NO:55, which may recognize a PAM sequence in the target nucleic acid of

TACC, AATC, GATA, AATA, AATG, GATG, GATC, TATA,

TATC, and/or TATG.

As would be understood, any single Cas12a polypeptide having two or more mutations would comprise only a single mutation at any given position. Thus, for example, a polypeptide may have mutation at position D535 that would be only one of the mutations of D535A, D535H, D535K, D535N, D535S, D535T, or D535V.

In some embodiments, a Cas12a polypeptide for use with the methods of this invention exhibits an altered protospacer adjacent motif (PAM) specificity as compared to wild type Cas12a (e.g., SEQ ID NO:180, SEQ ID NO:51, SEQ ID NO:55), wherein the altered PAM specificity may result in recognition of a non-natural PAM sequence of an one or more of

TTAA, TTAC, ACCA, ACCC, ACCG, ATCA, ATCC, ATCG,

CCCA, CCCG, CTCA, CTCC, CTCG, GCCA, GCCC, GCCG,

GTCA, GTCC, GTCG, GTCT, TCCT, TTCT, ACTA, ACTC,

ACTG, ATTA, ATTC, ATTG, CCTA, CCTC, CCTG, CTTA,

CTTC, CTTG, GCTA, GCTC, GCTG, GTTA, GTTC, GTTG,

TCTA, TCTC, TCTG, TCTT, TTTT, CCCC, TCCA, TCCC,

TCCG, TTCA, TTCC, and/or TTCG, and/or AACC,

TACC, AATC, GATA, AATA, AATG, GATG, GATC, TATA,

TATC, and/or TATG.

In some embodiments, the altered PAM specificity for a Cas12a polypeptide having a mutation of an arginine at position 532 and at 595, the positions of which in the Cas12a polypeptide of (a) are in reference to the position numbering of the amino acid sequence of SEQ ID NO:180 (Cas12a polypeptide of (a)) may result in recognition of a non-natural PAM sequence of any one or more of

TTAA, TTAC, ACCA, ACCC, ACCG, ATCA, ATCC, ATCG,

CCCA, CCCG, CTCA, CTCC, CTCG, GCCA, GCCC, GCCG,

GTCA, GTCC, GTCG, GTCT, TCCT, TTCT, ACTA, ACTC,

ACTG, ATTA, ATTC, ATTG, CCTA, CCTC, CCTG, CTTA,

CTTC, CTTG, GCTA, GCTC, GCTG, GTTA, GTTC, GTTG,

TCTA, TCTC, TCTG, TCTT, TTTT, CCCC, TCCA, TCCC,

TCCG, TTCA, TTCC, and/or TTCG).

In some embodiments, the altered PAM specificity for a Cas12a polypeptide having a mutation of an arginine at position 532 and 542 and a valine at position 538, the positions of which in the Cas12a polypeptide of (b) are in reference to position numbering of the amino acid sequence of SEQ ID NO:180 (Cas12a polypeptide of (b)) may in result in recognition of a non-natural PAM sequence of any one or more of

AACC, TACC, AATC, GATA, AATA, AATG, GATG, GATC,

TATA, TATC, and/or TATG.

In addition to having an altered PAM recognition specificity a Cas12a polypeptide useful with this invention may further comprise a mutation in the nuclease active site (e.g., RuvC domain) (e.g., deadCas12a, dCas12a). Such modifications may result in the Cas12a polypeptide having reduced nuclease activity (e.g., nickase activity) or no nuclease activity.

In some embodiments, provided are systems that can be used with the methods of the invention, the system comprising Cas12a polypeptides having altered PAM specificity and a guide nucleic acid (CRISPR RNA, CRISPR DNA, crRNA, crDNA) comprising a spacer sequence and a repeat sequence, and/or a fusion proteins comprising a Cas12a polypeptide having altered PAM specificity and a polypeptide of interest; or nucleic acids encoding Cas12a polypeptides having altered PAM specificity, and nucleic acids encoding polypeptide(s) of interest, wherein the guide nucleic acid is capable of forming a complex with the Cas12a polypeptide or the fusion protein and the spacer sequence is capable of hybridizing to a target nucleic acid, thereby guiding the Cas12a polypeptide and the polypeptide of interest to the target nucleic acid, whereby the target nucleic acid is modified or edited. In some embodiments, the Cas12a polypeptide comprises a mutation in the nuclease domain, e.g., the RuvC domain. In some embodiments, a system may comprise a polypeptide of interest linked to the C-terminus and/or the N-terminus of the Cas12a polypeptide (e.g., a fusion protein), optionally via a peptide linker. In some embodiments, a polypeptide of interest may comprise at least one polypeptide or protein domain having, for example, deaminase (deamination) activity, nickase activity, recombinase activity, transposase activity, methylase activity, glycosylase (DNA glycosylase) activity, glycosylase inhibitor activity (e.g., uracil-DNA glycosylase inhibitor (UGI)). demethylase activity, transcription activation activity, transcription repression activity, transcription release factor activity, histone modification activity, nuclease activity, single-strand RNA cleavage activity, double-strand RNA cleavage activity, restriction endonuclease activity (e.g., Fok1), nucleic acid binding activity, methyltransferase activity, DNA repair activity, DNA damage activity, dismutase activity, alkylation activity, depurination activity, oxidation activity, pyrimidine dimer forming activity, integrase activity, transposase activity, polymerase activity, ligase activity, helicase activity, and/or photolyase activity, optionally wherein the polypeptide of interest comprises at least one polypeptide or protein domain having deaminase activity. In some embodiments, a polypeptide of interest may comprise a uracil-DNA glycosylase inhibitor (UGI).

Additionally, provided herein are fusion proteins that comprise a Cas12a polypeptide with altered PAM specificity as described herein. In some embodiments, a fusion protein is provided that comprises a Cas12a polypeptide with altered PAM specificity as described herein and a linker, optionally a peptide linker. In some embodiments, a peptide linker may be linked to the C-terminus and/or the N-terminus of the Cas12a polypeptide. In some embodiments, a fusion protein may comprise a polypeptide of interest linked to the C-terminus and/or to the N-terminus of the Cas12a polypeptide with altered PAM specificity as described herein. In some embodiments, a fusion protein is provided comprising a Cas12a polypeptide with altered PAM specificity as described herein and an optional intervening linker linking the polypeptide of interest.

In some embodiments, the invention provides a polynucleotide encoding a Cas12a polypeptide with altered PAM specificity as described herein or a fusion protein comprising the Cas12a polypeptide with altered PAM specificity. In some embodiments, a polynucleotide may be optimized, for example, optimized for expression in an organism, e.g., in the cell of an organism, optionally wherein the organism may include but is not limited to, an animal, a plant, a fungus, an archaeon, or a bacterium. In some embodiments, the cell is not an animal cell. In some embodiments, the cell is not a mammalian cell. In some embodiments, the cell is not a human cell. In some embodiments, the invention provides a cell comprising the polynucleotide of the invention, the nucleic acid construct of the invention, the expression cassette or vector of the invention, and/or the system of the invention.

Any linker known in the art or later identified that does not interfere with the activity of the fusion protein may be used. A linker that does not "interfere" with the activity of a fusion protein is a linker that does not reduce or eliminate the activity of the polypeptides of the fusion protein (e.g., the nuclease and/or the polypeptide of interest); that is, the nuclease activity, nucleic acid binding activity, editing activity, and/or any other activity of the nuclease or peptide of interest is maintained in a fusion protein in which the nuclease and the polypeptide of interest are tethered to one another via the linker. In some embodiments, a peptide linker may be linked (e.g., at its N-terminus) to the C-terminus of a Cas12a polypeptide having altered PAM specificity as described herein, optionally wherein the fusion protein may further comprise a polypeptide of interest linked to the C-terminus of the linker. In some embodiments, a peptide linker may be linked (e.g., at its C-terminus) to the N-terminus of the Cas12a polypeptide, optionally wherein the fusion protein may further comprise a polypeptide of interest linked to the N-terminus of the linker. In some embodiments, a Cas12a polypeptide having altered PAM specificity as described herein may be linked at both its C-terminus and N-terminus to a linker and/or a polypeptide of interest (directly or via a linker).

A polypeptide of interest useful with this invention can include, but is not limited to, a polypeptide or protein domain having deaminase (deamination) activity, nickase activity, recombinase activity, transposase activity, methylase activity, glycosylase (DNA glycosylase) activity, glycosylase inhibitor activity (e.g., uracil-DNA glycosylase inhibitor (UGI)). demethylase activity, transcription activation activity, transcription repression activity, transcription release factor activity, histone modification activity, nuclease activity, single-strand RNA cleavage activity, double-strand RNA cleavage activity, restriction endonuclease activity (e.g., Fok1), nucleic acid binding activity, methyltransferase activity, DNA repair activity, DNA damage activity, dismutase activity, alkylation activity, depurination activity, oxidation activity, pyrimidine dimer forming activity, integrase activity, transposase activity, polymerase activity, ligase activity, helicase activity, and/or photolyase activity.

In some embodiments, a polypeptide of interest may comprise at least one polypeptide or protein domain having deaminase activity. In some embodiments, the at least one polypeptide or protein domain may be an adenine deaminase domain. An adenine deaminase (or adenosine deaminase) useful with this invention may be any known or later identified adenine deaminase from any organism (see, e.g., U.S. Pat. No. 10,113,163, which is incorporated by reference herein for its disclosure of adenine deaminases). An adenine deaminase can catalyze the hydrolytic deamination of adenine or adenosine. In some embodiments, the adenine deaminase may catalyze the hydrolytic deamination of adenosine or deoxyadenosine to inosine or deoxyinosine, respectively. In some embodiments, the adenosine deaminase may catalyze the hydrolytic deamination of adenine or adenosine in DNA. In some embodiments, an adenine deaminase encoded by a nucleic acid construct of the invention may generate an A→G conversion in the sense (e.g., "+"; template) strand of the target nucleic acid or a T→C conversion in the antisense (e.g., "−", complementary) strand of the target nucleic acid.

In some embodiments, a Cas12a nuclease of the invention may comprise a mutation in its nuclease active site (e.g., RuvC). A Cas12a nuclease having a mutation in its nuclease active site(s) and no longer comprising nuclease activity are commonly referred to as "dead," e.g., dCas12a. In some embodiments, a Cas12a domain or polypeptide of the invention having a mutation in its nuclease active site(s) may have impaired activity or reduced activity (e.g., nickase activity) as compared to the same Cas12a nuclease without the mutation.

Cas12a nucleases of the invention may be used in combination with a guide RNA (gRNA, CRISPR array, CRISPR RNA, crRNA), designed to function with the Cas12a nuclease, to modify a target nucleic acid. A guide nucleic acid useful with this invention comprises at least a spacer sequence and a repeat sequence. The guide nucleic acid is capable of forming a complex with the Cas12a nuclease domain encoded and expressed by a polynucleotide/nucleic acid construct of the invention encoding a Cas12a nuclease and the spacer sequence is capable of hybridizing to a target nucleic acid, thereby guiding the nucleic acid construct (e.g., a Cas12a nuclease of the invention (and/or a polypeptide of interest)) to the target nucleic acid, wherein the target nucleic acid may be modified (e.g., cleaved or edited) or modulated (e.g., modulating transcription) by the Cas12a nuclease (and/or an encoded deaminase domain and/or polypeptide of interest). As an example, a nucleic acid construct encoding aCas12a domain linked to a cytosine deaminase domain (e.g., a fusion protein) may be used in combination with guide nucleic acid to modify a target nucleic acid, wherein the cytosine deaminase domain of the fusion protein deaminates a cytosine base in the target nucleic acid, thereby editing the target nucleic acid. In a further example, a nucleic acid construct encoding a Cas12a domain (e.g., a Cas12a nuclease modified as described herein) linked to an adenine deaminase domain (e.g., a fusion protein) may be used in combination with a guide nucleic acid to modify a target nucleic acid, wherein the adenine deaminase domain of the fusion protein deaminates an adenosine base in the target nucleic acid, thereby editing the target nucleic acid.

A "guide nucleic acid," "guide RNA," "gRNA," "CRISPR RNA/DNA" "crRNA" or "crDNA" as used herein means a nucleic acid that comprises at least one spacer sequence, which is complementary to (and hybridizes to) a target nucleic acid (e.g., protospacer), and at least one repeat sequence (e.g., a repeat of a Type V Cas12a CRISPR-Cas system, or a fragment or portion thereof), wherein the repeat sequence may be linked to the 5' end and/or the 3' end of the spacer sequence. The design of a gRNA of this invention may be based on a Type V Cas12a system. In some embodiments, a "guide nucleic acid," as used herein means a nucleic acid that comprises at least one spacer sequence, which is complementary to (and hybridizes to) a target nucleic acid (e.g., a target DNA and/or a protospacer), and at least one repeat sequence (e.g., a repeat of a Type V Cas12a CRISPR-Cas system, or a fragment or portion thereof; a repeat of a Type II Cas9 CRISPR-Cas system, or fragment thereof; a repeat of a Type V C2c1 CRISPR Cas system, or a fragment thereof; a repeat of a CRISPR-Cas system of, for example, C2c3, Cas12a (also referred to as Cpf1), Cas12b, Cas12c, Cas12d, Cas12e, Cas12f, Cas12i, Cas13a, Cas13b, Cas13c, Cas13d, Casl, CaslB, Cas2, Cas3, Cas3', Cas3", Cas4, Cas5, Cas6, Cas7, Cas8, Cas9 (also known as Csnl and Csx12), Cas10, Csyl, Csy2, Csy3, Csel, Cse2, Cscl, Csc2, Csa5, Csn2, Csm2, Csm3, Csm4, Csm5, Csm6, Cmrl, Cmr3, Cmr4, Cmr5, Cmr6, Csbl, Csb2, Csb3, Csx17, Csx14, Csx10, Csx16, CsaX, Csx3, Csxl, Csx15, Csfl, Csf2, Csf3, Csf4 (dinG), and/or Csf5, or a fragment thereof), wherein the repeat sequence may be linked to the 5' end and/or the 3' end of the spacer sequence. In some embodiments, the guide nucleic acid comprises DNA.

In some embodiments, the guide nucleic acid comprises RNA (e.g., is a guide RNA). The design of a gRNA of this invention may be based on a Type I, Type II, Type III, Type IV, Type V, or Type VI CRISPR-Cas system.

In some embodiments, a Cas12a gRNA may comprise, from 5' to 3', a repeat sequence (full length or portion thereof ("handle"); e.g., pseudoknot-like structure) and a spacer sequence.

In some embodiments, a guide nucleic acid may comprise more than one "repeat sequence-spacer" sequence (e.g., 2, 3, 4, 5, 6, 7, 8, 9, 10, or more repeat-spacer sequences) (e.g., repeat-spacer-repeat, e.g., repeat-spacer-repeat-spacer-repeat-spacer-repeat-spacer-repeat-spacer, and the like). The guide nucleic acids of this invention are synthetic, human-made and not found in nature. A gRNA can be quite long and may be used as an aptamer (like in the MS2 recruitment strategy) or other RNA structures hanging off the spacer.

In some embodiments, a "repeat sequence" as used herein, refers to, for example, any repeat sequence of a wild-type Cas12a locus (e.g., a LbCas12a locus, a AsCas12a Locus, a FnCas12a locus) or a repeat sequence of a synthetic crRNA that is functional with a Cas12a polypeptide having altered PAM specificity and encoded by a nucleic acid construct useful with the invention. A repeat sequence useful with this invention can be any known or later identified repeat sequence of a Cas12a locus or it can be a synthetic repeat designed to function in a Cas12a Type V CRISPR-Cas system. A repeat sequence may comprise a hairpin structure and/or a stem loop structure. In some embodiments, a repeat sequence may form a pseudoknot-like structure at its 5' end (i.e., "handle"). Thus, in some embodiments, a repeat sequence can be identical to or substantially identical to a repeat sequence from a wild-type V CRISPR-Cas locus (e.g., a wild type Cas12a locus). A repeat sequence from a wild-type Cas12a locus may be determined through established algorithms, such as using the CRISPRfinder offered through CRISPRdb (see, Grissa et al. *Nucleic Acids Res.* 35 (Web Server issue):W52-7). In some embodiments, a repeat sequence or portion thereof is linked at its 3' end to the 5' end of a spacer sequence, thereby forming a repeat-spacer sequence (e.g., guide RNA, crRNA). In some embodiments, a "repeat sequence" as used herein, refers to, for example, any repeat sequence of a wild-type CRISPR Cas locus (e.g., a Cas9 locus, a Cas12a locus, a C2c1 locus, etc.) or a repeat sequence of a synthetic crRNA that is functional with the CRISPR-Cas effector protein encoded by the nucleic acid constructs of the invention. A repeat sequence useful with this invention can be any known or later identified repeat sequence of a CRISPR-Cas locus (e.g., Type I, Type II, Type III, Type IV, Type V or Type VI) or it can be a synthetic repeat designed to function in a Type I, II, III, IV, V or VI CRISPR-Cas system. A repeat sequence may comprise a hairpin structure and/or a stem loop structure. In some embodiments, a repeat sequence may form a pseudoknot-like structure at its 5' end (i.e., "handle"). Thus, in some embodiments, a repeat sequence can be identical to or substantially identical to a repeat sequence from wild-type Type I CRISPR-Cas loci, Type II, CRISPR-Cas loci, Type III, CRISPR-Cas loci, Type IV CRISPR-Cas loci, Type V CRISPR-Cas loci and/or Type VI CRISPR-Cas loci. A repeat sequence from a wild-type CRISPR-Cas locus may be determined through established algorithms, such as using the CRISPRfinder offered through CRISPRdb (see, Grissa et al. *Nucleic Acids Res.* 35 (Web Server issue):W52-7). In some embodiments, a repeat sequence or portion thereof is linked at its 3' end to the 5' end of a spacer sequence, thereby forming a repeat-spacer sequence (e.g., guide nucleic acid, guide RNA/DNA, crRNA, crDNA).

In some embodiments, a repeat sequence comprises, consists essentially of, or consists of at least 10 nucleotides depending on the particular repeat and whether the guide RNA comprising the repeat is processed or unprocessed (e.g., about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 to 100 or more nucleotides, or any range or value therein; e.g., about). In some embodiments, a repeat sequence comprises, consists essentially of, or consists of about 10 to about 20, about 10 to about 30, about 10 to about 45, about 10 to about 50, about 15 to about 30, about 15 to about 40, about 15 to about 45, about 15 to about 50, about 20 to about 30, about 20 to about 40, about 20 to about 50, about 30 to about 40, about 40 to about 80, about 50 to about 100, or more nucleotides.

A repeat sequence linked to the 5' end of a spacer sequence can comprise a portion of a repeat sequence (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more consecutive nucleotides of a wild type repeat sequence). In some embodiments, a portion of a repeat sequence linked to the 5' end of a spacer sequence can be about five to about ten consecutive nucleotides in length (e.g., about 5, 6, 7, 8, 9, 10 nucleotides) and have at least 90% identity (e.g., at least about 90%, 91%, 92%, 93%, 94%, 95%, 96%, 97%, 98%, 99%, or more) to the same region (e.g., 5 end) of a wild type CRISPR Cas repeat nucleotide sequence. In some embodiments, a portion of a repeat sequence may comprise a pseudoknot-like structure at its 5' end (e.g., "handle").

A "spacer sequence" as used herein is a nucleotide sequence that is complementary to a target nucleic acid (e.g., target DNA) (e.g., protospacer). The spacer sequence can be fully complementary or substantially complementary (e.g., at least about 70% complementary (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more, and any range or value therein)) to a target nucleic acid. Thus, in some embodiments, the spacer sequence can have one, two, three, four, or five mismatches as compared to the target nucleic acid, which mismatches can be contiguous or non-contiguous. In some embodiments, the spacer sequence can have about 70% complementarity to a target nucleic acid. In other embodiments, the spacer nucleotide sequence can have about 80% complementarity to a target nucleic acid. In still other embodiments, the spacer nucleotide sequence can have about 85%, 90%, 95%, 96%, 97%, 98%, 99% or 99.5% complementarity, and the like, to the target nucleic acid (protospacer). In some embodiments, the spacer sequence is 100% complementary to the target nucleic acid. A spacer sequence may have a length from about 15 nucleotides to about 30 nucleotides (e.g., about 15, 16, 17, 18, 19, 20, 21, 22, 23, 24, 25, 26, 27, 28, 29, or 30 nucleotides, or any range or value therein). Thus, in some embodiments, a spacer sequence may have complete complementarity or substantial complementarity over a region of a target nucleic acid (e.g., protospacer) that may be at least about 15 nucleotides to about 30 nucleotides in length. In some embodiments, the spacer may be about 20, 21, 22, 23, 24, or 25 nucleotides in length. In some embodiments, the spacer may be 23 nucleotides in length.

In some embodiments, the 5' region of a spacer sequence of a guide RNA may be identical to a target nucleic acid, while the 3' region of the spacer may be substantially complementary to the target nucleic acid (e.g., Type V CRISPR-Cas), or the 3' region of a spacer sequence of a guide RNA may be identical to a target nucleic acid, while the 5' region of the spacer may be substantially complementary to the target nucleic acid (e.g., Type II CRISPR-Cas), and therefore, the overall complementarity of the spacer sequence to the target nucleic acid may be less than 100%. Thus, for example, in a guide for a Type V CRISPR-Cas system, the first 1, 2, 3, 4, 5, 6, 7, 8, 9, 10 nucleotides in the 5' region (i.e., seed region) of, for example, a 20 nucleotide spacer sequence, may be 100% complementary to the target nucleic acid, while the remaining nucleotides in the 3' region of the spacer sequence may be substantially complementary (e.g., at least about 70% complementary) to the target nucleic acid. In some embodiments, the first 1 to 8 nucleotides (e.g., the first 1, 2, 3, 4, 5, 6, 7, 8, nucleotides, and any range therein) of a 5' end of the spacer sequence may be 100% complementary to the target nucleic acid, while the remaining nucleotides in the 3' region of the spacer sequence may be substantially complementary (e.g., at least about 50% complementary (e.g., about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to the target nucleic acid.

As a further example, in a guide nucleic acid for a Type II CRISPR-Cas system, the first 1, 2, 3, 4, 5, 6, 7, 8, 9, 10 nucleotides in the 3' region (i.e., seed region) of, for example, a 20 nucleotide spacer sequence may be 100% complementary to the target nucleic acid, while the remaining nucleotides in the 5' region of the spacer sequence are substantially complementary (e.g., at least about 70% complementary) to the target nucleic acid. In some embodiments, the first 1 to 10 nucleotides (e.g., the first 1, 2, 3, 4, 5, 6, 7, 8, 9, 10 nucleotides, and any range therein) of the 3' end of the spacer sequence may be 100% complementary to the target nucleic acid, while the remaining nucleotides in the 5' region of the spacer sequence are substantially complementary (e.g., at least about 50% complementary (e.g., at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more or any range or value therein)) to the target nucleic acid. A recruiting guide RNA further comprises one or more recruiting motifs as described herein, which may be linked to the 5' end of the guide or the 3' end or it may be inserted into the recruiting guide nucleic acid (e.g., within the hairpin loop).

In some embodiments, a seed region of a spacer may be about 8 to about 10 nucleotides in length, about 5 to about 6 nucleotides in length, or about 6 nucleotides in length.

As used herein, a "target nucleic acid", "target DNA," "target nucleotide sequence," "target region," or a "target region in the genome" refer to a region of an organism's genome that is fully complementary (100% complementary) or substantially complementary (e.g., at least 70% complementary (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or more, and any range or value therein)) to a spacer sequence in a guide RNA of this invention. In some embodiments, a target region useful for a Type V CRISPR-Cas system (e.g., LbCas12a, AsCas12a, FnCas12a) is located immediately 3' to a PAM sequence in the genome of the organism (e.g., a plant genome, an animal genome, a bacterial genome). In some embodiments, a target region may be selected from any at least 15 consecutive nucleotides (e.g., 15, 16, 17, 18, 19, 20, 21, 22, 23, 24, 25, 26, 27, 28, 29, 30 or more nucleotides, and any range or value therein; e.g., about 19 to about 25 nucleotides, about 20 to about 24 nucleotides in length, and the like) located immediately adjacent to a PAM sequence.

A "protospacer sequence" refers to the target nucleic acid and specifically to the portion of the target nucleic acid (e.g., or target region in the genome) that is fully or substantially complementary (and hybridizes) to the spacer sequence of the CRISPR repeat-spacer sequences (e.g., guide RNAs, CRISPR arrays, crRNAs).

In the case of Type V CRISPR-Cas Cas12a systems, the protospacer sequence is flanked (immediately adjacent to) a protospacer adjacent motif (PAM). The PAM is located at the 5' end on the non-target strand and at the 3' end of the target strand (see below, as an example).

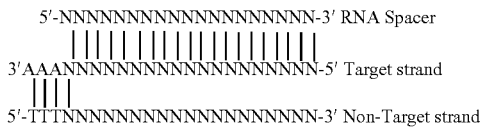

In the case of Type II CRISPR-Cas (e.g., Cas9) systems, the PAM is located immediately 3' of the target region. The PAM for Type I CRISPR-Cas systems is located 5' of the target strand. There is no known PAM for Type III CRISPR-Cas systems. Makarova et al. describes the nomenclature for all the classes, types and subtypes of CRISPR systems (*Nature Reviews Microbiology* 13:722-736 (2015)). Guide structures and PAMs are described by R. Barrangou (*Genome Biol.* 16:247 (2015)).

Canonical Cas12a PAMs are T rich. In some embodiments, a canonical Cas12a PAM sequence may be 5'-TTN, 5'-TTTN, or 5'-TTTV.

The polypeptides, fusion proteins and/or systems useful with the invention may be encoded by polynucleotides or nucleic acid constructs. In some embodiments, a polynucleotide/nucleic acid construct encoding the polypeptides, fusion proteins and/or systems may be operably associated with regulatory elements (e.g., promotors, terminators and the like) for expression in an organism of interest and/or a cell of an organism of interest as described herein. In some embodiments, a polynucleotide/nucleic acid construct encoding a polypeptide, fusion protein and/or system of the invention may be optimized for expression in an organism.

In some embodiments, the present invention provides a complex comprising (a) a Cas12a polypeptide having altered PAM specificity as described herein or a fusion protein comprising the same and (b) a guide nucleic acid (e.g., CRISPR RNA, CRISPR DNA, crRNA, crDNA) useful with the methods of the invention.

In some embodiments, the present invention provides a composition comprising (a) a Cas12a polypeptide having altered PAM specificity as described herein or a fusion protein comprising the same and (b) a guide nucleic acid useful with the methods of the invention.

In some embodiments, the present invention provides expression cassettes and/or vectors comprising the polynucleotides/nucleic acid constructs useful with the methods of the invention. In some embodiments, expression cassettes and/or vectors comprising the polynucleotides/nucleic acid constructs encoding the Cas12a polypeptides having altered PAM specificity and/or one or more guide nucleic acids may be provided. In some embodiments, a nucleic acid construct encoding the Cas12a polypeptides having altered PAM specificity and/or a fusion protein comprising a modified CRISPR-Cas nuclease of the invention may be comprised in the same or a separate expression cassette or vector from that comprising the guide nucleic acid. In some embodiments, a nucleic acid construct encoding an engineered protein as described herein and having altered PAM specificity and/or a fusion protein comprising the same may be comprised in the same or a separate expression cassette or vector from that comprising the guide nucleic acid. When the nucleic acid construct is comprised in a separate expression cassette or vector from that comprising the guide nucleic acid, a target nucleic acid may be contacted with (e.g., provided with) the expression cassette or vector comprising the nucleic acid construct of the invention prior to, concurrently with, or after the expression cassette comprising the guide nucleic acid is provided (e.g., contacted with the target nucleic acid).

In some embodiments, the present invention provides expression cassettes and/or vectors encoding compositions and/or complexes and/or systems that may be used with methods of the invention.

In some embodiments, the polynucleotides, nucleic acid constructs, expression cassettes and/or vectors of the invention that are optimized for expression in an organism may be about 70% to about 100% identical (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100%, and any value or range therein) to the polynucleotides, nucleic acid constructs, expression cassettes and/or vectors encoding the same modified CRISPR-Cas nuclease or fusion protein of the invention but which has not been optimized for expression in an organism. An organism for which a polynucleotide or nucleic acid construct may be optimized may include but is not limited to, an animal, a plant, a fungus, an archaeon, or a bacterium. In some embodiments, a polynucleotide or nucleic acid construct of the invention is optimized for expression in a plant.

In some embodiments, the invention provides cells comprising one or more polynucleotides, guide nucleic acids, nucleic acid constructs, systems, expression cassettes and/or vectors of the invention.

The nucleic acid constructs of the invention (e.g., encoding a modified CRISPR-Cas nuclease of the invention and/or a fusion protein comprising a modified CRISPR-Cas nuclease of the invention) and expression cassettes/vectors comprising the same may be used for modifying target nucleic acids and/or their expression in vivo (e.g., in an organism or the cell of an organism; e.g., a plant) and in vitro (e.g., in a cell or a cell free system).

In some embodiments, a method of modifying a target nucleic acid is provided comprising contacting the target nucleic acid with (a) a Cas12a polypeptide having a mutation, wherein the mutation is an arginine at position 532 and at 595, or (b) a Cas12a polypeptide having a mutation, wherein the mutation is an arginine at position 532 and 542 and a valine at position 538, each of which position in the Cas12a polypeptide of (a) and/or (b) is in reference to position numbering of the amino acid sequence of SEQ ID NO:180, wherein the Cas12a polypeptide of (a) recognizes a PAM sequence in the target nucleic acid of

```
TTAA, TTAC, ACCA, ACCC, ACCG, ATCA, ATCC, ATCG,
CCCA, CCCG, CTCA, CTCC, CTCG, GCCA, GCCC, GCCG,
GTCA, GTCC, GTCG, GTCT, TCCT, TTCT, ACTA, ACTC,
ACTG, ATTA, ATTC, ATTG, CCTA, CCTC, CCTG, CTTA,
CTTC, CTTG, GCTA, GCTC, GCTG, GTTA, GTTC, GTTG,
TCTA, TCTC, TCTG, TCTT, TTTT, CCCC, TCCA, TCCC,
TCCG, TTCA, TTCC, and/or TTCG,
``` and the Cas12a polypeptide of (b) recognizes a PAM sequence in the target nucleic acid of

```
AACC, TACC, AATC, GATA, AATA, AATG, GATG, GATC,
TATA, TATC, and/or TATG,
```

(b) a fusion protein comprising the Cas12a polypeptide of (a) and/or (b) and a guide nucleic acid (e.g., CRISPR RNA, CRISPR DNA, crRNA, crDNA); (c) a complex comprising the Cas12a polypeptide of (a) and/or (b) and a guide nucleic acid, or comprising the fusion protein of (b); and/or (d) a composition comprising the Cas12a polypeptide of (a) and/or (b) and a guide nucleic acid or comprising the fusion protein of (b), thereby modifying the target nucleic acid. In some embodiments, the Cas12a polypeptide of (a) may comprise an arginine at position G532 and at K595, or the Cas12a polypeptide of (b) may comprise an arginine at position G532 and Y542 and a valine at position K538, each of which position in the Cas12a polypeptide of (a) and/or (b) is in reference to position numbering of the amino acid sequence of SEQ ID NO:180. In some embodiments, the Cas12a polypeptide of (a) comprises the mutation of G532R and K595R with reference to position numbering of SEQ ID NO:180 and recognizes a PAM sequence in the target nucleic acid of

```
TTAA, TTAC, ACCA, ACCC, ACCG, ATCA, ATCC, ATCG,
CCCA, CCCG, CTCA, CTCC, CTCG, GCCA, GCCC, GCCG,
GTCA, GTCC, GTCG, GTCT, TCCT, TTCT, ACTA, ACTC,
ACTG, ATTA, ATTC, ATTG, CCTA, CCTC, CCTG, CTTA,
CTTC, CTTG, GCTA, GCTC, GCTG, GTTA, GTTC, GTTG,
TCTA, TCTC, TCTG, TCTT, TTTT, CCCC, TCCA, TCCC,
TCCG, TTCA, TTCC, and/or TTCG,
``` or the Cas12a polypeptide comprises the mutations of G532R, K538V and Y542R with reference to position numbering of SEQ ID NO:180 and recognizes a PAM sequence in the target nucleic acid of

```
AACC, TACC, AATC, GATA, AATA, AATG, GATG, GATC,
TATA, TATC, and/or TATG.
```

In some embodiments, a method of editing a target nucleic acid is provided, comprising contacting the target nucleic acid with: (a) a Cas12a polypeptide having a mutation, wherein the mutation is an arginine at position 532 and at 595, or (b) a Cas12a polypeptide having a mutation, wherein the mutation is an arginine at position 532 and 542 and a valine at position 538, each of which position in the Cas12a polypeptide of (a) and/or (b) is in reference to position numbering of the amino acid sequence of SEQ ID NO:180, wherein the Cas12a polypeptide of (a) recognizes a PAM sequence in the target nucleic acid of

```
TTAA, TTAC, ACCA, ACCC, ACCG, ATCA, ATCC, ATCG,
CCCA, CCCG, CTCA, CTCC, CTCG, GCCA, GCCC, GCCG,
GTCA, GTCC, GTCG, GTCT, TCCT, TTCT, ACTA, ACTC,
ACTG, ATTA, ATTC, ATTG, CCTA, CCTC, CCTG, CTTA,
CTTC, CTTG, GCTA, GCTC, GCTG, GTTA, GTTC, GTTG,
TCTA, TCTC, TCTG, TCTT, TTTT, CCCC, TCCA, TCCC,
TCCG, TTCA, TTCC, and/or TTCG,
``` and the Cas12a polypeptide of (b) recognizes a PAM sequence in the target nucleic acid of

```
AACC, TACC, AATC, GATA, AATA, AATG, GATG,
GATC, TATA, TATC, and/or TATG;
```

(b) a fusion protein comprising the Cas12a polypeptide of (a) and/or (b) and a guide nucleic acid (e.g., CRISPR RNA, CRISPR DNA, crRNA, crDNA); (c) a complex comprising the Cas12a polypeptide of (a) and/or (b) and a guide nucleic acid, or comprising the fusion protein of (b); and/or (d) a composition comprising the Cas12a polypeptide of (a) and/or (b) and a guide nucleic acid or comprising the fusion protein of (b), thereby editing the target nucleic acid. In some embodiments, the Cas12a polypeptide of (a) may comprise an arginine at position G532 and at K595, or the Cas12a polypeptide of (b) may comprise an arginine at position G532 and Y542 and a valine at position K538, each of which position in the Cas12a polypeptide of (a) and/or (b) is in reference to position numbering of the amino acid sequence of SEQ ID NO:180. In some embodiments, the Cas12a polypeptide of (a) comprises the mutation of G532R and K595R with reference to position numbering of SEQ ID NO:180 and recognizes a PAM sequence in the target nucleic acid of

```
TTAA, TTAC, ACCA, ACCC, ACCG, ATCA, ATCC, ATCG,
CCCA, CCCG, CTCA, CTCC, CTCG, GCCA, GCCC, GCCG,
GTCA, GTCC, GTCG, GTCT, TCCT, TTCT, ACTA, ACTC,
ACTG, ATTA, ATTC, ATTG, CCTA, CCTC, CCTG, CTTA,
CTTC, CTTG, GCTA, GCTC, GCTG, GTTA, GTTC, GTTG,
TCTA, TCTC, TCTG, TCTT, TTTT, CCCC, TCCA, TCCC,
TCCG, TTCA, TTCC, and/or TTCG,
``` or the Cas12a polypeptide comprises the mutations of G532R, K538V and Y542R with reference to position numbering of SEQ ID NO:180 and recognizes a PAM sequence in the target nucleic acid of

AACC, TACC, AATC, GATA, AATA, AATG, GATG, GATC,

TATA, TATC, and/or TATG.

In some embodiments, a method of editing a target nucleic acid is provided comprising contacting a cell or a cell free system comprising the target nucleic acid with: (a) a Cas12a polypeptide having a mutation, wherein the mutation is an arginine at position 532 and at 595, or (b) a Cas12a polypeptide having a mutation, wherein the mutation is an arginine at position 532 and 542 and a valine at position 538, each of which position in the Cas12a polypeptide of (a) and/or (b) is in reference to position numbering of the amino acid sequence of SEQ ID NO:180, wherein the Cas12a polypeptide of (a) recognizes a PAM sequence in the target nucleic acid of

TTAA, TTAC, ACCA, ACCC, ACCG, ATCA, ATCC, ATCG,

CCCA, CCCG, CTCA, CTCC, CTCG, GCCA, GCCC, GCCG,

GTCA, GTCC, GTCG, GTCT, TCCT, TTCT, ACTA, ACTC,

ACTG, ATTA, ATTC, ATTG, CCTA, CCTC, CCTG, CTTA,

CTTC, CTTG, GCTA, GCTC, GCTG, GTTA, GTTC, GTTG,

TCTA, TCTC, TCTG, TCTT, TTTT, CCCC, TCCA, TCCC,

TCCG, TTCA, TTCC, and/or TTCG, and the Cas12a polypeptide of (b) recognizes a PAM sequence in the target nucleic acid of

AACC, TACC, AATC, GATA, AATA, AATG, GATG, GATC,

TATA, TATC, and/or TATG, or an expression cassette or vector comprising the same and a guide nucleic acid, or an expression cassette or vector comprising the same; and/or (b) a nucleic acid construct encoding a complex comprising a fusion protein that comprises the Cas12a polypeptide of (a) and/or (b) and a guide nucleic acid, or an expression cassette or vector comprising the same, thereby editing the target nucleic acid. In some embodiments, the Cas12a polypeptide of (a) may comprise an arginine at position G532 and at K595, or the Cas12a polypeptide of (b) may comprise an arginine at position G532 and Y542 and a valine at position K538, each of which position in the Cas12a polypeptide of (a) and/or (b) is in reference to position numbering of the amino acid sequence of SEQ ID NO:180. In some embodiments, the Cas12a polypeptide of (a) comprises the mutation of G532R and K595R with reference to position numbering of SEQ ID NO:180 and recognizes a PAM sequence in the target nucleic acid of

TTAA, TTAC, ACCA, ACCC, ACCG, ATCA, ATCC, ATCG,

CCCA, CCCG, CTCA, CTCC, CTCG, GCCA, GCCC, GCCG,

GTCA, GTCC, GTCG, GTCT, TCCT, TTCT, ACTA, ACTC,

ACTG, ATTA, ATTC, ATTG, CCTA, CCTC, CCTG, CTTA,

CTTC, CTTG, GCTA, GCTC, GCTG, GTTA, GTTC, GTTG,

TCTA, TCTC, TCTG, TCTT, TTTT, CCCC, TCCA, TCCC,

TCCG, TTCA, TTCC, and/or TTCG, or the Cas12a polypeptide comprises the mutations of G532R, K538V and Y542R with reference to position numbering of SEQ ID NO:180 and recognizes a PAM sequence in the target nucleic acid of

AACC, TACC, AATC, GATA, AATA, AATG, GATG, GATC,

TATA, TATC, and/or TATG.

In some embodiments, a Cas12a polypeptide and/or a engineered protein having altered specificity as described herein may further comprise a mutation in the RuvC domain.

In some embodiments, a fusion protein comprising a Cas12a polypeptide and/or a engineered protein useful with the methods of the invention may further comprise a polypeptide of interest, optionally wherein the polypeptide of interest may comprise at least one polypeptide or protein domain having deaminase (deamination) activity, nickase activity, recombinase activity, transposase activity, methylase activity, glycosylase (DNA glycosylase) activity, glycosylase inhibitor activity (e.g., uracil-DNA glycosylase inhibitor (UGI)), demethylase activity, transcription activation activity, transcription repression activity, transcription release factor activity, histone modification activity, nuclease activity, single-strand RNA cleavage activity, double-strand RNA cleavage activity, restriction endonuclease activity, nucleic acid binding activity, methyltransferase activity, DNA repair activity, DNA damage activity, dismutase activity, alkylation activity, depurination activity, oxidation activity, pyrimidine dimer forming activity, integrase activity, transposase activity, polymerase activity, ligase activity, helicase activity, and/or photolyase activity. In some embodiments, a polypeptide of interest may comprises at least one polypeptide or protein domain having deaminase activity. In some embodiments, the at least one polypeptide or protein domain having deaminase activity is a cytosine deaminase domain or an adenine deaminase domain. In some embodiments, the polypeptide of interest may have glycosylase inhibitor activity, optionally wherein the polypeptide of interest is a uracil-DNA glycosylase inhibitor (UGI).

In some embodiments, the target nucleic acid is in a plant cell and the plant cell may be regenerated into a plant. In some embodiments, the target nucleic acid is in a plant cell and the plant cell may is not regenerable into a plant.

In some embodiments, the guide nucleic acid is capable of forming a complex with the Cas12a polypeptide having altered PAM specificity or with the fusion protein comprising the Cas12a polypeptide Cas12a polypeptide having altered PAM specificity, and the spacer sequence is capable of hybridizing to the target nucleic acid, thereby guiding the Cas12a polypeptide Cas12a polypeptide having altered PAM specificity and, when present, the polypeptide of interest, to the target nucleic acid, whereby the target nucleic acid is modified and/or edited.

The CRISPR-Cas nucleases having altered PAM recognition specificities may be utilized in many ways including, but not limited to, creating indels (NHEJ), in homology directed repair, as a genome recognition element without a nuclease function (dead Cas12a), as a genome recognition element with a partially functional nuclease (nickase Cas12a), in fusion proteins for catalytic editing of genomic DNA (DNA base editors), in fusions proteins for catalytic editing of RNA (RNA base editors), for targeting of other macromolecules to specific genomic regions; for targeting of small chemicals to specific genomic regions, for labeling of specific genomic regions and/or for CRISPR-directed genomic recombination strategies.

When provided on different nucleic acid constructs, expression vectors, and/or vectors, a nucleic acid construct of the invention may be contacted with a target nucleic acid prior to, concurrently with or after contacting the target nucleic acid with a guide nucleic acid.

The CRISPR-Cas polypeptides and engineered proteins having altered PAM specificity and nucleic acid constructs encoding the same may be used for modifying a target nucleic acid in any organism, including but not limited to, an animal, a plant, a fungus, an archaeon, or a bacterium. An animal can include, but is not limited to, a mammal, an insect, a fish, a bird, and the like. Exemplary mammals for which this invention may be useful include, but are not limited to, primates (human and non-human (e.g., a chimpanzee, baboon, monkey, gorilla, etc.)), cats, dogs, mice, rats, ferrets, gerbils, hamsters, cows, pigs, horses, goats, donkeys, or sheep. In some embodiments, the methods of the invention are not used for modifying a target nucleic acid in an animal. In some embodiments, the methods of the invention are not used for modifying a target nucleic acid in a mammal. In some embodiments, the methods of the invention are not used for modifying a target nucleic acid in a human.

In some embodiments, an engineered protein of the invention may exhibit an altered PAM (protospacer adjacent motif) specificity compared to the PAM specificity for LbCas12a.

In some embodiments, an engineered protein of the invention may further comprise a mutation in a nuclease active site (e.g., RuvC domain) (e.g., deadLbCas12a, dLbCas12a), optionally wherein the modified protein comprises an amino acid sequence having at least 80%, 85%, 90%, or 95% identity to the amino acid sequence of SEQ ID NO:50.

In some embodiments, the first polypeptide of an engineered protein of the invention may comprise an amino acid residue 1 to about amino residue 250, 300, or 350 with reference to the position numbering of the modified protein, optionally wherein the first polypeptide comprises the mutation and/or the first polypeptide comprises amino acid residue 1 to about amino residue 282, 283, 284, 285, 286, 287, 288, 289, 290, 291, 292, or 293 with reference to the position numbering of the modified protein (e.g., SEQ ID NO:180).

In some embodiments, the second polypeptide has a length of about 10, 50, 100, or 150 to about 200, 250, or 300 amino acids and/or the first polypeptide has a length of about 100, 200, or 250 to about 300, 350, or 400 amino acids, optionally wherein the second polypeptide has a length of about 140 or 150 to about 160, 170, 180, 190, 200, 210, 220, 230, 240, or 250 amino acids and/or the first polypeptide has a length of about 250 or 275 to about 300 or 350 amino acids.

In some embodiments, the second polypeptide comprises a first nuclease domain or a portion thereof. In some embodiments, the second polypeptide comprises a target strand nickase domain or a portion thereof, optionally wherein the second polypeptide comprises a target strand specific nickase domain, a nontarget strand specific nickase domain, or a target and nontarget strand nickase domain.

In some embodiments, the engineered protein of the invention further comprises a third polypeptide that comprises a second nuclease domain or a portion thereof, optionally wherein the third polypeptide comprises the mutation and/or wherein the first polypeptide and the third polypeptide are non-continuous (i.e., are separated from each (optionally by at least 10, 50, 100, or more amino acids) and are not directly attached to each other).

In some embodiments, the second polypeptide may be heterologous to the third polypeptide.

In some embodiments, the third polypeptide may be a Type V CRISPR-Cas effector polypeptide, optionally wherein the third polypeptide may be a second portion of the modified protein and may be different than the first polypeptide.

In some embodiments, the second nuclease domain or a portion thereof may be a nontarget and target strand nickase domain or a portion thereof.

In some embodiments, the second nuclease domain may be active. In some embodiments, the second nuclease domain may be inactive.

In some embodiments, the second polypeptide may comprise a HNH domain, optionally wherein the HNH domain comprises a mutation that modifies the activity of the HNH domain (e.g., a H840A mutation).

In some embodiments, the first and third polypeptides are each a portion of the modified protein and the second polypeptide is between and/or linked to (e.g., directly or indirectly) two amino acids that are two consecutive or nonconsecutive amino acids of the modified protein.

In some embodiments, the second polypeptide may be positioned in the engineered protein in a location that corresponds to an interdomain linker region of the modified protein.

In some embodiments, the second polypeptide comprises an amino acid sequence having at least 70%, 75%, 80%, 85%, 90%, 95%, 96%, 97%, 98%, 99%, or more sequence identity to one or more of SEQ ID NOs:1 or 169-174, optionally wherein the second polypeptide comprises an amino acid sequence of any one of SEQ ID NOs:1 or 169-174.

In some embodiments, the engineered protein comprises, in the amino terminal to carboxy terminal direction, the first polypeptide, the second polypeptide, and the third polypeptide, optionally wherein the third polypeptide has a length of about 800 or 850 to about 900, 1,000, or 1,100 amino acids (e.g., about 900 to about 950 or 1,000 amino acids).

In some embodiments, the engineered protein may further comprise all or a portion of a wedge domain, a Rec1 domain, a Rec2 domain, a PAM-interacting domain, a RuvC domain, a bridge helix, and/or a Nuc domain of the modified protein, optionally wherein the engineered protein comprises all or a portion of a wedge domain, a Rec1 domain, a Rec2 domain, a PAM-interacting domain, a RuvC domain, a bridge helix, and/or a Nuc domain of LbCas12a. In some embodiments, the engineered protein may comprise a Rec1 domain and a Rec2 domain and the second polypeptide may be located between the Rec1 domain and the Rec2 domain.

In some embodiments, an engineered protein of the invention may be devoid of at least a portion of the modified protein, optionally wherein the engineered protein may be devoid of at least a portion of LbCas12a.

In some embodiments, an engineered protein of the invention may further comprise a first linker between the first polypeptide and the second polypeptide and/or a second linker between the second polypeptide and the third polypeptide, optionally wherein the first linker and/or second linker comprises an amino acid sequence of $(GGS)_n$, wherein n is an integer of 1-20; GS; SG; and/or an amino acid sequence of one of SEQ ID NOs:18-47 or 176-179. In some embodiments, the first linker and/or the second linker may comprise 1 to 10 amino acids, optionally wherein the first linker and/or the second linker may comprise 1, 2, 3, or 4 amino acids. In some embodiments, the first linker and/or second linker may comprise glycine and/or serine.

In some embodiments, an engineered protein of the invention may comprise an amino acid sequence having about 70%, 75%, 80%, 85%, 90%, 95%, 96%, 97%, 98%, 99%, or more sequence identity to the amino acid sequence of a wild-type CRISPR-Cas effector protein, optionally wherein the engineered protein comprises an amino acid sequence having at least 70%, 75%, 80%, 85%, 90%, 95%, 96%, 97%, 98%, 99%, or more sequence identity to one or more of SEQ ID NOs:50-66 151, or 180.

In some embodiments, when the modified protein of an engineered protein is optimally aligned to any one of the amino acid sequences of SEQ ID NO:50, 58, or 180, the second polypeptide may be between any one of the following sets of amino acid residues that is present in the engineered protein: amino acid residues 290 and 291 of SEQ ID NO:50, amino acid residues 291 and 292 of SEQ ID NO:50, amino acid residues 291 and 292 of SEQ ID NO:58, or amino acid residues 292 and 293 of SEQ ID NO:58, amino acid residues 290 and 291 of SEQ ID NO:180, amino acid residues 291 and 292 of SEQ ID NO:180, or amino acid residues 292 and 293 of SEQ ID NO:180.

In some embodiments, the engineered protein may be a nuclease, optionally wherein the engineered protein is a target strand nickase, a nontarget strand nickase, or a target and nontarget strand nickase.

In some embodiments, the engineered protein of the invention has increased efficiency in nicking the target strand and/or nontarget strand of a target nucleic acid compared to a CRISPR-Cas effector protein (e.g., a wild-type CRISPR-Cas effector protein and/or a protein having a sequence of one of SEQ ID NOs:50-66 or 151, or 180).

In some embodiments, the engineered protein recognizes a non-natural protospacer adjacent motif (PAM) site and/or sequence (e.g., the engineered protein comprises an altered PAM specificity compared to wild-type LbCas12a). As used herein, a "non-natural PAM site" is any PAM site that is not recognized by a wild type LbCas12 nuclease. Thus, for a wild type LbCas12a nuclease this would be any PAM sequence other than the PAM sequence of TTTV, wherein V is A, C or G.

In some embodiments, the present invention provides expression cassettes and/or vectors comprising the nucleic acid constructs of the invention (e.g., one or more components of an editing system of the invention). In some embodiments, expression cassettes and/or vectors comprising the nucleic acid constructs of the invention and/or one or more guide nucleic acids may be provided. In some embodiments, a nucleic acid construct of the invention encodes an engineered protein, and/or a deaminase, and each may be comprised on the same or on a separate expression cassette or vector from that comprising the one or more guide nucleic acids. When the nucleic acid construct encoding an engineered protein or the components of an editing system is/are comprised on separate expression cassette(s) or vector(s) from that comprising the guide nucleic acid, a target nucleic acid may be contacted with (e.g., provided with) the expression cassette(s) or vector(s) encoding the engineered protein or components of an editing system in any order from one another and the guide nucleic acid, e.g., prior to, concurrently with, or after the expression cassette comprising the guide nucleic acid is provided (e.g., contacted with the target nucleic acid).

Methods of recruiting one or more components of an editing system to each other and/or to a target nucleic acid are known in the art and may include the use of a peptide tag or an affinity polypeptide that interacts with the peptide tag. In some embodiments, a guide nucleic acid may be linked to an RNA recruiting motif and a deaminase may be linked to an affinity polypeptide capable of interacting with the RNA recruiting motif, thereby recruiting the deaminase to the target nucleic acid. Alternatively, chemical interactions may be used to recruit a polypeptide (e.g., a deaminase) to a target nucleic acid.

A "recruiting motif" as used herein refers to one half of a binding pair that may be used to recruit a compound to which the recruiting motif is bound to another compound that includes the other half of the binding pair (i.e., a "corresponding motif"). The recruiting motif and corresponding motif may bind covalently and/or noncovalently. In some embodiments, a recruiting motif is an RNA recruiting motif (e.g., an RNA recruiting motif that is capable of binding and/or configured to bind to an affinity polypeptide), an affinity polypeptide (e.g., an affinity polypeptide that is capable of binding and/or configured to bind an RNA recruiting motif and/or a peptide tag), or a peptide tag (e.g., a peptide tag that is capable of binding and/or configured to bind an affinity polypeptide). For example, when a recruiting motif is an RNA recruiting motif, the corresponding motif for the RNA recruiting motif may be an affinity polypeptide that binds the RNA recruiting motif. A further example is that when a recruiting motif is a peptide tag, the corresponding motif for the peptide tag may be an affinity polypeptide that binds the peptide tag. Thus, a compound comprising a recruiting motif (e.g., an affinity polypeptide) may be recruited to another compound (e.g., a guide nucleic acid) comprising a corresponding motif for the recruiting motif (e.g., an RNA recruiting motif).

A peptide tag (e.g., epitope) useful with this invention may include, but is not limited to, a GCN4 peptide tag (e.g., Sun-Tag), a c-Myc affinity tag, an HA affinity tag, a His affinity tag, an S affinity tag, a methionine-His affinity tag, an RGD-His affinity tag, a FLAG octapeptide, a strep tag or strep tag II, a V5 tag, and/or a VSV-G epitope. Any epitope that may be linked to a polypeptide and for which there is a corresponding affinity polypeptide that may be linked to another polypeptide may be used with this invention as a peptide tag. In some embodiments, a peptide tag may comprise 1 or 2 or more copies of a peptide tag (e.g., repeat unit, multimerized epitope (e.g., tandem repeats)) (e.g., 1, 2, 3, 4, 5, 6, 7, 8, 9, 10, 11, 12, 13, 14, 15, 16, 17, 18, 19, 20, 21, 22, 23, 24, 25 or more repeat units. In some embodiments, an affinity polypeptide that interacts with/binds to a peptide tag may be an antibody. In some embodiments, the antibody may be a scFv antibody. In some embodiments, an affinity polypeptide that binds to a peptide tag may be synthetic (e.g., evolved for affinity interaction) including, but not limited to, an affibody, an anticalin, a monobody and/or a DARPin (see, e.g., Sha et al., *Protein Sci.* 26(5): 910-924 (2017)); Gilbreth (*Curr Opin Struc Biol* 22(4):413-420 (2013)), U.S. Pat. No. 9,982,053, each of which are incorporated by reference in their entireties for the teachings relevant to affibodies, anticalins, monobodies and/or DARPins.

In some embodiments, a guide nucleic acid may be linked to an RNA recruiting motif, and a polypeptide to be recruited (e.g., a deaminase) may be fused to an affinity polypeptide that binds to the RNA recruiting motif, wherein the guide binds to the target nucleic acid and the RNA recruiting motif binds to the affinity polypeptide, thereby recruiting the polypeptide to the guide and contacting the target nucleic acid with the polypeptide (e.g., deaminase). In some embodiments, two or more polypeptides may be recruited to a guide nucleic acid, thereby contacting the target nucleic acid with two or more polypeptides (e.g., deaminases).

In some embodiments of the invention, a guide RNA may be linked to one or to two or more RNA recruiting motifs (e.g., 1, 2, 3, 4, 5, 6, 7, 8, 9, 10 or more motifs; e.g., at least 10 to about 25 motifs), optionally wherein the two or more RNA recruiting motifs may be the same RNA recruiting motif or different RNA recruiting motifs. In some embodiments, an RNA recruiting motif and corresponding affinity polypeptide may include, but is not limited to, a telomerase Ku binding motif (e.g., Ku binding hairpin) and the corresponding affinity polypeptide Ku (e.g., Ku heterodimer), a telomerase Sm7 binding motif and the corresponding affinity polypeptide Sm7, an MS2 phage operator stem-loop and the corresponding affinity polypeptide MS2 Coat Protein (MCP), a PP7 phage operator stem-loop and the corresponding affinity polypeptide PP7 Coat Protein (PCP), an SfMu phage Com stem-loop and the corresponding affinity polypeptide Com RNA binding protein, a PUF binding site (PBS) and the affinity polypeptide Pumilio/fem-3 mRNA binding factor (PUF), and/or a synthetic RNA-aptamer and the aptamer ligand as the corresponding affinity polypeptide. In some embodiments, the RNA recruiting motif and corresponding affinity polypeptide may be an MS2 phage operator stem-loop and the affinity polypeptide MS2 Coat Protein (MCP). In some embodiments, the RNA recruiting motif and corresponding affinity polypeptide may be a PUF binding site (PBS) and the affinity polypeptide Pumilio/fem-3 mRNA binding factor (PUF). Exemplary RNA recruiting motifs and corresponding affinity polypeptides that may be useful with this invention can include, but are not limited to, SEQ ID NOs:108-118.

In some embodiments, the components for recruiting polypeptides and nucleic acids may include those that function through chemical interactions that may include, but are not limited to, rapamycin-inducible dimerization of FRB-FKBP; Biotin-streptavidin; SNAP tag; Halo tag; CLIP tag; DmrA-DmrC heterodimer induced by a compound; bifunctional ligand (e.g., fusion of two protein-binding chemicals together; e.g., dihydrofolate reductase (DHFR)).

In some embodiments, the nucleic acid constructs, expression cassettes or vectors of the invention that are optimized for expression in a plant may be about 70% to 100% identical (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100%) to the nucleic acid constructs, expression cassettes or vectors comprising the same polynucleotide(s) but which have not been codon optimized for expression in a plant.

As described herein, a "peptide tag" may be employed to recruit one or more polypeptides. A peptide tag may be any polypeptide that is capable of being bound by a corresponding motif such as an affinity polypeptide. A peptide tag may also be referred to as an "epitope" and when provided in multiple copies, a "multimerized epitope." Example peptide tags can include, but are not limited to, a GCN4 peptide tag (e.g., Sun-Tag), a c-Myc affinity tag, an HA affinity tag, a His affinity tag, an S affinity tag, a methionine-His affinity tag, an RGD-His affinity tag, a FLAG octapeptide, a strep tag or strep tag II, a V5 tag, and/or a VSV-G epitope. In some embodiments, a peptide tag may also include phosphorylated tyrosines in specific sequence contexts recognized by SH2 domains, characteristic consensus sequences containing phosphoserines recognized by 14-3-3 proteins, proline rich peptide motifs recognized by SH3 domains, PDZ protein interaction domains or the PDZ signal sequences, and an AGO hook motif from plants. Peptide tags are disclosed in WO2018/136783 and U.S. Patent Application Publication No. 2017/0219596, which are incorporated by reference for their disclosures of peptide tags. Peptide tags that may be useful with this invention can include, but are not limited to, SEQ ID NO:119 and SEQ ID NO:120. An affinity polypeptide useful with peptide tags includes, but is not limited to, SEQ ID NO:121.

A peptide tag may comprise or be present in one copy or in 2 or more copies of the peptide tag (e.g., multimerized peptide tag or multimerized epitope) (e.g., about 2, 3, 4, 5, 6, 7, 8, 9, 10, 11, 12, 13, 14, 15, 16, 17, 18, 9, 20, 21, 22, 23, 24, or 25 or more peptide tags). When multimerized, the peptide tags may be fused directly to one another or they may be linked to one another via one or more amino acids (e.g., 1, 2, 3, 4, 5, 6, 7, 8, 9, 10, 11, 12, 13, 14, 15, 16, 17, 18, 19, 20), or more amino acids), optionally about 3 to about 10, about 4 to about 10, about 5 to about 10, about 5 to about 15, or about 5 to about 20 amino acids, and the like, and any value or range therein. Thus, in some embodiments, a CRISPR-Cas effector protein of the invention may comprise a CRISPR-Cas effector protein domain fused to one peptide tag or to two or more peptide tags, optionally wherein the two or more peptide tags are fused to one another via one or more amino acid residues. In some embodiments, a peptide tag useful with the invention may be a single copy of a GCN4 peptide tag or epitope or may be a multimerized GCN4 epitope comprising about 2 to about 25 or more copies of the peptide tag (e.g., about 2, 3, 4, 5, 6, 7, 8, 9, 10, 11, 12, 13, 14, 15, 16, 17, 18, 19, 20, 21, 22, 23, 24, 25 or more copies of a GCN4 epitope or any range therein).

In some embodiments, a peptide tag may be fused to a CRISPR-Cas polypeptide or domain. In some embodiments, a peptide tag may be fused or linked to the C-terminus of a CRISPR-Cas effector protein to form a CRISPR-Cas fusion protein. In some embodiments, a peptide tag may be fused or linked to the N-terminus of a CRISPR-Cas effector protein to form a CRISPR-Cas fusion protein. In some embodiments, a peptide tag may be fused within a CRISPR-Cas effector protein (e.g., a peptide tag may be in a loop region of a CRISPR-Cas effector protein). In some embodiments, peptide tag may be fused to a cytosine deaminase and/or to an adenine deaminase.

An "affinity polypeptide" (e.g., "recruiting polypeptide") refers to any polypeptide that is capable of binding to its corresponding peptide tag, peptide tag, or RNA recruiting motif. An affinity polypeptide for a peptide tag may be, for example, an antibody and/or a single chain antibody that specifically binds the peptide tag, respectively. In some embodiments, an antibody for a peptide tag may be, but is not limited to, an scFv antibody. In some embodiments, an affinity polypeptide may be fused or linked to the N-terminus of a deaminase (e.g., a cytosine deaminase or an adenine deaminase). In some embodiments, the affinity polypeptide is stable under the reducing conditions of a cell or cellular extract.

The nucleic acid constructs of the invention and/or guide nucleic acids may be comprised in one or more expression cassettes as described herein. In some embodiments, a nucleic acid construct of the invention may be comprised in the same or in a separate expression cassette or vector from that comprising a guide nucleic acid and/or a recruiting guide nucleic acid.

In some embodiments, a nucleic acid construct, expression cassette, or vector of the invention that is optimized for expression in an organism (e.g., a human or plant) may be about 70% to 100% identical (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100%) to a nucleic acid construct, expression cassette or vector comprising the same polynucleotide(s) but which have not been codon optimized for expression in the organism.

When used in combination with a guide nucleic acid, a nucleic acid construct of the invention (and a expression cassette and/or a vector comprising the same) may be used to modify a target nucleic acid and/or its expression. A target nucleic acid may be contacted with a nucleic acid construct of the invention and/or expression cassettes and/or vectors comprising the same prior to, concurrently with or after contacting the target nucleic acid with the guide nucleic acid/recruiting guide nucleic acid (and/or expression cassettes and vectors comprising the same.

According to embodiments of the present invention, provided herein are engineered proteins. An "engineered protein" as used herein refers to a polypeptide or protein that is not found naturally in nature. In some embodiments, the engineered protein refers to a polypeptide that comprises a first polypeptide from a first protein and a second polypeptide from a second protein, wherein the first and second proteins are different from each other. In some embodiments, an engineered protein of the present invention comprises a polypeptide from a CRISPR-Cas effector protein (i.e., a CRISPR-Cas effector polypeptide) and a polypeptide that is heterologous to the CRISPR-Cas effector polypeptide (i.e., a heterologous polypeptide). A polypeptide from a CRISPR-Cas effector protein is referred to herein as a "CRISPR-Cas effector polypeptide" and a "CRISPR-Cas effector polypeptide" is all or a portion of a CRISPR-Cas effector protein. In some embodiments, a "CRISPR-Cas effector polypeptide" does not include all of a CRISPR-Cas effector protein and, thus, has a reduced number of amino acids compared to the number of amino acids for the CRISPR-Cas effector protein. In some embodiments, the CRISPR-Cas effector polypeptide is a Type V CRISPR-Cas effector polypeptide (i.e., all or a portion of a Type V CRISPR-Cas effector protein). In some embodiments, a Type V CRISPR-Cas effector polypeptide is a portion of a Type V CRISPR-Cas effector protein. In some embodiments, an engineered protein of the present invention is a target strand nickase that has about 50%, 55%, 60%, 65%, 70%, 75%, 80%, 85%, 90%, 95%, 96%, 97%, 98%, 99%, or more sequence identity to one or more wild-type CRISPR-Cas effector protein(s) (e.g., a Type V CRISPR-Cas effector protein) and/or to an amino acid sequence of one or more of SEQ ID NOs:50-66, 151, and/or 180. In some embodiments, an engineered protein of the present invention is a target strand nickase that has at least about 70%, 75%, 80%, 85%, 90%, 95%, 96%, 97%, 98%, 99%, or more sequence identity to one or more wild-type CRISPR-Cas effector protein(s) (e.g., a Type V CRISPR-Cas effector protein) and/or to an amino acid sequence of one or more of SEQ ID NOs:50-66, 151, and/or 180.

In some embodiments, an engineered protein and/or modified protein of the present invention may comprise an altered protospacer adjacent motif (PAM) specificity as compared to wild type LbCas12a (e.g., SEQ ID NO:180), LbCas12a comprising the mutations S542R/K607R (e.g., LbCas12a-RR; e.g., SEQ ID NO: 182), and/or LbCas12a comprising the mutations S542R/K548V/N552R (e.g., LbCas12a-RVR; e.g., SEQ ID NO: 183). An engineered protein and/or modified protein of the present invention may have an altered PAM specificity, wherein the altered PAM specificity includes, but is not limited to,

NNNG, NNNT, NNNA, NNNC, NNG, NNT, NNC, NNA, NG,

NT, NC, NA, NN, NNN, NNNN, wherein each N of each sequence is independently selected from any of T, C, G, or A. In some embodiments, the altered PAM specificity may include, but is not limited to,

TTAA, TTAC, ACCA, ACCC, ACCG, ATCA, ATCC, ATCG,

CCCA, CCCG, CTCA, CTCC, CTCG, GCCA, GCCC, GCCG,

GTCA, GTCC, GTCG, GTCT, TCCT, TTCT, ACTA, ACTC,

ACTG, ATTA, ATTC, ATTG, CCTA, CCTC, CCTG, CTTA,

CTTC, CTTG, GCTA, GCTC, GCTG, GTTA, GTTC, GTTG,

TCTA, TCTC, TCTG, TCTT, TTTT, CCCC, TCCA, TCCC,

TCCG, TTCA, TTCC, and/or TTCG.

In some embodiments, the altered PAM specificity may include, but is not limited to,

AACC, TACC, AATC, GATA, AATA, AATG, GATG, GATC,

TATA, TATC, and/or TATG.

In addition to having an altered PAM recognition specificity an engineered protein and/or modified protein of the present invention may further comprise a mutation in the nuclease active site (e.g., RuvC domain) (e.g., deadLbCas12a, dLbCas12a). Such modifications may result in the engineered protein and/or modified protein having reduced nuclease activity (e.g., nickase activity) or no nuclease activity.

In some embodiments, a CRISPR-Cas effector polypeptide (e.g., a Type V CRISPR-Cas effector polypeptide) of an engineered protein of the present invention is devoid of a nuclease domain (e.g., devoid of a RuvC domain). The polypeptide that is heterologous to the CRISPR-Cas effector polypeptide may be referred to herein as a heterologous polypeptide. The heterologous polypeptide may be a polypeptide of interest as described herein. In some embodiments, an engineered protein comprises all or a portion of a deaminase domain (e.g., a cytosine deaminase and/or adenine deaminase), which may be linked to any portion of the engineered protein. For example, in some embodiments, all or a portion of a deaminase domain is linked to the N- or C-terminus of the CRISPR-Cas effector polypeptide and/or to the N- or C-terminus of the engineered protein. In some embodiments, all or a portion of a deaminase domain is between two portions of an engineered protein. In some embodiments, an engineered protein comprises all or a portion of a polypeptide of interest, which may be linked to any portion of the engineered protein.

An engineered protein may cleave, cut, or nick a nucleic acid; bind a nucleic acid (e.g., a target nucleic acid and/or a guide nucleic acid); and/or identify, recognize, or bind a guide nucleic acid as defined herein. In some embodiments, an engineered protein or a portion thereof may be an enzyme (e.g., a nuclease, endonuclease, nickase, etc.) and/or may function as an enzyme. In some embodiments, an engineered protein of the present invention is an RNA-guided DNA-binding protein. In some embodiments, an engineered protein is present in and/or forms a complex with a guide nucleic acid that is a single guide nucleic acid (e.g., a gRNA, CRISPR array, and/or crRNA), optionally wherein the guide nucleic acid is a single crRNA. In some embodiments, a complex comprises an engineered protein and a guide nucleic acid and the guide nucleic acid and/or complex consists of a single guide nucleic acid (e.g., a single crRNA). In some embodiments, an engineered protein binds a single guide nucleic acid (e.g., a single crRNA), recognizes and/or binds a target nucleic acid, and has nuclease activity, optionally wherein the engineered protein cleaves the target strand of the target nucleic acid.

In some embodiments, an engineered protein comprises a first CRISPR-Cas effector polypeptide and a heterologous polypeptide. The first CRISPR-Cas effector polypeptide may be referred to herein as a first polypeptide and may be a Type V CRISPR-Cas effector polypeptide. The heterologous polypeptide may be referred to herein as a second polypeptide. The first polypeptide may be devoid of a nuclease domain, optionally devoid of a RuvC domain. The second polypeptide may be linked to the N- or C-terminus of the first polypeptide, optionally with or without a linker (e.g., a peptide linker). In some embodiments, the second polypeptide is linked to the N- or C-terminus of the first polypeptide with a peptide linker, optionally wherein the peptide linker is a GS linker. In some embodiments, the peptide linker is a GS linker having 1, 2, 3, or 4 amino acid residues, optionally 2 or 4 amino acid residues. In some embodiments, the peptide linker has one of the amino acid sequences of SEQ ID NOs:18-47 or 175-179. In some embodiments, the peptide linker may comprise an amino acid sequence of (GGS)$_n$, GS, SG, GSSG (SEQ ID NO:175), GSSGSS (SEQ ID NO:176), GSSGSSGS (SEQ ID NO:177), (GSS)$_n$ (SEQ ID NO:178), (GSS)$_n$GS (SEQ ID NO:179), S(GGS)$_n$ (SEQ ID NO:42), SGGS (SEQ ID NO:43), or (GGGGS)$_n$ (SEQ ID NO:44), wherein n is an integer of 1-20 (e.g., 1, 2, 3, 4, 5, 6, 7, 8, 9, 10, 11, 12, 13, 14, 15, 16, 17, 18, 19, or 20).

In some embodiments, the first polypeptide is a portion of a first CRISPR-Cas effector protein (e.g., a portion of a Type V CRISPR-Cas effector protein such as a portion of a Cas12a). In some embodiments, the heterologous polypeptide (e.g., second polypeptide) comprises a nuclease domain, optionally a HNH domain (e.g., an HNH domain comprising a sequence having at least 70%, 75%, 80%, 85%, 90%, 95%, 96%, 97%, 98%, 99%, or 100% sequence identity to the amino acid sequence of one or more of SEQ ID NOs:1 or 169-174). In some embodiments, the second polypeptide comprises a HNH domain that is from a CRISPR-Cas effector protein and/or comprises a sequence having at least 70%, 75%, 80%, 85%, 90%, 95%, 96%, 97%, 98%, 99%, or 100% sequence identity to the amino acid sequence of any one of SEQ ID NOs:1 or 172. In some embodiments, the second polypeptide comprises a HNH domain that is not from a CRISPR-Cas effector protein and/or comprises a sequence having at least 70%, 75%, 80%, 85%, 90%, 95%, 96%, 97%, 98%, 99%, or 100% sequence identity to the amino acid sequence of any one of SEQ ID NOs:169-171 or 173-174. In some embodiments, the second polypeptide is a polypeptide from a CRISPR-Cas effector protein, optionally wherein the second polypeptide is from a different type of CRISPR-Cas effector protein (e.g., a Type II CRISPR-Cas effector protein) than the type of the first CRISPR-Cas effector protein (e.g., a Type V CRISPR-Cas effector protein (e.g., a Type V CRISPR-Cas effector protein) from which the first CRISPR-Cas effector polypeptide is a portion of.

In some embodiments, an engineered protein comprises a first polypeptide, a second polypeptide, and a third polypeptide, which may be linked together in any order. In some embodiments, the first polypeptide may be devoid of a RuvC domain. The second polypeptide may be linked to the N- or C-terminus of the first polypeptide, optionally with or without a linker (e.g., a peptide linker), and/or the second polypeptide may be linked to the N- or C-terminus of the third polypeptide, optionally with or without a linker (e.g., a peptide linker). In some embodiments, the second polypeptide is between the first polypeptide and the third polypeptide. In some embodiments, the first polypeptide is a portion of a first CRISPR-Cas effector protein (e.g., a portion of a Type V CRISPR-Cas effector protein such as a portion of a Cas12a) and the third polypeptide is a portion of a second CRISPR-Cas effector protein (e.g., a portion of a Type V CRISPR-Cas effector protein such as a portion of a Cas12a), wherein the first CRISPR-Cas effector protein and second CRISPR-Cas effector protein may be the same protein or different proteins. In some embodiments, the first CRISPR-Cas effector protein and the second CRISPR-Cas effector protein are the same, thereby the first polypeptide and third polypeptide are portions from the same protein, but may be different portions of the CRISPR-Cas effector protein. The first polypeptide and third polypeptide may have different sequences. In some embodiments, the first polypeptide and third polypeptide may comprise a sequence that is the same. In some embodiments, the first polypeptide and third polypeptide together provide the full sequence of the CRISPR-Cas effector protein. In some embodiments, the first polypeptide and third polypeptide together do not make up the full sequence of the CRISPR-Cas effector protein (i.e., a portion of the sequence of the CRISPR-Cas effector protein is not present in the two sequences of the first polypeptide and third polypeptide); for example, 1 or 5 to 10, 15, 20, 25, 30, or more amino acids (e.g., 1, 2, 3, 4, 5, 6, 7, 8, 9, 10, 15, 20, 25, 30, or more amino acid(s)) of the CRISPR-Cas effector protein may not be present in the sequences of the first and third effector polypeptides. In some embodiments, the second polypeptide comprises a nuclease domain, optionally a HNH domain (e.g., an HNH domain from a Type II CRISPR-Cas effector protein). In some embodiments, the second polypeptide comprises a HNH domain that is not from a CRISPR-Cas effector protein. In some embodiments, the second polypeptide is a polypeptide from a CRISPR-Cas effector protein, optionally wherein the second polypeptide is from a different type of CRISPR-Cas effector protein (e.g., a Type II CRISPR-Cas effector protein) than the type of the first CRISPR-Cas effector protein (e.g., a Type V CRISPR-Cas effector protein) from which the first polypeptide is a portion of and/or than the type of the second CRISPR-Cas effector protein (e.g., a Type V CRISPR-Cas effector protein) from which the third polypeptide is a portion of. In some embodiments, the second polypeptide is from a Type II CRISPR-Cas effector protein (e.g., is a portion (e.g., the HNH domain or a portion thereof) of the Type II CRISPR-Cas effector protein), the first polypeptide is a portion of a Type V CRISPR-Cas effector protein, and the third polypeptide is a portion of a Type V CRISPR-Cas effector protein, wherein the first and second CRISPR-Cas effector polypeptides are different. In some embodiments, the second polypeptide is heterologous to one of the first polypeptide and third polypeptide. In some embodiments, the second polypeptide is heterologous to both the first polypeptide and the third polypeptide.

"Heterologous polypeptide" as used herein refers to a non-naturally occurring polypeptide compared to a CRISPR-Cas effector polypeptide present in an engineered protein. Accordingly, a heterologous polypeptide of an engineered protein is not found in nature in at least one CRISPR-Cas effector polypeptide of the engineered protein, so the heterologous polypeptide is non-naturally occurring with respect the at least one CRISPR-Cas effector polypeptide. For example, an engineered protein of the present invention may include a CRISPR-Cas effector polypeptide that is a portion of a CRISPR-Cas effector protein and a heterologous polypeptide (that is optionally from a CRISPR-Cas effector protein), and the heterologous polypeptide is non-naturally occurring compared to the CRISPR-Cas effector polypeptide in the absence of the heterologous polypeptide (e.g., the CRISPR-Cas effector polypeptide without or prior to including (e.g., insertion or fusion of) the heterologous polypeptide and the CRISPR-Cas effector polypeptide); in some embodiments, the heterologous polypeptide is heterologous to the CRISPR-Cas effector protein from which the CRISPR-Cas effector polypeptide is a portion of. In some embodiments, an engineered protein includes a heterologous polypeptide, a first CRISPR-Cas effector polypeptide that is a portion of a first CRISPR-Cas effector protein, and a second CRISPR-Cas effector polypeptide that is a portion of a second CRISPR-Cas effector protein, and the heterologous polypeptide is non-naturally occurring in (i.e., heterologous to) the first CRISPR-Cas effector polypeptide, the first CRISPR-Cas effector protein, the second CRISPR-Cas effector, and the second CRISPR-Cas effector protein. Similarly, a nucleotide sequence encoding a heterologous polypeptide is heterologous to (i.e., non-naturally occurring compared to) a nucleotide sequence encoding a CRISPR-Cas effector polypeptide of an engineered protein.

In some embodiments, the heterologous polypeptide comprises a polypeptide or domain from a different type of protein than a CRISPR-Cas effector polypeptide of the engineered protein (e.g., a Type V CRISPR-Cas effector polypeptide). For example, a heterologous polypeptide of an engineered protein of the present invention may be a portion of a first CRISPR-Cas effector protein (e.g., a Type II CRISPR-Cas effector polypeptide) and the heterologous polypeptide is heterologous to another CRISPR-Cas effector polypeptide that is present in the engineered protein (e.g., a Type V CRISPR-Cas effector polypeptide). In some embodiments, an engineered protein comprises one or more (e.g., 1, 2, 3, or more) portion(s) of (i.e., one or more CRISPR-Cas effector polypeptide(s) from) a Type V CRISPR-Cas effector protein (e.g., Cas 12a) and one or more (e.g., 1, 2, 3, or more) polypeptide(s) from a different type of CRISPR-Cas effector protein such as a Type II CRISPR-Cas effector protein. When two or more portions or polypeptides are from the same protein and each are present in an engineered protein, the two or more portions or polypeptides may be separated from each other in the engineered protein by a linker and/or a heterologous polypeptide (i.e., the two or more portions or polypeptides may not be directly linked) or may be in a different order than that of the protein from which they are from (e.g., a wild-type protein and/or CRISPR-Cas effector protein). In some embodiments, an engineered protein comprises one or more (e.g., 1, 2, 3, or more) portion(s) of (i.e., one or more CRISPR-Cas effector polypeptide(s) from) a Type V CRISPR-Cas effector protein (e.g., Cas 12a) and at least one polypeptide from and/or portion of a Type II CRISPR-Cas effector protein (e.g., Cas 9). In some embodiments, an engineered protein comprises a first CRISPR-Cas effector polypeptide that is a portion of a Type V CRISPR-Cas effector protein (e.g., Cas 12a) and a heterologous polypeptide from a Type II CRISPR-Cas effector protein (e.g., Cas 9). In some embodiments, an engineered protein comprises a first CRISPR-Cas effector polypeptide that is a portion of a Type V CRISPR-Cas effector protein (e.g., Cas 12a), a heterologous polypeptide from a Type II CRISPR-Cas effector protein (e.g., Cas 9), and a second CRISPR-Cas effector polypeptide that is a portion of a Type V CRISPR-Cas effector protein (e.g., Cas 12a), optionally wherein the first and second CRISPR-Cas effector polypeptides are different portions from the same Type V CRISPR-Cas effector protein (e.g., Cas 12a). In some embodiments, an engineered protein comprises a first CRISPR-Cas effector polypeptide that is a portion of a Type V CRISPR-Cas effector protein (e.g., Cas 12a), a heterologous polypeptide that comprises a HNH domain or a portion thereof, and a second CRISPR-Cas effector polypeptide that is a portion of a Type V CRISPR-Cas effector protein (e.g., Cas 12a), optionally wherein the first and second CRISPR-Cas effector polypeptides are different portions from the same Type V CRISPR-Cas effector protein (e.g., Cas 12a).

In some embodiments, an engineered protein comprises one or more (e.g., 1, 2, 3, or more) domain(s) or a portion thereof from a Type V CRISPR-Cas effector protein (e.g., Cas 12a) and one or more (e.g., 1, 2, 3, or more) domain(s) or a portion thereof from a different type of CRISPR-Cas effector protein such as a Type II CRISPR-Cas effector protein. In some embodiments, an engineered protein comprises one or more (e.g., 1, 2, 3, or more) domain(s) or a portion thereof from a Type V CRISPR-Cas effector protein (e.g., Cas 12a) and at least one domain or a portion thereof from a Type II CRISPR-Cas effector protein (e.g., Cas 9). In some embodiments, the heterologous polypeptide of an engineered protein does not interfere with or adversely affect the activity of a CRISPR-Cas effector polypeptide and/or of one or more domain(s) of the CRISPR-Cas effector polypeptide (e.g., a RuvC domain).

The second polypeptide and/or heterologous polypeptide of an engineered protein of the present invention may have a length of about 10 to about 300 amino acids such as about 10, 20, 30, 40, 50, 60, 70, 80, 90, or 100 amino acids to about 110, 125, 150, 175, 200, 225, 250, 275, or 300 amino acids. In some embodiments, the second polypeptide and/or heterologous polypeptide has a length of about 10, 20, 30, 40, 50, 60, 70, 80, 90, 100, 110, 120, 130, 140, 150, 160, 170, 180, 190, 200, 210, 220, 230, 240, 250, 260, 270, 280, 290, or 300 amino acids. In some embodiments, the second polypeptide and/or heterologous polypeptide has a length of about 120, 125, 130, 135, or 140 amino acids to about 145, 150, 155, or 160 amino acids. In some embodiments, the second polypeptide and/or heterologous polypeptide has a length of 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, or 160 amino acids. In some embodiments, the second polypeptide and/or heterologous polypeptide is between a first CRISPR-Cas effector polypeptide and a third CRISPR-Cas effector polypeptide and the second polypeptide and/or heterologous polypeptide is heterologous to one or both of the first and third CRISPR-Cas effector polypeptides.

In some embodiments, a CRISPR-Cas effector polypeptide (e.g., a first and/or third polypeptide) of an engineered protein of the present invention has a length of about 100, 150, 200, or 250 amino acids to about 300, 350, or 400 amino acids. In some embodiments, a CRISPR-Cas effector polypeptide has a length of about 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, or 400 amino acids. In some embodiments, a CRISPR-Cas effector polypeptide has a length of about 800, 850, or 900 amino acids to about 950, 1,000, 1,050, or 1,100 amino acids. In some embodiments, a CRISPR-Cas effector polypeptide has a length of about 800, 810, 820, 830, 840, 850, 860, 870, 880, 890, 900, 910, 920, 930, 940, 950, 960, 970, 980, 990, 1,000, 1,010, 1,020, 1,030, 1,040, 1,050, 1,060, 1,070, 1,080, 1,090, 1,100 amino acids. In some embodiments, an engineered protein comprises a first CRISPR-Cas effector polypeptide having a length of about 100, 150, 200, or 250 amino acids to about 300, 350, or 400 amino acids, a heterologous polypeptide having a length of about 10, 50, 100, or 140 amino acids to about 160, 200, 250, or 300 amino acids; and a second CRISPR-Cas effector polypeptide having a length of about 100, 200, 300, 400, 500, 600, 700, 800, 850, or 900 amino acids to about 950, 1,000, 1,050, or 1,100 amino acids.

In some embodiments, the heterologous polypeptide (e.g., a second polypeptide) comprises a nuclease domain or a portion thereof, which can be referred to herein as a "heterologous nuclease domain or a portion thereof" since the nuclease domain or a portion thereof from the heterologous polypeptide is heterologous to one or more CRISPR-Cas effector polypeptide(s) present in the engineered protein. The heterologous polypeptide may be a DNA nuclease domain or a portion thereof. In some embodiments, the heterologous nuclease domain or a portion thereof is from a CRISPR-Cas effector protein. In some embodiments, the heterologous nuclease domain or a portion thereof is not from a CRISPR-Cas effector protein. In some embodiments, the heterologous nuclease domain or a portion thereof is from a bacterial protein, optionally wherein the heterologous nuclease domain or a portion thereof is from a restriction endonuclease, homing endonuclease, colicin, pyocin, reverse transcriptase, DNase, and/or a standalone HNH domain. In some embodiments, an engineered protein comprises a heterologous polypeptide that includes a nuclease domain or a portion thereof (i.e., a heterologous nuclease domain or a portion thereof), and the engineered protein is a nuclease that optionally cleaves the target strand of a target nucleic acid and/or the non-target stand of a target nucleic acid. In some embodiments, the engineered protein cleaves the target strand of a target nucleic acid and the non-target stand of the target nucleic acid and provides either a blunt-ended double strand break of the target nucleic acid or a staggered double-strand break of the target nucleic acid. In some embodiments, the engineered protein cleaves the target strand of a target nucleic acid and the non-target stand of the target nucleic acid and the distance (e.g., number of nucleotides) between the cut sites is 0, 1, 2, 3, 4, or 5 nucleotides to about 6, 7, 8, 9, 10, 11, 12, 13, 14, 15, 16, 17, 18, 19, or 20 nucleotides.

In some embodiments, the heterologous nuclease domain or a portion thereof may be a target strand nickase domain or a portion thereof. A "target strand nickase domain or a portion thereof" as used herein refers to a polypeptide that has nickase activity to the target strand of a target nucleic acid when the domain or portion thereof is in its native protein. That is, a target strand nickase domain or a portion thereof can or is capable of nicking (e.g., cleaving or breaking) the target strand (also referred to as the sense (e.g., "+"; template) strand) of the target nucleic acid when the domain or portion thereof is in its native protein. For example, the HNH domain of Cas9 nicks and/or has nickase activity to the target strand of a target nucleic acid. "Nickase activity" as used herein refers to a single-strand break in a nucleic acid.

In some embodiments, a target strand nickase domain or a portion thereof, when present in an engineered protein, may have nickase activity to the target strand of a target nucleic acid. In some embodiments, a target strand nickase domain or a portion thereof, when present in an engineered protein, may have nickase activity to the nontarget strand (also referred to as the antisense (e.g., "−", complementary) strand) of a target nucleic acid. When a target strand nickase domain or a portion thereof in an engineered protein has nickase activity to both the target strand and nontarget strand, the target strand nickase domain or a portion thereof may cleave both strands sequentially. In some embodiments, a target strand nickase domain or a portion thereof in an engineered protein has more activity (e.g., enzymatic activity) towards the target strand than the nontarget strand of a target nucleic acid. For example, when present in an engineered protein, the target strand nickase domain or a portion thereof may prefer or cleave faster the target strand of a target nucleic acid than the nontarget strand of the target nucleic acid.

A "target strand specific nickase domain" as used herein refers to a polypeptide that has nickase activity only to the target strand of a target nucleic acid and does not nick the nontarget strand of the target nucleic acid. A "nontarget strand specific nickase domain" as used herein refers to a polypeptide that has nickase activity only to the nontarget strand of a target nucleic acid and does not nick the target strand of the target nucleic acid. A "target and nontarget strand nickase domain" as used herein refers to a polypeptide that has nickase activity to both the target strand and the nontarget strand of a target nucleic acid. In some embodiments, an engineered protein comprises a target strand nickase domain or a portion thereof and the target strand nickase domain or a portion thereof is a target strand specific nickase domain in the engineered protein. In some embodiments, an engineered protein comprises a target strand nickase domain or a portion thereof and the target strand nickase domain or a portion thereof is a nontarget strand specific nickase domain in the engineered protein. In some embodiments, an engineered protein comprises a target strand nickase domain or a portion thereof and the target strand nickase domain or a portion thereof is a target and nontarget strand nickase domain in the engineered protein.

An engineered protein may comprise a heterologous polypeptide (e.g., a second polypeptide) that comprises target strand nickase domain or a portion thereof. Accordingly, the engineered protein may have nickase activity to the target strand of a target nucleic acid and/or to the nontarget strand of the target nucleic acid. Thereby, the engineered protein may be a target strand nickase and/or a nontarget strand nickase. A "target strand nickase" as used herein in reference to an engineered protein refers to an engineered protein that can or is capable of cleaving the target strand of a target nucleic acid. A "nontarget strand nickase" as used herein in reference to an engineered protein refers to an engineered protein that can or is capable of cleaving the nontarget strand of a target nucleic acid. A "target and nontarget strand nickase" as used herein in reference to an engineered protein refers to an engineered protein that can or is capable of cleaving both the target and nontarget strand of a target nucleic acid in any order (e.g., sequentially or simultaneously). In some embodiments, the engineered protein is a target strand nickase and/or has nickase activity to the target strand of a target nucleic acid. In some embodiments, the engineered protein is a nontarget strand nickase and/or has nickase activity to the nontarget strand of a target nucleic acid. In some embodiments, the engineered protein is a target and nontarget strand nickase and/or has nickase activity to the target strand and nontarget strand of a target nucleic acid.

In some embodiments, the heterologous polypeptide of an engineered protein comprises a target strand nickase domain or a portion thereof and the target strand nickase domain or a portion thereof of the engineered protein has nickase activity to the target strand of a target nucleic acid, thereby the engineered protein is a target strand nickase. In some embodiments, the heterologous polypeptide of an engineered protein comprises a target strand nickase domain or a portion thereof and the target strand nickase domain or a portion thereof of the engineered protein has nickase activity to the nontarget strand of a target nucleic acid, thereby the engineered protein is a nontarget strand nickase. In some embodiments, the heterologous polypeptide of an engineered protein comprises a target strand nickase domain or a portion thereof and the target strand nickase domain or a portion thereof of the engineered protein has nickase activity to the both the target and nontarget strand of a target nucleic acid, thereby the engineered protein is a target and nontarget strand nickase. In some embodiments, the heterologous polypeptide of an engineered protein comprises a target strand nickase domain or a portion thereof and the target strand nickase domain or a portion thereof of the engineered protein has nickase activity to at least the target strand of a target nucleic acid and a CRISPR-Cas effector polypeptide of the engineered protein comprises a nuclease domain or a portion thereof that has nickase activity to at least the nontarget strand of the target nucleic acid, thereby the engineered protein is a target and nontarget strand nickase. In some embodiments, the CRISPR-Cas effector polypeptide of the engineered protein comprises a nuclease domain or portion thereof that is a target and nontarget strand nickase domain or portion thereof, but the nuclease domain or portion thereof is inactivated so that nuclease activity to the target strand is inactivated, thereby the target strand of the target nucleic acid is not nicked by the nuclease domain or portion thereof.

In some embodiments, an engineered protein may comprise one or more (e.g., 1, 2, or more) nuclease domain(s) or a portion thereof. In some embodiments, an engineered protein comprises at least two different nuclease domains or a portion thereof. In some embodiments, an engineered protein may comprise a native nuclease domain, optionally one or more (e.g., 1, 2, or more) native nuclease domain(s). A "native nuclease domain" as used herein refers to a nuclease domain that is naturally present in a CRISPR-Cas effector protein. In some embodiments, an engineered protein comprises a first heterologous nuclease domain (e.g., from and/or present in the heterologous polypeptide) and a second nuclease domain. The second nuclease domain may be from and/or present in CRISPR-Cas effector protein. In some embodiments, the first nuclease domain may be a native nuclease domain and/or the second nuclease domain may be a native nuclease domain. In some embodiments, the second nuclease domain is a target and nontarget strand nickase domain or a portion thereof. A "nontarget and target strand nickase domain or a portion thereof" as used herein refers to a polypeptide that has nickase activity to the nontarget strand of a target nucleic acid and to the target strand of the target nucleic acid when the domain or portion thereof is in its native protein, and cleaves the nontarget strand before the target strand or prefers or cleaves faster the nontarget strand than the target strand. A nontarget and target strand nickase domain or a portion thereof may provide a staggered double strand break in the target nucleic acid. In some embodiments, the second nuclease domain is active. In some embodiments, the second nuclease domain is deactivated (i.e., dead, inactive, or devoid of nickase activity). In some embodiments, the second nuclease domain only nicks the nontarget strand of a target nucleic acid and/or comprises a mutation that inactivates nickase activity to the target strand of a target nucleic acid. A nuclease domain or portion thereof in an engineered protein may be deactivated by a mutation in the nuclease domain or portion thereof that removes or inactivates nickase activity. In some embodiments, an engineered protein comprises a nuclease domain or portion thereof from a Type V CRISPR-Cas effector protein such as a Cas12a (e.g., from one of SEQ ID NO:50-66 or 180) or Cas12b (e.g., from SEQ ID NO:151). In some embodiments, the nuclease domain is a RuvC domain from a Type V CRISPR-Cas effector protein such as a Cas12a or Cas12b. An engineered protein may comprise one or more nuclease domain(s) that provide a blunt-ended double strand break of a target nucleic acid or a staggered double-strand break of a target nucleic acid.

In some embodiments, the heterologous polypeptide (e.g., a second polypeptide) of an engineered protein comprises all or a portion of a HNH domain of a CRISPR-Cas effector protein. The heterologous polypeptide and/or HNH domain may comprise and/or form a zinc finger motif. In some embodiments, the heterologous polypeptide and/or HNH domain has a length of about 10, 20, 30, 40, 50, 60, 70, 80, 90, or 100 amino acids to about 110, 125, 150, 175, 200, 225, 250, 275, or 300 amino acids. The heterologous polypeptide and/or HNH domain may comprise about 25 or 30 to about 40 or 45 amino acids and/or may comprise one or at least two histidines and an asparagine that are optionally in a nucleic acid binding and cleavage site. In some embodiments, the heterologous polypeptide and/or HNH domain may comprise about 25 or 30 to about 40 or 45 amino acids that include two histidines and one asparagine that are present in and/or form a zinc finger motif. The heterologous polypeptide and/or HNH domain may comprise and/or form two antiparallel beta-strands that are linked by a loop and/or may comprise an alpha helix, optionally wherein a histidine is present in at least one of the beta-strands, an asparagine is present in the loop, and/or a histidine or asparagine is present in the alpha-helix. The heterologous polypeptide may comprise all or a portion of a HNH domain having a structure as described in Pediaditakis M, et al. *Journal of Bacteriology* 194(22); 6184-6194. In some embodiments, the heterologous polypeptide of an engineered protein comprises all or a portion of a HNH domain of a Type II CRISPR-Cas effector protein such as a Cas9 HNH domain. The heterologous polypeptide of an engineered protein may comprise all or a portion of a HNH domain (e.g., a Cas9 HNH domain) that is inactive. The HNH domain or a portion thereof may have an inactivating mutation (e.g., a mutation that removes nickase activity). In some embodiments, the heterologous polypeptide of an engineered protein comprises all or a portion of an HNH domain that has an inactivating mutation and/or the HNH domain is inactive (e.g., does not have nickase activity). In some embodiments, the heterologous polypeptide of an engineered protein comprises all or a portion of an inactivated HNH domain that has a H840A mutation. In some embodiments, the heterologous polypeptide of an engineered protein comprises an amino acid sequence having at least 70%, 75%, 80%, 85%, 90%, 95%, 96%, 97%, 98%, 99%, or 100% sequence identity to the amino acid sequence of one or more of SEQ ID NOs:1 or 169-174. In some embodiments, the heterologous polypeptide of an engineered protein comprises the amino acid sequence of any one of SEQ ID NOs:1 or 169-174.

In some embodiments, the heterologous polypeptide of an engineered protein comprises an amino acid sequence that has an amino acid residue that is not a histidine residue at a position corresponding to amino acid residue number 839 of SEQ ID NO:81, when the amino acid sequence of the heterologous polypeptide and SEQ ID NO:81 are optimally aligned. In some embodiments, the heterologous polypeptide of an engineered protein comprises an amino acid sequence that has an amino acid residue that is not a histidine residue at a position corresponding to amino acid residue number 75 of SEQ ID NO:1, when the amino acid sequence of the heterologous polypeptide and SEQ ID NO:1 are optimally aligned. In some embodiments, the heterologous polypeptide of an engineered protein comprises an amino acid sequence that has an alanine residue at a position corresponding to amino acid residue number 839 of SEQ ID NO:81, when the amino acid sequence of the heterologous polypeptide and SEQ ID NO:81 are optimally aligned. In some embodiments, the heterologous polypeptide of an engineered protein comprises an amino acid sequence that has an alanine residue at a position corresponding to amino acid residue number 75 of SEQ ID NO:1, when the amino acid sequence of the heterologous polypeptide and SEQ ID NO:1 are optimally aligned.

In some embodiments, the heterologous polypeptide of an engineered protein may be between and/or linked to (e.g., directly or indirectly) two consecutive or nonconsecutive amino acids that are present in a CRISPR-Cas effector protein. In some embodiments, the engineered protein is prepared by inserting a heterologous polypeptide between two consecutive or nonconsecutive amino acids of a CRISPR-Cas effector protein or a portion thereof. In some embodiments, an engineered protein may comprise in the amino terminal to carboxy terminal direction, a first CRISPR-Cas effector polypeptide, a heterologous polypeptide, and a second CRISPR-Cas effector polypeptide, with the first and second CRISPR-Cas effector polypeptides being from the same CRISPR-Cas effector protein.

In some embodiments, a CRISPR-Cas effector polypeptide comprises a portion of a Type V CRISPR-Cas effector protein such as Cas12a or Cas12b. The CRISPR-Cas effector polypeptide may comprise all or a portion of a nucleic acid binding domain such as a nucleic acid binding domain from a Type V CRISPR-Cas effector protein (e.g., Cas12a or Cas12b). In some embodiments, a CRISPR-Cas effector polypeptide of an engineered protein comprises an amino acid sequence having at least 70%, 75%, 80%, 85%, 90%, 95%, 96%, 97%, 98%, 99%, or 100% sequence identity to a portion of the amino acid sequence of one or more of SEQ ID NOs:50-66, 151, or 180. In some embodiments, a CRISPR-Cas effector polypeptide comprises a portion of the amino acid sequence of any one of SEQ ID NOs:50-66, 151, or 180. In some embodiments, an engineered protein comprises two or more (e.g., 2, 3, 4, or more) separate portions of the amino acid sequence of any one of SEQ ID NOs:50-66, 151, or 180.

In some embodiments, an engineered protein of the present invention may be devoid of about 5, 10, 15, 20, 25, 30, 35, 40, 45, 50, 55, 60, 65, 70, 75, 80, 85, 90, 95, 100 or more amino acids that are present in a CRISPR-Cas effector protein such as one having a sequence of any one of SEQ ID NOs:50-66, 151, or 180. In some embodiments, an engineered protein of the present invention may be devoid of 0, 1, 2, 3, 4, 5, 6, 7, 8, 9, 10, 11, 12, 13, 14, or 15 amino acids that are present in a CRISPR-Cas effector protein such as one having a sequence of any one of SEQ ID NOs:50-66, 151, or 180. For example, an engineered protein may be devoid of one or more amino acids from amino acid residue 283 to amino acid residue 293 of SEQ ID NO:50 or SEQ ID NO:58 or SEQ ID NO:180; from amino acid residue 331 to amino acid residue 341 of SEQ ID NO:55; from amino acid residue 312 to amino acid residue 322 of SEQ ID NO:51; or from corresponding amino acid residues for a sequence that is optimally aligned to one of SEQ ID NOs:50, 51, 58, 55, or 180 (e.g., from amino acid residues that correspond to amino acid residues 283-293 when a sequence (e.g., SEQ ID NO:52) is optimally aligned to SEQ ID NO:50). In some embodiments, an engineered protein is devoid of one or more (e.g., 1, 2, 3, 4, or more) interdomain linker region(s) (e.g., a region that is between two domains such as two adjacent domains) that are present in a CRISPR-Cas effector protein (e.g., one having a sequence of any one of SEQ ID NOs:50-66, 151, or 180) from which a CRISPR-Cas effector is a portion of and that is present in the engineered protein.

In some embodiments, the heterologous polypeptide of an engineered protein may be between and/or linked to (e.g., directly or indirectly) two consecutive or nonconsecutive amino acids of a CRISPR-Cas effector protein (e.g., a CRISPR-Cas effector protein having an amino acid sequence of any one of SEQ ID NOs:50-66, 151, or 180). For example, an engineered protein may comprise, from the N- to C-terminus, a first CRISPR-Cas effector polypeptide, an HNH domain, and a second CRISPR-Cas effector polypeptide, wherein the first and second CRISPR-Cas effector polypeptides are each a portion of a CRISPR-Cas effector protein and the last amino acid residue at the C-terminus of the first CRISPR-Cas effector polypeptide and the first amino acid reside at the N-terminus of the second CRISPR-Cas effector polypeptide are two consecutive or nonconsecutive amino acid residues of the a CRISPR-Cas effector protein. The heterologous polypeptide may be linked directly to one or both of the two consecutive or nonconsecutive amino acids of the CRISPR-Cas effector protein (i.e., no linker is used to attach one terminus of the heterologous polypeptide to a terminus of a CRISPR-Cas effector polypeptide that is a portion of the CRISPR-Cas effector protein). In some embodiments, the heterologous polypeptide may be linked indirectly (e.g., via a linker such as a peptide linker) to one or both of the two consecutive or nonconsecutive amino acids of the CRISPR-Cas effector protein. In some embodiments, the heterologous polypeptide of an engineered protein may be between and/or linked to (e.g., directly or indirectly) two consecutive amino acids of a CRISPR-Cas effector protein (e.g., a CRISPR-Cas effector protein having an amino acid sequence of any one of SEQ ID NOs:50-66, 151, or 180). In some embodiments, the heterologous polypeptide of an engineered protein may be between and/or linked to (e.g., directly or indirectly) two nonconsecutive amino acids of a CRISPR-Cas effector protein (e.g., a CRISPR-Cas effector protein having an amino acid sequence of any one of SEQ ID NOs:50-66, 151, or 180).

In some embodiments, the two consecutive or nonconsecutive amino acids are two of the amino acid residues from amino acid residue 250, 260, 270, or 280 to amino acid residue 290, 300, 310, 320, 330, 340, or 350 that are consecutive or nonconsecutive, respectively. In some embodiments, the heterologous polypeptide may be between and/or linked to (e.g., directly or indirectly) two consecutive or nonconsecutive amino acids that are two of the following amino acid residues: amino acid residues 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, and 350 of a CRISPR-Cas effector protein (e.g., a CRISPR-Cas effector protein having an amino acid sequence of any one of SEQ ID NOs:50-66, 151, or 180). In some embodiments, the heterologous polypeptide of an engineered protein may be between and/or linked to (e.g., directly or indirectly) two nonconsecutive amino acids of a CRISPR-Cas effector protein (e.g., a CRISPR-Cas effector protein having an amino acid sequence of any one of SEQ ID NOs:50-66, 151, or 180), wherein one of the two nonconsecutive amino acid residues is amino acid residue 270, 271, 272, 273, 274, 275, 276, 277, 278, 279, 280, 281, 282, 283, 284, or 285 and the other of the two nonconsecutive amino acid residues is amino acid residue 286, 287, 288, 289, 290, 291, 292, 293, 294, 295, 296, 297, 298, 299, 300, 301, 302, 303, 304, or 305, optionally of SEQ ID NOs:50-66, 151, or 180. In some embodiments, the heterologous polypeptide is between and/or linked to (e.g., directly or indirectly) amino acid residues 290 and 291, amino acid residues 291 and 292, amino acid residues 292 and 293, amino acid residues 293 and 294, amino acid residues 320 and 321, amino acid residues 321 and 322, amino acid residues 339 and 340, or amino acid residues 340 and 341 of a CRISPR-Cas effector protein such as a CRISPR-Cas effector protein having an amino acid sequence of any one of SEQ ID NOs:50-66, 151, or 180. For example, in some embodiments, the heterologous polypeptide may be between and/or linked to (e.g., directly or indirectly) amino acid residues 290 and 291 of SEQ ID NO:50; amino acid residues 291 and 292 of SEQ ID NO:50; amino acid residues 291 and 292 of SEQ ID NO:58; amino acid residues 292 and 293 of SEQ ID NO:58; amino acid residues 320 and 321 of SEQ ID NO:51; amino acid residues 321 and 322 of SEQ ID NO:51; amino acid residues 322 and 323 of SEQ ID NO:51; amino acid residues 339 and 340 of SEQ ID NO:55; amino acid residues 340 and 341 of SEQ ID NO:55; amino acid residues 290 and 291 of SEQ ID NO:180; amino acid residues 291 and 292 of SEQ ID NO:180; amino acid residues 292 and 293 of SEQ ID NO:180; or corresponding amino acid residues for a sequence that is optimally aligned to one of SEQ ID NOs:50, 51, 58, 55, or 180 (e.g., amino acid residues that correspond to amino acid residues 291 and 292 when a sequence (e.g., SEQ ID NO:52) is optimally aligned to SEQ ID NO:50). In some embodiments, the heterologous polypeptide of an engineered protein may be in an interdomain linker region (e.g., a region that is between two domains such as two adjacent domains) of a CRISPR-Cas effector protein. In some embodiments, the heterologous polypeptide may be positioned in an engineered protein such that it is adjacent to an exposed portion of the target strand of a target nucleic acid.

In some embodiments, an engineered protein comprises all or a portion of a wedge domain, a Rec1 domain, a Rec2 domain, a PAM-interacting domain, a RuvC domain, a bridge helix, and/or a Nuc domain each of which may be from a Type V CRISPR-Cas effector protein such as Cas12a, Cas12b, and/or a protein having a sequence of any one of SEQ ID NOs:50-66, 151, or 180. In some embodiments, an engineered protein comprises all or a portion of a Cas12a domain having a structure as described in Yamano, Takashi, et al., *Mol Cell* 67: 633-645 (2017). In some embodiments, an engineered protein comprises all or a portion of an alpha-helical recognition (REC) lobe, optionally wherein the domains of all or a portion of the REC lobe in the engineered protein may be in a different order and/or structure than in a Type V CRISPR-Cas effector protein. A REC lobe may contain a Rec1 domain and Rec2 domain. A Rec1 domain may comprise 13 alpha helices and/or a Rec2 domain may comprise 10 alpha helices and two beta strands that may form a small antiparallel sheet. In some embodiments, the heterologous polypeptide of an engineered protein may be between a polypeptide for all or a portion of a Rec1 domain and a polypeptide for all or a portion of a Rec2 domain each of which may be from a Type V CRISPR-Cas effector protein such as Cas12a, Cas12b, and/or a protein having a sequence of any one of SEQ ID NOs:50-66, 151, or 180. In some embodiments, all or a portion of the heterologous polypeptide is at an exposed surface or interface of the engineered protein. In some embodiments, the CRISPR-Cas effector polypeptide of an engineered protein comprises all or a portion of a RuvC domain. As one of skill in the art would understand, some domains (e.g., the wedge and RuvC domains of Cas12a) are not continuous in sequence and may be split into two or more (e.g., 2, 3, 4, or more) non-continuous sequences. For example, the polypeptide for Cas12 may have the following from the N- to C-terminus: first portion of the wedge domain (WED-1), Rec1 domain, Rec2 domain, second portion of the wedge domain (WED-2), PAM-interacting domain (PI), third portion of the wedge domain (WED-3), first portion of the RuvC domain (RuvC-1), bridge helix, second portion of the RuvC domain (RuvC-2), Nuc domain, and third portion of the RuvC domain (RuvC-3). In some embodiments, an engineered protein comprises all or a portion of an active RuvC domain. In some embodiments, an engineered protein comprises all or a portion of an inactivated RuvC domain, optionally all or a portion of an inactivated RuvC domain that has a D10A mutation. In some embodiments, an engineered protein comprises all or a portion of an inactivated RuvC domain and the polypeptide comprising all or a portion of the inactivated RuvC domain has an alanine at a position corresponding to amino acid residue 831 of SEQ ID NO:50 when the polypeptide is optimally aligned to SEQ ID NO:50, optionally wherein the mutation is referred to as a D10A and/or D832A mutation.

A CRISPR-Cas effector polypeptide may comprise a nuclease, optionally a RuvC like nuclease. In some embodiments, a CRISPR-Cas effector polypeptide comprises a RuvC domain or a portion thereof. In some embodiments, a CRISPR-Cas effector polypeptide comprises a nuclease in the Rnase H superfamily. In some embodiments, a CRISPR-Cas effector polypeptide comprises RNase H-like enzyme having a catalytic core that may include a β-sheet comprising five β-strands, ordered 32 145, optionally where the β-strand 2 is antiparallel to the other β-strands. On both sides the central β-sheet may be flanked by α-helices, the number of which may differ between related enzymes. In some embodiments, a CRISPR-Cas effector polypeptide comprises a RNase H-like catalytic core where the active site residues include one or more of aspartic acid, glutamic acid and histidine. In some embodiments, a CRISPR-Cas effector polypeptide comprising a RNase H-like catalytic core may include negatively charged side chains in the active sites of the RNase H-like polypeptide that, directly or through a water molecule, are involved in coordinating a divalent metal ion. In some embodiments, a CRISPR-Cas effector polypeptide comprises RNase H-like catalytic core that uses a two ion-dependent mechanism of catalysis, optionally wherein the ion is $Mg^{2+}$ and/or $Mn^{2+}$. In some embodiments, a CRISPR-Cas effector polypeptide comprises nuclease and/or RNase H-like nuclease as described in Majorek K A, et al. *Nucleic Acids Res.* 2014; 42(7):4160-4179, which is incorporated herein by reference in its entirety.

In some embodiments, a CRISPR-Cas effector polypeptide comprises one or more (e.g., 1, 2, 3, 4 or more) mutations. The one or more mutations may be to improve or modify the activity of a heterologous polypeptide and/or the activity of a CRISPR-Cas effector polypeptide. In some embodiments, a CRISPR-Cas effector polypeptide may comprise an inactivating mutation such as a D10A mutation in the RuvC domain. In some embodiments, a CRISPR-Cas effector polypeptide comprises all or a portion of a Rec1 domain that comprises one or more (e.g., 1, 2, 3, 4 or more) mutations such as in one or more of amino acid residue(s) 243-253 of a CRISPR-Cas effector protein (e.g., a CRISPR-Cas effector protein having an amino acid sequence of any one of SEQ ID NOs:50-66, 151, or 180) and/or in the sequence GFVTESGEKIK (SEQ ID NO:122). In some embodiments, a CRISPR-Cas effector polypeptide comprises a hairpin and/or the sequence GFVTESGEKIK (SEQ ID NO:122), and one or more of the amino acid residue(s) in the hairpin and/or sequence may be mutated. In some embodiments, a CRISPR-Cas effector polypeptide comprises a hairpin and/or the sequence GFVTESGEKIK (SEQ ID NO:122), and all or a portion of the hairpin and/or sequence is deleted. In some embodiments, a CRISPR-Cas effector polypeptide comprises a hairpin and/or the sequence GFVTESGEKIK (SEQ ID NO:122), and 1, 2, 3, 4, 5, or more amino acid residues are added to one or both ends of the hairpin and/or sequence.

In some embodiments, an engineered protein comprises, from the N- to C-terminus, a first CRISPR-Cas effector polypeptide, an HNH domain, and a second CRISPR-Cas effector polypeptide, wherein the first and second CRISPR-Cas effector polypeptides are each a portion of deactivated LbCas12a (e.g., LbCas12a having a sequence of SEQ ID NO:50) and the last amino acid residue at the C-terminus of the first CRISPR-Cas effector polypeptide and the first amino acid reside at the N-terminus of the second CRISPR-Cas effector polypeptide are two consecutive amino acid residues of the deactivated LbCas12a. The HNH domain may be from *Streptococcus pyogenes* Cas9 (SpCas9) and/or may have a sequence comprising SEQ ID NO:1. In some embodiments, the HNH domain may have a sequence of any one of SEQ ID NOs:1 or 169-174. The HNH domain may be positioned in the engineered protein such that it is adjacent to an exposed portion of the target strand of a target nucleic acid. The engineered protein may be a target strand nickase. In some embodiments, the engineered protein only nicks the target DNA strand. In some embodiments, the engineered protein is a target and nontarget strand nickase.

One or more (e.g., 1, 2, 3, 4, or more) linker(s) may be present in an engineered protein. For example, a linker may be present between a CRISPR-Cas effector polypeptide and a heterologous polypeptide (e.g., a second polypeptide). In some embodiments, a linker may be present between a first CRISPR-Cas effector polypeptide and a heterologous polypeptide and a linker may be present between the heterologous polypeptide and a second CRISPR-Cas effector polypeptide. Exemplary linkers include, but are not limited to, those described herein. In some embodiments, the linker comprises 1 to 2, 3, 4, 5, 6, 7, 8, 9, or 10 amino acids and/or comprises glycine and/or serine. In some embodiments, the linker comprises 1, 2, 3, or 4 amino acids that are glycine and/or serine (i.e., a GS linker). In some embodiments, the engineered protein is devoid of a linker between a CRISPR-Cas effector polypeptide and a heterologous polypeptide. In some embodiments, the heterologous polypeptide is indirectly linked to an amino acid residue at the N-terminus of a CRISPR-Cas effector polypeptide via a linker and/or the heterologous polypeptide is indirectly linked to an amino acid residue at the C-terminus of a CRISPR-Cas effector polypeptide via a linker. Two or more peptide linkers present in an engineered protein of the present invention may be independently selected from each other and may be the same or different from each other. In some embodiments, an engineered protein comprises a peptide linker that is a GS linker having 1, 2, 3, or 4 amino acid residues, optionally 2 or 4 amino acid residues. In some embodiments, an engineered protein comprises a peptide linker that has an amino acid sequence of $(GGS)_n$ wherein n is an integer of 1-20; GS; SG; and/or an amino acid sequence of any one of SEQ ID NOs:18-47 or 176-179.

In some embodiments, the heterologous polypeptide is directly linked (i.e., without a linker) to an amino acid residue at the N-terminus of a CRISPR-Cas effector polypeptide and/or the heterologous polypeptide is directly linked (i.e., without a linker) to an amino acid residue at the C-terminus of a CRISPR-Cas effector polypeptide.

An engineered protein may comprise an amino acid sequence having at least 70%, 75%, 80%, 85%, 90%, 95%, 96%, 97%, 98%, 99%, or more sequence identity to any one of SEQ ID NOs:2-17, 125-132, or 157-168. In some embodiments, an engineered protein comprises and/or has an amino acid sequence of any one of SEQ ID NOs:2-17, 125-132, or 157-168. An engineered protein may have at least 70%, 75%, 80%, 85%, 90%, 95%, 96%, 97%, 98%, 99%, or more sequence identity to all or a portion of an amino acid sequence of a wild-type CRISPR-Cas effector protein. In some embodiments, the engineered protein has at least 70%, 75%, 80%, 85%, 90%, 95%, 96%, 97%, 98%, 99%, or more sequence identity to all or a portion of the amino acid sequence of any one of SEQ ID NOs:50-66, 151, or 180. In some embodiments, the engineered protein has about 70%, 75%, or 80% to about 85%, 90%, 95%, or 98% sequence identity to all or a portion of the amino acid sequence of any one of SEQ ID NOs:50-66, 151, or 180.

An engineered protein may have increased efficiency compared to a CRISPR-Cas effector protein (e.g., Cas12a, a CRISPR-Cas effector protein having a sequence of SEQ ID NOs:50-66, 151, or 180, and/or a wild-type CRISPR-Cas effector protein) such as increased efficiency in nicking the target strand and/or nontarget strand of a target nucleic acid. In some embodiments, an engineered protein may have increased efficiency compared to a CRISPR-Cas effector protein (e.g., Cas12a, a CRISPR-Cas effector protein having a sequence of SEQ ID NOs:50-66, 151, or 180, and/or a wild-type CRISPR-Cas effector protein) in nicking the target strand of a target nucleic acid. In some embodiments, an engineered protein may provide for an increased number of target strand breaks in a target nucleic acid compared to the number of target strand breaks in the target nucleic acid with a CRISPR-Cas effector protein (e.g., Cas12a, a CRISPR-Cas effector protein having a sequence of SEQ ID NOs:50-66, 151, or 180, and/or a wild-type CRISPR-Cas effector protein). In some embodiments, an engineered protein may have increased efficiency compared to a CRISPR-Cas effector protein (e.g., Cas12a, a CRISPR-Cas effector protein having a sequence of SEQ ID NOs:50-66, 151, or 180, and/or a wild-type CRISPR-Cas effector protein) in modifying a target nucleic acid.

Compositions, complexes, and systems comprising an engineered protein may be provided according to embodiments of the present invention. In some embodiments, a composition, complex and/or system comprising an engineered protein may be a base editing composition, complex, and/or system. A composition, complex, and/or system of the present invention may include a guide nucleic acid (e.g., a guide RNA) and/or a deaminase (e.g., a cytosine deaminase and/or an adenine deaminase). In some embodiments, an engineered protein, guide nucleic acid, and optionally deaminase form a complex or are comprised in a complex (e.g., a ribonucleoprotein). The engineered protein, guide nucleic acid, and optionally deaminase may not naturally occur together and/or a complex comprising the engineered protein, guide nucleic acid, and optionally deaminase may not naturally occur together. In some embodiments, an engineered protein comprises and/or is fused to a deaminase (e.g., an adenine deaminase and/or a cytosine deaminase).

Also provided herein are nucleic acid molecules encoding an engineered protein of present invention along with an expression cassettes and/or vector comprising a nucleic acid molecule of the present invention.

According to some embodiments, a method is provided that comprises contacting a target nucleic acid with: an engineered protein of the present invention, a guide nucleic acid (e.g., a guide RNA), and optionally a deaminase. In some embodiments, the engineered protein, the guide nucleic acid, and/or deaminase form a complex or are comprised in a complex. In some embodiments, the method may modify the target nucleic acid and/or may provide one or more single strand breaks in the target nucleic acid.

In some embodiments, a composition, system, method, and/or complex comprising an engineered protein may have increased efficiency compared to a composition, system, method, and/or complex comprising a CRISPR-Cas effector protein (e.g., Cas12a, a CRISPR-Cas effector protein having a sequence of SEQ ID NOs:50-66, 151, or 180, and/or a wild-type CRISPR-Cas effector protein). In some embodiments, a composition, system, method, and/or complex comprising an engineered protein that is a target strand nickase may have increased efficiency compared to a composition, system, method, and/or complex comprising a CRISPR-Cas effector protein (e.g., Cas12a, a CRISPR-Cas effector protein having a sequence of SEQ ID NOs:50-66, 151, or 180, and/or a wild-type CRISPR-Cas effector protein). This may be because nicking the target strand may increase the efficiency of genome editing tools such as base editors and/or base diversifiers. In some embodiments, a composition, system, method, and/or complex comprising an engineered protein may provide for an increased number of target strand breaks in a target nucleic acid compared to the number of target strand breaks in the target nucleic acid with a composition, system, method, and/or complex comprising a CRISPR-Cas effector protein (e.g., Cas12a, a CRISPR-Cas effector protein having a sequence of SEQ ID NOs:50-66, 151, or 180, and/or a wild-type CRISPR-Cas effector protein).

An engineered protein and/or a composition, system, method, and/or complex comprising an engineered protein may provide improved or altered insertion and/or deletion (e.g., indel) size and/or composition, improved or altered deletion size in a target nucleic acid, improved or altered nicking ability on either strand (i.e., target or nontarget strand of a target nucleic acid), and/or increased nuclease activity compared to a CRISPR-Cas effector protein (e.g., Cas12a, a CRISPR-Cas effector protein having a sequence of SEQ ID NOs:50-66, 151, or 180, and/or a wild-type CRISPR-Cas effector protein) and/or to a composition, system, method, and/or complex comprising a CRISPR-Cas effector protein (e.g., Cas12a, a CRISPR-Cas effector protein having a sequence of SEQ ID NOs:50-66, 151, or 180, and/or a wild-type CRISPR-Cas effector protein). In some embodiments, an engineered protein and/or a composition, system, method, and/or complex comprising an engineered protein imparts nuclease function onto a catalytically inactivated CRISPR-Cas effector protein. In some embodiments, an engineered protein and/or a composition, system, method, and/or complex comprising an engineered protein provides a different editing profile and/or a different cleavage pattern for a target nucleic acid compared to the editing profile and/or a different cleavage pattern of the target nucleic acid for a Cas effector protein ((e.g., Cas12a, a CRISPR-Cas effector protein having a sequence of SEQ ID NOs:50-66, 151, or 180, and/or a wild-type CRISPR-Cas effector protein) and/or a composition, system, method, and/or complex comprising a CRISPR-Cas effector protein (e.g., Cas12a, a CRISPR-Cas effector protein having a sequence of SEQ ID NOs:50-66, 151, or 180, and/or a wild-type CRISPR-Cas effector protein).

In some embodiments, a method of the present invention may have increased efficiency in modifying a target nucleic acid compared to the efficiency of a control method (e.g., a method comprising contacting the target nucleic acid with a CRISPR-Cas effector protein (e.g., Cas12a, a CRISPR-Cas effector protein having a sequence of SEQ ID NOs:50-66, 151, or 180, and/or a wild-type CRISPR-Cas effector protein) and/or that is devoid of an engineered protein).

As described herein, the polypeptides, engineered proteins, nucleic acids, expression cassettes, and/or vectors of the present invention may be optimized for expression in an organism. An organism useful with this invention may be any organism or cell thereof for which nucleic acid modification may be useful. An organism can include, but is not limited to, any animal (e.g., a mammal), any plant, any fungus, any archaeon, or any bacterium. In some embodiments, the organism may be a plant or cell thereof. In some embodiments, the organism is an animal such as a mammal (e.g., a human).

The target nucleic acid may be a genomic sequence from any organism (e.g., eukaryote such as a mammal or a plant). In some embodiments, the target nucleic acid is a genomic sequence from a model organism such as, but not limited to, *Escherichia coli*, an immortalized human cell line (e.g., HEK293, HeLa, etc.), *Caenorhabditis elegans*, and/or *Drosophila melanogaster*. In some embodiments, the target nucleic acid is a genomic sequence from a non-model organism. Exemplary non-model organisms include, but are not limited to crop plants (e.g., fruit crop plants, vegetable crop plants, and/or field crop plants) and/or animals such as humans, primates and/or mice. In some embodiments, the non-model organism is a crop plant such as corn, soybean, wheat, or canola. In some embodiments, the non-model organism is an animal for testing and/or use of a human therapeutic.

A target nucleic acid of any plant or plant part may be modified and/or edited (e.g., mutated, e.g., base edited, cleaved, nicked, and the like) using the nucleic acid constructs of the invention. Any plant (or groupings of plants, for example, into a genus or higher order classification) may be modified using the nucleic acid constructs of this invention including an angiosperm, a gymnosperm, a monocot, a dicot, a C3, C4, CAM plant, a bryophyte, a fern and/or fern ally, a microalgae, and/or a macroalgae. A plant and/or plant part useful with this invention may be a plant and/or plant part of any plant species/variety/cultivar. The term "plant part," as used herein, includes but is not limited to, embryos, pollen, ovules, seeds, leaves, stems, shoots, flowers, branches, fruit, kernels, ears, cobs, husks, stalks, roots, root tips, anthers, plant cells including plant cells that are intact in plants and/or parts of plants, plant protoplasts, plant tissues, plant cell tissue cultures, plant calli, plant clumps, and the like. As used herein, "shoot" refers to the above ground parts including the leaves and stems. Further, as used herein, "plant cell" refers to a structural and physiological unit of the plant, which comprises a cell wall and also may refer to a protoplast. A plant cell can be in the form of an isolated single cell or can be a cultured cell or can be a part of a higher-organized unit such as, for example, a plant tissue or a plant organ.

Non-limiting examples of plants useful with the present invention include turf grasses (e.g., bluegrass, bentgrass, ryegrass, fescue), feather reed grass, tufted hair grass, miscanthus, arundo, switchgrass, vegetable crops, including artichokes, kohlrabi, arugula, leeks, asparagus, lettuce (e.g., head, leaf, romaine), malanga, melons (e.g., muskmelon, watermelon, crenshaw, honeydew, cantaloupe), cole crops (e.g., brussels sprouts, cabbage, cauliflower, broccoli, collards, kale, Chinese cabbage, bok choy), cardoni, carrots, napa, okra, onions, celery, parsley, parsnips, chicory, peppers, potatoes, cucurbits (e.g., marrow, cucumber, zucchini, squash, pumpkin, honeydew melon, watermelon, cantaloupe), radishes, dry bulb onions, rutabaga, eggplant, salsify, escarole, shallots, endive, garlic, spinach, green onions, squash, greens, beet (sugar beet and fodder beet), sweet potatoes, chard, horseradish, tomatoes, turnips, and spices; a fruit crop such as apples, apricots, cherries, nectarines, peaches, pears, plums, prunes, cherry, quince, fig, nuts (e.g., chestnuts, pecans, pistachios, hazelnuts, pistachios, peanuts, walnuts, macadamia nuts, almonds, and the like), citrus (e.g., clementine, kumquat, orange, grapefruit, tangerine, mandarin, lemon, lime, and the like), blueberries, black raspberries, boysenberries, cranberries, currants, gooseberries, loganberries, raspberries, strawberries, blackberries, grapes (wine and table), avocados, bananas, kiwi, persimmons, pomegranate, pineapple, tropical fruits, pomes, melon, mango, papaya, and lychee, a field crop plant such as clover, alfalfa, timothy, evening primrose, meadow foam, corn/maize (field, sweet, popcorn), hops, jojoba, buckwheat, safflower, *quinoa*, wheat, rice, barley, rye, millet, sorghum, oats, triticale, sorghum, tobacco, kapok, a leguminous plant (beans (e.g., green and dried), lentils, peas (e.g., field peas, snow peas, snap peas), soybeans, garbanzo beans (chickpeas)), an oil plant (rape, canola, mustard, poppy, olive, sunflower, coconut, castor oil plant, cocoa bean, groundnut, oil palm), duckweed, *Arabidopsis*, a fiber plant (cotton, flax, hemp, jute), *Cannabis* (e.g., *Cannabis sativa, Cannabis indica*, and *Cannabis ruderalis*), lauraceae (cinnamon, camphor), or a plant such as coffee, sugar cane, tea, and natural rubber plants; and/or a bedding plant such as a flowering plant, a cactus, a succulent and/or an ornamental plant (e.g., roses, tulips, violets), as well as trees such as forest trees (broad-leaved trees and evergreens, such as conifers; e.g., elm, ash, oak, maple, fir, spruce, cedar, pine, birch, cypress, eucalyptus, willow), as well as shrubs and other nursery stock. In some embodiments, the nucleic acid constructs of the invention and/or expression cassettes and/or vectors encoding the same may be used to modify maize, soybean, wheat, canola, rice, tomato, pepper, sunflower, raspberry, blackberry, black raspberry and/or cherry.

The present invention further comprises a kit to carry out methods of this invention. A kit of this invention can comprise reagents, buffers, and/or apparatus for mixing, measuring, sorting, labeling, etc., as well as instructions and the like as would be appropriate for modifying a target nucleic acid.

In some embodiments, the invention provides a kit comprising one or more polynucleotides and/or nucleic acid constructs of the invention, and/or expression cassettes and/or vectors comprising the same, with optional instructions for the use thereof. In some embodiments, a kit may further comprise a polypeptide of interest and/or polynucleotide encoding the same and expression cassette and/or vector comprising the same. In some embodiments, a guide nucleic acid may be provided on the same expression cassette and/or vector as a nucleic acid construct of the invention. In some embodiments, a guide nucleic acid may be provided on a separate expression cassette or vector from that comprising the nucleic acid construct of the invention.

Accordingly, in some embodiments, kits are provided comprising a nucleic acid construct comprising (a) a polynucleotide encoding a Cas12a polypeptide with altered PAM specificity as provided herein and (b) a promoter that drives expression of the polynucleotide of (a). in some embodiments, kits are provided comprising a nucleic acid construct comprising (a) a polynucleotide encoding an engineered protein with altered PAM specificity as provided herein and (b) a promoter that drives expression of the polynucleotide of (a). In some embodiments, the kit may further comprise a nucleic acid construct encoding a guide nucleic acid, wherein the construct comprises a cloning site for cloning into the backbone of the guide nucleic acid a nucleic acid sequence that is identical or complementary to a target nucleic acid sequence.

In some embodiments, the kit may comprise a nucleic acid construct comprising/encoding one or more nuclear localization signals, wherein the nuclear localization signals are fused to the CRISPR-Cas polypeptide. In some embodiments, kits are provided comprising a nucleic acid construct of the invention encoding a CRISPR-Cas polypeptide having altered PAM specificity or, and/or an expression cassette and/or vector comprising the same, wherein the nucleic acid constructs, expression cassettes and/or vectors may further encode one or more selectable markers useful for identifying transformants (e.g., a nucleic acid encoding an antibiotic resistance gene, herbicide resistance gene, and the like). In some embodiments, the nucleic acid construct may be an mRNA that encodes one or more introns within the encoded CRISPR-Cas polypeptide. In some embodiments, a kit may comprise promoters and promoters with introns for use in expression of the polypeptides and nucleic acid constructs of the invention.

A polypeptide, polynucleotide, nucleic acid construct, expression cassette, vector, composition, kit, system and/or cell of the present invention may comprise all or a portion of a sequence of one or more of SEQ ID NOs:1-271. In some embodiments, a polypeptide, polynucleotide, nucleic acid construct, expression cassette, vector, composition, kit, system and/or cell of the present invention may comprise at least about 20%, 25%, 30%, 35%, 40%, 45%, 50%, 55%, 60%, 65%, 70%, 75%, 80%, 85%, 90%, 95%, 96%, 97%, 98%, 99%, or more consecutive amino acids of a sequence of one or more of SEQ ID NOs:1-271.

The invention will now be described with reference to the following examples. It should be appreciated that these examples are not intended to limit the scope of the claims to the invention, but are rather intended to be exemplary of certain embodiments. Any variations in the exemplified methods that occur to the skilled artisan are intended to fall within the scope of the invention.

EXAMPLES

Example 1

Figure 3:
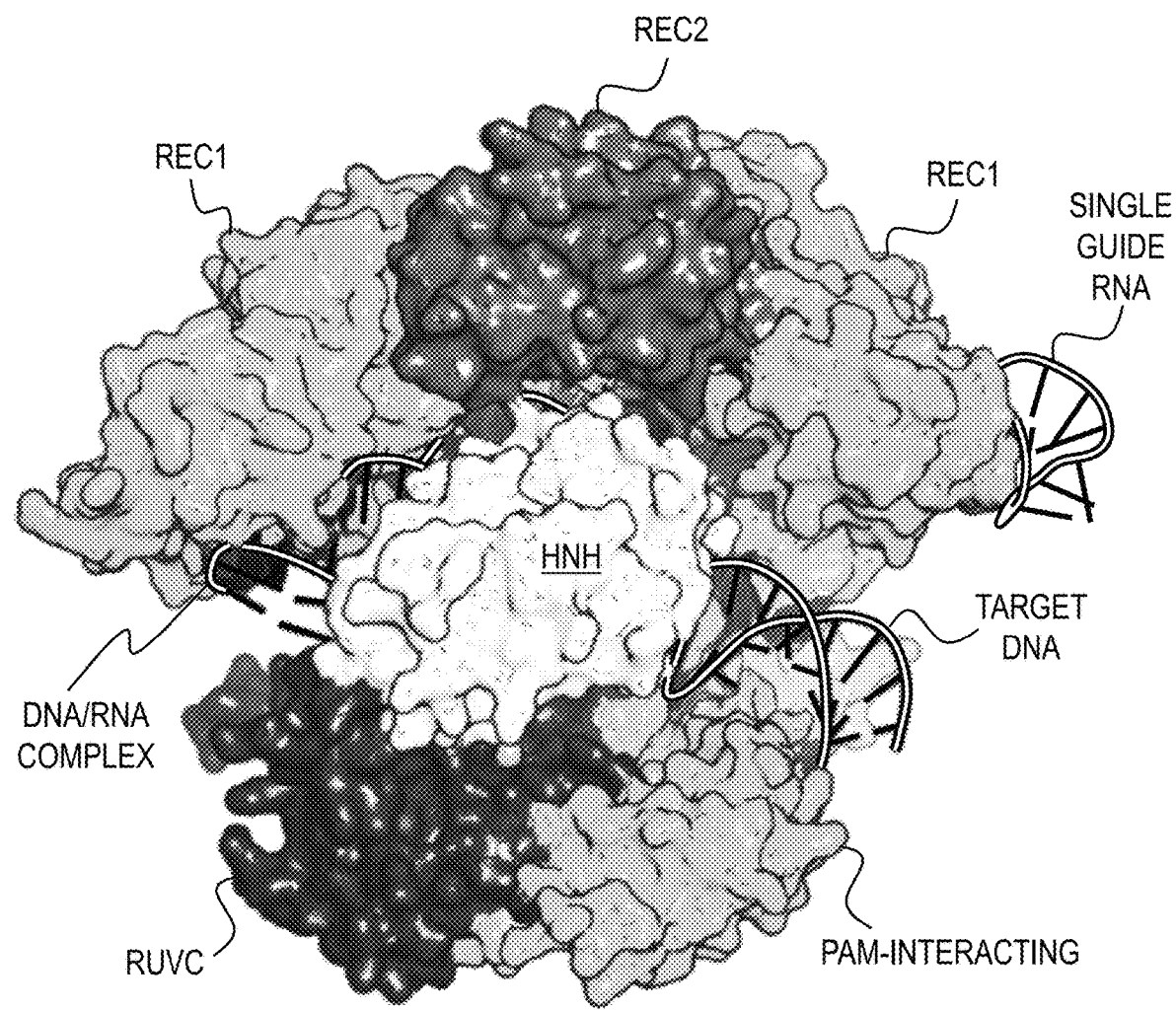
FIG. 3 is the crystal structure of SpCas9 (PDB ID 4UN3) bound to a single guide RNA (sgRNA) and target DNA. Domains shown are as follows: RuvC, bridge helix, Rec1, Rec2, HNH, and PAM-interacting.

Using existing domain annotations along with visual inspection of the SpCas9 crystal structure (PDB ID 4UN3) in PyMOL (The PyMOL Molecular Graphics System, Version 2.0. Schrodinger, LLC), the full HNH domain from SpCas9 (FIG. 3) was first identified and its residue boundaries determined. The domain is largely resolved in the crystal structure, but several residues connecting the N terminus of the HNH domain to the Rec1 domain are unresolved in the crystal structure. The location of Cas9 target DNA strand cleavage site relative to the HNH domain was also noted. This relative orientation was mimicked in subsequent rational positioning of the HNH domain relative to the target DNA strand of Cas12a.

Figure 4:
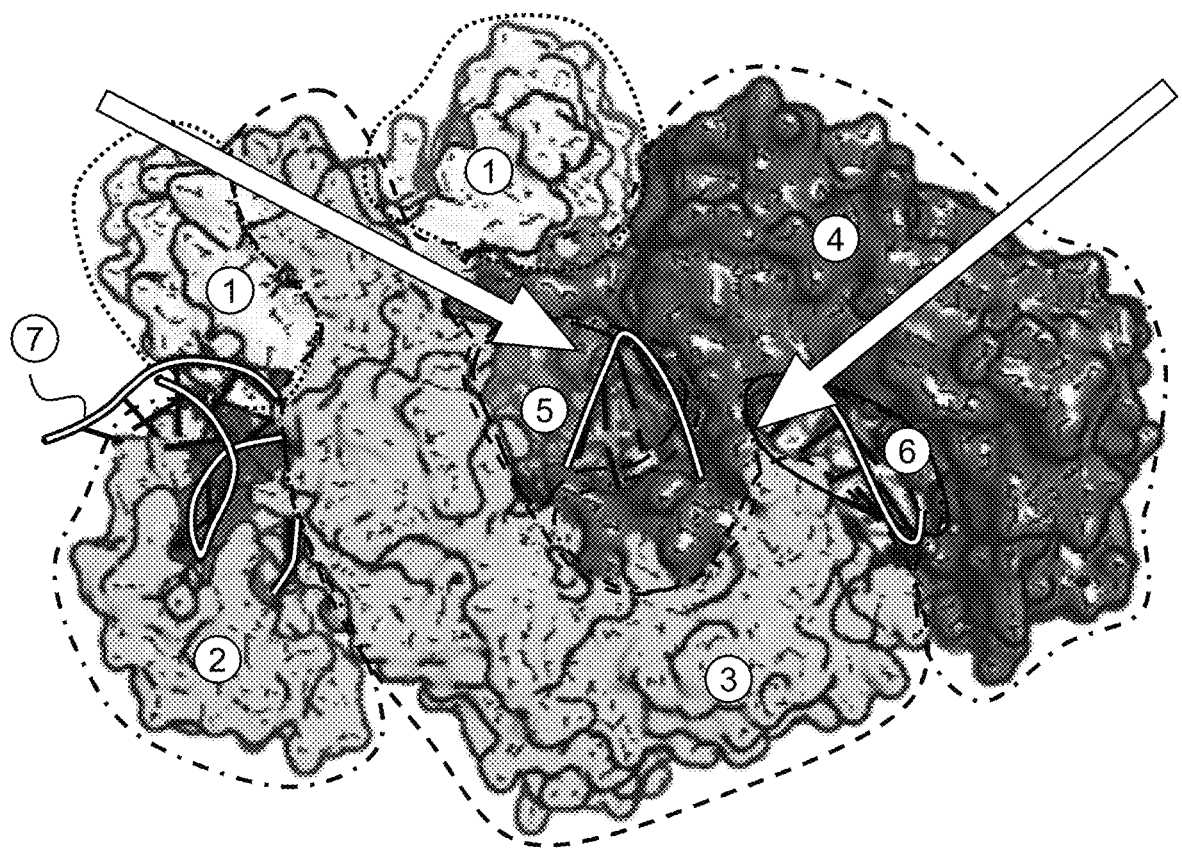

The crystal structure of the LbCas12a ternary complex (PDB ID 5XUS) was next examined to locate an accessible region of the target DNA strand. Although the side of the target DNA/crRNA duplex closest to the RuvC domain is heavily shielded by other Cas12a domains, there is an exposed portion of the target DNA (indicated by the left arrow in FIG. 4) on the opposite side of the protein at the interface between the Rec1 and Rec2 domains (FIG. 4). A linker (indicated by the right arrow in FIG. 4) connecting the two domains sits adjacent to this exposed site and has few interactions with other residues in LbCas12a; this linker was chosen as a candidate site for domain insertion.

To determine the precise placement of the SpCas9 HNH domain relative to LbCas12a, the exposed DNA bases in the groove between the Rec1 and Rec2 domains of LbCas12a were next identified. Then, treating the HNH domain and its target DNA (four bases with two on each side of the cleavage site) as a unit, alignments of the HNH target DNA to the exposed target strand of LbCas12a were tested in a sliding window using PyMOL until an alignment was identified that would place the HNH domain near the insertion loop and would minimize clashes with other domains of LbCas12a. The position of the HNH domain was then adjusted manually using PyMOL to minimize clashes between HNH and Cas12a.

Figure 5:
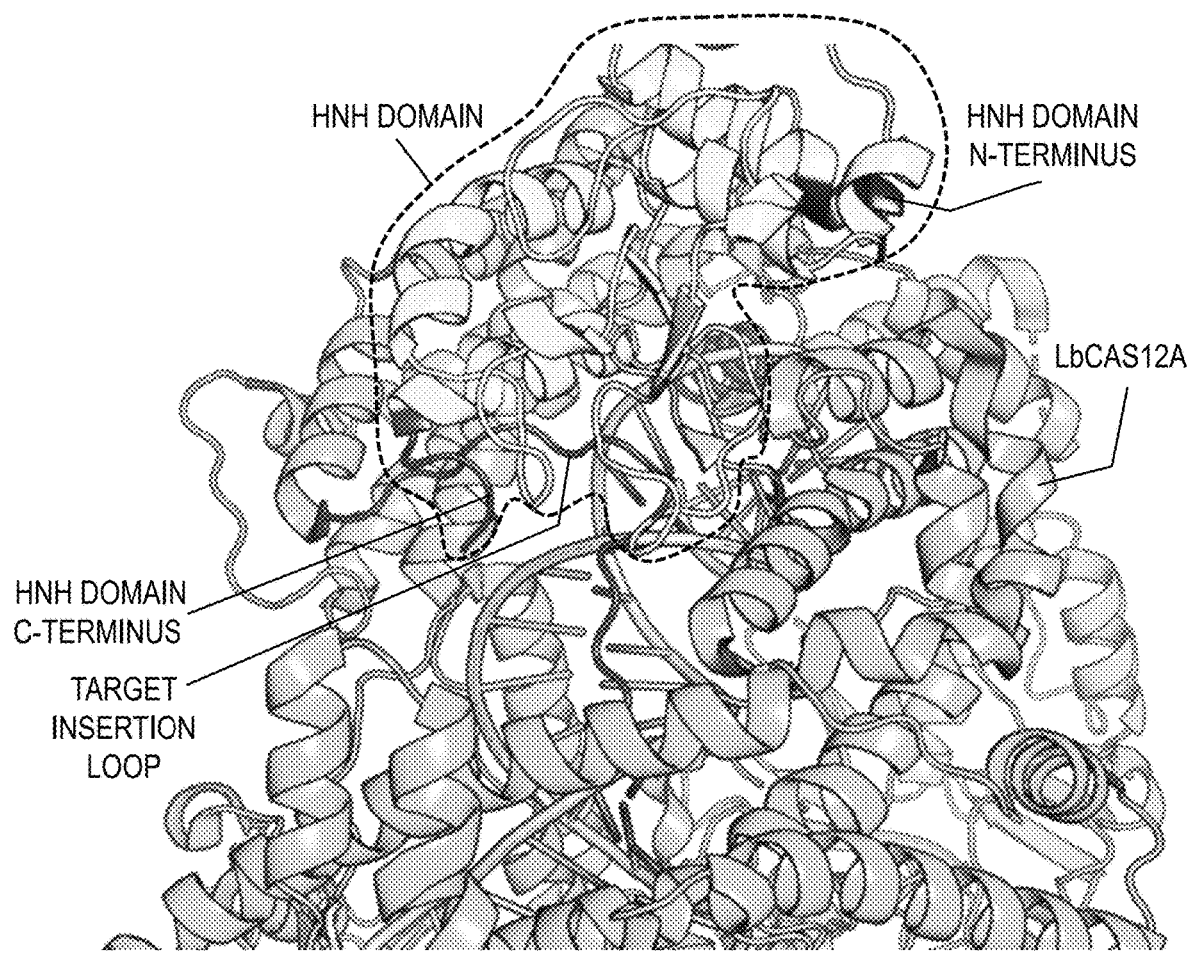

The final selected position of the HNH domain is shown in FIG. 5. While the C terminus of the HNH domain is very close to the C terminal end of the insertion loop, the HNH N terminus is relatively far from the insertion loop; however, this structure does not include the unstructured residues linking the SpCas9 Rec1 and HNH domains. A highly conserved hairpin in this region that interacts with the target DNA/crRNA duplex was further identified as a potential site for later design.

To prepare the Cas12a-HNH fusion structure for computational linker modeling, the N terminus of the HNH domain was initially extended by appending residues from SpCas9 that connect the Rec1 and HNH domains (and which are unresolved in the SpCas9 crystal structure) using PyMOL. The resulting structure was exported and prepared for linker modeling using custom Python scripts that inserted the HNH domain residues into possible insertion sites throughout the insertion loop as shown in Table 1.

TABLE 1

Results of preliminary computational screening of possible insertion sites in Cas12a.

| Insertion Site | # successful closures/10 attempts | Observations |
| --- | --- | --- |
| 282 | 0 | |
| 283 | 0 | |
| 284 | 0 | |
| 285 | 3 | |
| 286 | 0 | |
| 287 | 1 | |
| 288 | 3 | When loop closure does occur, it would likely offer little flexibility for the N-terminal linker. The C-terminal linker seems long enough to be flexible. |
| 289 | 2 | |
| 290 | 0 | |
| 291 | 9 | Insertion in a flexible location between glycine and glutamate residues |
| 292 | 9 | Insertion in a flexible location between glutamate and glycine residues |
| 293 | 6 | Insertion would be immediately before a tyrosine that interacts with other Cas12a residues |

A rapid computational screen was then performed to test the ability of the HNH domain termini to connect to the two ends of the linker cut site using the Rosetta Remodel protocol (Huang P. S. et al. (2011) *PLoS ONE* 6(8): e24109) included in the Rosetta macromolecular modeling software package. For each insertion point, ten iterations of loop closure (with no sequence design or insertions) were performed. The number of times that the linkers were able to successfully connect out of those ten iterations were tallied and compared (Table 1). Two of these insertion sites were then selected for more thorough linker modeling, including variations in linker lengths, based on a combination of their rate of successful loop closure and manual inspection (shown in bold in Table 1).

For the two selected insertion sites, fine-grained testing was then performed with small (2 to 4 residue) glycine-serine insertions or deletions in the N-terminal and C-terminal linkers and with more thorough sampling (100 iterations each). Possible residues for deletion were selected based on manual inspection of the sequence. Based on the linker modeling results, eight designs (four for each insertion site) were selected for experimental testing including extensions of 0, 2, or 4 residues of the N-terminal linker and extensions of 0 or 2 residues of the C-terminal linker.

Example 2

Figure 6:
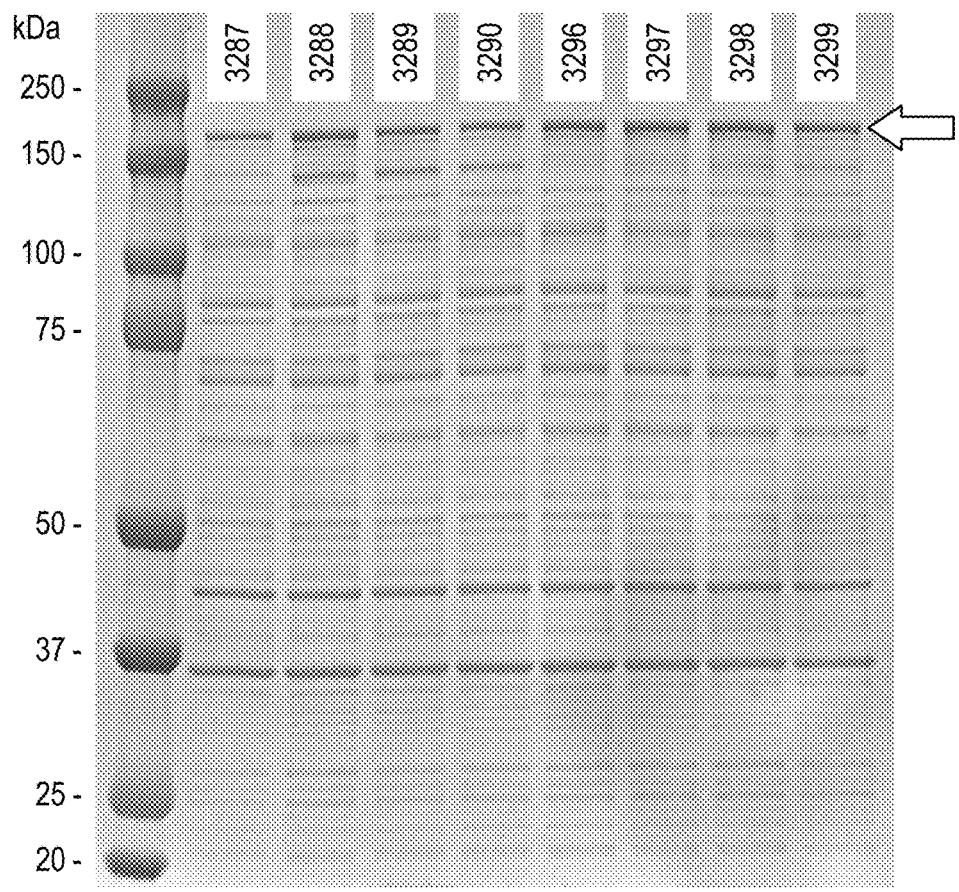
FIG. 6 is an illustration depicting the soluble fraction lysed *Escherichia coli* expressing HNH-3287, 3288, 3289, 3290, 3296, 3297, 3298, and 3299.

DNA coding regions for 8 LbCas12a-HNH constructs (HNH-3287, HNH-3288, HNH-3289, HNH-3290, HNH-3296, HNH-3297, HNH-3298, and HNH-3299) were synthesized with a 6-Histidine tag using solid state synthesis. The coding regions were coned into a pET28a plasmid (Novagen) behind an inducible T7 promoter and transfected into BL21(DE3)-Star cells (Invitrogen) and plated on kanamycin. Single colonies were grown in 30 ml of Luria Broth at 37° C. to an A600 optical density of 0.5. 500 mM IPTG was added and the temperature was lowered to 18° C. for 18 hours of expression. Cells were pelleted and lysed with BugBuster Master Mix (Millipore) according to the manufacturer's directions. Cell debris was pelleted and a soluble fraction was imaged on a 4-12% Bis-Tris PAGE gel (Invitrogen) under reducing conditions, and visualized using Coomassie staining. All eight HNH constructs showed soluble protein expression at the approximate MW of 160 kDa (FIG. 6, arrow).

Soluble protein expression for all eight constructs containing HNH nuclease in the middle of the Cas12a protein speaks to the quality of the fusion designs. Large domain insertions into the middle of proteins often results in insoluble protein expression or no expression in *Escherichia coli*. The observation of all eight proteins being highly expressed suggests the chimeric protein is folding properly and has not led to the disruption of either protein folds.

The expression protocol was repeated to generate proteins suitable for nuclease assays. After pelleting the eight constructs, the *E. coli* cells were frozen, thawed, and were suspended in Buffer A (20 mM HEPES-KOH pH 7.5, 500 mM NaCl, 10% glycerol, 2 mM TCEP, and 10 mM Imidazole pH 7.5). 0.3 mg/ml lysozyme was added, and the cells were incubated at room temperature for 20 minutes, followed by sonication (QSonica) with a ⅛-inch tip, 25% power, 10 second bursts followed by 30 second rests for 2.25 minutes. Cell debris was pelleted, and the supernatant was loaded onto Ni-NTA Agarose (Bio-Rad), washed with 20 mM imidazole in buffer A, and eluted with 300 mM imidazole in Buffer A. Approximate concentrations of proteins were 0.5 to 2 mg/ml (estimated by NanoDrop A280 absorbances) in a total eluate of 200 μL.

Example 3

A plasmid-based assay was used to assess nicking activity by purified HNH-3287, HNH-3288, HNH-3289, HNH-3290, HNH-3296, HNH-3297, and HNH-3298. Plasmid nicking assays work on the principle that supercoiled plasmids extracted from bacteria run smaller on agarose gels than linearized, double-cut plasmid. Furthermore, if only one strand is nicked the plasmid runs even larger than linearized plasmid. This assay has been used extensively in the CRISPR field to assess if an enzyme is a double-stranded nuclease or a single-stranded nuclease (Jinek et al., Science. 2012 Aug. 17; 337(6096):816-21) (Zetsche et al., Cell. 2015 Oct. 22; 163(3):759-71).

The sequence (SEQ ID NO: 123)
5'-TTTAGGAAT CCCTTCTGC AGCACCTGG-3', where the protospacer-adjacent motif (PAM) is in bold, was synthesized and cloned into a pUC18 plasmid. The plasmid was expressed in DH5a cells and purified using plasmid miniprep kits (Qiagen). CRISPR RNA molecules were synthesized (Synthego) without any chemical modifications with the sequence (SEQ ID NO: 124)
5'-AAUUUCUACU AAGUGUAGAU GGAAUCCCUU CUGCAGCACC

UGG-3' where the portion complimentary to the plasmid is emboldened. 30 μL reactions were assembled with a 10:10:1 RNA:Protein:Plasmid ratio, incubated for 15 minutes at 37° C., heat-inactivated at 85° C. for 2 minutes, and loaded on a 1% agarose gel containing 1/100 v/v SYBR-Safe stain (Invitrogen).

Proteins tested were wildtype LbCas12a (wtLbCas12a), LbCas12a-R1138A, and the various chimeric HNH proteins. The R1138A is a point mutation in LbCas12a which corresponds to a known non-template strand nickase mutation for AsCas12a (R1226A) (Yamano T, et al. Cell. 2016 May 5; 165(4):949-62). Concentrations tested were 33 nM for wtLbCas12a and LbCas12a-R1138. A lower 9 nM was used for the various HNH constructs to distinguish the most active nucleases by being somewhat near the expected Kd rather than generating complete nicking.

Figure 7:
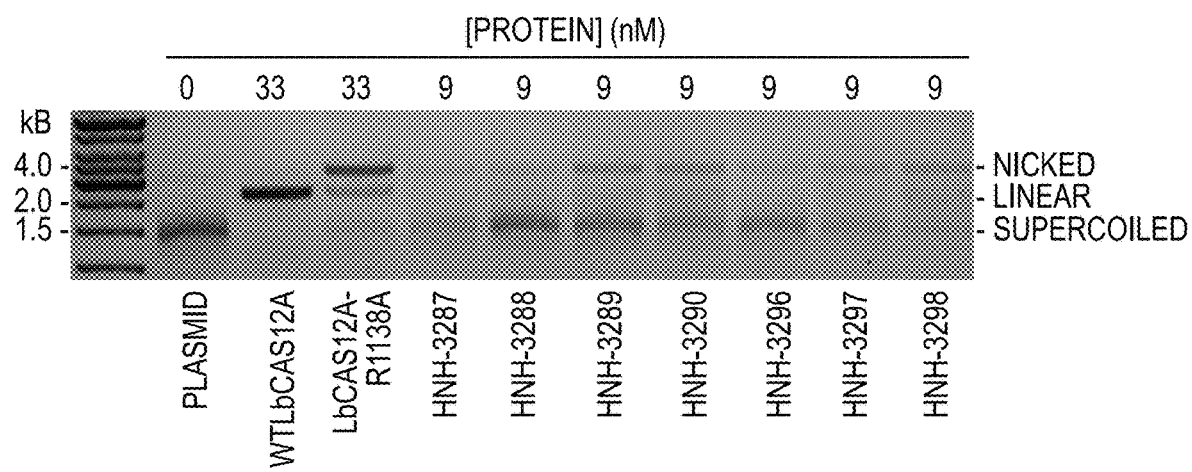
FIG. 7 is an illustration depicting the nicking activity of purified HNH-3287, 3288, 3289, 3290, 3296, 3297, and 3298.

The resulting gel (FIG. 7) indicates that HNH-3287, HNH-3288, HNH-3289, HNH-3290, HNH-3296, HNH-3297, and HNH-3298 are all nickases with percentages of nicking from ~25% efficiency to ~75% efficiency (upper bands, the nicked plasmids, compared to lower bands, the supercoiled plasmids) at these low 9 nM protein concentrations. Longer incubations or higher concentrations result in complete nicking, but do not allow for comparing relative mutant activities. Chimera HNH-3298 appears to have the highest percentage of nicking activity with 9 nM [protein] for 15 minutes at 37° C.

Example 4

Methods

Protein Expression and Purification

For initial testing of expression and activity, His-tagged proteins, SYN3287 (SEQ ID NO:125), SYN3288 (SEQ ID NO:126), SYN3289 (SEQ ID NO:127), SYN3290 (SEQ ID NO:128), SYN3296 (SEQ ID NO:129), SYN3297 (SEQ ID NO:130), SYN3298 (SEQ ID NO:131), and SYN3299 (SEQ ID NO:132), were expressed in BL21 cells in 30 mL cultures. Each of the proteins included an active HNH domain and an inactivated RuvC domain. Cells were pelleted, frozen overnight, and lysed by sonication. Proteins were then crudely purified from the lysate using HisPur™ Ni-NTA Spin Columns.

For assays of SYN3298 and SYN3289, proteins were expressed in the same way with the following changes: proteins were expressed in 1 L cultures and purified using HisTrap-HF columns by FPLC. Fractions containing the protein of interest were further purified by cation exchange and stored in 50% glycerol.

Plasmid Nickase Assay

To determine the activity of purified proteins as nickases or nucleases, 30 μL reactions were prepared containing 1×NEBuffer 3.1, 100 femtomoles of the DNA substrate, and equal parts purified protein and an appropriate guide RNA (1 picomole of each unless otherwise noted). Reactions were incubated at 37° C. for 30 minutes, stopped by a 20 minute Proteinase K digestion at room temperature, and separated on a 1% agarose gel. The target site for the plasmid nickase assay had a sequence of SEQ ID NO:133.

Fluorescent Nickase Assay

DNA substrates were produced by annealing one labeled (SEQ ID NO:134) and one unlabeled (SEQ ID NO:135) DNA strand to produce substrates labeled with Cy5 either on the PAM-containing or non-PAM-containing strand. The spacer for this assay included a sequence of SEQ ID NO:150. Nicking reactions were prepared as described for the plasmid nickase assay an incubated at 37° C. for 30 minutes. Reactions were stopped by digesting samples with Proteinase K for 10 minutes. All samples were then mixed with urea loading buffer to 1× concentration and heated to 90° C. for 5 minutes to denature the substrates. Samples were separated by running on a 6% TBE Urea gel at 4° C. and 100V.

HEK293T Cell Transfection

Eukaryotic HEK293T (ATCC CRL-3216) cells were cultured in Dulbecco's Modified Eagle's Medium plus GlutaMax (ThermoFisher) supplemented with 10% (v/v) FBS (FBS), at 37° C. with 5% $CO_2$. Protein components were synthesized using gene synthesis and subsequently cloned into plasmids with a CMV promoter. Guide RNAs were cloned with a human U6 promoter. HEK293T cells were seeded on 48-well collagen-coated BioCoat plates (Corning). Cells were transfected at about 70% confluency. 375 ng of CRISPR plasmid and 125 ng of guide RNA expression plasmids were transfected using 1.5 µl of Lipofectamine 3000 (ThermoFisher Scientific) per well according to the manufacturer's protocol. Genomic DNA from transfected cells were obtained after 3 days and indels were detected and quantified using high-throughput Illumina amplicon sequencing.

To determine which strand the designed proteins preferentially nick, pairs of guides were designed such that a Cas9 guide and a guide for the designed proteins on the same strand would cut close to each other (within ~10 bp). Each tested design was paired with either a nuclease-dead SpCas9, a SpCas9 D10A target strand nickase, or a SpCas9 H840A nontarget strand nickase. If the synthetic nickase and its paired Cas9 nickase cut opposite strands, then a greater editing frequency was expected than if they cut the same strand due to the production of double-stranded breaks.

Results

His-Tagged Designed Synthetic Nickases were Successfully Expressed in BL21 *E. coli*

Figure 8:
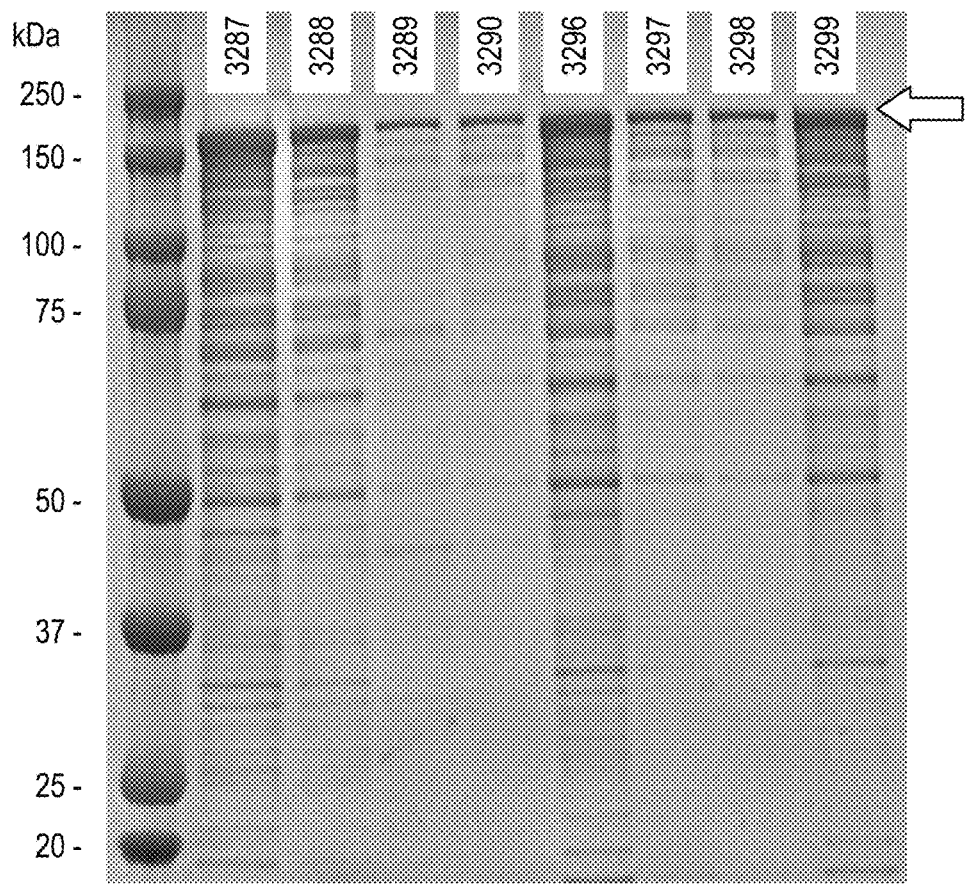
FIG. 8 is an image of a gel that indicates that nickases according to some embodiments of the present invention were solubly expressed in *E. coli*.

After crude purification of the designed nickases as described above, all samples showed a band at the expected size (~160 kDa) as shown in FIG. 8, indicating that the nickases were solubly expressed in *E. coli*.

Initial Plasmid Nicking Activity Observed from Crude Purifications of Synthetic Nickases.

Figure 9:
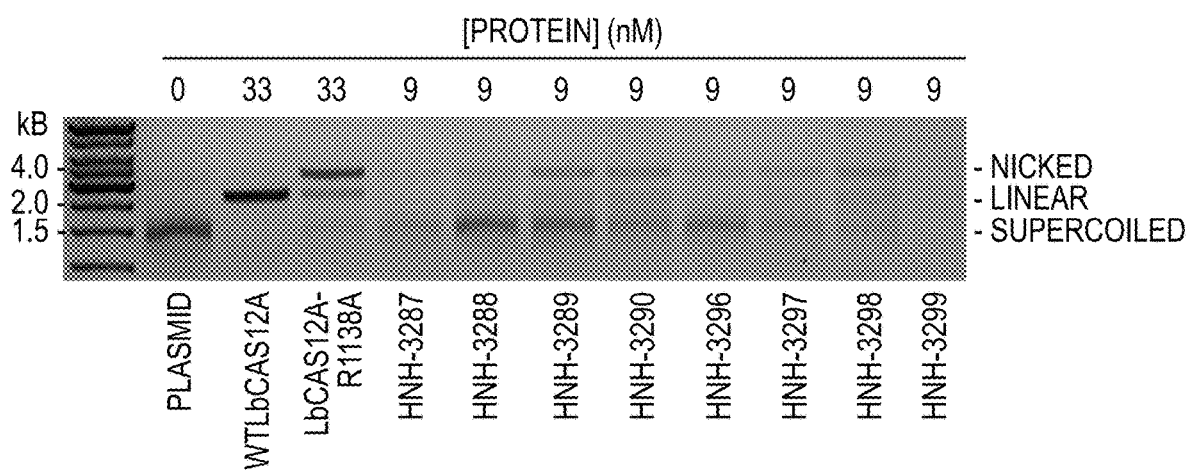
FIG. 9 is an image of a gel that indicates that nickases according to some embodiments of the present invention can nick a DNA substrate.

Plasmid nickase assays were performed as described in the methods section above using the crude nickase purifications shown in FIG. 8. Due to low yields from some of the purifications, all designed nickases were tested at low concentrations so that they could be compared directly. As can be seen in FIG. 9, all but one of the designs showed a band indicating the presence of nicked plasmid that was more prominent than in the negative control sample, suggesting that the designs are capable of nicking a DNA substrate.

RNA Dependence of Plasmid Nicking Using Crudely Purified Synthetic Nickases.

Figure 10:
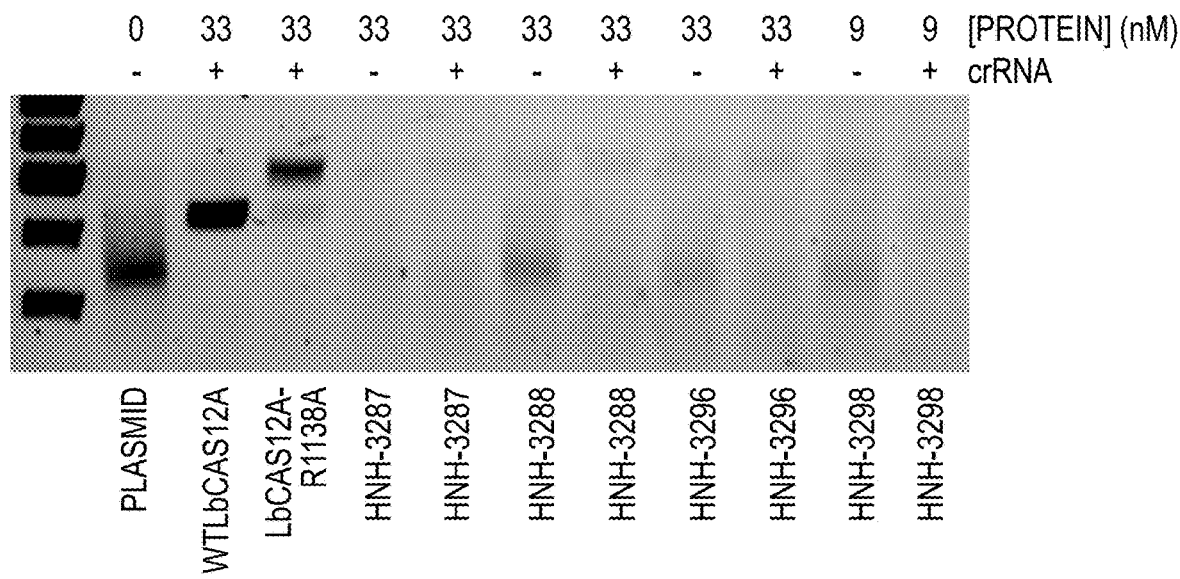
FIG. 10 is an image of a gel that indicates that nickases according to some embodiments of the present invention can be RNA-dependent.

To ensure that the observed nicking and cleavage of the plasmid were guide-dependent and not due to random nuclease activity, the plasmid nickase assay was repeated for selected designs in both the presence of a targeting crRNA. Designs SYN3288, SYN3296, and SYN3298 all showed a reduction in the amount of uncleaved plasmid present in the presence of crRNA as can be seen in FIG. 10, indicating that their nuclease activity is RNA-dependent.

Plasmid Nicking Activity of Purified Synthetic Nickase SYN3298.

Figure 11:
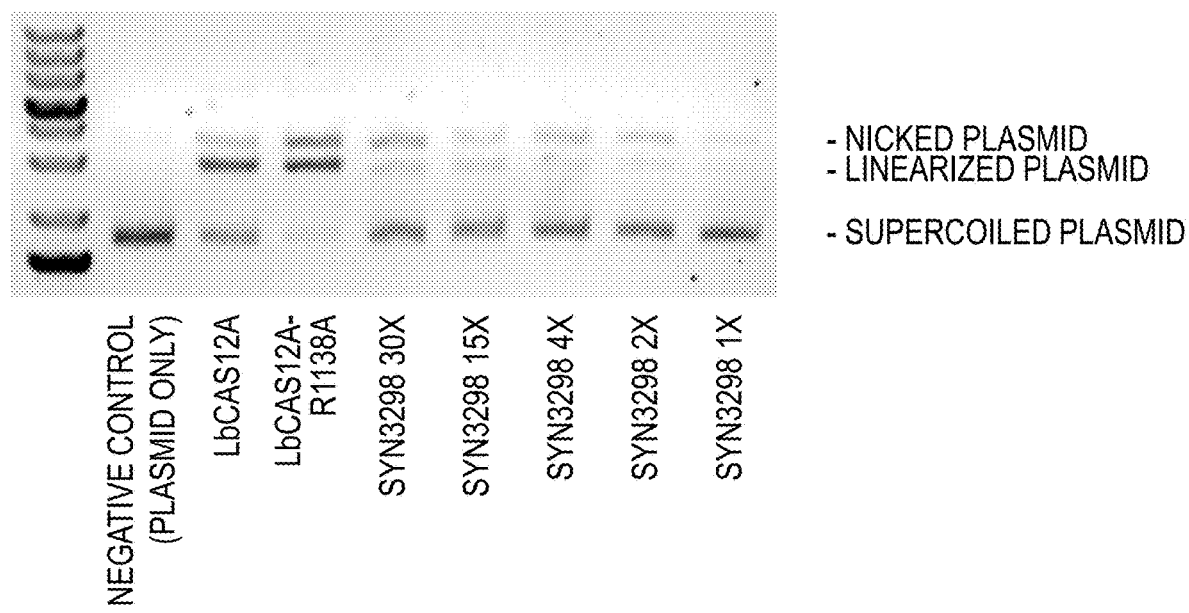
FIG. 11 is an image of a gel that indicates that nickases according to some embodiments of the present invention can act as a DNA nickase.

Different quantities of protein+guide were tested relative to the concentration of LbCas12a control used (e.g. 30× indicates that 30 picomoles of protein and guide were included in the reaction). Nicking and, to a lesser extent, cleavage of the plasmid were observed at all tested concentrations of SYN3298 (FIG. 11), confirming that this design acts as a DNA nickase.

Fluorescent Nickase Assay Using Purified Synthetic Nickases SYN3298 and SYN3289.

Figure 12:
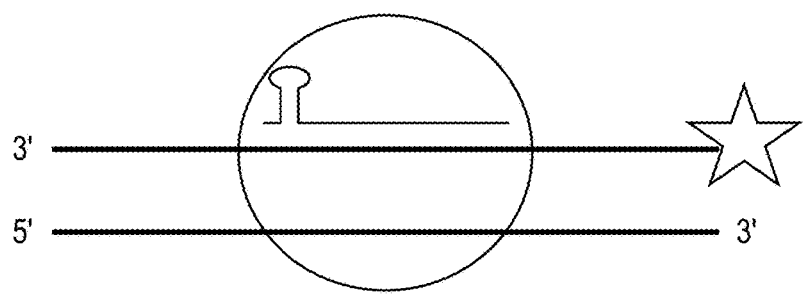
FIG. 12 is an illustration showing a labeled target strand.
Figure 13:
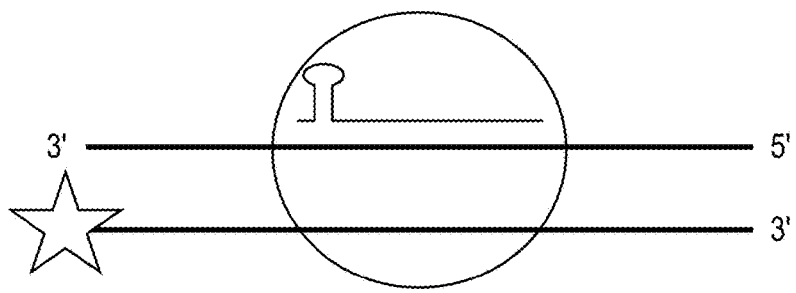
FIG. 13 is an illustration showing a labeled non-target strand.
Figure 14:
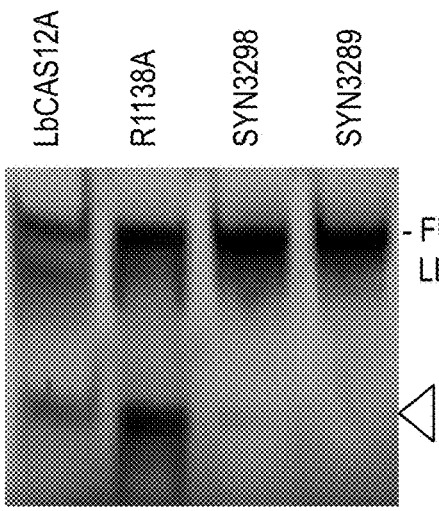
FIG. 14 is an image of a gel including samples incubated with a labeled target strand.
Figure 15:
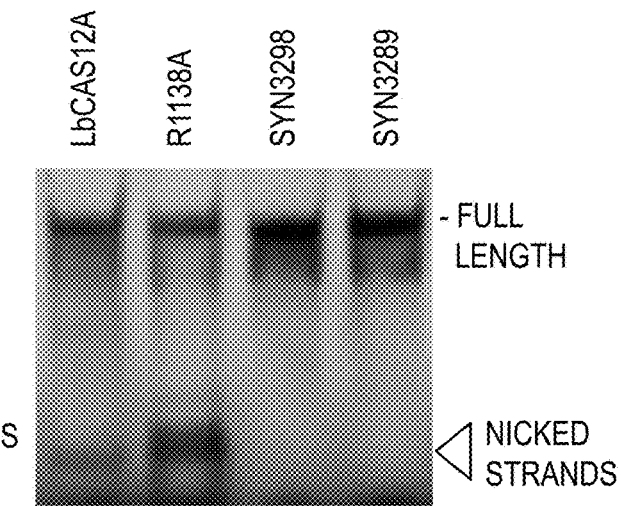
FIG. 15 is an image of a gel including samples incubated with a labeled non-target strand.
Figure 16:
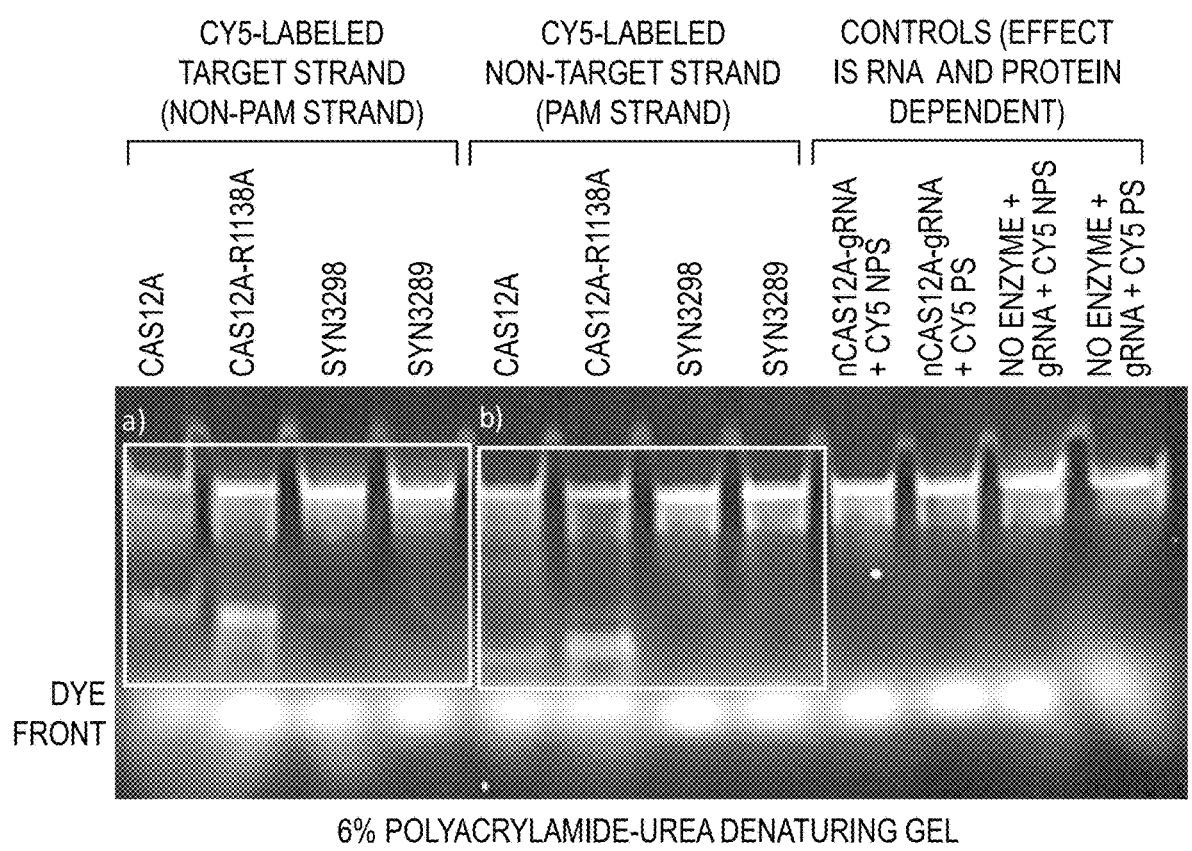
FIG. 16 is an image of the entire gel showing the lanes of FIG. 14 and FIG. 15 along with the lanes for the controls.

Substrates with a fluorescent Cy5 label on either the target (FIG. 12) or the nontarget (FIG. 13) were incubated with the designed nickases (which included an active HNH domain and an inactivated RuvC domain), LbCas12a, or the LbCas12a R1138A mutant (a nontarget strand nickase) and separated on a denaturing TBE-Urea gel. A shift in the position of the labeled band indicates that that strand was cleaved. FIG. 14 shows a portion of the gel for the samples incubated with the labeled target strand, FIG. 15 shows a portion of the gel for the samples incubated with the labeled non-target strand, and FIG. 16 shows the entire gel with lanes for the controls, the samples incubated with the labeled target strand (the boxed lanes denoted as "a)"), and the samples incubated with the labeled non-target strand (the boxed lanes denoted as "b)"). SYN3298 shows bands at the expected location for a cleaved substrate for the target DNA strand but not the nontarget DNA strand, indicating that it acts as a target strand nickase.

Sequence-Based Strand-Specific Nickase Assay of Genomic DNA in HEK293T Cells.

Synthetic nickases were co-transfected with nearby Cas9 nickases (e.g., Cas9(H840A) or Cas9(D10A) cutting either the target strand (e.g., Cas9(D10A)) or nontarget strand (e.g., Cas9(H840A)). Information on the spacers used in the sequence based, strand specific nickase assay is provided in Table 2. Upstream guide refers to which spacer would be expected to cut closer to the 5' end of the PAM-containing DNA strand. Estimated distance between the cut sites was determined based on the predicted cut site for each native nuclease domain.

TABLE 2

Spacer information for the sequence based, strand specific nickase assay.

| Target | Cas9 spacer sequence | Cas12a/synthetic nickase spacer sequence | Estimated distance between cut sites | Upstream guide |
|---|---|---|---|---|
| RUNX1 | GCATTTTCAGGAGGAAGCGA (SEQ ID NO: 136) | CAGGAGGAAGCGATGGCTTCAGA (SEQ ID NO: 137) | 7-12 bp | Cas9 |
| AAV1 | GTCCCCTCCACCCCACAGTG (SEQ ID NO: 138) | TCTGTCCCCTCCACCCCACAGTG (SEQ ID NO: 139) | 2-7 bp | Cas 12a/ synthetic nuclease |

Figure 17:
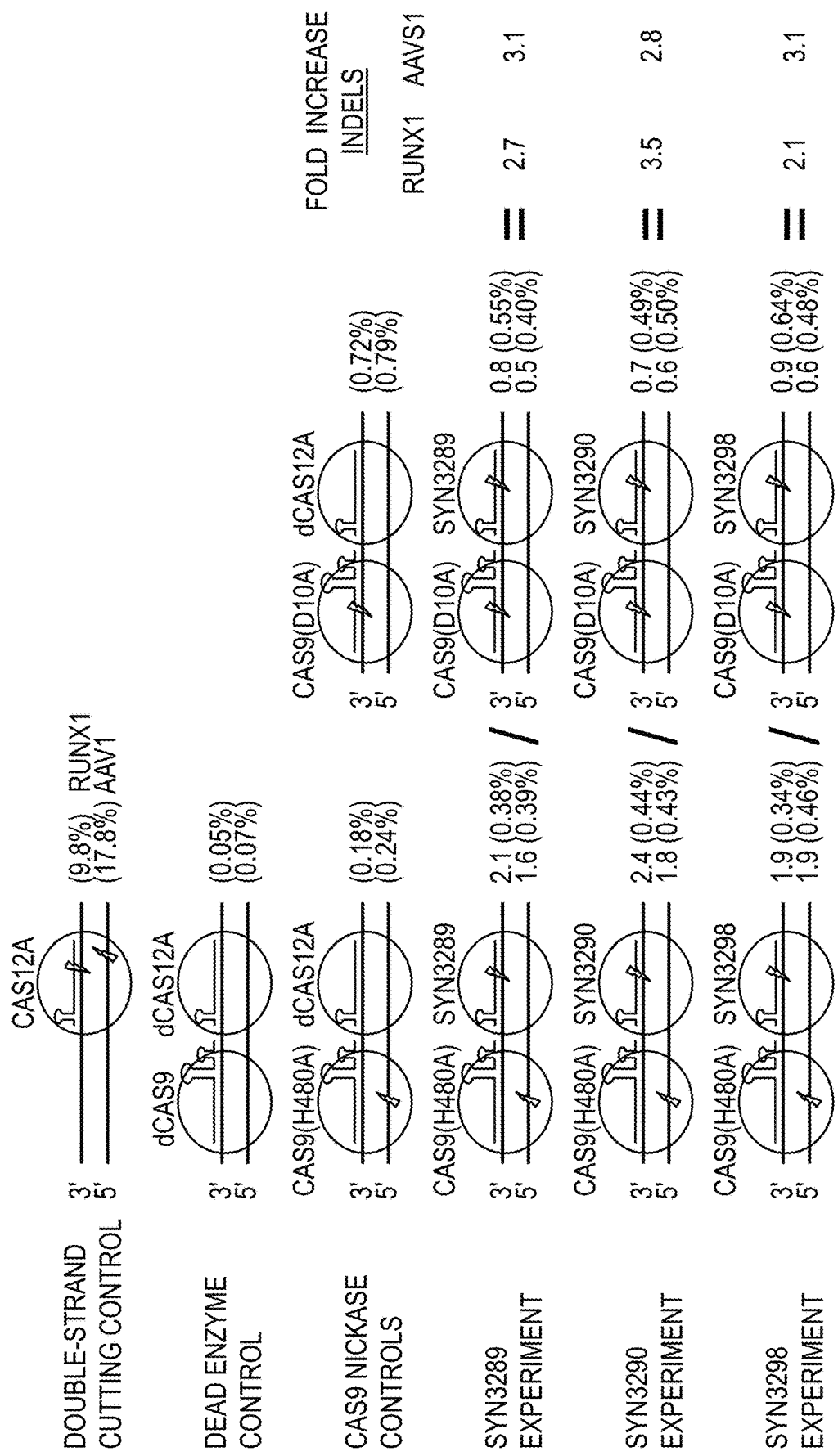
FIG. 17 is an illustration showing editing efficiencies for respective enzyme pairs according to some embodiments of the present invention.
Figure 18:
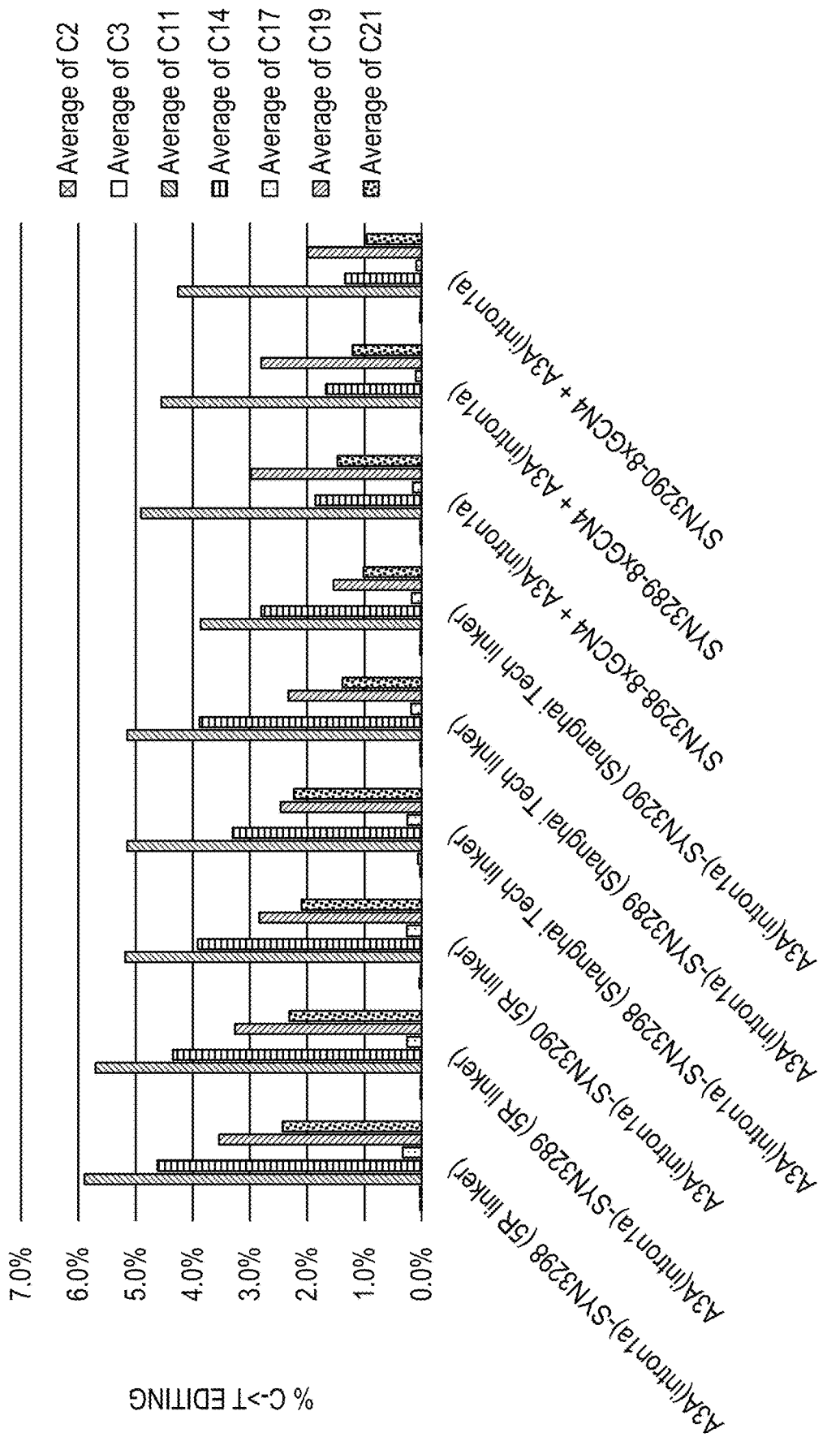
FIGS. 18-21 are graphs showing the percentage of C to T editing for various target regions corresponding to the respective spacers: FANCF spacer 1 (FIG. 18), FANCF spacer 2 (FIG. 19), AAVS1 spacer 1 (FIG. 20), and AAVS1 spacer 2 (FIG. 21).
Figure 19:
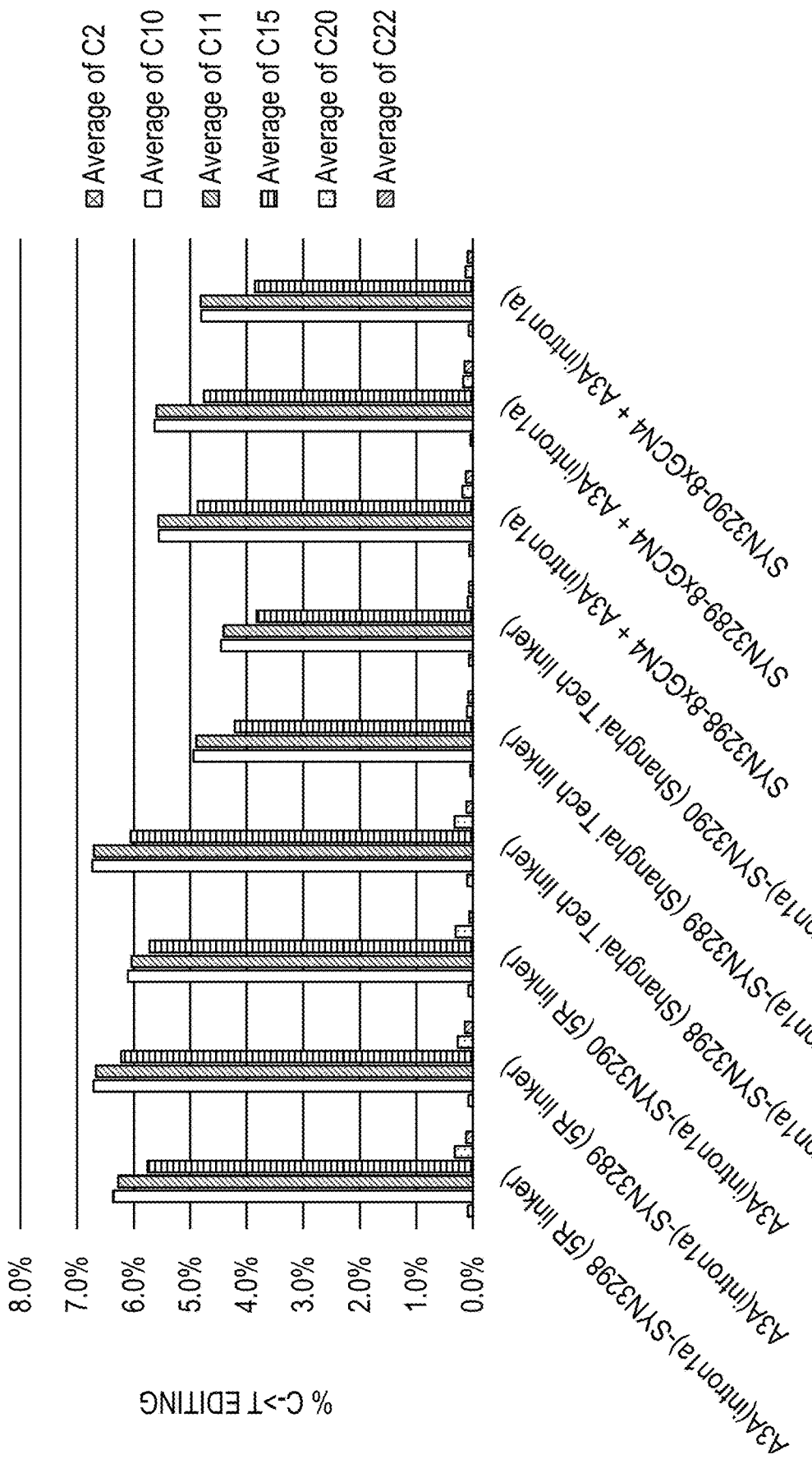
Figure 20:
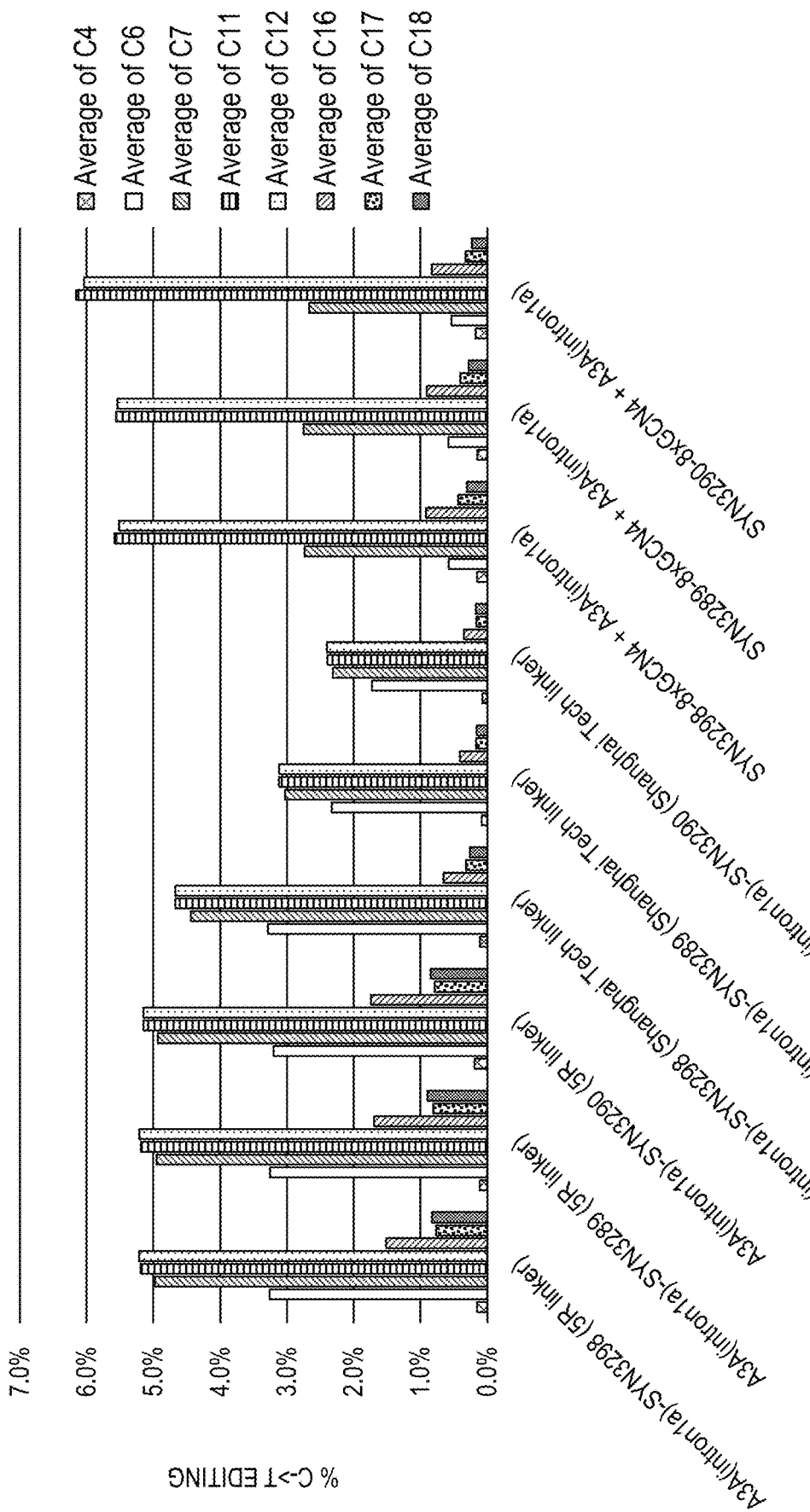
Figure 21:
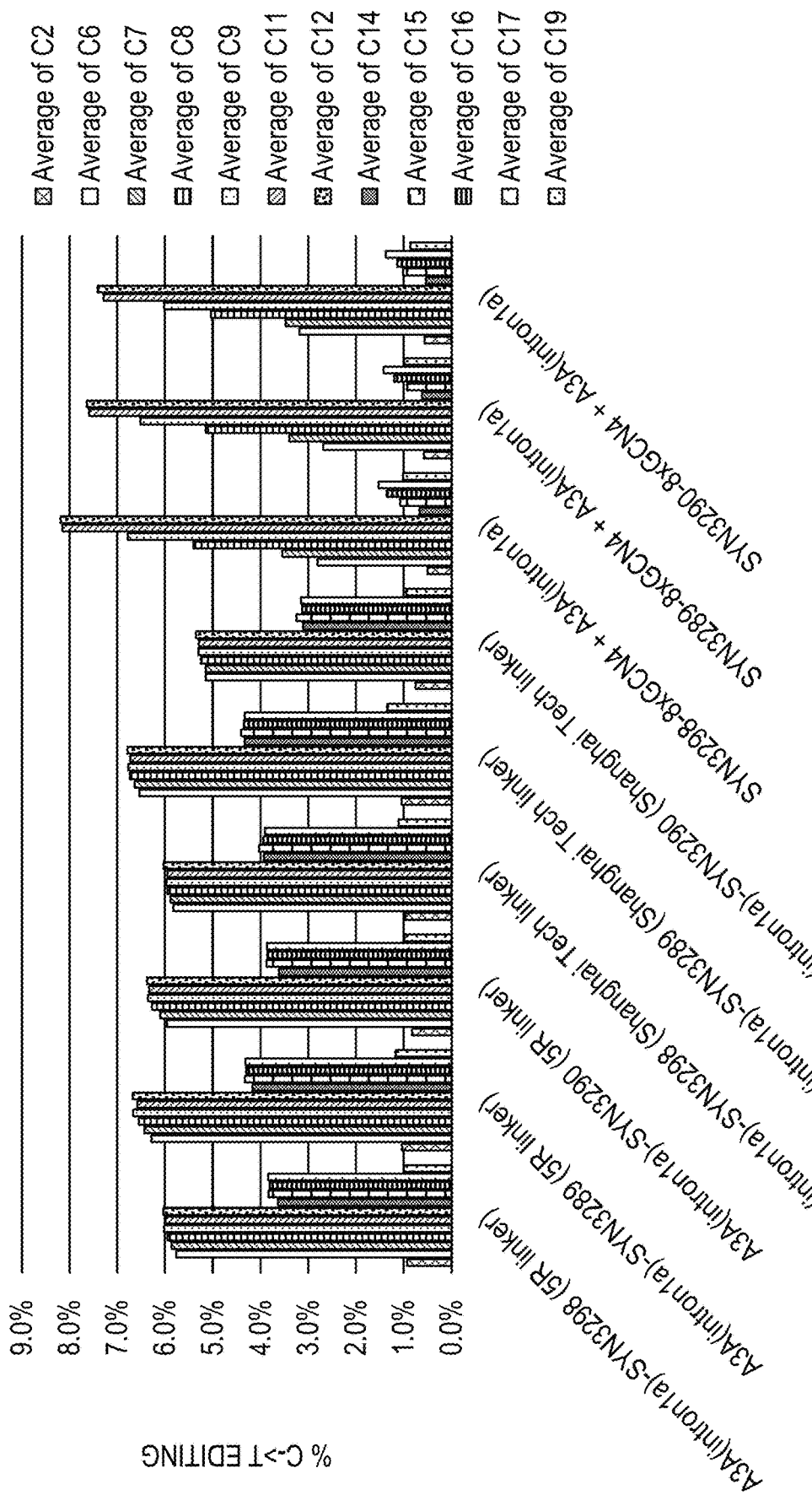

Editing efficiencies for each enzyme pair were normalized to the observed level of indels when the Cas9 nickase was paired with a nuclease-dead LbCas12a at the same target site (FIG. 17). Numbers in parentheses in FIG. 17 indicate the observed editing efficiencies prior to normalization. If the synthetic enzyme (SYN) (i.e., SYN3289, SYN3290, or SYN3298) preferentially cuts the target strand then (H480A::SYN)/(D10A::SYN)>1. If the synthetic enzyme (SYN) (i.e., SYN3289, SYN3290, or SYN3298) preferentially cuts the nontarget strand then (H480A::SYN)/(D10A::SYN)<1.

To determine which strand the designed proteins preferentially nick, pairs of guides were designed such that a Cas9 guide and a guide for the designed proteins on the same strand would cut close to each other (within ~10 bp). Each tested design was paired with either a nuclease-dead SpCas9, a SpCas9 D10A target strand nickase, or a SpCas9 H840A nontarget strand nickase. If the synthetic nickase and its paired Cas9 nickase cut opposite strands, then a greater editing frequency was expected to be seen than if they cut the same strand due to the production of double-stranded breaks. Increased (about a 3-fold increase) indel frequency was consistently observed when all designed nickases were paired with a Cas9 nontarget strand nickase compared to a Cas9 target strand nickase, indicating that the designed nickases preferentially cut the target DNA strand.

Example 5

Cytosine base editing data for base editors combining the A3A cytosine deaminase (SEQ ID NO:152) with SYN3289, SYN3290, or SYN3298 was obtained (FIGS. 18-21). Three architectures were tested for each enzyme: fusion of A3A to the N-terminus of the synthetic enzyme using a linker (SEQ ID NO:22) along with fusion of UGI (SEQ ID NO:104) to the C-terminus of the synthetic enzyme using a linker of SEQ ID NO:45 to provide SEQ ID NOs:160-162; fusion of A3A to the N terminus of the synthetic enzyme using a previously published linker (SEQ ID NO:153; Li et al. *Nat Biotechnol* 36, 324-327 (2018)) along with fusion of UGI (SEQ ID NO:104) to the C-terminus of the synthetic enzyme using a linker of SEQ ID NO:154 to provide SEQ ID NOs:163-165; or Suntag-based recruitment of UGI (SEQ ID NO:104) fused to the C-terminus of A3A (SEQ ID NO:152) to provide SEQ ID NO:156 recruited to the peptide tagged synthetic enzyme of one of SEQ ID NOs:157-159. All percentages shown in FIGS. 18-21 indicate averages across three data points. All of the tested enzymes demonstrated cytosine base editing in all three of the tested configurations. The spacer for FIG. 18 was SEQ ID NO:144, the spacer for FIG. 19 was SEQ ID NO:145, spacer for FIG. 20 was SEQ ID NO:146, and the spacer for FIG. 21 was SEQ ID NO:147.

Example 6

Figure 22:
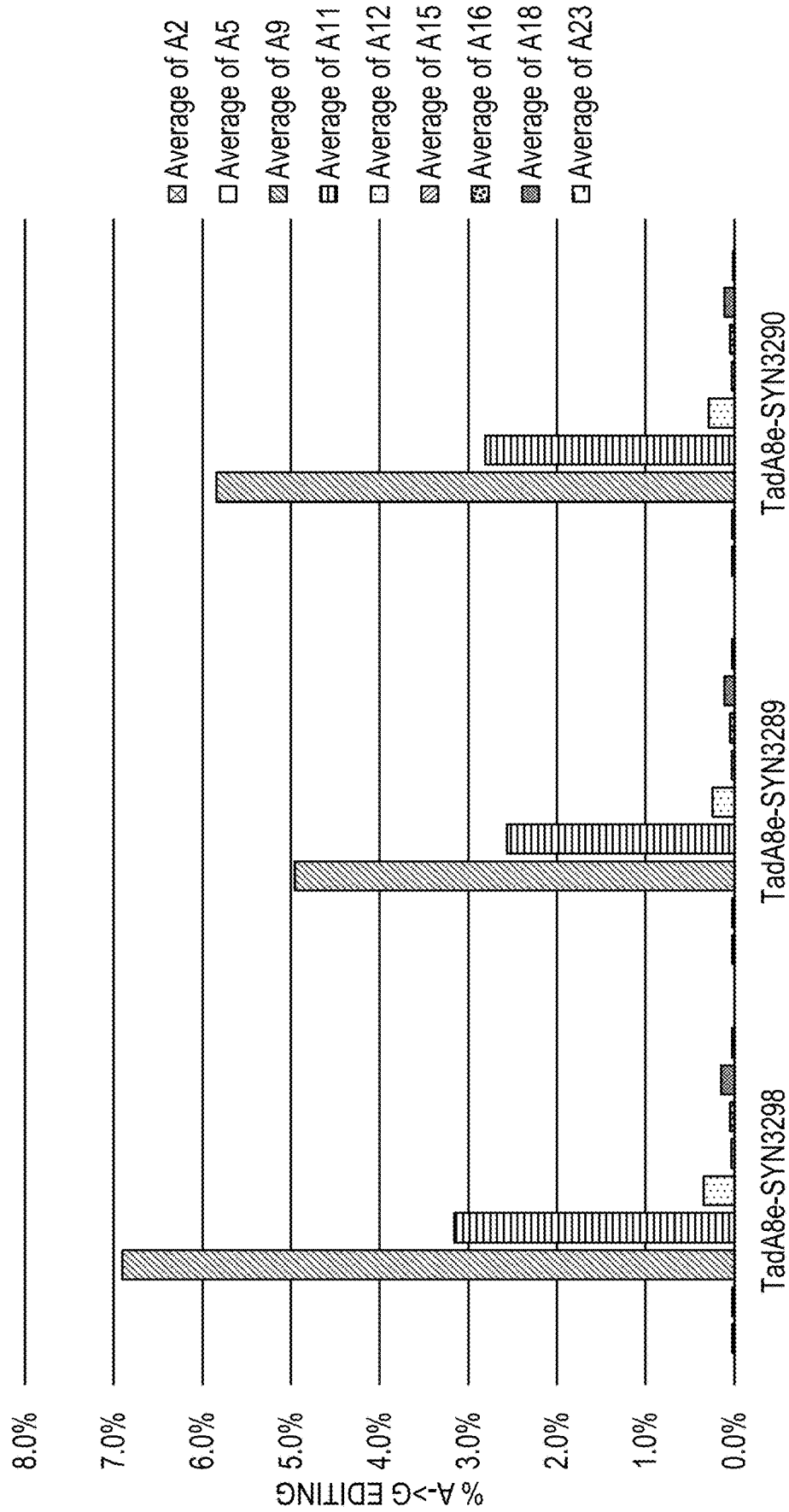
FIGS. 22-23 are graphs showing the percentage of A to G editing for various target regions corresponding to the respective spacers: RNF2 spacer 1 (FIG. 22) and RNF2 spacer 2 (FIG. 23).
Figure 23:
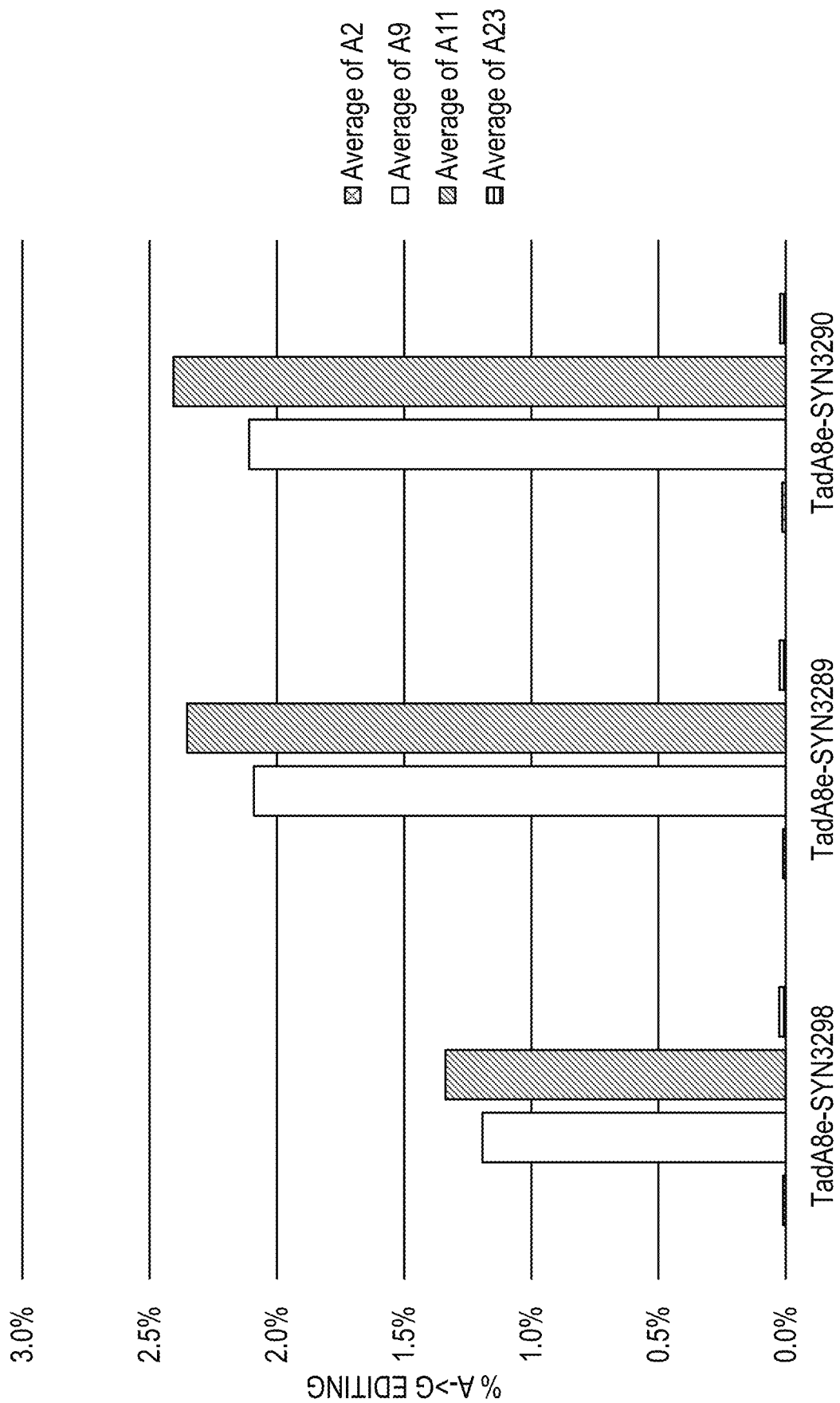
Figure 24:
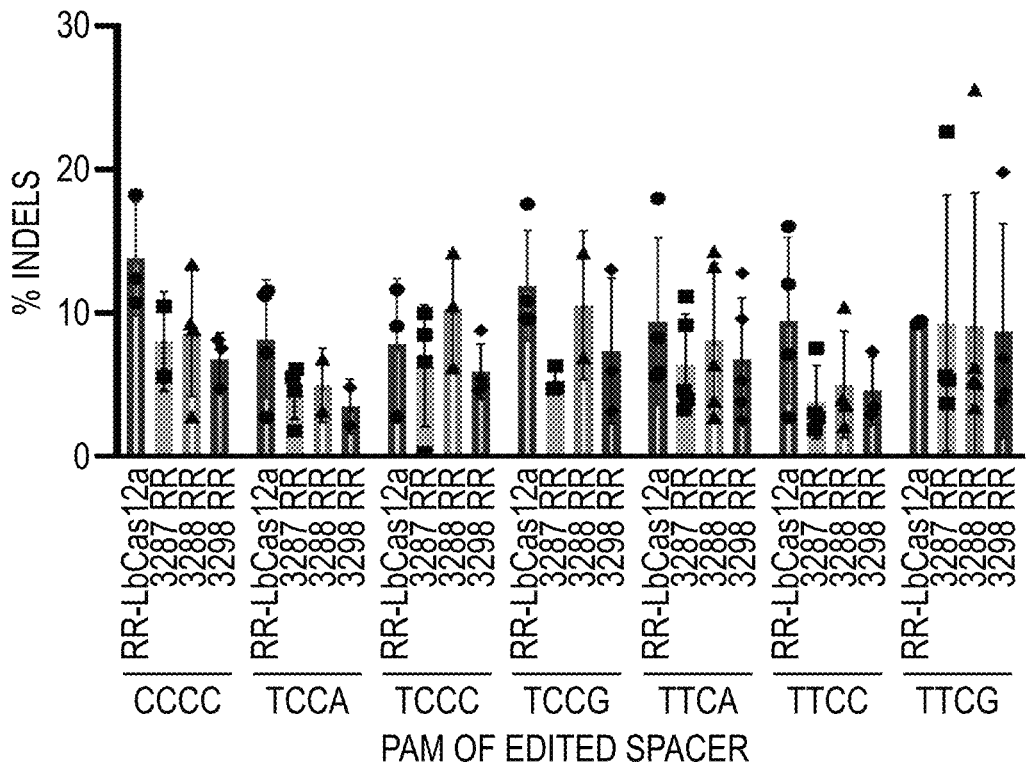
FIG. 24 is a graph showing the indel generation frequency of RR-LbCas12a and three synthetic enzymes (3287 RR, 3288 RR, and 3298RR), which each included G532R and K595R (RR) mutations with reference to position numbering of SEQ ID NO:180 (LbCas12a), at known, non-native protospacer adjacent motif (PAM) sequences.
Figure 25:
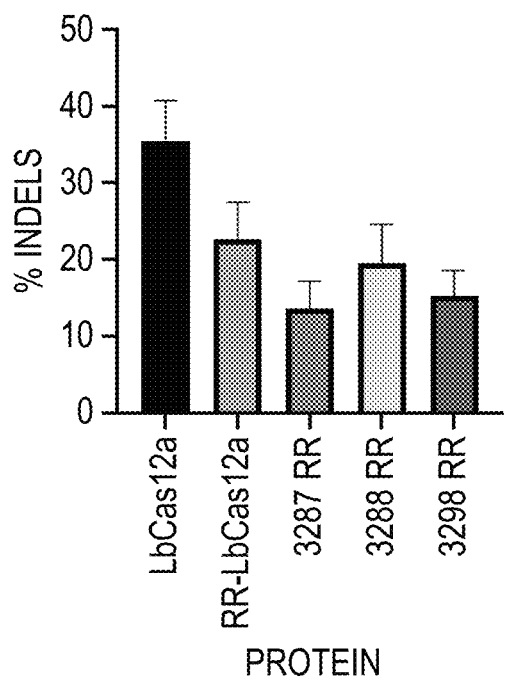
FIG. 25 is a graph showing the indel generation frequency of LbCas12a, RR-LbCas12a, 3287 RR, 3288 RR, and 3298 RR at native TTTV PAM sequences.
Figure 26:
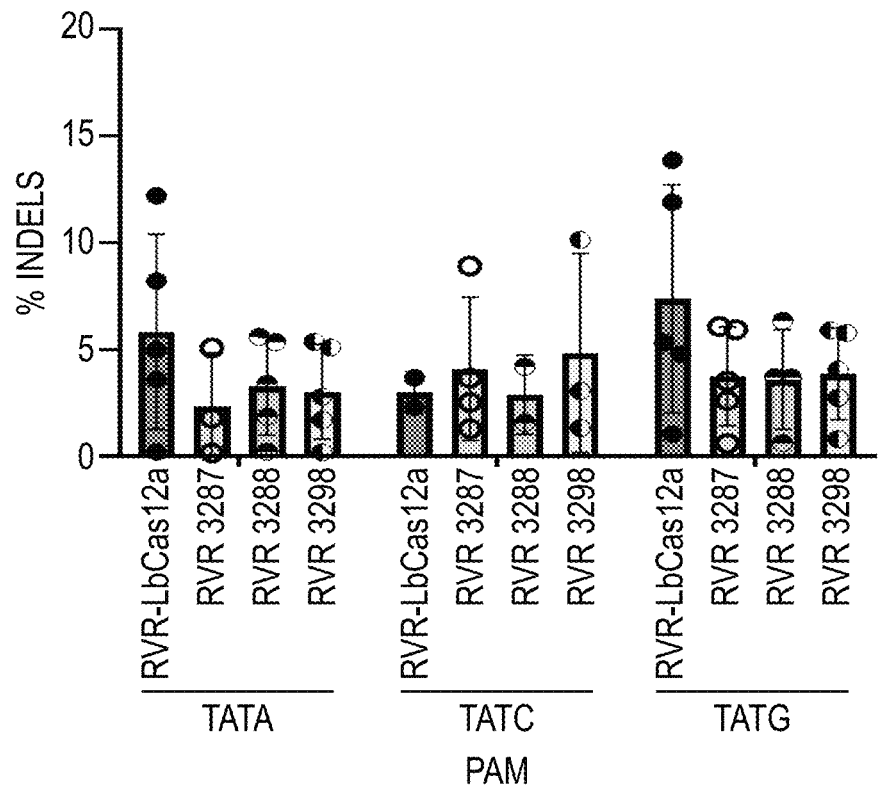
FIG. 26 is a graph showing the indel generation frequency of RVR-LbCas12a (having G532R, K538V, and Y542R (RVR) mutations) and RVR 3287, RVR 3288, and RVR 3298, which each included G532R, K538V, and Y542R (RVR) mutations with reference to position numbering of SEQ ID NO:180 (LbCas12a), at known, non-native PAM sequences.
Figure 27:
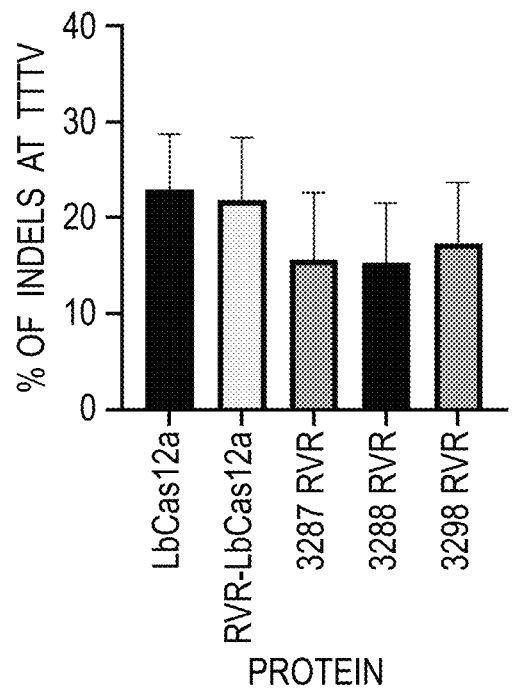
FIG. 27 is a graph showing the indel generation frequency of LbCas12a, RVR-LbCas12a (having G532R, K538V, and Y542R (RVR) mutations) and 3287 RVR, 3288 RVR, and 3298 RVR, which each included G532R, K538V, and Y542R (RVR) mutations with reference to position numbering of SEQ ID NO:180 (LbCas12a), at native TTTV PAM sequences.

Adenine base editing data for synthetic enzymes SYN3289, SYN3290, and SYN3298 as N-terminal fusions to the TadA8e adenine deaminase was obtained (FIGS. 22-23). The synthetic enzymes were fused to TadA8e (SEQ ID NO:155) using a linker (SEQ ID NO:47) to provide SEQ ID NOs:166-168. All percentages shown in FIGS. 22-23 indicate averages across three data points. The three tested designs all demonstrated adenine base editing activity when fused with TadA8e. The spacer for FIG. 22 was SEQ ID NO:148 and the spacer for FIG. 23 was SEQ ID NO:149.

Example 7

The PAM specificity of the engineered proteins described herein will be tested using the PAM-SCANR assay (Leenay, R. T. et al. *Mol Cell* 62, 137-147 (2016)) Briefly, an inactivated version of the synthetic enzyme (e.g., SYN3298 having a H370A mutation (i.e., SYN3298 with an alanine at amino acid residue number 370 to provide an inactivating mutation in the HNH domain)) will be expressed in a library of bacteria containing all 256 possible 4-base 5' PAMs in the promoter of a lacI gene and a GFP gene controlled by a lacZ promoter. In cells where the synthetic enzyme binds to the PAM, the lacI protein will not be expressed, allowing the expression of GFP, and the cells will fluoresce. Fluorescent cells will then be isolated by cell sorting and sequenced to determine which PAMs can be bound by the synthetic enzyme.

Example 8

The PAM specificity for synthetic enzymes SYN3287, SYN3288, and SYN3298 and mutants thereof was tested with native TTTV PAM sequences (where V is A, G, or C) and/or non-native PAM sequences (e.g., CCCC, TCCA, TCCC, TCCG, TTCA, TTCC, TTCG, TATA, TATC, or TATG). Specifically, SYN3287, SYN3288, or SYN3298 with either G532R and K595R (RR) mutations with reference to position numbering of SEQ ID NO:180 (LbCas12a); G532R, K538V, and Y542R (RVR) mutations with reference to position numbering of SEQ ID NO:180 (LbCas12a); or D156R mutation were tested, and the indel generation frequency was determined. RR-LbCas12a has G532R and K595R mutations (SEQ ID NO:181); 3298 RR has G680R and K743R mutations (SEQ ID NO:184); 3287 RR has G676R and K739R mutations (SEQ ID NO:187); 3288 RR has G678R and K741R mutations (SEQ ID NO:190); RVR-LbCas12a has G532R, K538V, and Y542R mutations (SEQ ID NO:182); 3298 RVR has G680R, K686V, and Y690R mutations (SEQ ID NO:185); 3287 RVR has G676R, K682V, and Y686R mutations (SEQ ID NO:188); 3288 RVR has G678R, K684V, and Y688R mutations (SEQ ID NO:191); LbCas12a D156R has a D156R mutation (SEQ ID NO:183); 3298 D156R has a D156R mutation (SEQ ID NO:186); 3287 D156R has a D156R mutation (SEQ ID NO:189); and 3288 D156R has a D156R mutation (SEQ ID NO:192), each with reference to the referred to sequence's own position numbering.

HEK293-T Cell Testing

HEK293T cells were seeded into 48-well collagen-coated plates (Corning) in the absence of antibiotic using DMEM media. At 70-80% confluency, cells were transfected with 1.5 µL of Lipofectamine 3000 (ThermoFisher Scientific) using 750 ng of editor plasmid and 250 ng of guide RNA plasmid according to manufacturer's protocol. After 3 days, cells were lysed, and DNA was extracted using MagMax DNA extraction kit (Applied Biosystems). Samples were sequenced using NGS, and editing efficiencies were calculated as the average percentage of reads containing desired edits across all available technical replicates.

Plant Testing

For each PAM sequence to be tested, five spacers each in corn and soy were designed, each spacer targeting a unique locus. Plasmids expressing the editor and spacers to be tested were transformed into corn or soy dried excised embryos (DEEs) via a standard *Agrobacterium* transformation protocol. After 10 weeks, plantlets were sampled destructively, and all editing targets were sequenced using NGS. Editing efficiencies were calculated for each target as the percentage of analyzed samples containing desired edits comprising at least 1% or 10% of sequenced reads.

Results

Figure 28:
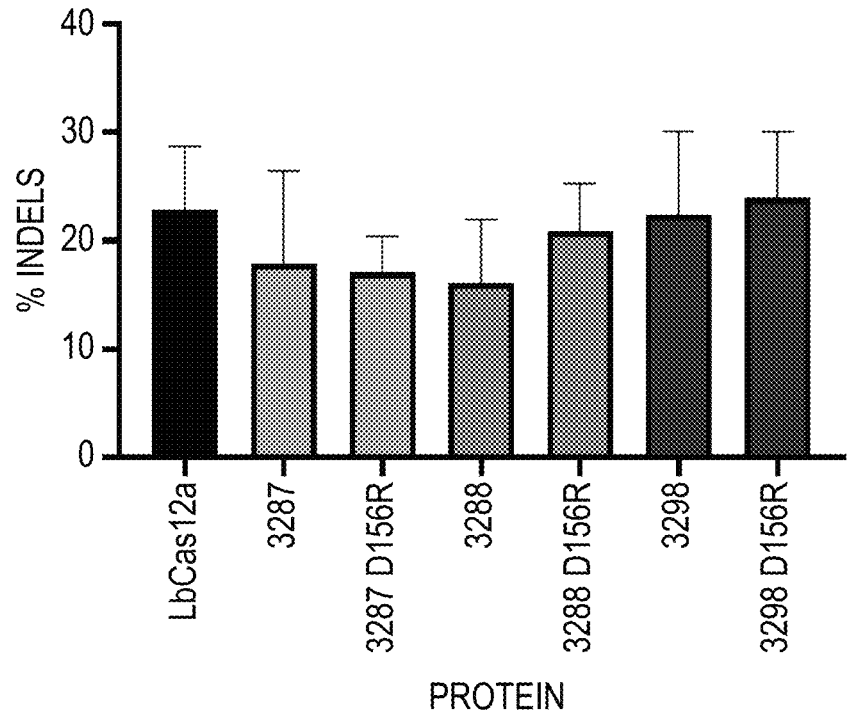
FIGS. 28-31 are graphs showing biological replicates of the indel generation frequency of LbCas12a, 3287, 3288, and 3298; as well as 3287 D156R, 3288 D156R, and 3298 D156R, which included a D156R mutation with reference to position numbering of SEQ ID NO:180 (LbCas12a), at native TTTV PAM sequences.
Figure 29:
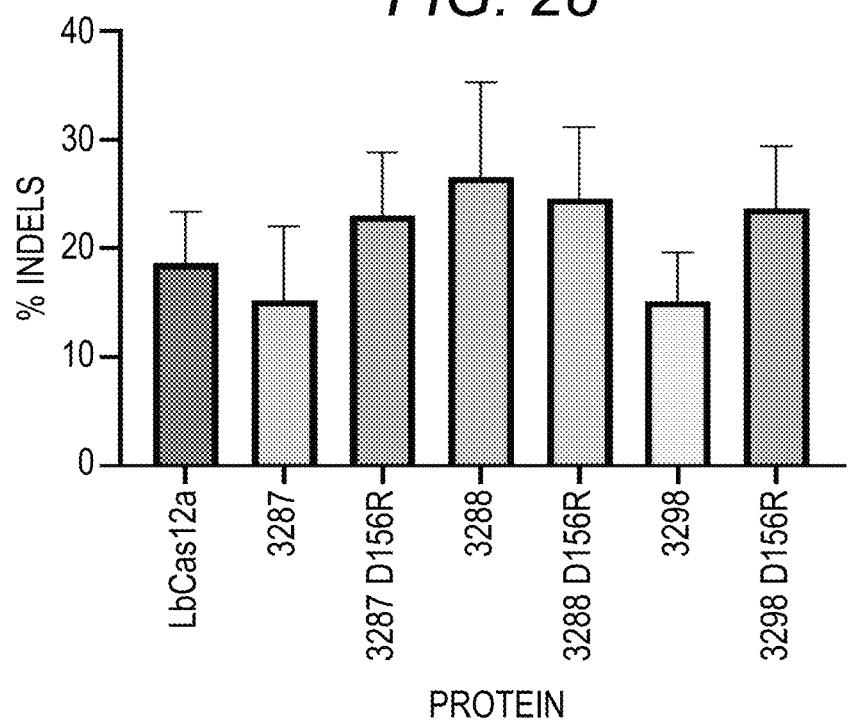
Figure 30:
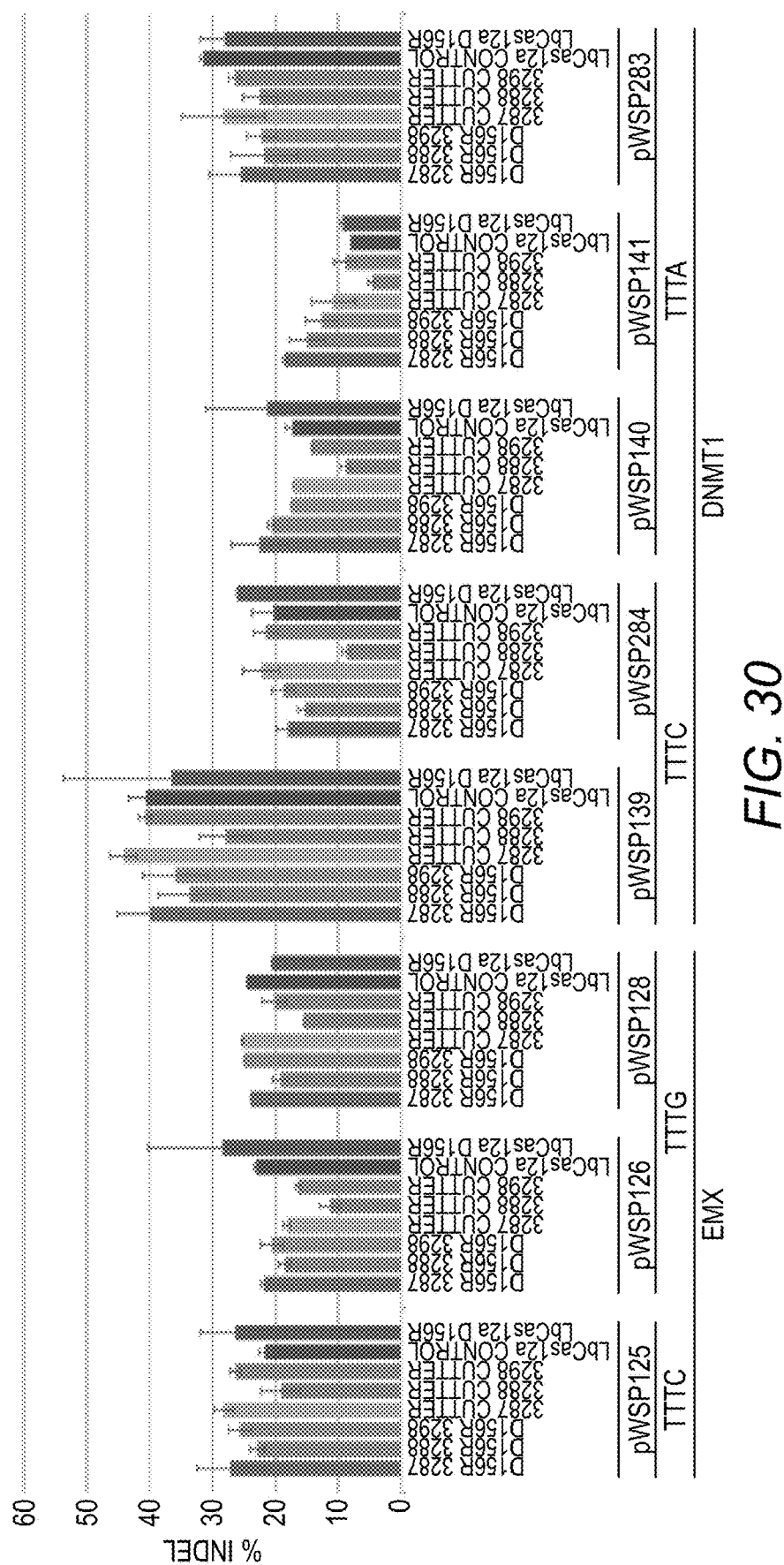
Figure 31:
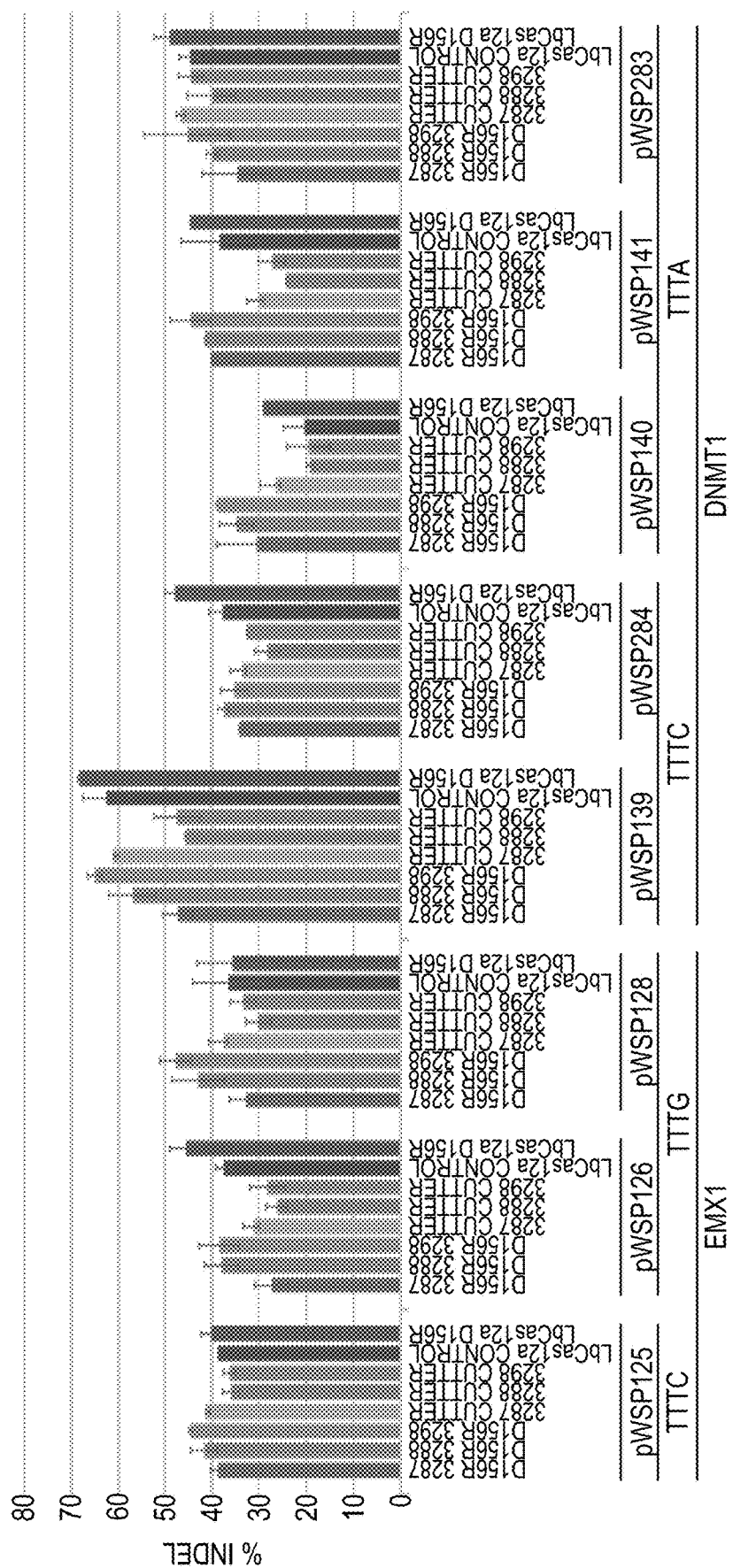
Figure 32:
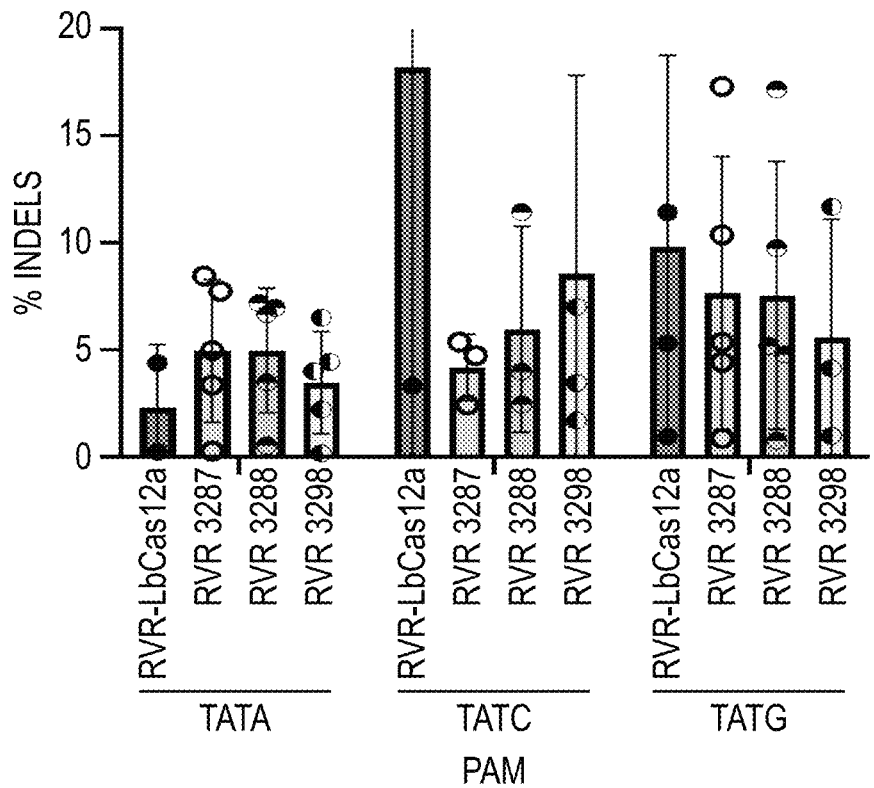
FIG. 32 is a graph showing the indel generation frequency of RVR-LbCas12a, RVR 3287, RVR 3288, and RVR 3298 at known, non-native PAM sequences.
Figure 33:
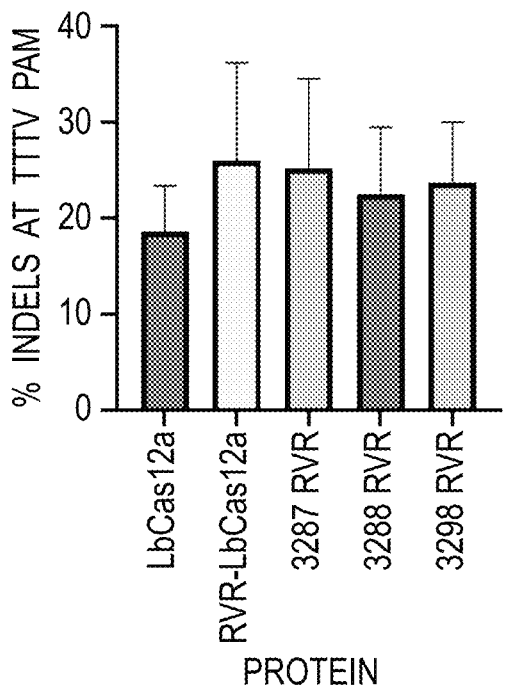
FIG. 33 is a graph showing the indel generation frequency LbCas12a, RVR-LbCas12a, 3287 RVR, 3288 RVR, and 3298 RVR at native TTTV PAM sequences.

The results are provided in FIGS. 24-33 and Tables 3-10. All proteins tested, with the exception of SYN3288, appear to be as efficient as LbCas12a and D156R controls against all eight TTTV spacers tested. The D156R mutants did not significantly alter PAM specificity and did not negatively affect recognition of TTTV PAM sequences (FIGS. 28-29).

In soy and corn plants, the RR and RVR mutations in SYN3298 (SYN3298-RR and SYN3298-RVR) were shown to have binding affinity for native TTTV PAM sequences and for non-native PAM sequences (Tables 3-10). SYN3298 (SEQ ID NO:131), SYN3298-RR (SEQ ID NO:184), and SYN3298-RVR (SEQ ID NO: 185).

TABLE 3

Total counts of desired edit for five different spacers testing SYN3298, SYN3298-RR, and SYN3298-RVR in soy.

| Protein | PAM type | PAM sequence | Spacer 1 total counts | Spacer 2 total counts | Spacer 3 total counts | Spacer 4 total counts | Spacer 5 total counts |
|---|---|---|---|---|---|---|---|
| SYN3298 | Native | TTTV | 174 | 118 | 148 | 134 | 151 |
| SYN3298-RR | Native | TTTA | 8 | 6 | 7 | 8 | 9 |
|  |  | TTTC | 12 | 7 | 12 | 8 | 10 |
|  |  | TTTG | 40 | 27 | 40 | 40 | 40 |
|  | Non-native | CCCC | 1 | 0 | 0 | 0 | 0 |
|  |  | TCCA | 2 | 0 | 0 | 1 | 1 |
|  |  | TCCC | 40 | 38 | 36 | 39 | 31 |
|  |  | TCCG | 40 | 39 | 26 | 40 | 36 |
|  |  | TTCA | 1 | 17 | 1 | 47 | 3 |
|  |  | TTCC | 0 | 32 | 0 | 0 | 0 |
|  |  | TTCG | 39 | 40 | 17 | 40 | 39 |
| SYN3298-RVR | Native | TTTG | 37 | 40 | 40 | 40 | 14 |
|  | Non-native | TATA | 34 | 37 | 39 | 36 | 38 |
|  |  | TATC | 29 | 40 | 0 | 20 | 35 |
|  |  | TATG | 0 | 39 | 28 | 36 | 40 |

TABLE 4

Percentage of samples with ≥1% editing for each of the five different spacers used to test SYN3298, SYN3298-RR, and SYN3298-RVR in soy. A "—" indicates that no data were returned for a given spacer.

| | | % Samples with ≥1% editing | | | | |
|---|---|---|---|---|---|---|
| Enzyme | PAM | Spacer 1 | Spacer 2 | Spacer 3 | Spacer 4 | Spacer 5 |
| SYN3298 | TTTV | 64.9 | 78 | 3.4 | 26.9 | 68.5 |
| SYN3298-RR | TTTA | 87.5 | 100 | 14.3 | 62.5 | 77.8 |
|  | TTTC | 0 | 0 | 0 | 50 | 100 |
|  | TTTG | 2.5 | 77.8 | 80 | 0 | 2.5 |
|  | CCCC | 100 | — | — | — | — |
|  | TCCA | 0 | — | — | 0 | 0 |
|  | TCCC | 75 | 79 | 33.3 | 30.8 | 0 |
|  | TCCG | 100 | 33.3 | 19.2 | 42.5 | 0 |
|  | TTCA | 0 | 58.8 | 0 | 23.4 | 66.7 |
|  | TTCC | — | 19 | — | — | — |
|  | TTCG | 51.3 | 0 | 0 | 0 | 20.5 |
| SYN3298-RVR | TTTG | 2.7 | 60 | 57.5 | 2.5 | 0 |
|  | TATA | 2.9 | 0 | 2.6 | 0. | 0 |
|  | TATC | 0.00 | 0 | — | 15 | 0 |
|  | TATG | — | 0 | 0 | 0 | 0 |

TABLE 5

Percentage of samples with ≥10% editing for each of the five different spacers used to test SYN3298, SYN3298-RR, and SYN3298-RVR in soy. A "—" indicates that no data were returned for a given spacer.

| | | % Samples with ≥10% Editing | | | | |
| --- | --- | --- | --- | --- | --- | --- |
| Enzyme | PAM | Spacer 1 | Spacer 2 | Spacer 3 | Spacer 4 | Spacer 5 |
| SYN3298 | TTTV | 29.2 | 44.7 | 1.6 | 8.9 | 31.4 |
| SYN3298-RR | TTTA | 75 | 66.7 | 0 | 0 | 22 |
| | TTTC | 0 | 0 | 0 | 25 | 10 |
| | TTTG | 2.5 | 14.8 | 30 | 0 | 0 |
| | CCCC | 10 | — | — | — | — |
| | TCCA | 0 | — | — | 0 | 0 |
| | TCCC | 22.5 | 18.4 | 2.8 | 2.6 | 0 |
| | TCCG | 30 | 15.4 | 0 | 12.5 | 0 |
| | TTCA | 0 | 29.4 | 0 | 2.1 | 0 |
| | TTCC | — | 9.4 | — | — | — |
| | TTCG | 2.6 | 0 | 0 | 0 | 2.6 |
| SYN3298-RVR | TTTG | 0 | 22.5 | 17.5 | 0 | 0 |
| | TATA | 0 | 0 | 0 | 0 | 0 |
| | TATC | 0 | 0 | — | 0 | 0 |
| | TATG | — | 0 | 0 | 0 | 0 |

TABLE 6

Overall PAM specificity of SYN3298, SYN3298-RR, and SYN3298-RVR in soy.

| Protein | PAM type | PAM sequence | Samples with desired edits comprising at least 1% of total sequence reads | Samples with desired edits comprising at least 10% of total sequence reads | Total samples |
| --- | --- | --- | --- | --- | --- |
| SYN3298 | Native | TTTV | 48.2% | 19.6% | 725 |
| SYN3298-RR | Native | TTTA | 68.4% | 31.6% | 38 |
| | | TTTC | 28.6% | 6.1% | 49 |
| | | TTTG | 29.4% | 9.1% | 187 |
| | Non-native | CCCC | 100% | 100% | 1 |
| | | TCCA | 0% | 0% | 4 |
| | | TCCC | 45.7% | 9.8% | 184 |
| | | TCCG | 41.4% | 12.7% | 181 |
| | | TTCA | 33.3% | 8.7% | 69 |
| | | TTCC | 18.8% | 9.4% | 32 |
| | | TTCG | 16% | 1.1% | 175 |
| SYN3298-RVR | Native | TTTG | 28.7% | 9.4% | 171 |
| | Non-native | TATA | 1.1% | 0% | 184 |
| | | TATC | 2.4% | 0% | 124 |
| | | TATG | 0% | 0% | 143 |

TABLE 7

Total counts of desired edit for five different spacers testing SYN3298, SYN3298-RR, and SYN3298-RVR in corn.

| Protein | PAM type | PAM sequence | Spacer 1 total counts | Spacer 2 total counts | Spacer 3 total counts | Spacer 4 total counts | Spacer 5 total counts |
| --- | --- | --- | --- | --- | --- | --- | --- |
| SYN3298 | Native | TTTV | 0 | 401 | 452 | 405 | 509 |
| SYN3298-RR | Native | TTTA | 83 | 77 | 107 | 97 | 89 |
| | | TTTC | 0 | 60 | 77 | 80 | 54 |
| | | TTTG | 39 | 47 | 48 | 47 | 44 |
| | Non-native | TTCA | 91 | 36 | 65 | 0 | 62 |
| | | TCCG | 34 | 20 | 0 | 27 | 28 |
| | | CCCC | 58 | 37 | 81 | 91 | 0 |
| | | TCCA | 33 | 24 | 28 | 0 | 25 |

TABLE 7-continued

Total counts of desired edit for five different spacers testing SYN3298, SYN3298-RR, and SYN3298-RVR in corn.

| Protein | PAM type | PAM sequence | Spacer 1 total counts | Spacer 2 total counts | Spacer 3 total counts | Spacer 4 total counts | Spacer 5 total counts |
|---|---|---|---|---|---|---|---|
| | | TCCC | 18 | 30 | 39 | 0 | 37 |
| | | TTCC | 0 | 47 | 46 | 49 | 2 |
| | | TTCG | 33 | 39 | 13 | 15 | 0 |
| SYN3298-RVR | Native | TTTA | 15 | 12 | 13 | 0 | 6 |
| | | TTTC | 0 | 16 | 19 | 0 | 13 |
| | | TTTG | 17 | 16 | 0 | 20 | 22 |

TABLE 8

Percentage of samples with ≥1% editing for each of the five different spacers used to test SYN3298, SYN3298-RR, and SYN3298-RVR in corn. A "—" indicates that no data were returned for a given spacer.

| | | % Samples with ≥1% editing | | | | |
|---|---|---|---|---|---|---|
| Protein | PAM | Spacer 1 | Spacer 2 | Spacer 3 | Spacer 4 | Spacer 5 |
| SYN3298 | TTTV | 509 | — | 20.5 | 0.9 | 18.8 |
| SYN3298-RR | TTTA | 89 | 12.1 | 32.5 | 32.7 | 0 |
| | TTTC | 54 | — | 3.3 | 9.1 | 8.8 |
| | TTTG | 44 | 0 | 0 | 6.3 | 4.3 |
| | CCCC | 0 | 12.1 | 0 | 0 | 4.4 |
| | TCCA | 25 | 9.1 | 0 | 0 | — |
| | TCCC | 37 | 16.7 | 16.7 | 2.6 | — |
| | TCCG | 28 | 0 | 5 | — | 3.7 |
| | TTCA | 62 | 7.7 | 2.8 | 9.2 | — |
| | TTCC | 2 | — | 34.1 | 52.2 | 10.2 |
| | TTCG | 0 | 3 | 10.3 | 30.8 | 0 |
| SYN3298-RVR | TTTA | 6 | 0 | 0 | 7.7 | — |
| | TTTC | 13 | — | 0.00 | 10.5 | — |
| | TTTG | 22 | 5.9 | 0 | — | 5 |

TABLE 9

Percentage of samples with ≥10% editing for each of the five different spacers used to test SYN3298, SYN3298-RR, and SYN3298-RVR in corn. A "—" indicates that no data were returned for a given spacer.

| | | % Samples with ≥10% Editing | | | | |
|---|---|---|---|---|---|---|
| Protein | PAM | Spacer 1 | Spacer 2 | Spacer 3 | Spacer 4 | Spacer 5 |
| SYN3298 | TTTV | 27.9 | — | 15.7 | 0.4 | 13.8 |
| SYN3298-RR | TTTA | 19.1 | 6 | 28.6 | 28 | 0 |
| | TTTC | 5.6 | — | 1.7 | 6.5 | 8.8 |
| | TTTG | 0 | 0 | 0 | 6.3 | 2 |
| | CCCC | — | 12.1 | 0 | 0 | 3.3 |
| | TCCA | 0 | 5.5 | 0 | 0 | — |
| | TCCC | 5.4 | 11.1 | 16.7 | 2.6 | — |
| | TCCG | 0 | 0 | 5 | — | 0 |
| | TTCA | 0 | 4.4 | 0 | 3.1 | — |
| | TTCC | 0 | — | 17.9 | 33.3 | 6.8 |
| | TTCG | — | 3 | 10.3 | 23.1 | 0 |
| SYN3298-RVR | TTTA | 0 | 0 | 0 | 0 | — |
| | TTTC | 7.7 | — | 0 | 10.5 | — |
| | TTTG | 0 | 5.9 | 0 | — | 5 |

TABLE 10

PAM specificity of SYN3298, SYN3298-RR, and SYN3298-RVR in corn.

| Protein | PAM type | PAM sequence | Samples with desired edits comprising at least 1% of total sequence reads | Samples with desired edits comprising at least 10% of total sequence reads | Total samples |
|---|---|---|---|---|---|
| SYN3298 | Native | TTTV | 17.2% | 13.9% | 1767 |
| SYN3298-RR | Native | TTTA | 19.2% | 15% | 453 |
|  |  | TTTC | 7% | 5.9% | 271 |
|  |  | TTTG | 2.2% | 1.8% | 225 |
|  | Non-native | TTCA | 5.5% | 2.4% | 254 |
|  |  | TCCG | 1.8% | 0.9% | 109 |
|  |  | CCCC | 4.1% | 3.7% | 267 |
|  |  | TCCA | 2.7% | 1.6% | 110 |
|  |  | TCCC | 8.9% | 8.1% | 124 |
|  |  | TTCC | 31.3% | 18.9% | 144 |
|  |  | TTCG | 9% | 8% | 100 |
| SYN3298-RVR | Native | TTTA | 2.2% | 0% | 46 |
|  |  | TTTC | 6.3% | 6.3% | 48 |
|  |  | TTTG | 2.7% | 2.7% | 75 |

Example 9

A LbCas12a mutant as described herein was tested for its ability to recognize non-native PAM sequences. The ability of LbCas2a-RR to recognize non-native PAM sequences was tested by measuring INDEL % in HEK293T cells using spacers immediately following the non-native PAM sequences indicated in the table below.

TABLE 11

Average INDEL% generated by LbCas12a-RR with spacers having the indicated PAMs in HEK293T cells.
LbCas12a-RR Non-native PAM Recognition in HEK293Ts

| PAM | Type of PAM Access | Average INDEL % | Number of Spacers |
|---|---|---|---|
| TTTA | LbCas12a-Wildtype | 37.7 | 3 |
| TTTC | LbCas12a-Wildtype | 39.5 | 3 |
| TTTG | LbCas12a-Wildtype | 42.5 | 2 |
| TTAA | Expanded Access | 16.7 | 3 |
| TTAC | Expanded Access | 30.7 | 3 |
| ACCA | Expanded Access | 17.4 | 3 |
| ACCC | Expanded Access | 22.1 | 3 |
| ACCG | Expanded Access | 24.6 | 3 |
| ATCA | Expanded Access | 1.9 | 5 |
| ATCC | Expanded Access | 7.1 | 3 |
| ATCG | Expanded Access | 0.8 | 4 |
| CCCA | Expanded Access | 29.1 | 3 |
| CCCC | Published Access | 13.8 | 3 |
| CCCG | Expanded Access | 37.4 | 2 |
| CTCA | Expanded Access | 18.9 | 3 |
| CTCC | Expanded Access | 19.6 | 3 |
| CTCG | Expanded Access | 16.4 | 3 |
| GCCA | Expanded Access | 19.6 | 3 |
| GCCC | Expanded Access | 41.7 | 3 |
| GCCG | Expanded Access | 8.9 | 3 |
| GTCA | Expanded Access | 16.2 | 3 |
| GTCC | Expanded Access | 14.1 | 3 |
| GTCG | Expanded Access | 10.9 | 3 |
| GTCT | Expanded Access | N/A | N/A |
| TCCA | Published Access | 8.2 | 4 |
| TCCC | Published Access | 7.9 | 3 |
| TCCG | Published Access | 11.9 | 4 |
| TCCT | Published Access | 9.9 | 3 |
| TTCA | Published Access | 9.5 | 4 |
| TTCC | Published Access | 9.5 | 4 |
| TTCG | Published Access | 9.4 | 2 |
| TTCT | Expanded Access | 2.3 | 5 |
| ACTA | Expanded Access | 27 | 4 |
| ACTC | Expanded Access | 10.3 | 3 |
| ACTG | Expanded Access | 11.8 | 3 |
| ATTA | Expanded Access | 21.9 | 3 |

TABLE 11-continued

Average INDEL% generated by LbCas12a-RR with spacers having the indicated PAMs in HEK293T cells.
LbCas12a-RR Non-native PAM Recognition in HEK293Ts

| PAM | Type of PAM Access | Average INDEL % | Number of Spacers |
|---|---|---|---|
| ATTC | Expanded Access | 15 | 3 |
| ATTG | Expanded Access | 18.3 | 3 |
| CCTA | Expanded Access | 18.6 | 4 |
| CCTC | Expanded Access | 22.2 | 1 |
| CCTG | Expanded Access | 13 | 2 |
| CTTA | Expanded Access | 3.2 | 4 |
| CTTC | Expanded Access | 1.5 | 5 |
| CTTG | Expanded Access | 1.5 | 5 |
| GCTA | Expanded Access | 23.3 | 3 |
| GCTC | Expanded Access | 13.9 | 3 |
| GCTG | Expanded Access | 18 | 3 |
| GTTA | Expanded Access | 26.9 | 3 |
| GTTC | Expanded Access | 9.0 | 3 |
| GTTG | Expanded Access | 9.3 | 3 |
| TCTA | Expanded Access | 34 | 4 |
| TCTC | Expanded Access | 25.1 | 3 |
| TCTG | Expanded Access | 20.7 | 3 |
| TCTT | Expanded Access | 15.6 | 2 |
| TTTT | Expanded Access | 25.7 | 2 |

LbCas12a-RR "expanded access" and LbCas12a-RR "published access" comprise a mutation located at position 532 and at 595 with reference to position numbering of the amino acid sequence of SEQ ID NO:180, which alters PAM recognition specificity. Specifically, the mutation at position 532 is G532R and at position 595, the mutation is K595R. As shown in Table 11 above, LbCas12a-RR was able to generate INDELs using spacers that required the enzyme to recognize non-native PAMs (the non-native PAM was immediately upstream of the spacer). In addition to the Cas12a-wildtype TTTV PAMs and the previously published Cas12a-RR PAMs, the enzyme was able to recognize an additional 44 PAMs.

Example 10

A LbCas12a mutant as described herein was tested for its ability to recognize non-native PAM sequences. The ability of LbCas12a-RVR to recognize non-native PAM sequences was tested by measuring INDEL % in HEK293T cells using spacers immediately following the non-native PAM sequences indicated in the table below.

TABLE 12

Average INDEL% generated by LbCas 12a-RVR with spacers having the indicated PAMs in HEK293T cells.
LbCas12a-RVR Non-native PAM Recognition in HEK293Ts

| PAM | Type of PAM Access | Average INDEL % | Number of Spacers |
|---|---|---|---|
| TTTA | Wild-Type LbCas12a | 21.1 | 3 |
| TTTC | Wild-Type LbCas12a | 27.7 | 3 |
| TTTG | Wild-Type LbCas12a | 18.6 | 2 |
| AACC | Expanded access | 8.6 | 3 |
| TACC | Expanded access | 22.3 | 3 |
| AATC | Expanded access | 17.2 | 3 |
| GATA | Expanded access | 14.9 | 3 |
| GATC | Expanded access | 11.8 | 2 |
| GATG | Expanded access | 13.7 | 3 |
| TATA | Published Access | 2.3 | 2 |
| TATC | Published Access | 18.2 | 2 |
| TATG | Published Access | 9.8 | 4 |

LbCas12a-RVR expanded polypeptide mutant and LbCas12a-RVR published access polypeptide mutant each comprise a mutation located at position 532, 542 and at 538 with reference to position numbering of the amino acid sequence of SEQ ID NO:180, which alters PAM recognition specificity. Specifically, the mutation at position 532 is G532R, the mutation at position 542 is Y542R and the mutation at position 538 is K538V. As shown in the table above, LbCas12a-RVR was able to generate INDELs using spacers that required the enzyme to recognize non-native PAMs (the non-native PAM was immediately upstream of the spacer). In addition to the Cas12a-wildtype TTTV PAMs and the previously published Cas12a-RVR PAMs, the enzyme was able to recognize an additional 8 PAMs.

Example 11

An engineered protein as described herein was tested for its ability to recognize non-native PAM sequences. The ability of SYN3298 (G680R+K743R) to recognize non-native PAM sequences was tested by measuring INDEL % in HEK293T cells using spacers immediately following the non-native PAM sequences shown in Table 13 below.

TABLE 13

Average INDEL% generated by an engineered protein (SEQ ID NO: 184) with spacers having the indicated PAMs in HEK293T cells.
Engineered Protein (SEQ ID NO: 184) Non-native PAM Recognition in HEK293Ts

| PAM | Average INDEL % | Number of Spacers |
|---|---|---|
| TTTA | 11.2 | 3 |
| TTTC | 14.7 | 3 |
| TTTG | No data received | 3 |
| TTAA | | |

TABLE 13-continued

Average INDEL% generated by an engineered protein (SEQ ID NO: 184) with spacers having the indicated PAMs in HEK293T cells. Engineered Protein (SEQ ID NO: 184) Non-native PAM Recognition in HEK293Ts

| PAM | Average INDEL % | Number of Spacers |
|---|---|---|
| TTAC | | |
| ACCA | | |
| ACCC | | |
| ACCG | | |
| ATCA | | |
| ATCC | | |
| ATCG | | |
| CCCA | | |
| CCCC | 6.8 | 3 |
| CCCG | | |
| CTCA | | |
| CTCC | | |
| CTCG | | |
| GCCA | | |
| GCCC | | |
| GCCG | | |
| GTCA | | |
| GTCC | | |
| GTCG | | |
| GTCT | | |
| TCCA | 3.5 | 2 |
| TCCC | 6 | 4 |
| TCCG | 7.4 | 3 |
| TCCT | | |
| TTCA | 6.8 | 5 |
| TTCC | 4.6 | 3 |
| TTCG | 8.8 | 4 |
| TTCT | | |
| ACTA | | |
| ACTC | | |
| ACTG | | |
| ATTA | | |
| ATTC | | |
| ATTG | | |
| CCTA | | |
| CCTC | | |
| CCTG | | |
| CTTA | | |
| CTTC | | |
| CTTG | | |
| GCTA | | |
| GCTC | | |
| GCTG | | |
| GTTA | | |
| GTTC | | |
| GTTG | | |
| TCTA | | |
| TCTC | | |
| TCTG | | |
| TCTT | | |
| TTTT | | |

Engineered protein SYN3298 (SEQ ID NO:184) comprising a mutation located at position 680 and at 743 with reference to position numbering of the amino acid sequence of SEQ ID NO:184 and having altered PAM specificity was tested for the ability to recognize natural (wild-type LbCas12a) PAM sequences and non-natural PAM sequences. Specifically, the mutation located at position 680 is G680R and the mutation located at position 743 is K743R. As shown Table 13 above, the engineered protein SEQ ID NO:184 was able to generate INDELs using spacers that required the enzyme to recognize non-native PAMs (the non-native PAM was immediately upstream of the spacer). In addition to the expected TTTV PAMs, the enzyme was able to recognize an additional 7 PAMs in human cells. Note that PAMs having blank rows were not tested in HEK293 Ts with the engineered protein (SEQ ID NO:184).

Example 12

An engineered protein as described herein was tested for its ability to recognize non-native PAM sequences. The ability of SYN3298 (G680R+K686V+Y690R) to recognize non-native PAM sequences was tested by measuring INDEL % in HEK293T cells using spacers immediately following the non-native PAM sequences indicated in Table 14 below.

TABLE 14

Average INDEL% generated by an engineered protein (SEQ ID NO: 185) with spacers having the indicated PAMs in HEK293T cells. Engineered Protein (SEQ ID NO: 185) Non-native PAM Recognition in HEK293Ts

| PAM | Average INDEL % | Number of Spacers |
|---|---|---|
| TTTA | 16.3 | 3 |
| TTTC | 24.3 | 3 |
| TTTG | 24.9 | 2 |
| TATA | 5 | 2 |
| TATC | 4.7 | 2 |
| TATG | 7.2 | 4 |
| AACC | To be tested | |
| TACC | To be tested | |
| AATC | To be tested | |
| GATA | To be tested | |
| GATC | To be tested | |
| GATG | To be tested | |
| AATA | To be tested | |
| AATG | To be tested | |

Engineered protein SYN3298 (SEQ ID NO:185) comprising a mutation located at position 680, at position 690, and at position 686 with reference to position numbering of the amino acid sequence of SEQ ID NO:185 and having altered PAM specificity was tested for the ability to recognize natural (wild-type LbCas12a) PAM sequences and non-natural PAM sequences. Specifically, the mutation located at position 680 is G680R, the mutation located at position 690 is Y690R, and the mutation located at position 686 is K686V. As shown in Table 14 above, the engineered protein SEQ ID NO:185 was able to generate INDELs using spacers that required the enzyme to recognize non-native PAMs (the non-native PAM was immediately upstream of the spacer). In addition to the expected TTTV PAMs, the enzyme was able to recognize an additional 3 PAMs in human cells. Note that PAMs having blank rows were not tested in HEK293 Ts with the engineered protein (SEQ ID NO:185).

Example 13

An engineered protein as described herein was tested for its ability to recognize non-native PAM sequences. The ability of SYN3298 (G680R+K743R) to recognize non-native PAM sequences was tested by measuring INDEL % in both corn and soy using spacers immediately following the non-native PAM sequences shown in Tables 15 and 16 below.

TABLE 15

Average INDEL% generated by an engineered protein (SEQ ID NO: 184) with spacers having the indicated PAMs in soy.
INDEL % in soy using SYM3298(G680R+K743R), with specifiec PAMs and spacers.

| PAM | Type of Access | PWspID | Spacer Sequence | SEQ ID NO: | Number of Plants Screened | % of Plants having 1% or Greater Editing Efficiency |
|---|---|---|---|---|---|---|
| TTTA | Wild-Type Cas12a | 1215 | TTGTAACCAACA TCCCCTGATGA | 201 | 6 | 100% |
| TTTC | Wild-Type Cas12a | 2593 | GGGTAAGTGGTG ATGACCCTACA | 202 | 10 | 100% |
| TTTG | Wild-Type Cas12a | 1931 | ATTTCTGGTCAC AACAGAAATAA | 203 | 40 | 80% |
| CCCC | Published Access | 2555 | TTGCTACCGACC CAGTGAGTGGT | 204 | 1 | 100% |
| TCCC | Published Access | 2562 | TCTCAGAGTTAA CAACTCTTTGC | 205 | 38 | 79% |
| TCCG | Published Access | 2569 | TTGCTACCGACC CAGTGAGTGGT | 206 | 40 | 100% |
| TTCA | Published Access | 2575 | CCAGTCCTTCTT CCCTTATCATC | 207 | 3 | 67% |
| TTCC | Published Access | 2580 | ATTTGAAGGTCT GAACCGGAATT | 208 | 32 | 19% |
| TTCG | Published Access | 2584 | TGTCCGTTGCTA CCGACCCAGTG | 209 | 39 | 51% |
| ACCG | Expanded Access | 2667 | ACCCAGTGAGTG GTCCACCACAC | 210 | 39 | 74% |

TABLE 15-continued

Average INDEL% generated by an engineered protein (SEQ ID NO: 184) with spacers having the indicated PAMs in soy.
INDEL % in soy using SYM3298(G680R+K743R), with specifiec PAMs and spacers.

| PAM | Type of Access | PWspID | Spacer Sequence | SEQ ID NO: | Number of Plants Screened | % of Plants having 1% or Greater Editing Efficiency |
|---|---|---|---|---|---|---|
| CCCA | Expanded Access | 2823 | GAAGAAGAAGTGAATCGTGCGGG | 211 | 41 | 29% |
| CCCG | Expanded Access | 2831 | GTGTGCCAGCCAATGTGCTCACA | 212 | 28 | 17% |
| CCTA | Expanded Access | 2834 | CCGGAGCCAAGGTCACCAAGGCT | 213 | 40 | 3% |
| GCCC | Expanded Access | 2684 | AGAAGCCGACACGTGGCTTCCCT | 214 | 4 | 75% |
| ACCC | Expanded Access | 2663 | AGTGAGTGGTCCACCACACCTTA | 215 | 2 | 50% |
| ATTA | Expanded Access | 2677 | GTGGAGAAATTACTTCAGCAACT | 216 | 39 | 3% |
| GCCA | Expanded Access | 2862 | GGGACAGATATGGTCAATTCCAA | 217 | 27 | 7% |
| GTCA | Expanded Access | 2873 | CCAAGGCTGCCCAGAAGAAGAAG | 218 | 32 | 3% |
| GTCC | Expanded Access | 2878 | GGGCAGTGTACTCAGCAAAGGTT | 219 | 30 | 20% |
| GTCG | Expanded Access | 2692 | GCTTCTGGGCTCGTCCGCGTGGA | 220 | 37 | 68% |
| GTTA | Expanded Access | 2883 | CTGAGTGGTGTGGCCTATGCGCA | 221 | 28 | 4% |
| TCTA | Expanded Access | 2890 | CTTTGCAGCCCGCAACCTGACAC | 222 | 26 | 4% |
| TCTC | Expanded Access | 2700 | ACTATTGAATGTAGGGTCATCAC | 223 | 30 | 37% |
| TCTG | Expanded Access | 2709 | AGAGGGAGAGATTTGAGAAAGAA | 224 | 16 | 6% |
| ACTC | Expanded Access | 2991 | CAAGTCCCCTACTGTCACTGTTG | 225 | 27 | 4% |
| GCTA | Expanded Access | 3006 | CCTAGAAAAGAAGACACAAGAGT | 226 | 40 | 3% |
| GTTC | Expanded Access | 3012 | ATCAGGGGATGTTGGTTACAATA | 227 | 40 | 3% |
| TCCT | Expanded Access | 3022 | ACCGGAGCCAAGGTCACCAAGGC | 228 | 40 | 5% |
| ATCA | Expanded Access | 3161 | GGGGATGTTGGTTACAATAAATG | 229 | 40 | 10% |
| ATCC | Expanded Access | 3167 | CCTGATGAACCAGCCCGCACGAT | 230 | 39 | 5% |
| CTTA | Expanded Access | 3180 | CCAGATGATAAGGGAAGAAGGAC | 231 | 36 | 3% |
| TTCT | Expanded Access | 3191 | TCTTCTGGGCAGCCTTGGTGACC | 232 | 40 | 5% |

TABLE 16

Average INDEL% generated by an engineered protein (SEQ ID NO: 184) with spacers having the indicated PAMs in corn.
INDEL % in corn using SYN3298(G680R+K743R), with specified PAMs and spacers.

| PAM | Type of Access | PWspID | Spacer Sequence | SEQ ID NO: | Number of Plants Screened | % of Plants having 1% or Greater Editing Efficiency |
|---|---|---|---|---|---|---|
| TTTA | Wild-Type Cas12a | 2544 | TGGGATTGGCAT TCTCCTATTGG | 233 | 107 | 33% |
| TTTC | Wild-Type Cas12a | 2548 | CGAGGACTGTCC AGTTGAGAGAT | 234 | 77 | 9% |
| TTTG | Wild-Type Cas12a | 2551 | CTTATTATTAGTT AGATATAACT | 235 | 48 | 6% |
| CCCC | Publi-shed Access | 2515 | GACCTCCACGTT CTCGATCTTCA | 236 | 58 | 12% |
| TCCA | Publi-shed Access | 2516 | ACAACATCCTCC TCGACGCCGAC | 237 | 33 | 9% |
| TCCC | Publi-shed Access | 2525 | ACTCGGCTTGTC GTCGAGGTAGT | 238 | 30 | 17% |
| TCCG | Publi-shed Access | 2527 | AGGACTGTCCAG TTGAGAGATAC | 239 | 20 | 5% |
| TTCA | Publi-shed Access | 2532 | TTGCCCACTGGA GGAACGTGCTC | 240 | 65 | 9% |
| TTCC | Publi-shed Access | 2535 | CTGCAGCCCTCT AGGAGAGAGCA | 241 | 46 | 52% |
| TTCG | Publi-shed Access | 2538 | AAAAGATGGATC CATTTCCTTCT | 242 | 13 | 31% |
| ACCC | Expanded Access | 2615 | GTCGCAGTAGCG TCCGTCTCTGG | 243 | 40 | 13% |
| ACCG | Expanded Access | 2617 | GGATGTCAAGTC AAATAATATAC | 244 | 20 | 30% |
| ATTA | Expanded Access | 2625 | TACAAGGGCAGT GAGTGATTTGT | 245 | 88 | 7% |
| ATTC | Expanded Access | 2720 | GGGGCACTATTG GGCATATTGCT | 246 | 40 | 3% |
| CCCA | Expanded Access | 2729 | AAGTCGGCCACA TGAGCTTCAAA | 247 | 34 | 7% |
| CCCG | Expanded Access | 2733 | GAGGAACTTGGC GAGCCCGAAGT | 248 | 31 | 13% |
| CCTC | Expanded Access | 2747 | CAAAGACCTGCA CCCAGCCAGCG | 249 | 36 | 3% |
| CTCC | Expanded Access | 2753 | TCGACGCCGACT TCGAGGCCCAC | 250 | 31 | 3% |
| CTCG | Expanded Access | 2759 | GGGGCATCTGAA TGCATGTCTGC | 251 | 21 | 5% |
| GCCA | Expanded Access | 2767 | GCGGCAGGGGA ATCTCCCCAGAT | 252 | 19 | 16% |
| GCCC | Expanded Access | 2630 | CGGAGGAACTTG GCGAGCCCGAA | 253 | 24 | 38% |
| GCCG | Expanded Access | 2635 | GCGTTGCCCCG GAGGAACTTGGC | 254 | 40 | 8% |
| GCTC | Expanded Access | 2768 | GCCAAGTTCCTC CGGGGCAACGC | 255 | 11 | 9% |
| GTCA | Expanded Access | 2781 | GGAAATGAGATC TCCGGTGAGCT | 256 | 20 | 5% |

TABLE 16-continued

Average INDEL% generated by an engineered protein (SEQ ID NO: 184) with spacers having the indicated PAMs in corn.
INDEL % in corn using SYN3298(G680R+K743R), with specified PAMs and spacers.

| PAM | Type of Access | PWspID | Spacer Sequence | SEQ ID NO: | Number of Plants Screened | % of Plants having 1% or Greater Editing Efficiency |
|---|---|---|---|---|---|---|
| GTCC | Expanded Access | 2783 | GCTATCGCCGGC TCGTACGGCTA | 257 | 9 | 11% |
| GTTA | Expanded Access | 2788 | GGGCATGTACCG TGGGGTGTCTT | 258 | 40 | 8% |
| TCTC | Expanded Access | 2651 | CAGCACCCGGCCG CCGCCACCGC | 259 | 32 | 3% |
| TCTG | Expanded Access | 2656 | GCCTCCTACATC GTACAGCCTAT | 260 | 67 | 4% |
| TTTT | Expanded Access | 2804 | CAGGAGGATGTG CTTCATGCAAG | 261 | 38 | 24% |
| TCCT | Expanded Access | 2990 | CTCCATCGTGAC GACGACGACCA | 262 | 95 | 1% |
| ATCA | Expanded Access | 3130 | GGTGCGGCGCT ACGTGTACCATG | 263 | 100 | 1% |
| CTTA | Expanded Access | 3143 | GGACCAGTAATC AGTTCCAATAG | 264 | 61 | 7% |
| TTCT | Expanded Access | 3159 | GCATGAGTTGAC ATTAGCAAAGG | 265 | 45 | 9% |

Engineered protein SYN3298 (SEQ ID NO:184) comprising a mutation located at position 680 and at 743 with reference to position numbering of the amino acid sequence of SEQ ID NO:184 and having altered PAM specificity was tested for the ability to recognize natural (wild-type LbCas12a) PAM sequences and non-natural PAM sequences. Specifically, the mutation located at position 680 is G680R and the mutation located at position 743 is K743R. As shown in Tables 15 and 16 above, the engineered protein SEQ ID NO:184 was able to generate INDELs using spacers that required the enzyme to recognize non-native PAMs (the non-native PAM was immediately upstream of the spacer).

In addition to the expected TTTV PAMs, the enzyme was able to recognize an additional 29 PAMs in soy and an additional 30 PAMs in corn.

Example 14

An engineered protein as described herein was tested for its ability to recognize non-native PAM sequences. The ability of SYN3298 (G680R+K686V+Y690R) to recognize non-native PAM sequences was tested by measuring INDEL % in soy using spacers immediately following the non-native PAM sequences indicated in Table 17 below.

TABLE 17

Average INDEL% generated by an engineered protein (SEQ ID NO:185) with spacers having the indicated PAMs in soy.
INDEL % in soy using SYN3298(G680R+K686V+Y690R), with specified PAMs and spacers.

| PAM | Type of Access | PWspID | Spacer Sequence | SEQ ID NO: | Number of Plants Screened | % of Plants having 1% or Greater Editing Efficiency |
|---|---|---|---|---|---|---|
| TTTG | Wild-Type Cas12a | 2594 | AAGGTCTGAACC GGAATTTCCTA | 266 | 40 | 60% |
| TATA | Published Access | 3106 | ACCCATCCATGT TCTTTCTCAAA | 267 | 34 | 3% |
| TATC | Published Access | 3114 | TTGGGGGAGTCT TTGATGTTGAG | 268 | 20 | 15% |
| GATC | Expanded Access | 3091 | CTACCGGAGCCA AGGTCACCAAG | 269 | 40 | 8% |

TABLE 17-continued

Average INDEL% generated by an engineered protein (SEQ ID NO:185) with spacers having the indicated PAMs in soy.
INDEL % in soy using SYN3298(G680R+K686V+Y690R), with specified PAMs and spacers.

| PAM | Type of Access | PWspID | Spacer Sequence | SEQ ID NO: | Number of Plants Screened | % of Plants having 1% or Greater Editing Efficiency |
|---|---|---|---|---|---|---|
| GATG | Expanded Access | 3098 | TTGAGTCATTAG TGGAGAAATTA | 270 | 31 | 3% |
| TACC | Expanded Access | 3101 | GGAGCCAAGGTC ACCAAGGCTGC | 271 | 39 | 28% |

Engineered protein SYN3298 (SEQ ID NO:185) comprising a mutation located at position 680, at position 690, and at position 686 with reference to position numbering of the amino acid sequence of SEQ ID NO:185 and having altered PAM specificity was tested for the ability to recognize natural (wild-type LbCas12a) PAM sequences and non-natural PAM sequences. Specifically, the mutation located at position 680 is G680R, the mutation located at position 690 is Y690R, and the mutation located at position 686 is K686V. As shown in Table 17 above, the engineered protein SEQ ID NO:185 was able to generate INDELs using spacers that required the enzyme to recognize non-native PAMs (the non-native PAM was immediately upstream of the spacer). In addition to the expected TTTV PAMs, the enzyme was able to recognize an additional 3 PAMs in soy.

The foregoing is illustrative of the present invention, and is not to be construed as limiting thereof. The invention is defined by the following claims, with equivalents of the claims to be included therein.

What is claimed is:

1. A method of modifying a target nucleic acid, comprising:
    contacting the target nucleic acid with:
    (a) a LbCas12a polypeptide having a mutation, wherein the mutation is an arginine at position 532 and at 595, and a guide nucleic acid,
    (b) a LbCas12a polypeptide having a mutation, wherein the mutation is an arginine at position 532 and 542 and a valine at position 538, each of which position in the LbCas12a polypeptide of (a) and/or (b) is in reference to position numbering of the amino acid sequence of SEQ ID NO:180, and a guide nucleic acid,
    wherein the LbCas12a polypeptide of (a) recognizes a PAM sequence in the target nucleic acid of

TTAA, TTAC, GTCT, ACTA, ACTC, ACTG, ATTA, ATTC,

ATTG, CCTA, CCTC, CCTG, CTTA, CTTC, CTTG, GCTA,

GCTC, GCTG, GTTA, GTTC, and/or GTTG, and the LbCas12a polypeptide of (b) recognizes a PAM sequence in the target nucleic acid of AACC, TACC, AATC, GATA, AATA, AATG, GATG, and/or

GATC, and/or
    (c) a fusion protein and a guide nucleic acid, the fusion protein comprising (i) the LbCas12a polypeptide of (a) and (b), (ii) the LbCas12a polypeptide of (a) and a polypeptide of interest, or (iii) the LbCas12a polypeptide of (b) and a polypeptide of interest.

2. The method of claim 1, wherein the LbCas12a polypeptide further comprises a mutation in the RuvC domain.

3. The method of claim 1, wherein the polypeptide of interest comprises at least one polypeptide or protein domain having deaminase (deamination) activity, nickase activity, recombinase activity, transposase activity, methylase activity, glycosylase (DNA glycosylase) activity, glycosylase inhibitor activity, demethylase activity, transcription activation activity, transcription repression activity, transcription release factor activity, histone modification activity, nuclease activity, single-strand RNA cleavage activity, double-strand RNA cleavage activity, restriction endonuclease activity, nucleic acid binding activity, methyltransferase activity, DNA repair activity, DNA damage activity, dismutase activity, alkylation activity, depurination activity, oxidation activity, pyrimidine dimer forming activity, integrase activity, transposase activity, polymerase activity, ligase activity, helicase activity, and/or photolyase activity.

4. The method of claim 3, wherein the polypeptide of interest comprises at least one polypeptide or protein domain having deaminase activity, optionally wherein the at least one polypeptide or protein domain having deaminase activity is a cytosine deaminase domain or an adenine deaminase domain.

5. The method of claim 3, wherein the polypeptide of interest has glycosylase inhibitor activity, optionally wherein the polypeptide of interest is a uracil-DNA glycosylase inhibitor (UGI).

6. A method of editing a target nucleic acid, comprising contacting the target nucleic acid with:
    (a) a LbCas12a polypeptide having a mutation, wherein the mutation is an arginine at position 532 and at 595, and a guide nucleic acid,
    (b) a LbCas12a polypeptide having a mutation, wherein the mutation is an arginine at position 532 and 542 and a valine at position 538, each of which position in the LbCas12a polypeptide of (a) and/or (b) is in reference to position numbering of the amino acid sequence of SEQ ID NO:180, and a guide nucleic acid,
    wherein the LbCas12a polypeptide of (a) recognizes a PAM sequence in the target nucleic acid of

TTAA, TTAC, GTCT, ACTA, ACTC, ACTG, ATTA, ATTC,

ATTG, CCTA, CCTC, CCTG, CTTA, CTTC, CTTG, GCTA,

GCTC, GCTG, GTTA, GTTC, and/or GTTG, and the LbCas12a polypeptide of (b) recognizes a PAM sequence in the target nucleic acid of AACC, TACC, AATC, GATA, AATA, AATG, GATG, and/or

GATC, and/or
    (c) a fusion protein and a guide nucleic acid, the fusion protein comprising (i) the LbCas12a polypeptide of (a) and (b), (ii) the LbCas12a polypeptide of (a) and a polypeptide of interest, or (iii) the LbCas12a polypeptide of (b) and a polypeptide of interest;
    thereby editing the target nucleic acid.

7. The method of claim 6, wherein the polypeptide of interest comprises at least one polypeptide or protein domain having deaminase (deamination) activity, nickase activity, recombinase activity, transposase activity, methylase activity, glycosylase (DNA glycosylase) activity, glycosylase inhibitor activity, demethylase activity, transcription activation activity, transcription repression activity, transcription release factor activity, histone modification activity, nuclease activity, single-strand RNA cleavage activity, double-strand RNA cleavage activity, restriction endonuclease activity, nucleic acid binding activity, methyltransferase activity, DNA repair activity, DNA damage activity, dismutase activity, alkylation activity, depurination activity, oxidation activity, pyrimidine dimer forming activity, integrase activity, transposase activity, polymerase activity, ligase activity, helicase activity, and/or photolyase activity.

8. The method of claim 7, wherein the polypeptide of interest comprises at least one polypeptide or protein domain having deaminase activity, optionally, wherein the at least one polypeptide or protein domain having deaminase activity is a cytosine deaminase domain or an adenine deaminase domain.

9. The method of claim 7, wherein the polypeptide of interest has glycosylase inhibitor activity, optionally wherein the polypeptide of interest is a uracil-DNA glycosylase inhibitor (UGI).

10. A method of editing a target nucleic acid, comprising contacting a cell or a cell free system comprising the target nucleic acid with:
   (a) a LbCas12a polypeptide having a mutation, wherein the mutation is an arginine at position 532 and at 595, and a guide nucleic acid,
   (b) a LbCas12a polypeptide having a mutation, wherein the mutation is an arginine at position 532 and 542 and a valine at position 538, each of which position in the LbCas12a polypeptide of (a) and/or (b) is in reference to position numbering of the amino acid sequence of SEQ ID NO:180, and a guide nucleic acid,
   wherein the LbCas12a polypeptide of (a) recognizes a PAM sequence in the target nucleic acid of TTAA, TTAC, GTCT, ACTA, ACTC, ACTG, ATTA, ATTC, ATTG, CCTA, CCTC, CCTG, CTTA, CTTC, CTTG, GCTA, GCTC, GCTG, GTTA, GTTC, and/or GTTG, and the LbCas12a polypeptide of (b) recognizes a PAM sequence in the target nucleic acid of AACC, TACC, AATC, GATA, AATA, AATG, GATG, and/or GATC, or an expression cassette or vector comprising the same and a guide nucleic acid, or an expression cassette or vector comprising the same; and/or (c) a nucleic acid construct encoding a complex comprising a fusion protein and a guide nucleic acid, the fusion protein comprising (i) the LbCas12a polypeptide of (a) and (b), (ii) the LbCas12a polypeptide of (a) and a polypeptide of interest, or (iii) the LbCas12a polypeptide of (b) and a polypeptide of interest, or an expression cassette or vector comprising the same, thereby editing the target nucleic acid.

11. The method of claim 10, wherein the polypeptide of interest comprises at least one polypeptide or protein domain having deaminase (deamination) activity, nickase activity, recombinase activity, transposase activity, methylase activity, glycosylase (DNA glycosylase) activity, glycosylase inhibitor activity, demethylase activity, transcription activation activity, transcription repression activity, transcription release factor activity, histone modification activity, nuclease activity, single-strand RNA cleavage activity, double-strand RNA cleavage activity, restriction endonuclease activity, nucleic acid binding activity, methyltransferase activity, DNA repair activity, DNA damage activity, dismutase activity, alkylation activity, depurination activity, oxidation activity, pyrimidine dimer forming activity, integrase activity, transposase activity, polymerase activity, ligase activity, helicase activity, and/or photolyase activity.

12. The method of claim 11, wherein the polypeptide of interest comprises at least one polypeptide or protein domain having deaminase activity, optionally, wherein the at least one polypeptide or protein domain having deaminase activity is a cytosine deaminase domain or an adenine deaminase domain.

13. The method of claim 11, wherein the polypeptide of interest has glycosylase inhibitor activity, optionally wherein the polypeptide of interest is a uracil-DNA glycosylase inhibitor (UGI).

* * * * *

SEQUENCE LISTING

```
Sequence total quantity: 271
SEQ ID NO: 1            moltype = AA  length = 144
FEATURE                 Location/Qualifiers
source                  1..144
                        mol_type = protein
                        organism = Streptococcus sp.
SEQUENCE: 1
ENQTTQKGQK NSRERMKRIE EGIKELGSQI LKEHPVENTQ LQNEKLYLYY LQNGRDMYVD   60
QELDINRLSD YDVDHIVPQS FLKDDSIDNK VLTRSDKNRG KSDNVPSEEV VKKMKNYWRQ  120
LLNAKLITQR KFDNLTKAER GGLS                                        144

SEQ ID NO: 2            moltype = AA  length = 1373
FEATURE                 Location/Qualifiers
source                  1..1373
                        mol_type = protein
                        organism = synthetic construct
SEQUENCE: 2
MGSKLEKFTN CYSLSKTLRF KAIPVGKTQE NIDNKRLLVE DEKRAEDYKG VKKLLDRYYL   60
SFINDVLHSI KLKNLNNYIS LFRKKTRTEK ENKELENLEI NLRKEIAKAF KGNEGYKSLF  120
KKDIIETILP EFLDDKDEIA LVNSFNGFTT AFTGFFDNRE NMFSEEAKST SIAFRCINEN  180
LTRYISNMDI FEKVDAIFDK HEVQEIKEKI LNSDYDVEDF FEGEFFNFVL TQEGIDVYNA  240
IIGGFVTESG EKIKGLNEYI NLYNQKTKQK LPKFKPLYKQ VLSDRESLSF YGENQTTQKG  300
QKNSRERMKR IEEGIKELGS QILKEHPVEN TQLQNEKLYL YYLQNGRDMY VDQELDINRL  360
SDYDVDHIVP QSFLKDDSID NKVLTRSDKN RGKSDNVPSE EVVKKMKNYW RQLLNAKLIT  420
QRKFDNLTKA ERGGLSEGYT SDEEVLEVFR NTLNKNSEIF SSIKKLEKLF KNFDEYSSAG  480
IFVKNGPAIS TISKDIFGEW NVIRDKWNAE YDDIHLKKKA VVTEKYEDDR RKSFKKIGSF  540
SLEQLQEYAD ADLSVVEKLK EIIIQKVDEI YKVYGSSEKL FDADFVLEKS LKKNDAVVAI  600
MKDLLDSVKS FENYIKAFFG EGKETNRDES FYGDFVLAYD ILLKVDHIYD AIRNYVTQKP  660
YSKDKFKLYF QNPQFMGGWD KDKETDYRAT ILRYGSKYYL AIMDKKYAKC LQKIDKDDVN  720
GNYEKINYKL LPGPNKMLPK VFFSKKWMAY YNPSEDIQKI YKNGTFKKGD MFNLNDCHKL  780
IDFFKDSISR YPKWSNAYDF NFSETEKYKD IAGFYREVEE QGYKVSFESA SKKEVDKLVE  840
EGKLYMFQIY NKDFSDKSHG TPNLHTMYFK LLFDENNHGQ IRLSGGAELF MRRASLKKEE  900
LVVHPANSPI ANKNPDNPKK TTTLSYDVYK DKRFSEDQYE LHIPIAINKC PKNIFKINTE  960
VRVLLKHDDN PYVIGIARGE RNLLYIVVVD GKGNIVEQYS LNEIINNFNG IRIKTDYHSL 1020
LDKKEKERFE ARQNWTSIEN IKELKAGYIS QVVHKICELV EKYDAVIALE DLNSGFKNSR 1080
VKVEKQVYQK FEKMLIDKLN YMVDKKSNPC ATGGALKGYQ ITNKFESFKS MSTQNGFIFY 1140
IPAWLTSKID PSTGFVNLLK TKYTSIADSK KFISSFDRIM YVPEEDLFEF ALDYKNFSRT 1200
DADYIKKWKL YSYGNRIRIF RNPKKNNVFD WEEVCLTSAY KELFNKYGIN YQQGDIRALL 1260
CEQSDKAFYS SFMALMSLML QMRNSITGRT DVDFLISPVK NSDGIFYDSR NYEAQENAIL 1320
PKNADANGAY NIARKVLWAI GQFKKAEDEK LDKVKIAISN KEWLEYAQTS VKH        1373

SEQ ID NO: 3            moltype = AA  length = 1375
FEATURE                 Location/Qualifiers
source                  1..1375
```

```
                        mol_type = protein
                        organism = synthetic construct
SEQUENCE: 3
MGSKLEKFTN CYSLSKTLRF KAIPVGKTQE NIDNKRLLVE DEKRAEDYKG VKKLLDRYYL    60
SFINDVLHSI KLKNLNNYIS LFRKKTRTEK ENKELENLEI NLRKEIAKAF KGNEGYKSLF   120
KKDIIETILP EFLDDKDEIA LVNSFNGFTT AFTGFFDNRE NMFSEEAKST SIAFRCINEN   180
LTRYISNMDI FEKVDAIFDK HEVQEIKEKI LNSDYDVEDF FEGEFFNFVL TQEGIDVYNA   240
IIGGFVTESG EKIKGLNEYI NLYNQKTKQK LPKFKPLYKQ VLSDRESLSF YGSGENQTTQ   300
KGQKNSRERM KRIEEGIKEL GSQILKEHPV ENTQLQNEKL YLYYLQNGRD MYVDQELDIN   360
RLSDYDVDHI VPQSFLKDDS IDNKVLTRSD KNRGKSDNVP SEEVVKKMKN YWRQLLNAKL   420
ITQRKFDNLT KAERGGLSEG YTSDEEVLEV FRNTLNKNSE IFSSIKKLEK LFKNFDEYSS   480
AGIFVKNGPA ISTISKDIFG EWNVIRDKWN AEYDDIHLKK KAVVTEKYED DRRKSFKKIG   540
SFSLEQLQEY ADADLSVVEK LKEIIIQKVD EIYKVYGSSE KLFDADFVLE KSLKKNDAVV   600
AIMKDLLDSV KSFENYIKAF FGEGKETNRD ESFYGDFVLA YDILLKVDHI YDAIRNYVTQ   660
KPYSKDKFKL YFQNPQFMGG WDKDKETDYR ATILRYGSKY YLAIMDKKYA KCLQKIDKDD   720
VNGNYEKINY KLLPGPNKML PKVFFSKKWM AYYNPSEDIQ KIYKNGTFKK GDMFNLNDCH   780
KLIDFFKDSI SRYPKWSNAY DFNFSETEKY KDIAGFYREV EEQGYKVSFE SASKKEVDKL   840
VEEGKLYMFQ IYNKDFSDKS HGTPNLHTMY FKLLFDENNH GQIRLSGGAE LFMRRASLKK   900
EELVVHPANS PIANKNPDNP KKTTTLSYDV YKDKRFSEDQ YELHIPIAIN KCPKNIFKIN   960
TEVRVLLKHD DNPYVIGIAR GERNLLYIVV VDGKGNIVEQ YSLNEIINNF NGIRIKTDYH  1020
SLLDKKEKER FEARQNWTSI ENIKELKAGY ISQVVHKICE LVEKYDAVIA LEDLNSGFKN  1080
SRVKVEKQVY QKFEKMLIDK LNYMVDKKSN PCATGGALKG YQITNKFESF KSMSTQNGFI  1140
FYIPAWLTSK IDPSTGFVNL LKTKYTSIAD SKKFISSFDR IMYVPEEDLF EFALDYKNFS  1200
RTDADYIKKW KLYSYGNRIR IFRNPKKNNV FDWEEVCLTS AYKELFNKYG INYQQGDIRA  1260
LLCEQSDKAF YSSFMALMSL MLQMRNSITG RTDVDFLISP VKNSDGIFYD SRNYEAQENA  1320
ILPKNADANG AYNIARKVLW AIGQFKKAED EKLDKVKIAI SNKEWLEYAQ TSVKH       1375

SEQ ID NO: 4              moltype = AA   length = 1377
FEATURE                   Location/Qualifiers
source                    1..1377
                          mol_type = protein
                          organism = synthetic construct
SEQUENCE: 4
MGSKLEKFTN CYSLSKTLRF KAIPVGKTQE NIDNKRLLVE DEKRAEDYKG VKKLLDRYYL    60
SFINDVLHSI KLKNLNNYIS LFRKKTRTEK ENKELENLEI NLRKEIAKAF KGNEGYKSLF   120
KKDIIETILP EFLDDKDEIA LVNSFNGFTT AFTGFFDNRE NMFSEEAKST SIAFRCINEN   180
LTRYISNMDI FEKVDAIFDK HEVQEIKEKI LNSDYDVEDF FEGEFFNFVL TQEGIDVYNA   240
IIGGFVTESG EKIKGLNEYI NLYNQKTKQK LPKFKPLYKQ VLSDRESLSF YGGSSGENQT   300
TQKGQKNSRE RMKRIEEGIK ELGSQILKEH PVENTQLQNE KLYLYYLQNG RDMYVDQELD   360
INRLSDYDVD HIVPQSFLKD DSIDNKVLTR SDKNRGKSDN VPSEEVVKKM KNYWRQLLNA   420
KLITQRKFDN LTKAERGGLS EGYTSDEEVL EVFRNTLNKN SEIFSSIKKL EKLFKNFDEY   480
SSAGIFVKNG PAISTISKDI FGEWNVIRDK WNAEYDDIHL KKKAVVTEKY EDDRRKSFKK   540
IGSFSLEQLQ EYADADLSVV EKLKEIIIQK VDEIYKVYGS SEKLFDADFV LEKSLKKNDA   600
VVAIMKDLLD SVKSFENYIK AFFGEGKETN RDESFYGDFV LAYDILLKVD HIYDAIRNYV   660
TQKPYSKDKF KLYFQNPQFM GGWDKDKETD YRATILRYGS KYYLAIMDKK YAKCLQKIDK   720
DDVNGNYEKI NYKLLPGPNK MLPKVFFSKK WMAYYNPSED IQKIYKNGTF KKGDMFNLND   780
CHKLIDFFKD SISRYPKWSN AYDFNFSETE KYKDIAGFYR EVEEQGYKVS FESASKKEVD   840
KLVEEGKLYM FQIYNKDFSD KSHGTPNLHT MYFKLLFDEN NHGQIRLSGG AELFMRRASL   900
KKEELVVHPA NSPIANKNPD NPKKTTTLSY DVYKDKRFSE DQYELHIPIA INKCPKNIFK   960
INTEVRVLLK HDDNPYVIGI ARGERNLLYI VVVDGKGNIV EQYSLNEIIN NFNGIRIKTD  1020
YHSLLDKKEK ERFEARQNWT SIENIKELKA GYISQVVHKI CELVEKYDAV IALEDLNSGF  1080
KNSRVKVEKQ VYQKFEKMLI DKLNYMVDKK SNPCATGGAL KGYQITNKFE SFKSMSTQNG  1140
FIFYIPAWLT SKIDPSTGFV NLLKTKYTSI ADSKKFISSF DRIMYVPEED LFEFALDYKN  1200
FSRTDADYIK KWKLYSYGNR IRIFRNPKKN NVFDWEEVCL TSAYKELFNK YGINYQQGDI  1260
RALLCEQSDK AFYSSFMALM SLMLQMRNSI TGRTDVDFLI SPVKNSDGIF YDSRNYEAQE  1320
NAILPKNADA NGAYNIARKV LWAIGQFKKA EDEKLDKVKI AISNKEWLEY AQTSVKH    1377

SEQ ID NO: 5              moltype = AA   length = 1379
FEATURE                   Location/Qualifiers
source                    1..1379
                          mol_type = protein
                          organism = synthetic construct
SEQUENCE: 5
MGSKLEKFTN CYSLSKTLRF KAIPVGKTQE NIDNKRLLVE DEKRAEDYKG VKKLLDRYYL    60
SFINDVLHSI KLKNLNNYIS LFRKKTRTEK ENKELENLEI NLRKEIAKAF KGNEGYKSLF   120
KKDIIETILP EFLDDKDEIA LVNSFNGFTT AFTGFFDNRE NMFSEEAKST SIAFRCINEN   180
LTRYISNMDI FEKVDAIFDK HEVQEIKEKI LNSDYDVEDF FEGEFFNFVL TQEGIDVYNA   240
IIGGFVTESG EKIKGLNEYI NLYNQKTKQK LPKFKPLYKQ VLSDRESLSF YGGSSGENQT   300
TQKGQKNSRE RMKRIEEGIK ELGSQILKEH PVENTQLQNE KLYLYYLQNG RDMYVDQELD   360
INRLSDYDVD HIVPQSFLKD DSIDNKVLTR SDKNRGKSDN VPSEEVVKKM KNYWRQLLNA   420
KLITQRKFDN LTKAERGGLS GSEGYTSDEE VLEVFRNTLN KNSEIFSSIK KLEKLFKNFD   480
EYSSAGIFVK NGPAISTISK DIFGEWNVIR DKWNAEYDDI HLKKKAVVTE KYEDDRRKSF   540
KKIGSFSLEQ LQEYADADLS VVEKLKEIII QKVDEIYKVY GSSEKLFDAD FVLEKSLKKN   600
DAVVAIMKDL LDSVKSFENY IKAFFGEGKE TNRDESFYGD FVLAYDILLK VDHIYDAIRN   660
YVTQKPYSKD KFKLYFQNPQ FMGGWDKDKE TDYRATILRY GSKYYLAIMD KKYAKCLQKI   720
DKDDVNGNYE KINYKLLPGP NKMLPKVFFS KKWMAYYNPS EDIQKIYKNG TFKKGDMFNL   780
NDCHKLIDFF KDSISRYPKW SNAYDFNFSE TEKYKDIAGF YREVEEQGYK VSFESASKKE   840
VDKLVEEGKL YMFQIYNKDF SDKSHGTPNL HTMYFKLLFD ENNHGQIRLS GGAELFMRRA   900
SLKKEELVVH PANSPIANKN PDNPKKTTTL SYDVYKDKRF SEDQYELHIP IAINKCPKNI   960
```

```
FKINTEVRVL LKHDDNPYVI GIARGERNLL YIVVVDGKGN IVEQYSLNEI INNFNGIRIK   1020
TDYHSLLDKK EKERFEARQN WTSIENIKEL KAGYISQVVH KICELVEKYD AVIALEDLNS   1080
GFKNSRVKVE KQVYQKFEKM LIDKLNYMVD KKSNPCATGG ALKGYQITNK FESFKSMSTQ   1140
NGFIFYIPAW LTSKIDPSTG FVNLLKTKYT SIADSKKFIS SFDRIMYVPE EDLFEFALDY   1200
KNFSRTDADY IKKWKLYSYG NRIRIFRNPK KNNVFDWEEV CLTSAYKELF NKYGINYQQG   1260
DIRALLCEQS DKAFYSSFMA LMSLMLQMRN SITGRTDVDF LISPVKNSDG IFYDSRNYEA   1320
QENAILPKNA DANGAYNIAR KVLWAIGQFK KAEDEKLDKV KIAISNKEWL EYAQTSVKH    1379

SEQ ID NO: 6              moltype = AA   length = 1373
FEATURE                   Location/Qualifiers
source                    1..1373
                          mol_type = protein
                          organism = synthetic construct
SEQUENCE: 6
MGSKLEKFTN CYSLSKTLRF KAIPVGKTQE NIDNKRLLVE DEKRAEDYKG VKKLLDRYYL    60
SFINDVLHSI KLKNLNNYIS LFRKKTRTEK ENKELENLEI NLRKEIAKAF KGNEGYKSLF   120
KKDIIETILP EFLDDKDEIA LVNSFNGFTT AFTGFFDNRE NMFSEEAKST SIAFRCINEN   180
LTRYISNMDI FEKVDAIFDK HEVQEIKEKI LNSDYDVEDF FEGEFFNFVL TQEGIDVYNA   240
IIGGFVTESG EKIKGLNEYI NLYNQKTKQK LPKFKPLYKQ VLSDRESLSF YGEENQTTQK   300
GQKNSRERMK RIEEGIKELG SQILKEHPVE NTQLQNEKLY LYYLQNGRDM YVDQELDINR   360
LSDYDVDHIV PQSFLKDDSI DNKVLTRSDK NRGKSDNVPS EEVVKKMKNY WRQLLNAKLI   420
TQRKFDNLTK AERGGLSGYT SDEEVLEVFR NTLNKNSEIF SSIKKLEKLF KNFDEYSSAG   480
IFVKNGPAIS TISKDIFGEW NVIRDKWNAE YDDIHLKKKA VVTEKYEDDR RKSFKKIGSF   540
SLEQLQEYAD ADLSVVEKLK EIIIQKVDEI YKVYGSSEKL FDADFVLEKS LKKNDAVVAI   600
MKDLLDSVKS FENYIKAFFG EGKETNRDES FYGDFVLAYD ILLKVDHIYD AIRNYVTQKP   660
YSKDKFKLYF QNPQFMGGWD KDKETDYRAT ILRYGSKYYL AIMDKKYAKC LQKIDKDDYN   720
GNYEKINYKL LPGPNKMLPK VFFSKKWMAY YNPSEDIQKI YKNGTFKKGD MFNLNDCHKL   780
IDFFKDSISR YPKWSNAYDF NFSETEKYKD IAGFYREVEE QGYKVSFESA SKKEVDKLVE   840
EGKLYMFQIY NKDFSDKSHG TPNLHTMYFK LLFDENNHGQ IRLSGGAELF MRRASLKKEE   900
LVVHPANSPI ANKNPDNPKK TTTLSYDVYK DKRFSEDQYE LHIPIAINKC PKNIFKINTE   960
VRVLLKHDDN PYVIGIARGE RNLLYIVVVD GKGNIVEQYS LNEIINNFNG IRIKTDYHSL  1020
LDKKEKERFE ARQNWTSIEN IKELKAGYIS QVVHKICELV EKYDAVIALE DLNSGFKNSR  1080
VKVEKQVYQK FEKMLIDKLN YMVDKKSNPC ATGGALKGYQ ITNKFESFKS MSTQNGFIFY  1140
IPAWLTSKID PSTGFVNLLK TKYTSIADSK KFISSFDRIM YVPEEDLFEF ALDYKNFSRT  1200
DADYIKKWKL YSYGNRIRIF RNPKKNNVFD WEEVCLTSAY KELFNKYGIN YQQGDIRALL  1260
CEQSDKAFYS SFMALMSLML QMRNSITGRT DVDFLISPVK NSDGIFYDSR NYEAQENAIL  1320
PKNADANGAY NIARKVLWAI GQFKKAEDEK LDKVKIAISN KEWLEYAQTS VKH         1373

SEQ ID NO: 7              moltype = AA   length = 1375
FEATURE                   Location/Qualifiers
source                    1..1375
                          mol_type = protein
                          organism = synthetic construct
SEQUENCE: 7
MGSKLEKFTN CYSLSKTLRF KAIPVGKTQE NIDNKRLLVE DEKRAEDYKG VKKLLDRYYL    60
SFINDVLHSI KLKNLNNYIS LFRKKTRTEK ENKELENLEI NLRKEIAKAF KGNEGYKSLF   120
KKDIIETILP EFLDDKDEIA LVNSFNGFTT AFTGFFDNRE NMFSEEAKST SIAFRCINEN   180
LTRYISNMDI FEKVDAIFDK HEVQEIKEKI LNSDYDVEDF FEGEFFNFVL TQEGIDVYNA   240
IIGGFVTESG EKIKGLNEYI NLYNQKTKQK LPKFKPLYKQ VLSDRESLSF YGEGSENQTT   300
QKGQKNSRER MKRIEEGIKE LGSQILKEHP VENTQLQNEK LYLYYLQNGR DMYVDQELDI   360
NRLSDYDVDH IVPQSFLKDD SIDNKVLTRS DKNRGKSDNV PSEEVVKKMK NYWRQLLNAK   420
LITQRKFDNL TKAERGGLSG YTSDEEVLEV FRNTLNKNSE IFSSIKKLEK LFKNFDEYSS   480
AGIFVKNGPA ISTISKDIFG EWNVIRDKWN AEYDDIHLKK KAVVTEKYED DRRKSFKKIG   540
SFSLEQLQEY ADADLSVVEK LKEIIIQKVD EIYKVYGSSE KLFDADFVLE KSLKKNDAVV  600
AIMKDLLDSV KSFENYIKAF FGEGKETNRD ESFYGDFVLA YDILLKVDHI DAIRNYVTQ   660
KPYSKDKFKL YFQNPQFMGG WDKDKETDYR ATILRYGSKY YLAIMDKKYA KCLQKIDKDD   720
VNGNYEKINY KLLPGPNKML PKVFFSKKWM AYYNPSEDIQ KIYKNGTFKK GDMFNLNDCH   780
KLIDFFKDSI SRYPKWSNAY DFNFSETEKY KDIAGFYREV EEQGYKVSFE SASKKEVDKL   840
VEEGKLYMFQ IYNKDFSDKS HGTPNLHTMY FKLLFDENNH GQIRLSGGAE LFMRRASLKK   900
EELVVHPANS PIANKNPDNP KKTTTLSYDV YKDKRFSEDQ YELHIPIAIN KCPKNIFKIN   960
TEVRVLLKHD DNPYVIGIAR GERNLLYIVV VDGKGNIVEQ YSLNEIINNF NGIRIKTDYH  1020
SLLDKKEKER FEARQNWTSI ENIKELKAGY ISQVVHKICE LVEKYDAVIA LEDLNSGFKN  1080
SRVKVEKQVY QKFEKMLIDK LNYMVDKKSN PCATGGALKG YQITNKFESF KSMSTQNGFI  1140
FYIPAWLTSK IDPSTGFVNL LKTKYTSIAD SKKFISSFDR IMYVPEEDLF EFALDYKNFS  1200
RTDADYIKKW KLYSYGNRIR IFRNPKKNNV FDWEEVCLTS AYKELFNKYG INYQQGDIRA  1260
LLCEQSDKAF YSSFMALMSL MLQMRNSITG RTDVDFLISP VKNSDGIFYD SRNYEAQENA  1320
ILPKNADANG AYNIARKVLW AIGQFKKAED EKLDKVKIAI SNKEWLEYAQ TSVKH        1375

SEQ ID NO: 8              moltype = AA   length = 1377
FEATURE                   Location/Qualifiers
source                    1..1377
                          mol_type = protein
                          organism = synthetic construct
SEQUENCE: 8
MGSKLEKFTN CYSLSKTLRF KAIPVGKTQE NIDNKRLLVE DEKRAEDYKG VKKLLDRYYL    60
SFINDVLHSI KLKNLNNYIS LFRKKTRTEK ENKELENLEI NLRKEIAKAF KGNEGYKSLF   120
KKDIIETILP EFLDDKDEIA LVNSFNGFTT AFTGFFDNRE NMFSEEAKST SIAFRCINEN   180
LTRYISNMDI FEKVDAIFDK HEVQEIKEKI LNSDYDVEDF FEGEFFNFVL TQEGIDVYNA   240
IIGGFVTESG EKIKGLNEYI NLYNQKTKQK LPKFKPLYKQ VLSDRESLSF YGEGSSGENQ   300
```

-continued

```
TTQKGQKNSR ERMKRIEEGI KELGSQILKE HPVENTQLQN EKLYLYYLQN GRDMYVDQEL  360
DINRLSDYDV DHIVPQSFLK DDSIDNKVLT RSDKNRGKSD NVPSEEVVKK MKNYWRQLLN  420
AKLITQRKFD NLTKAERGGL SGYTSDEEVL EVFRNTLNKN SEIFSSIKKL EKLFKNFDEY  480
SSAGIFVKNG PAISTISKDI FGEWNVIRDK WNAEYDDIHL KKKAVVTEKY EDDRRKSFKK  540
IGSFSLEQLQ EYADADLSVV EKLKEIIIQK VDEIYKVYGS SEKLFDADFV LEKSLKKNDA  600
VVAIMKDLLD SVKSFENYIK AFFGEGKETN RDESFYGDFV LAYDILLKVD HIYDAIRNYV  660
TQKPYSKDKF KLYFQNPQFM GGWDKDKETD YRATILRYGS KYYLAIMDKK YAKCLQKIDK  720
DDVNGNYEKI NYKLLPGPNK MLPKVFFSKK WMAYYNPSED IQKIYKNGTF KKGDMFNLND  780
CHKLIDFFKD SISRYPKWSN AYDFNFSETE KYKDIAGFYR EVEEQGYKVS FESASKKEVD  840
KLVEEGKLYM FQIYNKDFSD KSHGTPNLHT MYFKLLFDEN NHGQIRLSGG AELFMRRASL  900
KKEELVVHPA NSPIANKNPD NPKKTTTLSY DVYKDKRFSE DQYELHIPIA INKCPKNIFK  960
INTEVRVLLK HDDNPYVIGI ARGERNLLYI VVVDGKGNIV EQYSLNEIIN NFNGIRIKTD 1020
YHSLLDKKEK ERFEARQNWT SIENIKELKA GYISQVVHKI CELVEKYDAV IALEDLNSGF 1080
KNSRVKVEKQ VYQKFEKMLI DKLNYMVDKK SNPCATGGAL KGYQITNKFE SFKSMSTQNG 1140
FIFYIPAWLT SKIDPSTGFV NLLKTKYTSI ADSKKFISSF DRIMYVPEED LFEFALDYKN 1200
FSRTDADYIK KWKLYSYGNR IRIFRNPKKN NVFDWEEVCL TSAYKELFNK YGINYQQGDI 1260
RALLCEQSDK AFYSSFMALM SLMLQMRNSI TGRTDVDFLI SPVKNSDGIF YDSRNYEAQE 1320
NAILPKNADA NGAYNIARKV LWAIGQFKKA EDEKLDKVKI AISNKEWLEY AQTSVKH    1377

SEQ ID NO: 9          moltype = AA   length = 1379
FEATURE               Location/Qualifiers
source                1..1379
                      mol_type = protein
                      organism = synthetic construct
SEQUENCE: 9
MGSKLEKFTN CYSLSKTLRF KAIPVGKTQE NIDNKRLLVE DEKRAEDYKG VKKLLDRYYL   60
SFINDVLHSI KLKNLNNYIS LFRKKTRTEK ENKELENLEI NLRKEIAKAF KGNEGYKSLF  120
KKDIIETILP EFLDDKDEIA LVNSFNGFTT AFTGFFDNRE NMFSEEAKST SIAFRCINEN  180
LTRYISNMDI FEKVDAIFDK HEVQEIKEKI LNSDYDVEDF FEGEFFNFVL TQEGIDVYNA  240
IIGGFVTESG EKIKGLNEYI NLYNQKTKQK LPKFKPLYKQ VLSDRESLSF YGEGSSGENQ  300
TTQKGQKNSR ERMKRIEEGI KELGSQILKE HPVENTQLQN EKLYLYYLQN GRDMYVDQEL  360
DINRLSDYDV DHIVPQSFLK DDSIDNKVLT RSDKNRGKSD NVPSEEVVKK MKNYWRQLLN  420
AKLITQRKFD NLTKAERGGL SGSGYTSDEE VLEVFRNTLN KNSEIFSSIK KLEKLFKNFD  480
EYSSAGIFVK NGPAISTISK DIFGEWNVIR DKWNAEYDDI HLKKKAVVTE KYEDDRRKSF  540
KKIGSFSLEQ LQEYADADLS VVEKLKEIII QKVDEIYKVY GSSEKLFDAD FVLEKSLKKN  600
DAVVAIMKDL LDSVKSFENY IKAFFGEGKE TNRDESFYGD FVLAYDILLK VDHIYDAIRN  660
YVTQKPYSKD KFKLYFQNPQ FMGGWDKDKE TDYRATILRY GSKYYLAIMD KKYAKCLQKI  720
DKDDVNGNYE KINYKLLPGP NKMLPKVFFS KKWMAYYNPS EDIQKIYKNG TFKKGDMFNL  780
NDCHKLIDFF KDSISRYPKW SNAYDFNFSE TEKYKDIAGF YREVEEQGYK VSFESASKKE  840
VDKLVEEGKL YMFQIYNKDF SDKSHGTPNL HTMYFKLLFD ENNHGQIRLS GGAELFMRRA  900
SLKKEELVVH PANSPIANKN PDNPKKTTTL SYDVYKDKRF SEDQYELHIP IAINKCPKNI  960
FKINTEVRVL LKHDDNPYVI GIARGERNLL YIVVVDGKGN IVEQYSLNEI INNFNGIRIK 1020
TDYHSLLDKK EKERFEARQN WTSIENIKEL KAGYISQVVH KICELVEKYD AVIALEDLNS 1080
GFKNSRVKVE KQVYQKFEKM LIDKLNYMVD KKSNPCATGG ALKGYQITNK FESFKSMSTQ 1140
NGFIFYIPAW LTSKIDPSTG FVNLLKTKYT SIADSKKFIS SFDRIMYVPE EDLFEFALDY 1200
KNFSRTDADY IKKWKLYSYG NRIRIFRNPK KNNVFDWEEV CLTSAYKELF NKYGINYQQG 1260
DIRALLCEQS DKAFYSSFMA LMSLMLQMRN SITGRTDVDF LISPVKNSDG IFYDSRNYEA 1320
QENAILPKNA DANGAYNIAR KVLWAIGQFK KAEDEKLDKV KIAISNKEWL EYAQTSVKH  1379

SEQ ID NO: 10         moltype = AA   length = 1373
FEATURE               Location/Qualifiers
source                1..1373
                      mol_type = protein
                      organism = synthetic construct
SEQUENCE: 10
MGSKLEKFTN CYSLSKTLRF KAIPVGKTQE NIDNKRLLVE DEKRAEDYKG VKKLLDRYYL   60
SFINDVLHSI KLKNLNNYIS LFRKKTRTEK ENKELENLEI NLRKEIAKAF KGNEGYKSLF  120
KKDIIETILP EFLDDKDEIA LVNSFNGFTT AFTGFFDNRE NMFSEEAKST SIAFRCINEN  180
LTRYISNMDI FEKVDAIFDK HEVQEIKEKI LNSDYDVEDF FEGEFFNFVL TQEGIDVYNA  240
IIGGFVTESG EKIKGLNEYI NLYNQKTKQK LPKFKPLYKQ VLSDRESLSF YGENQTTQKG  300
QKNSRERMKR IEEGIKELGS QILKEHPVEN TQLQNEKLYL YYLQNGRDMY VDQELDINRL  360
SDYDVDHIVP QSFLKDDSID NKVLTRSDKN RGKSDNVPSE EVVKKMKNYW RQLLNAKLIT  420
QRKFDNLTKA ERGGLSEGYT SDEEVLEVFR NTLNKNSEIF SSIKKLEKLF KNFDEYSSAG  480
IFVKNGPAIS TISKDIFGEW NVIRDKWNAE YDDIHLKKKA VVTEKYEDDR RKSFKKIGSF  540
SLEQLQEYAD ADLSVVEKLK EIIIQKVDEI YKVYGSSEKL FDADFVLEKS LKKNDAVVAI  600
MKDLLDSVKS FENYIKAFFG EGKETNRDES FYGDFVLAYD ILLKVDHIYD AIRNYVTQKP  660
YSKDKFKLYF QNPQFMGGWD KDKETDYRAT ILRYGSKYYL AIMDKKYAKC LQKIDKDDVN  720
GNYEKINYKL LPGPNKMLPK VFFSKKWMAY YNPSEDIQKI YKNGTFKKGD MFNLNDCHKL  780
IDFFKDSISR YPKWSNAYDF NFSETEKYKD IAGFYREVEE QGYKVSFESA SKKEVDKLVE  840
EGKLYMFQIY NKDFSDKSHG TPNLHTMYFK LLFDENNHGQ IRLSGGAELF MRRASLKKEE  900
LVVHPANSPI ANKNPDNPKK TTTLSYDVYK DKRFSEDQYE LHIPIAINKC PKNIFKINTE  960
VRVLLKHDDN PYVIGIDRGE RNLLYIVVVD GKGNIVEQYS LNEIINNFNG IRIKTDYHSL 1020
LDKKEKERFE ARQNWTSIEN IKELKAGYIS QVVHKICELV EKYDAVIALE DLNSGFKNSR 1080
VKVEKQVYQK FEKMLIDKLN YMVDKKSNPC ATGGALKGYQ ITNKFESFKS MSTQNGFIFY 1140
IPAWLTSKID PSTGFVNLLK TKYTSIADSK KFISSFDRIM YVPEEDLFEF ALDYKNFSRT 1200
DADYIKKWKL YSYGNRIRIF RNPKNNVFD WEEVCLTSAY KELFNKYGIN YQQGDIRALL 1260
CEQSDKAFYS SFMALMSLML QMRNSITGRT DVDFLISPVK NSDGIFYDSR NYEAQENAIL 1320
PKNADANGAY NIARKVLWAI GQFKKAEDEK LDKVKIAISN KEWLEYAQTS VKH        1373
```

```
SEQ ID NO: 11           moltype = AA  length = 1375
FEATURE                 Location/Qualifiers
source                  1..1375
                        mol_type = protein
                        organism = synthetic construct
SEQUENCE: 11
MGSKLEKFTN CYSLSKTLRF KAIPVGKTQE NIDNKRLLVE DEKRAEDYKG VKKLLDRYYL    60
SFINDVLHSI KLKNLNNYIS LFRKKTRTEK ENKELENLEI NLRKEIAKAF KGNEGYKSLF   120
KKDIIETILP EFLDDKDEIA LVNSFNGFTT AFTGFFDNRE NMFSEEAKST SIAFRCINEN   180
LTRYISNMDI FEKVDAIFDK HEVQEIKEKI LNSDYDVEDF FEGEFFNFVL TQEGIDVYNA   240
IIGGFVTESG EKIKGLNEYI NLYNQKTKQK LPKFKPLYKQ VLSDRESLSF YGGSENQTTQ   300
KGGQKNSRERM KRIEEGIKEL GSQILKEHPV ENTQLQNEKL YLYYLQNGRD MYVDQELDIN   360
RLSDYDVDHI VPQSFLKDDS IDNKVLTRSD KNRGKSDNVP SEEVVKKMKN YWRQLLNAKL   420
ITQRKFDNLT KAERGGLSEG YTSDEEVLEV FRNTLNKNSE IFSSIKKLEK LFKNFDEYSS   480
AGIFVKNGPA ISTISKDIFG EWNVIRDKWN AEYDDIHLKK KAVVTEKYED DRRKSFKKIG   540
SFSLEQLQEY ADADLSVVEK LKEIIIQKVD EIYKVYGSSE KLFDADFVLE KSLKKNDAVV   600
AIMKDLLDSV KSFENYIKAF FGEGKETNRD ESFYGDFVLA YDILLKVDHI YDAIRNYVTQ   660
KPYSKDKFKL YFQNPQFMGG WDKDKETDYR ATILRYGSKY YLAIMDKKYA KCLQKIDKDD   720
VNGNYEKINY KLLPGPNKML PKVFFSKKWM AYYNPSEDIQ KIYKNGTFKK GDMFNLNDCH   780
KLIDFFKDSI SRYPKWSNAY DFNFSETEKY KDIAGFYREV EEQGYKVSFE SASKKEVDKL   840
VEEGKLYMFQ IYNKDFSDKS HGTPNLHTMY FKLLFDENNH GQIRLSGGAE LFMRRASLKK   900
EELVVHPANS PIANKNPDNP KKTTTLSYDV YKDKRFSEDQ YELHIPIAIN KCPKNIFKIN   960
TEVRVLLKHD DNPYVIGIDR GERNLLYIVV VDGKGNIVEQ YSLNEIINNF NGIRIKTDYH  1020
SLLDKKEKER FEARQNWTSI ENIKELKAGY ISQVVHKICE LVEKYDAVIA LEDLNSGFKN  1080
SRVKVEKQVY QKFEKMLIDK LNYMVDKKSN PCATGGALKG YQITNKFESF KSMSTQNGFI  1140
FYIPAWLTSK IDPSTGFVNL LKTKYTSIAD SKKFISSFDR IMYVPEEDLF EFALDYKNFS  1200
RTDADYIKKW KLYSYGNRIR IFRNPKKNNV FDWEEVCLTS AYKELFNKYG INYQQGDIRA  1260
LLCEQSDKAF YSSFMALMSL MLQMRNSITG RTDVDFLISP VKNSDGIFYD SRNYEAQENA  1320
ILPKNADANG AYNIARKVLW AIGQFKKAED EKLDKVKIAI SNKEWLEYAQ TSVKH       1375

SEQ ID NO: 12           moltype = AA  length = 1377
FEATURE                 Location/Qualifiers
source                  1..1377
                        mol_type = protein
                        organism = synthetic construct
SEQUENCE: 12
MGSKLEKFTN CYSLSKTLRF KAIPVGKTQE NIDNKRLLVE DEKRAEDYKG VKKLLDRYYL    60
SFINDVLHSI KLKNLNNYIS LFRKKTRTEK ENKELENLEI NLRKEIAKAF KGNEGYKSLF   120
KKDIIETILP EFLDDKDEIA LVNSFNGFTT AFTGFFDNRE NMFSEEAKST SIAFRCINEN   180
LTRYISNMDI FEKVDAIFDK HEVQEIKEKI LNSDYDVEDF FEGEFFNFVL TQEGIDVYNA   240
IIGGFVTESG EKIKGLNEYI NLYNQKTKQK LPKFKPLYKQ VLSDRESLSF YGGSSGENQT   300
TQKGQKNSRE RMKRIEEGIK ELGSQILKEH PVENTQLQNE KLYLYYLQNG RDMYVDQELD   360
INRLSDYDVD HIVPQSFLKD DSIDNKVLTR SDKNRGKSDN VPSEEVVKKM KNYWRQLLNA   420
KLITQRKFDN LTKAERGGLS EGYTSDEEVL EVFRNTLNKN SEIFSSIKKL EKLFKNFDEY   480
SSAGIFVKNG PAISTISKDI FGEWNVIRDK WNAEYDDIHL KKKAVVTEKY EDDRRKSFKK   540
IGSFSLEQLQ EYADADLSVV EKLKEIIIQK VDEIYKVYGS SEKLFDADFV LEKSLKKNDA   600
VVAIMKDLLD SVKSFENYIK AFFGEGKETN RDESFYGDFV LAYDILLKVD HIYDAIRNYV   660
TQKPYSKDKF KLYFQNPQFM GGWDKDKETD YRATILRYGS KYYLAIMDKK YAKCLQKIDK   720
DDVNGNYEKI NYKLLPGPNK MLPKVFFSKK WMAYYNPSED IQKIYKNGTF KKGDMFNLND   780
CHKLIDFFKD SISRYPKWSN AYDFNFSETE KYKDIAGFYR EVEEQGYKVS FESASKKEVD   840
KLVEEGKLYM FQIYNKDFSD KSHGTPNLHT MYFKLLFDEN NHGQIRLSGG AELFMRRASL   900
KKEELVVHPA NSPIANKNPD NPKKTTTLSY DVYKDKRFSE DQYELHIPIA INKCPKNIFK   960
INTEVRVLLK HDDNPYVIGI DRGERNLLYI VVVDGKGNIV EQYSLNEIIN NFNGIRIKTD  1020
YHSLLDKKEK ERFEARQNWT SIENIKELKA GYISQVVHKI CELVEKYDAV IALEDLNSGF  1080
KNSRVKVEKQ VYQKFEKMLI DKLNYMVDKK SNPCATGGAL KGYQITNKFE SFKSMSTQNG  1140
FIFYIPAWLT SKIDPSTGFV NLLKTKYTSI ADSKKFISSF DRIMYVPEED LFEFALDYKN  1200
FSRTDADYIK KWKLYSYGNR IRIFRNPKKN NVFDWEEVCL TSAYKELFNK YGINYQQGDI  1260
RALLCEQSDK AFYSSFMALM SLMLQMRNSI TGRTDVDFLI SPVKNSDGIF YDSRNYEAQE  1320
NAILPKNADA NGAYNIARKV LWAIGQFKKA EDEKLDKVKI AISNKEWLEY AQTSVKH    1377

SEQ ID NO: 13           moltype = AA  length = 1379
FEATURE                 Location/Qualifiers
source                  1..1379
                        mol_type = protein
                        organism = synthetic construct
SEQUENCE: 13
MGSKLEKFTN CYSLSKTLRF KAIPVGKTQE NIDNKRLLVE DEKRAEDYKG VKKLLDRYYL    60
SFINDVLHSI KLKNLNNYIS LFRKKTRTEK ENKELENLEI NLRKEIAKAF KGNEGYKSLF   120
KKDIIETILP EFLDDKDEIA LVNSFNGFTT AFTGFFDNRE NMFSEEAKST SIAFRCINEN   180
LTRYISNMDI FEKVDAIFDK HEVQEIKEKI LNSDYDVEDF FEGEFFNFVL TQEGIDVYNA   240
IIGGFVTESG EKIKGLNEYI NLYNQKTKQK LPKFKPLYKQ VLSDRESLSF YGGSSGENQT   300
TQKGQKNSRE RMKRIEEGIK ELGSQILKEH PVENTQLQNE KLYLYYLQNG RDMYVDQELD   360
INRLSDYDVD HIVPQSFLKD DSIDNKVLTR SDKNRGKSDN VPSEEVVKKM KNYWRQLLNA   420
KLITQRKFDN LTKAERGGLS EGYTSDEE VLEVFRNTLN KNSEIFSSIK KLEKLFKNFD   480
EYSSAGIFVK NGPAISTISK DIFGEWNVIR DKWNAEYDDI HLKKKAVVTE KYEDDRRKSF   540
KKIGSFSLEQ LQEYADADLS VVEKLKEIII QKVDEIYKVY GSSEKLFDAD FVLEKSLKKN   600
DAVVAIMKDL LDSVKSFENY IKAFFGEGKE TNRDESFYGD FVLAYDILLK VDHIYDAIRN   660
YVTQKPYSKD KFKLYFQNPQ FMGGWDKDKE TDYRATILRY GSKYYLAIMD KKYAKCLQKI   720
DKDDVNGNYE KINYKLLPGP NKMLPKVFFS KKWMAYYNPS EDIQKIYKNG TFKKGDMFNL   780
```

```
NDCHKLIDFF KDSISRYPKW SNAYDFNFSE TEKYKDIAGF YREVEEQGYK VSFESASKKE    840
VDKLVEEGKL YMFQIYNKDF SDKSHGTPNL HTMYFKLLFD ENNHGQIRLS GGAELFMRRA    900
SLKKEELVVH PANSPIANKN PDNPKKTTTL SYDVYKDKRF SEDQYELHIP IAINKCPKNI    960
FKINTEVRVL LKHDDNPYVI GIDRGERNLL YIVVVDGKGN IVEQYSLNEI INNFNGIRIK   1020
TDYHSLLDKK EKERFEARQN WTSIENIKEL KAGYISQVVH KICELVEKYD AVIALEDLNS   1080
GFKNSRVKVE KQVYQKFEKM LIDKLNYMVD KKSNPCATGG ALKGYQITNK FESFKSMSTQ   1140
NGFIFYIPAW LTSKIDPSTG FVNLLKTKYT SIADSKKFIS SFDRIMYVPE EDLFEFALDY   1200
KNFSRTDADY IKKWKLYSYG NRIRIFRNPK KNNVFDWEEV CLTSAYKELF NKYGINYQQG   1260
DIRALLCEQS DKAFYSSFMA LMSLMLQMRN SITGRTDVDF LISPVKNSDG IFYDSRNYEA   1320
QENAILPKNA DANGAYNIAR KVLWAIGQFK KAEDEKLDKV KIAISNKEWL EYAQTSVKH    1379

SEQ ID NO: 14           moltype = AA  length = 1373
FEATURE                 Location/Qualifiers
source                  1..1373
                        mol_type = protein
                        organism = synthetic construct
SEQUENCE: 14
MGSKLEKFTN CYSLSKTLRF KAIPVGKTQE NIDNKRLLVE DEKRAEDYKG VKKLLDRYYL     60
SFINDVLHSI KLKNLNNYIS LFRKKTRTEK ENKELENLEI NLRKEIAKAF KGNEGYKSLF    120
KKDIIETILP EFLDDKDEIA LVNSFNGFTT AFTGFFDNRE NMFSEEAKST SIAFRCINEN    180
LTRYISNMDI FEKVDAIFDK HEVQEIKEKI LNSDYDVEDF FEGEFFNFVL TQEGIDVYNA    240
IIGGFVTESG EKIKGLNEYI NLYNQKTKQK LPKFKPLYKQ VLSDRESLSF YGEENQTTQK    300
GQKNSRERMK RIEEGIKELG SQILKEHPVE NTQLQNEKLY LYYLQNGRDM YVDQELDINR    360
LSDYDVDHIV PQSFLKDDSI DNKVLTRSDK NRGKSDNVPS EEVVKKMKNY WRQLLNAKLI    420
TQRKFDNLTK AERGGLSGYT SDEEVLEVFR NTLNKNSEIF SSIKKLEKLF KNFDEYSSAG    480
IFVKNGPAIS TISKDIFGEW NVIRDKWNAE YDDIHLKKVA VVTEKYEDDR RKSFKKIGSF    540
SLEQLQEYAD ADLSVVEKLK EIIIQKVDEI YKVYGSSEKL FDADFVLEKS LKKNDAVVAI    600
MKDLLDSVKS FENYIKAFFG EGKETNRDES FYGDFVLAYD ILLKVDHIYD AIRNYVTQKP    660
YSKDKFKLYF QNPQFMGGWD KDKETDYRAT ILRYGSKYYL AIMDKKYAKC LQKIDKDDVN    720
GNYEKINYKL LPGPNKMLPK VFFSKKWMAY YNPSEDIQKY YKNGTFKKGD MFNLNDCHKL    780
IDFFKDSISR YPKWSNAYDF NFSETEKYKD IAGFYREVEE QGYKVSFESA SKKEVDKLVE    840
EGKLYMFQIY NKDFSDKSHG TPNLHTMYFK LLFDENNHGQ IRLSGGAELF MRRASLKKEE    900
LVVHPANSPI ANKNPDNPKK TTTLSYDVYK DKRFSEDQYE LHIPIAINKC PKNIFKINTE    960
VRVLLKHDDN PYVIGIDRGE RNLLYIVVVD GKGNIVEQYS LNEIINNFNG IRIKTDYHSL   1020
LDKKEKERFE ARQNWTSIEN IKELKAGYIS QVVHKICELV EKYDAVIALE DLNSGFKNSR   1080
VKVEKQVYQK FEKMLIDKLN YMVDKKSNPC ATGGALKGYQ ITNKFESFKS MSTQNGIFY    1140
IPAWLTSKID PSTGFVNLLK TKYTSIADSK KFISSFDRIM YVPEEDLFEF ALDYKNFSRT   1200
DADYIKKWKL YSYGNRIRIF RNPKKNNVFD WEEVCLTSAY KELFNKYGIN YQQGDIRALL   1260
CEQSDKAFYS SFMALMSLML QMRNSITGRT DVDFLISPVK NSDGIFYDSR NYEAQENAIL   1320
PKNADANGAY NIARKVLWAI GQFKKAEDEK LDKVKIAISN KEWLEYAQTS VKH          1373

SEQ ID NO: 15           moltype = AA  length = 1375
FEATURE                 Location/Qualifiers
source                  1..1375
                        mol_type = protein
                        organism = synthetic construct
SEQUENCE: 15
MGSKLEKFTN CYSLSKTLRF KAIPVGKTQE NIDNKRLLVE DEKRAEDYKG VKKLLDRYYL     60
SFINDVLHSI KLKNLNNYIS LFRKKTRTEK ENKELENLEI NLRKEIAKAF KGNEGYKSLF    120
KKDIIETILP EFLDDKDEIA LVNSFNGFTT AFTGFFDNRE NMFSEEAKST SIAFRCINEN    180
LTRYISNMDI FEKVDAIFDK HEVQEIKEKI LNSDYDVEDF FEGEFFNFVL TQEGIDVYNA    240
IIGGFVTESG EKIKGLNEYI NLYNQKTKQK LPKFKPLYKQ VLSDRESLSF YGEGSENQTT    300
QKGQKNSRER MKRIEEGIKE LGSQILKEHP VENTQLQNEK LYLYYLQNGR DMYVDQELDI    360
NRLSDYDVDH IVPQSFLKDD SIDNKVLTRS DKNRGKSDNV PSEEVVKKMK NYWRQLLNAK    420
LITQRKFDNL TKAERGGLSG YTSDEEVLEV FRNTLNKNSE IFSSIKKLEK LFKNFDEYSS    480
AGIFVKNGPA ISTISKDIFG EWNVIRDKWN AEYDDIHLKK AVVTEKYED DRRKSFKKIG    540
SFSLEQLQEY ADADLSVVEK LKEIIIQKVD EIYKVYGSSE KLFDADFVLE KSLKKNDAVV    600
AIMKDLLDSV KSFENYIKAF FGEGKETNRD ESFYGDFVLA YDILLKVDHI YDAIRNYVTQ    660
KPYSKDKFKL YFQNPQFMGG WDKDKETDYR ATILRYGSKY YLAIMDKKYA KCLQKIDKDD    720
VNGNYEKINY KLLPGPNKML PKVFFSKKWM AYYNPSEDIQ KIYKNGTFKK GDMFNLNDCH    780
KLIDFFKDSI SRYPKWSNAY DFNFSETEKY KDIAGFYREV EEQGYKVSFE SASKKEVDKL    840
VEEGKLYMFQ IYNKDFSDKS HGTPNLHTMY FKLLFDENNH GQIRLSGGAE LFMRRASLKK    900
EELVVHPANS PIANKNPDNP KKTTTLSYDV YKDKRFSEDQ YELHIPIAIN KCPKNIFKIN    960
TEVRVLLKHD DNPYVIGIDR GERNLLYIVV VDGKGNIVEQ YSLNEIINNF NGIRIKTDYH   1020
SLLDKKEKER FEARQNWTSI ENIKELKAGY ISQVVHKICE LVEKYDAVIA LEDLNSGFKN   1080
SRVKVEKQVY QKFEKMLIDK LNYMVDKKSN PCATGGALKG YQITNKFESF KSMSTQNGIF   1140
YIPAWLTSK IDPSTGFVNL LKTKYTSIAD SKKFISSFDR IMYVPEEDLF EFALDYKNFS    1200
RTDADYIKKW KLYSYGNRIR IFRNPKKNNV FDWEEVCLTS AYKELFNKYG INYQQGDIRA   1260
LLCEQSDKAF YSSFMALMSL MLQMRNSITG RTDVDFLISP VKNSDGIFYD SRNYEAQENA   1320
ILPKNADANG AYNIARKVLW AIGQFKKAED EKLDKVKIAI SNKEWLEYAQ TSVKH        1375

SEQ ID NO: 16           moltype = AA  length = 1377
FEATURE                 Location/Qualifiers
source                  1..1377
                        mol_type = protein
                        organism = synthetic construct
SEQUENCE: 16
MGSKLEKFTN CYSLSKTLRF KAIPVGKTQE NIDNKRLLVE DEKRAEDYKG VKKLLDRYYL     60
SFINDVLHSI KLKNLNNYIS LFRKKTRTEK ENKELENLEI NLRKEIAKAF KGNEGYKSLF    120
```

```
KKDIIETILP EFLDDKDEIA LVNSFNGFTT AFTGFFDNRE NMFSEEAKST SIAFRCINEN    180
LTRYISNMDI FEKVDAIFDK HEVQEIKEKI LNSDYDVEDF FEGEFFNFVL TQEGIDVYNA    240
IIGGFVTESG EKIKGLNEYI NLYNQKTKQK LPKFKPLYKQ VLSDRESLSF YGEGSSGENQ    300
TTQKGQKNSR ERMKRIEEGI KELGSQILKE HPVENTQLQN EKLYLYYLQN GRDMYVDQEL    360
DINRLSDYDV DHIVPQSFLK DDSIDNKVLT RSDKNRGKSD NVPSEEVVKK MKNYWRQLLN    420
AKLITQRKFD NLTKAERGGL SGYTSDEEVL EVFRNTLNKN SEIFSSIKKL EKLFKNFDEY    480
SSAGIFVKNG PAISTISKDI FGEWNVIRDK WNAEYDDIHL KKKAVVTEKY EDDRRKSFKK    540
IGSFSLEQLQ EYADADLSVV EKLKEIIIQK VDEIYKVYGS SEKLFDADFV LEKSLKKNDA    600
VVAIMKDLLD SVKSFENYIK AFFGEGKETN RDESFYGDFV LAYDILLKVD HIYDAIRNYV    660
TQKPYSKDKF KLYFQNPQFM GGWDKDKETD YRATILRYGS KYYLAIMDKK YAKCLQKIDK    720
DDVNGNYEKI NYKLLPGPNK MLPKVFFSKK WMAYYNPSED IQKIYKNGTF KKGDMFNLND    780
CHKLIDFFKD SISRYPKWSN AYDFNFSETE KYKDIAGFYR EVEEQGYKVS FESASKKEVD    840
KLVEEGKLYM FQIYNKDFSD KSHGTPNLHT MYFKLLFDEN NHGQIRLSGG AELFMRRASL    900
KKEELVVHPA NSPIANKNPD NPKKTTTLSY DVYKDKRFSE DQYELHIPIA INKCPKNIFK    960
INTEVRVLLK HDDNPYVIGI DRGERNLLYI VVVDGKGNIV EQYSLNEIIN NFNGIRIKTD   1020
YHSLLDKKEK ERFEARQNWT SIENIKELKA GYISQVVHKI CELVEKYDAV IALEDLNSGF   1080
KNSRVKVEKQ VYQKFEKMLI DKLNYMVDKK SNPCATGGAL KGYQITNKFE SFKSMSTQNG   1140
FIFYIPAWLT SKIDPSTGFV NLLKTKYTSI ADSKKFISSF DRIMYVPEED LFEFALDYKN   1200
FSRTDADYIK KWKLYSYGNR IRIFRNPKKN NVFDWEEVCL TSAYKELFNK YGINYQQGDI   1260
RALLCEQSDK AFYSSFMALM SLMLQMRNSI TGRTDVDFLI SPVKNSDGIF YDSRNYEAQE   1320
NAILPKNADA NGAYNIARKV LWAIGQFKKA EDEKLDKVKI AISNKEWLEY AQTSVKH      1377

SEQ ID NO: 17           moltype = AA   length = 1379
FEATURE                 Location/Qualifiers
source                  1..1379
                        mol_type = protein
                        organism = synthetic construct
SEQUENCE: 17
MGSKLEKFTN CYSLSKTLRF KAIPVGKTQE NIDNKRLLVE DEKRAEDYKG VKKLLDRYYL     60
SPINDVLHSI KLKNLNNYIS LFRKKTRTEK ENKELENLEI NLRKEIAKAF KGNEGYKSLF    120
KKDIIETILP EFLDDKDEIA LVNSFNGFTT AFTGFFDNRE NMFSEEAKST SIAFRCINEN    180
LTRYISNMDI FEKVDAIFDK HEVQEIKEKI LNSDYDVEDF FEGEFFNFVL TQEGIDVYNA    240
IIGGFVTESG EKIKGLNEYI NLYNQKTKQK LPKFKPLYKQ VLSDRESLSF YGEGSSGENQ    300
TTQKGQKNSR ERMKRIEEGI KELGSQILKE HPVENTQLQN EKLYLYYLQN GRDMYVDQEL    360
DINRLSDYDV DHIVPQSFLK DDSIDNKVLT RSDKNRGKSD NVPSEEVVKK MKNYWRQLLN    420
AKLITQRKFD NLTKAERGGL SGSGYTSDEE VLEVFRNTLN KNSEIFSSIK KLEKLFKNFD    480
EYSSAGIFVK NGPAISTISK DIFGEWNVIR DKWNAEYDDI HLKKKAVVTE KYEDDRRKSF    540
KKIGSFSLEQ LQEYADADLS VVEKLKEIII QKVDEIYKVY GSSEKLFDAD FVLEKSLKKN    600
DAVVAIMKDL LDSVKSFENY IKAFFGEGKE TNRDESFYGD FVLAYDILLK VDHIYDAIRN    660
YVTQKPYSKD KFKLYFQNPQ FMGGWDKDKE TDYRATILRY GSKYYLAIMD KKYAKCLQKI    720
DKDDVNGNYE KINYKLLPGP NKMLPKVFFS KKWMAYYNPS EDIQKIYKNG TFKKGDMFNL    780
NDCHKLIDFF KDSISRYPKW SNAYDFNFSE TEKYKDIAGF YREVEEQGYK VSFESASKKE    840
VDKLVEEGKL YMFQIYNKDF SDKSHGTPNL HTMYFKLLFD ENNHGQIRLS GGAELFMRRA    900
SLKKEELVVH PANSPIANKN PDNPKKTTTL SYDVYKDKRF SEDQYELHIP IAINKCPKNI    960
FKINTEVRVL LKHDDNPYVI GIDRGERNLL YIVVVDGKGN IVEQYSLNEI INNFNGIRIK   1020
TDYHSLLDKK EKERFEARQN WTSIENIKEL KAGYISQVVH KICELVEKYD AVIALEDLNS   1080
GFKNSRVKVE KQVYQKFEKM LIDKLNYMVD KKSNPCATGG ALKGYQITNK FESFKSMSTQ   1140
NGFIFYIPAW LTSKIDPSTG FVNLLKTKYT SIADSKKFIS SFDRIMYVPE EDLFEFALDY   1200
KNFSRTDADY IKKWKLYSYG NRIRIFRNPK KNNVFDWEEV CLTSAYKELF NKYGINYQQG   1260
DIRALLCEQS DKAFYSSFMA LMSLMLQMRN SITGRTDVDF LISPVKNSDG IFYDSRNYEA   1320
QENAILPKNA DANGAYNIAR KVLWAIGQFK KAEDEKLDKV KIAISNKEWL EYAQTSVKH    1379

SEQ ID NO: 18           moltype = AA   length = 36
FEATURE                 Location/Qualifiers
source                  1..36
                        mol_type = protein
                        organism = synthetic construct
SEQUENCE: 18
EKSKNDRSKP QPSDDRDRQP PSGEDYPEWK APGEYE                               36

SEQ ID NO: 19           moltype = AA   length = 34
FEATURE                 Location/Qualifiers
source                  1..34
                        mol_type = protein
                        organism = synthetic construct
SEQUENCE: 19
QEPKPQDQSS EVPPPPGSQK PGTKEPHDSK SSGP                                 34

SEQ ID NO: 20           moltype = AA   length = 34
FEATURE                 Location/Qualifiers
source                  1..34
                        mol_type = protein
                        organism = synthetic construct
SEQUENCE: 20
PDNSSGQKLQ LPQPSDKPQD SREKSDSLPS DKRD                                 34

SEQ ID NO: 21           moltype = AA   length = 36
FEATURE                 Location/Qualifiers
source                  1..36
```

```
                              mol_type = protein
                              organism = synthetic construct
SEQUENCE: 21
PDNSTLQTLQ LPQPTPSSTD TQQTSDTDPE DTTDVI                                36

SEQ ID NO: 22                 moltype = AA   length = 30
FEATURE                       Location/Qualifiers
source                        1..30
                              mol_type = protein
                              organism = synthetic construct
SEQUENCE: 22
STSQSDGSSV PADIDQSSDS DQSSSQGQPG                                       30

SEQ ID NO: 23                 moltype = AA   length = 14
FEATURE                       Location/Qualifiers
source                        1..14
                              mol_type = protein
                              organism = synthetic construct
SEQUENCE: 23
AKPDDESQKP PQDD                                                        14

SEQ ID NO: 24                 moltype = AA   length = 14
FEATURE                       Location/Qualifiers
source                        1..14
                              mol_type = protein
                              organism = synthetic construct
SEQUENCE: 24
LQLEPGPTTP EYPI                                                        14

SEQ ID NO: 25                 moltype = AA   length = 14
FEATURE                       Location/Qualifiers
source                        1..14
                              mol_type = protein
                              organism = synthetic construct
SEQUENCE: 25
IQLPPSDTTP ENPI                                                        14

SEQ ID NO: 26                 moltype = AA   length = 12
FEATURE                       Location/Qualifiers
source                        1..12
                              mol_type = protein
                              organism = synthetic construct
SEQUENCE: 26
ESNDNSQVPP SL                                                          12

SEQ ID NO: 27                 moltype = AA   length = 10
FEATURE                       Location/Qualifiers
source                        1..10
                              mol_type = protein
                              organism = synthetic construct
SEQUENCE: 27
SEQQEYPGSG                                                             10

SEQ ID NO: 28                 moltype = AA   length = 10
FEATURE                       Location/Qualifiers
source                        1..10
                              mol_type = protein
                              organism = synthetic construct
SEQUENCE: 28
NNSEQQENPA                                                             10

SEQ ID NO: 29                 moltype = AA   length = 12
FEATURE                       Location/Qualifiers
source                        1..12
                              mol_type = protein
                              organism = synthetic construct
SEQUENCE: 29
STDGSGQPKH KP                                                          12

SEQ ID NO: 30                 moltype = AA   length = 20
FEATURE                       Location/Qualifiers
source                        1..20
                              mol_type = protein
                              organism = synthetic construct
SEQUENCE: 30
PKPSSESGER YEQQPEPPPP                                                  20

SEQ ID NO: 31                 moltype = AA   length = 16
FEATURE                       Location/Qualifiers
```

```
source                      1..16
                            mol_type = protein
                            organism = synthetic construct
SEQUENCE: 31
KGGGGEPDEK RPSQSS                                                              16

SEQ ID NO: 32               moltype = AA   length = 14
FEATURE                     Location/Qualifiers
source                      1..14
                            mol_type = protein
                            organism = synthetic construct
SEQUENCE: 32
YAGGTPKEPP PPNS                                                                14

SEQ ID NO: 33               moltype = AA   length = 14
FEATURE                     Location/Qualifiers
source                      1..14
                            mol_type = protein
                            organism = synthetic construct
SEQUENCE: 33
PLVAGGTPFE PPPP                                                                14

SEQ ID NO: 34               moltype = AA   length = 14
FEATURE                     Location/Qualifiers
source                      1..14
                            mol_type = protein
                            organism = synthetic construct
SEQUENCE: 34
PQPDERSQIP DNKE                                                                14

SEQ ID NO: 35               moltype = AA   length = 10
FEATURE                     Location/Qualifiers
source                      1..10
                            mol_type = protein
                            organism = synthetic construct
SEQUENCE: 35
YTDEKPLPRS                                                                     10

SEQ ID NO: 36               moltype = AA   length = 12
FEATURE                     Location/Qualifiers
source                      1..12
                            mol_type = protein
                            organism = synthetic construct
SEQUENCE: 36
SHPPQEPPQS NL                                                                  12

SEQ ID NO: 37               moltype = AA   length = 16
FEATURE                     Location/Qualifiers
source                      1..16
                            mol_type = protein
                            organism = synthetic construct
SEQUENCE: 37
SESPSKQQPE PKSSKG                                                              16

SEQ ID NO: 38               moltype = AA   length = 16
FEATURE                     Location/Qualifiers
source                      1..16
                            mol_type = protein
                            organism = synthetic construct
SEQUENCE: 38
SESPTNQQPE PQWTTD                                                              16

SEQ ID NO: 39               moltype = AA   length = 16
FEATURE                     Location/Qualifiers
source                      1..16
                            mol_type = protein
                            organism = synthetic construct
SEQUENCE: 39
GGSKGPPPSP PPPQPE                                                              16

SEQ ID NO: 40               moltype = AA   length = 16
FEATURE                     Location/Qualifiers
source                      1..16
                            mol_type = protein
                            organism = synthetic construct
SEQUENCE: 40
GPLPAPPPQP PPPQPN                                                              16

SEQ ID NO: 41               moltype = AA   length = 14
```

```
FEATURE                 Location/Qualifiers
source                  1..14
                        mol_type = protein
                        organism = synthetic construct
SEQUENCE: 41
RPLPHDNNKQ DYSK                                                        14

SEQ ID NO: 42           moltype = AA  length = 61
FEATURE                 Location/Qualifiers
VARIANT                 5..61
                        note = Residue may be present or absent
source                  1..61
                        mol_type = protein
                        organism = synthetic construct
SEQUENCE: 42
SGGSGGSGGS GGSGGSGGSG GSGGSGGSGG SGGSGGSGGS GGSGGSGGSG GSGGSGGSGG       60
S                                                                      61

SEQ ID NO: 43           moltype = AA  length = 4
FEATURE                 Location/Qualifiers
source                  1..4
                        mol_type = protein
                        organism = synthetic construct
SEQUENCE: 43
SGGS                                                                    4

SEQ ID NO: 44           moltype = AA  length = 100
FEATURE                 Location/Qualifiers
VARIANT                 6..100
                        note = Residue may be present or absent
source                  1..100
                        mol_type = protein
                        organism = synthetic construct
SEQUENCE: 44
GGGGSGGGGS GGGGSGGGGS GGGGSGGGGS GGGGSGGGGS GGGGSGGGGS GGGGSGGGGS       60
GGGGSGGGGS GGGGSGGGGS GGGGSGGGGS GGGGSGGGGS                            100

SEQ ID NO: 45           moltype = AA  length = 10
FEATURE                 Location/Qualifiers
source                  1..10
                        mol_type = protein
                        organism = synthetic construct
SEQUENCE: 45
SGGSGGSGGS                                                             10

SEQ ID NO: 46           moltype = AA  length = 16
FEATURE                 Location/Qualifiers
source                  1..16
                        mol_type = protein
                        organism = synthetic construct
SEQUENCE: 46
SGSETPGTSE SATPES                                                      16

SEQ ID NO: 47           moltype = AA  length = 32
FEATURE                 Location/Qualifiers
source                  1..32
                        mol_type = protein
                        organism = synthetic construct
SEQUENCE: 47
SGGSSGGSSG SETPGTSESA TPESSGGSSG GS                                    32

SEQ ID NO: 48           moltype = DNA  length = 1592
FEATURE                 Location/Qualifiers
source                  1..1592
                        mol_type = other DNA
                        organism = Medicago truncatula
SEQUENCE: 48
actgttaata attttaaac gtcagcgcac taaaaaaacg aaaagacgga cacgtgaaaa        60
taaaaaacac acactagttt atgacgcaat actattttac ttatgatttg ggtacattag     120
acaaaaccgt gaaagagatg tatcagctat gaaacctgta tacttcaata cagagactta    180
ctcatatcgg atacgtacgc acgaagtatc atattaatta tttttaatttt taataaatat   240
tttatcggat acttatgtga tactctacat atacacaagg atatttctaa gatactttat    300
agatacgtat cctagaaaaa catgaagagt aaaaaagtga gacaatgttg taaaaattca    360
ttataaatgt atatgattca attttagata tgcatcagta taattgattc tcgatgaaac    420
acttaaaatt atatttcttg tggaagaacg tagcgagaga ggtgattcag ttagacaaca    480
ttaaataaaa ttaatgttaa gttctttttaa tgatgtttct ctcaatatca catcatatga    540
aaatgtaata tgatttataa gaaaatttt aaaaaattta ttttaataat cacatgtact     600
attttttaaa aattgtatct tttataataa tacaataata aagagtaatc agtgttaatt    660
tttcttcaaa tataagtttt attataaatc attgttaacg tatcataagt cattaccgta    720
```

```
tcgtatctta attttttttt aaaaaccgct aattcacgta cccgtattgt attgtacccg    780
cacctgtatc acaatcgatc ttagttagaa gaattgtctc gaggcggtgc aagacagcat    840
ataatagacg tggactctct tataccaaac gttgtcgtat cacaaagggt taggtaacaa    900
gtcacagttt gtccacgtgt cacgtttaa ttggaagagg tgccgttggc gtaatataac     960
agccaatcga tttttgctat aaaagcaaat caggtaaact aaacttcttc attctttct   1020
tccccatcgc tacaaaaccg gttcctttgg aaaagagatt cattcaaacc tagcacccaa   1080
ttccgtttca aggtataatc tactttctat tcttcgatta ttttattatt attagctact   1140
atcgtttaat cgatcttttc ttttgatccg tcaaatttaa attcaattag ggttttgttc   1200
ttttctttca tctgattgaa atccttctga attgaaccgt ttacttgatt ttactgttta   1260
ttgtatgatt taatcctttg tttttcaaag acagtcttta gattgtgatt aggggttcat   1320
ataaattttt agatttggat ttttgtattg tatgattcaa aaaatacgtc ctttaattag   1380
attagtacat ggatatttt tacccgattt attgattgtc agggagaatt tgatgagcaa    1440
gttttttga tgtctgttgt aaattgaatt gattataatt gctgatctgc tgcttccagt    1500
tttcataacc catattcttt taaccttgtt gtacacacaa tgaaaaattg gtgattgatt   1560
catttgtttt tctttgtttt ggattataca gg                                 1592

SEQ ID NO: 49           moltype = DNA   length = 2000
FEATURE                 Location/Qualifiers
source                  1..2000
                        mol_type = other DNA
                        organism = Zea mays
SEQUENCE: 49
gtcgtgcccc tctctagaga taaagagcat tgcatgtcta aagtataaaa aattaccaca     60
tatttttttg tcacacttat ttgaagtgta gtttatctat ctctatacat atatttaaac    120
ttcactctac aaataatata gtctataata ctaaaataat attagtgttt tagaggatca    180
tataaataaa ctgctagaca tggtctaaag gataattgaa tattttgaca atctacagtt    240
ttatcttttt agtgtgcatg tgatctctct gttttttttg caaatagctt gacctatata    300
atacttcatc cattttatta gtacatccat ttaggattta gggttgatgg tttcatagaa    360
ctaattttta gtacatccat tttattcttt ttagtctcta aattttttaa aactaaaact    420
ctattttgat tttttattta ataatttaga tataaaatga aataaaataa attgactaca    480
aataaaacaa atacccttta agaaataaaa aaactaagca aacatttttc ttgtttcgag    540
tagataatga caggctgttc aacgccgtcg acgagtctaa cggacaccaa ccagcgaacc    600
agcagcgtcg cgtcgggcca agcgaagcag acggcacggc atctctgtag ctgcctctgg    660
accctcgtcg agagttccgc tccaccgttg gacttgctcc gctgtcggca tccagaaatt    720
gcgtggcgga gcggcagacg tgaggcggca cggcaggcgg cctcttcctc ctctcacggc    780
accggcagct acggggatt cctttcccac cgctccttcg cttccctcc ctcgcccgcc      840
gtaataaata gacacccct ccacaccctc tttccccaac ctcgtgttcg ttcggagcgc     900
acacacacgc aaccagatct ccccaaaatc cagccgtcgg cacctccgct tcaaggtacg    960
ccgctcatcc tccccccc cctctctcta ccttctctag atcggcgatc cggtccatgg     1020
ttagggcccg gtagttctac ttctgttcat gtttgtgtta gagcaaacat gttcatgttc   1080
atgtttgtga tgatgtggtc tggttgggcg gtcgttctag atcggagtag gatactgttt   1140
caagctacct ggtggattta ttaatttgt atctgtatgt gtgtgccata catcttcata    1200
gttacgagtt taagatgatg gatggaaata tcgatctaga ataggtatac atgttgatgc   1260
gggttttact gatgcatata cagagatgct tttttctcg cttggttgtg atgatatggt    1320
ctggttgggc ggtcgttcta gatcggagta gaatactgtt tcaaactacc tggtggattt   1380
attaaaggat aaagggtcgt tctagatcgg agtagaaatc tgtttcaaac tacctggtgg   1440
atttattaaa ggatctgtat gtatgtgcct acatcttcat agttacgagt ttaagatgat   1500
ggatggaaat atcgatctag ataggtata catgttgatg cgggttttac tgatgcatat    1560
acagagatgc tttttttcgc ttggttgtga tgatgtggtc tggttgggcg gtcgttctag   1620
atcggagtag aatactgttt caaactacct ggtggattta ttaattttgt atctttatgt   1680
gtgtgccata catcttcata gttacgagtt taagatgatg gatggaaata ttgatctagg   1740
ataggtatac atgttgatgt gggttttact gatgcatata catgatggca tatgcggcat   1800
ctattcatat gctctaacct tgagtaccta tctattataa taaacaagta tgttttataa   1860
ttattttgat cttgatatac ttggatgatg gcatatgcag cagctatatg tggatttttt   1920
agccctgcct tcatacgcta ttatttgct tggtactgtt tcttttgtcc gatgctcacc    1980
ctgttgtttg gtgatacttc                                               2000

SEQ ID NO: 50           moltype = AA   length = 1227
FEATURE                 Location/Qualifiers
source                  1..1227
                        mol_type = protein
                        note = Lachnospiraceae bacterium
                        organism = unidentified
SEQUENCE: 50
SKLEKFTNCY SLSKTLRFKA IPVGKTQENI DNKRLLVEDE KRAEDYKGVK KLLDRYYLSF      60
INDVLHSIKL KNLNNYISLF RKKTRTEKEN KELENLEINL RKEIAKAFKG NEGYKSLFKK    120
DIIETILPEF LDDKDEIALV NSFNGFTTAF TGFFDNRENM FSEEAKSTSI AFRCINENLT    180
RYISNMDIFE KVDAIFDKHE VQEIKEKILN SDYDVEDFPE GEFFNFVLTQ EGIDVYNAII    240
GGFVTESGEK IKGLNEYINL YNQKTKQKLP KFKPLYKQVL SDRESLSFYG EGYTSDEEVL    300
EVFRNTLNKN SEIFSSIKKL EKLFKNFDEY SSAGIFVKNG PAISTISKDI FGEWNVIRDK    360
WNAEYDDIHL KKKAVVTEKY EDDRRKSFKK IGSFSLEQLQ EYADADLSVV EKLKEIIIQK    420
VDEIYKVYGS SEKLFDADFV LEKSLKKNDA VVAIMKDLLD SVKSFENYIK AFFGEGKETN    480
RDESFYGDFV LAYDILLKVD HIYDAIRNYV TQKPYSKCDF KLYFQNPQFM GGWDKDKETD    540
YRATILRYGS KYYLAIMDKK YAKCLQKIDK DDVNGNYEKI NYKLLPGPNK MLPKVFFSKK    600
WMAYYNPSED IQKIYKNGTF KKGDMFNLND CHKLIDFFKD SISRYPKWSN AYDFNFSETE    660
KYKDIAGFYR EVEEQGYKVS FESASKKEVD KLVEEGKLYM FQIYNKDPSD KSHGTPNLHT    720
MYFKLLFDEN NHGQIRLSGG AELFMRRASL KKEELVVHPA NSPIANKNPD NPKKTTTLSY    780
DVYKDKRFSE DQYELHIPIA INKCPKNIFK INTEVRVLLK HDDNPYVIGI ARGERNLLYI    840
VVVDGKGNIV EQYSLNEIIN NFNGIRIKTD YHSLLDKKEK ERFEARQNWT SIENIKELKA    900
```

```
                                    -continued
GYISQVVHKI CELVEKYDAV IALEDLNSGF KNSRVKVEKQ VYQKFEKMLI DKLNYMVDKK      960
SNPCATGGAL KGYQITNKFE SFKSMSTQNG FIFYIPAWLT SKIDPSTGFV NLLKTKYTSI     1020
ADSKKFISSF DRIMYVPEED LFEFALDYKN FSRTDADYIK KWKLYSYGNR IRIFRNPKKN     1080
NVFDWEEVCL TSAYKELFNK YGINYQQGDI RALLCEQSDK AFYSSFMALM SLMLQMRNSI     1140
TGRTDVDFLI SPVKNSDGIF YDSRNYEAQE NAILPKNADA NGAYNIARKV LWAIGQFKKA     1200
EDEKLDKVKI AISNKEWLEY AQTSVKH                                        1227

SEQ ID NO: 51           moltype = AA  length = 1307
FEATURE                 Location/Qualifiers
source                  1..1307
                        mol_type = protein
                        organism = Acidaminococcus sp.
SEQUENCE: 51
MTQFEGFTNL YQVSKTLRFE LIPQGKTLKH IQEQGFIEED KARNDHYKEL KPIIDRIYKT       60
YADQCLQLVQ LDWENLSAAI DSYRKEKTEE TRNALIEEQA TYRNAIHDYF IGRTDNLTDA      120
INKRHAEIYK GLFKAELFNG KVLKQLGTVT TTEHENALLR SFDKFTTYFS GFYENRKNVF      180
SAEDISTAIP HRIVQDNFPK FKENCHIFTR LITAVPSLRE HFENVKKAIG IFVSTSIEEV      240
FSFPFYNQLL TQTQIDLYNQ LLGGISREAG TEKIKGLNEV LNLAIQKNDE TAHIIASLPH      300
RFIPLFKQIL SDRNTLSFIL EEFKSDEEVI QSFCKYKTLL RNENVLETAE ALFNELNSID      360
LTHIFISHKK LETISSALCD HWDTLRNALY ERRISELTGK ITKSAKEKVQ RSLKHEDINL      420
QEIISAAGKE LSEAFKQKTS EILSHAHAAL DQPLPTTLKK QEEKEILKSQ LDSLLGYHL       480
LDWFAVDESN EVDPEFSARL TGIKLEMEPS LSFYNKARNY ATKKPYSVEK FKLNFQMPTL      540
ASGWDVNKEK NNGAILFVKN GLYYLGIMPK QKGRYKALSF EPTEKTSEGF DKMYYDYFPD      600
AAKMIPKCST QLKAVTAHFQ THTTPILLSN NFIEPLEITK EIYDLNNPEK EPKKFQTAYA      660
KKTGDQKGYR EALCKWIDFT RDFLSKYTKT TSIDLSSLRP SSQYKDLGEY YAELNPLLYH     720
ISFQRIAEKE IMDAVETGKL YLFQIYNKDF AKGHHGKPNL HTLYWTGLFS PENLAKTSIK     780
LNGQAELFYR PKSRMKRMAH RLGEKMLNKK LKDQKTPIPD TLYQELYDYV NHRLSHDLSD     840
EARALLPNVI TKEVSHEIIK DRRFTSDKFF FHVPITLNYQ AANSPSKFNQ RVNAYLKEHP     900
ETPIIGIDRG ERNLIYITVI DSTGKILEQR SLNTIQQFDY QKKLDNREKE RVAARQAWSV     960
VGTIKDLKQG YLSQVIHEIV DLMIHYQAVV VLENLNFGFK SKRTGIAEKA VYQQFEKMLI    1020
DKLNCLVLKD YPAEKVGGVL NPYQLTDQFT SFAKMGTQSG FLFYVPAPYT SKIDPLTGFV    1080
DPFVWKTIKN HESRKHFLEG FDFLHYDVKT GDFILHFKMN RNLSFQRGLP GFMPAWDIVF    1140
EKNETQFDAK GTPFIAGKRI VPVIENHRFT GRYRDLYPAN ELIALLEEKG IVFRDGSNIL    1200
PKLLENDDSH AIDTMVALIR SVLQMRNSNA ATGEDYINSP VRDLNGVCFD SRFQNPEWPM    1260
DADANGAYHI ALKGQLLLNH LKESKDLKLQ NGISNQDWLA YIQELRN                 1307

SEQ ID NO: 52           moltype = AA  length = 1241
FEATURE                 Location/Qualifiers
source                  1..1241
                        mol_type = protein
                        organism = Butyrivibrio proteoclasticus
SEQUENCE: 52
MLLYENYTKR NQITKSLRLE LRPQGKTLRN IKELNLLEQD KAIYALLERL KPVIDEGIKD       60
IARDTLKNCE LSFEKLYEHF LSGDKKAYAK ESERLKKEIV KTLIKNLPEG IGKISEINSA      120
KYLNGVLYDF IDKTHKDSEE KQNILSDILE TKGYLAFSK FLTSRITTLE QSMPKRVIEN      180
FEIYAANIPK MQDALERGAV SFAIEYESIC SVDYYNQILS QEDIDSYNRL ISGIMDEDGA      240
KEKGINQTIS EKNIKIKSEH LEEKPFRILK QLHKQILEER EKAFTIDHID SDEEVVQVTK      300
EAFEQTKEQW ENIKKINGFY AKDPGDITLF IVVGPNQTHV LSQLIYGEHD RIRLLLEEYE      360
KNTLEVLPRR TKSEDARYDK FVNAVPKKVA KESHTFDGLQ KMTGDDRLFI LYRDELARNY     420
MRIKEAYGTF ERDILKSRRG IKGNRDVQES LVSFYDELTK FRSALRIINS GNDEKADPIF     480
YNTFDGIFEK ANRTYKAENL CRNYVTKSPA DDARIMASCL GTPARLRTHW WNGEENFAIN    540
DVAMIRRGDE YYYFVLTPDV KPVDLKTKDE TDAQIFVQRK GAKSFLGLPK ALFKCILEPY    600
FESPEHKNDK NCVIEEYVSK PLTIDRRAYD IFKNGTFKKT NIGIDGLTEE KPKDDCRYLI    660
DVYKEFIAVY TRYSCFNMSG LKRADEYNDI GEFFSDVDTR LCTMEWIPVS FERINDMVDK    720
KEGLLFLVRS MFLYNRPRKP YERTFIQLFS DSNMEHTSML LNSRAMIQYR AASLPRRVTH    780
KKGSILVALR DSNGEHIPMH IREAIYKMKN NFDISSEDFI MAKAYLAEHD VAIKKANEDI    840
IRNRRYTEDK FFLSLSYTKN ADISARTLDY INDKVEEDTQ DSRMAVIVTR NLKDLTYVAV    900
VDEKNNVLEE KSLNEIDGVN YRELLKERTK IKYHDKTRLW QYDVSSKGLK EAYVELAVTQ    960
ISKLATKYNA VVVVESMSST FKDKFSFLDE QIFKAFEARL CARMSDLSFN TIKEGEAGSI   1020
SNPIQVSNNN GNSYQDGVIY FLNNAYTRTL CPDTGFVDVF DKTRLITMQS KRQFFAKMKD   1080
IRIDDGEMLF TFNLEEYPTK RLLDRKEWTV KIAGDGSYFD KDKGEYVYVN DIVREQIIPA   1140
LLEDKAVFDG NMAEKFLDKT AISGKSVELI YKWFANALYG IITKKDGEKI YRSPITGTEI   1200
DVSKNTTYNF GKKFMFKQEY RGDGDFLDAF LNYMQAQDIA V                       1241

SEQ ID NO: 53           moltype = AA  length = 1238
FEATURE                 Location/Qualifiers
source                  1..1238
                        mol_type = protein
                        organism = Methanoplasma termitum
SEQUENCE: 53
MNNYDEFTKL YPIQKTIRFE LKPQGRTMEH LETFNFFEED RDRAEKYKIL KEAIDEYHKK       60
FIDEHLTNMS LDWNSLKQIS EKYYKSREEK DKKVFLSEQK RMRQEIVSEF KKDDRFKDLF      120
SKKLFSELLK EEIYKKGNHQ EIDALKSFDK FSGYFIGLHE NRKNMYSDGD EITAISNRIV      180
NENFPKFLDN LQKYQEARKK YPEWIIKAES ALVAHNIKMD IVFSLEYFNK VLNQEGIQRY     240
NLALGGYVTK SGEKMMGLND ALNLAHQSEK SSKGRIHMTP LFKQILSEKE SFSYIPDVFT     300
EDSQLLPSIG GFFAQIENDK DGNIFDRALE LISSYAEYDT ERIYIRQADI NRVSNVIFGE     360
WGTLGGLMRE YKADSINDIN LERTCKKVDK WLDSKEFALS DVLEAIDRTG NNDAFNEYIS     420
KMRTAREKID AARKEMKFIS EKISGDEESI HIIKTLLDSV QQFLHFFNLF KARQDIPLDG     480
AFYAEFDEVH SKLFAIVPLY NKVRNYLTKN NLNTKKIKLN FKNPTLANGW DQNKVYDYAS    540
```

-continued

```
LIFLRDGNYY LGIINPKRKK NIKFEQGSGN GPFYRKMVYK QIPGPNKNLR PVFLTSTKGK  600
KEYKPSKEII EGYEADKHIR GDKFDLDFCH KLIDFFKESI EKHKDWSKFN FYFSPTESYG  660
DISEFYLDVE KQGYRMHFEN ISAETIDEYV EKGDLFLFQI YNKDFVKAAT GKKDMHTIYW  720
NAAFSPENLQ DVVVKLNGEA ELFYRDKSDI KEIVHREGEI LVNRTYNGRT PVPDKIHKKL  780
TDYHNGRTKD LGEAKEYLDK VRYFKAHYDI TKDRRYLNDK IYFHVPLTLN FKANGKKNLN  840
KMVIEKFLSD EKAHIIGIDR GERNLLYYSI IDRSGKIIDQ QSLNVIDGFD YREKLNQREI  900
EMKDARQSWN AIGKIKDLKE GYLSKAVHEI TKMAIQYNAI VVMEELNYGF KRGRFKVEKQ  960
IYQKFENMLI DKMNYLVFKD APDESPGGVL NAYQLTNPLE SFAKLGKQTG ILFYVPAAYT  1020
SKIDPTTGFV NLFNTSSKTN AQERKEFLQK FESISYSAKD GGIFAFAFDY RKFGTSKTDH  1080
KNVWTAYTNG ERMRYIKEKK RNELFDPSKE IKEALTSSGI KYDGGQNILP DILRSNNNGL  1140
IYTMYSSFIA AIQMRVYDGK EDYIISPIKN SKGEFFRTDP KRRELPIDAD ANGAYNIALR  1200
GELTMRAIAE KFDPDSEKMA KLELKHKDWF EFMQTRGD                          1238

SEQ ID NO: 54          moltype = AA  length = 1281
FEATURE                Location/Qualifiers
source                 1..1281
                       mol_type = protein
                       organism = Eubacterium eligens
SEQUENCE: 54
MNGNRSIVYR EFVGVIPVAK TLRNELRPVG HTQEHIIQNG LIQEDELRQE KSTELKNIMD  60
DYYREYIDKS LSGVTDLDFT LLFELMNLVQ SSPSKDNKKA LEKEQSKMRE QICTHLQSDS  120
NYKNIFNAKL LKEILPDFIK NYNQYDVKDK AGKLETLALF NGFSTYFTDF FEKRKNVFTK  180
EAVSTSIAYR IVHENSLIFL ANMTSYKKIS EKALDEIEVI EKNNQDKMGD WELNQIFNPD  240
FYNMVLIQSG IDFYNEICGV VNAHMNLYCQ QTKNNYNLFK MRKLHKQILA YTSTSFEVPK  300
MFEDDMSVYN AVNAFIDETE KGNIIGKLKD IVNKYDELDE KRIYISKDFY ETLSCFMSGN  360
WNLITGCVEN FYDENIHAKG KSKEEKVKKA VKEDKYKSIN DVNDLVEKYI DEKERNEFKN  420
SNAKQYIREI SNIITDTETA HLEYDDHISL IESEEKADEM KKRLDMYMNM YHWAKAFIVD  480
EVLDRDEMFY SDIDDIYNIL ENIVPLYNRV RNYVTQKPYN SKKIKLNFQS PTLANGWSQS  540
KEFDNNAIIL IRDNKYYLAI FNAKNKPDKK IIQGNSDKKN DNDYKKMVYN LLPGANKMLP  600
KVFLSKKGIE TFKPSDYIIS GYNAHKHIKT SENFDISFCR DLIDYFKNSI EKHAEWRKYE  660
FKFSATDSYS DISEFYREVE MQGYRIDWTY ISEADINKLD EEGKIYLFQI YNKDFAENST  720
GKENLHTMYF KNIFSEENLD KIIKLNGQAE LFYRRASVKN PVKHKKDSVL VNKTYKNQLD  780
NGDVVRIPIP DDIYNEIYKM YNGYIKESDL SEAAKEYLDK VEVRTAQKDI VKDYRYTVDK  840
YFIHTPITIN YKVTARNNVN DMVVKYIAQN DDIHVIGIDR GERNLIYISV IDSHGNIVKQ  900
KSYNILNNYD YKKKLVEKEK TREYARKNWK SIGNIKELKE GYISGVVHEI AMLIVEYNAI  960
IAMEDLNYGF KRGRFKVERQ VYQKFESMLI NKLNYFASKE KSVDEPGGLL KGYQLTYVPD  1020
NIKNLGKQCG VIFYVPAAFT SKIDPSTGFI SAFNFKSIST NASRKQFFMQ FDEIRYCAEK  1080
DMFSFGFDYN NFDTYNITMG KTQWTVYTNG ERLQSEFNNA RRTGKTKSIN LTETIKLLLE  1140
DNEINYADGH DIRIDMEKMD EDKKSEFFAQ LLSLYKLTVQ MRNSYTEAEE QENGISYDKI  1200
ISPVINDEGE FFDSDNYKES DDKECKMPKD ADANGAYCIA LKGLYEVLKI KSEWTEDGFD  1260
RNCLKLPHAE WLDFIQNKRY E                                            1281

SEQ ID NO: 55          moltype = AA  length = 1300
FEATURE                Location/Qualifiers
source                 1..1300
                       mol_type = protein
                       organism = Francisella tularensis
SEQUENCE: 55
MSIYQEFVNK YSLSKTLRFE LIPQGKTLEN IKARGLILDD EKRAKDYKKA KQIIDKYHQF  60
FIEEILSSVC ISEDLLQNYS DVYFKLKKSD DDNLQKDFKS AKDTIKKQIS EYIKDSEKFK  120
NLFNQNLIDA KKGQESDLIL WLKQSKDNGI ELFKANSDIT DIDEALEIIK SFKGWTTYFK  180
GFHENRKNVY SSNDIPTSII YRIVDDNLPK FLENKAKYES LKDKAPEAIN YEQIKKDLAE  240
ELTFDIDYKT SEVNQRVFSL DEVFEIANFN NYLNQSGITK FNTIIGGKFV NGENTKRKGI  300
NEYINLYSQQ INDKTLKKYK MSVLFKQILS DTESKSFVID KLEDDSDVVT TMQSFYEQIA  360
AFKTVEEKSI KETLSLLFDD LKAQKLDLSK IYFKNDKSLT DLSQQVFDDY SVIGTAVLEY  420
ITQQIAPKNL DNPSKKEQEL IAKKTEKAKY LSLETIKLAL EEFNKHRDID KQCRFEEILA  480
NFAAIPMIFD EIAQNKDNLA QISIKYQNQG KKDLLQASAE DDVKAIKDLL DQTNNLLHKL  540
KIFHISQSED KANILDKDEH FYLVFEECYF ELANIVPLYN KIRNYITQKP YSDEKFKLNF  600
ENSTLANGWD KNKEPDNTAI LFIKDDKYYL GVMNKKNNKI FDDKAIKENK GEGYKKIVYK  660
LLPGANKMLP KVFFSAKSIK FYNPSEDILR IRNHSTHTKN GSPQKGYEKF EFNIEDCRKF  720
IDFYKQSISK HPEWKDFGFR FSDTQRYNSI DEFYREVENQ GYKLTFENIS ESYIDSVVNQ  780
GKLYLFQIYN KDFSAYSKGR PNLHTLYWKA LFDERNLQDV VYKLNGEAEL FYRKQSIPKK  840
ITHPAKEAIA NKNKDNPKKE SVFEYDLIKD KRFTEDKFFF HCPITINFKS SGANKFNDEI  900
NLLLKEKAND VHILSIDRGE RHLAYYTLVD GKGNIIKQDT FNIIGNDRMK TNYHDKLAAI  960
EKDRDSARKD WKKINNIKEM KEGYLSQVVH EIAKLVIEYN AIVVFEDLNF GFKRGRFKVE  1020
KQVYQKLEKM LIEKLNYLVF KDNEFDKTGG VLRAYQLTAP FETFKKMGKQ TGIIYYVPAG  1080
FTSKICPVTG FVNQLYPKYE SVSKSQEFFS KFDKICYNLD KGYFEFSFDY KNFGDKAAKG  1140
KWTIASFGSR LINFRNSDKN HNWDTREVYP TKELEKLLKD YSIEYGHGEC IKAAICGESD  1200
KKFFAKLTSV LNTILQMRNS KTGTELDYLI SPVADVNGNF FDSRQAPKNM PQDADANGAY  1260
HIGLKGLMLL GRIKNNQEGK KLNLVIKNEE YFEFVQNRNN                        1300

SEQ ID NO: 56          moltype = AA  length = 1206
FEATURE                Location/Qualifiers
source                 1..1206
                       mol_type = protein
                       note = Lachnospiraceae bacterium
                       organism = unidentified
SEQUENCE: 56
MYYESLTKQY PVSKTIRNEL IPIGKTLDNI RQNNILESDV KRKQNYEHVK GILDEYHKQL  60
```

```
INEALDNCTL PSLKIAAEIY LKNQKEVSDR EDFNKTQDLL RKEVVEKLKA HENFTKIGKK   120
DILDLLEKLP SISEDDYNAL ESFRNFYTYF TSYNKVRENL YSDKEKSSTV AYRLINENFP   180
KPLDNVKSYR FVKTAGILAD GLGEEEQDSL FIVETFNKTL TQDGIDTYNS QVGKINSSIN   240
LYNQKNQKAN GFRKIPKMKM LYKQILSDRE ESFIDEFQSD EVLIDNVESY GSVLIESLKS   300
SKVSAFFDAL RESKGKNVYV KNDLAKTAMS VIVFENWRTF DDLLNQEYDL ANENKKKDDK   360
YFEKRQKELK KNKSYSLEHL CNLSEDSCNL IENYIHQISD DIENIIINNE TFLRIVINEH   420
DRSRKLAKNR KAVKAIKDFL DSIKVLEREL KLINSSGQEL EKDLIVYSAH EELLVELKQV   480
DSLYNMTRNY LTKKPFSTEK VKLNFNRSTL LNGWDRNKET DNLGVLLLKD GKYYLGIMNT   540
SANKAFVNPP VAKTEKVFKK VDYKLLPVPN QMLPKVFFAK SNIDFYNPSS EIYSNYKKGT   600
HKKGNMFSLE DCHNLIDFFK ESISKHEDWS KFGFKFDTQA SYNDISEFYR EVEKQGYKLT   660
YTDIDETYIN DLIERNELYL FQIYNKDFSM YSKGKLNLHT LYFMMLFDQR NIDDVVYKLN   720
GEAEVFYRPA SISEDELIIH KAGEEIKNKN PNRARTKETS TFSYDIVKDK RYSKDKFTLH   780
IPITMNFGVD EVKRFNDAVN SAIRIDENVN VIGIDRGERN MLYVVVIDSK GNILEQISLN   840
SIINKEYDIE TDYHALLDER EGGRDKARKD WNTVENIRDL KAGLYLQVVN VVAKLVLKYN   900
AIICLEDLNF GFKRGRQKVE KQVYQKFEKM LIDKLNYLVI DKSREQTSPK ELGGALNALQ   960
LTSKFKSFKE LGKQSGVIYY VPAYLTSKID PTTGFANLFY MKCENVEKSK RFFDGFDFIR  1020
FNALENVFEF GFDYRSFTQR ACGINSKWTV CTNGERIIKY RNPDKNNMFD EKVVVVTDEM  1080
KNLFEQYKIP YEDGRNVKDM IISNEEAEFY RRLYRLLQQT LQMRNSTSDG TRDYIISPVK  1140
NKREAYFNSE LSDGSVPKDA DANGAYNIAR KGLWVLEQIR QKSEGEKINL AMTNAEWLEY  1200
AQTHLL                                                            1206

SEQ ID NO: 57           moltype = AA   length = 1233
FEATURE                 Location/Qualifiers
source                  1..1233
                        mol_type = protein
                        note = Lachnospiraceae bacterium
                        organism = unidentified
SEQUENCE: 57
MDYGNGQFER RAPLTKTITL RLKPIGETRE TIREQKLLEQ DAAFRKLVET VTPIVDDCIR    60
KIADNALCHF GTEYDFSCLG NAISKNDSKA IKKETEKVEK LLAKVLTENL PDGLRKVNDI   120
NSAAFIQDTL TSFVQDDADK RVLIQELKGK TVLMQRFLTT RITALTVWLP DRVFENFNIF   180
IENAEKMRIL LDSPLNEKIM KFDPDAEQYA SLEFYGQCLS QKDIDSYNLI ISGIYADDEV   240
KNPGINEIVK EYNQQIRGDK DESPLPKLKK LHQILMPVE KAFFVRVLSN DSDARSILEK   300
ILKDTEMLPS KIIEAMKEAD AGDIAVYGSR LHELSHVIYG DHGKLSQIIY DKESKRISEL   360
METLSPKERK ESKKRLEGLE EHIRKSTYTF DELNRYAEKN VMAAYIAAVE ESCAEIMRKE   420
KDLRTLLSKE DVKIRGNRHN TLIVKNYFNA WTVFRNLIRI LRRKSEAEID SDFYDVLDDS   480
VEVLSLTYKG ENLCRSYITK KIGSDLKPEI ATYGSALRPN SRWWSPGEKF NVKFHTIVRR   540
DGRLYYFILP KGAKPVELED MDGDIECLQM RKIPNGPITL PKLVFKDPEA FFRDNPEADE   600
FVFLSGMKAP VTITRETYEA YRYKLYTVGK LRDGEVSEEE YKRALLQVLT AYKEFLENRM   660
IYADLNFGFK DLEEYKDSSE FIKQVETHNT FMCWAKVSSS QLDDLVKSGN GLLFEIWSER   720
LESYYKGYNE KVLRGYEGVL LSILKDENLV SMRTLLNSRP MLVYRPKESS KPMVVHRDGS   780
RVVDRFDKDG KYIPPEVHDE LYRFFNNLLI KEKLGEKARK ILDNKKVVK VLESERVKWS   840
KFYDEQFAVT FSVKKNADCL DTTKDLNAEV MEQYSESNRL ILIRNTTDIL YYLVLDKNGK   900
VLKQRSLNII NDGARDVDWK ERFRQVTKDR NEGYNEWDYS RTSNDLKEVY LNYALKEIAE   960
AVIEYNAILI IEKMSNAFKD KYSFLDDVTF KGFETKKLAK LSDLHFRGIK DGEPCSFTNP  1020
LQLCQNDSNK ILQDGVIFMV PNSMTRSLDP DTGFIFAIND HNIRTKKAKL NFLSKFDQLK  1080
VSSEGCLIMK YSGDSLPTHN TDNRVWNCCC NHPITNYDR TKKVEFIEEP VEELSRVLEE  1140
NGIETDTELN KLNERENVPG KVVDAIYSLV LNYLRGTVSG VAGQRAVYYS PVTGKKYDIS  1200
FIQAMNLNRK CDYYRIGSKE RGEWTDFVAQ LIN                              1233

SEQ ID NO: 58           moltype = AA   length = 1227
FEATURE                 Location/Qualifiers
source                  1..1227
                        mol_type = protein
                        note = Lachnospiraceae bacterium
                        organism = unidentified
SEQUENCE: 58
MSKLEKFTNC YSLSKTLRFK AIPVGKTQEN IDNKRLLVED EKRAEDYKGV KKLLDRYYLS    60
FINDVLHSIK LKNLNNYISL FRKKTRTEKE NKELENLEIN LRKEIAKAFK GNEGYKSLFK   120
KDIIETILPE FLDDKDEIAL VNSFNGFTTA FTGFFDNREN MFSEEAKSTS IAFRCINENL   180
TRYISNMDIF EKVDAIFDKH EVQEIKEKIL NSDYDVEDFF EGEFFNFVLT QEGIDVYNAI   240
IGGFVTESGE KIKGLNEYIN LYNQKTKQKL PKFKPLYKQV LSDRESLSFY GEGYTSDEEV   300
LEVFRNTLNK NSEIFSSIKK LEKLFKNFDE YSSAGIFVNK GPAISTISKD IPGEWNVIRD   360
KWNAEYDDIH LKKKAVVTEK YEDDRRKSFK KIGSFSLEQL QEYADADLSV VEKLKEIIIQ   420
KVDEIYKVYG SSEKLFDADF VLEKSLKKND AVVAIMKDLL DSVKSFENYI KAFFGEGKET   480
NRDESFYGDF VLAYDILLKV DHIYDAIRNY VTQKPYSKDK FKLYFQNPQF MGGWDKDKET   540
DYRATILRYG SKYYLAIMDK KYAKCLQKID KDDVNGNYEK INYKLLPGPN KMLPKVFFSK   600
KWMAYYNPSE DIQKIYKNGT FKKGDMFNLN DCHKLIDFFK DSISRYPKWS NAYDFNFSET   660
EKYKDIAGFY REVEEQGYKV SFESASKKEV DKLVEEGKLY MFQIYNKDFS DKSHGTPNLH   720
TMYFKLLFDE NNHGQIRLSG GAELFMRRAS LKKEELVVHP ANSPIANKNP DNPKKTTTLS   780
YDVYKDKRFS EDQYELHIPI ANINKCPKNI FKINTEVRVL LKHDDNPYVI GIDRGERNLL   840
YIVVVDGKGN IVEQYSLNEI INNFNGIRIK TDYHSLLDKK EKERFEARQN WTSIENIKEL   900
KAGYISQVVH KICELVEKYD AVIALEDLNS GFKNSRVKVE SQVVQKFEKM LIDKLNYMVD   960
KKSNPCATGG ALKGYQITNK FESFKSMSTQ NGFIFYIPAW LTSKIDPSTG FVNLLKTKYT  1020
SIADKKFISS FDRIMYVPEE DLFEFALDYK NFSRTDADYI KKWKLYSYGN RIRIFRNPKK  1080
NNVFDWEEVC LTSAYKELFN KYGINYQQGD IRALLCEQSD KAPYSSFMAL MSLMLQMRNS  1140
ITGRTDVDFL ISPVKNSDGI FYDSRNYEAQ ENAILPKNAD ANGAYNIARK VLWAIGQFKK  1200
AEDEKLDKVK IASNKEWLEY AQTSVKH                                     1227
```

```
SEQ ID NO: 59            moltype = AA   length = 1264
FEATURE                  Location/Qualifiers
source                   1..1264
                         mol_type = protein
                         organism = Leptospira inadai
SEQUENCE: 59
MEDYSGFVNI YSIQKTLRFE LKPVGKTLEH IEKKGFLKKD KIRAEDYKAV KKIIDKYHRA    60
YIEEVFDSVL HQKKKKDKTR FSTQFIKEIK EFSELYYKTE KNIPDKERLE ALSEKLRKML   120
VGAFKGEFSE EVAEKYNKNL FSKELIRNEI EKFCETDEER KQVSNFKSFT TYFTGPHSNR   180
QNIYSDEKKS TAIGYRIIHQ NLPKFLDNLK IIESIQRRFK DFPWSDLKKN LKKIDKNIKL   240
TEYFSIDGFV NVLNQKGIDA YNTILGGKSE ESGEKIQGLN EYINLYRQKN NIDRKNPLNV   300
KILFKQILGD RETKSFIPEA FPDDQSVLNS ITEFAKYLKL DKKKKSIIAE LKKFLSSFNR   360
YELDGIYLAN DNSLASISTF LFDDWSFIKK SVSFKYDESV GDPKKKIKSP LKYEKEKEKW   420
LKQKYYTISF LNDAIESYSK SQDEKRVKIR LEAYFAEFKS KDDAKKQFDL LERIEEAYAI   480
VEPLLGAEYP RDRNLKADKK EVGKIKDFLD SIKSLQFFLK PLLSAEIFDE KDLGFYNQLE   540
GYYEEIDISG HLYNKVRNYL TGKIYSKEKF KLNFENSTLL KGWDENREVA NLCVIFREDQ   600
KYYLGVMDKE NNTILSDIPK VKPNELFYEK MVYKLIPTPH MQLPRIIFSS DNLSIYNPSK   660
SILKIREAKS FKEGKNFKLK DCHKFIDFYK ESISKNEDWS RFDFKFSKTS SYENISEFYR   720
EVERQGYNLD FKKVSKFYID SLVEDGKLYL FQIYNKDFSI FSKGKPNLHT IYFRSLFSKE   780
NLKDVCLKLN GEAEMFFRKK SINYDEKKKR EGHHPELFEK LKYPILKDKR YSEDKFQFHL   840
PISLNFKSKE RLNFNLKVNE FLKRNDINI IGIDRGERNL LYLVMINQKG EILKQTLLDS   900
MQSGKGRPEI NYKEKLQEKE IERDKARKSW GTVENIKELK EGYISIVIHQ ISKLMVENNA   960
IVVLEDLNIG FKRGRQKVER QVYQKFEKML IDKLNFLVFK ENKPTEPGGV LKAYQLTDEF  1020
QSFEKLSKQT GFLFYVPSWN TSKIDPRTGF IDFLHPAYEN IEKAKQWINK FDSIRFNSKM  1080
DWFEFTADTR KFSENLMLGK NRVWVICTTN VERYFTSKTA NSSIQYNSIQ ITEKLKELFV  1140
DIPFSNGQDL KPEILRKNDA VFFKSLLFYI KTTLSLRQNN GKKGEEEKDF ILSPVVDSKG  1200
RFFNSLEASD DEPKDADANG AYHIALKGLM NLLVLNETKE ENLSRPKWKI KNKDWLEFVW  1260
ERNR                                                              1264

SEQ ID NO: 60            moltype = AA   length = 1373
FEATURE                  Location/Qualifiers
source                   1..1373
                         mol_type = protein
                         organism = Moraxella bovoculi
SEQUENCE: 60
MLFQDFTHLY PLSKTVRFEL FIDRTLEHIH AKNFLSQDET MADMHQKKVK ILDDYHRDFI    60
ADMMGEVKLT KLAEFYDVYL KFRKNPKDDE LQKAQLKDLQ AVLRKEIVKP IGNGGKYKAG   120
YDRLFGAKLF KDGKELGDLA KFVIAQEGES SPKLAHLAHF EKFSTYFTGF HDNRKNMYSD   180
EDKHTAIAYR LIHENLPRFI DNLQILTTIK QKHSALYDQI INELTASGLD VSLASHLDGY   240
HKLLTQEGIT AYNTLLGGIS GEAGSPKIQG INELINSHHN QHCHKSERIA KLRPLHKQIL   300
SDGMSVSFLP SKFADDSEMC QAVNEFYRHY ADVFAKVQSL FDGFDDHQKD GIYVEHKNLN   360
ELSKQAFGDF ALLGRVLDGY YVDVVNPEFN ERFAKAKTDN AKAKLTKEKD KFIKGVHSLA   420
SLEQAIEHYT ARHDDESVQA GKLGQYFKHG LAGVDNPIQK IHNNHSTIKG FLERERPAGE   480
RALPKIKSGK NPEMTQLRQL KELLDNALNV AHFAKLLTTK TTLDNQDGNF YGEFGVLYDE   540
LAKIPTLYNK VRDYLSQKPF STEKYKLNFG NPTLLNGWDL NKEKDNFGVI LQKDGCYYLA   600
LLDKAHKKVF DNAPNTGKSI YQKMIYKYLE VRKQFPKVFF SKEAIAINYH PSKELVEIKD   660
KGRQRSDDER LKLYRFILEC LKIHPKYDKK FEGAIGDIQL FKKDKKGREV PISEKDLFKD   720
INGIFSSKPK LEMEDFFIGE FKRYNPSQDL VDQYNIYKKI DSNDNRKKEN FYNNHPKFKK   780
DLVRYYYESM CKHEEWEESF EFSKKLQDIG CYVDVNELFT EIETRRLNYK ISFCNINADY   840
IDELVEQGQL YLFQIYNKDF SPKAHGKPNL HTLYFKALFS EDNLADPIYK LNGEAQIFYR   900
KASLDMNETT IHRAGEVLEN KNPDNPKKRQ FVYDIIKDKR YTQKDFMLHV PITMNFGVQG   960
MTIKEFNKKV NQSIQQYDEV NVIGIDRGER HLLYLTVINS KGEILEQCSL NDITTASANG  1020
TQMTTPYHKI LDKREIERLN ARVGWGEIET IKELKSGYLS HVVHQISQLM LKYNAIVVLE  1080
DLNFGFKRGR FKVEKQIYQN FENALIKKLN HLVLKDKADD EIGSYKNALQ LTNNFTDLKS  1140
IGKQTGFLFY VPAWNTSKID PETGFVDLLK PRYENIQASQ AFFGKFDKIC YNADKDYFEF  1200
HIDYAKFTDK AKNSRQIWTI CSHGDKRYVY DKTANQNKGA AKGINVNDIL KSLFARHHIN  1260
EKQPNLVMDI CQNNDKEFHK SLMYLLKTLL ALRYSNASSD EDFILSPVAN DEGVFFNSAL  1320
ADDTQPQNAD ANGAYHIALK GLWLLNELKN SDDLNKVKLA IDNQTWLNFA QNR         1373

SEQ ID NO: 61            moltype = AA   length = 1352
FEATURE                  Location/Qualifiers
source                   1..1352
                         mol_type = protein
                         note = Parcubacteria bacterium
                         organism = unidentified
SEQUENCE: 61
MENIFDQFIG KYSLSKTLRF ELKPVGKTED FLKINKVFEK DQTIDDSYNQ AKFYFDSLHQ    60
KFIDAALASD KTSELSFQNF ADVLEKQNKI ILDKKREMGA LRKRDKNAVG IDRLQKEIND   120
AEDIIQKEKE KIYKDVRTLF DNEAESWKTY YQEREVDGKK ITESKADLKQ KGADFLTAAG   180
ILKVLKYEFP EEKEKEFQAK NQPSLFVEEK ENPGQKRYIF DSFDKFAGYL TKFQQTKKNL   240
YAADGTSTAV ATRIADNFII FHQNTKVFRD KYKNNHTDLG FDEENIFEIE RYKNCLLQRE   300
IEHIKNENSY NKIIGRINKK IKEYRDQKAK DTKLTKSDFP FFKNLDKQIL GEVEKEKQLI   360
EKTREKTEED VLIERFKEFI ENNEERFTAA KKLMNAFCNG EFESEYEGIY LKNKAINTIS   420
RRWFVSDRDF ELKLPQQKSK NKSEKNEPKV KKFISIAEIK NAVEELDGDI FKAVFYDKKI   480
IAQGGSKLEQ FLVIWKYEFE YLFRDIEREN GEKLLGYDSC LKIAKQLGIF PQEKEAREKA   540
TAVIKNYADA GLGIFQMMKY FSLDDKDRKN TPGQLSTNFY AEYDGYYKDF EPIKYYNEFR   600
NFITKKPFDE DKIKLNFENG ALLKGWDENK EYDFMGVILK KEGRLYLGIM HKNHRKLFQS   660
MGNAKGDNAN RYQKMIYKQI ADASKDVPRL LLTSKKAMEK FKPSQEILRI KKEKTFKRES   720
KNFSLRDLHA LIEYYRNCIP QYSNWSFYDF QFQDTGKYQN IKEFTDDVQK YGYKISFRDI  780
```

```
DDEYINQALN EGKMYLFEVV NKDIYNTKNG SKNLHTLYFE HILSAENLND PVFKLSGMAE    840
IFQRQPSVNE REKITTQKNQ CILDKGDRAY KYRRYTEKKI MFHMSLVLNT GKGEIKQVQF    900
NKIINQRISS SDNEMRVNVI GIDRGEKNLL YYSVVKQNGE IIEQASLNEI NGVNYRDKLI    960
EREKERLKNR QSWKPVVKIK DLKKGYISHV IHKICQLIEK YSAIVVLEDL NMRFKQIRGG   1020
IERSVYQQFE KALIDKLGYL VFKDNRDLRA PGGVLNGYQL SAPFVSFEKM RKQTGILFYT   1080
QAEYTSKTDP ITGFRKNVYI SNSASLDKIK EAVKKFDAIG WDGKEQSYFF KYNPYNLADE   1140
KYKNSTVSKE WAIFASAPRI RRQKGEDGYW KYDRVKVNEE FEKLLKVWNF VNPKATDIKQ   1200
EIIKKIKAGD LQGEKELDGR LRNFWHSFIY LFNLVLELRN SFSLQIKIKA GEVIAVDEGV   1260
DFIASPVKPF FTTPNPYIPS NLCWLAVENA DANGAYNIAR KGVMILKKIR EHAKKDPEFK   1320
KLPNLFISNA EWDEAARDWG KYAGTTALNL DH                                 1352

SEQ ID NO: 62           moltype = AA  length = 1260
FEATURE                 Location/Qualifiers
source                  1..1260
                        mol_type = protein
                        organism = Porphyromonas crevioricanis
SEQUENCE: 62
MDSLKDFTNL YPVSKTLRFE LKPVGKTLEN IEKAGILKED EHRAESYRRV KKIIDTYHKV     60
FIDSSLENMA KMGIENEIKA MLQSFCELYK KDHRTEGEDK ALDKIRAVLR GLIVGAFTGV    120
CGRRENTVQN EKYESLFKEK LIKEILPDFV LSTEAESLPF SVEEATRSLK EFDSFTSYFA    180
GFYENRKNIY STKPQSTAIA YRLIHENLPK FIDNILVFQK IKEPIAKELE HIRADFSAGG    240
YIKKDERLED IFSLNYYIHV LSQAGIEKYN ALIGKIVTEG DGEMKGLNEH INLYNQQRGR    300
EDRLPLFRPL YKQILSDREQ LSYLPESFEK DEELLRALKE FYDHIAEDIL GRTQQLMTSI    360
SEYDLSRIYV RNDSQLTDIS KKMLGDWNAI YMARERAYDH EQAPKRITAK YERDRIKALK    420
GEESISLANL NSCIAFLDNV RDCRVDTYLS TLGQKEGPHG LSNLVENVFA SYHEAEQLLS    480
FPYPEENNLI QDKDNVVLIK NLLDNISDLQ RFLKPLWGMG DCKDERFY GEYNYIRGAL     540
DQVIPLYNKV RNYLTRKPYS TRKVKLNFGN SQLLSGWDRN KEKDNSCVIL RKGQNFYLAI    600
MNNRHKRSFE NKMLPEYKEG EPYFEKMDYK FLPDPNKMLP KVFLSKKGIE IYKPSPKLLE    660
QYGHGTHKKG DTFSMDDLHE LIDFFKHSIE AHEDWKQFGF KFSDTATYEN VSSFYREVED    720
QGYKLSFRKV SESYVYSLID QGKLYLFQIY NKDFSPCSLG TPNLHTLYWR MLFDERNLAD    780
VIYKLDGKAE IFFREKSLKN DHPTHPAGKP IKKKSRQKKG EESLFEYDLV KDRRYTMDKF    840
QFHVPITMNF KCSAGSKVND MVNAHIREAK DMHVIGIDRG ERNLLYICVI DSRGTILDQI    900
SLNTINDIDY HDLLESRDKD RQQEHRNWQT IEGIKELKQG YLSQAVHRIA ELMVAYKAVV    960
ALEDLNMGFK RGRQKVESSV YQQFEKQLID KLNYLVDKKR RPEDIGGLLR AYQFTAPFKS   1020
FKEMGKQNGF LFYIPAWNTS NIDPTTGFVN LPHVQYENVD KAKSFFQKFD SISYNPKKDW   1080
FEFAFDYKNF TKKAEGSRSM WILCTHGSRI KNFRNSQKNG QWDSEEFALT EAFKSLFVRY   1140
EIDYTADLKT AIVDEKQKDF FVDLLKLFKL TVQMRNSWKE KDLDYLISPV AGADGRFFDT   1200
REGNKSLPKD ADANGAYNIA LKGLWALRQI RQTSEGGKLK LAISNKEWLQ FVQERSYEKD   1260

SEQ ID NO: 63           moltype = AA  length = 1324
FEATURE                 Location/Qualifiers
source                  1..1324
                        mol_type = protein
                        organism = Prevotella disiens
SEQUENCE: 63
MENYQEFTNL FQLNKTLRFE LKPIGKTCEL LEEGKIFASG SFLEKDKVRA DNVSYVKKEI     60
DKKHKIFIEE TLSSFSISND LLKQYFDCYN ELKAFKKDCK KDEEEVKKTA LRNKCTSIQR    120
AMREAISQAF LKSPQKKLLA IKNLIENVFK ADENVQHFSE FTSYFSGFET NRENFYSDEE    180
KSTSIAYRLV HDNLPIFIKN IYIFEKLKEQ FDAKTLSEIF ENYKLYVAGS SLDEVFSLEY    240
FNNTLTQKGI DNYNAVIGKI VKEDKQEIQG LNEHINLYNQ KHKDRRLPFF ISLKKQILSD    300
REALSWLPDM FKNDSEVIDA LKGFYIEDGF ENNVLTPLAT LLSSLDKYNL NGIFIRNNEA    360
LSSSLSQNVYR NFSIDEAIDA QNAELQTFNN YELIANALRA KIKKETKQGR KSFEKYEEYI    420
DKKVKAIDSL SIQEINELVE NYVSEFNSNS GNMPRKVEDY FSLMRKGDFG SNDLIENIKT    480
KLSAAEKLLG TKYQETAKDI FKKDENSKLI KELLDATKQF QHFIKPLLGT GEEADRDLVF    540
YGDFLPLYEK FEELTLLYNK VRNRLTQKPY SKDKIRLCFN KPKLMTGWVD SKTEKSDNGT    600
QYGGYLFRKK NEIGEYDYFL GISSKAQLFR KNEAVIGDYE RLDYYQPKAN TIYGSAYEGE    660
NSYKEDKKRL NKVIIAYIEQ IKQTNIKKSI IESISKYPNI SDDDKVTPSS LLEKIKKVSI    720
DSYNGILSFK SFQSVNKEVI DNLLKTISPL KNKAEFLDLI NKDYQIFTEV QAVIDEICKQ    780
KTFIYFPISN VELEKEMGDK DKPLCLFQIS NKDLSFAKTF SANLRKKRGA ENLHTMLFKA    840
LMEGNQDNLD LGSGAIFYRA KSLDGNKPTH PANEAIKCRN VANKDKVSLF TYDIYKNRRY    900
MENKFLPHLS IVQNYKAAND SAQLNSSATE YIRKADDLHI IGIDRGERNL LYYSVIDMKG    960
NIVEQDSLNI IRNNDLETDY HDLLDKREKE RKANRQNWEA VEGIKDLKKG YLSQAVHQIA   1020
QLMLKYNAII ALEDLNSGQMFV TRGQKIEKAV YQQFEKSLVD KKR PYNELGGILK        1080
AYQLASSITK NNSDKQNGFL FYVPAWNTSK IDPVTGFTDL LRPKAMTIKE AQDFFGAFDN   1140
ISYNDKGYFE FETNYDKFKI RMKSAQTRWT ICTFGNRIKR KKDKNYWNYE EVELTEEFKK   1200
LFKDSNIDYE NCNLKEEIQN KDNRKFFDDL IKLLQLTLQM RNSDDKGNDY IISPVANAEG   1260
QFFDSRNGDK KLPLDADANG AYNIARKGLW NIRQIKQTKN KDDLNLSISS TEWLDFVREK   1320
PYLK                                                               1324

SEQ ID NO: 64           moltype = AA  length = 1484
FEATURE                 Location/Qualifiers
VARIANT                 1073
                        note = Xaa can be any naturally occurring amino acid
source                  1..1484
                        mol_type = protein
                        note = Peregrinibacteria bacterium
                        organism = unidentified
SEQUENCE: 64
MSNFFKNFTN LYELSKTLRF ELKPVGDTLT NMKDHLEYDE KLQTFLKDQN IDDAYQALKP     60
```

```
QFDEIHEEFI TDSLESKKAK EIDFSEYLDL FQEKKELNDS EKKLRNKIGE TFNKAGEKWK    120
KEKYPQYEWK KGSKIANGAD ILSCQDMLQF IKYKNPEDEK IKNYIDDTLK GFFTYFGGFN    180
QNRANYYETK KEASTAVATR IVHENLPKFC DNVIQFKHII KRKKDGTVEK TERKTEYLNA    240
YQYLKNNNKI TQIKDAETEK MIESTPIAEK IFDVYYFSSC LSQKQIEEYN RIIGHYNLLI    300
NLYNQAKRSE GKHLSANEKK YKDLPKFKTL YKQIGCGKEK DLFYTIKCDT EEEANKSRNE    360
GKEESHSVEEI INKAQEAINK YFKSNNDCEN INTVPDFINY ILTKENYEGV YWSKAAMNTI    420
SDKYFANYHD LQDRLKEAKV FQKADKKSED DIKIPEAIEL SGLFGVLDSL ADWQTTLFKS    480
SILSNEKLKI ITDSQTPSEA LLKMIFNDIE KNMESFLKET NDIITLKKYK GNKEGTEKIK    540
QWFDYTLAIN RMLKYFLVKE NKIKGNSLDT NISEALKTLI YSDDAEWFKW YDALRNYLTQ    600
KPQDEAKENK LKLNFDNPSL AGGWDVNKEC SNFCVILKDK NEKKYLAMIK KGENTLFQKE    660
WTEGRGKNLT KKSNPLFEIN NCEILSKMEY DFWADVSKMI PKCSTQLKAV VNHFKQSDNE    720
FIFPIGYKVT SGEKFREECK ISKQDFELNN KVFNKNELSV TAMRYDLSST QEKQYIKAFQ    780
KEYWELLFKQ EKRDTKLTNN EIFNEWINFC NKKYSELLSW ERKYKDALTN WINFCKYFLS    840
KYPKTTLFNY SFKESENYNS LDEFYRDVDI CSYKLNINTT INKSILDRLV EEGKLYLFEI    900
KNQDSNDGKS IGHKNNLHTI YWNAIFENFD NRPKLNGEAE IFYRKAISKD KLGIVKGKKT    960
KNGTWIIKNY RFSKEKFILH VPITLNFCSN NEYVNDIVNT KFYNFSNLHF LGIDRGEKHL   1020
AYYSLVNKNG EIVDQGTLNL PFTDKDGNQR SIKKEKYFYN KQEDKWEAKE VDXWNYNDLL   1080
DAMASNRDMA RKNWQRIGTI KEAKNGYVSL VIRKIADLAV NNERPAFIVL EDLNTGFKRS   1140
RQKIDKSVYQ KFELALAKKL NFLVDKNAKR DEIGSPTKAL QLTPPVNNYG DIENKKQAGI   1200
MLYTRANYTS QTDPATGWRK TIYLKAGPEE TTYKKDGKIK NKSVKDQIIE TFTDIGFDGK   1260
DYYFEYDKGE FVDEKTGEIK PKKWRLYSGE NGKSLDRFRG EREKDKYEWK IDKIDIVKIL   1320
DDLFVNFDKN ISLLKQLKEG VELTRNNEHG TGESLRFAIN LIQQIRNTGN NERDNDFILS   1380
PVRDENGKHF DSREYWDKET KGEKISMPSS GDANGAFNIA RKGIIMNAHI LANSDSKDLS   1440
LFVSDEEWDL HLNNKTEWKK QLNIFSSRKA MAKRKKKRPA ATKK                    1484

SEQ ID NO: 65          moltype = AA  length = 1245
FEATURE                Location/Qualifiers
source                 1..1245
                       mol_type = protein
                       organism = Porphyromonas macacae
SEQUENCE: 65
MKTQHFFEDF TSLYSLSKTI RFELKPIGKT LENIKKNGLI RRDEQRLDDY EKLKKVIDEY     60
HEDFIANILS SFSFSEEILQ SYIQNLSISE ARAKIEKTMR DTLAKAFSED ERYKSIFKKE    120
LVKKDIPVWC PAYKSLCKKF DNFTTSLVPF HENRKNLYTS NEITASIPYR IVHVNLPKFI    180
QNIEALCELQ KKMGADLYLE MMENLRNVWP SFVKTPDDLC NLKTYNHLMV QSSISEYNRF    240
VGGYSTEDGT KHQGINEWIN IYRQRNKEMR LPGLVFLHKQ ILAKVDSSSF ISDTLENDDQ    300
VFCVLRQFRK LFWNTVSSKE DDAASLKDLF CGLSGYDPEA IYVSDAHLAT ISKNIFDRWN    360
YISDAIRRKT EVLMPRKKES VERYAEKISK QIKKRQSYSL AELDDDLLAHY SEESLPAGFS    420
LLSYFTSLGG QKYLVSDGEV ILYEEGSNIW DEVLIAFRDL QVILDKDFTE KKLGKDEEAV    480
SVIKKALDSA LRLRKFFDLL SGTGAEIRRD SSFYALYTDR MDKLKGLLKM YDKVRNYLTK    540
KPYSIEKFKL HFDNPSLLSG WDKNKELNNL SVIFRQNGYY YLGIMTPKGK NLFKTLPKLG    600
AEEMFYEKME YKQIAEPMLM LPKVFFPKKT KPAPAPDQSV VDIYNKKTFK TGQKGFNKKS    660
LYRLIDFYKE ALTVHEWKLF NFSFSPTEQY RNIGEFFDEV REQAYKVSMV NVPASYIDEA    720
VENGKLYLFQ IYNKDFSPYS KGIPNLHTLY WKALFSEQNQ SRVYKLCGGG ELFYRKASLH    780
MQDTTVHPKG ISIHKKNLNK KGETSLFNYD LVKDKRFTED KFFFHVPISI NYKNKKITNV    840
NQMVRDYIAQ NDDLQHGIDR GERNLLYISR IDTRGNLLEQ FSLNVIESDK GDLRTDYQKI    900
LGDREQERLR RRQEWKSIES IKDLKDGYMS QVVHKICNMV VEHKAIVVLE NLNLSFMKGR    960
KKVEKSVYEK FERMLVDKLN YLVVDKKNLS NEPGGLYAAY QLTNPLFSFE ELHRYPQSGI   1020
LFFVDPWNTS LTDPSTGFVN LLGRINYTNV GDARKFFDRF NAIRYDGKGN ILFDLDLSRF   1080
DVRVETQRKL WTLTTFGSRI AKSKKSGKWM VERIENLSLC FLELFEQFNI GYRVEKDLKK   1140
AILSQDRKEF YVRLIYLFNL MMQIRNSDGE EDYILSPALN EKNLQFDSRL IEAKDLPVDA   1200
DANGAYNVAR KGLMVVQRIK RGDHESIHRI GRAQWLRYVQ EGIVE                   1245

SEQ ID NO: 66          moltype = AA  length = 1250
FEATURE                Location/Qualifiers
source                 1..1250
                       mol_type = protein
                       organism = Smithella sp.
SEQUENCE: 66
MQTLFENFTN QYPVSKTLRF ELIPQGKTKD FIEQKGLLKK DEDRAEKYKK VKNIIDEYHK     60
DFIEKSLNGL KLDGLEKYKT LYLKQEKDDK DKKAFDKEKE NLRKQIANAF RNNEKPFKTLF    120
AKELIKNDLM SFACEEDKKN VKEFEAFTTY FTGFHQNRAN MYVADEKRTA IASRLIHENL    180
PKFIDNIKIF EKMKKEAPEL LSPFNQTLKD MKDVIKGTTL EEIFSLDYFN KTLTQSGIDI    240
YNSVIGGRTP EEGKTIKGL NEYINTDFNQ KQTDKKKRQP KFKQLYKQIL SDRQSLSFIA    300
EAFKNDTEIL EAIEKFYVNE LLHFSNEGKS TNVLDAIKNA VSNLESFNLT KMYFRSGASL    360
TDVSRKVFGE WSIINRALDN YYATTYPIKP REKSEKYEER KEKWLKQDFN VSLIQTAIDE    420
YDNETVKGKN SGKVIADYFA KFCDDKETDL IQKVNEGYIA VKDLLNTPCP ENEKLGSNKD    480
QVKQIKAFMD SIMDIMHFVR PLSLKDTDKE KDETFYSLFT PLYDHLTQTI ALYNKVRNYL    540
TQKPYSTEKI KLNFENSTLL GGWDLNKETD NTAIILRKDN LYYLGIMDKR HNRIFRNVPK    600
ADKKDFCYEK MVYKLLPGAN KMLPKVFFSQ SRIQEFTPSA KLLENYANET HKKGDNFNLN    660
HCHKLIDFFK DSINKHEDWK NFDFRFSATS TYADLSGFYH EVEHQGYKIS FQSVADSFID    720
DLVNEGKLYL FQIYNKDFSP FSKGKPNLHT LYWKMLFDEN NLKDVVYKLN GEAEVFYRKK    780
SIAEKNTTIH KANESIINKN PDNPKATSTF NYDIVKDKRY HFIKFQFHIP ITMNFKAEGI    840
FNMNQRVNQF LKANPDINII GIDRGERHLL YYALINQKGK ILKQDTLNVI ANEKQKVDYH    900
NLLDKKEGDR ATARQEWGVI ETIKELKEGY LSQVIHKLTD LMIENNAIIV MEDLNFGFKR    960
GRQKVEKQVY QKFEKMLIDK LNYLVDKNKK ANELGGLLNA FQLANKFESF QKMGKQNGFI   1020
FYVPAWNTSK TDPATGFIDF LKPRYENLNQ AKDFFEKFDS IRLNSKADYF EFAFDFKNFT   1080
EKADGGRTKW TVCTTNEDRY QWNRALNNNR GSQEKYDITA ELKSLFDGKV DYKSGKDLKQ   1140
QIASQESADF FKALMKNLSI TLSLRHNNGE KGDNEQDYIL SPVADSKGRF FDSRKADDDM   1200
```

PKNADANGAY HIALKGLWCL EQISKTDDLK KVKLAISNKE WLEFVQTLKG                1250

SEQ ID NO: 67           moltype = DNA   length = 3987
FEATURE                 Location/Qualifiers
source                  1..3987
                        mol_type = other DNA
                        organism = synthetic construct SEQUENCE: 67
atggccggga gcaagaagcg ccggataaag caggacacgc agttcgaggg cttcaccaac    60
ctgtaccaag tctccaagac gctccggttc gagcttatcc cgcaagggaa gaccctgaaa   120
cacatccagg aacaaggttt catcgaggag gacaaggccc gcaacgacca ctacaaggag   180
ctcaagccca taatcgatcg gatctacaag acgtacgccg accagtgcct ccaactggtg   240
cagctcgact gggagaacct gagcgccgcc attgacagct accgcaagga aaagaccgag   300
gagacgcgca acgcccttat tgaggacgca gccacctacc gcaacgccat ccacgactac   360
ttcatcgggc gcaccgacaa cctgacggac gcgatcaaca agcgccacgc ggaaatctac   420
aagggccttt tcaaggccga gctcttcaac gggaaggtcc taaaacagct cgggactgtc   480
acgacaaccg agcatgagaa cgccctcctt cgcagcttcg acaagttcac cacatacttc   540
tcgggcttct accggaaccg caagaacgtt ttcagcgccg aggacatctc caccgccatc   600
ccgcacagga tcgtccagga caacttcccc aagttcaagg agaactgcca catcttcacg   660
cgcctgatta cagccgtacc ttcacttcgt gagcacttcg agaacgtcaa aaaggccatc   720
gggatcttcg tctccacgtc catcgaggag gtattctctt tcccgttcta taccagctc   780
ctgacccaga cgcagatcga cctctacaac cagctactgg ggcatcag ccgggaggcc   840
gggaccgaga aaataaaggg cctcaacgaa gttctcaacc tggccatcca gaagaacgac   900
gagaccgcgc atatcatcgc atccctgccg catcgcttca ttcctttgtt caagcagata   960
ttgagcgacc ggaacaccct ctcgttcatc ctcgaagaat tcaagagcga cgaggaggtc  1020
attcagtctt tctgcaagta caagacgctc tacggagaatg agaatgtgct ggagaccgcg  1080
gaggcactct tcaatgagct gaactccatt gacctgaccc acatcttcat tagccacaag  1140
aaactggaga cgatctccag cgccctgtgc gaccactggg acactctccg caacgccctc  1200
tacgaacgcc ggatctccga acttaccggc aagataacta agtcggctaa ggagaaggtg  1260
caacgagcc tcaagcacga ggacatcaac cttcaggaaa tcatctcagc cgcgggcaag  1320
gagctgagcg aggcgtttaa gcagaaaaca tcggagatac tgagccacgc gcacgcggcc  1380
ctggatcaac cgctgccgac gactctcaag aagcaagagg agaaggaaat ccttaagtcc  1440
cagctcgact cgctgctcgg cctctatcac ttgctcgact ggttcgcggt tgatgagtcc  1500
aacgaggtgg acccggagtt ctccgcgcgc ctcacggta ttaagctgga gatggagcca  1560
agcttaagct tctacaacaa ggcccgcaac tacgcgacta aaaaaccgta ctcagtcgag  1620
aaattcaagc tgaatttcca gatgcctaca ttggcgaggg ggtgggacgt gaaccgcgag  1680
aagaacaatg gagccatcct gttcgtcaaa aatgggttgt actacctggg catcatgccc  1740
aagcagaagg gccgttacaa ggccctgtca ttcgagccta ccgagaagac ctcggagggc  1800
ttcgacaaga tgtactacga ctatttcccg gacgccgaca aagatgatccc gaagtgctcc  1860
acgcagctca aagccgtcac ggcccacttc cagacgcata ccacgccgat acttctgagc  1920
aacaacttca ttgagccgct agagatcacg aaggagatat cgacctaaa caaccccgaa  1980
aaggagccca agaagttcca gacagcctac gctaagaaga caggtgatca agagggatat  2040
agggacgcac tctgcaagtg gatcgactte acgcgcgact tcctgtcgaa atatacaaag  2100
acgaccagca ttgacctaag ttctctccgc ccatcctccc agtacaagga tctgggcgag  2160
tattatgcgg agctgaaccc attgctgtac cacatcagct tccagaggat cgccgagaag  2220
gagattatgc acgcggtgga gacggggaaa ctatacctgt tccaaatata taacaaggac  2280
ttcgctaaag ggcaccacgg gaagcccaac ctgcacacac tctactggac gggcttgttt  2340
tcgccagaaa atttggccaa gacttcgatc aagctcaacg gccaggcgga gttgttttac  2400
cgtcccaagt ctcgcatgaa gcgcatggcg catcgcctcg gagagaaaat gcttaacaag  2460
aagctcaagg atcagaagac gcccatacct gatacgttgt accaggaatt gtacgactac  2520
gtgaaccacc gctatcgca cgacctctca gacgaggccc gcgccctcct cccaaacgtg  2580
attactaagg aggtttccca tgaaataatc aaggaccgac ggttcaccag cgacaaatttt  2640
ttttccacg tgcctatcac gctcaattac caggcgccaa actccccatc gaagttcaac  2700
cagcgcgtga cgcctacct taaggagcac ccggagaccc caatcatcgg gatcgaccgt  2760
ggcgagcga acctgatcta tattacggtg atcgatgca ccgggaagat cctggagcag  2820
cgctccctga acacaatcca gcagtttgac taccagaaga aactcgacaa ccggagaag  2880
gagcgcgtcg cagcccggca agcatggagt gtggtcggca ccataaagga cctgaaacag  2940
ggttacctaa gtcaagttat ccacgagatc gttgacctga tgatacacta tcaagccgta  3000
gtcgtgctgg agaacctcaa cttcgggttt aagtccaagc gcaccggcat cgccggaggag  3060
gcggtgtacc agcagttcga gaagatgctg atcgacaagc tgaactgcct ggtgctcaag  3120
gactaccctg cggagaaggt cggcgggggtc ttgaacccgt accagctaac cgaccagttc  3180
acgagcttcg ccaaaatggg cacgcagtcc ggattcttgt tttatgtccc ggctccatat  3240
acaagtaaga tcgacccgct gacagggttt gttgacccat tcgtgtggaa gaccatcaag  3300
aaccacgaga gcaggaaaca cttcttagag gcttcgact tcctgcatta cgacgttaag  3360
acaggcgact tcatcctgca cttcaagatg aaccgcaacc tgtcgttcca gagggcctca  3420
cccggcttca tgcccgcctg ggatatcgtc tttgagaaga tgagacgca gttcgacgcg  3480
aaggggacgc cgttcatcgc tggaaagcgg atcgtgccgg tcatcgagaa ccaccgcttc  3540
acgggtcgct accgagattt ataccccgcc aacgaactaa ttgcgctgct ggaggagaag  3600
gggatcgtgt tccgagatgg cagcaacatt ctcccgaagc tgctggaga cgacgactcg  3660
cacgctattg acacgatggt cgccctcata cggagcgtgc ttcagatgcg gaacagtaac  3720
gctgccacgg gcgaggacta cattaactcc ccgtccgcg acctcaacgg ggtctgcttc  3780
gatagccgct tccagaaccc ggagtggcct atggatgcgg acgcgaacgg ggcctaccac  3840
atcgccctca gggccaact cctgctcaac cacttgaagg aaagcaaaga cctcaaattg  3900
cagaatggca tcagtaacca ggactggctc gcgtacatcc aggaactgag aaacgggtcc  3960
aagaagcggc gtatcaagca agattga                                       3987

SEQ ID NO: 68           moltype = DNA   length = 3987
FEATURE                 Location/Qualifiers
source                  1..3987

```
                         mol_type = other DNA
                         organism = synthetic construct
SEQUENCE: 68
atggcgggaa gcaaaaagcg ccggattaag caagacacgc agttcgaggg cttcacgaac    60
ctctaccaag tcagcaagac cctccggttc gagctgatac cacagggaaa gacgctcaag   120
cacatccagg aacagggctt catcgaggag gacaaggcgc gcaacgacca ctacaaggag   180
ttgaaaccga tcatcgaccg catctacaag acgtacgccg accagtgcct ccagctcgtg   240
cagctcgact gggagaacct ctccgccgcc attgactcgt accggaagga gaagactgag   300
gagacccgca acgccctgat cgaggagcaa gcaacctacc ggaacgccat ccacgactac   360
ttcatcggcc gcaccgacaa cctcaccgac gcgatcaaca agcgcacgc ggagatatac    420
aaagggctgt tcaaggcgga gctgttcaac ggcaaggtgc tcaagcagct agggacggtg   480
accacgaccg agcacgagaa cgcgctcctc cgcagcttcg acaagttcac cacctacttc   540
agcggcttct accggaaccg caagaatgtg ttcagcgcgg aggacatcag cacggccatc   600
ccgcaccgca tcgtccagga caacttcccg aagttcaagg agaactgcca catcttcacc   660
cgcctgataa ccgccgtccc ctccctgcgg gagcacttcg agaacgtcaa aaaggcaatt   720
gggatcttcg tctcgaccag cattgaggag gtgttcagct ccccttcta caaccagctc    780
ctcacccaga cgcagatcga cctgtacaat cagttgctcg gcgggataag ccgcgaggcg   840
ggaaccgaaa aaatcaaggg gctgaaccga agtgttgaac tcgccatcca gaagaacgac   900
gagaccgcgc acatcatcgc ctccctgccc caccggttca tcccgctgtt caagcagatc   960
ctctctgacc ggaacaccct gtccttcatt cttgaggagt tcaagtcgga cgaggaggtc  1020
atccagagct tctgcaagta caagacgctg ctacggaacg agaacgtgct ggagacggcg  1080
gaggcactgt tcaacgagct aaacagcatc gacctcacgc acatcttcat cagtcacaag  1140
aaactggaga ccatctcctc cgcgctgtgc gaccactggg acacgctcag gaacgcgctc  1200
tacgagcgcc gaatcagtga gctgacgggc aagatcacga agtccgcgaa ggagaaggtg  1260
cagcggtccc tcaagcacga ggacatcaac ctccaggaga tcatctcagc ggctgggaaa  1320
gagctgtccg aggcgttcaa gcagaaaacg agcgaaatcc tgtcccacgc gcacgcgccc  1380
ctggatcagc ctctgccgac gaccctcaag aaacaagaag aaaaggaaat cctcaagtcc  1440
cagctcgact cgctgctggg cctgtaccat ctcctcgact ggttcgccgt ggacgagagc  1500
aacgaggtgg accccgagtt ctccgcgcgg cttacgggga tcaagctgga gatggagccc  1560
agcctgtcct tctacaacaa ggcgcgcaac tacgccacca agaagcccta cagcgtggag  1620
aagttcaagc tcaacttcca gatgcccact ctcgcacgtg ggtgggacgt caaccgcgaa  1680
aaaaataatg gggcgatcct gttcgtcaag aacggcctgt actacttggg catcatgccg  1740
aaacagaagg gccgctacaa ggccctgagc ttcgaaccga ccgagaaaac gagcgagggg  1800
ttcgacaaga tgtactacga ctacttcccc gacgccgcga agatgattcc aaagtgctcc  1860
acgcagctta aggccgtgac ggcccacttc cagacgcaca cgaccccgat cctcctcagc  1920
aacaacttca tcgagcccct ggagatcacg aaggagatat acgacctgaa caacccggag  1980
aaggagccca gaaattcca gaccgcctac gccaagaaga caggcgacca aaagggttac    2040
agggaggccc tctgcaagtg gatcgacttc actagggact tcctgtccaa gtacaccaag  2100
actacctcta tcgacctgtc cagcctccgc ccgtcgtccc agtacaaaga tttgggcgag  2160
tattacgcgg agctgaaccc actgctctac cacatcagct tccacgcat cgcggagaag    2220
gagatcatgg acgcagtgga cgggcaagg ctatacctat ttcagatata caacaaagac    2280
ttcgctaagg acaccacgg caagcctaac ctgcacaccc tctactggac ggggctcttc    2340
agcccggaga acctcgccaa gacctcgatc aagctcaagg aggccgca gctgttctac     2400
cggcccaagt cccgcatgaa gcggatggcc caccggctcg gggagaaaat gctcaacaag  2460
aaattgaagg accaaaaac gccgataccc gacaccctat accaggagct gtacgactat    2520
gtgaaccacc gcctgagcca cgacctcagc gacgaggcgc gggccctcct gccgaacgtc  2580
atcacaaagg aggtcagcca cgagatcact aaggaccggc gcttcacctc cgacaagttt  2640
ttctttcacg tgcccatcac gctcaactac caggccgcca actcgccgtc caagttcaac  2700
cagcgcgtga acgcctacct caaggagcac cccgagaccc cgatcatcgg gattgaccga  2760
ggggagcgga acctcatcta catcaccgtc atcgacagca ccgggaagat ccttgaacag  2820
cggtcgctca acaccatcca gcagttcgac taccagaaga aactcgacaa ccgggagaag  2880
gagagagtgg cggcccgcca ggcttggtcc gtcgtcgga cgattaagga cttgaaacaa    2940
ggttacctgt cgcaagtgat ccacgagatc gttgacctga tgatccacta ccaagccgtc  3000
gtggtcctga agaacctcaa cttcggcttc aagagcaaac gaaccggcat cgcggagaag  3060
gccgtgtacc agcagttcga aaaaatgctg atcgacaagc tgaactgcct cgtgctcaag  3120
gactaccccg ctgagaaggt cggcgggggtg ctgaacccgt accagctcac tgaccagttc  3180
accagcttcg caaagatggg cacccagtcc ggcttcctgt tctacgtgcc tgcgccatac  3240
acctcgaaga tcgacccgct caccgggttc gtggaccct cgtctggaa gaccatcaag    3300
aaccacgaga gccgcaagca cttcctggag ggcttcgact tcctccacta cgacgtcaag  3360
accggggact tcatcctgca cttcaagatg aaccgcaacc tcagtttcca gcgcggcctg  3420
ccggggttca tgcccgcttg ggatatagtc ttcgaagaaga atgagacgca gttcgacgcg  3480
aagggcaccc cgttcatcgc cgggaagcgc atcgtgccgg tcatcgagaa ccaccggttc  3540
accgggcgct accgcgacct ataccccgcg aacgagttga tcgccctcct ggaggagaag  3600
ggcatcgtgt tccgcgacgg ctccaacatc ctcccgaacg tcgaaaa cgacgactcc     3660
cacgccatcg acacgatggt cgcgctgatc cggtcggtgc tccagatgcg gaactccaac  3720
gccgcgacgg gcgaggacta catcaacagt ccggtccgcg atctgaacgg cgtctgcttc  3780
gactccggt tccagaaccc cgagtggccg atggacgcgg acgcgaacgg cgcataccac    3840
atcgccctaa aagggcaatt gctgctcaac cacctcaagg aatccaaaga cctaaagctc  3900
cagaacggca tctccaacca ggactggctg gcgtacatcc aggaactgcg gaacgggagc  3960
aaaaaacgtc ggatcaagca agattga                                      3987

SEQ ID NO: 69           moltype = DNA  length = 3987
FEATURE                 Location/Qualifiers
source                  1..3987
                        mol_type = other DNA
                        organism = synthetic construct
SEQUENCE: 69
atggcgggct ccaagaaacg ccggattaag caagatacc agttcgaggg gttcacgaac      60
ctctaccaag tgagcaagac cctccgattc gaactgattc tcaggggaa gaccctcaag     120
```

```
cacatccagg agcaagggtt catcgaggag gacaaggcgc ggaacgacca ctacaaggaa    180
ctcaaaccca tcatcgaccg catctacaag acctacgccg atcagtgcct ccagctcgtg    240
cagttggact gggagaacct cagcgcggcc attgactcct accggaagga gaaaacggag    300
gagacgcgca acgcgctcat cgaggaacag gcaacctatc gcaacgccat ccacgactac    360
ttcatcggga ggactgacaa cctcactgac gcgattaaca agcgccacgc ggagatatac    420
aagggactct tcaaagcgga gctgtttaac ggcaaggttc tcaagcaact cggcactgtg    480
accacgaccg agcatgagaa cgccctgctc cgctccttcg acaagttcac cacctacttc    540
tccgggttct accgcaaccg caagaatgtc ttcagcgcgg aggacatcag cacggccatt    600
ccacatcgaa tcgtccaaga taacttcccg aagttcaagg agaactgcca catcttcacc    660
cgactcatta ctgctgtacc gtcgttacgc gaacacttcg agaacgtcaa gaaggcaatt    720
ggaatcttcg tctctacgtc aatagaggag gtgttcagct tccctttcta caaccagctc    780
cttacgcaga cccagataga cctgtacaat cagctcctcg gtgggatcag ccgggaggcg    840
gggactgaga agattaaagg gctcaacgag gtcttgaacc tggccatcca aaaaaacgat    900
gagacggcgc acatcatcgc ctcgctgccc caccggttca tcccgctgtt caagcagatc    960
ctcagtgaca ggaacacctt gagctttatc ctagaggagt tcaagagcga cgaggggtg   1020
atccagagct tctgcaagta caaaaccctg ctgaggaacg agaacgtcct ggagacggcg   1080
gaggcgctgt tcaacgagct gaactctatc gacttaactc acatattcat ctcgcacaag   1140
aagctggaga ctattagctc tgcactctgc gaccactggg acaccctccg caacgcgctc   1200
tacgagcgcc gcatctcgga gctgaccggg aagatcacca atccgcgaa ggaaaaggtc   1260
cagcgttccc tcaaacacga ggatattaac ttacaggaga ttatctcagc ggctgggaag   1320
gagttgtcag aggcgttcaa gcagaaaact tccgagatcc tgagccacgc gcacgcagcg   1380
ctcgaccagc ctctgcccac caccctcaaa aagcaggaag aaaaagagat cctcaagagc   1440
cagttggact ccctgctggg gctctatcac cttctcgact ggttcgccgt cgatgagtcg   1500
aacgaggtgg accccgagtt ctccgcccgg ctgaccggca tcaagctaga gatgagccg   1560
tccctcagct tctacaataa ggcccgcaac tacgcgacca aaaaaccta cagcgtggag   1620
aagttcaagc tgaacttcca gatgccgacc ttagcacgcg gttgggacgt aaacagggag   1680
aagaacaatg gagccatcct gttcgtcaag aacgggcttt actacctcgg gataatgccc   1740
aagcagaagg gccgctacaa ggccctttcc ttcgagccga cggagaaaac ctccgagggg   1800
ttcgacaaga tgtactacga ctacttcccc gacgccgcca agatgatccc gaagtgctca   1860
acgcagctaa aagccgtgac cgcccacttc cagacccaca gcagccgcgat cctgctgagc   1920
aacaacttca tcgagcccct tgagatcact aaggagatat acgacctgaa caaccccgag   1980
aaggagccca gaagtttca aaccgcctac gccaaaaaaa ctggcgacca aaagggctac   2040
agggaggcgc tgtgtaagtg gatcgacttc acacgcgact tcctttcgaa gtatacgaag   2100
acaacctcta ttgacctgag cagcctgcgt cctagctccc agtacaaaga tttgggcgag   2160
tactacgcgg agcttaatcc actactctac cacatctcat tccagcgcat cgctgagaag   2220
gaaatcatgg acgcggtgga gacaggcaaa ctgtacctct tccagatata caacaaagac   2280
ttcgctaagg gcaccacgg gaagcccaac cttcatacgc tctactggac gggcctattc   2340
agccccgaaa atctggccaa gacctccatc aagctgaacg gccaagcgga gctgttctac   2400
agacccaaga gccggatgaa gcggatggcc cacaggctcg gcgagaaaat gcttaacaaa   2460
aagttgaagg accagaaaac ccctatcccc gacaccctct accaggaact gtacgactac   2520
gtgaaccaca ggctctcgca cgacctttcc gacgaggccc gtgccctact cccgaacgtc   2580
attaccaaag aggtttcgca cgagatcatc aaggaccggc ggttcacgag cgacaagttt   2640
ttctttcacg tccccatcac ccttaactac caggcggcca actccccatc caagttcaac   2700
cagcgtgtga atgcctacct caaggagcac ccagagaccc cgatcattgg gatcgaccgg   2760
ggcgagcgga acctgatcta catcaccgtc atcgactcga cggcaagat tcttgagcag   2820
agatcgttga ataccataca gcagttcgac taccagaaga aactcgacaa ccgcgagaag   2880
gagcgcgtgg cggcccgcca ggcgtggtcc gtcgttggga cgattaagga cttgaaacaa   2940
ggttatctgt cccaagtcat ccacgagatc gttgatctga tgatccacta tcaggcagtg   3000
gtggtgctgg agaatctcaa cttcggcttc aagagtaagc ggacgggaat cgccgagaag   3060
gccgtgtacc agcagttcga gaagatgctg atcgacaagc tcaactgcct tgtgctgaaa   3120
gactacccgg ccgagaaggt cggcggcgtc ctcaaccgt accaacttac cgaaccagttc   3180
acctccttcg ccaagatggg cactcagtcc gggttcttgt tctacgtccc cgcaccttac   3240
acctctaaga tcgaccctct gactggcttc gtagatccat tcgtgtggaa gaccattaag   3300
aaccacgaga gccgcaagca cttcctggag ggcttcgact tcctgcacta cgacgtgaag   3360
accggggact tcatccttca cttcaagatg aaccggaacc tcagcttcca gcggggcctg   3420
ccgggggttca tgcccgcctg ggacatcgtg ttcgagaaga acgagaccca gttcgacgcg   3480
aagggcacgc ccttcatcgc cgggaagcgt atcgtgccgg tgatcgagaa ccatcgtttc   3540
acgggtcgct accgtgacct ctaccgcgcg aacgagctta tcgcactcct ggaggagaag   3600
ggcatcgtct tcccggacgg ctccaacatc ctcccgaaac tgctggaaaa cgacgactct   3660
cacgccatcg acacgatggt ggccctcatc cggtcgtgc tccaaatgcg gaacagcaac   3720
gccgccaccg gtgaggacta catcaacagc ccggtccggg atctgaacgg ggtgtgcttc   3780
gattcgcggt tccagaatcc tgagtggccg atggacgcgg atgcaaacgg ggcgtaccac   3840
atcgcgctca agggccagtt acttctgaac caccttaagg agtctaaaga tttgaaactc   3900
cagaacggga tctcgaacca ggactggctg gcctacatcc aagagttgcg gaacggcagc   3960
aagaagcggc ggattaagca agattag                                       3987

SEQ ID NO: 70         moltype = DNA  length = 4101
FEATURE               Location/Qualifiers
source                1..4101
                      mol_type = other DNA
                      organism = synthetic construct
SEQUENCE: 70
gacaagaagt acagcatcgg gctggcgatc gggaccaact ccgtcggctg ggctgtgatt     60
accgacgagt acaaggtgcc atccaagaag ttcaaggtcc tcggcaacac tgaccgcac    120
agcattaaga agaacctgat tggggcgctg ctgttcgatt cgggggagac tgcggaggcg    180
accaggctga agcggactgc gcgccggagg tacaccagga ggaagaatcg gatctgctac    240
ctccaggaga ttttctcgaa tgagatggcc aaggtgacga ttccttcttc catcgcctg    300
gaggagtcgt tcctcgttga ggaggacaag aagcatgaga ggcatccat tttcgggaat    360
atcgttgacg aggtggctta ccatgagaag tacccgacca tctaccatct gcggaagaag    420
```

```
ctcgtcgatt cgaccgataa ggccgacctg cggctgatct acctggccct cgcgcacatg   480
attaagttcc ggggccattt cctcatcgag ggcgacctca acccggacaa ctcggacgtg   540
gataagctct tcattcagct cgtgcagaca tacaaccagc tcttcgagga gaatcccatt   600
aacgcctcgg gggtcgacgc taaggctatt ctctcggctc ggctgtcgaa gtcgcgccgg   660
ctggagaatc tcattgccca gctcccaggc gagaagaaga acggcctctt cggcaacctg   720
attgccctgt cgctggggct cacaccgaat ttcaagtcga acttcgacct cgccgaggac   780
gctaagctcc agctcagcaa ggatacttac gatgatgacc tcgataacct gctcgcccag   840
attgggatc agtacgcgga tctgttcctc gcggccaaga atctcagcga tgctattctc    900
ctgtcggaca ttctccgcgt caacacagag attactacgg ccccactgtc ggcgagcatg   960
attaagaggt acgatgagca tcatcaggac ctgacactgc tcaaggcgct ggtccggcag  1020
cagctccccg agaagtacaa ggagattttc ttcgatcagt caaagaatgg gtacgcgggc  1080
tacattgatg gcgcgcgtc ccaggaggag ttctacaagt tcattaagcc catcctggag   1140
aagatgacg ggaccgagga gctgctggtg aagctcaatc gggaggacct gctccggaag   1200
cagcgcacat tcgacaatgg ctcgattcct caccagattc acctgggcga gctgcacgcc  1260
attctccgca ggcaggagga cttctacccg ttcctcaagg acaaccgcga gaagatcgag  1320
aagatcctga ccttccggat tccatactac gtggggccgc tcgcgcgggg gaactcccgg  1380
ttcgcgtgga tgactcgcaa gtccgaagaa acgattacac cgtggaattt cgaggaggtc  1440
gtcgacaagg gcgctagtgc gcagtcattc attgagagga tgaccaattt cgataagaac  1500
ctgcctaacg agaaggtgct gccgaagcat tcgctgctct acgagtactt caccgttttac  1560
aatgagctga ccaaggtgaa gtatgtgact gagggcatga ggaagccagc gttcctgagc  1620
ggcgagcaga agaaggctat cgtggacctg ctcttcaaga ctaaccggaa ggtgactgtg  1680
aagcagctca aggaggacta cttcaagaag attgagtgct tcgattccgt tgagattagc  1740
gggtggagg atcggttcaa tgcttcgctc gggacatacc acgatctcct gaagatcatt  1800
aaggataagg acttcctcga caacgaggag aacgaggaca ttctcgaaga tattgtcctg  1860
accctcaccc tcttcgagga tcgggagatg atcgaggaga ggctcaagac atacgctcat  1920
ctgttcgatg ataaggtcat gaagcagctg aagcgcacag ggtacacagg gtgggggcgg  1980
ctgagccgga agctgatcaa cgggattcgg gataagcagt ccggggaagc aaattctcgac  2040
ttcctcaagt ccgacgggtt cgctaaccgg aacttcatgc agctcattca tgatgactcg  2100
ctgacattca aggaggatat tcagaaggcg caggtttcgg ggcagggcga ctcgctccac  2160
gagcatattg cgaatctggc gggctccccc gcgattaaga agggcattct gcaaaccgtc  2220
aaggtggttg atgagctggt caaggtcatg gggcggcata agccagaaa tattgtcatc  2280
gagatggcgc gggagaatca gaccacacag aaggggcaga agaactcacg ggagcggatg  2340
aagcgcatcg aggagggcat caaggagctg gggtcgcaga tcctgaagga gcatcccgtg  2400
gagaacactc agctgcaaaa tgagaagctg tacctctact acctccagaa cgggagggac  2460
atgtatgtgg atcaggagct ggatattaat aggctgagcg attacgatgt cgaccacatt  2520
gtcccacagt cgttcctgaa ggacgacagc attgacaaca aggtgctgac ccgctcggat  2580
aagaacaggg gcaagagcga taatgttcca agcgaggagg ttgtgaagaa gatgaagaac  2640
tactggcggc agctcctgaa cgcgaagctc atcacacagc ggaagttcga caacctcacc  2700
aaggctgagc gcgggggcct gagcgagctg gacaaggcgg ggttcattaa gaggcagctg  2760
gtcgagacac ggcagattac aaagcatgtt cgcgcagattc tcgattcccg gatgaacacc  2820
aagtacgatg agaacgataa gctgattcgg gaggtcaagg taattaccct gaagtccaag  2880
ctggtgtccg acttcaggaa ggacttccag ttctacaagg ttcgggagat caacaactac  2940
caccacgcgc atgatgccta cctcaacgcg gtcgtggggc ccgctctcat caagaagtac  3000
ccaaagctgg agtcagagtt cgtctacggg gattacaagg tttacgacgt gcggaagatg  3060
atcgctaaga gcgagcagga gattggcaag gctaccgcta agtacttctt ctactccaac  3120
atcatgaact tcttcaagac agagattacc ctcgcgaatg gcgagatccg gaagaggccc  3180
ctcatcgaga caaatgggga gacagggggag atttgtctggg ataaggggcg ggatttcgcg  3240
accgtccgga aggtcctgtc gatgcccag gttaatattg tcaagaagac tgaggtccaa   3300
actggcggct tctcaaagga gtcgattctc ccaaagagga actccgataa gctcattgct  3360
cggaagaagg attgggaccc caagaagtac ggggggattcg actcccccac tgttgcttac  3420
tctgttctgg ttgttgctaa ggtggagaag gggaagtcga agaagctgaa gagcgtgaa  3480
gagctgctcg ggattacaat tatgagagg tcatccttcg agaagaatcc catcgacttc  3540
ctggaggcca agggctacaa ggaggtgaag aaggacctga ttattaagct gcccaagtac  3600
tcgctcttcg agctggagaa tgggcggaag cggatgctgg cgtccgcggg ggagctgcaa  3660
aaggggaacg agctggcgct cccctccaag tatgtgaagt tcctctacct ggcgtcgaa   3720
tacgagaagc tgaaggggtc cccagaggat aatgagcaga agcagctctt cgtcgagcag  3780
cataagcact acctggacga gattatcgag cagattagcg agttctcgaa gcgggtcatc  3840
ctcgcggatg cgaacctgga taaggtgctc agcgcctaca ataagcaccg ggacaagccg  3900
attcgggagc aggcggagaa tattattcac ctcttcacac tcaccaacct cggggcacca  3960
gctgcgttca agtacttcga cactactatc gaccggaagc ggtacacctc gacgaaggag  4020
gtgctcgacg ccaccctcat tcaccagtcg atcacaggcc tgtacgagac acggattgac  4080
ctgtcccagc tcggggcga c                                             4101
SEQ ID NO: 71         moltype = DNA  length = 4101
FEATURE               Location/Qualifiers
source                1..4101
                      mol_type = other DNA
                      organism = synthetic construct
SEQUENCE: 71
gacaagaagt actccattgg cctggcgatt gggacaaact cggtggggtg ggccgtgatt    60
acggatgagt acaaggttcc aagcaagaag ttcaaggtcc tcgggaacac agatcggcat   120
tcgattaaga gaatctcat tggggcgctc ctcttcgact cggggggagac agcggaggct   180
accaggctca agcggacagc caggcggcgg tacacaaggg ggaagaatcg catctgctac   240
ctccagagta ttttctcgaa tgagatgcg aaggtggacg acagctttctt ccatcgactg   300
gaggagtcct tcctggtgga ggaggataag aagcacggaa ggcatccaat tttcggggaac   360
atcgtggacg aggttcgcta ccatgagaag taccctacaa tctaccatct gcggaagaag   420
ctggttgact ccacagacaa ggcggacctg aggctgatct acctcgctct ggcccacatg   480
attaagttcc gcgggcattt cctgatcgag ggggacctga atcccgacaa ttcggatgtg   540
gacaagctct tcatccagct ggtgcagacc tacaaccagc tgttcgagga gaatcccatc   600
```

```
aatgcgtcgg gcgttgacgc taaggccatt ctgtccgcta ggctgtcgaa gagcaggagg    660
ctggagaacc tgatcgccca gctgccaggc gagaagaaga atgggctctt cgggaatctg    720
attgcgctct ccctggggct gacaccgaac ttcaagagca atttcgatct ggctgaggac    780
gcgaagctcc agctctcgaa ggacacttac gacgatgacc tcgataacct cctcgcgcag    840
atcggggacc agtacgctga tctcttcctc gccgctaaga acctctcgga tgctatcctg    900
ctctccgaca ttctccgggt taataccgag attacaaagg ccccactgtc ggcgtccatg    960
atcaagcggt acgatgagca tcatcaggat ctcaccctgc tcaaggccct cgtgcggcag   1020
cagctgcccg agaagtacaa ggagattttc ttcgaccaga gcaagaatgg gtacgctggc   1080
tacattgacg gcggggcctc acaggaggag ttctacaagt tcatcaagcc aatcctggag   1140
aagatggatg ggacagagga gctgctggtg aagctcaacc gggaggatct gctcaggaag   1200
cagcggacgt cgacaacgg gtcgattccc catcagatcc acctggggga gctgcacgcg   1260
atcctgcgcc ggcaggagga tttctaccct tcctgaagg ataatcggga gaagatcgag   1320
aagattctca ccttccggat tccctactac gtcgggccac tcgcgcgggg caatagcagg   1380
ttcgcctgga tgacacggaa gagcgaggag acaatcaccc cctggaactt cgaggaggtt   1440
gtcgacaagg gggcgtccgc ccagtcattc attgagcgga tgaccaattt cgacaagaat   1500
ctgccaaatg agaaggttct cccaaagcat agcctcctct acgagtactt cactgtttac   1560
aacgagctga ccaaggtgaa gtatgtgacc gagggcatgc ggaagcccgc gttcctgtcc   1620
ggcgagcaga agaaggccat tgtggacctc ctgttcaaga ccaatcgcaa ggtcacagtc   1680
aagcagctca aggaggatta cttcaagaag atcgagtgct tcgactcggt tgagattagc   1740
ggggtggagg atcggttcaa cgcgagcctc ggcacttacc acgacctcct gaagatcatc   1800
aaggataagg acttcctcga caacgaggag aacgaggata ttctggagga catcgtgctc   1860
accctgacgc tgttcgagga tcgggagatg atcgaggacg gcctgaaagac ctacgctcat   1920
ctcttcgatg ataaggtcat gaagcagctg aagaggaggc ggtacaccgg gtggggccgc   1980
ctgagcagga agctcattaa cgggatcagg gacaagcaga gcggcaagac catcctggac   2040
ttcctcaaga gcgatggctt cgccaaccgg aatttcatgc agctcatcca cgacgactcc   2100
ctcaccttca aggaggacat tcagaaggct caggtcaggg gccaggggca ctcgctgcat   2160
gagcacatcg ctaacctggc gggcagccca gccatcaaga agggcatcct ccagacagtg   2220
aaggtcgtgg atgagctggt gaaggtcatg ggccggcata agcccgagaa tattgtgatt   2280
gagatggcgc gggagaatca gaccactcag aagggccaga agaactcgcg ggagcgcatg   2340
aagaggatcg aggagggggat taaggagctg ggcagccaga ttctcaagga gcaccccgtg   2400
gagaataccc agctccagaa cgagaagctg tacctctact acctccagaa tgggcgggac   2460
atgtatgttg atcaggagct ggacatcaat cgcctctcgg attacgacgt ggaccacatc   2520
gtgccccaga gcttcctgaa ggatgatagc atcgacaata aggtcctgac ccgctccgac   2580
aagaatccgg gcaagagcga caacgtgccg agcgaggagg tcgtgaagaa gatgaagaac   2640
tactggcggc agctgctgaa cgcgaagctc attacacagc ggaagttcga taacctgacg   2700
aaggcggaga ggggcggcct ctccgagctg gacaaggcgg gcttcattaa gaggcagctc   2760
gtggagactc gccagatcac caagcacgtg gctcagatcc tcgatagccg gatgaatacg   2820
aagtacgatg agaatgacaa gctcatccgg gaggtgaagg taatcaccct gaagtcaaag   2880
ctcgttagcg atttccggaa ggacttccag ttctacaaga tgcgggagat taacaactac   2940
catcatgcgc acgatgcgta cctcaatgcg gtggtgggca cagccctgat taagaagtac   3000
cccaagctgg agagcgagtt cgtctacggg gactacaagg tgtacgatgt tcggaagatg   3060
atcgccaaga gcgagcagga gattgggaag gccaccgcta agtacttctt ctactcgaat   3120
attatgaatt tcttcaagac cgagatcaca ctcgctaatg gggagattcg gaagcggccc   3180
ctcatcgaga ctaacgggga gactggcgag attgtgtggg acaagggggcg cgacttcgct   3240
accgtgcgca aggtcctctc gatgcccccag gttaatattg ttaagaagac agaggtgcag   3300
acgggcgggt tctccaagga gtctatcctg ccgaagcgga actcggacaa gctgatcgcc   3360
cgcaagaagg attgggaccc caagaagacg ggggggattg atagcccaac cgtggcttac   3420
agcgtcctgg tggtcgccaa ggttgagaag gggaagtcga agaagctcaa gagcgttaag   3480
gagctgctgg gcatcaccat catggagcgg tccagcttcg agaagaatcc tatcgacttc   3540
ctggaggcta agggggtacaa ggaggtcaag aaggacctga tcattaagct gcccaagtac   3600
tctctgtttcg agctggagaa cgggagagg cggatgctgg cgtctgctgg cgagctacag   3660
aagggcaatg agctgcgcct ccccctcgaag tatgtcaact tcctctacct ggcttcccat   3720
tacgagaagc tgaagggctc gcccgaggat aatgagcaga agcagctctt cgtggagcag   3780
cacaagcact acctcgacga gatcattgag cagtttcgg agttctcgaa gcgggtcatt   3840
ctcgcggaca cgaacctcga caaggtcctc tcggcgtaca acaagcaccg ggacaagccc   3900
atccgggagc aggccgagaa cattatccac ctcttcacac tgaccaacct cggcgctccc   3960
gccgcgttca gtacttcga caccaccatt gaccgcaaga gatacacatc caccaaggag   4020
gtgctggacg cgaccctcat ccaccagagc atcacaggcc tctacgagac acggatcgac   4080
ctctcgcagc tcgggggcga t                                            4101
SEQ ID NO: 72          moltype = DNA  length = 4092
FEATURE                Location/Qualifiers
source                 1..4092
                       mol_type = other DNA
                       organism = synthetic construct
SEQUENCE: 72
gacaagaagt actcgatcgg cctggcgatt ggcacaaaca gcgtgggtg ggctgtgatc     60
actgatgagt acaaggtgcc atcgaagaag ttcaaggtgt tggggaatac agaccggcat   120
tcgatcaaga agaatctcat tggcgctctc ctcttcgata ccgcgagac tgctgaggcg   180
acccgcctga agcgcaccgc ccggcggcgc tacactcggc ggaagaatag gatttgctac   240
ctccaggaga tttttctcga atgagatggcc aaggtggatg acagcttctt ccaccgcctg   300
gaggagtcgt tcctggtcga ggaggacaag aagcatgagc ggcacccctat cttcgggaat   360
atcgttgatg aggtcgccta ccacgagaag tacccccacta tctaccatct ccgcaagaag   420
ctcgtggaca gcacagataa ggccgacctc cgcctgatct acctcgccct cgcgcacatg   480
attaagttcc gggggcactt cctcattgag gggatctga atcccgataa ctccgacgtg   540
gacaagctgt tcatccagct ggtgcagaca taaccagc tgttcgagga gaatcccatc   600
aacgcgagcg gcgtggacgc taaggccatt ctgtcggcta ggctctcgaa gtcgaggcgg   660
ctggagaacc tgattgcgca gctccccggc gagaagaaga acgggctgtt cgggaatctc   720
atcgccctct ccctcggcct cacaccaaac ttcaagagca atttcgacct ggctgaggac   780
```

```
gctaagctgc aactctcaaa ggatacatac gatgacgacc tggacaatct cctggctcag    840
atcggcgacc agtacgctga cctgttcctc gcggccaaga atctgtcgga cgcgattctc    900
ctcagcgaca tcctgcgcgt caataccgag attacgaagg ctccactgtc tgcgtcaatg    960
attaagcggt acgatgagca tcaccaggat ctgaccctcc tgaaggcgct cgtgcggcag   1020
cagctgcccg agaagtacaa ggagattttc ttcgatcaga gcaagaatgg ctacgccggc   1080
tacatcgacg ggggcgcgag ccaggaggag ttctacaagt tcatcaagcc catcctggag   1140
aagatgacg gcaccgagga gctactcgtg aagctcaatc gggaggatct cctccggaag   1200
cagcggacat tcgataacgg gtctatccca caccagatcc acctcggcga gctgcatgcg   1260
attctgcggc ggcaggagga tttctaccct ttcctgaagg acaaccggga gaagatcgag   1320
aagatcctca cattccggat tccatactac gtcggccccc tggcgagggg caatagccgg   1380
ttcgcgtgga tgacaaggaa gtccgaggag actattaccc cgtggaattt cgaggaggtg   1440
gttgacaagg gcgcttccgc gcagagcttc attgagcgga tgacaaactt cgacaagaat   1500
ctccccaacg agaaggtcct gccgaagcat agcctcctgt acgagtactt caccgtctac   1560
aatgagctaa ctaaggtcaa gtatgtgaca gagggcatga ggaagccagc cttcctctca   1620
ggcgagcaga agaaggccat tgtggacctc ctgttcaaga caaaccgcaa ggtgacagtg   1680
aagcagctga aggaggatta cttcaagaag attgagtgct tcgactcagt ggagatttca   1740
ggcgtggagg atcggttcaa cgcgagcctg ggacttacc acgacctgct gaagattatt   1800
aaggacaagg acttcctgga taacgaggag aatgaggaca tcctggagga tattgtgctc   1860
accctcaccc tgttcgagga cagggagatg attgaggaga ggctcaagac ctacgcgcac   1920
ctgttcgatg acaaggtcat gaagcagctg aagaggcggc gctacactgg gtggggccgc   1980
ctgtcgcgga agctgatcaa cggcattcgg ataagcagt ccgggaagac cattctggat   2040
ttcctgaagt cggacggctt cgccaacagg aatttcatgc agctgatcca cgacgactcc   2100
ctcaccttca aggaggacat tcagaaggcc caggttagcg gccaggggga ctcactccac   2160
gagcatattg ccaatctggc cggctctcca gctatcaaga agggcatcct gcaaacagtt   2220
aaggttgttg acgagctggt taaggtcatg ggcggcata agcccgagaa cattgtcatc   2280
gagatggctc ggggagaacca gacaactcag aagggccaga agaactccag ggagcgcagc   2340
aagcggattg aggagggcat taaggagctg gggtcccaga tcctcaagga gcaccctgtc   2400
gagaacactc agctgcaaaa cgagaagctc tacctgtact acctccagaa cgggcgggat   2460
atgtatgtgg atcaggagct ggacatcaac aggctctccg actacgacgt ggatcacatt   2520
gtcccacagt cttttcctcaa ggatgattcc atcgacaaca aggtgctgac gcgcagcgac   2580
aagaataggg ggaagtcgga caacgttccg agcgaggagg tcgtgaagaa gatgaagaat   2640
tactggaggc agctcctgaa tgcgaagctg atcactcaga ggaagttcga caatctgaca   2700
aaggcggaga ggggcgggct ctcggagctg gataagcgg gcttcatcaa gcggcagctc   2760
gttgaaaccc ggcagatcac caagcatgtc gcccagatcc tcgatagccg catgaacacc   2820
aagtacgatg agaacgacaa gctcattcgg gaggttaagg tcattacgct gaagtccaag   2880
ctcgtcagcg acttcaggaa ggatttccag ttctacaagg ttcgggagat taacaactac   2940
caccacgcgc atgatgcgta cctgaacgct gttgtcggca ctgctctcat caagaagtac   3000
ccaaagctgg agtccgagtt cgtctacggg gactacaagg tctacgatgt ccggaagatg   3060
atcgccaagt cggagcagga gatcgggaag gctactcttt ctacagcaac               3120
attatgaatt tcttcaagac ggagattacg ctggcgaacg gggagattag gaagaggccc   3180
ctcattgaga ctaatgggga gacaggcgag attgttggg acaagggccg cgacttcgcg   3240
actgtgcgga aggtcctgtc catgccacag gtgaatattg ttaagaagac agaggtgcag   3300
actgggggct tctcgaagga gagcattctc ccaaagcgga acagcgataa gctcatcgcg   3360
cgcaagaagg attgggaccc taagaagtac ggcggcttcg attctcccac tgtggcctac   3420
tccgttctcg tggttgccaa ggttgagaag gggaagtcga agaagctgaa gtcggtcaag   3480
gagctgctcg ggattacaat catggagcgg agcagcttcg agaagaaccc tattgatttc   3540
ctggaggcca agggctacaa ggaggttaag aaggatctca ttatcaagct ccctaagtac   3600
tctctgttcg agctggagaa tggccggaag aggatgctgg cctcggctgg cgagctacag   3660
aaggggaatg agctggcccct cccgtcgaag tatgtgaatt tcctgtacct cgcgtcgcac   3720
tacgagaagc tcaagggcag cccggaggat aatgagcaga agcagctctt cgtggagcag   3780
cataagcact acctggacga gatcattgag cagatcgcg agttctcgaa gcggggtttt   3840
ctggctgatg ctaacctgga caaggttctg agcgcctaca ataagcatcg cgacaagccg   3900
attcgcgagc aggcggagaa tattatccac ctgttcaccc tcactaacct cggggctccc   3960
gcggccttca gtacttcga taccacaata gataggaagc ggtacacctc gacgaaggag   4020
gtcctcgacg ccacactcat ccatcagtcg attacaggcc tgtacgagac acggattgac   4080
ctctcgcagc tg                                                      4092
SEQ ID NO: 73           moltype = DNA  length = 4101
FEATURE                 Location/Qualifiers
source                  1..4101
                        mol_type = other DNA
                        organism = synthetic construct
SEQUENCE: 73
gacaagaagt attccatagg cctggctatc ggcaccaaca gcgtgggctg ggccgtcatc     60
accgacgagt acaaagtgcc gagtaaaaag ttcaaagtgc tcggcaacac cgaccgccac    120
tccataaaga aaaacctgat cggggcgctc ctgttcgaca cggcgagac ggcggaggcc    180
acccgcttga aacgcacggc ccgacggcgc tacacgcggc gcaagaaccg gatctgttac    240
ctacaggaga ttttctctaa cgagatggcg aaggtggacg actcgttctt tcaccgcctc    300
gaagagtcct tcctcgtgga ggaggacaag aaacacggat gccaccgac cttcggcaac    360
atcgtggacg aggtggccta ccacgagaag taccgacca tctaccacct ccggaagaaa    420
ctcgtggaca gcacggacaa ggcgacctg aggctcatct acctcgccct ggcgcacatg    480
attaagttcc ggggccactt cctgatcgag ggcgacctga cccggacaa cagcgacgtg    540
gacaagctgt tcatccagct agtccagacc tacaaccagc ttttcgagga aaaccccatc    600
aacgccacg gggtggacgc gaaggcgatc ctgtccgccc ggctgagcaa gtccgggcgg    660
ctggagaacc tcatcgcgca gttgcccggc gagaagaaga cgggctgtt cgggaacctg    720
atcgccctct ccctggggct caccccgaac ttcaagtcca acttcgacct cgccgaggac    780
gccaaactac agctgagcaa ggacacctac gacgacgacc tcgacaacct gctgcccag    840
atcggggacc agtacgcaga cctgttcctc gccgccaaga acctctccga cgccatcctg    900
ctgtcggaca tcctgcgggt gaacacggag atcacgaagg ccccgctctc ggcctcgatg    960
```

```
attaaacgct acgacgagca ccaccaggac ttgaccctcc tcaaggcgct ggtccgccag 1020
cagcttcccg agaagtacaa ggaaatcttt ttcgatcaga gcaagaacgg gtacgccggg 1080
tacatcgacg gcgggcgtc ccaggaggag ttctacaagt tcatcaagcc catcctggag 1140
aaaatggacg ggaccgagga gctgctcgtg aagctcaacc gcgaagattt gctccgcaag 1200
cagcgcacgt tcgacaacgg gtcgatcccg caccagatcc cctgggcga gctgcacgcg 1260
atcctcaggc gtcaggaaga cttctacccg ttcctcaagg acaaccgcga gaagatagag 1320
aagattctga ccttcagaat tccttattac gtggggcccgc tggctcgggg caactcgcgc 1380
ttcgcctgga tgacgcgcaa gtccgaggag accatcaccc cgtggaactt cgaggaggtg 1440
gtggataagg gtgcctcggc ccagtccttc atcgagcgga tgaccaactt cgacaagaac 1500
ctgccgaacg agaaggtgct ccccaagcac agcctgctct acgaatattt cacggtgtac 1560
aacgagctga cgaaggtcaa gtacgtgacc gagggaatga ggaaacctgc attcctctcc 1620
ggggagcaga agaaagccat agtcgacctc ctgttcaaga ccaaccggaa ggtcaccgtc 1680
aagcagctca aggaggacta cttcaagaag atcgagtgct tcgattcagt ggagatcagc 1740
ggcgtcgagg accggttcaa cgccagcctg ggcacctacc acgacctgct caagatcatc 1800
aaggacaagg acttcctcga caacgaggag aacgaggaca tcctggagga catcgtgctg 1860
accctgacgc tcttcgagga ccgcgagatg atcgaggagc gcctcaagac ctacgcccac 1920
ctgttcgacg acaaggtgat gaagcagctc aagcggcgga gatatactgg gtggggccgc 1980
ctctcccgga agctcattaa cggtatcagg gataagcgat ccggaaagac gatcctcgac 2040
ttcctcaagt cggacgggtt cgccaaccgc aacttcatgc agctcatcca cgacgactcc 2100
ctgacgttca aggaggacat ccagaaggcc caagtgtctg gtcaaggtga ctcgctccac 2160
gagcacatcg ccaacctcgc gggcagcccg gccatcaaga agggaatact ccagaccgtc 2220
aaggtggtgg acgagctggt gaagtgctcg ggccgccaca gccggagaa catcgtcatc 2280
gagatggcgc gggagaacca gaccacgcag aaggggcaga aaaatagccg tgagcgcatg 2340
aagcgcatcg aggaggggat taaggagttg ggcagccaga tcctcaagga gcaccctgtg 2400
gagaacacgc agttgcaaaa cgagaagctc tacctgtact acctcagaa cgggagggat 2460
atgtcgtgg accaagaact ggacatcaac cgcctgtccg actacgacgt ggaccacatc 2520
gtgccgcaga gcttcctcaa ggacgacagc atcgacaaca aggtgctcac ccggtccgac 2580
aagaatcggg gcaagtccga caacgtgccc agcgaggagg tcgtcaaaaa gatgaaaaac 2640
tactggcgac aactactgaa cgccaagctc atcacccagc gcaagttcga caacctcaca 2700
aaagccggac gcggcgggtt gagcgagctg gacaaggccg ggttcatcaa gcgccagctc 2760
gtcgagacgc gccagatcac gaagcacgtc gcgcagatac tcgacagccg gatgaacacc 2820
aagtacgacg agaacgacaa gctcatccgg gaggtgaagg tcatcaccct caagtcgaag 2880
ctcgtgagcg acttccgcaa ggacttccag ttctacaagg tccgggagat caacaactac 2940
caccacgccc acgatgctta tcttaacgcc gtggtgggga cggccctcat taagaaatac 3000
ccgaagctgg agtcggagtt cgtgtacggc gactacagg tgtacgacgt caggaagatg 3060
atcgccaagt ccgaacagga gatcgggaag gccacggcga atacttctt ctacagcaac 3120
atcatgaact tcttcaagac cgagatcacc ctcgccaacg gcgagatccg caagcgcccg 3180
ctcatcgaga cgaacgggga gaccggcgag atcgtctggg acaaggggcg cgacttcgcc 3240
actgtgcgga aggtgctgtc gatgccccag gtcaacatcg tcaagaagac ggaggtccag 3300
acgggcgggt tcagcaagga gagcatcctg ccgaagcgca acagcgacaa gctgatcgcc 3360
cgcaaaaagg actgggatcc aaaaaagtac ggcggcttcg acagcccac cgtcgcctac 3420
agcgtcctcg tcgtcgctaa agtcgagaag ggcaagtcca aaaagctcaa gagcgtcaag 3480
gagctgctcg ggatcaccat catggagcgg tccagcttgc agaagaaccc aattgatttc 3540
ctggaggcga agggctacaa ggaggtcaag aaagacctca tcataaagct gccgaagtac 3600
tcactcttcg agctggagaa cgggcgcaag cggatgctgg cgtcggccgg agagctccaa 3660
aagggcaacg agctggcgct gccgagcaag tacgtgaact tcctctacct ggcgtcccac 3720
tacgagaagc tcaagggcag tccagaggat aacgagcaga agcagctatt cgtggagcag 3780
cacaagcact acctggacga gatcatcgag cagatcagcg agttctccaa gcgcgtcatc 3840
ctggcggacg ccaacctgga caaggtgctg tccgcgtaca acaagcaccg cgacaagccg 3900
atccgcgagc aagccgagaa catcatccac ctgttcaccc tcacgaacct cggggcaccc 3960
gccgccttca aatatttcga cacgaccatc gaccgcaagc gctacaccag cacgaaggag 4020
gtgctcgacg ccaccctgat ccaccagagc atcaccgggc tgtacgagac ccgcatcgac 4080
ctctcgcagc tcggcgggga c 4101
```

SEQ ID NO: 74      moltype = DNA  length = 4101
FEATURE              Location/Qualifiers
source               1..4101
                       mol_type = other DNA
                       organism = synthetic construct
SEQUENCE: 74

```
gacaagaagt acagtattgg attggccatc gggacgaaca gcgtgggctg ggccgtcatc 60
accgacgagt acaaggtgcc atccaagaag tttaaggttc tggggaatac cgaccgccac 120
tcgatcaaga aaaatctcat cggggcgctg cttttcgaca gcggcgagac ggcggaagcg 180
acgcggctca agcggacggc tcgtcgccgt tacacccggc gtaagaaccg catctgttac 240
ctccaggaga tattcagcaa cgagatggcc aaggtggacg actcctttt ccaccgtctt 300
gaggagtcct tcctggtcga ggaggacaag aagcacgagc gccacccgat cttcgggaac 360
atcgtggacg aggtggccta ccacgagaag taccccacga tctaccacct ccgcaaaaaa 420
ctcgtggact caactgacaa ggcgatttg aggcttatct acctcgccct cgccacacatg 480
attaagttcc gtgggcactt cctaatcgag ggtgacctca accccgacaa ctctgacgtg 540
gacaagctgt tcatccagct tgtgcagacc tacaatcagc tctttgagga gaatccgatc 600
aacgcatctg gtgtggacgc aaaggccatc ctcagcgcgc ggctgagcaa gtctaggcgg 660
ttggagaacc tgatcgccca actgcccggc gagaagaaa atggcctctt cggcaacctg 720
atcgcctgt cgctggggct cacgccgaac ttcaagagta actttgacct ggcggaggac 780
gctaagctca agtatctaa ggacacatac gacgacgacc tggacaagct gctggccaag 840
atcggcgacc agtacgccga cctcttccta gccgccaaga acctgtccga cgccatcctc 900
ctcagcgaca cctgcgcgt gaacacggag atcacgaagg ctccgctcag cgcctccatg 960
attaagcggt acgacgagca ccaccaagac ctaactttac tcaaagccct cgtgcggcag 1020
cagcttcccg agaagtacaa agagatattt tttgatcagt ccaagaacgg ttatgcgggc 1080
tacatcgacg gcggcgcgag ccaggaggag ttctacaagt tcatcaagcc catcctggag 1140
```

```
aagatggacg gcacggagga gctgctcgtg aagctcaacc gtgaagacct cctgcgaaag 1200
cagcgaacct tcgacaacgg ttcgatcccg caccagatcc acctcgggga gctgcacgcc 1260
atcctgaggc gacaggagga cttctaccct ttcctaaagg acaaccgcga gaagattgaa 1320
aaaatcctga cgtttcgcat accctactac gtcggcccgc tggcgcgcgg caactcccgg 1380
ttcgcctgga tgacccgtaa gagcgaggag acgatccgcc cgtggaactt cgaggaggtc 1440
gtggacaagg gcgcgagcgc gcagagcttc atcgagcgca tgaccaactt cgacaagaac 1500
ctcccgaacg agaaggtgct cccaaagcac tccctcctgt acgagtattt caccgtgtac 1560
aacgagttga caaaggtgaa gtacgtgacg gagggaatgc ggaagcctgc gttcctctcg 1620
ggcgagcaga agaaggcaat cgtggacctg ctcttcaaga ccaaccggaa ggtgacggtg 1680
aagcagctca aggaggacta cttcaaaaaa atcgagtgct tcgactccgt ggagataagc 1740
ggcgtggagg accgattcaa cgcctccctc ggcacctacc acgacctcct taagatcatc 1800
aaggacaagg acttcctgga caacgaggag aacgaggaca tcctggagga catcgtgctc 1860
accctgaccc tcttcgagga ccgggagatg atcgaggagc gcctcaagac gtacgccacg 1920
ttgttcgacg acaaggtgat gaagcggcgc aagcggcgac gataccacgg gtggggccgc 1980
ctatcccgca aacttatcaa cggcatccgc gacaagcagt ccggcaagac gatcctggat 2040
ttcctcaagt cggacgggtt cgccaaccgg aacttcatgc agctcatcca cgacgacagc 2100
ctcacgttca aggaggacat ccagaaggcc aagtgagcg tcaagggga cagcctccac 2160
gagcacattg cgaaccttgc tgggagccct gcgatcaaga aggggatatt gcaaaccgtg 2220
aaggtcgtgg acgagttggt gaaggtcatg gggcgacaca agcccgagaa catcgtgatc 2280
gagatggcca gggaaaatca gaccacgcag aagggccaaa aaaacagccg cgagcggatg 2340
aagcggatcg aggagggcat caaggagctg gggtcgcaga tcctcaagga gcacccggtg 2400
gagaacaccg agctccagaa cgagaagctg tacctctatt acctacagaa cggcgggat 2460
atgtacgtgg accaggagct agacatcaac cgcctgtccg actacgacgt ggaccatatc 2520
gtcccgcagt cgttcttgaa ggacgacagc atcgacaaca aggtgctcac aagatcggat 2580
aagaatcgag gcaagtccga caacgtgccc tcggaggagg tggtcaagaa aatgaaaaac 2640
tactggccgc agttgctgaa cgccaagctc attacgcagc ggaagttcga caacctgacg 2700
aaggctgaac gtggtgggct cagcgagcta gacaaggcgg ggttcatcaa gcggcagctc 2760
gtcgagaccc ggcagatcac caagcacgtg gcgcagatcc tggactcgcg catgaacacc 2820
aagtacgacg agaacgacaa gctcatccgt gaggtgaagg tcatcaccct taagtctaag 2880
ctggtcagtg acttccgcaa ggacttccag ttctacaagg tccgggagat caacaactac 2940
caccacgcgc acgacgccta cctcaacgcg gtggtgggga cggcgcttat taagaaatat 3000
cccaagctgg aaagcgagtt cgtttacggc gactacaagg tgtacgacgt ccgcaagatg 3060
atcgcaaagt cggaacagga aatcggaaag gcgacggcca aatatttctt ttactccaac 3120
atcatgaatt ttttttaagac ggagatcacc ctggcgaggg gggagatccg caagcggccc 3180
ctcatcgaga ccaacgggga gacgggcgag atcgtctggg acaagggccg ggacttcgcc 3240
accgtgcgca aggtgctttc tatgcctcaa gtcaatatcg tcaaaaagac agaggtgcag 3300
accggcgggt tcagcaagga gtctatcctg ccgaagcgca actcggacaa gctcatccgc 3360
cgcaagaaag actgggaccc caaaaaatat ggcgggttcg actcgccgac cgtcgcctac 3420
agcgtcctcg tggtggctaa ggtcgagaag ggcaagagca aaaagctaaa gtcggtgaag 3480
gagctgctgg gcatcaccat catggagcgc tcgtctttcg agaagaatcc aatcgacttc 3540
ctagaggcga aggggtacaa ggaggtcaaa aaggatctta tcatcaaact gccgaagtac 3600
agtctgttcg agctggagaa cgggcggaag cggatgctgg ctagtgcggg cgagttgcag 3660
aagggcaacg agttggcact gccctccaag tacgtgaact tcctgtacct ggcctcccac 3720
tacgagaagc tcaaggggag ccccgaggac aacgagcaga agcagctatt cgtcgagcag 3780
cacaagcact acctggacga gatcatcgag cagatcagtg agttctccaa gcgggtcatc 3840
ctcgcggacg ccaacctgga caaggtgctg agcgcgtaca caagcacag ggacaagcca 3900
atcagggaac aggccgagaa catcatccac ctgttcaacc tgaccaacct gggtgcaccg 3960
gctgccttca agtactttga cacgaccatc gaccggaagc gctacacctc cacgaaggag 4020
gtgctggacg ccacgctgat ccaccagagc atcaccgggc tctacgagac acggatcgac 4080
ctgagccagc ttggcgggga c                                       4101

SEQ ID NO: 75           moltype = DNA   length = 4092
FEATURE                 Location/Qualifiers
source                  1..4092
                        mol_type = other DNA
                        organism = synthetic construct
SEQUENCE: 75
gacaaaaagt attccattgg actcgctatc ggcacgaaca gcgtcgggtg ggcggtcatc 60
actgacgagt acaaggtgcc gagcaagaag tttaaggtgc tgggaaacac cgacaggcac 120
tcgatcaaga aaaatcttat cggggcccta ctcttcgact cggagaaac cgccgaggcc 180
acccggttga agcgcacggc ccgccgtcgc tacaccagge gcaagaaccg gatctgctac 240
ctccaggaga tattcagcaa tgagatggcg aaggtggacg actcgttttt tcacaggcta 300
gaggagtctt tcctcgtgga ggaggacaag aaacacgagc gccaccccat cttcggcaac 360
atcgtggatg aggtggcata tcacgagaag tacccaacca tctaccacct cgcaaaaag 420
ctcgtggact ctaccgacaa ggccgacctc cgtctgatct acctcgcgct ggcccacatg 480
attaagttcc gaggacactt tctgatcgag ggcgacctga acccagacaa cagcgacgtg 540
gacaagctgt tcatccaact tgtccagacc tacaatcagc tcttcgagga aaccctatc 600
aacgcctcgg gcgtggacgc gaaggccatc ctgtccgccc gcctgagcaa gtcgcggcgg 660
ctggagaacc tgatcgccca gctccccggc gaaaaaaaga acggcctctt cggcaacctc 720
atcgcgttgt cgctggggct caccccgaac ttcaagtcca acttcgacct ggccgaggac 780
gctaaactcc agctctcgaa ggatacctac gacgacgacc tcgacaacct gctgcccag 840
atcggcgacc agtacgcgga cctttttcctg gcggccaaga acctgagcga cgcgatcctc 900
cttagcgaca tactccgtgt gaacaccgag atcacgaagg cccccgctctc cgcgtccatg 960
attaagcgct acgacgagca ccaccaagac ctaccctgcg ttaaggcgct ggtcaggcag 1020
cagttaccgg agaagtacaa ggagatcttt tttgatcaat ctaagaacgg ttacgccggg 1080
tacatcgacg gcggcgcgtc ccaggaggag ttctacaagt tcatcaagcc gatcttggag 1140
aaaatggacg gaccgagga gctgctcgtg aagctcaacc gcgaagacct cctccgcaag 1200
cagcgcacct tcgacaacgg gagcatcccg caccagatcc acctgggaga gctgcacgcg 1260
atcctgcgga gacaagagga cttctacccc ttcctcaagg acaaccggga gaagattgaa 1320
```

```
aaaatactta cttttcgtat cccgtactac gtcgggcccc ttgcgagggg caactccaga   1380
ttcgcgtgga tgacccgcaa gtccgaggag accatcaccc cgtggaactt cgaggaggtg   1440
gtggacaagg gcgcgtcggc ccagtcgttc atcgagcgca tgaccaactt cgacaagaac   1500
cttccgaacg agaaggtgct cccgaagcac agcctgctct acgaatattt tactgtgtac   1560
aacgagctga cgaaggtcaa gtacgttacg gaggggatga ggaagcccgc cttcctctcc   1620
ggcgagcaga agaaagccat tgtggatctc ctgttcaaga ccaaccgcaa ggtgacggtg   1680
aaacagctca agaggactta cttcaaggaag atcgagtgct tcgactccgt agagatcagc   1740
ggggtcgagg accgcttcaa cgcctcgctg ggcacgtacc acgacctgct aaagattatc   1800
aaggacaaag acttcctaga caatgaggag aacgaggaca tttctggagga catcgtgctg   1860
actctgacgc tgttcgaaga ccgcgagatg atcgaggagc ggcttaagac gtacgcccac   1920
ctgttcgacg acaaggtgat gaagcagttg aaacggcggc gctacaccgg gtggggccgc   1980
ctctcccgca agctcatcaa cggcatccgc gacaagcagt cggggaagac gatcctggac   2040
ttcctcaaga gcgacggctt cgccaaccga aacttcatgc agctaatcca cgacgacagc   2100
ctgacgttca aggaggacat ccagaaggcc caagtgacgg gccagggaga ctcgctacac   2160
gagcatatcg ccaacctggc tggcagcccg gcgattaaga aaggaatcct ccaaaccgtc   2220
aaagtggtgg acgagctggt gaaggtgatg ggccgccaca gcccgagaa cattgtgatc   2280
gagatggcgc gggagaacca gacgacgcag aagggcaaa aaaatagcag ggaaaggatg   2340
aagcgaatag aggaggggat caaggagctg gggagccaga ttctcaaaga gcacccggtc   2400
gagaacacac agctccagaa cgagaagctg tacctctact acctccaaaa cggccgcgat   2460
atgtacgtgg accaggaact agacatcaac cggctgagcg actatgacgt ggaccacatc   2520
gtgccgcagt ccttcctcaa ggacgactcg attgacaaca agtgctcac tagatccgac   2580
aagaacagag gcaagagcga taacgtcccg tcggagggag tcgtcaagaa aatgaaaaac   2640
tactggcggc agctcctaaa cgccaagctc atcacgcagc gtaagttcga caacctgacg   2700
aaggcggagc ggggcgggct gagcgagctg gacaaagcgg ggttcatcaa gcggcagctc   2760
gttgagacgc ggcagatcac aaagcacgtc gcgcaaatcc tcgactcccg catgaacacc   2820
aagtacgacg agaacgacaa gctcatccgg gaggtgaagg tcattaccct taaatcgaag   2880
ctcgtcagcg actttcgtaa ggacttccag ttctacaagg tcagagagat caacaactac   2940
caccacgccc acgacgccta tctgaacgcc gtggtgggca ccgcgcttat taagaagtac   3000
cccaagctgg agtccgagtt cgtgtacggc gactacaagg tttatgacgt caggaagatg   3060
atcgccaagt cggaacagga gatcggaaaa gctaccgcca aatatttctt ctatagcaac   3120
atcatgaact tcttcaaaac cgagatcacc ctcgccaacg gcgagatccg gaagcgcccc   3180
ctcatcgaga ccaacgggga gaccgggag atcgtctggg acaaggggcg ggacttcgct   3240
actgtccgaa aggtgctctc catgccacaa gtgaatatcg tcaagaaaac agaggtgcag   3300
accggagggt tcagtaagga gtccatcctg cccaagcgga actccgacaa gctaattgct   3360
cgcaaaaagg attgggatcc taaaaaatat ggcggcttcg actcgcccac ggtcgcctac   3420
tctgtgctgg tcgtggcgaa ggtggagaag ggcaagtcca agaagctcaa gagcgtcaag   3480
gagctgctgg ggatcacgat catggagcgt agttcgtttg agaagaatcc catcgacttc   3540
ctggaggcta agggctacaa ggaggtcaaa aaggacctca tcattaagct gccgaagtac   3600
agcctcttcg agctggagaa cgggcggaag cgtatgctac ctccgctggg ggagttacaa   3660
aaggggaacg agctggcgct gccgtctaag tacgtcaact tcctgtacct ggcctcccac   3720
tacgagaagc tcaaggggtc gccggaggac aacgagcaga agcagctctt cgtagagcag   3780
cacaagcact acctggacga gatcatcgag cagatttcag agttctcaaa gcgggtcatc   3840
ctcgccgacg ccaacctgga caaggtgctc tcggcctaca acaagcaccg ggacaagccg   3900
atccgcgaac aggccgaaaa catcatccac ctgttcacgc tcaccaacct cggtgccccg   3960
gcggccttca gtactttga cacgaccatc gaccggaagc gctatacctc gacgaaggag   4020
gtgctggacg ccaccctgat ccaccagtcc atcaccgggc tttacgagac ccggatcgac   4080
ctctcgcagc ta                                                     4092
```

| | | |
|---|---|---|
| SEQ ID NO: 76 | moltype = DNA   length = 4101 | |
| FEATURE | Location/Qualifiers | |
| source | 1..4101 | |
| | mol_type = other DNA | |
| | organism = synthetic construct | |

SEQUENCE: 76

```
gacaagaagt atagtattgg actcgccatc ggaaccaact ctgtggggtg ggctgttatt   60
acagatgaat ataaggtgcc atccaaaaag tttaaagttc tgggcaatac tgatagacac   120
tcaatcaaga agaatctgat aggtgcactt ctgtttgata gtggagagac tgccgaggca   180
accagactta aaaggactgc aagaagaaga tataccagaa gaaagaatag gatttgctat   240
ttgcaggaaa tcttcagcaa cgaaatggcc aaggttgatg actcatttt ccataggttg   300
gaggagagtt tcttgtgga ggaagataag aagcacgaaa gacacccaat tttcgggaat   360
atagtggacg aggtggctta tcatgagaag tatcccacta tctaccacct gagaaagaaa   420
cttgtgacta caaccgataa ggctgatctt aggcttatat acttggccct tgcacatatg   480
atcaaattca ggggccattt tcttatcgaa ggcgatctta tcccgataa ctcagatgtg   540
gacaagctgt ttatacaact tgtgcaaacc tacaatcaac tcttcgagga taatcccatt   600
aacgcctccg gcgtggatgc aaaagccata ctgtcagcca gactgagcaa agtaggaga   660
ctggagaatc ttatagccca actgcccggt gaaaagaaga tgggctctt cggaaatctg   720
atcgctcttt cattggggtt gacacccaac tttaagagta ctttgactt ggcagaagat   780
gcaaagttgc agctcagtaa agacacatat gatgacgacc ttgacaatct cttggcacaa   840
ataggggatc aatacgctga ccttttcctc gctgccaaga acctcagcga cgctatactg   900
ttgtccgaca ttcttaggt taataccgaa attacaaagg cccctcttag tgcaagtatg   960
atcaaaaggt atgatgagca tcaccaagac cttacactgc tgaaggctct ggttagacag   1020
caactccctg aaaagtataa ggaaatattc ttcgaccaaa gtaagaacgg gtacgccggt   1080
tatattgatg ggggcgcaag tcaagaagaa ttttacaaat tcatcaagcc aattcttgaa   1140
aagatgacg ggactgagga attgctggtg aaactgaata gagaggacct tctagaaaa   1200
cagaggacat tgacaatgg gtccatccca caccagattc atctggggga actcacgca   1260
atattgagga acaagaaga ctttttaccca ttccttaagg ataatagaga gaaatcgaa   1320
aaaatcctga ctttcaggat tccttactat gttgggccac tggccagggg gaactcaaga   1380
ttcgcttgga tgacaaggaa gtcagaagaa accataaccc cttggaattt tgaagaggtg   1440
gttgataagg gggcatcagc ccagtcttc atagagagga tgaccaactt tgataaaaat   1500
```

```
cttccaaatg agaaggtttt gccaaaacat agtcttttgt acgagtactt tactgtttat  1560
aacgaattga ccaaggtgaa gtatgtgacc gagggaatga ggaagccagc attttttgtcc  1620
ggggagcaaa agaaagcaat cgttgatctt ctcttcaaga ccaacagaaa agtgaccgtg  1680
aaacaactga aggaagacta cttcaaaaag atagaatgtt tcgattcagt ggaaattagc  1740
ggtgttgaag acaggttcaa tgcttcattg ggtacttacc acgacctgtt gaagataatc  1800
aaagacaagg actttctcga taatgaggag aacgaagaca tcttggaaga cattgtgctt  1860
acactcactt tgtttgagga cagggaaatg attgaggaaa gactcaaaac ttacgctcat  1920
ttgtttgatg ataaggttat gaaacaacta aaaagaagaa ggtacaccgg ctggggaaga  1980
ttgagtagga aactgatcaa cggtattaga gataaacaat ccggaaaagc tatcctcgat  2040
ttccttaaga gtgatggctt tgcaaatagg aattttatgc agctgattca tgacgactca  2100
cttaccttca aagaagacat ccaaaaagct caggtgtctg gcaaggcga cagtctgcat  2160
gaacatatag ctaacttggc tgggagtccc gccatcaaga aggggatact tcaaacagtt  2220
aaagttgtgg acgaattggt gaaggtaatg ggaaggcaca agcctgaaaa tatagtgata  2280
gaaatggcaa gggaaatca aacaacccag aagggacaga agaacagtag ggaaaggatg  2340
aaaaggatag aagagggat caaagagctt ggtagccaga tcctcaagga acatccagtg  2400
gagaataccc aacttcaaaa cgagaaactc tatttgtact acttgcagaa cggaagagat  2460
atgtatgtgg accaagagct tgatattaac aggctgagcg attatgacgt tgaccacata  2520
gtgccccaat cattcctcaa ggatgactct attgataata aggtgctgac aaggagtgac  2580
aagaatagag ggaaatccga caacgttcca tccgaggaag ttgtgaagaa gatgaagaac  2640
tactggaggc agttgctgaa cgctaagctc attacccaga ggaaattcga taacctgacc  2700
aaagcagaga gaggcgggct gagcgaactc gataaagcag gtttcatcaa gagacaactc  2760
gtggagacta ggcaaattac taagcacgtg gctcaaatac tcgacagcag ggtgaacaca  2820
aagtacgacg agaacgacaa gctcattaga gaggttaagg ttattactct gaaaagtaaa  2880
ttggttagcg atttcagaaa ggatttccaa ttctataagg ttagagagat caacaattat  2940
catcatgcac atgatgccta tctgaatgct gtggttggta cagcccttat caagaagtac  3000
cctaagctag agagcgagtt tgtgtacgga gattataagg tgtatgatgt gaggaaaatg  3060
atcgctaaaa gtgagcaaga gattggaaag gctaccgcca aatacttctt ttattccaat  3120
attatgaatt tcttcaagac agaaatcacc ctggctaacg gcgagataag gaagaggccg  3180
cttatcgaaa ctaatgggga gacaggcgaa atagtgtggg acaaagggag ggatttcgca  3240
actgtgagga aggttttgag catgcctcag gtgaatatcg ttaagaaaac cgaagttcaa  3300
actggagggt tctctaagga aagcattctc cccaagagga actccgacaa gctgattgct  3360
agaaagaaag actgggaccc caagaagtat ggcggattcg actcacccac tgtggcatat  3420
agcgttctcg tggtggcaaa ggttgaaaag ggtaaatcca aaaaactcaa atccgtgaag  3480
gaactcctg gcataactat tatggaaagg agtagcttc aaaagaatcc catcgacttt  3540
ctcgaagcta agggctataa ggaagttaag aaggaccta taatcaaact tccaaaatac  3600
tcccttttg agttggaaaa cggcagaaag agaatgttgg ccagtgccgg ggagcttcaa  3660
aagggcaacg aactggctct gcctagcaaa tatgtgaact ttttgtatct ggcatcacac  3720
tacgagaaac ttaaaggctc tcctgaggac aacgagcaaa aacagctctt tgttaacag  3780
cataagcact acctcgacga gattattgag cagatcgacg agttctcaaa gagagttatt  3840
ctggctgacg ctaatcttga caaggttttg tccgcttaca acaaacagg gataagcca  3900
atcagggagc aggcagaaa cataatccat ctctttaccc tgacaaacct cggtgccccc  3960
gctgctttca agtatttga tactaccatt gacaggaaga gatatacttc cactaaggaa  4020
gtgctcgacg caacccctcat acaccaaagt atcacaggcc tctatgaaac taggatagat  4080
ttgtctcaac ttggggcga t                                             4101
SEQ ID NO: 77        moltype = DNA  length = 4101
FEATURE              Location/Qualifiers
source               1..4101
                     mol_type = other DNA
                     organism = synthetic construct
SEQUENCE: 77
gacaaaaagt attccatcgg gcttgctatc ggaaccaact ctgtggggtg ggcagttatt    60
accgacgaat acaaggtgcc cagcaagaag tttaaggttc tggggaacac agatagacat   120
agcataaaga aaaacctgat aggcgcactg ttgttcgact ccggggaaac agccgaagct   180
accaggctga agaactgc aagaagaagg tacaccagaa gaaaaaacag aatatgttat   240
ctccaagaga ttttctctaa cgagatggcc aaggtggacg actcattctt tcacagactg   300
gaagaatctt tccttgtgga agaagataag aaacacgaga ggcacccat ttttggcaat   360
atcgtgatg aggtggctta ccacgaaaaa taccctacaa tataccacct caggaaaaaa   420
ttggttgata gtacagacaa ggccgacctc aggctcatct atttggccct ggccacatat   480
attaaattca gggggcactt tctcatcgag ggagatttga acccccgacaa cagtgatgtt   540
gataagctct ttattcagct cgtgcagact tacaatcagt tgtttgagga aaaccccatt   600
aatgcttccg gggtggacgc caaggcaatc ctttctgcaa gactctcaaa gtcaaggaga   660
ctcgaaaatc tgatagcaca gcttccagga gagaagaaga acgggctctt tggaaacctg   720
atcgctctgt cactcggact cacacccaat ttcaaagca attttgattt ggcagaggac   780
gctaagctgc aactcagtaa ggataccta cgacgatgact tggataatct gctcgcacaa   840
attgggacc agtatgcaga cctgtttctc gcagctaaga acttgagtga cgccatattg   900
ctcagtgaca tcctcaggg taataccgag attacaaaag ctccactctc tgcaagcatg   960
atcaagaggt atgacgagca ccatcaagac ctgacactcc ttaaggcgtt ggttaggcag  1020
caacttcctg aaaagtataa ggaaatcttc ttcgatcaaa gcaaaaacgg ctacgccggc  1080
tatatagacg ggggagcatc ccaagaagaa ttttataagt tcataaaacc tatattggag  1140
aagatggacg ggacagagga attgctcgtg aaactgaaca gggaggatct cctcaggaag  1200
caaaggacct tcgacaatgg ctccatccca atcagattc acctcggcga actgcacgca  1260
atactgagaa gacaagagga ctttttatcct ttcctgaagg acaacaggga gaaatcgag  1320
aaaatcttga cattcagaat cccatactac gttgggcctc tggccagagg taacagtagg  1380
ttcgcctgga tgactaggaa atcagaggag actattacac cctgaacctt tgaagaagtt  1440
gttgataagg gagcttcagc acaatcattc atcgaaagaa tgacaaactt tgacaaaaat  1500
ctgcctaatg agaagtgct cccaaaacat tccctgctgt atgagtattt taccgtttat  1560
aacgagctta ccaaggtgaa atacgttact gaaggtatga gaaagccagc ttttctttca  1620
ggggagcaaa agaaggctat cgtggatctt ctctttaaga ccaacagaaa ggttaccgtg  1680
```

```
aagcagctta aggaagacta cttaaaaag atcgagtgtt ttgactcagt ggaaataagc  1740
ggtgttgaag atagattcaa cgcatccttg ggaacttatc atgatcttct taagataatc  1800
aaggataaag actttctcga caacgaggaa acgaagata tactggagga catagttctg  1860
acacttactt tgttcgagga tagggagatg atcgaggaaa gactgaaaac atatgctcac  1920
cttttcgacg acaaagttat gaaacaactc aagagaagga gatatacaag gtgggggaga  1980
ttgagcagga aactgattaa tggtatcaga gacaaacagt caggaaaaac aatactcgac  2040
tttttgaaat cagacgggtt cgcaaatagg aatttcatgc agcttataca cgacgattca  2100
cttactttta aagaggacat tcaaaaggct caagttagtg gacaaggtga ctccctccac  2160
gaacacatcg caaatctcgc tggcagccct gcaattaaga agggtatact ccagacagtt  2220
aaggttgttg acgagctggt taaagtgatg ggaagacaca aacccgagaa catagtgata  2280
gagatggcca gggaaaacca aaccactcaa aaagggcaga aaaattccag agagaggatg  2340
aaaaggattg aagaaggtat caaggagctg ggtagccaaa ttctgaaaga acatcctgtg  2400
gaaaacactc aactccagaa tgagaaactc tatctgtact atctgtcaaa tgggagagat  2460
atgtatgtgg accaggaact ggacataaac aggctctcag attacgatgt ggatcatatc  2520
gtgccacagt cctttcttaa ggatgatagc atcgacaata aggtgcttac caggtccgac  2580
aagaacaggg gaaagtcaga taacgtgcct tctgaagaag ttgttaaaaa gatgaagaac  2640
tactggagac agctgcttaa cgctaagctc ataacacaga ggaagtttga caacttgacc  2700
aaggccgaga gaggcggact ctcagaattg gataaggcag ggttcataaa aaggcagctg  2760
gtggaaacaa ggcagataac taaacatgtg gctcagatcc tcgatagtag gatgaataca  2820
aaatacgatg agaacgacaa gctcataagg gaggttaaag tgataactct gaaatccaaa  2880
ctggttagcg atttaggaa ggatttccag ttttacaaag ttagggagat caacaattat  2940
catcacgccc acgatgccta cttgaacgca gttgtgggta ctgcacttat caaaagtac  3000
cctaagctgg aatccgagtt tgtttatgga gactataagg tgtacgacgt tagaaaaatg  3060
attgcaaagt cagagcagga gatagggaaa gccactgcaa aatatttctt ttatagcaat  3120
atcatgaatt tctttaagac agaaatcaca ctggccaatg gggaaataag gaagaggccc  3180
ctgatcgaaa ctaatggcga gacagggagg attgtgtgga ataaaggtag ggactttgca  3240
acagtgagga aagtgctgag catgcccaa gttaatatcg ttaaaaagac cgaggttcaa  3300
acaggggggct ttagtaagga aagcattttg cccaagagga atagtgacaa attgattgct  3360
aggaaaaaag attgggaccc caaaaagtat ggcggatttg atagccccac tgttgcttac  3420
tccgtgctcg tggttgcaaa ggtggagaag ggaaagaca agaaactgaa gtcagttaag  3480
gaactcctg gtatcactat catggaaaga agctcctttg agaagaaccc tattgacttc  3540
ctggaggcta aagggtacaa agaggttaag aaagaccta tcattaaatt gcccaaatat  3600
agtctttcg agcttgaaaa cggaagaaag aggatgcttg catccgctgg cgaattgcaa  3660
aagggcaatg agcttgctct cccttccaag tatgtgaact tcctttatct tgcctcacac  3720
tatgaaaaac tcaaaggttc acccgaagac aacgaacaaa agcaactatt tgtggaacaa  3780
cacaagcact acctggacga aatcattgag caatttctg agttttcaaa aagggtaatc  3840
ttggctgacg caaatctcga caagttttg tcagcttaca caaacatag agataagcca  3900
attagagagc aagctgagaa tatcatccat ctgtttaccc tgactaacct tggagcgcct  3960
gctgctttta aatatcga caccacaatc gacaggaaga ggtacactag cactaaggaa  4020
gttctcgacg ccaccctcat ccaccagagt attacaggcc tgtacgagac aagaattgat  4080
cttttctcaac ttggtggtga c                                           4101
```

SEQ ID NO: 78    moltype = DNA  length = 4101
FEATURE      Location/Qualifiers
source       1..4101
          mol_type = other DNA
          organism = synthetic construct
SEQUENCE: 78

```
gataagaagt actcaatcgg tctggcaatc ggaaccaact ctgtgggttg ggcagtgatt  60
acagatgagt ataaggtgcc aagcaaaaaa ttcaaggtgc tgggtaatac cgacagacac  120
agcattaaga agaattgat tggagcactc tctctttgact caggggaaac agcagaggca  180
acaaggctga agaggacagc aaggcggagg tacacaaggc ggaaaaacag gatatgctac  240
ctccaggaaa tctttagcaa cgagatggct aaagtggatg atagcttttt ccatagactc  300
gaagaatcct tcttgttga agaggacaaa aagcatgaaa ggcatccat cttcggcaat  360
atagttgatg aggttgcata ccatgagaag tacccacaa tctaccacct cagaaagaaa  420
cttgtggact ccacagataa agcagacctg aggctcatat acctcgcact cgcacacatg  480
atcaagttca gagggcactt tctcatcgaa ggtgacctga tccagataa ttcgagatgtg  540
gataaactgt ttatacagct ggtgcaaaca tacaaccaac ttttcgagga aaacccaatc  600
aatgcctccg gtgttgatgc aaaggccatc ctgtcagcag gactcagcaa aagcaggcgg  660
ctcgaaaacc tcatcgccca gcttccggt gaaaagaaga acgggctctt tggtaatctc  720
atcgcattga gccttggtct tactccaaac ttcaagagca attttgatct ggcagaggat  780
gctaaactgc aactctcaaa ggacacatat gacgatgacc ttgacaatct gttggcccag  840
atcggggacc aatatgcaga cctcttcctg gccgcaaaga atcgtgcaga tgcaatcctc  900
ttgtccgaca tactgagagt taactctgag atcacaaagg cacctctgtc cgcctccatg  960
attaagagat acgatgagca tcaccaggat ctgactttgc tcaaagcccc cgttagacag  1020
cagttgccag aaaagtacaa agaaatattc tttgatcaat caaaaacgg atatgcaggg  1080
tacatcgacg gtggggcaag ccaggaagag ttctacaaat tcatcaaacc tatcctggaa  1140
aagatggatg gacagaaga gctgctggtt aagctgaata gggaagacct cctcagaaag  1200
cagaggacat tgataacgg gagcatccct catcaaatcc acctcggtga actccatgct  1260
atcctgagaa ggcaggaaga cttttatcca tttttgaagg acaatagga gaaaatcgaa  1320
aaaatcctga cattcagaat cccatactac gttggtcctc tggcaagagg taacagtagg  1380
ttcgcatgga tgcaaggaa aagcgaggag acaatcacac cctggaattt tgaggaagtt  1440
gttgacaagg tgccagcgc acaatccttt atcgaaagaa tgacaaattt cgacaagaat  1500
ctgcctaacg aaaaggttct cccaaagcat tcactcctgt acgaatattt tacagtttat  1560
aacgaactga ctaaagttaa atacgttacc gagggtatga ggaagccagc attccttcc  1620
ggggaacaga agaagctat tgtggacctc ctgttcaaga caatagaaa agtgacagtt  1680
aagcaactca agaggattta cttcaaaaag atcgaatgtt ttgactctgt ggagatcagc  1740
ggggtggagg atagattcaa cgccagcctg ggtacatatc atgatctcct gaaatcatt  1800
aaagacaagg acttccttga caacgaggag aacgaggaca ttctggaaga cattgttctg  1860
```

```
acccctcacac tctttgagga tagggagatg attgaggaaa gactgaagac ctacgcccac 1920
ctctttgacg ataaagtgat gaaacagctc aagagaagaa ggtatacagg ttggggaga  1980
ctgagcagga agttgatcaa tgggattagg acaaacagt ccgggaaaac aatcctcgat   2040
tttctgaagt cagacggttt cgcaaacaga aattttatgc agctcattca cgatgacagc  2100
ttgacattca aggaagacat ccaaaaggct caagtgagcg gccaagggga tagcctccac  2160
gagcatattg caaatctggc aggttcacca gccatcaaaa agggcatact tcagacagtt  2220
aaggttgtgg acgaattggt taaagttatg ggcaggcata agccagagaa tatcgttatc  2280
gaaatggcaa gggagaacca aacaactcaa aaagggcaga aaaatagcag agagaggatg  2340
aaaagaatcg aggaagggat caaggaactt gggtcccaaa tcctcaagga gcacccagtt  2400
gaaaatactc aactgcaaaa cgagaagctc tatctctact atctccaaaa cgggagggat  2460
atgtatgttg accaggagct ggatattaac agactgtcag attatgatgt tgatcatatc  2520
gtgccccagt cattcctgaa ggacgattcc atcgacaaca aagttctcac aaggtccgat  2580
aaaaacaggg gcaagtccga taacgttcca agcgaagaag tggtgaaaaa gatgaaaaac  2640
tattggagac aacttctgaa tgcaaagttg attactcaga gaaagtttga caacctcaca  2700
aaagcagaaa gaggcgggct tagcgaactc gataaggcag ggtttatcaa agacagctg   2760
gttgagacaa ggcagatcac aaaacatgtg gcacagatcc ttgactcaag gatgaatacc  2820
aagtatgatg agaatgataa gttgatcagg gaggttaaag ttatcacact caaatccaaa  2880
ctggtgtcag acttcaggaa agactttcaa ttttataagg tgaggggagt caataactac  2940
caccatgcac atgacgccta cctgaacgca gtggtgggta cagcattgat taaaaaatac  3000
cctaagctgg agtctgagtt tgtgtacggg gactacaagg tgtacgacgt gagggaaatg  3060
atagccaagt ccgagcagga gatcgggaaa gcaacagcta agtatttctt ttacagtaat  3120
atcatgaatt tctttaaaac tgagattact ctggcaaacg gggagatcag gaaaagaccc  3180
ctcatcgaga ctaatggtga aacaggtgag atcgtttggg acaaggggag ggattttgct  3240
actgttagaa aagttctgag tatgccacaa gtgaatattg tgaaaagac agaagttcag   3300
acaggtgggt tctccaaaga atccatcctg cccaagagaa attcagacaa gctcatcgca  3360
agaaagaagg actgggaccc taagaagtac ggaggtttga acagcccac cgtggcctat  3420
tccgtgcttg ttgtggcaaa ggtggagaaa gggaagagca aaaaactgaa atccgtgaaa  3480
gaactgctgg gaattaccat catggaaaga agctccttg agaagaaccc aatcgacttc   3540
ctggaagcaa aaggatataa ggaagtgaaa aaggacctca ttatcaagct cccaaaatac  3600
tcactttcg agttggagaa cggtagaaag aggatgctgg caagcgcagg ggaacttcag   3660
aaaggcaatg agctggcatt gccatcaaag tatgtgaact tcctctactt ggccagccat  3720
tacgagaaac ttaaaggtag cccagaagat aacgagcaaa aacagctctt tgtggaacag  3780
cataagcatt atctggatga gatcatgaaa caaatctcag agttttccaa gagagttatc  3840
ctcgcagatg caaacctgga taaggttctc tcagcctata taagcatag agacaagcca   3900
attagagagc aagcagagaa cattatccac ttgttcactc ttacaaacct gggggcacca  3960
gccgccttca aatatttcga tacaacaata gacagaaaga ggtataccag caccaaagaa  4020
gttctcgacg ccacactgat ccatcaatca atcacaggcc tttacgaaac taggatcgac  4080
ttgtcacaac tgggtgggga t                                            4101

SEQ ID NO: 79            moltype = DNA   length = 3307
FEATURE                  Location/Qualifiers
source                   1..3307
                         mol_type = other DNA
                         organism = synthetic construct
SEQUENCE: 79
gagcaaggac acctacgacg acgacttgga caacctattg gcccagatag gtgaccagta  60
tgcagacctc ttccttgcgg ccaagaactt gagtgacgct atactgctca gtgacatcct  120
gagggtgaac actgagatca ctaaggcccc tctctctgcc tcaatgatta agcgttacga  180
cgagcatcac caggatctca ccctgcttaa ggcccttgtt cggcagcagc tccctgagaa  240
gtacaaggag atattttttg accagtctaa gaacggctac gccggttaca ttgacggtgg  300
ggcaagccag gaggagttct acaagttcat caagccgatc cttgagaaga tggacggcac  360
cgaggagcta cttgtcaagt tgaaccggga agacctgctc cggaaacagc gtacattcga  420
caacggcagc atccctcacc agatccacct gggcgaacta cacgccatcc tccgacgtca  480
ggaggacttc tatccattct tgaaagataa cagggaaaaa atcgaaaaaa tacttacgtt  540
tcgaataccg tactacgtgg ggccccttgc tcggggaaac tccagattcg catgatgac   600
caggaagtca gaggagacca tcacaccctg gaactttgag gaggtggttg acaaaggtgc  660
ttctgcccag tccttcattg agcggatgac taacttcgac aagaacctgc ccaacgagaa  720
ggtgctgcca aagcacagcc tgctctacga atactttact gtgtacaatg agctgacgaa  780
ggtgaagtac gtgacagagg ggatgcgtaa gcccgcttc ctgacgcggcg agcaaaaaaa   840
agcaatcgtg gacctactgt tcaagaacaa ccgaaggtg acagtgaagc agctcaagga   900
ggactacttc aaaaaaatcg agtgcttcga ctctgttgag ataagcggcg tggaggaccg  960
attcaacgcc tcattgggaa cctatcacga cctgctcaag atcattaagg acaaggactt  1020
cctggataat gaggagaatg aggacatcct ggaggatatt gtgctgaccc ttactctatt  1080
cgaggacagg gagatgatcg aggagcgact caagacctac gctcacctgt tcgacgacaa  1140
ggttatgaag caattgaagc gtaggcgata cacggggtgg gaagactct cccgaaaact   1200
gataaacggc atcagggaca agcagtcagg gaagacgatc ttggacttcc tgaaatccga  1260
cgggttcgcc aaccgcaact tcatgcagct cattcacgac gactcactaa cgttcaaaga  1320
ggacattcag aaggctcaag tcagtggaca aggcgactcc ctgcacgagc acattgcaaa  1380
ccttgcgggc tccccggcga ttaaaaaggg cattctccaa acggttaggg tgttggacga  1440
gctggtgaag gtgatgggcc gacacaagcc tgagaacatc gtgatcgaga tggcccaggga  1500
gaaccagact acccagaagg gtcagaagaa ctctcgggaa cgtatgaagc gtattgagga  1560
gggattaag gagttgggct ctcaaatcct caaggagcac cctgtggaga acactcagct   1620
ccaaaacgag aagctgtacc tgtactacct gcaaaacgg cgcgatatgt acgtggatca   1680
ggagttgaa atcagcagc ttagcgatta cgacgtggac cacatcgtgc cacagtcatt    1740
cttaaaggac gacagcatcg acaacaaggt tctgacgagg agcgacaaga tcgaggaa    1800
aagtgacaat gttccatccg aggaggtggt caagaaaatg aagaactatt ggcgtcagct  1860
tctgaacgcc aagctcatca cccagcgaaa attcgacaac ctgactaagg ctgagcgagg  1920
cggactctcc gagcttgaca aggctggctt catcaagcgg cagttggtcg aaacccgaca  1980
gataacgaag cacgttgccc agatacttga ctcccgtatg aacaccaagt acgacgagaa  2040
```

```
cgacaagctc atcagggagg tgaaggtcat tacccttaag tccaaactcg tcagcgactt  2100
tcgtaaggac ttccagttct acaaggtgcg cgagatcaat aactaccacc acgcacacga  2160
cgcctacctg aacgcagtgg ttggaaccgc gttgattaaa aagtacccca agttggagtc  2220
ggagttcgtt tacggggact acaaggtgta cgacgttcgg aagatgatcg ccaagtctga  2280
acaggagatc gggaaagcaa ccgccaagta tttcttctat agcaacatca tgaacttctt  2340
taaaaccgag atcacacttg ccaatggcga gatccgtaag aggccgctga tcgagacaaa  2400
tggggagact ggcgagatcg tgtgggacaa gggccgcgac ttcgcaaccg ttcggaaagt  2460
cttgtccatg cctcaagtca acatcgtcaa gaagactgag gtgcaaacag gcgggttctc  2520
gaaggagtcc atactgccca agaggaactc agacaagctc atagcacgca aaaaagactg  2580
ggatccaaag aaatacggcg ggttcgactc gccgacagtc gcatactccg tgttagtggt  2640
ggctaaagtg gaaaagggga agtccaagaa gctcaagtcc gtcaaggagt tgctcgggat  2700
caccattatg aacggtcct cattcgaaa gaatcccatt gacttcctag aggcgaaggg  2760
ctacaaagag gtcaaaaagg acctaattat taagctcccc aagtattcac tcttcgaact  2820
tgaaaatggt cgtaagcgga tgttggcaag cgctggaagg cttcagaagg ggaacgagct  2880
tgcactgcct tccaagtacg tgaacttcct gtacctcgcc tctcattacg agaagttgaa  2940
gggctcaccg gaggacaacg agcagaagca gttgttcgtg gagcagcaca agcactacct  3000
cgacgagatc attgagcaga taagtgagtt cagcaaacgg gtgatccttg ccgacgctaa  3060
cctggacaag gtgctgagcg cctacaacaa gcacagagac aagccgatcc gagagcaagc  3120
ggagaacatc atacacctgt tcaccctcac gaacctcggg gctcccgcag ccttcaaata  3180
ttttgacacg accatcgacc gtaaacgcta cactagcacg aaggaggtgc tggacgctac  3240
ccttatccac cagtccatca ccggcctgta cgagacgaga atcgacttgt cgcagctcgg  3300
tggtgac                                                           3307
```

| SEQ ID NO: 80 | moltype = DNA  length = 4101 |
|---|---|
| FEATURE | Location/Qualifiers |
| source | 1..4101 |
| | mol_type = other DNA |
| | organism = synthetic construct |

SEQUENCE: 80

```
gacaaaaaat actcaattgg tctggcaatt gggaccaaca gtgtcggatg ggccgtgatt  60
accgacgagt acaaggtgcc gtccaaaaaa ttcaaggtgc ttgggaacac cgaccgccac  120
tcgatcaaga aaaacctaat cggtgcgttg cttttcgaca gtggggagac cgccgaggca  180
acacgcttaa aacgcacagc taggaggaga tatacacggc gcaagaaccg aatatgctac  240
ttacaggaga tattctccaa tgagatggcg aaggtggacg actctttctt ccatcggctt  300
gaggaatcct tcctggtcga ggaggacaag aagcacgagc gacacccgat attcgggaac  360
atcgttgatg aggtggcgta ccacgagaag tacccaacga tataccactt acgcaagaag  420
ctcgtggact ctacggacaa ggccgacttg cgccttatct acttggcact ggcccacatg  480
attaagttcc gaggccactt ccttatcgag ggtgacctga accccgataa ctccgacgtg  540
gacaagctct tcatccaact cgtccagaca tacaaccagc tattcgagga gaatcctatc  600
aacgcctctg gggtggacgc taaagctatc ctctcagccc gcctgtcaaa gtcgaggagg  660
ttggagaacc taatcgccca gcttccaggc gagaagaaaa atgggctgtt cggaaacctt  720
atcgcactct cactgggcct aaccccgaac ttcaagtcca acttcgacct ggcagaggac  780
gcgaaattgc agttgtcgaa agacacctat gacgatgacc tggacaacct gttggcccaa  840
ataggggacc agtacgccga cctgttccta gcgccaaaga acctgtccga cgccatcttg  900
ctgtcggata tactgcgggt gaacaccgag atcactaaag cacctctctc cgccagcatg  960
attaagcgtt acgacgagca ccaccaagat ttgaccctgc taaaggcact tgtacggcag  1020
cagcttcccg agaagtacaa ggagatcttt tcgaccaaag acaagaacgg ctacgccggg  1080
tacatcgacg gaggtgccag ccaggaggag ttctacaagt tcattaagcc catcctggag  1140
aagatggacg ggactgagga actacttgtg aagctgaacc gggaagactt actacggaag  1200
cagcgtacct tcgacaacgg ttctatccca catcagatcc atcttgggga gttgcacgcg  1260
atcctgcgac gccaggagga cttttacccc ttcctgaaag acaaccgcga gaaaatcgaa  1320
aagatactga ccttcagaat accttactac gtcggacccc ttgcgcgagg caactcaaga  1380
ttcgcgtgga tgaccaggaa atcagaggag accatcacac cctggaattt cgaggaggtg  1440
gttgacaagg gtgcctccgc ccagtccttt atcgaacgaa tgaccaactt cgacaagaac  1500
ttgccaaacg agaaggtgct ccccaaacac agcctctct acgaatattt cacagtgtac  1560
aacgagctta ctaaagttaa gtatgttact gagggcatga ggaaaccgc cttcctgtca  1620
ggcgagcaga agaaagctat tgtggacctc cttttcaaga ccaaccggaa ggtgacagtg  1680
aagcagctca aggaggacta cttcaagaag atagagtgct tcgacagcgt ggagatcagc  1740
ggggtggagg acagattcaa tgcctctctc ggaacatacc acgacttgct taagatcatc  1800
aaggacaagg acttcctcga caacgaggaa aacgaggata ttctggagga tattgttctg  1860
actcttaccc tgttcgagga ccgggagatg atcgaggagc gtctcaagac ctacgcccac  1920
ctgttcgacg acaaagttat gaagcagctc aagcgtcgga gatataccgg atggggccgt  1980
ctgtctcgga agctcatcaa cgggatcagg gacaagcagt cagggaagac gatcttagac  2040
ttccttaagt ctgacggctt cgccaacagg aacttcatgc agttgatcca cgacgacagc  2100
cttaccttca aggaggacat ccagaaggcc caagtgagtg gccagggtga cagcctccac  2160
gagcatattg ctaatcttgc gggttcccca gcgattaaaa agggcatact tcaaaccgtt  2220
aaggtggtgg acgagcttgt caaggtgatg gggcgacaca gcccgagaa catcgtgatc  2280
gagatggcca gggagaacca gaccacccag aaggggcaga agaatagccg agaacgcatg  2340
aagcgcatca aggagggat taaggagcta gggagccaga tcctcaagga acatcccgtc  2400
gagaacaccc agctccggaa cgagaagcta tacctctact acttgcaaaa cgggagggat  2460
atgtacgtgg atcaggagtt ggacattaac cgcctaagcg actacgacgt agatcacatc  2520
gtgcctcagt cattcctcaa agacgacagc attgacaaca agtcttgac ccgatccgac  2580
aagaaccgag gaaaatccga caatgtgccc tcagaggagg tcgtcaagaa aatgaagaac  2640
tattggaggc agctacttaa cgccaaactc ataacccagc ggaagttcga caacctgaca  2700
aaggctgagc ggggtgggct cagcgagctt gacaaggctg gcttcatcaa gcggcagttg  2760
gtggagacaa gacagataac gaagcacgtg gctcagatcc tggactctcg catgaacacg  2820
aagtacgacg agaacgacaa attgatccgc gaggtcaagg ttattacgct caagagcaaa  2880
cttgtcagca atttccgcaa ggacttccag ttctacaagg tgagggagat taacaactac  2940
caccatgcac atgatgccta cttgaacgca gtggtgggga ccgcgcttat taaaaagtac  3000
```

```
cctaagttgg agtcagagtt cgtttatggg gactacaagg tgtacgacgt ccggaagatg 3060
attgcaaagt ctgaacagga aatcgggaag gccaccgcca aatatttctt ctacagtaac 3120
attatgaatt tttttaagac tgaaattact ctcgcaaacg gcgagatcag gaagcgtccc 3180
ctcatcgaga caaacgggga gaccggggag atagtctggg acaaggggcg ggacttcgct 3240
acggtgagga aggtgctctc gatgccacaa gtgaacatcg tcaaaaagac agaggtgcag 3300
accggtggct tctcaaagga gtcaatcctg ccaaaacgta acagcgacaa gctcatcgcc 3360
cgcaagaaag actgggaccc taagaagtat ggtgggttcg actcaccgac ggtcgcatac 3420
tccgttctgg tcgtggcaaa ggtggaaaag ggcaagtcca aaaaactgaa atccgtgaag 3480
gagttgcttg gcattaccat catggaacgc agcagcttcg agaagaaccc cattgacttc 3540
ctggaggcta aagggtacaa ggaggtcaag aaagatttaa ttattaagct acctaagtac 3600
agcttgttcg agctggagaa cggccgaaaa cgaatgctcg catccgccgg ggaacttcaa 3660
aagggcaacg agcttgcgct gccctccaag tacgtgaact tcctgtactt ggcatcccac 3720
tacgagaaac tcaagggtag cccagaggac aacgagcaga agcagctatt cgtggagcag 3780
cacaagcact acctcgacga gataatcgag cagatccgat cgttcagtaa gcgggtgata 3840
ctcgcggacg ccaacttgga caaggtgctt agtgcctaca acaagcaccg tgacaagccc 3900
atccgagaac aggctgagaa catcatccac ctttcactc tgacaaacct cggtgctccc 3960
gccgccttca aatacttcga cactaccatc gacaggaagc gctacacatc tacgaaggaa 4020
gttcttgacg ctacgcttat tcatcagtct atcacgggc tgtacgagac aaggatcgac 4080
cttagccaac tcggcgggga t                                             4101

SEQ ID NO: 81      moltype = AA  length = 1367
FEATURE            Location/Qualifiers
source             1..1367
                   mol_type = protein
                   organism = synthetic construct
SEQUENCE: 81
DKKYSIGLAI GTNSVGWAVI TDEYKVPSKK FKVLGNTDRH SIKKNLIGAL LFDSGETAEA   60
TRLKRTARRR YTRRKNRICY LQEIFSNEMA KVDDSFFHRL EESFLVEEDK KHERHPIFGN  120
IVDEVAYHEK YPTIYHLRKK LVDSTDKADL RLIYLALAHM IKFRGHFLIE GDLNPDNSDV  180
DKLFIQLVQT YNQLFEENPI NASGVDAKAI LSARLSKSRR LENLIAQLPG EKKNGLFGNL  240
IALSLGLTPN FKSNFDLAED AKLQLSKDTY DDDLDNLLAQ IGDQYADLFL AAKNLSDAIL  300
LSDILRVNTE ITKAPLSASM IKRYDEHHQD LTLLKALVRQ QLPEKYKEIF FDQSKNGYAG  360
YIDGGASQEE FYKFIKPILE KMDGTEELLV KLNREDLLRK QRTFDNGSIP HQIHLGELHA  420
ILRRQEDFYP FLKDNREKIE KILTFRIPYY VGPLARGNSR FAWMTRKSEE TITPWNFEEV  480
VDKGASAQSF IERMTNFDKN LPNEKVLPKH SLLYEYFTVY NELTKVKYVT EGMRKPAFLS  540
GEQKKAIVDL LFKTNRKVTV KQLKEDYFKK IECFDSVEIS GVEDRFNASL GTYHDLLKII  600
KDKDFLDNEE NEDILEDIVL TLTLFEDREM IEERLKTYAH LFDDKVMKQL KRRRYTGWGR  660
LSRKLINGIR DKQSGKTILD FLKSDGFANR NFMQLIHDDS LTFKEDIQKA QVSGQGDSLH  720
EHIANLAGSP AIKKGILQTV KVVDELVKVM GRHKPENIVI EMARENQTTQ KGQKNSRERM  780
KRIEEGIKEL GSQILKEHPV ENTQLQNEKL YLYYLQNGRD MYVDQELDIN RLSDYDVDHI  840
VPQSFLKDDS IDNKVLTRSD KNRGKSDNVP SEEVVKKMKN YWRQLLNAKL ITQRKFDNLT  900
KAERGGLSEL DKAGFIKRQL VETRQITKHV AQILDSRMNT KYDENDKLIR EVKVITLKSK  960
LVSDFRKDFQ FYKVREINNY HHAHDAYLNA VVGTALIKKY PKLESEFVYG DYKVYDVRKM 1020
IAKSEQEIGK ATAKYFFYSN IMNFFKTEIT LANGEIRKRP LIETNGETGE IVWDKGRDFA 1080
TVRKVLSMPQ VNIVKKTEVQ TGGFSKESIL PKRNSDKLIA RKKDWDPKKY GGFDSPTVAY 1140
SVLVVAKVEK GKSKKLKSVK ELLGITIMER SSFEKNPIDF LEAKGYKEVK KDLIIKLPKY 1200
SLFELENGRK RMLASAGELQ KGNELALPSK YVNFLYLASH YEKLKGSPED NEQKQLFVEQ 1260
HKHYLDEIIE QISEFSKRVI LADANLDKVL SAYNKHRDKP IREQAENIIH LFTLTNLGAP 1320
AAFKYFDTTI DRKRYTSTKE VLDATLIHQS ITGLYETRID LSQLGGD               1367

SEQ ID NO: 82      moltype = AA  length = 1367
FEATURE            Location/Qualifiers
source             1..1367
                   mol_type = protein
                   organism = synthetic construct
SEQUENCE: 82
DKKYSIGLAI GTNSVGWAVI TDEYKVPSKK FKVLGNTDRH SIKKNLIGAL LFDSGETAEA   60
TRLKRTARRR YTRRKNRICY LQEIFSNEMA KVDDSFFHRL EESFLVEEDK KHERHPIFGN  120
IVDEVAYHEK YPTIYHLRKK LVDSTDKADL RLIYLALAHM IKFRGHFLIE GDLNPDNSDV  180
DKLFIQLVQT YNQLFEENPI NASGVDAKAI LSARLSKSRR LENLIAQLPG EKKNGLFGNL  240
IALSLGLTPN FKSNFDLAED AKLQLSKDTY DDDLDNLLAQ IGDQYADLFL AAKNLSDAIL  300
LSDILRVNTE ITKAPLSASM IKRYDEHHQD LTLLKALVRQ QLPEKYKEIF FDQSKNGYAG  360
YIDGGASQEE FYKFIKPILE KMDGTEELLV KLNREDLLRK QRTFDNGSIP HQIHLGELHA  420
ILRRQEDFYP FLKDNREKIE KILTFRIPYY VGPLARGNSR FAWMTRKSEE TITPWNFEEV  480
VDKGASAQSF IERMTNFDKN LPNEKVLPKH SLLYEYFTVY NELTKVKYVT EGMRKPAFLS  540
GEQKKAIVDL LFKTNRKVTV KQLKEDYFKK IECFDSVEIS GVEDRFNASL GTYHDLLKII  600
KDKDFLDNEE NEDILEDIVL TLTLFEDREM IEERLKTYAH LFDDKVMKQL KRRRYTGWGR  660
LSRKLINGIR DKQSGKTILD FLKSDGFANR NFMQLIHDDS LTFKEDIQKA QVSGQGDSLH  720
EHIANLAGSP AIKKGILQTV KVVDELVKVM GRHKPENIVI EMARENQTTQ KGQKNSRERM  780
KRIEEGIKEL GSQILKEHPV ENTQLQNEKL YLYYLQNGRD MYVDQELDIN RLSDYDVDHI  840
VPQSFLADDS IDNKVLTRSD KNRGKSDNVP SEEVVKKMKN YWRQLLNAKL ITQRKFDNLT  900
KAERGGLSEL DKAGFIKRQL VETRQITKHV AQILDSRMNT KYDENDKLIR EVKVITLKSK  960
LVSDFRKDFQ FYKVREINNY HHAHDAYLNA VVGTALIKKY PALESEFVYG DYKVYDVRKM 1020
IAKSEQEIGK ATAKYFFYSN IMNFFKTEIT LANGEIRKAP LIETNGETGE IVWDKGRDFA 1080
TVRKVLSMPQ VNIVKKTEVQ TGGFSKESIL PKRNSDKLIA RKKDWDPKKY GGFDSPTVAY 1140
SVLVVAKVEK GKSKKLKSVK ELLGITIMER SSFEKNPIDF LEAKGYKEVK KDLIIKLPKY 1200
SLFELENGRK RMLASAGELQ KGNELALPSK YVNFLYLASH YEKLKGSPED NEQKQLFVEQ 1260
HKHYLDEIIE QISEFSKRVI LADANLDKVL SAYNKHRDKP IREQAENIIH LFTLTNLGAP 1320
AAFKYFDTTI DRKRYTSTKE VLDATLIHQS ITGLYETRID LSQLGGD               1367
```

```
SEQ ID NO: 83              moltype = AA  length = 228
FEATURE                    Location/Qualifiers
source                     1..228
                           mol_type = protein
                           organism = Rattus norvegicus
SEQUENCE: 83
SSETGPVAVD PTLRRRIEPH EFEVFFDPRE LRKETCLLYE INWGGRHSIW RHTSQNTNKH   60
VEVNFIEKFT TERYFCPNTR CSITWFLSWS PCGECSRAIT EFLSRYPHVT LFIYIARLYH  120
HADPRNRQGL RDLISSGVTI QIMTEQESGY CWRNFVNYSP SNEAHWPRYP HLWVRLYVLE  180
LYCIILGLPP CLNILRRKQP QLTFFTIALQ SCHYQRLPPH ILWATGLK              228

SEQ ID NO: 84              moltype = AA  length = 199
FEATURE                    Location/Qualifiers
source                     1..199
                           mol_type = protein
                           organism = Homo sapiens
SEQUENCE: 84
MEASPASGPR HLMDPHIFTS NFNNGIGRHK TYLCYEVERL DNGTSVKMDQ HRGFLHNQAK   60
NLLCGFYGRH AELRFLDLVP SLQLDPAQIY RVTWFISWSP CFSWGCAGEV RAFLQENTHV  120
RLRIFAARIY DYDPLYKEAL QMLRDAGAQV SIMTYDEFKH CWDTFVDHQG CPFQPWDGLD  180
EHSQALSGRL RAILQNQGN                                              199

SEQ ID NO: 85              moltype = DNA  length = 621
FEATURE                    Location/Qualifiers
source                     1..621
                           mol_type = other DNA
                           organism = Petromyzon marinus
SEQUENCE: 85
acagatgcag agtatgtgag aattcacgaa aagctggaca tctataccct caagaagcag   60
ttctttaaca ataagaagtc tgtgagccat aggtgctacg tgctgttcga gctgaagaga  120
aggggtgaaa aagggcatg tttttggggg tatgctgtga acaagcccca gtctggaact  180
gagagaggca ttcacgccga aattttcagc atcagaaagg tggaggaata cctgagggat  240
aaccctggac agtttacaat taattggtat tctagctggt ctccatgcgc tgactgtgcc  300
gagaagatcc tggaatggta caaccaggag ctgagaggaa atggccatac cctgaagatt  360
tgggcctgca agctgtacta tgaaaagaac gcaagaaatc agatcggact gtggaacctg  420
agggataatg tgtggggct gaacgtgatg gtgtccgagc actatcagtg ctgtagaaag  480
attttcattc agtcctcaca taatcagctg aacgagaata gatggctgga aaagactctg  540
aagagggctg agaagagaag gtccgaactg tcaattatga tccaggtgaa gatcctgcac  600
accactaagt cacctgccgt g                                            621

SEQ ID NO: 86              moltype = AA  length = 160
FEATURE                    Location/Qualifiers
source                     1..160
                           mol_type = protein
                           organism = synthetic construct
SEQUENCE: 86
FERNYDPREL RKETYLLYEI KWGKSGKLWR HWCQNNRTQH AEVYFLENIF NARRFNPSTH   60
CSITWYLSWS PCAECSQKIV DFLKEHPNVL EIYVARLYYH EDERNRQGLR DLVNSGVTIR  120
IMDLPDYNYC WKTFVSDQGG DEDYWPGHFA PWIKQYSLKL                       160

SEQ ID NO: 87              moltype = AA  length = 229
FEATURE                    Location/Qualifiers
source                     1..229
                           mol_type = protein
                           organism = Rattus norvegicus
SEQUENCE: 87
MSSETGPVAV DPTLRRRIEP HEFEVFFDPR ELRKETCLLY EINWGGRHSI WRHTSQNTNK   60
HVEVNFIEKF TTERYFCPNT RCSITWFLSW SPCGECSRAI TEFLSRYPHV TLFIYIARLY  120
HHADPRNRQG LRDLISSGVT IQIMTEQESG YCWRNFVNYS PSNEAHWPRY PHLWVRLYVL  180
ELYCIILGLP PCLNILRRKQ PQLTFFTIAL QSCHYQRLPP HILWATGLK             229

SEQ ID NO: 88              moltype = AA  length = 198
FEATURE                    Location/Qualifiers
source                     1..198
                           mol_type = protein
                           organism = Homo sapiens
SEQUENCE: 88
MDSLLMNRRK FLYQFKNVRW AKGRRETYLC YVVKRRDSAT SFSLDFGYLR NKNGCHVELL   60
FLRYISDWDL DPGRCYRVTW FTSWSPCYDC ARHVADFLRG NPNLSLRIFT ARLYFCEDRK  120
AEPEGLRRLH RAGVQIAIMT FKDYFYCWNT FVENHERTFK AWEGLHENSV RLSRQLRRIL  180
LPLYEVDDLR DAFRTLGL                                               198

SEQ ID NO: 89              moltype = AA  length = 197
FEATURE                    Location/Qualifiers
source                     1..197
                           mol_type = protein
                           organism = synthetic construct
SEQUENCE: 89
```

```
MDSLLMNRRE FLYQFKNVRW AKGRRETYLC YVVKRRDSAT SFSLDFGYLR NKNGCHVELL    60
FLRYISDWDL DPGRCYRVTW FISWSPCYDC ARHVADFLRG NPNLSLRIFT ARLYFCEDRK   120
AEPEGLRRLH RAGVQIAIMT FKDYFYCWNT FVENHGRTFK AWEGLHENSV RLSRQLRRIL   180
LPLYEVDDLR DAFRTCT                                                  197

SEQ ID NO: 90           moltype = AA   length = 207
FEATURE                 Location/Qualifiers
source                  1..207
                        mol_type = protein
                        organism = synthetic construct
SEQUENCE: 90
TDAEYVRIHE KLDIYTFKKQ FSNNKKSVSH RCYVLFELKR RGERRACFWG YAVNKPQSGT    60
ERGIHAEIFS IRKVEEYLRD NPGQFTINWY SSWSPCADCA EKILEWYNQE LRGNGHTLKI   120
WVCKLYYEKN ARNQIGLWNL RDNGVGLNVM VSEHYQCCRK IFIQSSHNQL NENRWLEKTL   180
KRAEKRRSEL SIMFQVKILH TTKSPAV                                       207

SEQ ID NO: 91           moltype = AA   length = 228
FEATURE                 Location/Qualifiers
source                  1..228
                        mol_type = protein
                        organism = synthetic construct
SEQUENCE: 91
SSKTGPVAVD PTLRRRIEPH EFEVFFDPRE LRKETCLLYE INWGGRHSIW RHTSQNTNKH    60
VEVNFIEKFT TERYFCPNTR CSITWFLSWS PCGECSRAIT EFLSRYPNVT LFIYIARLYH   120
LANPRNRQGL RDLISSGVTI QIMTEQESGY CWHNFVNYSP SNESHWPRYP HLWVRLYVLE   180
LYCIILGLPP CLNILRRKQS QLTSFTIALQ SCHYQRLPPH ILWATGLK                228

SEQ ID NO: 92           moltype = AA   length = 162
FEATURE                 Location/Qualifiers
source                  1..162
                        mol_type = protein
                        organism = synthetic construct
SEQUENCE: 92
SFERNYDPRE LRKETYLLYE IKWGKSGKLW RHWCQNNRTQ HAEVYFLENI FNARRFNPST    60
HCSITWYLSW SPCAECSQKI VDFLKEHPNV NLEIYVARLY YPENERNRQG LRDLVNSGVT   120
IRIMDLPDYN YCWKTFVSDQ GGDEDYWPGH FAPWIKQYSL KL                      162

SEQ ID NO: 93           moltype = AA   length = 166
FEATURE                 Location/Qualifiers
source                  1..166
                        mol_type = protein
                        organism = Escherichia coli
SEQUENCE: 93
SEVEFSHEYW MRHALTLAKR AWDEREVPVG AVLVHNNRVI GEGWNRPIGR HDPTAHAEIM    60
ALRQGGLVMQ NYRLIDATLY VTLEPCVMCA GAMIHSRIGR VVFGARDAKT GAAGSLMDVL   120
HHHPGMNHRVE ITEGILADEC AALLSDFFRM RRQEIKAQKK AQSSTD                 166

SEQ ID NO: 94           moltype = AA   length = 166
FEATURE                 Location/Qualifiers
source                  1..166
                        mol_type = protein
                        organism = synthetic construct
SEQUENCE: 94
SEVEFSHEYW MRHALTLAKR ARDEREVPVG AVLVLNNRVI GEGWNRAIGL HDPTAHAEIM    60
ALRQGGLVMQ NYRLIDATLY VTFEPCVMCA GAMIHSRIGR VVFGVRNAKT GAAGSLMDVL   120
HYPGMNHRVE ITEGILADEC AALLCYFFRM PRQVFNAQKK AQSSTD                  166

SEQ ID NO: 95           moltype = AA   length = 166
FEATURE                 Location/Qualifiers
source                  1..166
                        mol_type = protein
                        organism = synthetic construct
SEQUENCE: 95
SEVEFSHEYW MRHALTLAKR AWDEREVPVG AVLVLNNRVI GEGWNRSIGL HDPTAHAEIM    60
ALRQGGLVMQ NYRLIDATLY VTFEPCVMCA GAMIHSRIGR VVFGVRNAKT GAAGSLMDVL   120
HYPGMNHRVE ITEGILADEC AALLCYFFRM RRQVFNAQKK AQSSTD                  166

SEQ ID NO: 96           moltype = AA   length = 166
FEATURE                 Location/Qualifiers
source                  1..166
                        mol_type = protein
                        organism = synthetic construct
SEQUENCE: 96
SEVEFSHEYW MRHALTLAKR ALDEREVPVG AVLVLNNRVI GEGWNRAIGL HDPTAHAEIM    60
ALRQGGLVMQ NYRLIDATLY VTFEPCVMCA GAMIHSRIGR VVFGVRNAKT GAAGSLMDVL   120
HYPGMNHRVE ITEGILADEC NALLCYFFRM RRQVFNAQKK AQSSTD                  166

SEQ ID NO: 97           moltype = AA   length = 166
FEATURE                 Location/Qualifiers
```

```
source                    1..166
                          mol_type = protein
                          organism = synthetic construct
SEQUENCE: 97
SEVEFSHEYW MRHALTLAKR ALDEREVPVG AVLVLNNRVI GEGWNRAIGL HDPTAHAEIM    60
ALRQGGLVMQ NYRLIDATLY VTFEPCVMCA GAMIHSRIGR VVFGVRNAKT GAAGSLMDVL   120
HYPGMNHRVE ITEGILADEC NALLCYFFRM PRQVFNAQKK AQSSTD                  166

SEQ ID NO: 98             moltype = AA  length = 1763
FEATURE                   Location/Qualifiers
source                    1..1763
                          mol_type = protein
                          organism = synthetic construct
SEQUENCE: 98
SEVEFSHEYW MRHALTLAKR AWDEREVPVG AVLVHNNRVI GEGWNRPIGR HDPTAHAEIM    60
ALRQGGLVMQ NYRLIDATLY VTLEPCVMCA GAMIHSRIGR VVFGARDAKT GAAGSLMDVL   120
HHPGMNHRVE ITEGILADEC AALLSDFFRM RRQEIKAQKK AQSSTDSGGS SGGSSGSETP   180
GTSESATPES SGGSSGGSSE VEFSHEYWMR HALTLAKRAR DEREVPVGAV LVLNNRVIGE   240
GWNRAIGLHD PTAHAEIMAL RQGGLVMQNY RLIDATLYVT FEPCVMCAGA MIHSRIGRVV   300
FGVRNAKTGA AGSLMDVLHY PGMNHRVEIT EGILADECAA LLCYFFRMPR QVFNAQKKAQ   360
SSTDSGGSSG GSSGSETPGT SESATPESSG GSSGGSDKKY SIGLAIGTNS VGWAVITDEY   420
KVPSKKFKVL GNTDRHSIKK NLIGALLFDS GETAEATRLK RTARRRYTRR KNRICYLQEI   480
FSNEMAKVDD SFFHRLEESF LVEEDKKHER HPIFGNIVDE VAYHEKYPTI YHLRKKLVDS   540
TDKADLRLIY LALAHMIKFR GHFLIEGDLN PDNSDVDKLF IQLVQTYNQL FEENPINASG   600
VDAKAILSAR LSKSRRLENL IAQLPGEKKN GLFGNLIALS LGLTPNFKSN FDLAEDAKLQ   660
LSKDTYDDDL DNLLAQIGDQ YADLFLAAKN LSDAILLSDI LRVNTEITKA PLSASMIKRY   720
DEHHQDLTLL KALVRQQLPE KYKEIFFDQS KNGYAGYIDG GASQEEFYKF IKPILEKMDG   780
TEELLVKLNR EDLLRKQRTF DNGSIPHQIH LGELHAILRR QEDFYPFLKD NREKIEKILT   840
FRIPYYVGPL ARGNSRFAWM TRKSEETITP WNFEEVVDKG ASAQSFIERM TNFDKNLPNE   900
KVLPKHSLLY EYFTVYNELT KVKYVTEGMR KPAFLSGEQK KAIVDLLFKT NRKVTVKQLK   960
EDYFKKIECF DSVEISGVED RFNASLGTYH DLLKIIKDKD FLDNEENEDI LEDIVLTLTL  1020
FEDREMIEER LKTYAHLFDD KVMKQLKRRR YTGWGRLSRK LINGIRDKQS GKTILDPLKS  1080
DGFANRNFMQ LIHDDSLTFK EDIQKAQVSG QGDSLHEHIA NLAGSPAIKK GILQTVKVVD  1140
ELVKVMGRHK PENIVIEMAR ENQTTQKGQK NSRERMKRIE EGIKELGSQI LKEHPVENTQ  1200
LQNEKLYLYY LQNGRDMYVD QELDINRLSD YDVDHIVPQS FLKDDSIDNK VLTRSDKNRG  1260
KSDNVPSEEV VKKMKNYWRQ LLNAKLITQR KFDNLTKAER GGLSELDKAG FIKRQLVETR  1320
QITKHVAQIL DSRMNTKYDE NDKLIREVKV ITLKSKLVSD FRKDFQFYKV REINNYHHAH  1380
DAYLNAVVGT ALIKKYPKLE SEFVYGDYKV YDVRKMIAKS EQEIGKATAK YPFYSNIMNF  1440
FKTEITLANG EIRKRPLIET NGETGEIVWD KGRDFATVRK VLSMPQVNIV KKTEVQTGGF  1500
SKESILPKRN SDKLIARKKD WDPKKYGGFD SPTVAYSVLV VAKVEKGKSK KLKSVKELLG  1560
ITIMERSSFE KNPIDFLEAK GYKEVKKDLI IKLPKYSLFE LENGRKRMLA SAGELQKGNE  1620
LALPSKYVNF LYLASHYEKL KGSPEDNEQK QLFVEQHKHY LDEIIEQISE FSKRVILADA  1680
NLDKVLSAYN KHRDKPIREQ AENIIHLFTL TNLGAPAAFK YFDTTIDRKR YTSTKEVLDA  1740
TLIHQSITGL YETRIDLSQL GGD                                         1763

SEQ ID NO: 99             moltype = AA  length = 1565
FEATURE                   Location/Qualifiers
source                    1..1565
                          mol_type = protein
                          organism = synthetic construct
SEQUENCE: 99
SEVEFSHEYW MRHALTLAKR ARDEREVPVG AVLVLNNRVI GEGWNRAIGL HDPTAHAEIM    60
ALRQGGLVMQ NYRLIDATLY VTFEPCVMCA GAMIHSRIGR VVFGVRNSKR GAAGSLMNVL   120
NYPGMNHRVE ITEGILADEC AALLCDFYRM PRQVFNAQKK AQSSINSGGS SGGSSGSETP   180
GTSESATPES SGGSSGGSDK KYSIGLAIGT NSVGWAVITD EYKVPSKKFK VLGNTDRHSI   240
KKNLIGALLF DSGETAEATR LKRTARRRYT RRKNRICYLQ EIFSNEMAKV DDSFFHRLEE   300
SFLVEEDKKH ERHPIFGNIV DEVAYHEKYP TIYHLRKKLV DSTDKADLRL IYLALAHMIK   360
FRGHFLIEGD LNPDNSDVDK LFIQLVQTYN QLFEENPINA SGVDAKAILS ARLSKSRRLE   420
NLIAQLPGEK KNGLFGNLIA LSLGLTPNFK SNFDLAEDAK LQLSKDTYDD DLDNLLAQIG   480
DQYADLFLAA KNLSDAILLS DILRVNTEIT KAPLSASMIK RYDEHHQDLT LLKALVRQQL   540
PEKYKEIFFD QSKNGYAGYI DGGASQEEFY KFIKPILEKM DGTEELLVKL NREDLLRKQR   600
TFDNGSIPHQ IHLGELHAIL RRQEDFYPFL KDNREKIEKI LTFRIPYYVG PLARGNSRFA   660
WMTRKSEETI TPWNFEEVVD KGASAQSFIE RMTNFDKNLP NEKVLPKHSL LYEYFTVYNE   720
LTKVKYVTEG MRKPAFLSGE QKKAIVDLLF KTNRKVTVKQ LKEDYFKKIE CFDSVEISGV   780
EDRFNASLGT YHDLLKIIKD KDFLDNEENE DILEDIVLTL TLFEDREMIE ERLKTYAHLF   840
DDKVMKQLKR RRYTGWGRLS RKLINGIRDK QSGKTILDPL KSDGFANRNF MQLIHDDSLT   900
FKEDIQKAQV SGQGDSLHEH IANLAGSPAI KKGILQTVKV VDELVKVMGR HKPENIVIEM   960
ARENQTTQKG QKNSRERMKR IEEGIKELGS QILKEHPVEN TQLQNEKLYL YYLQNGRDMY  1020
VDQELDINRL SDYDVDHIVP QSFLKDDSID NKVLTRSDKN RGKSDNVPSE EVVKKMKNYW  1080
RQLLNAKLIT QRKFDNLTKA ERGGLSELDK AGFIKRQLVE TRQITKHVAQ ILDSRMNTKY  1140
DENDKLIREV KVITLKSKLV SDFRKDFQFY KVREINNYHH AHDAYLNAVV GTALIKKYPK  1200
LESEFVYGDY KVYDVRKMIA KSEQEIGKAT AKYFFYSNIM NFFKTEITLA NGEIRKRPLI  1260
ETNGETGEIV WDKGRDFATV RKVLSMPQVN IVKKTEVQTG GFSKESILPK RNSDKLIARK  1320
KDWDPKKYGG FDSPTVAYSV LVVAKVEKGK SKKLKSVKEL LGITIMERSS FEKNPIDFLE  1380
AKGYKEVKKD LIIKLPKYSL FELENGRKRM LASAGELQKG NELALPSKYV NFLYLASHYE  1440
KLKGSPEDNE QKQLFVEQHK HYLDEIIEQI SEFSKRVILA DANLDKVLSA YNKHRDKPIR  1500
EQAENIIHLF TLTNLGAPAA FKYFDTTIDR KRYTSTKEVL DATLIHQSIT GLYETRIDLS  1560
QLGGD                                                             1565
```

```
SEQ ID NO: 100          moltype = AA   length = 1565
FEATURE                 Location/Qualifiers
source                  1..1565
                        mol_type = protein
                        organism = synthetic construct
SEQUENCE: 100
SEVEFSHEYW MRHALTLAKR ARDEREVPVG AVLVLNNRVI GEGWNRAIGL HDPTAHAEIM    60
ALRQGGLVMQ NYRLYDATLY STFEPCVMCA GAMIHSRIGR VVFGVRNAKT GAAGSLMDVL   120
HHPGMNHRVE ITEGILADEC AALLCRFFRM PRRVFNAQKK AQSSTDSGGS SGGSSGGSETP  180
GTSESATPES SGGSSGGSDK KYSIGLAIGT NSVGWAVITD EYKVPSKKFK VLGNTDRHSI   240
KKNLIGALLF DSGETAEATR LKRTARRRYT RRKNRICYLQ EIFSNEMAKV DDSFFHRLEE   300
SFLVEEDKKH ERHPIFGNIV DEVAYHEKYP TIYHLRKKLV DSTDKADLRL IYLALAHMIK   360
FRGHFLIEGD LNPDNSDVDK LFIQLVQTYN QLFEENPINA SGVDAKAILS ARLSKSRRLE   420
NLIAQLPGEK KNGLFGNLIA LSLGLTPNFK SNFDLAEDAK LQLSKDTYDD DLDNLLAQIG   480
DQYADLFLAA KNLSDAILLS DILRVNTEIT KAPLSASMIK RYDEHHQDLT LLKALVRQQL   540
PEKYKEIFFD QSKNGYAGYI DGGASQEEFY KFIKPILEKM DGTEELLVKL NREDLLRKQR   600
TFDNGSIPHQ IHLGELHAIL RRQEDFYPFL KDNREKIEKI LTFRIPYYVG PLARGNSRFA   660
WMTRKSEETI TPWNFEEVVD KGASAQSFIE RMTNFDKNLP NEKVLPKHSL LYEYFTVYNE   720
LTKVKYVTEG MRKPAFLSGE QKKAIVDLLF KTNRKVTVKQ LKEDYFKKIE CFDSVEISGV   780
EDRFNASLGT YHDLLKIIKD KDFLDNEENE DILEDIVLTL TLFEDREMIE ERLKTYAHLF   840
DDKVMKQLKR RRYTGWGRLS RKLINGIRDK QSGKTILDFL KSDGFANRNF MQLIHDDSLT   900
FKEDIQKAQV SGQGDSLHEH IANLAGSPAI KKGILQTVKV VDELVKVMGR HKPENIVIEM   960
ARENQTTQKG QKNSRERMKR IEEGIKELGS QILKEHPVEN TQLQNEKLYL YYLQNGRDMY  1020
VDQELDINRL SDYDVDHIVP QSFLKDDSID NKVLTRSDKN RGKSDNVPSE EVVKKMKNYW  1080
RQLLNAKLIT QRKFDNLTKA ERGGLSELDK AGFIKRQLVE TRQITKHVAQ ILDSRMNTKY  1140
DENDKLIREV KVITLKSKLV SDFRKDFQFY KVREINNYHH AHDAYLNAVV GTALIKKYPK  1200
LESEFVYGDY KVYDVRKMIA KSEQEIGKAT AKYFFYSNIM NFFKTEITLA NGEIRKRPLI  1260
ETNGETGEIV WDKGRDFATV RKVLSMPQVN IVKKTEVQTG GFSKESILPK RNSDKLIARK  1320
KDWDPKKYGG FDSPTVAYSV LVVAKVEKGK SKKLKSVKEL LGITIMERSS FEKNPIDFLE  1380
AKGYKEVKKD LIIKLPKYSL FELENGRKRM LASAGELGKG NELALPSKYV NFLYLASHYE  1440
KLKGSPEDNE QKQLFVEQHK HYLDEIIEQI SEFSKRVILA DANLDKVLSA YNKHRDKPIR  1500
EQAENIIHLF TLTNLGAPAA FKYFDTTIDR KRYTSTKEVL DATLIHQSIT GLYETRIDLS  1560
QLGGD                                                             1565

SEQ ID NO: 101          moltype = AA   length = 364
FEATURE                 Location/Qualifiers
source                  1..364
                        mol_type = protein
                        organism = synthetic construct
SEQUENCE: 101
SEVEFSHEYW MRHALTLAKR AWDEREVPVG AVLVHNNRVI GEGWNRPIGR HDPTAHAEIM    60
ALRQGGLVMQ NYRLIDATLY VTLEPCVMCA GAMIHSRIGR VVFGARDAKT GAAGSLMDVL   120
HHPGMNHRVE ITEGILADEC AALLSDFFRM RRQEIKAQKK AQSSTDSGGS SGGSSGSETP   180
GTSESATPES SGGSSGGSSE VEFSHEYWMR HALTLAKRAR DEREVPVGAV LVLNNRVIGE   240
GWNRAIGLHD PTAHAEIMAL RQGGLVMQNY RLIDATLYVT FEPCVMCAGA MIHSRIGRVV   300
FGVRNAKTGA AGSLMDVLHY PGMNHRVEIT EGILADECAA LLCYFFRMPR QVFNAQKKAQ   360
SSTD                                                               364

SEQ ID NO: 102          moltype = AA   length = 167
FEATURE                 Location/Qualifiers
source                  1..167
                        mol_type = protein
                        organism = synthetic construct
SEQUENCE: 102
MSEVEFSHEY WMRHALTLAK RARDEREVPV GAVLVLNNRV IGEGWNRAIG LHDPTAHAEI    60
MALRQGGLVM QNYRLYDATL YSTFEPCVMC AGAMIHSRIG RVVFGVRNAK TGAAGSLMDV   120
LHHPGMNHRV EITEGILADE CAALLCRFFR MPRRVFNAQK KAQSSTD                167

SEQ ID NO: 103          moltype = AA   length = 167
FEATURE                 Location/Qualifiers
source                  1..167
                        mol_type = protein
                        organism = synthetic construct
SEQUENCE: 103
MSEVEFSHEY WMRHALTLAK RARDEREVPV GAVLVLNNRV IGEGWNRAIG LHDPTAHAEI    60
MALRQGGLVM QNYRLIDATL YVTFEPCVMC AGAMIHSRIG RVVFGVRNSK RGAAGSLMNV   120
LNYPGMNHRV EITEGILADE CAALLCDFYR MPRQVFNAQK KAQSSIN                167

SEQ ID NO: 104          moltype = AA   length = 83
FEATURE                 Location/Qualifiers
source                  1..83
                        mol_type = protein
                        note = Bacillus phage AR9
                        organism = Takahashivirus sp.
SEQUENCE: 104
TNLSDIIEKE TGKQLVIQES ILMLPEEVEE VIGNKPESDI LVHTAYDEST DENVMLLTSD    60
APEYKPWALV IQDSNGENKI KML                                           83

SEQ ID NO: 105          moltype = AA   length = 1372
```

```
FEATURE                 Location/Qualifiers
source                  1..1372
                        mol_type = protein
                        organism = synthetic construct
SEQUENCE: 105
MSKLEKFTNC YSLSKTLRFK AIPVGKTQEN IDNKRLLVED EKRAEDYKGV KKLLDRYYLS    60
FINDVLHSIK LKNLNNYISL FRKKTRTEKE NKELENLEIN LRKEIAKAFK GNEGYKSLFK   120
KDIIETILPE FLDDKDEIAL VNSFNGFTTA FTGFFDNREN MFSEEAKSTS IAFRCINENL   180
TRYISNMDIF EKVDAIFDKH EVQEIKEKIL NSDYDVEDFF EGEFFNFVLT QEGIDVYNAI   240
IGGFVTESGE KIKGLNEYIN LYNQKTKQPL PKFKPLYKQV LSDRESLSFY GENQTTQKGQ   300
KNSRERMKRI EEGIKELGSQ ILKEHPVENT QLQNEKLYLY YLQNGRDMYV DQELDINRLS   360
DYDVDHIVPQ SFLKDDSIDN KVLTRSDKNR GKSDNVPSEE VVKKMKNYWR QLLNAKLITQ   420
RKFDNLTKAE RGGLSEGYTS DEEVLEVFRN TLNKNSEIFS SIKKLEKLFK NFDEYSSAGI   480
FVKNGPAIST ISKDIFGEWN VIRDKWNAEY DDIHLKKKAV VTEKYEDDRR KSFKKIGSFS   540
LEQLQEYADA DLSVVEKLKE IIIQKVDEIY KVYGSSEKLF DADFVLEKSL KKNDAVVAIM   600
KDLLDSVKSF ENYIKAFFGE GKETNRDESF YGDFVLAYDI LLKVDHIYDA IRNYVTQKPY   660
SKDKFKLYFQ NPQFMGGWDK DKETDYRATI LRYGSKYYLA IMDKKYAKCL QKIDKDDVNG   720
NYEKINYKLL PGPNKMLPKV FFSKKWMAYY NPSEDIQKIY KNGTFKKGDM FNLNDCHKLI   780
DFFKDSISRY PKWSNAYDFN FSETEKYKDI AGFYREVEEQ GYKVSFESAS KKEVDKLVEE   840
GKLYMFQIYN KDFSDKSHGT PNLHTMYFKL LFDENNHGQI RLSGGAELFM RRASLKKEEL   900
VVHPANSPIA NKNPDNPKKT TTLSYDVYKD KRFSEDQYEL HIPIAINKCP KNIFKINTEV   960
RVLLKHDDNP YVIGIDRGER NLLYIVVVDG KGNIVEQYSL NEIINNFNGI RIKTDYHSLL  1020
DKKEKERFEA RQNWTSIENI KELKAGYISQ VVHKICELVE KYDAVIALED LNSGFKNSRV  1080
KVEKQVYQKF EKMLIDKLNY MVDKKSNPCA TGGALKGYQI TNKFESFKSM STQNGFIFYI  1140
PAWLTSKIDP STGFVNLLKT KYTSIADSKK FISSSFDRIMY VPEEDLFEFA LDYKNFSRTD  1200
ADYIKKWKLY SYGNRIRIFR NPKKNNVFDW EEVCLTSAYK ELFNKYGINY QQGDIRALLC  1260
EQSDKAFYSS FMALMSLMLQ MRNSITGRTD VDFLISPVKN SDGIFYDSRN YEAQENAILP  1320
KNADANGAYN IARKVLWAIG QFKKAEDEKL DKVKIAISNK EWLEYAQTSV KH          1372

SEQ ID NO: 106          moltype = AA   length = 1374
FEATURE                 Location/Qualifiers
source                  1..1374
                        mol_type = protein
                        organism = synthetic construct
SEQUENCE: 106
MSKLEKFTNC YSLSKTLRFK AIPVGKTQEN IDNKRLLVED EKRAEDYKGV KKLLDRYYLS    60
FINDVLHSIK LKNLNNYISL FRKKTRTEKE NKELENLEIN LRKEIAKAFK GNEGYKSLFK   120
KDIIETILPE FLDDKDEIAL VNSFNGFTTA FTGFFDNREN MFSEEAKSTS IAFRCINENL   180
TRYISNMDIF EKVDAIFDKH EVQEIKEKIL NSDYDVEDFF EGEFFNFVLT QEGIDVYNAI   240
IGGFVTESGE KIKGLNEYIN LYNQKTKQPL PKFKPLYKQV LSDRESLSFY GSGENQTTQK   300
GQKNSRERMK RIEEGIKELG SQILKEHPVE NTQLQNEKLY LYYLQNGRDM YVDQELDINR   360
LSDYDVDHIV PQSFLKDDSI DNKVLTRSDK NRGKSDNVPS EEVVKKMKNY WRQLLNAKLI   420
TQRKFDNLTK AERGGLSEGY TSDEEVLEVF RNTLNKNSEI FSSIKKLEKL FKNFDEYSSA   480
GIFVKNGPAI STISKDIFGE WNVIRDKWNA EYDDIHLKKK AVVTEKYEDD RRKSFKKIGS   540
FSLEQLQEYA DADLSVVEKL KEIIIQKVDE IYKVYGSSEK LFDADFVLEK SLKKNDAVVA   600
IMKDLLDSVK SFENYIKAFF GEGKETNRDE SFYGDFVLAY DILLKVDHIY DAIRNYVTQK   660
PYSKDKFKLY FQNPQFMGGW DKDKETDYRA TILRYGSKYY LAIMDKKYAK CLQKIDKDDV   720
NGNYEKINYK LLPGPNKMLP KVFFSKKWMA YYNPSEDIQK IYKNGTFKKG DMFNLNDCHK   780
LIDFFKDSIS RYPKWSNAYD FNFSETEKYK DIAGFYREVE EQGYKVSFES ASKKEVDKLV   840
EEGKLYMFQI YNKDFSDKSH GTPNLHTMYF KLLFDENNHG QIRLSGGAEL FMRRASLKKE   900
ELVVHPANSP IANKNPDNPK KTTTLSYDVV YKDKRFSEDQ YELHIPIAINK CPKNIFKINT   960
EVRVLLKHDD NPYVIGIDRG ERNLLYIVVV DGKGNIVEQY SLNEIINNFN GIRIKTDYHS  1020
LLDKKEKERF EARQNWTSIE NIKELKAGYI SQVVHKICEL VEKYDAVIAL EDLNSGFKNS  1080
RVKVEKQVYQ KFEKMLIDKL NYMVDKKSNP CATGGALKGY QITNKFESFK SMSTQNGFIF  1140
YIPAWLTSKI DPSTGFVNLL KTKYTSIADS KKFISSFDRI MYVPEEDLFE FALDYKNFSR  1200
TDADYIKKWK LYSYGNRIRI FRNPKKNNVF DWEEVCLTSA YKELFNKYGI NYQQGDIRAL  1260
LCEQSDKAFY SSFMALMSLM LQMRNSITGR TDVDFLISPV KNSDGIFYDS RNYEAQENAI  1320
LPKNADANGA YNIARKVLWA IGQFKKAEDE KLDKVKIAIS NKEWLEYAQT SVKH        1374

SEQ ID NO: 107          moltype = AA   length = 1376
FEATURE                 Location/Qualifiers
source                  1..1376
                        mol_type = protein
                        organism = synthetic construct
SEQUENCE: 107
MSKLEKFTNC YSLSKTLRFK AIPVGKTQEN IDNKRLLVED EKRAEDYKGV KKLLDRYYLS    60
FINDVLHSIK LKNLNNYISL FRKKTRTEKE NKELENLEIN LRKEIAKAFK GNEGYKSLFK   120
KDIIETILPE FLDDKDEIAL VNSFNGFTTA FTGFFDNREN MFSEEAKSTS IAFRCINENL   180
TRYISNMDIF EKVDAIFDKH EVQEIKEKIL NSDYDVEDFF EGEFFNFVLT QEGIDVYNAI   240
IGGFVTESGE KIKGLNEYIN LYNQKTKQPL PKFKPLYKQV LSDRESLSFY GEGSSGENQT   300
TQKGQKNSRE RMKRIEEGIK ELGSQILKEH PVENTQLQNE KLYLYYLQNG RDMYVDQELD   360
INRLSDYDVD HIVPQSFLKD DSIDNKVLTR SDKNRGKSDN VPSEEVVKKM KNYWRQLLNA   420
KLITQRKFDN LTKAERGGLS GYTSDEEVLE VFRNTLNKNS EIFSSIKKLE KLFKNFDEYS   480
SAGIFVKNGP AISTISKDIF GEWNVIRDKW NAEYDDIHLK KKAVVTEKYE DDRRKSFKKI   540
GSFSLEQLQE YADADLSVVE KLKEIIIQKV DEIYKVYGSS EKLFDADFVL EKSLKKNDAV   600
VAIMKDLLDS VKSFENYIKA FFGEGKETNR DESFYGDFVL AYDILLKVDH IYDAIRNYVT   660
QKPYSKDKFK LYFQNPQFMG GWDKDKETDY RATILRYGSK YYLAIMDKKY AKCLQKIDKD   720
DVNGNYEKIN YKLLPGPNKM LPKVFFSKKW MAYYNPSEDI QKIYKNGTFK KGDMFNLNDC   780
HKLIDFFKDS ISRYPKWSNA YDFNFSETEK YKDIAGFYRE VEEQGYKVSF ESASKKEVDK   840
```

```
LVEEGKLYMF QIYNKDFSDK SHGTPNLHTM YFKLLFDENN HGQIRLSGGA ELFMRRASLK    900
KEELVVHPAN SPIANKNPDN PKKTTTLSYD VYKDKRFSED QYELHIPIAI NKCPKNIFKI    960
NTEVRVLLKH DDNPYVIGID RGERNLLYIV VVDGKGNIVE QYSLNEIINN FNGIRIKTDY   1020
HSLLDKKEKE RFEARQNWTS IENIKELKAG YISQVVHKIC ELVEKYDAVI ALEDLNSGFK   1080
NSRVKVEKQV YQKFEKMLID KLNYMVDKKS NPCATGGALK YQITNKFES FKSMSTQNGF    1140
IFYIPAWLTS KIDPSTGFVN LLKTKYTSIA DSKKFISSFD RIMYVPEEDL FEFALDYKNF   1200
SRTDADYIKK WKLYSYGNRI RIFRNPKKNN VFDWEEVCLT SAYKELFNKY GINYQQGDIR   1260
ALLCEQSDKA FYSSFMALMS LMLQMRNSIT GRTDVDFLIS PVKNSDGIFY DSRNYEAQEN   1320
AILPKNADAN GAYNIARKVL WAIGQFKKAE DEKLDKVKIA ISNKEWLEYA QTSVKH       1376

SEQ ID NO: 108          moltype = DNA   length = 66
FEATURE                 Location/Qualifiers
source                  1..66
                        mol_type = other DNA
                        organism = Saccharomyces bayanus
SEQUENCE: 108
ttcttgtcgt acttatagat cgctacgtta tttcaatttt gaaaatctga gtcctgggag    60
tgcgga                                                                66

SEQ ID NO: 109          moltype = AA    length = 605
FEATURE                 Location/Qualifiers
source                  1..605
                        mol_type = protein
                        organism = Homo sapiens
SEQUENCE: 109
MSGWESYYKT EGDEEAEEEQ EENLEASGDY KYSGRDSLIF LVDASKAMFE SQSEDELTPF    60
DMSIQCIQSV YISKIISSDR DLLAWFYGTE KDKNSVNFKI YVLQELDNPG AKRILELDQF   120
KGQQGQKRFQ DMMGHGSDYS LSEVLWVCAN LFSDVQFKMS HKRIMLFTNE DNPHGNDSAK   180
ASRARTKAGD LRDTGIFLDL HLKKPGGFDI SLFYRDIISI AEDEDLRVHF EESSKLEDLL   240
RKVRAKETRK RALSRLKLKL NKDIVISVGI YNLVQKALKP PPIKLYRETN EPVKTKTRTF   300
NTSTGGLLLP SDTKRSQIYG SRQIILEKEE TEELKRFDDP GLMLMGFKPL VLLKKHHYLR   360
PSLFVYPEES LVIGSSTLFS ALLIKCLEKE VAALCRYTPR RNIPPYFVAL VPQEEELDDQ   420
KIQVTPPGFQ LVFLPFADDK RKMPFTEKIM ATPEQVGKMK AIVEKLRFTY RSDSFENPVL   480
QQHFRNLEAL ALDLMEPEQA VDLTLPKVEA MNKRLGSLVD EFKELVYPPD YNPEGKVTKR   540
KHDNEGSGSK RPKVEYSEEE LKTHISKGTL GKFTVPLKEA CRAYGLKSGL KKQELLEALT   600
KHFQD                                                               605

SEQ ID NO: 110          moltype = AA    length = 482
FEATURE                 Location/Qualifiers
source                  1..482
                        mol_type = protein
                        organism = synthetic construct
SEQUENCE: 110
MVRSGNKAAW LCMDVGFTMS NSIPGIESPF EQAKKVITMF VQRQVFAENK DEIALVLFGT    60
DGTDNPLSGG DQYQNITVHR HLMLPDFDLL EDIESKIQPG SQQADFLDAL IVSMDVIQHE   120
TIGKKFEKRH IEIFTDLSSR FSKSQLDIII HSLKKCDISE RHSIHWPCRL TIGSNLSIRI   180
AAYKSILQER VKKTTWDAKT LKKEDIQKET VYCLNDDDET EVLKEDIIQG FRYGSDIVPF   240
SKVDEEQMKY KSEGKCFSVL GFCKSSVQVR RFFMGNQVLK VFAARDDEAA AVALSSLIHA   300
LDDLDIWAIV RYAYDKRANP QVGVAFPHIK HNYECLVYVQ LPFMEDLRQY MFSSLKNSKK   360
YAPTEAQLNA VDALIDSMSL AKKDEKTDTL EDLFPTTKIP NPRFQRLFQC LLHRALHPRE   420
PLPPIQQHIW NMLNPPAEVT TKSQIPLSKI KTLFPLIEAK KKDQVTAQEI FQDNHEDGPT   480
AK                                                                  482

SEQ ID NO: 111          moltype = DNA   length = 10
FEATURE                 Location/Qualifiers
source                  1..10
                        mol_type = other DNA
                        organism = Methanobacterium thermoautotrophicum
SEQUENCE: 111
aatttttgga                                                           10

SEQ ID NO: 112          moltype = AA    length = 83
FEATURE                 Location/Qualifiers
source                  1..83
                        mol_type = protein
                        organism = Methanobacterium thermoautotrophicum
SEQUENCE: 112
GSVIDVSSQR VNVQRPLDAL GNSLNSPVII KLKGDREFRG VLKSFDLHMN LVLNDAEELE    60
DGEVTRRLGT VLIRGDNIVY ISP                                            83

SEQ ID NO: 113          moltype = DNA   length = 25
FEATURE                 Location/Qualifiers
source                  1..25
                        mol_type = other DNA
                        organism = Emesvirus zinderi
SEQUENCE: 113
gcgcacatga ggatcaccca tgtgc                                          25

SEQ ID NO: 114          moltype = AA    length = 116
```

```
FEATURE                 Location/Qualifiers
source                  1..116
                        mol_type = protein
                        organism = Emesvirus zinderi
SEQUENCE: 114
MASNFTQFVL VDNGGTGDVT VAPSNFANGI AEISSNSRSQ AYKVTCSVRQ SSAQNRKYTI    60
KVEVPKGAWR SYLNMELTIP IFATNSDCEL IVKAMQGLLK DGNPIPSAIA ANSGIY       116

SEQ ID NO: 115          moltype = DNA  length = 26
FEATURE                 Location/Qualifiers
source                  1..26
                        mol_type = other DNA
                        organism = Pepevirus rubrum
SEQUENCE: 115
ataaggagtt tatatggaaa ccctta                                        26

SEQ ID NO: 116          moltype = AA  length = 127
FEATURE                 Location/Qualifiers
source                  1..127
                        mol_type = protein
                        organism = Pepevirus rubrum
SEQUENCE: 116
MSKTIVLSVG EATRTLTEIQ STADRQIFEE KVGPLVGRLR LTASLRQNGA KTAYRVNLKL    60
DQADWDCSTS VCGELPKVRY TQVWSHDVTI VANSTEASRK SLYDLTKSLV ATSQVEDLVV   120
NLVPLGR                                                             127

SEQ ID NO: 117          moltype = DNA  length = 19
FEATURE                 Location/Qualifiers
source                  1..19
                        mol_type = other DNA
                        organism = Shigella flexneri
SEQUENCE: 117
ctgaatgcct gcgagcatc                                                19

SEQ ID NO: 118          moltype = AA  length = 62
FEATURE                 Location/Qualifiers
source                  1..62
                        mol_type = protein
                        organism = Shigella flexneri
SEQUENCE: 118
MKSIRCKNCN KLLFKADSFD HIEIRCPRCK RHIIMLNACE HPTEKHCGKR EKITHSDETV    60
RY                                                                   62

SEQ ID NO: 119          moltype = AA  length = 24
FEATURE                 Location/Qualifiers
source                  1..24
                        mol_type = protein
                        organism = synthetic construct
SEQUENCE: 119
EELLSKNYHL ENEVARLKKG SGSG                                          24

SEQ ID NO: 120          moltype = AA  length = 241
FEATURE                 Location/Qualifiers
source                  1..241
                        mol_type = protein
                        organism = synthetic construct
SEQUENCE: 120
EEELLSKNYH LENEVARLKK GSGSGEELLS KNYHLENEVA RLKKGSGSGE ELLSKNYHLE    60
NEVARLKKGS GSGEELLSKN YHLENEVARL KKGSGSGEEL LSKNYHLENE VARLKKGSGS   120
GEELLSKNYH LENEVARLKK GSGSGEELLS KNYHLENEVA RLKKGSGSGE ELLSKNYHLE   180
NEVARLKKGS GSGEELLSKN YHLENEVARL KKGSGSGEEL LSKNYHLENE VARLKKGSGS   240
G                                                                   241

SEQ ID NO: 121          moltype = AA  length = 277
FEATURE                 Location/Qualifiers
source                  1..277
                        mol_type = protein
                        organism = synthetic construct
SEQUENCE: 121
MGPDIVMTQS PSSLSASVGD RVTITCRSST GAVTTSNYAS WVQEKPGKLF KGLIGGTNNR    60
APGVPSRFSG SLIGDKATLT ISSLQPEDFA TYFCALWYSN HWVFGQGTKV ELKRGGGGSG   120
GGGSGGGGSS GGGSEVKLLE SGGGLVQPGG SLKLSCAVSG FSLTDYGVNW VRQAPGRGLE   180
WIGVIWDGDI TDYNSALKDR FIISKDNGKN TVYLQMSKVR SDDTALYYCV TGLFDYWGQG   240
TLVTVSSYPY DVPDYAGGGG GSGGGGSGGG GSGGGGS                            277

SEQ ID NO: 122          moltype = AA  length = 11
FEATURE                 Location/Qualifiers
source                  1..11
                        mol_type = protein
```

```
                    note = Lachnospiraceae bacterium
                    organism = unidentified
SEQUENCE: 122
GFVTESGEKI K                                                        11

SEQ ID NO: 123      moltype = DNA   length = 27
FEATURE             Location/Qualifiers
source              1..27
                    mol_type = other DNA
                    organism = synthetic construct
SEQUENCE: 123
tttaggaatc ccttctgcag cacctgg                                       27

SEQ ID NO: 124      moltype = RNA   length = 43
FEATURE             Location/Qualifiers
source              1..43
                    mol_type = other RNA
                    organism = synthetic construct
SEQUENCE: 124
aatttctact aagtgtagat ggaatcccct ctgcagcacc tgg                     43

SEQ ID NO: 125      moltype = AA   length = 1373
FEATURE             Location/Qualifiers
source              1..1373
                    mol_type = protein
                    organism = synthetic construct
SEQUENCE: 125
MGSKLEKFTN CYSLSKTLRF KAIPVGKTQE NIDNKRLLVE DEKRAEDYKG VKKLLDRYYL    60
SFINDVLHSI KLKNLNNYIS LFRKKTRTEK ENKELENLEI NLRKEIAKAF KGNEGYKSLF   120
KKDIIETILP EFLDDKDEIA LVNSFNGFTT AFTGFFDNRE NMFSEEAKST SIAFRCINEN   180
LTRYISNMDI FEKVDAIFDK HEVQEIKEKI LNSDYDVEDF FEGEFFNFVL TQEGIDVYNA   240
IIGGFVTESG EKIKGLNEYI NLYNQKTKQK LPKFKPLYKQ VLSDRESLSF YGENQTTQKG   300
QKNSRERMKR IEEGIKELGS QILKEHPVEN TQLQNEKLYL YYLQNGRDMY VDQELDINRL   360
SDYDVDHIVP QSFLKDDSID NKVLTRSDKN RGKSDNVPSE EVVKKMKNYW RQLLNAKLIT   420
QRKFDNLTKA ERGGLSEGYT SDEEVLEVFR NTLNKNSEIF SSIKKLEKLF KNFDEYSSAG   480
IFVKNGPAIS TISKDIFGEW NVIRDKWNAE YDDIHLKKKA VVTEKYEDDR RKSFKKIGSF   540
SLEQLQEYAD ADLSVVEKLK EIIIQKVDEI YKVYGSSEKL FDADFVLEKS LKKNDAVVAI   600
MKDLLDSVKS FENYIKAFFG EGKETNRDES FYGDFVLAYD ILLKVDHIYD AIRNYVTQKP   660
YSKDKFKLYF QNPQFMGGWD KDKETDYRAT ILRYGSKYYL AIMDKKYAKC LQKIDKDDVN   720
GNYEKINYKL LPGPNKMLPK VFFSKKWMAY YNPSEDIQKI YKNGTFKKGD MFNLNDCHKL   780
IDFFKDSISR YPKWSNAYDF NFSETEKYKD IAGFYREVEE QGYKVSFESA SKKEVDKLVE   840
EGKLYMFQIY NKDFSDKSHG TPNLHTMYFK LLFDENNHGQ IRLSGGAELF MRRASLKKEE   900
LVVHPANSPI ANKNPDNPKK TTTLSYDVYK DKRFSEDQYE LHIPIAINKC PKNIFKINTE   960
VRVLLKHDDN PYVIGIDRGE RNLLYIVVVD GKGNIVEQYS LNEIINNFNG IRIKTDYHSL  1020
LDKKEKERFE ARQNWTSIEN IKELKAGYIS QVVHKICELV EKYDAVIALE DLNSGFKNSR  1080
VKVEKQVYQK FEKMLIDKLN YMDKKSNPC ATGGALKGYQ ITNKFESFKS MSTQNGFIFY   1140
IPAWLTSKID PSTGFVNLLK TKYTSIADSK KFISSFDRIM YVPEEDLFEF ALDYKNFSRT  1200
DADYIKKWKL YSYGNRIRIF RNPKKNNVFD WEEVCLTSAY KELFNKYGIN YQQGDIRALL  1260
CEQSDKAFYS SFMALMSLML QMRNSITGRT DVDFLISPVK NSDGIFYDSR NYEAQENAIL  1320
PKNADANGAY NIARKVLWAI GQFKKAEDEK LDKVKIAISN KEWLEYAQTS VKH         1373

SEQ ID NO: 126      moltype = AA   length = 1375
FEATURE             Location/Qualifiers
source              1..1375
                    mol_type = protein
                    organism = synthetic construct
SEQUENCE: 126
MGSKLEKFTN CYSLSKTLRF KAIPVGKTQE NIDNKRLLVE DEKRAEDYKG VKKLLDRYYL    60
SFINDVLHSI KLKNLNNYIS LFRKKTRTEK ENKELENLEI NLRKEIAKAF KGNEGYKSLF   120
KKDIIETILP EFLDDKDEIA LVNSFNGFTT AFTGFFDNRE NMFSEEAKST SIAFRCINEN   180
LTRYISNMDI FEKVDAIFDK HEVQEIKEKI LNSDYDVEDF FEGEFFNFVL TQEGIDVYNA   240
IIGGFVTESG EKIKGLNEYI NLYNQKTKQK LPKFKPLYKQ VLSDRESLSF YGSGENQTTQ   300
KGQKNSRERM KRIEEGIKEL GSQILKEHPV ENTQLQNEKL YLYYLQNGRD MYVDQELDIN   360
RLSDYDVDHI VPQSFLKDDS IDNKVLTRSD KNRGKSDNVP SEEVVKKMKN YWRQLLNAKL   420
ITQRKFDNLT KAERGGLSEG YTSDEEVLEV FRNTLNKNSE IFSSIKKLEK LFKNFDEYSS   480
AGIFVKNGPA ISTISKDIFG EWNVIRDKWN AEYDDIHLKK KAVVTEKYED DRRKSFKKIG   540
SFSLEQLQEY ADADLSVVEK LKEIIIQKVD EIYKVYGSSE KLFDADFVLE KSLKKNDAVV   600
AIMKDLLDSV KSFENYIKAF FGEGKETNRD ESFYGDFVLA YDILLKVDHI YDAIRNYVTQ   660
KPYSKDKFKL YFQNPQFMGG WDKDKETDYR ATILRYGSKY YLAIMDKKYA KCLQKIDKDD   720
VNGNYEKINY KLLPGPNKML PKVFFSKKWM AYYNPSEDIQ KIYKNGTFKK GDMFNLNDCH   780
KLIDFFKDSI SRYPKWSNAY DFNFSETEKY KDIAGFYREV EEQGYKVSFE SASKKEVDKL   840
VEEGKLYMFQ IYNKDFSDKS HGTPNLHTMY FKLLFDENNH GQIRLSGGAE LFMRRASLKK   900
EELVVHPANS PIANKNPDNP KKTTTLSYDV YKDKRFSEDQ YELHIPIAIN KCPKNIFKIN   960
TEVRVLLKHD DNPYVIGIDR GERNLLYIVV VDGKGNIVEQ YSLNEIINNF NGIRIKTDYH  1020
SLLDKKEKER FEARQNWTSI ENIKELKAGY ISQVVHKICE LVEKYDAVIA LEDLNSGFKN  1080
SRVKVEKQVY QKFEKMLIDK LNYMDKKSNP CATGGALKGY QITNKFESFK SMSTQNGFI   1140
FYIPAWLTSK IDPSTGFVNL LKTKYTSIAD SKKFISSFDR IMYVPEEDLF EFALDYKNFS  1200
RTDADYIKKW KLYSYGNRIR IFRNPKKNNV FDWEEVCLTS AYKELFNKYG INYQQGDIRA  1260
LLCEQSDKAF YSSFMALMSL MLQMRNSITG RTDVDFLISP VKNSDGIFYD SRNYEAQENA  1320
```

```
ILPKNADANG AYNIARKVLW AIGQFKKAED EKLDKVKIAI SNKEWLEYAQ TSVKH      1375

SEQ ID NO: 127          moltype = AA   length = 1377
FEATURE                 Location/Qualifiers
source                  1..1377
                        mol_type = protein
                        organism = synthetic construct
SEQUENCE: 127
MGSKLEKFTN CYSLSKTLRF KAIPVGKTQE NIDNKRLLVE DEKRAEDYKG VKKLLDRYYL  60
SFINDVLHSI KLKNLNNYIS LFRKKTRTEK ENKELENLEI NLRKEIAKAF KGNEGYKSLF  120
KKDIIETILP EFLDDKDEIA LVNSFNGFTT AFTGFFDNRE NMFSEEAKST SIAFRCINEN  180
LTRYISNMDI FEKVDAIFDK HEVQEIKEKI LNSDYDVEDF FEGEFFNFVL TQEGIDVYNA  240
IIGGFVTESG EKIKGLNEYI NLYNQKTKQK LPKFKPLYKQ VLSDRESLSF YGGSSGENQT  300
TQKGQKNSRE RMKRIEEGIK ELGSQILKEH PVENTQLQNE KLYLYYLQNG RDMYVDQELD  360
INRLSDYDVD HIVPQSFLKD DSIDNKVLTR SDKNRGKSDN VPSEEVVKKM KNYWRQLLNA  420
KLITQRKFDN LTKAERGGLS EGYTSDEEVL EVFRNTLNKN SEIFSSIKKL EKLFKNFDEY  480
SSAGIFVKNG PAISTISKDI FGEWNVIRDK WNAEYDDIHL KKKAVVTEKY EDDRRKSFKK  540
IGSFSLEQLQ EYADADLSVV EKLKEIIIQK VDEIYKVYGS SEKLFDADFV LEKSLKKNDA  600
VVAIMKDLLD SVKSFENYIK AFFGEGKETN RDESFYGDFV LAYDILLKVD HIYDAIRNYV  660
TQKPYSKDKF KLYFQNPQFM GGWDKDKETD YRATILRYGS KYYLAIMDKK YAKCLQKIDK  720
DDVNGNYEKI NYKLLPGPNK MLPKVFFSKK WMAYYNPSED IQKIYKNGTF KKGDMFNLND  780
CHKLIDFFKD SISRYPKWSN AYDFNFSETE KYKDIAGFYR EVEEQGYKVS FESASKKEVD  840
KLVEEGKLYM FQIYNKDFSD KSHGTPNLHT MYFKLLFDEN NHGQIRLSGG AELFMRRASL  900
KKEELVVHPA NSPIANKNPD NPKKTTTLSY DVYKDKRFSE DQYELHIPIA INKCPKNIFK  960
INTEVRVLLK HDDNPYVIGI DRGERNLLYI VVVDGKGNIV EQYSLNEIIN NFNGIRIKTD  1020
YHSLLDKKEK ERFEARQNWT SIENIKELKA GYISQVVHKI CELVEKYDAV IALEDLNSGF  1080
KNSRVKVEKQ VYQKFEKMLI DKLNYMVDKK SNPCATGGAL KGYQITNKFE SFKSMSTQNG  1140
FIFYIPAWLT SKIDPSTGFV NLLKTKYTSI ADSKKFISSF DRIMYVPEED LFEFALDYKN  1200
FSRTDADYIK KWKLYSYGNR IRIFRNPKKN NVFDWEEVCL TSAYKELFNK YGINYQQGDI  1260
RALLCEQSDK AFYSSFMALM SLMLQMRNSI TGRTDVDFLI SPVKNSDGIF YDSRNYEAQE  1320
NAILPKNADA NGAYNIARKV LWAIGQFKKA EDEKLDKVKI AISNKEWLEY AQTSVKH    1377

SEQ ID NO: 128          moltype = AA   length = 1379
FEATURE                 Location/Qualifiers
source                  1..1379
                        mol_type = protein
                        organism = synthetic construct
SEQUENCE: 128
MGSKLEKFTN CYSLSKTLRF KAIPVGKTQE NIDNKRLLVE DEKRAEDYKG VKKLLDRYYL  60
SFINDVLHSI KLKNLNNYIS LFRKKTRTEK ENKELENLEI NLRKEIAKAF KGNEGYKSLF  120
KKDIIETILP EFLDDKDEIA LVNSFNGFTT AFTGFFDNRE NMFSEEAKST SIAFRCINEN  180
LTRYISNMDI FEKVDAIFDK HEVQEIKEKI LNSDYDVEDF FEGEFFNFVL TQEGIDVYNA  240
IIGGFVTESG EKIKGLNEYI NLYNQKTKQK LPKFKPLYKQ VLSDRESLSF YGGSSGENQT  300
TQKGQKNSRE RMKRIEEGIK ELGSQILKEH PVENTQLQNE KLYLYYLQNG RDMYVDQELD  360
INRLSDYDVD HIVPQSFLKD DSIDNKVLTR SDKNRGKSDN VPSEEVVKKM KNYWRQLLNA  420
KLITQRKFDN LTKAERGGLS GSEGYTSDEE VLEVFRNTLN KNSEIFSSIK KLEKLFKNFD  480
EYSSAGIFVK NGPAISTISK DIFGEWNVIR DKWNAEYDDI HLKKKAVVTE KYEDDRRKSF  540
KKIGSFSLEQ LQEYADADLS VVEKLKEIII QKVDEIYKVY GSSEKLFDAD FVLEKSLKKN  600
DAVVAIMKDL LDSVKSFENY IKAFFGEGKE TNRDESFYGD FVLAYDILLK VDHIYDAIRN  660
YVTQKPYSKD KFKLYFQNPQ FMGGWDKDKE TDYRATILRY GSKYYLAIMD KKYAKCLQKI  720
DKDDVNGNYE KINYKLLPGP NKMLPKVFFS KKWMAYYNPS EDIQKIYKNG TFKKGDMFNL  780
NDCHKLIDFF KDSISRYPKW SNAYDFNFSE TEKYKDIAGF YREVEEQGYK VSFESASKKE  840
VDKLVEEGKL YMFQIYNKDF SDKSHGTPNL HTMYFKLLFD ENNHGQIRLS GGAELFMRRA  900
SLKKEELVVH PANSPIANKN PDNPKKTTTL SYDVYKDKRF SEDQYELHIP IAINKCPKNI  960
FKINTEVRVL LKHDDNPYVI DRGERNLL YIVVVDGKGN IVEQYSLNEI INNFNGIRIK  1020
TDYHSLLDKK EKERFEARQN WTSIENIKEL KAGYISQVVH KICELVEKYD AVIALEDLNS  1080
GFKNSRVKVE KQVYQKFEKM LIDKLNYMVD KKSNPCATGG ALKGYQITNK FESFKSMSTQ  1140
NGFIFYIPAW LTSKIDPSTG FVNLLKTKYT SIADSKKFIS SFDRIMYVPE EDLFEFALDY  1200
KNFSRTDADY IKKWKLYSYG NRIRIFRNPK KNNVFDWEEV CLTSAYKELF NKYGINYQQ  1260
DIRALLCEQS DKAFYSSFMA LMSLMLQMRN SITGRTDVDF LISPVKNSDG IFYDSRNYEA  1320
QENAILPKNA DANGAYNIAR KVLWAIGQFK KAEDEKLDKV KIAISNKEWL EYAQTSVKH  1379

SEQ ID NO: 129          moltype = AA   length = 1373
FEATURE                 Location/Qualifiers
source                  1..1373
                        mol_type = protein
                        organism = synthetic construct
SEQUENCE: 129
MGSKLEKFTN CYSLSKTLRF KAIPVGKTQE NIDNKRLLVE DEKRAEDYKG VKKLLDRYYL  60
SFINDVLHSI KLKNLNNYIS LFRKKTRTEK ENKELENLEI NLRKEIAKAF KGNEGYKSLF  120
KKDIIETILP EFLDDKDEIA LVNSFNGFTT AFTGFFDNRE NMFSEEAKST SIAFRCINEN  180
LTRYISNMDI FEKVDAIFDK HEVQEIKEKI LNSDYDVEDF FEGEFFNFVL TQEGIDVYNA  240
IIGGFVTESG EKIKGLNEYI NLYNQKTKQK LPKFKPLYKQ VLSDRESLSF YGEENQTTQK  300
GQKNSRERMK RIEEGIKELG SQILKEHPVE NTQLQNEKLY LYYLQNGRDM YVDQELDINR  360
LSDYDVDHIV PQSFLKDDSI DNKVLTRSDK NRGKSDNVPS EEVVKKMKNY WRQLLNAKLI  420
TQRKFDNLTK AERGGLSGYT SDEEVLEVFR NTLNKNSEIF SSIKKLEKLF KNFDEYSSAG  480
IFVKNGPAIS TISKDIFGEW NVIRDKWNAE YDDIHLKKKA VVTEKYEDDR RKSFKKIGSF  540
SLEQLQEYAD ADLSVVEKLK EIIIQKVDEI YKVYGSSEKL FDADFVLEKS LKKNDAVVAI  600
MKDLLDSVKS FENYIKAFFG EGKETNRDES FYGDFVLAYD ILLKVDHIYD AIRNYVTQKP  660
```

```
YSKDKFKLYF QNPQFMGGWD KDKETDYRAT ILRYGSKYYL AIMDKKYAKC LQKIDKDDVN    720
GNYEKINYKL LPGPNKMLPK VFFSKKWMAY YNPSEDIQKI YKNGTFKKGD MFNLNDCHKL    780
IDFFKDSISR YPKWSNAYDF NFSETEKYKD IAGFYREVEE QGYKVSFESA SKKEVDKLVE    840
EGKLYMFQIY NKDFSDKSHG TPNLHTMYFK LLFDENNHGQ IRLSGGAELF MRRASLKKEE    900
LVVHPANSPI ANKNPDNPKK TTTLSYDVYK DKRFSEDQYE LHIPIAINKC PKNIFKINTE    960
VRVLLKHDDN PYVIGIDRGE RNLLYIVVVD GKGNIVEQYS LNEIINNFNG IRIKTDYHSL   1020
LDKKEKERFE ARQNWTSIEN IKELKAGYIS QVVHKICELV EKYDAVIALE DLNSGFKNSR   1080
VKVEKQVYQK FEKMLIDKLN YMVDKKSNPC ATGGALKGYQ ITNKFESFKS MSTQNGFIFY   1140
IPAWLTSKID PSTGFVNLLK TKYTSIADSK KFISSFDRIM YVPEEDLFEF ALDYKNFSRT   1200
DADYIKKWKL YSYGNRIRIF RNPKKNNVFD WEEVCLTSAY KELFNKYGIN YQQGDIRALL   1260
CEQSDKAFYS SFMALMSLML QMRNSITGRT DVDFLISPVK NSDGIFYDSR NYEAQENAIL   1320
PKNADANGAY NIARKVLWAI GQFKKAEDEK LDKVKIAISN KEWLEYAQTS VKH          1373

SEQ ID NO: 130        moltype = AA  length = 1375
FEATURE               Location/Qualifiers
source                1..1375
                      mol_type = protein
                      organism = synthetic construct
SEQUENCE: 130
MGSKLEKFTN CYSLSKTLRF KAIPVGKTQE NIDNKRLLVE DEKRAEDYKG VKKLLDRYYL     60
SFINDVLHSI KLKNLNNYIS LFRKKTRTEK ENKELENLEI NLRKEIAKAF KGNEGYKSLF    120
KKDIIETILP EFLDDKDEIA LVNSFNGFTT AFTGFFDNRE NMFSEEAKST SIAFRCINEN    180
LTRYISNMDI FEKVDAIFDK HEVQEIKEKI LNSDYDVEDF FEGEFFNFVL TQEGIDVYNA    240
IIGGFVTESG EKIKGLNEYI NLYNQKTKQK LPKFKPLYKQ VLSDRESLSF YGEGSENQTT    300
QKGQKNSRER MKRIEEGIKE LGSQILKEHP VENTQLQNEK LYLYYLQNGR DMYVDQELDI    360
NRLSDYDVDH IVPQSFLKDD SIDNKVLTRS DKNRGKSDNV PSEEVVKKMK NYWRQLLNAK    420
LITQRKFDNL TKAERGGLSG YTSDEEVLEV FRNTLNKNSE IFSSIKKLEK LFKNFDEYSS    480
AGIFVKNGPA ISTISKDIFG EWNVIRDKWN AEYDDIHLKK KAVVTEKYED DRRKSFKKIG    540
SFSLEQLQEY ADADLSVVEK LKEIIIQKVD EIYKVYGSSE KLFDADFVLE KSLKKNDAVV    600
AIMKDLLDSV KSFENYIKAF FGEGKETNRD ESFYGDFVLA YDILLKVDHI YDAIRNYVTQ    660
KPYSKDKFKL YFQNPQFMGG WDKDKETDYR ATILRYGSKY YLAIMDKKYA KCLQKIDKDD    720
VNGNYEKINY KLLPGPNKML PKVFFSKKWM AYYNPSEDIQ KIYKNGTFKK GDMFNLNDCH    780
KLIDFFKDSI SRYPKWSNAY DFNFSETEKY KDIAGFYREV EEQGYKVSFE SASKKEVDKL    840
VEEGKLYMFQ IYNKDFSDKS HGTPNLHTMY FKLLFDENNH GQIRLSGGAE LFMRRASLKK    900
EELVVHPANS PIANKNPDNP KKTTTLSYDV YKDKRFSEDQ YELHIPIAIN KCPKNIFKIN    960
TEVRVLLKHD DNPYVIGIDR GERNLLYIVV VDGKGNIVEQ YSLNEIINNF NGIRIKTDYH   1020
SLLDKKEKER FEARQNWTSI ENIKELKAGY ISQVVHKICE LVEKYDAVIA LEDLNSGFKN   1080
SRVKVEKQVY QKFEKMLIDK LNYMVDKKSN PCATGGALKG YQITNKFESF KSMSTQNGFI   1140
FYIPAWLTSK IDPSTGFVNL LKTKYTSIAD SKKFISSFDR IMYVPEEDLF EFALDYKNFS   1200
RTDADYIKKW KLYSYGNRIR IFRNPKKNNV FDWEEVCLTS AYKELFNKYG INYQQGDIRA   1260
LLCEQSDKAF YSSFMALMSL MLQMRNSITG RTDVDFLISP VKNSDGIFYD SRNYEAQENA   1320
ILPKNADANG AYNIARKVLW AIGQFKKAED EKLDKVKIAI SNKEWLEYAQ TSVKH        1375

SEQ ID NO: 131        moltype = AA  length = 1375
FEATURE               Location/Qualifiers
source                1..1375
                      mol_type = protein
                      organism = synthetic construct
SEQUENCE: 131
SKLEKFTNCY SLSKTLRFKA IPVGKTQENI DNKRLLVEDE KRAEDYKGVK KLLDRYYLSF     60
INDVLHSIKL KNLNNYISLF RKKTREKEN KELENLEINL RKEIAKAFKG NEGYKSLFKK    120
DIIETILPEF LDDKDEIALV NSFNGFTTAF TGFFDNRENM FSEEAKSTSI AFRCINENLT    180
RYISNMDIFE KVDAIFDKHE VQEIKEKILN SDYDVEDFFE GEFFNFVLTQ EGIDVYNAII    240
GGFVTESGEK IKGLNEYINL YNQKTKQKLP KFKPLYKQVL SDRESLSFYG EGSSGENQTT    300
QKGQKNSRER MKRIEEGIKE LGSQILKEHP VENTQLQNEK LYLYYLQNGR DMYVDQELDI    360
NRLSDYDVDH IVPQSFLKDD SIDNKVLTRS DKNRGKSDNV PSEEVVKKMK NYWRQLLNAK    420
LITQRKFDNL TKAERGGLSG YTSDEEVLEV FRNTLNKNSE IFSSIKKLEK LFKNFDEYSS    480
AGIFVKNGPA ISTISKDIFG EWNVIRDKWN AEYDDIHLKK KAVVTEKYED DRRKSFKKIG    540
SFSLEQLQEY ADADLSVVEK LKEIIIQKVD EIYKVYGSSE KLFDADFVLE KSLKKNDAVV    600
AIMKDLLDSV KSFENYIKAF FGEGKETNRD ESFYGDFVLA YDILLKVDHI YDAIRNYVTQ    660
KPYSKDKFKL YFQNPQFMGG WDKDKETDYR ATILRYGSKY YLAIMDKKYA KCLQKIDKDD    720
VNGNYEKINY KLLPGPNKML PKVFFSKKWM AYYNPSEDIQ KIYKNGTFKK GDMFNLNDCH    780
KLIDFFKDSI SRYPKWSNAY DFNFSETEKY KDIAGFYREV EEQGYKVSFE SASKKEVDKL    840
VEEGKLYMFQ IYNKDFSDKS HGTPNLHTMY FKLLFDENNH GQIRLSGGAE LFMRRASLKK    900
EELVVHPANS PIANKNPDNP KKTTTLSYDV YKDKRFSEDQ YELHIPIAIN KCPKNIFKIN    960
TEVRVLLKHD DNPYVIGIDR GERNLLYIVV VDGKGNIVEQ YSLNEIINNF NGIRIKTDYH   1020
SLLDKKEKER FEARQNWTSI ENIKELKAGY ISQVVHKICE LVEKYDAVIA LEDLNSGFKN   1080
SRVKVEKQVY QKFEKMLIDK LNYMVDKKSN PCATGGALKG YQITNKFESF KSMSTQNGFI   1140
FYIPAWLTSK IDPSTGFVNL LKTKYTSIAD SKKFISSFDR IMYVPEEDLF EFALDYKNFS   1200
RTDADYIKKW KLYSYGNRIR IFRNPKKNNV FDWEEVCLTS AYKELFNKYG INYQQGDIRA   1260
LLCEQSDKAF YSSFMALMSL MLQMRNSITG RTDVDFLISP VKNSDGIFYD SRNYEAQENA   1320
ILPKNADANG AYNIARKVLW AIGQFKKAED EKLDKVKIAI SNKEWLEYAQ TSVKH        1375

SEQ ID NO: 132        moltype = AA  length = 1379
FEATURE               Location/Qualifiers
source                1..1379
                      mol_type = protein
                      organism = synthetic construct
SEQUENCE: 132
```

-continued

```
MGSKLEKFTN CYSLSKTLRF KAIPVGKTQE NIDNKRLLVE DEKRAEDYKG VKKLLDRYYL    60
SFINDVLHSI KLKNLNNYIS LFRKKTRTEK ENKELENLEI NLRKEIAKAF KGNEGYKSLF   120
KKDIIETILP EFLDDKDEIA LVNSFNGFTT AFTGFFDNRE NMFSEEAKST SIAFRCINEN   180
LTRYISNMDI FEKVDAIFDK HEVQEIKEKI LNSDYDVEDF FEGEFFNFVL TQEGIDVYNA   240
IIGGFVTESG EKIKGLNEYI NLYNQKTKQK LPKFKPLYKQ VLSDRESLSF YGEGSSGENQ   300
TTQKGQKNSR ERMKRIEEGI KELGSQILKE HPVENTQLQN EKLYLYYLQN GRDMYVDQEL   360
DINRLSDYDV DHIVPQSFLK DDSIDNKVLT RSDKNRGKSD NVPSEEVVKK MKNYWRQLLN   420
AKLITQRKFD NLTKAERGGL SGSGYTSDEE VLEVFRNTLN KNSEIFSSIK KLEKLFKNFD   480
EYSSAGIFVK NGPAISTISK DIFGEWNVIR DKWNAEYDDI HLKKKAVVTE KYEDDRRKSF   540
KKIGSFSLEQ LQEYADADLS VVEKLKEIII QKVDEIYKVY GSSEKLFDAD FVLEKSLKKN   600
DAVVAIMKDL LDSVKSFENY IKAFFGEGKE TNRDESFYGD FVLAYDILLK VDHIYDAIRN   660
YVTQKPYSKD KFKLYFQNPQ FMGGWDKDKE TDYRATILRY GSKYYLAIMD KKYAKCLQKI   720
DKDDVNGNYE KINYKLLPGP NKMLPKVFFS KKWMAYYNPS EDIQKIYKNG TFKKGDMFNL   780
NDCHKLIDFF KDSISRYPKW SNAYDFNFSE TEKYKDIAGF YREVEEQGYK VSFESASKKE   840
VDKLVEEGKL YMFQIYNKDF SDKSHGTPNL HTMYFKLLFD ENNHGQIRLS GGAELFMRRA   900
SLKKEELVVH PANSPIANKN PDNPKKTTTL SYDVYKDKRF SEDQYELHIP IAINKCPKNI   960
FKINTEVRVL LKHDDNPYVI GIDRGERNLL YIVVVDGKGN IVEQYSLNEI INNFNGIRIK  1020
TDYHSLLDKK EKERFEARQN WTSIENIKEL KAGYISQVVH KICELVEKYD AVIALEDLNS  1080
GFKNSRVKVE KQVYQKFEKM LIDKLNYMVD KKSNPCATGG ALKGYQITNK FESFKSMSTQ  1140
NGFIFYIPAW LTSKIDPSTG FVNLLKTKYT SIADSKKFIS SFDRIMYVPE EDLFEFALDY  1200
KNFSRTDADY IKKWKLYSYG NRIRIFRNPK KNNVFDWEEV CLTSAYKELF NKYGINYQQG  1260
DIRALLCEQS DKAFYSSFMA LMSLMLQMRN SITGRTDVDF LISPVKNSDG IFYDSRNYEA  1320
QENAILPKNA DANGAYNIAR KVLWAIGQFK KAEDEKLDKV KIAISNKEWL EYAQTSVKH   1379
```

SEQ ID NO: 133        moltype = DNA  length = 46
FEATURE                  Location/Qualifiers
source                   1..46
                           mol_type = other DNA
                           organism = synthetic construct
SEQUENCE: 133
gatgctttag gaatcccttc tgcagcacct gggcgcaggt cacgag                46

SEQ ID NO: 134        moltype = DNA  length = 99
FEATURE                  Location/Qualifiers
source                   1..99
                           mol_type = other DNA
                           organism = Homo sapiens
SEQUENCE: 134
cctccggatt cctacccga aaagacagtg gttaggacag ggatcaccgg ggtgacaccc  60
cacctcccct gtctattttc atgggtcttg gtctcggtg                          99

SEQ ID NO: 135        moltype = DNA  length = 99
FEATURE                  Location/Qualifiers
source                   1..99
                           mol_type = other DNA
                           organism = Homo sapiens
SEQUENCE: 135
ggaggcctaa ggatggggct tttctgtcac caatcctgtc cctagtggcc ccactgtggg  60
gtggaggga cagataaaag tacccagaac cagagccac                           99

SEQ ID NO: 136        moltype = DNA  length = 20
FEATURE                  Location/Qualifiers
source                   1..20
                           mol_type = other DNA
                           organism = Homo sapiens
SEQUENCE: 136
gcattttcag gaggaagcga                                                   20

SEQ ID NO: 137        moltype = DNA  length = 23
FEATURE                  Location/Qualifiers
source                   1..23
                           mol_type = other DNA
                           organism = Homo sapiens
SEQUENCE: 137
caggaggaag cgatggcttc aga                                          23

SEQ ID NO: 138        moltype = DNA  length = 20
FEATURE                  Location/Qualifiers
source                   1..20
                           mol_type = other DNA
                           organism = Homo sapiens
SEQUENCE: 138
gtcccctcca ccccacagtg                                                   20

SEQ ID NO: 139        moltype = DNA  length = 23
FEATURE                  Location/Qualifiers
source                   1..23
                           mol_type = other DNA
                           organism = Homo sapiens

```
SEQUENCE: 139
tctgtccct ccaccccaca gtg                                                  23

SEQ ID NO: 140          moltype = DNA  length = 4101
FEATURE                 Location/Qualifiers
source                  1..4101
                        mol_type = other DNA
                        organism = synthetic construct
SEQUENCE: 140
gacaagaagt acagcatcgg cctggacatc ggcaccaact ctgtgggctg ggccgtgatc        60
accgacgagt acaaggtgcc cagcaagaaa ttcaaggtgc tgggcaacac cgaccggcac       120
agcatcaaga agaacctgat cggagccctg ctgttcgaca cgggcgaaac agccgaggcc       180
acccggctga agagaaccgc cagaagaaga tacaccgacg gaagaaccg gatctgctat        240
ctgcaagaga tcttcagcaa cgagatggcc aaggtgacg aagcttctt ccacagactg         300
gaagagtcct tcctggtgga agaggataag aagcacgagc ggcaccccat cttcggcaac       360
atcgtggacg aggtggccta ccacgagaag taccccacca tctaccacct gagaaagaaa       420
ctggtggaca gcaccgacaa ggccgacctg cggctgatct atctggccct ggcccacatg       480
atcaagttcc ggggccactt cctgatcgag ggcgacctga accccgacaa cagcgacgtg       540
gacaagctgt tcatccagct ggtgcagacc tacaaccagc tgttcgagga aaacccatc        600
aacgccagcg gcgtcgacgc caaggccatc ctgtctgcca gactgagcaa gagcagacgg       660
ctggaaaatc tgatcgccca gctgcccggc gagaagaaga atggcctgtt cggaaacctg       720
attgccctga gcctgggcct gaccccaac ttcaagagca acttcgacct ggccgaggat        780
gccaaactgc agctgagcaa ggacacctac gacgacgacc tggacaacct gctggcccga       840
atcggcgacc agtacgccga cctgtttctg gccgccaaga acctgtccga cgccatcctg       900
ctgagcgaca tcctgagagt gaacaccgag atcaccaagg cccccctgag cgcctctatg       960
atcaagagat acgacgagca ccaccaggac ctgaccctgc tgaaagctct cgtgcggcag      1020
cagctgcctg agaagtacaa agagattttc ttcgaccaga gcaagaacgg ctacgccggc      1080
tacattgacg gcgcagccag ccaggaagag ttctacaagt catcaagcc catcctggaa       1140
aagatgacg gcaccgagga actgctcgtg aagctgaaca gagaggacct gctgcggaag      1200
cagcggacct tcgacaacgg cagcatcccc caccagatcc acctgggaga gctgcacgcc      1260
attctgcgc ggcaggaaga ttttaccca ttcctgaagg acaaccggga aagatcgag         1320
aagatcctga ccttccgcat ccctactac gtgggccctc tggccagggg aaacagcaga       1380
ttcgcctgga tgaccagaaa gagcgaggaa accatcaccc ctggaactt cgaggaagtg       1440
gtggacaagg gcgcttccgc ccagagcttc atcgagcgga tgaccaactt cgataagaac     1500
ctgcccaacg agaaggtgct gcccaagcac agcctgctgt acgagtactt caccgtgtat     1560
aacgagctga ccaaagtgaa atacgtgacc gagggaatga aaagcccgc cttcctgagc       1620
ggcgagcaga aaaggccat cgtggacctg ctgttcaaga ccaaccggaa agtgaccgtg       1680
aagcagctca aagaggacta cttcaagaaa atcgagtgct tcgactccgt ggaaatctcc      1740
ggcgtggaag atcggttcaa cgcctccctg ggcacatacc acgatctgct gaaaattatc      1800
aaggacaagg acttcctgga caatgaagaa aacgaggaca ttctggaaga tatcgtgctg      1860
accctgacac tgtttgagga cagagagatg atcgaggaac ggctgaaaac ctatgcccac      1920
ctgttcgacg acaaagtgat gaagcagctg aagcggcgga gatacaccgg ctggggcagg      1980
ctgagcgga agctgatcaa cggcatccgg gacaagcagt ccggcaagac aatcctggat      2040
ttcctgaagt ccgacggctt cgccaacaga aacttcatgc agctgatcca cgacgacagc     2100
ctgaccttta agaggacat ccagaaagcc caggtgtccg gccagggcga tagcctgcac       2160
gagcacattg ccaatctggc cggcagcccc gccattaaga agggcatcct gcagacagtg      2220
aaggtggtgg acgagctcgt gaaagtgatg ggccgcacaa agcccgagaa catcgtgatc     2280
gaaatggcca gagaaaacca gaccacccag aagggacaga gaacagccg cgagagaatg     2340
aagcggatcg aagagggcat caaagagctg ggcagccaga tcctgaagga acaccccgtg     2400
gaaacaccc agctgcagaa cgagaagctg tacctgtact acctgcagaa tgggcgggat      2460
atgtacgtga ccaggaact ggacatcaac cggctgtccg actacgatgt ggaccatatc      2520
gtgcctcaga gctttctgaa ggacgactcc atcgacaaca aggtgctgac cagaagcgac     2580
aagaaccggg gcaagagcga caacgtgccc tccgaagagg tcgtgaagaa gatgaagaac     2640
tactggcggc agctgctgaa cgccaagctg attcccaga gaaagttcga caatctgacc      2700
aaggccgaga gaggcggcct gagcgaactg gataaggccg gcttcatcaa gagacagctg     2760
gtggaaaccc ggcagatcac aaagcacgtg gcacagatcc tggactccg gatgaacact      2820
aagtacgacg agaatgacaa gctgatccgg gaagtgaaag tgatcaccct gaagtccaag     2880
ctggtgtccg atttccggaa ggatttccag ttttacaaag tgcgcgagat caacaactac     2940
caccacgccc acgacgccta cctgaacgcc gtcgtgggaa ccgccctgat caaaaagtac     3000
cctaagctgg aaagcgagtt cgtgtacggc gactacaagg tgtacgacgt gcggaagatg     3060
atcgccaaga gcgagcagga atcggcaag gctaccgcca gtactctt ctacagcaac        3120
atcatgaact ttttcaagac cgagattacc ctggccaacg gcgagatccg gaagcggcct     3180
ctgatcgaga caaacggcga aaccgggag atcgtgtggg ataagggccg ggattttgcc      3240
accgtgcgga agtgctgag catgccccaa gtgaatatcg tgaaaaagac cgaggtgcag      3300
acaggcggct tcagcaaaga gtctatcctg cccaaggga acagcgataa gctgatcgcc     3360
agaaagaagg actgggaccc taagaagtac ggcggcttcg acagccccac cgtgcctat     3420
tctgtgctgg tggtggccaa agtggaaag gcaagtcca agaaactgaa gagtgtgaaa      3480
gagctgctgg ggatcaccat catggaagga agcagctcg agaagaatcc catcgacttt     3540
ctggaagcca agggctacaa agaagtgaaa aaggacctga tcatcaagct gcctaagtac     3600
tccctgttcg agctgaaaa cggccggaag agaatgctgg cctctgccgg cgaactgcag     3660
aagggaaacg aactggccct gcccctccaa tatgtgaact tcctgtacct ggccagccac     3720
tatgagaagc tgaagggctc ccccgaggat aatgagcaga acagctgtt tgtggaacag     3780
cacaagcact acctggacga gatcatcgag cagatcagcg agttcccaa gagagtgatc     3840
ctggccgacg ctaatctgga caaagtgctg tccgcctaca acaagcaccg ggataagccc     3900
atcagagagc aggccgagaa tatcatccac ctgtttaccc tgaccaatct gggagccct      3960
gccgccttca gtactttga caccaccatc gaccggaaga gtacaccag caccaaagag      4020
gtgctggacg ccaccctgat ccaccagagc atcaccggcc tgtacgagac acggatcgac     4080
ctgtctcagc tgggaggtga c                                                4101
```

```
SEQ ID NO: 141         moltype = DNA   length = 4101
FEATURE                Location/Qualifiers
source                 1..4101
                       mol_type = other DNA
                       organism = synthetic construct
SEQUENCE: 141
gacaagaagt acagcatcgg cctggacatc ggcaccaact ctgtgggctg ggccgtgatc    60
accgacgagt caaggtgcc cagcaagaaa ttcaaggtgc tgggcaacac cgaccggcac   120
agcatcaaga agaacctgat cggagccctg ctgttcgaca gcggcgaaac agccgaggcc   180
acccggctga agagaaccgc cagaagaaga tacaccagac ggaagaaccg gatctgctat   240
ctgcaagaga tcttcagcaa cgagatggcc aaggtggacg acagcttctt ccacagactg   300
gaagagtcct tcctggtgga agaggataag aagcacgagc ggcaccccat cttcggcaac   360
atcgtggacg aggtggccta ccacgagaag taccccacca tctaccacct gagaaagaaa   420
ctggtggaca gcaccgacaa ggccgacctg cggctgatct atctggccct ggcccacatg   480
atcaagttcc ggggccactt cctgatcgag ggcgacctga accccgacaa cagcgacgtg   540
gacaagctgt tcatccagct ggtgcagacc tacaaccagc tgttcgagga aaaccccatc   600
aacgccagcg gcgtggacgc caaggccatc ctgtctgcca gactgagcaa gagcagacgg   660
ctggaaaaatc tgatcgccca gctgcccggc gagaagaaga atggcctgtt cggaaacctg   720
attgccctga gcctgggcct gacccccaac ttcaagagca acttcgacct ggccgaggat   780
gccaaactgc agctgagcaa ggacacctac gacgacgacc tggacaacct gctggcccag   840
atcggcgacc agtacgccga cctgtttctg gccgccaaga acctgtccga cgccatcctg   900
ctgagcgaca tcctgagagt gaacaccgag atcaccaagg cccccctgag cgcctctatg   960
atcaagagat acgacgagca ccaccaggac ctgaccctgc tgaaagctct cgtgcggcag  1020
cagctgcctg agaagtacaa agagattttc ttcgaccaga gcaagaacgg ctacgccggc  1080
tacattgacg gcggagccag ccaggaagag ttctacaagt tcatcaagcc catcctggaa  1140
aagatggacg gcaccgagga actgctcgtg aagctgaaca gagaggacct gctgcgaaag  1200
cagcggacct tcgacaacgg cagcatcccc accagatcc acctgggaga gctgcacgcc  1260
attctgcggc ggcaggaaga tttttaccca ttcctgaagg acaaccggga aaagatcgag  1320
aagatcctga ccttccgcat ccctactac gtgggccctc tggccagggg aaacagcaga  1380
ttcgcctgga tgaccagaaa gagcgaggaa accatccaga cctggaactt cgaggaagtg  1440
gtggacaagg gcgcttccgc ccagagcttc atcgagcgga tgaccaactt cgataagaac  1500
ctgcccaacg agaaggtgct gcccaagcac agcctgctgt acgagtactt caccgtgtat  1560
aacgagctga ccaaagtgaa atacgtgacc gagggaatga aaagcccgc cttcctgagc  1620
ggcgagcaga aaaaggccat cgtggacctg ctgttcaaga ccaaccggaa agtgaccgtg  1680
aagcagctga aagaggacta cttcaagaaa atcgagtgct tcgactccgt ggaaatctcc  1740
ggcgtggaag atcggttcaa cgcctccctg ggcacatacc acgatctgct gaaaattatc  1800
aaggacaagg acttcctgga caatgaggaa aacgaggaca ttctggaaga tatcgtgctg  1860
accctgacac tgtttgagga cagagagatg atcgaggaac ggctgaaaac ctatgcccac  1920
ctgttcgacg acaaagtgat gaagcagctg aagcggcgga gataccgg ctgggcagg  1980
ctgagccgga agctgatcaa cggcatccgg gacaagcagt ccggcaagac aatcctggat  2040
ttcctgaagt ccgacggctt cgccaacaga aacttcatgc agctgatcca cgacgacagc  2100
ctgacctttta aagaggacat ccagaaagcc caggtgtccg gccagggcga tagcctgcac  2160
gagcacattg ccaatctggc cggcagcccc gccattaaga gggcatct gcagacagtg  2220
aaggtggtgg acgagctcgt gaaagtgatg ggccggcaca gcccgagaa catcgtgatc  2280
gaaatggcca gagagaacca gaccacccag aagggacaga gaacagccg cgagagaatg  2340
aagcggatcg aagagggcat caaagagctg ggcagccaga tcctgaaaga caccccgtg  2400
gaaaacaccc agctgcagaa cgagaagctg tacctgtact acctgcagaa tgggcgggat  2460
atgtacgtgg accaggaact ggacatcaac cggctgtccg actacgatgt ggaccatatc  2520
gtgcctcaga gctttctggc cgacgactcc atcgacaaca aggtgctgac cagaagcgac  2580
aagaaccggg gcaagagcga caacgtgccc tccgaagagg tcgtgaagaa gatgaagaac  2640
tactgcgacg agctgctgaa cgccaagctg attacccaga gaaagttcga caatctgacc  2700
aaggccgaga gaggcggcct gagcgaactg gataaggccg gcttcatcaa gagacagctg  2760
gtggaaaccc ggcagatcac aaagcacgtg gcacagatcc tggactccg gatgaacact  2820
aagtacgacg agaatgacaa gctgatccgg gaagtgaaag tgatcaccct gaagtccaag  2880
ctggtgtccg atttccggaa ggatttccag ttttacaaag tgcgcgagat caacaactac  2940
caccacgccc acgacgccta cctgaacgcc gtcgtgggaa ccgccctgat caaaaagtac  3000
cctgccctgg aaagcgagtt cgtgtacggc gactacaagg tgtacgacgt gcggaagatg  3060
atcgccaaga gcgagcagga aatcggcaag gctaccgcca gtacttctt ctacagcaac  3120
atcatgaact ttttcaagac cgagattacc ctggccaacg gcgagatccg gaaggccct  3180
ctgatcgaga caaacggcga aaccgggagg atcgtgtggg ataagggccg ggattttgcc  3240
accgtgcgga aagtgctgag catgccccaa gtgaatatcg tgaaaaagac cgaggtgcag  3300
acaggcggct tcagcaaaga gtctatcctg cccaagagga cagcgataa gctgatcgcc  3360
agaaagaagg actgggaccc taagaagtac ggcggcttcg acagcccac cgtggcctat  3420
tctgtgctgg tggtggccaa agtggaaaag gcaagtcca gaaactgaa gagtgtgaaa  3480
gagctgctgg ggatcaccat catggaaaga agcagcttcg agaagaatcc catcgacttt  3540
ctggaagcca agggctacaa agaagtgaaa aaggacctga tcatcaagct gcctaagtac  3600
tccctgttcg agctggaaaa cggccggaag agaatgctgg cctctgccgg cgaactgcag  3660
aagggaaacg aactggccct gccctccaaa tatgtgaact tcctgtacct ggccagccac  3720
tatgagaagc tgaagggctc ccccgaggat aatgagcaga acagctgtt tgtggaacag  3780
cacaagcact acctggacga gatcatcgag cagatcagcg agttctccaa gagagtgatc  3840
ctggccgacg ctaatctgga caaagtgctg tccgcctaca acaagcaccg ggataagccc  3900
atcagagagc aggccgagaa tatcatccac ctgtttaccc tgaccaatct gggagcccct  3960
gccgccttca gtactttga caccaccatc gaccggaaga ggtacaccag caccaaagag  4020
ctgctggacg ccaccctgat ccaccagagc atcaccggcc tgtacgagac acggatcgac  4080
ctgtctcagc tgggaggtga c                                            4101

SEQ ID NO: 142         moltype = DNA   length = 4101
FEATURE                Location/Qualifiers
source                 1..4101
``` mol_type = other DNA
                    organism = synthetic construct
SEQUENCE: 142
gacaagaagt acagcatcgg cctggccatc ggcaccaact ctgtgggctg ggccgtgatc    60
accgacgagt acaaggtgcc cagcaagaaa ttcaaggtgc tgggcaacac cgaccggcac   120
agcatcaaga agaacctgat cggagccctg ctgttcgaca gcggcgaaac agccgaggcc   180
acccggctga agagaaccgc cagaagaaga tacaccagac ggaagaaccg gatctgctat   240
ctgcaagaga tcttcagcaa cgagatggcc aaggtggacg acagcttctt ccacagactg   300
gaagagtcct tcctggtgga agaggataag aagcacgagc ggcaccccat cttcggcaac   360
atcgtggacg aggtggccta ccacgagaag taccccacca tctaccacct gagaaagaaa   420
ctggtggaca gcaccgacaa ggccgacctg cggctgatct atctggccct ggcccacatg   480
atcaagttcc ggggccactt cctgatcgag ggcgacctga accccgacaa cagcgacgtg   540
gacaagctgt tcatccagct ggtgcagacc tacaaccagc tgttcgagga aaacccatc   600
aacgccagcg gcgtggacgc caaggccatc ctgtctgcca gactgagcaa gagcagacgg   660
ctggaaaatc tgatcgccca gctgcccggc gagaagaaga atggcctgtt cggaaacctg   720
attgccctga gcctgggcct gacccccaac ttcaagagca acttcgacct ggccgaggat   780
gccaaactgc agctgagcaa ggacacctac gacgacgacc tggacaacct gctggcccag   840
atcggcgacc agtacgccga cctgtttctg gccgccaaga acctgtccga cgccatcctg   900
ctgagcgaca tcctgagagt gaacaccgag atcaccaagg cccccctgag cgcctctatg   960
atcaagagat acgacgagca ccaccaggac ctgaccctgc tgaaagctct cgtgcggcag  1020
cagctgcctg agaagtacaa agattttttc ttcgaccaga gcaagaacgg ctacgccggc  1080
tacattgacg gcggagccag ccaggaagag ttctacaagt tcatcaagcc catcctggaa  1140
aagatggacg gcaccgagga actgctcgtg aagctgaaca gagaggacct gctgcggaag  1200
cagcggacct cgacaacgg cagcatcccc caccagatcc acctgggaga gctgcacgcc  1260
attctgcggc ggcaggaaga tttttaccca ttcctgaagg acaaccggga aaagatcgag  1320
aagatcctga ccttccgcat ccctactac gtgggccctc tggccagggg aaacagcaga  1380
ttcgcctgga tgaccagaaa gagcgaggaa accatcaccc cctggaactt cgaggaagtg  1440
gtggacaagg gcgcttccgc ccagagcttc atcgagcgga tgaccaactt cgataagaac  1500
ctgcccaacg agaaggtgct gcccaagcac agcctgctgt acgagtactt caccgtgtat  1560
aacgccatcg ccaaagtgaa atcgtgacc gagggaatga gaaagcccgc cttcctggc   1620
ggcgagcaga aaaaggccat cgtggacctg ctgttcaaga ccaaccggaa agtgaccgtg  1680
aagcagctga aagaggacta cttcaagaaa atcgagtgct tcgactccgt ggaaatctcc  1740
ggcgtggaag atcggttcaa cgcctccctg ggcacatacc acgatctgct gaaaattatc  1800
aaggacaagg acttcctgga caatgaggaa aacgaggaca ttctggaaga tatcgtgctg  1860
accctgacac tgtttgagga cagagagatg atcgaggaac ggctgaaaac ctatgcccac  1920
ctgttcgacg acaaagtgat gaagcagctg aagcggcgga gataccggg ctggggcagg  1980
ctgagccgga agctgatcaa cggcatccgg gacaagcagt ccggcaagac aatcctggat  2040
ttcctgaagt ccgacggctt cgccaacaga aacttcatgc agctgatcca cgacgacagc  2100
ctgaccttta aagaggacat ccagaaagcc caggtgtccg gccagggcga tagcctgcac  2160
gagcacattg ccaatctggc cggcagcccc gccattaaga agggcatcct gcagacagtg  2220
aaggtggtgg acgagctcgt gaaagtgatg ggccggcaca gcccgagaa catcgtgatc  2280
gaaatggcca gagagaacca gaccacccag aagggacaga gaacagccg cgagagaatg  2340
aagcggatcg aaggggcat caaagagctg ggcagccaga tcctgaaaga acaccccaag  2400
gaaaacaccc agctgcagaa cgagaagctg tacctgtact acctgcagaa tgggcgggat  2460
atgtacgtgg accaggaact ggacatcaac cggctgtccg actacgatgt ggaccatatc  2520
gtgcctcaga gctttctgaa ggacgactcc atcgacaaca aggtgctgac cagaagcgac  2580
aagaaccggg gcaagagcga caacgtgccc tccgaagagg tcgtgaagaa gatgaagaac  2640
tactggcggc agctgctgaa cgccaagctg attaccccaga gaaagttcga caatctgacc  2700
aaggccgaga gaggcggcct gagcgaactg gataaggccg gcttcatcaa gagacagctg  2760
gtggaaaccc ggcagatcac aaagcacgtg gcacagatcc tggactcccg gatgaacact  2820
aagtacgacg agaatgacaa gctgatccgg gaagtgaaag tgatcaccct gaagtccaag  2880
ctggtgtccg atttccggaa ggatttccag ttttacaaag tgcgcgagat caacaactac  2940
caccacgccc acgacgccta cctgaacgcc gtcgtgggaa ccgccctgat caaaagtac  3000
cctaagctgg aaagcgagtt cgtgtacggc gactacaagg tgtacgacgt gcggaagatg  3060
atcgccaaga gcgagcagga aatcggcaag gctaccgcca agtacttctt ctacagcaac  3120
atcatgaact tttcaagac cgagattacc ctggccaacg gcgagatccg gaagcggcct  3180
ctgatcgaga caaacggcga aaccggggag atcgtgtggg ataagggccg ggattttgcc  3240
accgtgcgga agtgctgag catgcccaa gtgaatatcg tgaaaagac cgaggtgcag  3300
acaggcggct tcagcaaaga gtctatctg cccaagagga acagcgataa gctgatcgcc  3360
agaaagaagg actgggaccc taagaagtac ggcggcttcg acagccccac cgtggcctat  3420
tctgtgctgg tggtggccaa agtggaaaag ggcaagtcca agaaactgaa gagtgtgaaa  3480
gagctgctgg gatcaccat catggaaaga agcagcttcg agaagaatcc catcgacttt  3540
ctggaagcca agggctacaa agaagtgaaa aaggacctga tcatcaagct gcctaagtac  3600
tccctgttcg agctggaaaa cggccggaag aatgctgg cctctgccgg cgaactgcag  3660
aagggaaacg aactgcccct gcctccaaa tatgtgaact tcctgtacct ggccagccac  3720
tatgagaagc tgaagggctc ccccgaggat aatgagcaga aacagctgtt tgtgaacag  3780
cacaagcact acctggacga gatcatcgag cagatcagcg agttctccaa gagagtgatc  3840
ctggccgacg ctaatctgga caaagtgctg tccgcctaca acaagcaccg ggataagccc  3900
atcagagagc aggccgagaa tatcatccac ctgtttaccc tgaccaatct ggagccctc  3960
gccgccttca gtactttga caccaccatc gaccggaaga ggtacaccag caccaaagag  4020
gtgctggacg ccaccctgat ccaccagagc atcaccggcc tgtacgagac acggatcgac  4080
ctgtctcagc tgggaggtga c                                             4101

SEQ ID NO: 143    moltype = DNA   length = 4101
FEATURE           Location/Qualifiers
source            1..4101
                    mol_type = other DNA
                    organism = synthetic construct
SEQUENCE: 143

```
gacaagaagt acagcatcgg cctggacatc ggcaccaact ctgtgggctg ggccgtgatc   60
accgacgagt acaaggtgcc cagcaagaaa ttcaaggtgc tgggcaacac cgaccggcac  120
agcatcaaga agaacctgat cggagccctg ctgttcgaca gcggcgaaac agccgaggcc  180
acccggctga agagaaccgc cagaagaaga tacaccagac ggaagaaccg gatctgctat  240
ctgcaagaga tcttcagcaa cgagatggcc aaggtggacg acagcttctt ccacagactg  300
gaagagtcct tcctggtgga agaggataag aagcacgagc ggcacccat cttcggcaac   360
atcgtggacg aggtggccta ccacgagaag tacccccacca tctaccacct gagaaagaaa  420
ctggtggaca gcaccgacaa ggccgacctg cggctgatct atctggccct ggcccacatg  480
atcaagttcc ggggccactt cctgatcgag ggcgacctga accccgacaa cagcgacgtg  540
gacaagctgt tcatccagct ggtgcagacc tacaaccagc tgttcgagga aaaccccatc  600
aacgccagcg gcgtggacgc caaggccatc ctgtctgcca gactgagcaa gagcagacgg  660
ctggaaaatc tgatcgccca gctgcccggc gagaagaaga atggcctgtt cggaaacctg  720
attgccctga gcctgggcct gacccccaac ttcaagagca acttcgacct ggccgaggat  780
gccaaactgc agctgagcaa ggacacctac gacgacgact tggacaacct gctggccgac  840
atcggcgacc agtacgccga cctgtttctg gccgccaaga acctgtccga cgccatcctg  900
ctgagcgaca tcctgagagt gaacaccgag atcaccaagg cccccctgag cgcctctatg  960
atcaagagat acgacgagca ccaccaggac ctgaccctgc tgaaagctct cgtgcggcag 1020
cagctgcctg agaagtacaa agagatttc ttcgaccaga cgaagaacgg ctacgccggc 1080
tacattgacg gcggagccag ccaggaagag ttctacaagt tcatcaagcc catcctggaa 1140
aagatggacg gcaccgagga actgctcgtg aagctgaaca gagaggacct gctgcgaaag 1200
cagcggacct tcgacaacgg cagcatcccc accagatcc acctgggaga gctgcacgcc 1260
attctgcggc ggcaggaaga ttttaccca ttcctgaaca caaccggaa aaagatccga 1320
aagatcctga ccttccgcat ccctactac gtgggccctc tggccagggg aaacagcaga 1380
ttcgcctgga tgaccagaaa gagcgaggaa accatcaccc cctggaactt cgaggaagtg 1440
gtggacaagg gcgcttccgc ccagagcttc atcgagcgga tgaccaactt cgataagaac 1500
ctgccaaacg agaaggtgct gcccaagcac agcctgctgt acgagtactt caccgtgtat 1560
aacgagctga ccaaagtgaa atacgtgacc gagggaatga gaaagcccgc cttcctgagc 1620
ggcgagcaga aaaaggccat cgtggacctg ctgttcaaga ccaaccggaa agtgaccgtg 1680
aagcagctga aagaggacta cttcaagaaa atcgagtgct tcgactccgt ggaaatctcc 1740
ggcgtggaag atcggttcaa cgcctccctg ggcacatacc acgatctgct gaaaattatc 1800
aaggacaagg acttcctgga caatgaggaa aacgaggaca ttctggaaga tatcgtgctg 1860
accctgacac tgtttgagga cagagagatg atcgaggaac ggctgaaaac ctatgcccac 1920
ctgttcgacg acaaagtgat gaagcagctg aagcggcgga gatacaccgg ctggggcagg 1980
ctgagccgga agctgatcaa cggcatccgg gacaagcagt ccggcaagac aatcctggat 2040
ttcctgaagt ccgacggctt cgccaacaga aacttcatgc agctgatcca cgacgacagc 2100
ctgacctta aagaggacat ccagaaagcc caggtgtccg gccagggcga tagcctgcac 2160
gagcacattg ccaatctggc cggcagcccc gccattaaga agggcatcct gcagacagtg 2220
aaggtggtgg acgagctcgt gaaagtgatg ggccggcaca gcccgagaa catcgtgatc 2280
gaaatggcca gagagaacca gaccacccag aagggacaga agaacagccg cgagagaatg 2340
aagcggatcg aagagggcat caaagagctg ggcagccaga tcctgaaaga cacccccgtg 2400
gaaaacaccc agctgcagaa cgagaagctg tacctgtact acctgcagaa tgggcgggat 2460
atgtacgtgg accaggaact ggacatcaac cggctgtccg actacgatgt ggacgccatc 2520
gtgcctcaga gctttctgaa ggacgactcc atcgacaaca aggtgctgac cagaagcgac 2580
aagaaccggg gcaagagcga caacgtgccc tccgaagagg tcgtgaagaa gatgaagaac 2640
tactggcggc agctgctgaa cgccaagctg attacccaga aaagttcga caatctgacc 2700
aaggccgaga gaggcggcct gagcgaactg gataaggccg gcttcatcaa gagacagctg 2760
gtggaaaccc ggcagatcac aaagcacgtg gcacagatcc tggactcccg gatgaacact 2820
aagtacgacg agaatgacaa gctgatccgg gaagtgaaag tgatcaccct gaagtccaag 2880
ctggtgtccg atttccggaa ggatttccag ttttacaaag tgcgcgagat caacaactac 2940
caccacgccc acgacgccta cctgaacgcc gtcgtgggaa ccgccctgat caaaaagtac 3000
cctaagctgg aaagcgagtt cgtgtacggc gactacaagg tgtacgacgt gcggaagatg 3060
atcgccaaga gcgagcagga aatcggcaag gctaccgcca agtacttctt ctacagcaac 3120
atcatgaact ttttcaagac cgagattacc ctggccaacg gcgagatccg gaagcggcct 3180
ctgatcgaga caaacggcga aaccggggag atcgtgtggg ataagggccg ggattttgcc 3240
accgtgcgga aagtgctgag catgccccaa gtgaatatcg tgaaaaagac cgaggtgcag 3300
acaggcggct tcagcaaaga gtctatcctg cccaagagga acagcgataa gctgatcgcc 3360
agaaagaagg actgggaccc taagaagtac ggcggcttcg acagcccac cgtgcctat   3420
tctgtgctgt tggtggccaa agtggaaaag ggcaagtcca gaaactgaa gagtgtgaaa  3480
gagctgctgg ggatcacat catggaaaga agcagcttc agaagaatcc catcgacttt  3540
ctggaagcca agggctacaa agaagtgaaa aaggacctga tcatcaagct gcctaagtac 3600
tccctgttcg agctgaaaaa cggccggaag agaatgctgg cctctgccgg cgaactgcag 3660
aagggaaacg aactggccct gccctccaaa tatgtgaact tcctgtacct ggccagccac 3720
tatgagaagc tgaagggctc ccccgaggat aatgagcaga acagctgtt tgtggaacag  3780
cacaagcact acctggacga gatcatcgaa cagatcagcg agttctccaa gagagtgatc 3840
ctggccgacg ctaatctgga caaagtgctg tccgcctaca acaagcaccg ggataagccc 3900
atcagagagc aggccgagaa tatcatccac ctgtttaccc tgaccaatct gggagcccct 3960
gccgccttca gtactttga caccaccatc gaccggaaga ggtacaccag caccaaagag  4020
gtgctggacg ccacccctgat ccaccagagc atcaccggcc tgtacgagac acggatcgac 4080
ctgtctcagc tgggaggtga c                                           4101

SEQ ID NO: 144         moltype = DNA  length = 23
FEATURE                Location/Qualifiers
source                 1..23
                       mol_type = other DNA
                       organism = synthetic construct
SEQUENCE: 144
accttggaga cggcgactct ctg                                           23

SEQ ID NO: 145         moltype = DNA  length = 23
```

```
FEATURE                 Location/Qualifiers
source                  1..23
                        mol_type = other DNA
                        organism = synthetic construct
SEQUENCE: 145
gcggatgttc caatcagtac gca                                               23

SEQ ID NO: 146          moltype = DNA   length = 23
FEATURE                 Location/Qualifiers
source                  1..23
                        mol_type = other DNA
                        organism = synthetic construct
SEQUENCE: 146
tgtcaccaat cctgtcccta gtg                                               23

SEQ ID NO: 147          moltype = DNA   length = 23
FEATURE                 Location/Qualifiers
source                  1..23
                        mol_type = other DNA
                        organism = synthetic construct
SEQUENCE: 147
tctgtccect ccaccccaca gtg                                               23

SEQ ID NO: 148          moltype = DNA   length = 23
FEATURE                 Location/Qualifiers
source                  1..23
                        mol_type = other DNA
                        organism = synthetic construct
SEQUENCE: 148
tatgagttac aacgaacacc tca                                               23

SEQ ID NO: 149          moltype = DNA   length = 23
FEATURE                 Location/Qualifiers
source                  1..23
                        mol_type = other DNA
                        organism = synthetic construct
SEQUENCE: 149
cacgtctcat atgcccettg gca                                               23

SEQ ID NO: 150          moltype = RNA   length = 23
FEATURE                 Location/Qualifiers
source                  1..23
                        mol_type = other RNA
                        organism = synthetic construct
SEQUENCE: 150
tgtcaccaat cctgtcccta gtg                                               23

SEQ ID NO: 151          moltype = AA    length = 1129
FEATURE                 Location/Qualifiers
source                  1..1129
                        mol_type = protein
                        organism = Alicyclobacillus acidoterrestris
SEQUENCE: 151
MAVKSIKVKL RLDDMPEIRA GLWKLHKEVN AGVRYYTEWL SLLRQENLYR RSPNGDGEQE         60
CDKTAEECKA ELLERLRARQ VENGHRGPAG SDDELLQLAR QLYELLVPQA IGAKGDAQQI        120
ARKFLSPLAD KDAVGGLGIA KAGNKPRWVR MREAGEPGWE EEKEKAETRK SADRTADVLR        180
ALADFGLKPL MRVYTDSEMS SVEWKPLRKG QAVRTWDRDM FQQAIERMMS WESWNQRVGQ        240
EYAKLVEQKN RFEQKNFVGQ EHLVHLVNQL QQDMKEASPG LESKEQTAHY VTGRALRGSD        300
KVFEKWGKLA PDAPFDLYDA EIKNVQRRNT RRFGSHDLFA KLAEPEYQAL WREDASFLTR        360
YAVYNSILRK LNHAKMFATF TLPDATAHPI WTRFDKLGGN LHQYTFLFNE FGERRHAIRF        420
HKLLKVENGV AREVDDVTVP ISMSEQLDNL LPRDPNEPIA LYFRDYGAEQ HFTGEFGGAK        480
IQCRRDQLAH MHRRRGARDV YLNVSVRVQS QSEARGERRP PYAAVFRLVG DNHRAFVHFD        540
KLSDYLAEHP DDGKLGSEGL LSGLRVMSVD LGLRTSASIS VFRVARKDEL KPNSKGRVPF        600
FFPIKGNDNL VAVHERSQLL KLPGETESKD LRAIREERQR TLRQLRTQLA YLRLLVRCGS        660
EDVGRRERSW AKLIEQPVDA ANHMTPDWRE AFENELQKLK SLHGICSDKE WMDAVYESVR        720
RVWRHMGKQV RDWRKDVRSG ERPKIRGYAK DVVGGNSIEQ IEYLERQYKF LKSWSFFGKV        780
SGQVIRAEKG SRFAITLREH IDHAKEDRLK KLADRIIMEA LGYVYALDER GKGKWVAKYP        840
PCQLILLEEL SEYQFNNDRP PSENNQLMQW SHRGVFQELI NQAQVHDLLV GTMYAAFSSR        900
FDARTGAPGI RCRRVPARCT QEHNPEPFPW WLNKFVVEHT LDACPLRADD LIPTGEGEIF        960
VSPFSAEEGD FHQIHADLNA AQNLQQRLWS DFDISQIRLR CDWGEVDGEL VLIPRLTGKR       1020
TADSYSNKVF YTNTGVTYYE RERGKKRRKV FAQEKLSEEE AELLVEADEA REKSVVLMRD       1080
PSGIINRGNW TRQKEFWSMV NQRIEGYLVK QIRSRVPLQD SACENTGDI                  1129

SEQ ID NO: 152          moltype = AA   length = 198
FEATURE                 Location/Qualifiers
source                  1..198
                        mol_type = protein
                        organism = synthetic construct
SEQUENCE: 152
```

```
EASPASGPRH LMDPHIFTSN FNNGIGRHKT YLCYEVERLD NGTSVKMDQH RGFLHNQAKN    60
LLCGFYGRHA ELRFLDLVPS LQLDPAQIYR VTWFISWSPC FSWGCAGEVR AFLQENTHVR   120
LRIFAARIYD YDPLYKEALQ MLRDAGAQVS IMTYDEFKHC WDTFVDHQGC PFQPWDGLDE   180
HSQALSGRLR AILQNQGN                                                198

SEQ ID NO: 153          moltype = AA  length = 17
FEATURE                 Location/Qualifiers
source                  1..17
                        mol_type = protein
                        organism = synthetic construct
SEQUENCE: 153
SGSETPGTSE SATPESM                                                  17

SEQ ID NO: 154          moltype = AA  length = 13
FEATURE                 Location/Qualifiers
source                  1..13
                        mol_type = protein
                        organism = synthetic construct
SEQUENCE: 154
GSPKKKRKVS GGS                                                      13

SEQ ID NO: 155          moltype = AA  length = 166
FEATURE                 Location/Qualifiers
source                  1..166
                        mol_type = protein
                        organism = Escherichia coli
SEQUENCE: 155
SEVEFSHEYW MRHALTLAKR ARDEREVPVG AVLVLNNRVI GEGWNRAIGL HDPTAHAEIM    60
ALRQGGLVMQ NYRLIDATLY VTFEPCVMCA GAMIHSRIGR VVFGVRNSKR GAAGSLMNVL   120
NYPGMNHRVE ITEGILADEC AALLCDFYRM PRQVFNAQKK AQSSIN                  166

SEQ ID NO: 156          moltype = AA  length = 397
FEATURE                 Location/Qualifiers
source                  1..397
                        mol_type = protein
                        organism = synthetic construct
SEQUENCE: 156
GSSETPGTSE SATPEGGSGG SGSEASPASG PRHLMDPHIF TSNFNNGIGR HKTYLCYEVE    60
RLDNGTSVKM DQHRGFLHNQ AKNLLCGFYG RHAELRFLDL VPSLQLDPAQ IYRVTWFISW   120
SPCFSWGCAG EVRAFLQENT HVRLRIFAAR IYDYDPLYKE ALQMLRDAGA QVSIMTYDEF   180
KHCWDTFVDH QGCPFQPWDG LDEHSQALSG RLRAILQNQG NGGGGSTNLS DIIEKETGKQ   240
LVIQESILML PEEVEEVIGN KPESDILVHT AYDESTDENV MLLTSDAPEY KPWALVIQDS   300
NGENKIKMLS GGSGGSGGSY KLILNGKTLK GETTTEAVDA ATAEKVFKQY ANDNGVDGEW   360
TYDDATKTFT VTESGGSKRT ADGSEFEPKK KRKVGSG                           397

SEQ ID NO: 157          moltype = AA  length = 1787
FEATURE                 Location/Qualifiers
source                  1..1787
                        mol_type = protein
                        organism = synthetic construct
SEQUENCE: 157
MKRTADGSEF ESPKKKRKVS KLEKFTNCYS LSKTLRFKAI PVGKTQENID NKRLLVEDEK    60
RAEDYKGVKK LLDRYYLSFI NDVLHSIKLK NLNNYISLFR KKTRTEKENK ELENLEINLR   120
KEIAKAFKGN EGYKSLFKKD IIETILPEFL DDKDEIALVN SFNGFTTAFT GFFDNRENMF   180
SEEAKSTSIA FRCINENLTR YISNMDIFEK VDAIFDKHEV QEIKEKILNS DYDVEDFFEG   240
EFFNVLTQE GIDVYNAIIG GFVTESGEKI KGLNEYINLY NQKTKQLPK FKPLYKQVLS    300
DRESLSFYGE GSSGENQTTQ KGQKNSRERM KRIEEGIKEL GSQILKEHPV ENTQLQNEKL   360
YLYYLQNGRD MYVDQELDIN RLSDYDVDHI VPQSFLKDDS IDNKVLTRSD KNRGKSDNVP   420
SEEVVKKMKN YWRQLLNAKL ITQRKFDNLT KAERGGLSGY TSDEEVLEVF RNTLNKNSEI   480
FSSIKKLEKL FKNFDEYSSA GIFVKNGPAI STISKDIFGE WNVIRDKWNA EYDDIHLKKK   540
AVVTEKYEDD RRKSFKKIGS FSLEQLQEYA DADLSVVEKL KEIIIQKVDE IYKVYGSSEK   600
LFDADFVLEK SLKKNDAVVA IMKDLLDSVK SFENYIKAFF GEGKETNRDE SFYGDFVLAY   660
DILLKVDHIY DAIRNYVTQK PYSKDKFKLY FQNPQFMGGW DKDKETDYRA TILRYGSKYY   720
LAIMDKKYAK CLQKIDKDDV NGNYEKINYK LLPGPNKMLP KVFFSKKWMA YYNPSEDIQK   780
IYKNGTFKKG DMFNLNDCHK LIDFFKDSIS RYPKWSNAYD FNFSETEKYK DIAGFYREVE   840
EQGYKVSFES ASKKEVDKLV EEGKLYMFQI YNKDFSDKSH GTPNLHTMYF KLLFDENNHG   900
QIRLSGGAEL FMRRASLKKE ELVVHPANSP IANKNPDNPK KTTTLSYDVY KDKRFSEDQY   960
ELHIPIAINK CPKNIFKINT EVRVLLKHDD NPYVIGIARG ERNLLYIVVV DGKGNIVEQY  1020
SLNEIINNFN GIRIKTDYHS LLDKKEKERF EARQNWTSIE NIKELKAGYI SQVVHKICEL  1080
VEKYDAVIAL EDLNSGFKNS RVKVEKQVYQ KFEKMLIDKL NYMVDKKSNP CATGGALKGY  1140
QITNKFESFK SMSTQNGFIF YIPAWLTSKI DPSTGFVNLL KTKYTSIADS KKFISSFDRI  1200
MYVPEEDLFE FALDYKNFSR TDADYIKKWK LYSYGNRIRI FRNPKKNNVF DWEEVCLTSA  1260
YKELFNKYGI NYQQGDIRAL LCEQSDKAFY SSFMALMSLM LQMRNSITGR TDVDFLISPV  1320
KNSDGIFYDS RNYEAQENAI LPKNADANGA YNIARKVLWA IGQFKKAEDE KLDKVKIAIS  1380
NKEWLEYAQT SVKHGGGGSG GGGSGGGGS PKKKRKVAAA GSEELLSKNY HLENEVARLK  1440
KGSGSGGSGS GGGSGSGGGS SGGGSGSGEE LLSKNYHLEN EVARLKKGSG SGGSGSGGSG  1500
SGGGSGSGG SGSGEELLSK NYHLENEVAR LKKGSGSGGS GSGGGSGSGG SGSGGSGSGG  1560
EELLSKNYHL ENEVARLKKG SGSGGSGSGG SGSGSGGSGG GGSGSGEELL SKNYHLENEV  1620
ARLKKGSGSG GSGSGGSGSG SGGSGSGSGG SGEELLSKNY HLENEVARLK KGSGGGGSGS  1680
```

```
GGSGSGSGGS GSGGSGSGEE LLSKNYHLEN EVARLKKGSG SGGSGSGGSG SGSGGSGSGG 1740
SGSGEELLSK NYHLENEVAR LKKSGGSKRT ADGSEFEPKK KRKVGSG              1787

SEQ ID NO: 158          moltype = AA  length = 1787
FEATURE                 Location/Qualifiers
source                  1..1787
                        mol_type = protein
                        organism = synthetic construct
SEQUENCE: 158
MKRTADGSEF ESPKKKRKVS KLEKFTNCYS LSKTLRFKAI PVGKTQENID NKRLLVEDEK 60
RAEDYKGVKK LLDRYYLSFI NDVLHSIKLK NLNNYISLFR KKTRTEKENK ELENLEINLR 120
KEIAKAFKGN EGYKSLFKKD IIETILPEFL DDKDEIALVN SFNGFTTAFT GFFDNRENMF 180
SEEAKSTSIA FRCINENLTR YISNMDIFEK VDAIFDKHEV QEIKEKILNS DYDVEDFFEG 240
EFFNFVLTQE GIDVYNAIIG GFVTESGEKI KGLNEYINLY NQKTKQKLPK FKPLYKQVLS 300
DRESLSFYGG SSGENQTTQK GQKNSRERMK RIEEGIKELG SQILKEHPVE NTQLQNEKLY 360
LYYLQNGRDM YVDQELDINR LSDYDVDHIV PQSFLKDDSI DNKVLTRSDK NRGKSDNVPS 420
EEVVKKMKNY WRQLLNAKLI TQRKFDNLTK AERGGLSEGY TSDEEVLEVF RNTLNKNSEI 480
FSSIKKLEKL FKNFDEYSSA GIFVKNGPAI STISKDIFGE WNVIRDKWNA EYDDIHLKKK 540
AVVTEKYEDD RRKSFKKIGS FSLEQLQEYA DADLSVVEKL KEIIIQKVDE IYKVYGSSEK 600
LFDADFVLEK SLKKNDAVVA IMKDLLDSVK SFENYIKAFF GEGKETNRDE SFYGDFVLAY 660
DILLKVDHIY DAIRNYVTQK PYSKDKFKLY FQNPQFMGGW DKDKETDYRA TILRYGSKYY 720
LAIMDKKYAK CLQKIDKDDV NGNYEKINYK LLPGPNKMLP KVFFSKKWMA YYNPSEDIQK 780
IYKNGTFKKG DMFNLNDCHK LIDFFKDSIS RYPKWSNAYD FNFSETEKYK DIAGFYREVE 840
EQGYKVSFES ASKKEVDKLV EEGKLYMFQI YNKDFSDKSH GTPNLHTMYF KLLFDENNHG 900
QIRLSGGAEL FMRRASLKKE ELVVHPANSP IANKNPDNPK KTTTLSYDVY KDKRFSEDQY 960
ELHIPIAINK CPKNIFKINT EVRVLLKHDD NPYVIGIARG ERNLLYIVVV DGKGNIVEQY 1020
SLNEIINNFN GIRIKTDYHS LLDKKEKERF EARQNWTSIE NIKELKAGYI SQVVHKICEL 1080
VEKYDAVIAL EDLNSGFKNS RVKVEKQVYQ KFEKMLIDKL NYMVDKKSNP CATGGALKGY 1140
QITNKFESFK SMSTQNGFIF YIPAWLTSKI DPSTGFVNLL KTKYTSIADS KKFISSFDRI 1200
MYVPEEDLFE FALDYKNFSR TDADYIKKWK LYSYGNRIRI FRNPKKNNVF DWEEVCLTSA 1260
YKELFNKYGI NYQQGDIRAL LCEQSDKAFY SSFMALMSLM LQMRNSITGR TDVDFLISPV 1320
KNSDGIFYDS RNYEAQENAI LPKNADANGA YNIARKVLWA IGQFKKAEDE KLDKVKIAIS 1380
NKEWLEYAQT SVKHGGGSG GGGSGGGSG PKKKRKVAAA GSEELLSKNY HLENEVARLK 1440
KGSGSGGSGS GSGGSGSGGS GSGGSGSGEE LLSKNYHLEN EVARLKKGSG SGGSGSGGSG 1500
SGSGGSGSGG SGSGEELLSK NYHLENEVAR LKKGSGSGGS GSGGSGSGSG SGSGGSGSGS 1560
EELLSKNYHL ENEVARLKKG SGGSGSGGS SGSGSGGSGS GGGSGEELL SKNYHLENEV 1620
ARLKKGSGSG GSGSGGSGSG SGGSGSGGSG SGEELLSKNY HLENEVARLK KGSGSGGSGS 1680
GGGSGSGGGS GGGGSGSGEE LLSKNYHLEN EVARLKKGSG SGGSGSGGSG SGSGGSGSGG 1740
SGSGEELLSK NYHLENEVAR LKKSGGSKRT ADGSEFEPKK KRKVGSG              1787

SEQ ID NO: 159          moltype = AA  length = 1789
FEATURE                 Location/Qualifiers
source                  1..1789
                        mol_type = protein
                        organism = synthetic construct
SEQUENCE: 159
MKRTADGSEF ESPKKKRKVS KLEKFTNCYS LSKTLRFKAI PVGKTQENID NKRLLVEDEK 60
RAEDYKGVKK LLDRYYLSFI NDVLHSIKLK NLNNYISLFR KKTRTEKENK ELENLEINLR 120
KEIAKAFKGN EGYKSLFKKD IIETILPEFL DDKDEIALVN SFNGFTTAFT GFFDNRENMF 180
SEEAKSTSIA FRCINENLTR YISNMDIFEK VDAIFDKHEV QEIKEKILNS DYDVEDFFEG 240
EFFNFVLTQE GIDVYNAIIG GFVTESGEKI KGLNEYINLY NQKTKQKLPK FKPLYKQVLS 300
DRESLSFYGG SSGENQTTQK GQKNSRERMK RIEEGIKELG SQILKEHPVE NTQLQNEKLY 360
LYYLQNGRDM YVDQELDINR LSDYDVDHIV PQSFLKDDSI DNKVLTRSDK NRGKSDNVPS 420
EEVVKKMKNY WRQLLNAKLI TQRKFDNLTK AERGGLSGSE GYTSDEEVLE VFRNTLNKNS 480
EIFSSIKKLE KLFKNFDEYS SAGIFVKNGP AISTISKDIF GEWNVIRDKW NAEYDDIHLK 540
KKAVVTEKYE DDRRKSFKKI GSFSLEQLQE YADADLSVVE KLKEIIIQKV DEIYKVYGSS 600
EKLFDADFVL EKSLKKNDAV VAIMKDLLDS VKSFENYIKA FFGEGKETNR DESFYGDFVL 660
AYDILLKVDH IYDAIRNYVT QKPYSKDKFK LYFQNPQFMG GWDKDKETDY RATILRYGSK 720
YYLAIMDKKY AKCLQKIDKD DVNGNYEKIN YKLLPGPNKM LPKVFFSKKW MAYYNPSEDI 780
QKIYKNGTFK KGDMFNLNDC HKLIDFFKDS ISRYPKWSNA YDFNFSETEK YKDIAGFYRE 840
VEEQGYKVSF ESASKKEVDK LVEEGKLYMF QIYNKDFSDK SHGTPNLHTM YFKLLFDENN 900
HGQIRLSGGA ELFMRRASLK KEELVVHPAN SPIANKNPDN PKKTTTLSYD VYKDKRFSED 960
QYELHIPIAI NKCPKNIFKI NTEVRVLLKH DDNPYVIGIA RGERNLLYIV VVDGKGNIVE 1020
QYSLNEIINN FNGIRIKTDY HSLLDKKEKE RFEARQNWTS IENIKELKAG YISQVVHKIC 1080
ELVEKYDAVI ALEDLNSGFK NSRVKVEKQV YQKFEKMLID KLNYMVDKKS NPCATGGALK 1140
GYQITNKFES FKSMSTQNGF IFYIPAWLTS KIDPSTGFVN LLKTKYTSIA DSKKFISSFD 1200
RIMYVPEEDL FEFALDYKNF SRTDADYIKK WKLYSYGNRI RIFRNPKKNN VFDWEEVCLT 1260
SAYKELFNKY GINYQQGDIR ALLCEQSDKA FYSSFMALMS LMLQMRNSIT GRTDVDFLIS 1320
PVKNSDGIFY DSRNYEAQEN AILPKNADAN GAYNIARKVL WAIGQFKKAE DEKLDKVKIA 1380
ISNKEWLEYA QTSVKHGGGS GGGGSGGGSG PKKKRKVAAA GSEELLSKNY HLENEVARLK 1440
LKKGSGSGGS GSGGSGSGSG SGSGGSGSGG EELLSKNYHL ENEVARLKKG SGGSGSGGG 1500
SGSGGGSGS GGSGSGEELL SKNYHLENEV ARLKKGSGSG GSGSGGSGSG SGSGGSGGS 1560
SGEELLSKNY HLENEVARLK KGSGSGGSGS GGGSGSGGGS GGGGSGSGEE LLSKNYHLEN 1620
EVARLKKGSG SGGSGSGGSG SGSGGSGSGG SGSGEELLSK NYHLENEVAR LKKGSGSGGS 1680
GSGGSGSGSG SGSGGSGSGS EELLSKNYHL ENEVARLKKG SGGSGSGGSG SGSGGSGSGS 1740
GGSGSGEELL SKNYHLENEV ARLKKSGGSK RTADGSEFEP KKKRKVGSG           1789

SEQ ID NO: 160          moltype = AA  length = 1739
FEATURE                 Location/Qualifiers
```

```
source                   1..1739
                         mol_type = protein
                         organism = synthetic construct
SEQUENCE: 160
MKRTADGSEF ESPKKKRKVE ASPASGPRHL MDPHIFTSNF NNGIGRHKTY LCYEVERLDN    60
GTSVKMDQHR GFLHNQAKNL LCGFYGRHAE LRFLDLVPSL QLDPAQIYRV TWFISWSPCF   120
SWGCAGEVRA FLQENTHVRL RIFAARIYDY DPLYKEALQM LRDAGAQVSI MTYDEFKHCW   180
DTFVDHQGCP FQPWDGLDEH SQALSGRLRA ILQNQGNSTS QSDGSSVPAD IDQSSDSDQS   240
SSQGQPGSKL EKFTNCYSLS KTLRFKAIPV GKTQENIDNK RLLVEDEKRA EDYKGVKKLL   300
DRYYLSFIND VLHSIKLKNL NNYISLFRKK TRTEKENKEL ENLEINLRKE IAKAFKGNEG   360
YKSLFKKDII ETILPEFLDD KDEIALVNSF NGFTTAFTGF FDNRENMFSE EAKSTSIAFR   420
CINENLTRYI SNMDIFEKVD AIFDKHEVQE IKEKILNSDY DVEDFFEGEF FNFVLTQEGI   480
DVYNAIIGGF VTESGEKIKG LNEYINLYNQ KTKQKLPKFK PLYKQVLSDR ESLSFYGEGS   540
SGENQTTQKG QKNSRERMKR IEEGIKELGS QILKEHPVEN TQLQNEKLYL YYLQNGRDMY   600
VDQELDINRL SDYDVDHIVP QSFLKDDSID NKVLTRSDKN RGKSDNVPSE EVVKKMKNYW   660
RQLLNAKLIT QRKFDNLTKA ERGGLSGYTS DEEVLEVFRN TLNKNSEIFS SIKKLEKLFK   720
NFDEYSSAGI FVKNGPAIST ISKDIFGEWN VIRDKWNAEY DDIHLKKKAV VTEKYEDDRR   780
KSFKKIGSFS LEQLQEYADA DLSVVEKLKE IIIQKVDEIY KVYGSSEKLF DADFVLEKSL   840
KKNDAVVAIM KDLLDSVKSF ENYIKAFFGE GKETNRDESF YGDFVLAYDI LLKVDHIYDA   900
IRNYVTQKPY SKDKFKLYFQ NPQFMGGWDK DKETDYRATI LRYGSKYYLA IMDKKYAKCL   960
QKIDKDDVNG NYEKINYKLL PGPNKMLPKV FFSKKWMAYY NPSEDIQKIY KNGTFKKGDM  1020
FNLNDCHKLI DFFKDSISRY PKWSNAYDFN FSETEKYKIY AGFYREVEEQ GYKVSFESAS  1080
KKEVDKLVEE GKLYMFQIYN KDFSDKSHGT PNLHTMYFKL LFDENNHGQI RLSGGAELFM  1140
RRASLKKEEL VVHPANSPIA NKNPDNPKKT TTLSYDVYKD KRFSEDQYEL HIPIAINKCP  1200
KNIFKINTEV RVLLKHDDNP YVIGIARGER NLLYIVVVDG KGNIVEQYSL NEIINNFNGI  1260
RIKTDYHSLL DKKEKERFEA RQNWTSIENI KELKAGYISQ VVHKICELVE KYDAVIALED  1320
LNSGFKNSRV KVEKQVYQKF EKMLIDKLNY MVDKKSNPCA TGGALKGYQI TNKFESFKSM  1380
STQNGFIFYI PAWLTSKIDP STGFVNLLKT KYTSIADSKK FISSFDRIMY VPEEDLFEFA  1440
LDYKNFSRTD ADYIKKWKLY SYGNRIRIFR NPKKNNVFDW EEVCLTSAYK ELFNKYGINY  1500
QQGDIRALLC EQSDKAFYSS FMALMSLMLQ MRNSITGRTD VDFLISPVKN SDGIFYDSRN  1560
YEAQENAILP KNADANGAYN IARKVLWAIG QFKKAEDEKL DKVKIAISNK EWLEYAQTSV  1620
KHSGGSGSG GSTNLSDIIE KETGKQLVIQ ESILMLPEEV EEVIGNKPES DILVHTAYDE  1680
STDENVMLLT SDAPEYKPWA LVIQDSNGEN KIKMLSGGSK RTADGSEFEP KKKRKVGSG   1739

SEQ ID NO: 161           moltype = AA  length = 1739
FEATURE                  Location/Qualifiers
source                   1..1739
                         mol_type = protein
                         organism = synthetic construct
SEQUENCE: 161
MKRTADGSEF ESPKKKRKVE ASPASGPRHL MDPHIFTSNF NNGIGRHKTY LCYEVERLDN    60
GTSVKMDQHR GFLHNQAKNL LCGFYGRHAE LRFLDLVPSL QLDPAQIYRV TWFISWSPCF   120
SWGCAGEVRA FLQENTHVRL RIFAARIYDY DPLYKEALQM LRDAGAQVSI MTYDEFKHCW   180
DTFVDHQGCP FQPWDGLDEH SQALSGRLRA ILQNQGNSTS QSDGSSVPAD IDQSSDSDQS   240
SSQGQPGSKL EKFTNCYSLS KTLRFKAIPV GKTQENIDNK RLLVEDEKRA EDYKGVKKLL   300
DRYYLSFIND VLHSIKLKNL NNYISLFRKK TRTEKENKEL ENLEINLRKE IAKAFKGNEG   360
YKSLFKKDII ETILPEFLDD KDEIALVNSF NGFTTAFTGF FDNRENMFSE EAKSTSIAFR   420
CINENLTRYI SNMDIFEKVD AIFDKHEVQE IKEKILNSDY DVEDFFEGEF FNFVLTQEGI   480
DVYNAIIGGF VTESGEKIKG LNEYINLYNQ KTKQKLPKFK PLYKQVLSDR ESLSFYGGSS   540
GENQTTQKGQ KNSRERMKRI EEGIKELGSQ ILKEHPVENT QLQNEKLYLY YLQNGRDMYV   600
DQELDINRLS DYDVDHIVPQ SFLKDDSIDN KVLTRSDKNR GKSDNVPSEE VVKKMKNYWR   660
QLLNAKLITQ RKFDNLTKAE RGGLSEGYTS DEEVLEVFRN TLNKNSEIFS SIKKLEKLFK   720
NFDEYSSAGI FVKNGPAIST ISKDIFGEWN VIRDKWNAEY DDIHLKKKAV VTEKYEDDRR   780
KSFKKIGSFS LEQLQEYADA DLSVVEKLKE IIIQKVDEIY KVYGSSEKLF DADFVLEKSL   840
KKNDAVVAIM KDLLDSVKSF ENYIKAFFGE GKETNRDESF YGDFVLAYDI LLKVDHIYDA   900
IRNYVTQKPY SKDKFKLYFQ NPQFMGGWDK DKETDYRATI LRYGSKYYLA IMDKKYAKCL   960
QKIDKDDVNG NYEKINYKLL PGPNKMLPKV FFSKKWMAYY NPSEDIQKIY KNGTFKKGDM  1020
FNLNDCHKLI DFFKDSISRY PKWSNAYDFN FSETEKYKDI AGFYREVEEQ GYKVSFESAS  1080
KKEVDKLVEE GKLYMFQIYN KDFSDKSHGT PNLHTMYFKL LFDENNHGQI RLSGGAELFM  1140
RRASLKKEEL VVHPANSPIA NKNPDNPKKT TTLSYDVYKD KRFSEDQYEL HIPIAINKCP  1200
KNIFKINTEV RVLLKHDDNP YVIGIARGER NLLYIVVVDG KGNIVEQYSL NEIINNFNGI  1260
RIKTDYHSLL DKKEKERFEA RQNWTSIENI KELKAGYISQ VVHKICELVE KYDAVIALED  1320
LNSGFKNSRV KVEKQVYQKF EKMLIDKLNY MVDKKSNPCA TGGALKGYQI TNKFESFKSM  1380
STQNGFIFYI PAWLTSKIDP STGFVNLLKT KYTSIADSKK FISSFDRIMY VPEEDLFEFA  1440
LDYKNFSRTD ADYIKKWKLY SYGNRIRIFR NPKKNNVFDW EEVCLTSAYK ELFNKYGINY  1500
QQGDIRALLC EQSDKAFYSS FMALMSLMLQ MRNSITGRTD VDFLISPVKN SDGIFYDSRN  1560
YEAQENAILP KNADANGAYN IARKVLWAIG QFKKAEDEKL DKVKIAISNK EWLEYAQTSV  1620
KHSGGSGSG GSTNLSDIIE KETGKQLVIQ ESILMLPEEV EEVIGNKPES DILVHTAYDE  1680
STDENVMLLT SDAPEYKPWA LVIQDSNGEN KIKMLSGGSK RTADGSEFEP KKKRKVGSG   1739

SEQ ID NO: 162           moltype = AA  length = 1741
FEATURE                  Location/Qualifiers
source                   1..1741
                         mol_type = protein
                         organism = synthetic construct
SEQUENCE: 162
MKRTADGSEF ESPKKKRKVE ASPASGPRHL MDPHIFTSNF NNGIGRHKTY LCYEVERLDN    60
GTSVKMDQHR GFLHNQAKNL LCGFYGRHAE LRFLDLVPSL QLDPAQIYRV TWFISWSPCF   120
SWGCAGEVRA FLQENTHVRL RIFAARIYDY DPLYKEALQM LRDAGAQVSI MTYDEFKHCW   180
```

```
DTFVDHQGCP FQPWDGLDEH SQALSGRLRA ILQNQGNSTS QSDGSSVPAD IDQSSDSDQS    240
SSQGQPGSKL EKFTNCYSLS KTLRFKAIPV GKTQENIDNK RLLVEDEKRA EDYKGVKKLL    300
DRYYLSFIND VLHSIKLKNL NNYISLFRKK TRTEKENKEL ENLEINLRKE IAKAFKGNEG    360
YKSLFKKDII ETILPEFLDD KDEIALVNSF NGFTTAFTGF FDNRENMFSE EAKSTSIAFR    420
CINENLTRYI SNMDIFEKVD AIFDKHEVQE IKEKILNSDY DVEDFFEGEF FNFVLTQEGI    480
DVYNAIIGGF VTESGEKIKG LNEYINLYNQ KTKQKLPKFK PLYKQVLSDR ESLSFYGGSS    540
GENQTTQKGQ KNSRERMKRI EEGIKELGSQ ILKEHPVENT QLQNEKLYLY YLQNGRDMYV    600
DQELDINRLS DYDVDHIVPQ SFLKDDSIDN KVLTRSDKNR GKSDNVPSEE VVKKMKNYWR    660
QLLNAKLITQ RKFDNLTKAE RGGLSGSEGY TSDEEVLEVF RNTLNKNSEI FSSIKKLEKL    720
FKNFDEYSSA GIFVKNGPAI STISKDIFGE WNVIRDKWNA EYDDIHLKKK AVVTEKYEDD    780
RRKSFKKIGS FSLEQLQEYA DADLSVVEKL KEIIIQKVDE IYKVYGSSEK LFDADFVLEK    840
SLKKNDAVVA IMKDLLDSVK SFENYIKAFF GEGKETNRDE SFYGDFVLAY DILLKVDHIY    900
DAIRNYVTQK PYSKDKFKLY FQNPQFMGGW DKDKETDYRA TILRYGSKYY LAIMDKKYAK    960
CLQKIDKDDV NGNYEKINYK LLPGPNKMLP KVFFSKKWMA YYNPSEDIQK IYKNGTFKKG   1020
DMFNLNDCHK LIDFFKDSIS RYPKWSNAYD FNFSETEKYK DIAGFYREVE EQGYKVSFES   1080
ASKKEVDKLV EEGKLYMFQI YNKDFSDKSH GTPNLHTMYF KLLFDENNHG QIRLSGGAEL   1140
FMRRASLKKE ELVVHPANSP IANKNPDNPK KTTTLSYDVY KDKRFSEDQY ELHIPIAINK   1200
CPKNIFKINT EVRVLLKHDD NPYVIGIARG ERNLLYIVVV DGKGNIVEQY SLNEIINNFN   1260
GIRIKTDYHS LLDKKEKERF EARQNWTSIE NIKELKAGYI SQVVHKICEL VEKYDAVIAL   1320
EDLNSGFKNS RVKVEKQVYQ KFEKMLIDKL NYMVDKKSNP CATGGALKGY QITNKFESFK   1380
SMSTQNGFIF YIPAWLTSKI DPSTGFVNLL KTKYTSIADS KKFISSFDRI MYVPEEDLFE   1440
FALDYKNFSR TDADYIKKWK LYSYGNRIRI FRNPKKNNVF DWEEVCLTSA YKELFNKYGI   1500
NYQQGDIRAL LCEQSDKAFY SSFMALMSLM LQMRNSITGR TDVDFLISPV KNSDGIFYDS   1560
RNYEAQENAI LPKNADANGA YNIARKVLWA IGQFKKAEDE KLDKVKIAIS NKEWLEYAQT   1620
SVKHSGGSGG SGGSTNLSDI IEKETGKQLV IQESILMLPE EVEEVIGNKP ESDILVHTAY   1680
DESTDENVML LTSDAPEYKP WALVIQDSNG ENKIKMLSGG SKRTADGSEF EPKKKRKVGS   1740
G                                                                  1741

SEQ ID NO: 163        moltype = AA  length = 1734
FEATURE               Location/Qualifiers
source                1..1734
                      mol_type = protein
                      organism = synthetic construct
SEQUENCE: 163
MKRTADGSEF ESPKKKRKVM EASPASGPRH LMDPHIFTSN FNNGIGRHKT YLCYEVERLD    60
NGTSVKMDQH RGFLHNQAKN LLCGFYGRHA ELRFLDLVPS LQLDPAQIYR VTWFISWSPC   120
FSWGCAGEVR AFLQENTHVR LRIFAARIYD YDPLYKEALQ MLRDAGAQVS IMTYDEFKHC   180
WDTFVDHQGC PFQPWDGLDE HSQALSGRLR AILQNQGNSG SETPGTSESA TPESMSKLEK   240
FTNCYSLSKT LRFKAIPVGK TQENIDNKRL LVEDEKRAED YKGVKKLLDR YYLSFINDVL   300
HSIKLKNLNN YISLFRKKTR TEKENKELEN LEINLRKEIA KAFKGNEGYK SLFKKDIIET   360
ILPEFLDDKD EIALVNSFNG FTTAFTGFFD NRENMFSEEA KSTSIAFRCI NENLTRYISN   420
MDIFEKVDAI FDKHEVQEIK EKILNSDYDV EDFFEGEFFN FVLTQEGIDV YNAIIGGFVT   480
ESGEKIKGLN EYINLYNQKT KQKLPKFKPL YKQVLSDRES LSFYGEGSSG ENQTTQKGQK   540
NSRERMKRIE EGIKELGSQI LKEHPVENTQ LQNEKLYLYY LQNGRDMYVD QELDINRLSD   600
YDVDHIVPQS FLKDDSIDNK VLTRSDKNRG KSDNVPSEEV VKKMKNYWRQ LLNAKLITQR   660
KFDNLTKAER GGLSGYTSDE EVLEVFRNTL NKNSEIFSSI KKLEKLFKNF DEYSSAGIFV   720
KNGPAISTIS KDIFGEWNVI RDKWNAEYDD IHLKKKAVVT EKYEDDRRKS FKKIGSFSLE   780
QLQEYADADL SVVEKLKEII IQKVDEIYKV YGSSEKLFDA DFVLEKSLKK NDAVVAIMKD   840
LLDSVKSFEN YIKAFFGEGK ETNRDESFYG DFVLAYDILL KVDHIYDAIR NYVTQKPYSK   900
DKFKLYFQNP QFMGGWDKDK ETDYRATILR YGSKYYLAIM DKKYAKCLQK IDKDDVNGNY   960
EKINYKLLPG PNKMLPKVFF SKKWMAYYNP SEDIQKIYKN GTFKKGDMFN LNDCHKLIDF  1020
FKDSISRYPK WSNAYDFNFS ETEKYKDIAG FYREVEEQGY KVSFESASKK EVDKLVEEGK  1080
LYMFQIYNKD FSDKSHGTPN LHTMYFKLLF DENNHGQIRL SGGAELFMRR ASLKKEELVV  1140
HPANSPIANK NPDNPKKTTT LSYDVYKDKR FSEDQYELHI PIAINKCPKN IFKINTEVRV  1200
LLKHDDNPYV IGIARGERNL LYIVVVDGKG NIVEQYSLNE IINNFNGIRI KTDYHSLLDK  1260
KEKERFEARQ NWTSIENIKE LKAGYISQVV HKICELVEKY DAVIALEDLN SGFKNSRVKV  1320
EKQVYQKFEK MLIDKLNYMV DKKSNPCATG GALKGYQITN KFESFKSMST QNGFIFYIPA  1380
WLTSKIDPST GFVNLLKTKY TSIADSKKFI SSFDRIMYVP EEDLFEFALD YKNFSRTDAD  1440
YIKKWKLYSY GNRIRIFRNP KKNNVFDWEE VCLTSAYKEL FNKYGINYQQ GDIRALLCEQ  1500
SDKAFYSSFM ALMSLMLQMR NSITGRTDVD FLISPVKNSD GIFYDSRNYE AQENAILPKN  1560
ADANGAYNIA RKVLWAIGQF KKAEDEKLDK VKIAISNKEW LEYAQTSVKH GSPKKKRKVS  1620
GGSTNLSDII EKETGKQLVI QESILMLPEE VEEVIGNKPE SDILVHTAYD ESTDENVMLL  1680
TSDAPEYKPW ALVIQDSNGE NKIKMLTKYD SGGSKRTADG SEFEPKKKRK VGSG        1734

SEQ ID NO: 164        moltype = AA  length = 1734
FEATURE               Location/Qualifiers
source                1..1734
                      mol_type = protein
                      organism = synthetic construct
SEQUENCE: 164
MKRTADGSEF ESPKKKRKVM EASPASGPRH LMDPHIFTSN FNNGIGRHKT YLCYEVERLD    60
NGTSVKMDQH RGFLHNQAKN LLCGFYGRHA ELRFLDLVPS LQLDPAQIYR VTWFISWSPC   120
FSWGCAGEVR AFLQENTHVR LRIFAARIYD YDPLYKEALQ MLRDAGAQVS IMTYDEFKHC   180
WDTFVDHQGC PFQPWDGLDE HSQALSGRLR AILQNQGNSG SETPGTSESA TPESMSKLEK   240
FTNCYSLSKT LRFKAIPVGK TQENIDNKRL LVEDEKRAED YKGVKKLLDR YYLSFINDVL   300
HSIKLKNLNN YISLFRKKTR TEKENKELEN LEINLRKEIA KAFKGNEGYK SLFKKDIIET   360
ILPEFLDDKD EIALVNSFNG FTTAFTGFFD NRENMFSEEA KSTSIAFRCI NENLTRYISN   420
MDIFEKVDAI FDKHEVQEIK EKILNSDYDV EDFFEGEFFN FVLTQEGIDV YNAIIGGFVT   480
ESGEKIKGLN EYINLYNQKT KQKLPKFKPL YKQVLSDRES LSFYGGSSGE NQTTQKGQKN   540
```

```
SRERMKRIEE GIKELGSQIL KEHPVENTQL QNEKLYLYYL QNGRDMYVDQ ELDINRLSDY    600
DVDHIVPQSF LKDDSIDNKV LTRSDKNRGK SDNVPSEEVV KKMKNYWRQL LNAKLITQRK    660
FDNLTKAERG GLSEGYTSDE EVLEVFRNTL NKNSEIFSSI KKLEKLFKNF DEYSSAGIFV    720
KNGPAISTIS KDIFGEWNVI RDKWNAEYDD IHLKKKAVVT EKYEDDRRKS FKKIGSFSLE    780
QLQEYADADL SVVEKLKEII IQKVDEIYKV YGSSEKLFDA DFVLEKSLKK NDAVVAIMKD    840
LLDSVKSFEN YIKAFFGEGK ETNRDESFYG DFVLAYDILL KVDHIYDAIR NYVTQKPYSK    900
DKFKLYFQNP QFMGGWDKDK ETDYRATILR YGSKYYLAIM DKKYAKCLQK IDKDDVNGNY    960
EKINYKLLPG PNKMLPKVFF SKKWMAYYNP SEDIQKIYKN GTFKKGDMFN LNDCHKLIDF   1020
FKDSISRYPK WSNAYDFNFS ETEKYKDIAG FYREVEEQGY KVSFESASKK EVDKLVEEGK   1080
LYMFQIYNKD FSDKSHGTPN LHTMYFKLLF DENNHGQIRL SGGAELFMRR ASLKKEELVV   1140
HPANSPIANK NPDNPKKTTT LSYDVYKDKR FSEDQYELHI PIAINKCPKN IPFKINTEVRV  1200
LLKHDDNPYV IGIARGERNL LYIVVVDGKG NIVEQYSLNE IINNFNGIRI KTDYHSLLDK   1260
KEKERFEARQ NWTSIENIKE LKAGYISQVV HKICELVEKY DAVIALEDLN SGFKNSRVKV   1320
EKQVYQKFEK MLIDKLNYMV DKKSNPCATG GALKGYQITN KFESFKSMST QNGFIFYIPA   1380
WLTSKIDPST GFVNLLKTKY TSIADSKKFI SSFDRIMYVP EEDLFEFALD YKNFSRTDAD   1440
YIKKWKLYSY GNRIRIFRNP KKNNVFDWEE VCLTSAYKEL FNKYGINYQQ GDIRALLCEQ   1500
SDKAFYSSFM ALMSLMLQMR NSITGRTDVD FLISPVKNSD GIFYDSRNYE AQENAILPKN   1560
ADANGAYNIA RKVLWAIGQF KKAEDEKLDK VKIAISNKEW LEYAQTSVKH GSPKKKRKVS   1620
GGSTNLSDII EKETGKQLVI QESILMLPEE VEEVIGNKPE SDILVHTAYD ESTDENVMLL   1680
TSDAPEYKPW ALVIQDSNGE NKIKMLTKYD SGGSKRTADG SEFEPKKKRK VGSG         1734

SEQ ID NO: 165          moltype = AA   length = 1736
FEATURE                 Location/Qualifiers
source                  1..1736
                        mol_type = protein
                        organism = synthetic construct
SEQUENCE: 165
MKRTADGSEF ESPKKKRKVM EASPASGPRH LMDPHIFTSN FNNGIGRHKT YLCYEVERLD     60
NGTSVKMDQH RGFLHNQAKN LLCGFYGRHA ELRFLDLVPS LQLDPAQIYR VTWFISWSPC    120
FSWGCAGEVR AFLQENTHVR LRIFAARIYD YDPLYKEALQ MLRDAGAQVS IMTYDEFKHC    180
WDTFVDHQGC PFQPWDGLDE HSQALSGRLR AILQNQGNSG SETPGTSESA TPESMSKLEK    240
FTNCYSLSKT LRFKAIPVGK TQENIDNKRL LVEDEKRAED YKGVKKLLDR YYLSFINDVL    300
HSIKLKNLNN YISLFRKKTR TEKENKELEN LEINLRKEIA KAFKGNEGYK SLFKKDIIET    360
ILPEFLDDKD EIALVNSFNG FTTAFTGFFD NRENMFSEEA KSTSIAFRCI NENLTRYISN    420
MDIFEKVDAI FDKHEVQEIK EKILNSDYDV EDFFEGEFFN FVLTQEGIDV YNAIIGGFVT    480
ESGEKIKGLN EYINLYNQKT KQKLPKFKPL YKQVLSDRES LSFYGGSSGE NQTTQKGQKN    540
SRERMKRIEE GIKELGSQIL KEHPVENTQL QNEKLYLYYL QNGRDMYVDQ ELDINRLSDY    600
DVDHIVPQSF LKDDSIDNKV LTRSDKNRGK SDNVPSEEVV KKMKNYWRQL LNAKLITQRK    660
FDNLTKAERG GLSGSEGYTS DEEVLEVFRN TLNKNSEIFS SIKKLEKLFK NFDEYSSAGI    720
FVKNGPAIST ISKDIFGEWN VIRDKWNAEY DDIHLKKKAV VTEKYEDDRR KSFKKIGSFS    780
LEQLQEYADA DLSVVEKLKE IIIQKVDEIY KVYGSSEKLF DADFVLEKSL KKNDAVVAIM    840
KDLLDSVKSF ENYIKAFFGE GKETNRDESF YGDFVLAYDI LLKVDHIYDA IRNYVTQKPY    900
SKDKFKLYFQ NPQFMGGWDK DKETDYRATI LRYGSKYYLA IMDKKYAKCL QKIDKDDVNG    960
NYEKINYKLL PGPNKMLPKV FFSKKWMAYY NPSEDIQKIY KNGTFKKGDM FNLNDCHKLI   1020
DFFKDSISRY PKWSNAYDFN FSETEKYKDI AGFYREVEEQ GYKVSFESAS KKEVDKLVEE   1080
GKLYMFQIYN KDFSDKSHGT PNLHTMYFKL LFDENNHGQI RLSGGAELFM RRASLKKEEL   1140
VVHPANSPIA NKNPDNPKKT TTLSYDVYKD KRFSEDQYEL HIPIAINKCP KNIFKINTEV   1200
RVLLKHDDNP YVIGIARGER NLLYIVVVDG KGNIVEQYSL NEIINNFNGI RIKTDYHSLL   1260
DKKEKERFEA RQNWTSIENI KELKAGYISQ VVHKICELVE KYDAVIALED LNSGFKNSRV   1320
KVEKQVYQKF EKMLIDKLNY MVDKKSNPCA TGGALKGYQI TNKFESFKSM STQNGFIFYI   1380
PAWLTSKIDP STGFVNLLKT KYTSIADSKK FISSFDRIMY VPEEDLFEFA LDYKNFSRTD   1440
ADYIKKWKLY SYGNRIRIFR NPKKNNVFDW EEVCLTSAYK ELFNKYGINY QQGDIRALLC   1500
EQSDKAFYSS FMALMSLMLQ MRNSITGRTD VDFLISPVKN SDGIFYDSRN YEAQENAILP   1560
KNADANGAYN IARKVLWAIG QFKKAEDEKL DKVKIAISNK EWLEYAQTSV KHGSPKKKRK   1620
VSGGSTNLSD IIEKETGKQL VIQESILMLP EEVEEVIGNK PESDILVHTA YDESTDENVM   1680
LLTSDAPEYK PWALVIQDSN GENKIKMLTK YDSGGSKRTA DGSEFEPKKK RKVGSG       1736

SEQ ID NO: 166          moltype = AA   length = 1616
FEATURE                 Location/Qualifiers
source                  1..1616
                        mol_type = protein
                        organism = synthetic construct
SEQUENCE: 166
MKRTADGSEF ESPKKKRKVS EVEFSHEYWM RHALTLAKRA RDEREVPVGA VLVLNNRVIG     60
EGWNRAIGLH DPTAHAEIMA LRQGGLVMQN YRLIDATLYV TFEPCVMCAG AMIHSRIGRV    120
VFGVRNSKRG AAGSLMNVLN YPGMNHRVEI TEGILADECA ALLCDFYRMP RQVFNAQKKA    180
QSSINSGGSS GGSSGSETPG TSESATPESS GGSSGGSSKL EKFTNCYSLS KTLRFKAIPV    240
GKTQENIDNK RLLVEDEKRA EDYKGVKKLL DRYYLSFIND VLHSIKLKNL NNYISLFRKK    300
TRTEKENKEL ENLEINLRKE IAKAFKGNEG YKSLFKKDII ETILPEFLDD KDEIALVNSF    360
NGFTTAFTGF FDNRENMFSE EAKSTSIAFR CINENLTRYI SNMDIFEKVD AIFDKHEVQE    420
IKEKILNSDY DVEDFFEGEF FNFVLTQEGI DVYNAIIGGF VTESGEKIKG LNEYINLYNQ    480
KTKQKLPKFK PLYKQVLSDR ESLSFYGGSS GENQTTQKGQ KNSRERMKRI EEGIKELGSQ    540
ILKEHPVENT QLQNEKLYLY YLQNGRDMYV DQELDINRLS DYDVDHIVPQ SFLKDDSIDN    600
KVLTRSDKNR GKSDNVPSEE VVKKMKNYWR QLLNAKLITQ RKFDNLTKAE RGGLSEGYTS    660
DEEVLEVFRN TLNKNSEIFS SIKKLEKLFK NFDEYSSAGI FVKNGPAIST ISKDIFGEWN    720
VIRDKWNAEY DDIHLKKKAV VTEKYEDDRR KSFKKIGSFS LEQLQEYADA DLSVVEKLKE    780
IIIQKVDEIY KVYGSSEKLF DADFVLEKSL KKNDAVVAIM KDLLDSVKSF ENYIKAFFGE    840
GKETNRDESF YGDFVLAYDI LLKVDHIYDA IRNYVTQKPY SKDKFKLYFQ NPQFMGGWDK    900
DKETDYRATI LRYGSKYYLA IMDKKYAKCL QKIDKDDVNG NYEKINYKLL PGPNKMLPKV    960
```

```
FFSKKWMAYY NPSEDIQKIY KNGTFKKGDM FNLNDCHKLI DFFKDSISRY PKWSNAYDFN   1020
FSETEKYKDI AGFYREVEEQ GYKVSFESAS KKEVDKLVEE GKLYMFQIYN KDFSDKSHGT   1080
PNLHTMYFKL LFDENNHGQI RLSGGAELFM RRASLKKEEL VVHPANSPIA NKNPDNPKKT   1140
TTLSYDVYKD KRFSEDQYEL HIPIAINKCP KNIFKINTEV RVLLKHDDNP YVIGIARGER   1200
NLLYIVVVDG KGNIVEQYSL NEIINNFNGI RIKTDYHSLL DKKEKERFEA RQNWTSIENI   1260
KELKAGYISQ VVHKICELVE KYDAVIALED LNSGFKNSRV KVEKQVYQKF EKMLIDKLNY   1320
MVDKKSNPCA TGGALKGYQI TNKFESFKSM STQNGFIFYI PAWLTSKIDP STGFVNLLKT   1380
KYTSIADSKK FISSFDRIMY VPEEDLFEFA LDYKNFSRTD ADYIKKWKLY SYGNRIRIFR   1440
NPKKNNVFDW EEVCLTSAYK ELFNKYGINY QQGDIRALLC EQSDKAFYSS FMALMSLMLQ   1500
MRNSITGRTD VDFLISPVKN SDGIFYDSRN YEAQENAILP KNADANGAYN IARKVLWAIG   1560
QFKKAEDEKL DKVKIAISNK EWLEYAQTSV KHSGGSKRTA DGSEFEPKKK RKVGSG      1616

SEQ ID NO: 167           moltype = AA  length = 1616
FEATURE                  Location/Qualifiers
source                   1..1616
                         mol_type = protein
                         organism = synthetic construct
SEQUENCE: 167
MKRTADGSEF ESPKKKRKVS EVEFSHEYWM RHALTLAKRA RDEREVPVGA VLVLNNRVIG    60
EGWNRAIGLH DPTAHAEIMA LRQGGLVMQN YRLIDATLYV TFEPCVMCAG AMIHSRIGRV   120
VFGVRNSKRG AAGSLMNVLN YPGMNHRVEI TEGILADECA ALLCDFYRMP RQVFNAQKKA   180
QSSINSGGSS GGSSGSETPG TSESATPESS GGSSGGSSKL EKFTNCYSLS KTLRFKAIPV   240
GKTQENIDNK RLLVEDEKRA EDYKGVKKLL DRYYLSFIND VLHSIKLKNL NNYISLFRKK   300
TRTEKENKEL ENLEINLRKE IAKAFKGNEG YKSLFKKDII ETILPEFLDD KDEIALVNSF   360
NGFTTAFTGF FDNRENMFSE EAKSTSIAFR CINENLTRYI SNMDIFEKVD AIFDKHEVQE   420
IKEKILNSDY DVEDFFEGEF FNFVLTQEGI DVYNAIIGGF VTESGEKIKG LNEYINLYNQ   480
KTKQKLPKFK PLYKQVLSDR ESLSFYGGSS GENQTTQKGQ KNSRERMKRI EEGIKELGSQ   540
ILKEHPVENT QLQNEKLYLY YLQNGRDMYV DQELDINRLS DYDVDHIVPQ SFLKDDSIDN   600
KVLTRSDKNR GKSDNVPSEE VVKKMKNYWR QLLNAKLITQ RKFDNLTKAE RGGLSEGYTS   660
DEEVLEVFRN TLNKNSEIFS SIKKLEKLFK NFDEYSSAGI FVKNGPAIST ISKDIFGEWN   720
VIRDKWNAEY DDIHLKKKAV VTEKYEDDRR KSFKKIGSFS LEQLQEYADA DLSVVEKLKE   780
IIIQKVDEIY KVYGSSEKLF DADFVLEKSL KKNDAVVAIM KDLLDSVKSF ENYIKAFFGE   840
GKETNRDESF YGDFVLAYDI LLKVDHIYDA IRNYVTQKPY SKDKFKLYFQ NPQFMGGWDK   900
DKETDYRATI LRYGSKYYLA IMDKKYAKCL QKIDKDDVNG NYEKINYKLL PGPNKMLPKV   960
FFSKKWMAYY NPSEDIQKIY KNGTFKKGDM FNLNDCHKLI DFFKDSISRY PKWSNAYDFN  1020
FSETEKYKDI AGFYREVEEQ GYKVSFESAS KKEVDKLVEE GKLYMFQIYN KDFSDKSHGT  1080
PNLHTMYFKL LFDENNHGQI RLSGGAELFM RRASLKKEEL VVHPANSPIA NKNPDNPKKT  1140
TTLSYDVYKD KRFSEDQYEL HIPIAINKCP KNIFKINTEV RVLLKHDDNP YVIGIARGER  1200
NLLYIVVVDG KGNIVEQYSL NEIINNFNGI RIKTDYHSLL DKKEKERFEA RQNWTSIENI  1260
KELKAGYISQ VVHKICELVE KYDAVIALED LNSGFKNSRV KVEKQVYQKF EKMLIDKLNY  1320
MVDKKSNPCA TGGALKGYQI TNKFESFKSM STQNGFIFYI PAWLTSKIDP STGFVNLLKT  1380
KYTSIADSKK FISSFDRIMY VPEEDLFEFA LDYKNFSRTD ADYIKKWKLY SYGNRIRIFR  1440
NPKKNNVFDW EEVCLTSAYK ELFNKYGINY QQGDIRALLC EQSDKAFYSS FMALMSLMLQ  1500
MRNSITGRTD VDFLISPVKN SDGIFYDSRN YEAQENAILP KNADANGAYN IARKVLWAIG  1560
QFKKAEDEKL DKVKIAISNK EWLEYAQTSV KHSGGSKRTA DGSEFEPKKK RKVGSG     1616

SEQ ID NO: 168           moltype = AA  length = 1618
FEATURE                  Location/Qualifiers
source                   1..1618
                         mol_type = protein
                         organism = synthetic construct
SEQUENCE: 168
MKRTADGSEF ESPKKKRKVS EVEFSHEYWM RHALTLAKRA RDEREVPVGA VLVLNNRVIG    60
EGWNRAIGLH DPTAHAEIMA LRQGGLVMQN YRLIDATLYV TFEPCVMCAG AMIHSRIGRV   120
VFGVRNSKRG AAGSLMNVLN YPGMNHRVEI TEGILADECA ALLCDFYRMP RQVFNAQKKA   180
QSSINSGGSS GGSSGSETPG TSESATPESS GGSSGGSSKL EKFTNCYSLS KTLRFKAIPV   240
GKTQENIDNK RLLVEDEKRA EDYKGVKKLL DRYYLSFIND VLHSIKLKNL NNYISLFRKK   300
TRTEKENKEL ENLEINLRKE IAKAFKGNEG YKSLFKKDII ETILPEFLDD KDEIALVNSF   360
NGFTTAFTGF FDNRENMFSE EAKSTSIAFR CINENLTRYI SNMDIFEKVD AIFDKHEVQE   420
IKEKILNSDY DVEDFFEGEF FNFVLTQEGI DVYNAIIGGF VTESGEKIKG LNEYINLYNQ   480
KTKQKLPKFK PLYKQVLSDR ESLSFYGGSS GENQTTQKGQ KNSRERMKRI EEGIKELGSQ   540
ILKEHPVENT QLQNEKLYLY YLQNGRDMYV DQELDINRLS DYDVDHIVPQ SFLKDDSIDN   600
KVLTRSDKNR GKSDNVPSEE VVKKMKNYWR QLLNAKLITQ RKFDNLTKAE RGGLSGEGEY   660
TSDEEVLEVF RNTLNKNSEI FSSIKKLEKL FKNFDEYSSA GIFVKNGPAI STISKDIFGE   720
WNVIRDKWNA EYDDIHLKKK AVVTEKYEDD RRKSFKKIGS FSLEQLQEYA DADLSVVEKL   780
KEIIIQKVDE IYKVYGSSEK LFDADFVLEK SLKKNDAVVA IMKDLLDSVK SFENYIKAFF   840
GEGKETNRDE SFYGDFVLAY DILLKVDHIY DAIRNYVTQK PYSKDKFKLY FQNPQFMGGW   900
DKDKETDYRA TILRYGSKYY LAIMDKKYAK CLQKIDKDDV NGNYEKINYK LLPGPNKMLP   960
KVFFSKKWMA YYNPSEDIQK IYKNGTFKKG DMFNLNDCHK LIDFFKDSIS RYPKWSNAYD  1020
FNFSETEKYK DIAGFYREVE EQGYKVSFES ASKKEVDKLV EEGKLYMFQI YNKDFSDKSH  1080
GTPNLHTMYF KLLFDENNHG QIRLSGGAEL FMRRASLKKE ELVVHPANSP IANKNPDNPK  1140
KTTTLSYDVY KDKRFSEDQY ELHIPIAINK CPKNIFKINT EVRVLLKHDD NPYVIGIARG  1200
ERNLLYIVVV DGKGNIVEQY SLNEIINNFN GIRIKTDYHS LDKKEKERF EARQNWTSIE  1260
NIKELKAGYI SQVVHKICEL VEKYDAVIAL EDLNSGFKNS RVKVEKQVYQ KFEKMLIDKL  1320
NYMVDKKSNP CATGGALKGY QITNKFESFK SMSTQNGFIF YIPAWLTSKI DPSTGFVNLL  1380
KTKYTSIADS KKFISSFDRI MYVPEEDLFE FALDYKNFSR TDADYIKKWK LYSYGNRIRI  1440
FRNPKKNNVF DWEEVCLTSA YKELFNKYGI NYQQGDIRAL CEQSDKAFY SSFMALMSLM  1500
LQMRNSITGR TDVDFLISPV KNSDGIFYDS RNYEAQENAI LPKNADANGA YNIARKVLWA  1560
IGQFKKAEDE KLDKVKIAIS NKEWLEYAQT SVKHSGGSKR TADGSEFEPK KKRKVGSG    1618
```

-continued

```
SEQ ID NO: 169          moltype = AA   length = 53
FEATURE                 Location/Qualifiers
source                  1..53
                        mol_type = protein
                        organism = Vibrio campbellii
SEQUENCE: 169
CRVTGVQLKN HLIASHIKPW AVSNNQERLD GHNGLLLAPH VDHLFDKGFI SFE        53

SEQ ID NO: 170          moltype = AA   length = 137
FEATURE                 Location/Qualifiers
source                  1..137
                        mol_type = protein
                        organism = Bacillus thermoleovorans
SEQUENCE: 170
MPNRPLKPCN KIGCTNLTRD RYCEQHKHLA EQRQRTRRND KEYDKHKRNQ QARAFYHSRE  60
WERVRLAVLA RDNYLCQHCL KEKKITRAVI VDHVVPLLVD WSKRLDMDNL QSLCQSCHNR 120
KTAEDKRRYG QGRSGKF                                               137

SEQ ID NO: 171          moltype = AA   length = 49
FEATURE                 Location/Qualifiers
source                  1..49
                        mol_type = protein
                        note = Bacillus phage SP01
                        organism = Okubovirus sp.
SEQUENCE: 171
KGKTFQVHRL VAIHFCEGYE EGLVVDHKDG NKDNNLSTNL RWVTQKINV             49

SEQ ID NO: 172          moltype = AA   length = 156
FEATURE                 Location/Qualifiers
source                  1..156
                        mol_type = protein
                        organism = Neisseria meningitidis
SEQUENCE: 172
SFKDRKEIEK RQEENRKDRE KAAAKFREYF PNFVGEPKSK DILKLRLYEQ QHGKCLYSGK  60
EINLGRLNEK GYVEIDHALP FSRTWDDSFN NKVLVLGSEN QNKGNQTPYE YFNGKDNSRE 120
WQEFKARVET SRFPRSKKQR ILLQKFDEDG FKERNL                          156

SEQ ID NO: 173          moltype = AA   length = 53
FEATURE                 Location/Qualifiers
source                  1..53
                        mol_type = protein
                        organism = Vibrio campbellii
SEQUENCE: 173
CRVTGVQLKN HLIASHIKPW AVSNNQERLD GHNGLLLAPH VDHLFDKGFI SFE        53

SEQ ID NO: 174          moltype = AA   length = 62
FEATURE                 Location/Qualifiers
source                  1..62
                        mol_type = protein
                        organism = Streptomyces coelicolor
SEQUENCE: 174
SARGAVLKRC QKRCENPECA GHPTELTKAG LPILQVDHVN DLAKGGPDVP WNMIALCPNC  60
HA                                                                62

SEQ ID NO: 175          moltype = AA   length = 4
FEATURE                 Location/Qualifiers
source                  1..4
                        mol_type = protein
                        organism = synthetic construct
SEQUENCE: 175
GSSG                                                               4

SEQ ID NO: 176          moltype = AA   length = 6
FEATURE                 Location/Qualifiers
source                  1..6
                        mol_type = protein
                        organism = synthetic construct
SEQUENCE: 176
GSSGSS                                                             6

SEQ ID NO: 177          moltype = AA   length = 8
FEATURE                 Location/Qualifiers
source                  1..8
                        mol_type = protein
                        organism = synthetic construct
SEQUENCE: 177
GSSGSSGS                                                           8
```

```
SEQ ID NO: 178           moltype = AA   length = 60
FEATURE                  Location/Qualifiers
source                   1..60
                         mol_type = protein
                         organism = synthetic construct
VARIANT                  4..60
                         note = Residue may be present or absent
SEQUENCE: 178
GSSGSSGSSG SSGSSGSSGS SGSSGSSGSS GSSGSSGSSG SSGSSGSSGS SGSSGSSGSS   60

SEQ ID NO: 179           moltype = AA   length = 62
FEATURE                  Location/Qualifiers
source                   1..62
                         mol_type = protein
                         organism = synthetic construct
VARIANT                  4..60
                         note = Residue may be present or absent
SEQUENCE: 179
GSSGSSGSSG SSGSSGSSGS SGSSGSSGSS GSSGSSGSSG SSGSSGSSGS SGSSGSSGSS   60
GS                                                                 62

SEQ ID NO: 180           moltype = AA   length = 1228
FEATURE                  Location/Qualifiers
source                   1..1228
                         mol_type = protein
                         note = Lachnospiraceae bacterium
                         organism = unidentified
SEQUENCE: 180
MSKLEKFTNC YSLSKTLRFK AIPVGKTQEN IDNKRLLVED EKRAEDYKGV KKLLDRYYLS   60
FINDVLHSIK LKNLNNYISL FRKKTRTEKE NKELENLEIN LRKEIAKAFK GNEGYKSLFK  120
KDIIETILPE FLDDKDEIAL VNSFNGFTTA FTGFFDNREN MFSEEAKSTS IAFRCINENL  180
TRYISNMDIF EKVDAIFDKH EVQEIKEKIL NSDYDVEDFF EGEFFNFVLT QEGIDVYNAI  240
IGGFVTESGE KIKGLNEYIN LYNQKTKQKL PKFKPLYKQV LSDRESLSFY GEGYTSDEEV  300
LEVFRNTLNK NSEIFSSIKK LEKLFKNFDE YSSAGIFVKN GPAISTISKD IFGEWNVIRD  360
KWNAEYDDIH LKKKAVVTEK YEDDRRKSFK KIGSFSLEQL QEYADADLSV VEKLKEIIIQ  420
KVDEIYKVYG SSEKLFDADF VLEKSLKKND AVVAIMKDLL DSVKSFENYI KAFFGEGKET  480
NRDESFYGDF VLAYDILLKV DHIYDAIRNY VTQKPYSKDK FKLYFQNPQF MGGWDKDKET  540
DYRATILRYG SKYYLAIMDK KYAKCLQKID KDDVNGNYEK INYKLLPGPN KMLPKVFFSK  600
KWMAYYNPSE DIQKIYKNGT FKKGDMFNLN DCHKLIDFFK DSISRYPKWS NAYDFNFSET  660
EKYKDIAGFY REVEEQGYKV SFESASKKEV DKLVEEGKLY MFQIYNKDFS DKSHGTPNLH  720
TMYFKLLFDE NNHGQIRLSG GAELFMRRAS LKKEELVVHP ANSPIANKNP DNPKKTTTLS  780
YDVYKDKRFS EDQYELHIPI AINKCPKNIF KINTEVRVLL KHDDNPYVIG IDRGERNLLY  840
IVVVDGKGNI VEQYSLNEII NNFNGIRIKT DYHSLLDKKE KERFEARQNW TSIENIKELK  900
AGYISQVVHK ICELVEKYDA VIALEDLNSG FKNSRVKVEK QVYQKFEKML IDKLNYMVDK  960
KSNPCATGGA LKGYQITNKF ESFKSMSTQN GFIFYIPAWL TSKIDPSTGF VNLLKTKYTS 1020
IADSKKFISS FDRIMYVPEE DLFEFALDYK NFSRTDADYI KKWKLYSYGN RIRIFRNPKK 1080
NNVFDWEEVC LTSAYKELFN KYGINYQQGD IRALLCEQSD KAFYSSFMAL MSLMLQMRNS 1140
ITGRTDVDFL ISPVKNSDGI FYDSRNYEAQ ENAILPKNAD ANGAYNIARK VLWAIGQFKK 1200
AEDEKLDKVK IAISNKEWLE YAQTSVKH                                   1228

SEQ ID NO: 181           moltype = AA   length = 1228
FEATURE                  Location/Qualifiers
source                   1..1228
                         mol_type = protein
                         organism = synthetic construct
SEQUENCE: 181
MSKLEKFTNC YSLSKTLRFK AIPVGKTQEN IDNKRLLVED EKRAEDYKGV KKLLDRYYLS   60
FINDVLHSIK LKNLNNYISL FRKKTRTEKE NKELENLEIN LRKEIAKAFK GNEGYKSLFK  120
KDIIETILPE FLDDKDEIAL VNSFNGFTTA FTGFFDNREN MFSEEAKSTS IAFRCINENL  180
TRYISNMDIF EKVDAIFDKH EVQEIKEKIL NSDYDVEDFF EGEFFNFVLT QEGIDVYNAI  240
IGGFVTESGE KIKGLNEYIN LYNQKTKQKL PKFKPLYKQV LSDRESLSFY GEGYTSDEEV  300
LEVFRNTLNK NSEIFSSIKK LEKLFKNFDE YSSAGIFVKN GPAISTISKD IFGEWNVIRD  360
KWNAEYDDIH LKKKAVVTEK YEDDRRKSFK KIGSFSLEQL QEYADADLSV VEKLKEIIIQ  420
KVDEIYKVYG SSEKLFDADF VLEKSLKKND AVVAIMKDLL DSVKSFENYI KAFFGEGKET  480
NRDESFYGDF VLAYDILLKV DHIYDAIRNY VTQKPYSKDK FKLYFQNPQF MRGWDKDKET  540
DYRATILRYG SKYYLAIMDK KYAKCLQKID KDDVNGNYEK INYKLLPGPN KMLPRVFFSK  600
KWMAYYNPSE DIQKIYKNGT FKKGDMFNLN DCHKLIDFFK DSISRYPKWS NAYDFNFSET  660
EKYKDIAGFY REVEEQGYKV SFESASKKEV DKLVEEGKLY MFQIYNKDFS DKSHGTPNLH  720
TMYFKLLFDE NNHGQIRLSG GAELFMRRAS LKKEELVVHP ANSPIANKNP DNPKKTTTLS  780
YDVYKDKRFS EDQYELHIPI AINKCPKNIF KINTEVRVLL KHDDNPYVIG IDRGERNLLY  840
IVVVDGKGNI VEQYSLNEII NNFNGIRIKT DYHSLLDKKE KERFEARQNW TSIENIKELK  900
AGYISQVVHK ICELVEKYDA VIALEDLNSG FKNSRVKVEK QVYQKFEKML IDKLNYMVDK  960
KSNPCATGGA LKGYQITNKF ESFKSMSTQN GFIFYIPAWL TSKIDPSTGF VNLLKTKYTS 1020
IADSKKFISS FDRIMYVPEE DLFEFALDYK NFSRTDADYI KKWKLYSYGN RIRIFRNPKK 1080
NNVFDWEEVC LTSAYKELFN KYGINYQQGD IRALLCEQSD KAFYSSFMAL MSLMLQMRNS 1140
ITGRTDVDFL ISPVKNSDGI FYDSRNYEAQ ENAILPKNAD ANGAYNIARK VLWAIGQFKK 1200
AEDEKLDKVK IAISNKEWLE YAQTSVKH                                   1228

SEQ ID NO: 182           moltype = AA   length = 1228
```

```
FEATURE                 Location/Qualifiers
source                  1..1228
                        mol_type = protein
                        organism = synthetic construct
SEQUENCE: 182
MSKLEKFTNC YSLSKTLRFK AIPVGKTQEN IDNKRLLVED EKRAEDYKGV KKLLDRYYLS    60
FINDVLHSIK LKNLNNYISL FRKKTRTEKE NKELENLEIN LRKEIAKAFK GNEGYKSLFK   120
KDIIETILPE FLDDKDEIAL VNSFNGFTTA FTGFFDNREN MFSEEAKSTS IAFRCINENL   180
TRYISNMDIF EKVDAIFDKH EVQEIKEKIL NSDYDVEDFF EGEFFNFVLT QEGIDVYNAI   240
IGGFVTESGE KIKGLNEYIN LYNQKTKQKL PKFKPLYKQV LSDRESLSFY GEGYTSDEEV   300
LEVFRNTLNK NSEIFSSIKK LEKLFKNFDE YSSAGIFVKN GPAISTISKD IFGEWNVIRD   360
KWNAEYDDIH LKKKAVVTEK YEDDRRKSFK KIGSFSLEQL QEYADADLSV VEKLKEIIIQ   420
KVDEIYKVYG SSEKLFDADF VLEKSLKKND AVVAIMKDLL DSVKSFENYI KAFFGEGKET   480
NRDESFYGDF VLAYDILLKV DHIYDAIRNY VTQKPYSKDK FKLYFQNPQF MRGWDKDVET   540
DRRATILRYG SKYYLAIMDK KYAKCLQKID KDDVNGNYEK INYKLLPGPN KMLPKVFFSK   600
KWMAYYNPSE DIQKIYKNGT FKKGDMFNLN DCHKLIDFFK DSISRYPKWS NAYDFNFSET   660
EKYKDIAGFY REVEEQGYKV SFESASKKEV DKLVEEGKLY MFQIYNKDFS DKSHGTPNLH   720
TMYFKLLFDE NNHGQIRLSG GAELFMRRAS LKKEELVVHP ANSPIANKNP DNPKKTTTLS   780
YDVYKDKRFS EDQYELHIPI AINKCPKNIF KINTEVRVLL KHDDNPYVIG IDRGERNLLY   840
IVVVDGKGNI VEQYSLNEII NNFNGIRIKT DYHSLLDKKE KERFEARQNW TSIENIKELK   900
AGYISQVVHK ICELVEKYDA VIALEDLNSG FKNSRVKVEK QVYQKFEKML IDKLNYMVDK   960
KSNPCATGGA LKGYQITNKF ESFKSMSTQN GFIFYIPAWL TSKIDPSTGF VNLLKTKYTS  1020
IADSKKFISS FDRIMYVPEE DLFEFALDYK NFSRTDADYI KKWKLYSYGN RIRIFRNPKK  1080
NNVFDWEEVC LTSAYKELFN KYGINYQQGD IRALLCEQSD KAFYSSFMAL MSLMLQMRNS  1140
ITGRTDVDFL ISPVKNSDGI FYDSRNYEAQ ENAILPKNAD ANGAYNIARK VLWAIGQFKK  1200
AEDEKLDKVK IAISNKEWLE YAQTSVKH                                    1228

SEQ ID NO: 183          moltype = AA    length = 1228
FEATURE                 Location/Qualifiers
source                  1..1228
                        mol_type = protein
                        organism = synthetic construct
SEQUENCE: 183
MSKLEKFTNC YSLSKTLRFK AIPVGKTQEN IDNKRLLVED EKRAEDYKGV KKLLDRYYLS    60
FINDVLHSIK LKNLNNYISL FRKKTRTEKE NKELENLEIN LRKEIAKAFK GNEGYKSLFK   120
KDIIETILPE FLDDKDEIAL VNSFNGFTTA FTGFFRNREN MFSEEAKSTS IAFRCINENL   180
TRYISNMDIF EKVDAIFDKH EVQEIKEKIL NSDYDVEDFF EGEFFNFVLT QEGIDVYNAI   240
IGGFVTESGE KIKGLNEYIN LYNQKTKQKL PKFKPLYKQV LSDRESLSFY GEGYTSDEEV   300
LEVFRNTLNK NSEIFSSIKK LEKLFKNFDE YSSAGIFVKN GPAISTISKD IFGEWNVIRD   360
KWNAEYDDIH LKKKAVVTEK YEDDRRKSFK KIGSFSLEQL QEYADADLSV VEKLKEIIIQ   420
KVDEIYKVYG SSEKLFDADF VLEKSLKKND AVVAIMKDLL DSVKSFENYI KAFFGEGKET   480
NRDESFYGDF VLAYDILLKV DHIYDAIRNY VTQKPYSKDK FKLYFQNPQF MGGWDKDKET   540
DYRATILRYG SKYYLAIMDK KYAKCLQKID KDDVNGNYEK INYKLLPGPN KMLPKVFFSK   600
KWMAYYNPSE DIQKIYKNGT FKKGDMFNLN DCHKLIDFFK DSISRYPKWS NAYDFNFSET   660
EKYKDIAGFY REVEEQGYKV SFESASKKEV DKLVEEGKLY MFQIYNKDFS DKSHGTPNLH   720
TMYFKLLFDE NNHGQIRLSG GAELFMRRAS LKKEELVVHP ANSPIANKNP DNPKKTTTLS   780
YDVYKDKRFS EDQYELHIPI AINKCPKNIF KINTEVRVLL KHDDNPYVIG IDRGERNLLY   840
IVVVDGKGNI VEQYSLNEII NNFNGIRIKT DYHSLLDKKE KERFEARQNW TSIENIKELK   900
AGYISQVVHK ICELVEKYDA VIALEDLNSG FKNSRVKVEK QVYQKFEKML IDKLNYMVDK   960
KSNPCATGGA LKGYQITNKF ESFKSMSTQN GFIFYIPAWL TSKIDPSTGF VNLLKTKYTS  1020
IADSKKFISS FDRIMYVPEE DLFEFALDYK NFSRTDADYI KKWKLYSYGN RIRIFRNPKK  1080
NNVFDWEEVC LTSAYKELFN KYGINYQQGD IRALLCEQSD KAFYSSFMAL MSLMLQMRNS  1140
ITGRTDVDFL ISPVKNSDGI FYDSRNYEAQ ENAILPKNAD ANGAYNIARK VLWAIGQFKK  1200
AEDEKLDKVK IAISNKEWLE YAQTSVKH                                    1228

SEQ ID NO: 184          moltype = AA    length = 1376
FEATURE                 Location/Qualifiers
source                  1..1376
                        mol_type = protein
                        organism = synthetic construct
SEQUENCE: 184
MSKLEKFTNC YSLSKTLRFK AIPVGKTQEN IDNKRLLVED EKRAEDYKGV KKLLDRYYLS    60
FINDVLHSIK LKNLNNYISL FRKKTRTEKE NKELENLEIN LRKEIAKAFK GNEGYKSLFK   120
KDIIETILPE FLDDKDEIAL VNSFNGFTTA FTGFFDNREN MFSEEAKSTS IAFRCINENL   180
TRYISNMDIF EKVDAIFDKH EVQEIKEKIL NSDYDVEDFF EGEFFNFVLT QEGIDVYNAI   240
IGGFVTESGE KIKGLNEYIN LYNQKTKQKL PKFKPLYKQV LSDRESLSFY GEGSSGENQT   300
TQKGQKNSRE RMKRIEEGIK ELGSQILKEH PVENTQLQNE KLYLYYLQNG RDMYVDQELD   360
INRLSDYDVD HIVPQSFLKD DSIDNKVLTR SDKNRGKSDN VPSEEVVKKM KNYWRQLLNA   420
KLITQRKFDN LTKAERGGLS GYTSDEEVLE VFRNTLNKNS EIFSSIKKLE KLFKNFDEYS   480
SAGIFVKNGP AISTISKDIF GEWNVIRDKW NAEYDDIHLK KKAVVTEKYE DDRRKSFKKI   540
GSFSLEQLQE YADADLSVVE KLKEIIIQKV DEIYKVYGSS EKLFDADFVL EKSLKKNDAV   600
VAIMKDLLDS VKSFENYIKA FFGEGKETNR DESFYGDFVL AYDILLKVDH IYDAIRNYVT   660
QKPYSKDKFK LYFQNPQFMR GWDKKETDY RATILRYGSK YYLAIMDKKY AKCLQKIDKD   720
DVNGNYEKIN YKLLPGPNKM LPRVFFSKKW MAYYNPSEDI QKIYKNGTFK KGDMFNLNDC   780
HKLIDFFKDS ISRYPKWSNA YDFNFSETEK YKDIAGFYRE VEEQGYKVSF ESASKKEVDK   840
LVEEGKLYMF QIYNKDFSDK SHGTPNLHTM YFKLLFDENN HGQIRLSGGA ELFMRRASLK   900
KEELVVHPAN SPIANKNPDN PKKTTTLSYD VYKDKRFSED QYELHIPIAI NKCPKNIFKI   960
NTEVRVLLKH DDNPYVIGID RGERNLLYIV VVDGKGNIVE QYSLNEIINN FNGIRIKTDY  1020
HSLLDKKEKE RFEARQNWTS IENIKELKAG YISQVVHKIC ELVEKYDAVI ALEDLNSGFK  1080
```

```
NSRVKVEKQV YQKFEKMLID KLNYMVDKKS NPCATGGALK GYQITNKFES FKSMSTQNGF  1140
IFYIPAWLTS KIDPSTGFVN LLKTKYTSIA DSKKFISSFD RIMYVPEEDL FEFALDYKNF  1200
SRTDADYIKK WKLYSYGNRI RIFRNPKKNN VFDWEEVCLT SAYKELFNKY GINYQQGDIR  1260
ALLCEQSDKA FYSSFMALMS LMLQMRNSIT GRTDVDFLIS PVKNSDGIFY DSRNYEAQEN  1320
AILPKNADAN GAYNIARKVL WAIGQFKKAE DEKLDKVKIA ISNKEWLEYA QTSVKH      1376

SEQ ID NO: 185          moltype = AA   length = 1376
FEATURE                 Location/Qualifiers
source                  1..1376
                        mol_type = protein
                        organism = synthetic construct
SEQUENCE: 185
MSKLEKFTNC YSLSKTLRFK AIPVGKTQEN IDNKRLLVED EKRAEDYKGV KKLLDRYYLS    60
FINDVLHSIK LKNLNNYISL FRKKTRTEKE NKELENLEIN LRKEIAKAFK GNEGYKSLFK   120
KDIIETILPE FLDDKDEIAL VNSFNGFTTA FTGFFDNREN MFSEEAKSTS IAFRCINENL   180
TRYISNMDIF EKVDAIFDKH EVQEIKEKIL NSDYDVEDFF EGEFFNFVLT QEGIDVYNAI   240
IGGFVTESGE KIKGLNEYIN LYNQKTKQKL PKFKPLYKQV LSDRESLSFY GEGSSGENQT   300
TQKGQKNSRE RMKRIEEGIK ELGSQILKEH PVENTQLQNE KLYLYYLQNG RDMYVDQELD   360
INRLSDYDVD HIVPQSFLKD DSIDNKVLTR SDKNRGKSDN VPSEEVVKKM KNYWRQLLNA   420
KLITQRKFDN LTKAERGGLS GYTSDEEVLE VFRNTLNKNS EIFSSIKKLE KLFKNFDEYS   480
SAGIFVKNGP AISTISKDIF GEWNVIRDKW NAEYDDIHLK KKAVVTEKYE DDRRKSFKKI   540
GSFSLEQLQE YADADLSVVE KLKKEIIIQKV DEIYKVYGSS EKLFDADFVL EKSLKKNDAV   600
VAIMKDLLDS VKSFENYIKA FFGEGKETNR DESFYGDFVL AYDILLKVDH IYDAIRNYVT   660
QKPYSKDKFK LYFQNPQFMR GWDKVETDR RATILRYGSK YYLAIMDKKY AKCLQKIDKD   720
DVNGNYEKIN YKLLPGPNKM LPKVFFSKKW MAYYNPSEDI QKIYKNGTFK KGDMFNLNDC   780
HKLIDFFKDS ISRYPKWSNA YDFNFSETEK YKDIAGFYRE VEEQGYKVSF ESASKKEVDK   840
LVEEGKLYMF QIYNKDFSDK SHGTPNLHTM YFKLLFDENN HGQIRLSGGA ELFMRRASLK   900
KEELVVHPAN SPIANKNPDN PKKTTTLSYD VYKDKRFSED QYELHIPIAI NKCPKNIFKI   960
NTEVRVLLKH DDNPYVIGID RGERNLLYIV VVDGKGNIVE QYSLNEIINN FNGIRIKTDY  1020
HSLLDKKEKE RFEARQNWTS IENIKELKAG YISQVVHKIC ELVEKYDAVI ALEDLNSGFK  1080
NSRVKVEKQV YQKFEKMLID KLNYMVDKKS NPCATGGALK GYQITNKFES FKSMSTQNGF  1140
IFYIPAWLTS KIDPSTGFVN LLKTKYTSIA DSKKFISSFD RIMYVPEEDL FEFALDYKNF  1200
SRTDADYIKK WKLYSYGNRI RIFRNPKKNN VFDWEEVCLT SAYKELFNKY GINYQQGDIR  1260
ALLCEQSDKA FYSSFMALMS LMLQMRNSIT GRTDVDFLIS PVKNSDGIFY DSRNYEAQEN  1320
AILPKNADAN GAYNIARKVL WAIGQFKKAE DEKLDKVKIA ISNKEWLEYA QTSVKH      1376

SEQ ID NO: 186          moltype = AA   length = 1376
FEATURE                 Location/Qualifiers
source                  1..1376
                        mol_type = protein
                        organism = synthetic construct
SEQUENCE: 186
MSKLEKFTNC YSLSKTLRFK AIPVGKTQEN IDNKRLLVED EKRAEDYKGV KKLLDRYYLS    60
FINDVLHSIK LKNLNNYISL FRKKTRTEKE NKELENLEIN LRKEIAKAFK GNEGYKSLFK   120
KDIIETILPE FLDDKDEIAL VNSFNGFTTA FTGFFDNREN MFSEEAKSTS IAFRCINENL   180
TRYISNMDIF EKVDAIFDKH EVQEIKEKIL NSDYDVEDFF EGEFFNFVLT QEGIDVYNAI   240
IGGFVTESGE KIKGLNEYIN LYNQKTKQKL PKFKPLYKQV LSDRESLSFY GEGSSGENQT   300
TQKGQKNSRE RMKRIEEGIK ELGSQILKEH PVENTQLQNE KLYLYYLQNG RDMYVDQELD   360
INRLSDYDVD HIVPQSFLKD DSIDNKVLTR SDKNRGKSDN VPSEEVVKKM KNYWRQLLNA   420
KLITQRKFDN LTKAERGGLS GYTSDEEVLE VFRNTLNKNS EIFSSIKKLE KLFKNFDEYS   480
SAGIFVKNGP AISTISKDIF GEWNVIRDKW NAEYDDIHLK KKAVVTEKYE DDRRKSFKKI   540
GSFSLEQLQE YADADLSVVE KLKKEIIIQKV DEIYKVYGSS EKLFDADFVL EKSLKKNDAV   600
VAIMKDLLDS VKSFENYIKA FFGEGKETNR DESFYGDFVL AYDILLKVDH IYDAIRNYVT   660
QKPYSKDKFK LYFQNPQFMG GWDKDKETDY RATILRYGSK YYLAIMDKKY AKCLQKIDKD   720
DVNGNYEKIN YKLLPGPNKM LPKVFFSKKW MAYYNPSEDI QKIYKNGTFK KGDMFNLNDC   780
HKLIDFFKDS ISRYPKWSNA YDFNFSETEK YKDIAGFYRE VEEQGYKVSF ESASKKEVDK   840
LVEEGKLYMF QIYNKDFSDK SHGTPNLHTM YFKLLFDENN HGQIRLSGGA ELFMRRASLK   900
KEELVVHPAN SPIANKNPDN PKKTTTLSYD VYKDKRFSED QYELHIPIAI NKCPKNIFKI   960
NTEVRVLLKH DDNPYVIGID RGERNLLYIV VVDGKGNIVE QYSLNEIINN FNGIRIKTDY  1020
HSLLDKKEKE RFEARQNWTS IENIKELKAG YISQVVHKIC ELVEKYDAVI ALEDLNSGFK  1080
NSRVKVEKQV YQKFEKMLID KLNYMVDKKS NPCATGGALK GYQITNKFES FKSMSTQNGF  1140
IFYIPAWLTS KIDPSTGFVN LLKTKYTSIA DSKKFISSFD RIMYVPEEDL FEFALDYKNF  1200
SRTDADYIKK WKLYSYGNRI RIFRNPKKNN VFDWEEVCLT SAYKELFNKY GINYQQGDIR  1260
ALLCEQSDKA FYSSFMALMS LMLQMRNSIT GRTDVDFLIS PVKNSDGIFY DSRNYEAQEN  1320
AILPKNADAN GAYNIARKVL WAIGQFKKAE DEKLDKVKIA ISNKEWLEYA QTSVKH      1376

SEQ ID NO: 187          moltype = AA   length = 1372
FEATURE                 Location/Qualifiers
source                  1..1372
                        mol_type = protein
                        organism = synthetic construct
SEQUENCE: 187
MSKLEKFTNC YSLSKTLRFK AIPVGKTQEN IDNKRLLVED EKRAEDYKGV KKLLDRYYLS    60
FINDVLHSIK LKNLNNYISL FRKKTRTEKE NKELENLEIN LRKEIAKAFK GNEGYKSLFK   120
KDIIETILPE FLDDKDEIAL VNSFNGFTTA FTGFFDNREN MFSEEAKSTS IAFRCINENL   180
TRYISNMDIF EKVDAIFDKH EVQEIKEKIL NSDYDVEDFF EGEFFNFVLT QEGIDVYNAI   240
IGGFVTESGE KIKGLNEYIN LYNQKTKQKL PKFKPLYKQV LSDRESLSFY GENQTTQKGQ   300
KNSRERMKRI EEGIKELGSQ ILKEHPVENT QLQNEKLYLY YLQNGRDMYV DQELDINRLS   360
DYDVDHIVPQ SFLKDDSIDN KVLTRSDKNR GKSDNVPSEE VVKKMKNYWR QLLNAKLITQ   420
```

```
RKFDNLTKAE RGGLSEGYTS DEEVLEVFRN TLNKNSEIFS SIKKLEKLFK NFDEYSSAGI    480
FVKNGPAIST ISKDIFGEWN VIRDKWNAEY DDIHLKKKAV VTEKYEDDRR KSFKKIGSFS    540
LEQLQEYADA DLSVVEKLKE IIIQKVDEIY KVYGSSEKLF DADFVLEKSL KKNDAVVAIM    600
KDLLDSVKSF ENYIKAFFGE GKETNRDESF YGDFVLAYDI LLKVDHIYDA IRNYVTQKPY    660
SKDKFKLYFQ NPQFMRGWDK DKETDYRATI LRYGSKYYLA IMDKKYAKCL QKIDKDDVNG    720
NYEKINYKLL PGPNKMLPRV FFSKKWMAYY NPSEDIQKIY KNGTFKKGDM FNLNDCHKLI    780
DFFKDSISRY PKWSNAYDFN FSETEKYKDI AGFYREVEEQ GYKVSFESAS KKEVDKLVEE    840
GKLYMFQIYN KDFSDKSHGT PNLHTMYFKL LFDENNHGQI RLSGGAELFM RRASLKKEEL    900
VVHPANSPIA NKNPDNPKKT TTLSYDVYKD KRFSEDQYEL HIPIAINKCP KNIFKINTEV    960
RVLLKHDDNP YVIGIDRGER NLLYIVVVDG KGNIVEQYSL NEIINNFNGI RIKTDYHSLL   1020
DKKEKERFEA RQNWTSIENI KELKAGYISQ VVHKICELVE KYDAVIALED LNSGFKNSRV   1080
KVEKQVYQKF EKMLIDKLNY MVDKKSNPCA TGGALKGYQI TNKFESFKSM STQNGFIFYI   1140
PAWLTSKIDP STGFVNLLKT KYTSIADSKK FISSFDRIMY VPEEDLFEFA LDYKNFSRTD   1200
ADYIKKWKLY SYGNRIRIFR NPKKNNVFDW EEVCLTSAYK ELFNKYGINY QQGDIRALLC   1260
EQSDKAFYSS FMALMSLMLQ MRNSITGRTD VDFLISPVKN SDGIFYDSRN YEAQENAILP   1320
KNADANGAYN IARKVLWAIG QFKKAEDEKL DKVKIAISNK EWLEYAQTSV KH           1372

SEQ ID NO: 188           moltype = AA   length = 1372
FEATURE                  Location/Qualifiers
source                   1..1372
                         mol_type = protein
                         organism = synthetic construct
SEQUENCE: 188
MSKLEKFTNC YSLSKTLRFK AIPVGKTQEN IDNKRLLVED EKRAEDYKGV KKLLDRYYLS     60
FINDVLHSIK LKNLNNYISL FRKKTRTEKE NKELENLEIN LRKEIAKAFK GNEGYKSLFK    120
KDIIETILPE FLDDKDEIAL VNSFNGFTTA FTGFFDNREN MFSEEAKSTS IAFRCINENL    180
TRYISNMDIF EKVDAIFDKH EVQEIKEKIL NSDYDVEDFF EGEFFNFVLT QEGIDVYNAI    240
IGGFVTESGE KIKGLNEYIN LYNQKTKQKL PKFKPLYKQV LSDRESLSFY GENQTTQKGQ    300
KNSRERMKRI EEGIKELGSQ ILKEHPVENT QLQNEKLYLY YLQNGRDMYV DQELDINRLS    360
DYDVDHIVPQ SFLKDDSIDN KVLTRSDKNR GKSDNVPSEE VVKKMKNYWR QLLNAKLITQ    420
RKFDNLTKAE RGGLSEGYTS DEEVLEVFRN TLNKNSEIFS SIKKLEKLFK NFDEYSSAGI    480
FVKNGPAIST ISKDIFGEWN VIRDKWNAEY DDIHLKKKAV VTEKYEDDRR KSFKKIGSFS    540
LEQLQEYADA DLSVVEKLKE IIIQKVDEIY KVYGSSEKLF DADFVLEKSL KKNDAVVAIM    600
KDLLDSVKSF ENYIKAFFGE GKETNRDESF YGDFVLAYDI LLKVDHIYDA IRNYVTQKPY    660
SKDKFKLYFQ NPQFMRGWDK DVETDRRATI LRYGSKYYLA IMDKKYAKCL QKIDKDDVNG    720
NYEKINYKLL PGPNKMLPKV FFSKKWMAYY NPSEDIQKIY KNGTFKKGDM FNLNDCHKLI    780
DFFKDSISRY PKWSNAYDFN FSETEKYKDI AGFYREVEEQ GYKVSFESAS KKEVDKLVEE    840
GKLYMFQIYN KDFSDKSHGT PNLHTMYFKL LFDENNHGQI RLSGGAELFM RRASLKKEEL    900
VVHPANSPIA NKNPDNPKKT TTLSYDVYKD KRFSEDQYEL HIPIAINKCP KNIFKINTEV    960
RVLLKHDDNP YVIGIDRGER NLLYIVVVDG KGNIVEQYSL NEIINNFNGI RIKTDYHSLL   1020
DKKEKERFEA RQNWTSIENI KELKAGYISQ VVHKICELVE KYDAVIALED LNSGFKNSRV   1080
KVEKQVYQKF EKMLIDKLNY MVDKKSNPCA TGGALKGYQI TNKFESFKSM STQNGFIFYI   1140
PAWLTSKIDP STGFVNLLKT KYTSIADSKK FISSFDRIMY VPEEDLFEFA LDYKNFSRTD   1200
ADYIKKWKLY SYGNRIRIFR NPKKNNVFDW EEVCLTSAYK ELFNKYGINY QQGDIRALLC   1260
EQSDKAFYSS FMALMSLMLQ MRNSITGRTD VDFLISPVKN SDGIFYDSRN YEAQENAILP   1320
KNADANGAYN IARKVLWAIG QFKKAEDEKL DKVKIAISNK EWLEYAQTSV KH           1372

SEQ ID NO: 189           moltype = AA   length = 1372
FEATURE                  Location/Qualifiers
source                   1..1372
                         mol_type = protein
                         organism = synthetic construct
SEQUENCE: 189
MSKLEKFTNC YSLSKTLRFK AIPVGKTQEN IDNKRLLVED EKRAEDYKGV KKLLDRYYLS     60
FINDVLHSIK LKNLNNYISL FRKKTRTEKE NKELENLEIN LRKEIAKAFK GNEGYKSLFK    120
KDIIETILPE FLDDKDEIAL VNSFNGFTTA FTGFFRNREN MFSEEAKSTS IAFRCINENL    180
TRYISNMDIF EKVDAIFDKH EVQEIKEKIL NSDYDVEDFF EGEFFNFVLT QEGIDVYNAI    240
IGGFVTESGE KIKGLNEYIN LYNQKTKQKL PKFKPLYKQV LSDRESLSFY GENQTTQKGQ    300
KNSRERMKRI EEGIKELGSQ ILKEHPVENT QLQNEKLYLY YLQNGRDMYV DQELDINRLS    360
DYDVDHIVPQ SFLKDDSIDN KVLTRSDKNR GKSDNVPSEE VVKKMKNYWR QLLNAKLITQ    420
RKFDNLTKAE RGGLSEGYTS DEEVLEVFRN TLNKNSEIFS SIKKLEKLFK NFDEYSSAGI    480
FVKNGPAIST ISKDIFGEWN VIRDKWNAEY DDIHLKKKAV VTEKYEDDRR KSFKKIGSFS    540
LEQLQEYADA DLSVVEKLKE IIIQKVDEIY KVYGSSEKLF DADFVLEKSL KKNDAVVAIM    600
KDLLDSVKSF ENYIKAFFGE GKETNRDESF YGDFVLAYDI LLKVDHIYDA IRNYVTQKPY    660
SKDKFKLYFQ NPQFMGGWDK DKETDYRATI LRYGSKYYLA IMDKKYAKCL QKIDKDDVNG    720
NYEKINYKLL PGPNKMLPKV FFSKKWMAYY NPSEDIQKIY KNGTFKKGDM FNLNDCHKLI    780
DFFKDSISRY PKWSNAYDFN FSETEKYKDI AGFYREVEEQ GYKVSFESAS KKEVDKLVEE    840
GKLYMFQIYN KDFSDKSHGT PNLHTMYFKL LFDENNHGQI RLSGGAELFM RRASLKKEEL    900
VVHPANSPIA NKNPDNPKKT TTLSYDVYKD KRFSEDQYEL HIPIAINKCP KNIFKINTEV    960
RVLLKHDDNP YVIGIDRGER NLLYIVVVDG KGNIVEQYSL NEIINNFNGI RIKTDYHSLL   1020
DKKEKERFEA RQNWTSIENI KELKAGYISQ VVHKICELVE KYDAVIALED LNSGFKNSRV   1080
KVEKQVYQKF EKMLIDKLNY MVDKKSNPCA TGGALKGYQI TNKFESFKSM STQNGFIFYI   1140
PAWLTSKIDP STGFVNLLKT KYTSIADSKK FISSFDRIMY VPEEDLFEFA LDYKNFSRTD   1200
ADYIKKWKLY SYGNRIRIFR NPKKNNVFDW EEVCLTSAYK ELFNKYGINY QQGDIRALLC   1260
EQSDKAFYSS FMALMSLMLQ MRNSITGRTD VDFLISPVKN SDGIFYDSRN YEAQENAILP   1320
KNADANGAYN IARKVLWAIG QFKKAEDEKL DKVKIAISNK EWLEYAQTSV KH           1372

SEQ ID NO: 190           moltype = AA   length = 1374
FEATURE                  Location/Qualifiers
```

| source | 1..1374 |
| --- | --- |
| | mol_type = protein |
| | organism = synthetic construct |

SEQUENCE: 190

```
MSKLEKFTNC YSLSKTLRFK AIPVGKTQEN IDNKRLLVED EKRAEDYKGV KKLLDRYYLS   60
FINDVLHSIK LKNLNNYISL FRKKTRTEKE NKELENLEIN LRKEIAKAFK GNEGYKSLFK  120
KDIIETILPE FLDDKDEIAL VNSFNGFTTA FTGFFDNREN MFSEEAKSTS IAFRCINENL  180
TRYISNMDIF EKVDAIFDKH EVQEIKEKIL NSDYDVEDFF EGEFFNFVLT QEGIDVYNAI  240
IGGFVTESGE KIKGLNEYIN LYNQKTKQKL PKFKPLYKQV LSDRESLSFY GSGENQTTQK  300
GQKNSRERMK RIEEGIKELG SQILKEHPVE NTQLQNEKLY LYYLQNGRDM YVDQELDINR  360
LSDYDVDHIV PQSFLKDDSI DNKVLTRSDK NRGKSDNVPS EEVVKKMKNY WRQLLNAKLI  420
TQRKFDNLTK AERGGLSEGY TSDEEVLEVF RNTLNKNSEI FSSIKKLEKL FKNFDEYSSA  480
GIFVKNGPAI STISKDIFGE WNVIRDKWNA EYDDIHLKKK AVVTEKYEDD RRKSFKKIGS  540
FSLEQLQEYA DADLSVVEKL KEIIIQKVDE IYKVYGSSEK LFDADFVLEK SLKKNDAVVA  600
IMKDLLDSVK SFENYIKAFF GEGKETNRDE SFYGDFVLAY DILLKVDHIY DAIRNYVTQK  660
PYSKDKFKLY FQNPQFMRGW DKDKETDYRA TILRYGSKYY LAIMDKKYAK CLQKIDKDDV  720
NGNYEKINYK LLPGPNKMLP RVFFSKKWMA YYNPSEDIQK IYKNGTFKKG DMFNLNDCHK  780
LIDFFKDSIS RYPKWSNAYD FNFSETEKYK DIAGFYREVE EQGYKVSFES ASKKEVDKLV  840
EEGKLYMFQI YNKDFSDKSH GTPNLHTMYF KLLFDENNHG QIRLSGGAEL FMRRASLKKE  900
ELVVHPANSP IANKNPDNPK KTTTLSYDVY KDKRFSEDQY ELHIPIAINK CPKNIFKINT  960
EVRVLLKHDD NPYVIGIDRG ERNLLYIVVV DGKGNIVEQY SLNEIINNFN GIRIKTDYHS 1020
LLDKKEKERF EARQNWTSIE NIKELKAGYI SQVVHKICEL VEKYDAVIAL EDLNSGFKNS 1080
RVKVEKQVYQ KFEKMLIDKL NYMVDKKSNP CATGGALKGY QITNKFESFK SMSTQNGFIF 1140
YIPAWLTSKI DPSTGFVNLL KTKYTSIADS KKFISSFDRI MYVPEEDLFE FALDYKNFSR 1200
TDADYIKKWK LYSYGNRIRI FRNPKKNNVF DWEECVLTSA YKELFNKYGI NYQQGDIRAL 1260
LCEQSDKAFY SSFMALMSLM LQMRNSITGR TDVDFLISPV KNSDGIFYDS RNYEAQENAI 1320
LPKNADANGA YNIARKVLWA IGQFKKAEDE KLDKVKIAIS NKEWLEYAQT SVKH        1374
```

| SEQ ID NO: 191 | moltype = AA  length = 1374 |
| --- | --- |
| FEATURE | Location/Qualifiers |
| source | 1..1374 |
| | mol_type = protein |
| | organism = synthetic construct |

SEQUENCE: 191

```
MSKLEKFTNC YSLSKTLRFK AIPVGKTQEN IDNKRLLVED EKRAEDYKGV KKLLDRYYLS   60
FINDVLHSIK LKNLNNYISL FRKKTRTEKE NKELENLEIN LRKEIAKAFK GNEGYKSLFK  120
KDIIETILPE FLDDKDEIAL VNSFNGFTTA FTGFFDNREN MFSEEAKSTS IAFRCINENL  180
TRYISNMDIF EKVDAIFDKH EVQEIKEKIL NSDYDVEDFF EGEFFNFVLT QEGIDVYNAI  240
IGGFVTESGE KIKGLNEYIN LYNQKTKQKL PKFKPLYKQV LSDRESLSFY GSGENQTTQK  300
GQKNSRERMK RIEEGIKELG SQILKEHPVE NTQLQNEKLY LYYLQNGRDM YVDQELDINR  360
LSDYDVDHIV PQSFLKDDSI DNKVLTRSDK NRGKSDNVPS EEVVKKMKNY WRQLLNAKLI  420
TQRKFDNLTK AERGGLSEGY TSDEEVLEVF RNTLNKNSEI FSSIKKLEKL FKNFDEYSSA  480
GIFVKNGPAI STISKDIFGE WNVIRDKWNA EYDDIHLKKK AVVTEKYEDD RRKSFKKIGS  540
FSLEQLQEYA DADLSVVEKL KEIIIQKVDE IYKVYGSSEK LFDADFVLEK SLKKNDAVVA  600
IMKDLLDSVK SFENYIKAFF GEGKETNRDE SFYGDFVLAY DILLKVDHIY DAIRNYVTQK  660
PYSKDKFKLY FQNPQFMRGW DKDVETDRRA TILRYGSKYY LAIMDKKYAK CLQKIDKDDV  720
NGNYEKINYK LLPGPNKMLP KVFFSKKWMA YYNPSEDIQK IYKNGTFKKG DMFNLNDCHK  780
LIDFFKDSIS RYPKWSNAYD FNFSETEKYK DIAGFYREVE EQGYKVSFES ASKKEVDKLV  840
EEGKLYMFQI YNKDFSDKSH GTPNLHTMYF KLLFDENNHG QIRLSGGAEL FMRRASLKKE  900
ELVVHPANSP IANKNPDNPK KTTTLSYDVY KDKRFSEDQY ELHIPIAINK CPKNIFKINT  960
EVRVLLKHDD NPYVIGIDRG ERNLLYIVVV DGKGNIVEQY SLNEIINNFN GIRIKTDYHS 1020
LLDKKEKERF EARQNWTSIE NIKELKAGYI SQVVHKICEL VEKYDAVIAL EDLNSGFKNS 1080
RVKVEKQVYQ KFEKMLIDKL NYMVDKKSNP CATGGALKGY QITNKFESFK SMSTQNGFIF 1140
YIPAWLTSKI DPSTGFVNLL KTKYTSIADS KKFISSFDRI MYVPEEDLFE FALDYKNFSR 1200
TDADYIKKWK LYSYGNRIRI FRNPKKNNVF DWEECVLTSA YKELFNKYGI NYQQGDIRAL 1260
LCEQSDKAFY SSFMALMSLM LQMRNSITGR TDVDFLISPV KNSDGIFYDS RNYEAQENAI 1320
LPKNADANGA YNIARKVLWA IGQFKKAEDE KLDKVKIAIS NKEWLEYAQT SVKH        1374
```

| SEQ ID NO: 192 | moltype = AA  length = 1374 |
| --- | --- |
| FEATURE | Location/Qualifiers |
| source | 1..1374 |
| | mol_type = protein |
| | organism = synthetic construct |

SEQUENCE: 192

```
MSKLEKFTNC YSLSKTLRFK AIPVGKTQEN IDNKRLLVED EKRAEDYKGV KKLLDRYYLS   60
FINDVLHSIK LKNLNNYISL FRKKTRTEKE NKELENLEIN LRKEIAKAFK GNEGYKSLFK  120
KDIIETILPE FLDDKDEIAL VNSFNGFTTA FTGFFRNREN MFSEEAKSTS IAFRCINENL  180
TRYISNMDIF EKVDAIFDKH EVQEIKEKIL NSDYDVEDFF EGEFFNFVLT QEGIDVYNAI  240
IGGFVTESGE KIKGLNEYIN LYNQKTKQKL PKFKPLYKQV LSDRESLSFY GSGENQTTQK  300
GQKNSRERMK RIEEGIKELG SQILKEHPVE NTQLQNEKLY LYYLQNGRDM YVDQELDINR  360
LSDYDVDHIV PQSFLKDDSI DNKVLTRSDK NRGKSDNVPS EEVVKKMKNY WRQLLNAKLI  420
TQRKFDNLTK AERGGLSEGY TSDEEVLEVF RNTLNKNSEI FSSIKKLEKL FKNFDEYSSA  480
GIFVKNGPAI STISKDIFGE WNVIRDKWNA EYDDIHLKKK AVVTEKYEDD RRKSFKKIGS  540
FSLEQLQEYA DADLSVVEKL KEIIIQKVDE IYKVYGSSEK LFDADFVLEK SLKKNDAVVA  600
IMKDLLDSVK SFENYIKAFF GEGKETNRDE SFYGDFVLAY DILLKVDHIY DAIRNYVTQK  660
PYSKDKFKLY FQNPQFMGGW DKDKETDYRA TILRYGSKYY LAIMDKKYAK CLQKIDKDDV  720
NGNYEKINYK LLPGPNKMLP KVFFSKKWMA YYNPSEDIQK IYKNGTFKKG DMFNLNDCHK  780
LIDFFKDSIS RYPKWSNAYD FNFSETEKYK DIAGFYREVE EQGYKVSFES ASKKEVDKLV  840
EEGKLYMFQI YNKDFSDKSH GTPNLHTMYF KLLFDENNHG QIRLSGGAEL FMRRASLKKE  900
```

```
ELVVHPANSP IANKNPDNPK KTTTLSYDVY KDKRFSEDQY ELHIPIAINK CPKNIFKINT   960
EVRVLLKHDD NPYVIGIDRG ERNLLYIVVV DGKGNIVEQY SLNEIINNFN GIRIKTDYHS  1020
LLDKKEKERF EARQNWTSIE NIKELKAGYI SQVVHKICEL VEKYDAVIAL EDLNSGFKNS  1080
RVKVEKQVYQ KFEKMLIDKL NYMVDKKSNP CATGGALKGY QITNKFESFK SMSTQNGFIF  1140
YIPAWLTSKI DPSTGFVNLL KTKYTSIADS KKFISSFDRI MYVPEEDLFE FALDYKNFSR  1200
TDADYIKKWK LYSYGNRIRI FRNPKKNNVF DWEEVCLTSA YKELFNKYGI NYQQGDIRAL  1260
LCEQSDKAFY SSFMALMSLM LQMRNSITGR TDVDFLISPV KNSDGIFYDS RNYEAQENAI  1320
LPKNADANGA YNIARKVLWA IGQFKKAEDE KLDKVKIAIS NKEWLEYAQT SVKH        1374

SEQ ID NO: 193         moltype = AA   length = 1328
FEATURE                Location/Qualifiers
source                 1..1328
                       mol_type = protein
                       organism = synthetic construct
SEQUENCE: 193
MAGSKKRRIK QDTQFEGFTN LYQVSKTLRF ELIPQGKTLK HIQEQGFIEE DKARNDHYKE    60
LKPIIDRIYK TYADQCLQLV QLDWENLSAA IDSYRKEKTE ETRNALIEEQ ATYRNAIHDY   120
FIGRTDNLTD AINKRHAEIY KGLFKAELFN GKVLKQLGTV TTTEHENALL RSFDKFTTYF   180
SGFYRNRKNV FSAEDISTAI PHRIVQDNPP KFKENCHIFT RLITAVPSLR EHFENVKKAI   240
GIFVSTSIEE VFSFPPYNQL LTQTQIDLYN QLLGGISREA GTEKIKGLNE VLNLAIQKND   300
ETAHIIASLP HRFIPLFKQI LSDRNTLSFI LEEFKSDEEV IQSFCKYKTL LRNENVLETA   360
EALFNELNSI DLTHIFISHK KLETISSALC DHWDTLRNAL YERRISELTG KITKSAKEKV   420
QRSLKHEDIN LQEIISAAGK ELSEAFKQKT SEILSHAHAA LDQPLPTTLK KQEEKEILKS   480
QLDSLLGLYH LLDWFAVDES NEVDPEFSAR LTGIKLEMEP SLSFYNKARN YATKKPYSVE   540
KFKLNFQMPT LARGWDVNRE KNNGAILFVK NGLYYLGIMP KQKGRYKALS FEPTEKTSEG   600
FDKMYYDYFP DAAKMIPKCS TQLKAVTAHF QTHTTPILLS NNFIEPLEIT KEIYDLNNPE   660
KEPKKFQTAY AKKTGDQKGY REALCKWIDF TRDFLSKYTK TTSIDLSSLR PSSQYKDLGE   720
YYAELNPLLY HISFQRIAEK EIMDAVETGK LYLFQIYNKD FAKGHHGKPN LHTLYWTGLF   780
SPENLAKTSI KLNGQAELFY RPKSRMKRMA HRLGEKMLNK KLKDQKTPIP DTLYQELYDY   840
VNHRLSHDLS DEARALLPNV ITKEVSHEII KDRRFTSDKF FPHVPITLNY QAANSPSKFN   900
QRVNAYLKEH PETPIIGIDR GERNLIYITV IDSTGKILEQ RSLNTIQQFD YQKKLDNREK   960
ERVAARQAWS VVGTIKDLKQ GYLSQVIHEI VDLMIHYQAV VVLENLNGF KSKRTGIAEK   1020
AVYQQFEKML IDKLNCLVLK DYPAEKVGGV LNPYQLTDQF TSFAKMGTQS GFLFYVPAPY  1080
TSKIDPLTGF VDPFVWKTIK NHESRKHFLE GFDFLHYDVK TGDFILHFKM NRNLSFQRGL  1140
PGFMPAWDIV FEKNETQOFDA KGTPFIAGKR IVPVIENHRF TGRYRDLYPA NELIALLEEK  1200
GIVFRDGSNI LPKLLENDDS HAIDTMVALI RSVLQMRNSN AATGEDYINS PVRDLNGVCF  1260
DSRFQNPEWP MDADANGAYH IALKGQLLLN HLKESKDLKL QNGISNQDWL AYIQELRNGS  1320
KKRRIKQD                                                          1328

SEQ ID NO: 194         moltype = DNA   length = 3790
FEATURE                Location/Qualifiers
source                 1..3790
                       mol_type = other DNA
                       organism = synthetic construct
SEQUENCE: 194
ccatgggcag caaactggaa aaatttacga attgttatag cctgtccaag accctgcgtt    60
tcaaagccat ccccgttggc aaaacccagg agaaattgaa taataaacgt ctgctggttg   120
aggatgaaaa aagagcagaa gactataagg gagtcaaaaa actgctggat cggtactacc   180
tgagctttat aaatgacgtg ctgcatagca ttaaactgaa aaatctgaat aactatatta   240
gtctgttccg caagaaaacc cgaacagaga aagaaaataa agagctggaa aacctggaga   300
tcaatctgcg taaagagatc gcaaaagctt ttaaaggaaa tgaaggttat aaaagcctgt   360
tcaaaaaaga cattattgaa accatcctgc cggaatttct ggatgataaa gacgagatag   420
cgctcgtgaa cagcttcaac gggttcacga ccgccttcac gggcttttttc gataacaggg   480
aaaatatgtt tcagaggaa gccaaaagca cctcgatagc gttccgttgc attaatgaaa    540
atttgacaag atatatcagc aacatggata ttttcgagaa agttgatgcg atctttgaca   600
aacatgaagt gcaggagatt aaggaaaaaa ttctgaacag cgattatgat gttgaggatt   660
ttttcgaggg ggaattttt aactttgtac tgacacagga aggtatagat gtgtataatg   720
ctattatcgg cgggttcgtt accgaatccg gcgagaaaat taagggtctg aatgagtaca   780
tcaatctgta taaccaaaag accaaacaga aactgccaaa attcaaaccg ctgtacaagg   840
aagtcctgag cgatcgggaa agcttgagct tttacggtga aggttatacc agcgacgagg   900
aggtactgga ggtctttcgc aataccctga caagaacag cgaaattttc agctccatta   960
aaaagctgga gaaactgttt aagaattttg acgagtacag cagcgcaggt atttttgtga  1020
agaacggacc tgccataagc accattagca aggatatttt tggagagtgg aatgttatcc  1080
gtgataaatg gaacgcggaa tatgatgaca tacacctgga tgggtaactg  1140
agaaatatga agacgatcgc cgcaaaagct ttaaaaaaaat cggcagcttt agcctggagc  1200
agctgcagga atatgcggac gccgacctga gcgtggtcga gaaactgaag gaaattatta  1260
tccaaaaagt ggatgagatt tacaaggtat atggtagcag cgaaaactg tttgatgcgg  1320
acttcgttct ggaaaaaagc ctgaaaaaaa atgatgctgt tgttgcgatc atgaaagacc  1380
tgctcgatag cgttaaagc tttgaaaatt acattaaagc attctttggc gagggcaaag  1440
aaacaaacag agacgaaagc ttttatggcg acttcgtcct ggcttatgac atcctgttga  1500
aggtagatca tatatatgat gcaattcgta attacgtaac caaaagccg tacagcaaag  1560
ataagttcaa actgtatttc cagaacccgc agtttatggg tggctgggac aaagacaagg  1620
agacagacta tcgcgccact attctgcgtt acggcagcaa gtactatctc gccatcatgg  1680
acaaaaaata tgcaaagtgt ctgcagaaaa tcgataaaga cgacgtgaac ggaaattacg  1740
aaaagattaa ttataagctg ctgccagggc ccaacaagtg gttaccgaaa tgattttttt  1800
ccaaaaaatg gatggcatac tataaccccga gcgaggatat acagaagatt tacaaaaatg  1860
ggaccttcaa aaaggggat atgttcaatc tgaatgactg ccacaaactg atcgattttt  1920
ttaaagatag catcagccgt tatcctaaat ggtcaaacgc gtatgatttt aatttctccg  1980
aaacggagaa atataaagac attgctggtt ctatccgcga agtcgaagaa cagggttata  2040
```

```
aagttagctt tgaatcggcc agcaagaaag aggttgataa actggtggag gagggtaagc    2100
tgtatatgtt tcagatttat aacaaagact ttagcgacaa aagccacggt actcctaatc    2160
tgcatacgat gtactttaaa ctgctgtttg atgagaataa ccacggccaa atccgtctct    2220
ccggtggagc agaactttt  atgcggcgtg cgagcctaaa aaaggaagaa ctggtggtgc    2280
atcccgccaa cagcccgatt gctaacaaaa atccagataa tcctaagaag accaccacac    2340
tgtcgtacga tgtctataag gataaacgtt tctcggaaga ccagtatgaa ttgcatatac    2400
cgatagcaat taataaatgc ccaaaaaaca ttttcaaaat caacactgaa gttcgtgtgc    2460
tgctgaaaca tgatgataat ccgtatgtga tcggaattga ccgtggggag agaaatctgc    2520
tgtatattgt agtcgttgat ggcaagggca acatgcttga gcagtatagc ctgaatgaaa    2580
taattaataa ttttaacggt atacgtatta aaaccgacta tcatagcctg ctggataaaa    2640
aggagaaaga gcgttttgag gcacgccaaa attggacgag catcgaaaac atcaaggaac    2700
tgaaggcagg atatatcagc caagtagtcc ataaaatctg tgaactggtg gagaagtacg    2760
acgctgtcat tgccctggaa gacctcaata gcggctttaa aaacagccgg gtgaaggtgg    2820
agaaacaggt ataccaaaag tttgaaaaga tgctcattga taagctgaac tatatggttg    2880
ataaaaagag caacccgtgc gccactggcg gtgcactgaa agggtaccaa attaccaata    2940
aatttgaaag cttaaaagc  atgagcacgc agaatgggtt tatttttat  ataccagcat    3000
ggctgacgag caagattgac cccagcactg gttttgtcaa tctgctgaaa accaaataca    3060
caagcattgc ggatagcaaa aaatttattt cgagcttcga ccgtattatg tatgttccgg    3120
aggaagatct gtttgaattt gccctggatt ataaaaactt cagccgcacc gatgcagatt    3180
atatcaaaaa atggaagctg tacagttatg gtaatcgtat acgtatcttc cgtaatccga    3240
agaaaaacaa tgtgttcgat tgggaagagg tctgtctgac cagcgcgtat aaagaactgt    3300
tcaacaagta cggaataaat tatcagcaag gtgacattcg cgcactgctg ggtgaacagt    3360
cagataaagc attttatagc agctttatgt cgctgatgag cctgatgctc cagatgcgca    3420
acagcataac cggtcgcaca gatgttgact ttctgatcag ccctgtgaag aatagcgacg    3480
gcatcttcta cgattccagg aactatgaag cacaggaaaa cgctattctg cctaaaaatg    3540
ccgatgccaa cggcgcctat aatattgcac ggaaggttct gtgggcgatt ggacagttca    3600
agaaagcgga agatgagaag ctggataagg taaaaattgc tattagcaat aaggaatggc    3660
tggagtacgc acagacatcg gttaaacacg gtagtaaaag gccggcggcc acgaaaaagg    3720
ccggccaggc aaaaaagaaa aagggagcgg ccgcactcga gcaccaccac caccaccact    3780
gagcggccgc                                                            3790
```

SEQ ID NO: 195        moltype = DNA  length = 8986
FEATURE              Location/Qualifiers
source               1..8986
                      mol_type = other DNA
                      organism = synthetic construct
SEQUENCE: 195

```
tggcgaatgg gacgcgccct gtagcggcgc attaagcgcg gcgggtgtgg tggttacgcg    60
cagcgtgacc gctacacttg ccagcgccct agcgcccgct cctttcgctt tcttcccttc    120
ctttctcgcc acgttcgccg gctttccccg tcaagctcta aatcgggggc tccctttagg    180
gttccgattt agtgctttac ggcacctcga ccccaaaaaa cttgattagg gtgatggttc    240
acgtagtggg ccatcgccct gatagacggt ttttcgccct ttgacgttgg agtccacgtt    300
ctttaatagt ggactcttgt tccaaactgg aacaacactc aaccctatct cggtctattc    360
ttttgattta taagggatttt tgccgatttc ggcctattgg ttaaaaaatg agctgattta    420
acaaaaattt aacgcgaatt ttaacaaaat attaacgttt acaatttcag gtggcacttt    480
tcggggaaat gtgcgcggaa cccctatttg tttatttttc taaatacatt caaatatgta    540
tccgctcatg aattaattct tagaaaaact catcgagcat caaatgaaac tgcaatttat    600
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa ataaggttat caagtgaga    780
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga cgagaaatac gcgatcgctg ttaaaaggac    960
aattacaaac aggaatcgaa tgcaaccggc gcaggaacac tgccagcgca tcaacaatat    1020
tttcacctga atcaggatat tcttctaata cctggaatgc tgttttcccg gggatcgcag    1080
tggtgagtaa ccatgcatca tcaggagtac ggataaaatg cttgatggtc ggaagaggca    1140
taaattccgt cagccagttt agtctgacca tctcatctgt aacatcattg gcaacgctac    1200
ctttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
cccttgtatt actgtttatg taagcagaca gttttattgt tcatgaccaa atcccttaa    1440
cgtgagtttt cgttccactg agcgtcagac cccgtagaaa agatcaaagg atcttcttga    1500
gatccttttt ttctgcgcgt aatctgctgc ttgcaaacaa aaaaaccacc gctaccagcg    1560
gtggtttgtt tgccggatca agagctacca actcttttc  cgaaggtaac tggcttcagc    1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata agtcgtgtct taccgggttg gactcaagac gatagttacc ggataaggcg    1800
cagcggtcgg gctgaacggg gggttcgtgc acacagccca gcttggagcg aacgacctac    1860
accgaactga gatacctaca gcgtgagcta tgagaaagcg ccacgcttcc cgaagggaga    1920
aaggcggaca ggtatccggt aagcggcagg gtcggaacag gagagcgcac gagggagctt    1980
ccagggggaa acgcctggta tctttatagt cctgtcgggt ttcgccacct ctgacttgag    2040
cgtcgatttt tgtgatgctc gtcagggggg cggagcctat ggaaaaacgc cagcaacgcg    2100
gcctttttac ggttcctggc cttttgctgg ccttttgctc acatgttctt tcctgcgtta    2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
```

```
gttttcaccg tcatcaccga aacgcgcgag gcagctgcgg taaagctcat cagcgtggtc 2580
gtgaagcgat tcacagatgt ctgcctgttc atccgcgtcc agctcgttga gtttctccag 2640
aagcgttaat gtctggcttc tgataaagcg ggccatgtta agggcggttt tttcctgttt 2700
ggtcactgat gcctccgtgt aagggggatt tctgttcatg ggggtaatga taccgatgaa 2760
acgagagagg atgctcacga tacgggttac tgatgatgaa catgcccggt tactggaacg 2820
ttgtgagggt aaacaactgg cggtatggat gcggcgggac cagagaaaaa tcactcaggg 2880
tcaatgccag cgcttcgtta atacagatgt aggtgttcca cagggtagcc agcagcatcc 2940
tgcgatgcag atccggaaca taatggtgca gggcgctgac ttccgcgttt ccagacttta 3000
cgaaacacgg aaaccgaaga ccattcatgt tgttgctgaa gtcgcagacg ttttgcagca 3060
gcagtcgctt cacgttcgct cgcgtatcgg tgattcattc tgctaaccag taaggcaacc 3120
ccgccagcct agccgggtcc tcaacgacag gagcacgatc atgcgcaccc gtggggccgc 3180
catgccggca taatggcct gcttctcgcc gaaacgtttg gtggcgggac cagtgacgaa 3240
ggcttgagcg agggcgtgca agattccgaa taccgcaagc gacaggccga tcatcgtcgc 3300
gctccagcga aagcggtcct cgccgaaaat gacccagagc gctgccggca cctgtcctac 3360
gagttgcatg ataaagaaga cagtcataag tgcggcgacg atagtcatgc cccgcgccca 3420
ccggaaggag ctgactgggt tgaaggctct caagggcatc ggtcgagatc ccggtgccta 3480
atgagtgagc taacttacat taattgcgtt gcgctcactg cccgctttcc agtcgggaaa 3540
cctgtcgtgc cagctgcatt aatgaatcgg ccaacgcgcg gggagaggcg gtttgcgtat 3600
tgggcgccag ggtggttttt cttttcacca gtgagacggg caacagctga ttgcccttca 3660
ccgcctggcc ctgagagagt gcagcaagc ggtccacgct ggtttgcccc agcaggcgaa 3720
aatcctgttt gatggtggtt aacggcggga tataacatga gctgtcttcg gtatcgtcgt 3780
atcccactac cgagatatcc gcaccaacgc gcagcccgga ctcggtaatg gcgcgcattg 3840
cgcccagcgc catctgatcg ttggcaacca gcatcgcagt gggaacgatg ccctcattca 3900
gcatttgcat ggtttgttga aaaccggaca tggcactcca gtcgccttcc cgttccgcta 3960
tcggctgaat ttgattgcga gtgagatatt tatgccagcc agccagacgc agacgcgccg 4020
agacagaact taatgggccc gctaacagcg cgatttgctg gtgacccaat gcgaccagat 4080
gctccacgcc cagtcgcgta ccgtcttcat gggagaaaat aatactgttg atgggtgtct 4140
ggtcagagac atcaagaaat aacgccgaaa cattagtgca ggcagcttcc acagcaatgg 4200
catcctggtc atccagcgga tagttaatga tcagcccact gacgcgttgc gcgagaagat 4260
tgtgcaccac cgctttacag gcttcgacgc cgcttcgttc taccatcgac accaccagc 4320
tggcacccag ttgatcggcg cgagatttaa tcgccgcgac aatttgcgac ggcgcgtgca 4380
gggccagact ggaggtggca acgccaatca gcaacgactg tttgcccgcc agttgttgtg 4440
ccacgcggtt gggaatgtaa ttcagctccg ccatcgccgc ttccactttt tcccgcgttt 4500
tcgcagaaac gtggctggcc tggttcacca cgcgggaacg ggtctgataa gagacaccgg 4560
catactctgc gacatcgtat aacgttactg gtttcacatt caccaccctg aattgactct 4620
cttccgggcg ctatcatgcc ataccgcgaa aggttttgcg ccattcgatg gtgtccggga 4680
tctcgacgct ctcccttatg cgactcctgc attaggaagc agcccagtag taggttgagg 4740
ccgttgagca ccgccgccgc aaggaatggt gcatgcaagg agatggcgcc caacagtccc 4800
ccggccacgg ggcctgccac catacccacg ccgaaacaag cgctcatgag cccgaagtgg 4860
cgagcccgat cttccccatc ggtgatgtcg gcgatatagg cgccagcaac cgcacctgtg 4920
gcgcggtga tgccggccac gatgcgtccg cgtagagga tcgagatctc gatcccgcga 4980
aattaatacg actcactata ggggaattgt gagcggataa caattcccct ctagaaataa 5040
ttttgtttaa cttaagaag gagatatacc atgggcagca aactgaaaa atttacgaat 5100
tgttatagcc tgtccaagac cctgcgtttc aaagccatcc ccgttggcaa aacccaggag 5160
aatattgata taaacgtct gctggttgag gatgaaaaaa gagcagaaga ctataaggga 5220
gtcaaaaaac tgctggatcg gtactacctg agctttataa atgacgtgct gcatagcatt 5280
aaactgaaaa atctgaataa ctatattagt ctgttccgca agaaaacccg aacagagaaa 5340
gaaaataaag agctggaaaa cctggagatc aatctgcgta aagagatcgc aaaagctttt 5400
aaaggaaatg aaggttataa aagcctgttc aaaaaagaca ttattgaaac catcctgccg 5460
gaattctggg atgataaaga cgagatagcg ctcgtgaaca gcttcaacgg gttcacgacc 5520
gccttcacgg gcttttttcga taacaggaa aaatatgtttt cagggaagc caaaagcacc 5580
tcgatagcgt tccgttgcat taatgaaaat ttgacaagat atatcagcaa catggatatt 5640
ttcgagaaag ttgatgcgat cttttgacaaa catgaagtgc aggagattaa ggaaaaaatt 5700
ctgaacagcg attatgatgt tgaggatttt tcgaggggg aatttttttaa ctttgtactg 5760
acacaggaga gtatagatgt gtataatgct attatcggcg ggttcgttac cgaatccgcc 5820
gagaaaatta agggtctgaa tgagtacatc aatctgtata accaaaagac caaacagaaa 5880
ctgccaaaat tcaaaccgct gtacaagcaa gtcctgagcg atcgggaaag cttgagcttt 5940
tacggtgaag gttataccag cgacgaggag gtactggagg tctttcgcaa tacccctgaac 6000
aagaacagcg aaattttcag ctccattaaa aagctggaga aactgtttaa gaattttgaa 6060
gagtacagca gcgcaggtat ttttgtgaag aacggactg ccataagcac cattagcaag 6120
gatatttttg gagagtggaa tgttatccgt gataaatgga acgcggaata tgatgacata 6180
cacctgaaaa agaaggctgt ggtaactgag aaatatgaag acgatcgccg caaaagcttt 6240
aaaaaatcg gcagctttag cctggagcag ctgcaggaat atgcggacgc cgacctgagc 6300
gtggtcgaga aactgaagga aattattatc caaaagtgg atgagatta caaggtatat 6360
ggtagcagcg aaaactgtt tgatgcggac ttcgttctgg aaaaaagcct gaaaaaaat 6420
gatgctgttg ttgcgatcat gaagacctg ctcgatagcg ttaagagctt tgaaaattac 6480
attaaagcat tctttggcga gggcaaagaa acaaacagag acgaaagctt ttatggcgac 6540
ttcgtcctgg cttatgacat cctgttgaag gtagatcata tatatgatgc aattcgtaat 6600
tacgtaaccc aaaagccgta cagcaaagat aagttcaaac tgtatttcca gaacccgcag 6660
tttatgggtg gctgggacaa agacaaggag acagactatc gcgccactat tctgcgttac 6720
ggcagcaagt actatctcgc catcatggac aaaaaatatg caaagtgtct gcagaaaatc 6780
gataaagacg acgtgaacgg aaattacgaa aagattaatt ataagctgct gccagggccc 6840
aacaagatgt taccgaaagt attttttttcc aaaaaatgaa tggcatacta taacccgagc 6900
gaggatatac agaagattta caaaatggg accttcaaag agggggatat gttcaatctg 6960
aatgactgcc acaaactgat cgattttttt aaagatagca tcagccgtta tcctaaatgg 7020
tcaaacgcgt atgatttaaa tttctccgaa acggagaaat ataaagacat tgctggtttc 7080
tatcgcgaag tcgaagaaca gggttataaa gttagctttg aatcggccag caagaaagag 7140
gttgataaac tggtggagga gggtaagctg tatatgtttc agatttataa caaagacttt 7200
agcgacaaaa gccacggtac tcctaatctg catacgatgt actttaaaact gctgtttgat 7260
```

```
gagaataacc acggccaaat ccgtctctcc ggtggagcag aacttttta t gcggcgtgcg 7320
agcctaaaaa aggaagaact ggtggtgcat cccgccaaca gcccgattgc taacaaaaat 7380
ccagataatc ctaagaagac caccacactg tcgtacgatg tctataagga taaacgtttc 7440
tcggaagacc agtatgaatt gcatataccg atagcaatta taaatgccc aaaaaacatt 7500
ttcaaaatca acactgaagt tcgtgtgctg ctgaaacatg atgataatcc gtatgtgatc 7560
ggaattgacc gtgggagag aaatctgctg tatattgtag tcgttgatgg caagggcaac 7620
atcgttgagc agtatagcct gaatgaaata attaataatt ttaacggtat acgtattaaa 7680
accgactatc atagcctgct ggataaaaag gagaaagagc gttttgaggc acgccaaaat 7740
tggacgagca tcgaaaacat caaggaactg aaggcaggat atatcagcca agtagtccat 7800
aaaatctgtg aactggtgga gaagtacgac gctgtcattg ccctggaaga cctcaatagc 7860
ggctttaaaa acagccgggt gaaggtggag aaacaggtat accaaaagtt tgaaaagatg 7920
ctcattgata agctgaacta tatgttgat aaaaagagca cccgtgcgc cactggcggt 7980
gcactgaaag ggtaccaaat taccaataaa tttgaaagct taaaagcat gagcacgcag 8040
aatgggttta tttttatat accagcatgg ctgacgagca agattgaccc cagcactggt 8100
tttgtcaatc tgctgaaaac caaatacaca agcattgcgg atagcaaaaa atttatttcg 8160
agcttcgacc gtattatgta tgttccggag gaagatctgt ttgaatttgc cctggattat 8220
aaaaacttca gccgcaccga tgcagattat atcaaaaaat ggaagctgta cagttatggt 8280
aatcgtatac gtatcttccg taatccgaag aaaaacaatg tgttcgattg ggaagaggtc 8340
tgtctgacca gcgcgtataa agaactgttc aacaagtacg gaataaatta tcagcaaggt 8400
gacattgccg cactgctgtg tgaacagtca gataaagcat tttatagcag ctttatggcg 8460
ctgatgagcc tgatgctcca gatgcgcaac agcataaccg tcgcacaga tgttgacttt 8520
ctgatcagcc ctgtgaagaa tagcgacggc atcttctacg attccaggaa ctatgaagca 8580
caggaaaacg ctattctgcc taaaaatgcc gatgccaacg gcgcctataa tattgcacgg 8640
aaggttctgt gggcgattgg acagttcaag aaagcggaag atgagaagct ggataaggta 8700
aaaattgcta ttagcaataa ggaatggctg gagtacgcac agacatcggt taaacacggt 8760
agtaaaagc cggcggccac gaaaaaggcc ggccaggcaa aaaagaaaaa gggagcggtg 8820
gcactcgagc accaccacca ccaccactga gatccggctg ctaacaaagc ccgaaaggaa 8880
gctgagttgg ctgctgccac cgctgagcaa taactagcat aacccttggg gcctctaaa 8940
cgggtcttga gggttttttt gctgaaagga ggaactatat ccggat           8986
```

```
SEQ ID NO: 196          moltype = DNA   length = 23
FEATURE                 Location/Qualifiers
source                  1..23
                        mol_type = other DNA
                        organism = synthetic construct
SEQUENCE: 196
tcatctgtgc ccctccctcc ctg                                        23

SEQ ID NO: 197          moltype = DNA   length = 23
FEATURE                 Location/Qualifiers
source                  1..23
                        mol_type = other DNA
                        organism = synthetic construct
SEQUENCE: 197
cagcccgctg gccctgtaaa gga                                        23

SEQ ID NO: 198          moltype = DNA   length = 23
FEATURE                 Location/Qualifiers
source                  1..23
                        mol_type = other DNA
                        organism = synthetic construct
SEQUENCE: 198
gaacatgaaa acttaaatag aac                                        23

SEQ ID NO: 199          moltype = DNA   length = 23
FEATURE                 Location/Qualifiers
source                  1..23
                        mol_type = other DNA
                        organism = synthetic construct
SEQUENCE: 199
gtcaggttgg ctgctgggct ggc                                        23

SEQ ID NO: 200          moltype = DNA   length = 23
FEATURE                 Location/Qualifiers
source                  1..23
                        mol_type = other DNA
                        organism = synthetic construct
SEQUENCE: 200
acagatgggg ctggacaatt ttt                                        23

SEQ ID NO: 201          moltype = DNA   length = 23
FEATURE                 Location/Qualifiers
source                  1..23
                        mol_type = other DNA
                        organism = synthetic construct
SEQUENCE: 201
ttgtaaccaa catcccctga tga                                        23

SEQ ID NO: 202          moltype = DNA   length = 23
```

```
FEATURE                 Location/Qualifiers
source                  1..23
                        mol_type = other DNA
                        organism = synthetic construct
SEQUENCE: 202
gggtaagtgg tgatgaccct aca                                              23

SEQ ID NO: 203          moltype = DNA   length = 23
FEATURE                 Location/Qualifiers
source                  1..23
                        mol_type = other DNA
                        organism = synthetic construct
SEQUENCE: 203
atttctggtc acaacagaaa taa                                              23

SEQ ID NO: 204          moltype = DNA   length = 23
FEATURE                 Location/Qualifiers
source                  1..23
                        mol_type = other DNA
                        organism = synthetic construct
SEQUENCE: 204
ttgctaccga cccagtgagt ggt                                              23

SEQ ID NO: 205          moltype = DNA   length = 23
FEATURE                 Location/Qualifiers
source                  1..23
                        mol_type = other DNA
                        organism = synthetic construct
SEQUENCE: 205
tctcagagtt aacaactctt tgc                                              23

SEQ ID NO: 206          moltype = DNA   length = 23
FEATURE                 Location/Qualifiers
source                  1..23
                        mol_type = other DNA
                        organism = synthetic construct
SEQUENCE: 206
ttgctaccga cccagtgagt ggt                                              23

SEQ ID NO: 207          moltype = DNA   length = 23
FEATURE                 Location/Qualifiers
source                  1..23
                        mol_type = other DNA
                        organism = synthetic construct
SEQUENCE: 207
ccagtccttc ttcccttatc atc                                              23

SEQ ID NO: 208          moltype = DNA   length = 23
FEATURE                 Location/Qualifiers
source                  1..23
                        mol_type = other DNA
                        organism = synthetic construct
SEQUENCE: 208
atttgaaggt ctgaaccgga att                                              23

SEQ ID NO: 209          moltype = DNA   length = 23
FEATURE                 Location/Qualifiers
source                  1..23
                        mol_type = other DNA
                        organism = synthetic construct
SEQUENCE: 209
tgtccgttgc taccgaccca gtg                                              23

SEQ ID NO: 210          moltype = DNA   length = 23
FEATURE                 Location/Qualifiers
source                  1..23
                        mol_type = other DNA
                        organism = synthetic construct
SEQUENCE: 210
acccagtgag tggtccacca cac                                              23

SEQ ID NO: 211          moltype = DNA   length = 23
FEATURE                 Location/Qualifiers
source                  1..23
                        mol_type = other DNA
                        organism = synthetic construct
SEQUENCE: 211
gaagaagaag tgaatcgtgc ggg                                              23
```

```
SEQ ID NO: 212          moltype = DNA   length = 23
FEATURE                 Location/Qualifiers
source                  1..23
                        mol_type = other DNA
                        organism = synthetic construct
SEQUENCE: 212
gtgtgccagc caatgtgctc aca                                              23

SEQ ID NO: 213          moltype = DNA   length = 23
FEATURE                 Location/Qualifiers
source                  1..23
                        mol_type = other DNA
                        organism = synthetic construct
SEQUENCE: 213
ccggagccaa ggtcaccaag gct                                              23

SEQ ID NO: 214          moltype = DNA   length = 23
FEATURE                 Location/Qualifiers
source                  1..23
                        mol_type = other DNA
                        organism = synthetic construct
SEQUENCE: 214
agaagccgac acgtggcttc cct                                              23

SEQ ID NO: 215          moltype = DNA   length = 23
FEATURE                 Location/Qualifiers
source                  1..23
                        mol_type = other DNA
                        organism = synthetic construct
SEQUENCE: 215
agtgagtggt ccaccacacc tta                                              23

SEQ ID NO: 216          moltype = DNA   length = 23
FEATURE                 Location/Qualifiers
source                  1..23
                        mol_type = other DNA
                        organism = synthetic construct
SEQUENCE: 216
gtggagaaat tacttcagca act                                              23

SEQ ID NO: 217          moltype = DNA   length = 23
FEATURE                 Location/Qualifiers
source                  1..23
                        mol_type = other DNA
                        organism = synthetic construct
SEQUENCE: 217
gggacagata tggtcaattc caa                                              23

SEQ ID NO: 218          moltype = DNA   length = 23
FEATURE                 Location/Qualifiers
source                  1..23
                        mol_type = other DNA
                        organism = synthetic construct
SEQUENCE: 218
ccaaggctgc ccagaagaag aag                                              23

SEQ ID NO: 219          moltype = DNA   length = 23
FEATURE                 Location/Qualifiers
source                  1..23
                        mol_type = other DNA
                        organism = synthetic construct
SEQUENCE: 219
gggcagtgta ctcagcaaag gtt                                              23

SEQ ID NO: 220          moltype = DNA   length = 23
FEATURE                 Location/Qualifiers
source                  1..23
                        mol_type = other DNA
                        organism = synthetic construct
SEQUENCE: 220
gcttctgggc tcgtccgcgt gga                                              23

SEQ ID NO: 221          moltype = DNA   length = 23
FEATURE                 Location/Qualifiers
source                  1..23
                        mol_type = other DNA
                        organism = synthetic construct
SEQUENCE: 221
ctgagtggtg tggcctatgc gca                                              23
```

```
SEQ ID NO: 222         moltype = DNA  length = 23
FEATURE                Location/Qualifiers
source                 1..23
                       mol_type = other DNA
                       organism = synthetic construct
SEQUENCE: 222
ctttgcagcc cgcaacctga cac                                              23

SEQ ID NO: 223         moltype = DNA  length = 23
FEATURE                Location/Qualifiers
source                 1..23
                       mol_type = other DNA
                       organism = synthetic construct
SEQUENCE: 223
actattgaat gtagggtcat cac                                              23

SEQ ID NO: 224         moltype = DNA  length = 23
FEATURE                Location/Qualifiers
source                 1..23
                       mol_type = other DNA
                       organism = synthetic construct
SEQUENCE: 224
agagggagag atttgagaaa gaa                                              23

SEQ ID NO: 225         moltype = DNA  length = 23
FEATURE                Location/Qualifiers
source                 1..23
                       mol_type = other DNA
                       organism = synthetic construct
SEQUENCE: 225
caagtcccct actgtcactg ttg                                              23

SEQ ID NO: 226         moltype = DNA  length = 23
FEATURE                Location/Qualifiers
source                 1..23
                       mol_type = other DNA
                       organism = synthetic construct
SEQUENCE: 226
cctagaaaag aagacacaag agt                                              23

SEQ ID NO: 227         moltype = DNA  length = 23
FEATURE                Location/Qualifiers
source                 1..23
                       mol_type = other DNA
                       organism = synthetic construct
SEQUENCE: 227
atcaggggat gttggttaca ata                                              23

SEQ ID NO: 228         moltype = DNA  length = 23
FEATURE                Location/Qualifiers
source                 1..23
                       mol_type = other DNA
                       organism = synthetic construct
SEQUENCE: 228
accggagcca aggtcaccaa ggc                                              23

SEQ ID NO: 229         moltype = DNA  length = 23
FEATURE                Location/Qualifiers
source                 1..23
                       mol_type = other DNA
                       organism = synthetic construct
SEQUENCE: 229
ggggatgttg gttacaataa atg                                              23

SEQ ID NO: 230         moltype = DNA  length = 23
FEATURE                Location/Qualifiers
source                 1..23
                       mol_type = other DNA
                       organism = synthetic construct
SEQUENCE: 230
cctgatgaac cagcccgcac gat                                              23

SEQ ID NO: 231         moltype = DNA  length = 23
FEATURE                Location/Qualifiers
source                 1..23
                       mol_type = other DNA
                       organism = synthetic construct
SEQUENCE: 231
```

-continued

```
ccagatgata agggaagaag gac                                          23

SEQ ID NO: 232         moltype = DNA   length = 23
FEATURE                Location/Qualifiers
source                 1..23
                       mol_type = other DNA
                       organism = synthetic construct
SEQUENCE: 232
tcttctgggc agccttggtg acc                                          23

SEQ ID NO: 233         moltype = DNA   length = 23
FEATURE                Location/Qualifiers
source                 1..23
                       mol_type = other DNA
                       organism = synthetic construct
SEQUENCE: 233
tgggattggc attctcctat tgg                                          23

SEQ ID NO: 234         moltype = DNA   length = 23
FEATURE                Location/Qualifiers
source                 1..23
                       mol_type = other DNA
                       organism = synthetic construct
SEQUENCE: 234
cgaggactgt ccagttgaga gat                                          23

SEQ ID NO: 235         moltype = DNA   length = 23
FEATURE                Location/Qualifiers
source                 1..23
                       mol_type = other DNA
                       organism = synthetic construct
SEQUENCE: 235
cttattatta gttagatata act                                          23

SEQ ID NO: 236         moltype = DNA   length = 23
FEATURE                Location/Qualifiers
source                 1..23
                       mol_type = other DNA
                       organism = synthetic construct
SEQUENCE: 236
gacctccacg ttctcgatct tca                                          23

SEQ ID NO: 237         moltype = DNA   length = 23
FEATURE                Location/Qualifiers
source                 1..23
                       mol_type = other DNA
                       organism = synthetic construct
SEQUENCE: 237
acaacatcct cctcgacgcc gac                                          23

SEQ ID NO: 238         moltype = DNA   length = 23
FEATURE                Location/Qualifiers
source                 1..23
                       mol_type = other DNA
                       organism = synthetic construct
SEQUENCE: 238
actcggcttg tcgtcgaggt agt                                          23

SEQ ID NO: 239         moltype = DNA   length = 23
FEATURE                Location/Qualifiers
source                 1..23
                       mol_type = other DNA
                       organism = synthetic construct
SEQUENCE: 239
aggactgtcc agttgagaga tac                                          23

SEQ ID NO: 240         moltype = DNA   length = 23
FEATURE                Location/Qualifiers
source                 1..23
                       mol_type = other DNA
                       organism = synthetic construct
SEQUENCE: 240
ttgcccactg gaggaacgtg ctc                                          23

SEQ ID NO: 241         moltype = DNA   length = 23
FEATURE                Location/Qualifiers
source                 1..23
                       mol_type = other DNA
                       organism = synthetic construct
```

```
SEQUENCE: 241
ctgcagccct ctaggagaga gca                                              23

SEQ ID NO: 242          moltype = DNA   length = 23
FEATURE                 Location/Qualifiers
source                  1..23
                        mol_type = other DNA
                        organism = synthetic construct
SEQUENCE: 242
aaaagatgga tccatttcct tct                                              23

SEQ ID NO: 243          moltype = DNA   length = 23
FEATURE                 Location/Qualifiers
source                  1..23
                        mol_type = other DNA
                        organism = synthetic construct
SEQUENCE: 243
gtcgcagtag cgtccgtctc tgg                                              23

SEQ ID NO: 244          moltype = DNA   length = 23
FEATURE                 Location/Qualifiers
source                  1..23
                        mol_type = other DNA
                        organism = synthetic construct
SEQUENCE: 244
ggatgtcaag tcaaataata tac                                              23

SEQ ID NO: 245          moltype = DNA   length = 23
FEATURE                 Location/Qualifiers
source                  1..23
                        mol_type = other DNA
                        organism = synthetic construct
SEQUENCE: 245
tacaagggca gtgagtgatt tgt                                              23

SEQ ID NO: 246          moltype = DNA   length = 23
FEATURE                 Location/Qualifiers
source                  1..23
                        mol_type = other DNA
                        organism = synthetic construct
SEQUENCE: 246
ggggcactat tgggcatatt gct                                              23

SEQ ID NO: 247          moltype = DNA   length = 23
FEATURE                 Location/Qualifiers
source                  1..23
                        mol_type = other DNA
                        organism = synthetic construct
SEQUENCE: 247
aagtcggcca catgagcttc aaa                                              23

SEQ ID NO: 248          moltype = DNA   length = 23
FEATURE                 Location/Qualifiers
source                  1..23
                        mol_type = other DNA
                        organism = synthetic construct
SEQUENCE: 248
gaggaacttg gcgagcccga agt                                              23

SEQ ID NO: 249          moltype = DNA   length = 23
FEATURE                 Location/Qualifiers
source                  1..23
                        mol_type = other DNA
                        organism = synthetic construct
SEQUENCE: 249
caaagacctg cacccagcca gcg                                              23

SEQ ID NO: 250          moltype = DNA   length = 23
FEATURE                 Location/Qualifiers
source                  1..23
                        mol_type = other DNA
                        organism = synthetic construct
SEQUENCE: 250
tcgacgccga cttcgaggcc cac                                              23

SEQ ID NO: 251          moltype = DNA   length = 23
FEATURE                 Location/Qualifiers
source                  1..23
                        mol_type = other DNA
```

-continued

```
                        organism = synthetic construct
SEQUENCE: 251
ggggcatctg aatgcatgtc tgc                                           23

SEQ ID NO: 252          moltype = DNA   length = 23
FEATURE                 Location/Qualifiers
source                  1..23
                        mol_type = other DNA
                        organism = synthetic construct
SEQUENCE: 252
gcggcagggg aatctcccca gat                                           23

SEQ ID NO: 253          moltype = DNA   length = 23
FEATURE                 Location/Qualifiers
source                  1..23
                        mol_type = other DNA
                        organism = synthetic construct
SEQUENCE: 253
cggaggaact tggcgagccc gaa                                           23

SEQ ID NO: 254          moltype = DNA   length = 23
FEATURE                 Location/Qualifiers
source                  1..23
                        mol_type = other DNA
                        organism = synthetic construct
SEQUENCE: 254
gcgttgcccc ggaggaactt ggc                                           23

SEQ ID NO: 255          moltype = DNA   length = 23
FEATURE                 Location/Qualifiers
source                  1..23
                        mol_type = other DNA
                        organism = synthetic construct
SEQUENCE: 255
gccaagttcc tccggggcaa cgc                                           23

SEQ ID NO: 256          moltype = DNA   length = 23
FEATURE                 Location/Qualifiers
source                  1..23
                        mol_type = other DNA
                        organism = synthetic construct
SEQUENCE: 256
ggaaatgaga tctccggtga gct                                           23

SEQ ID NO: 257          moltype = DNA   length = 23
FEATURE                 Location/Qualifiers
source                  1..23
                        mol_type = other DNA
                        organism = synthetic construct
SEQUENCE: 257
gctatcgccg gctcgtacgg cta                                           23

SEQ ID NO: 258          moltype = DNA   length = 23
FEATURE                 Location/Qualifiers
source                  1..23
                        mol_type = other DNA
                        organism = synthetic construct
SEQUENCE: 258
gggcatgtac cgtggggtgt ctt                                           23

SEQ ID NO: 259          moltype = DNA   length = 23
FEATURE                 Location/Qualifiers
source                  1..23
                        mol_type = other DNA
                        organism = synthetic construct
SEQUENCE: 259
cagcacccgg ccgccgccac cgc                                           23

SEQ ID NO: 260          moltype = DNA   length = 23
FEATURE                 Location/Qualifiers
source                  1..23
                        mol_type = other DNA
                        organism = synthetic construct
SEQUENCE: 260
gcctcctaca tcgtacagcc tat                                           23

SEQ ID NO: 261          moltype = DNA   length = 23
FEATURE                 Location/Qualifiers
source                  1..23
```

```
                        mol_type = other DNA
                        organism = synthetic construct
SEQUENCE: 261
caggaggatg tgcttcatgc aag                                              23

SEQ ID NO: 262          moltype = DNA   length = 23
FEATURE                 Location/Qualifiers
source                  1..23
                        mol_type = other DNA
                        organism = synthetic construct
SEQUENCE: 262
ctccatcgtg acgacgacga cca                                              23

SEQ ID NO: 263          moltype = DNA   length = 23
FEATURE                 Location/Qualifiers
source                  1..23
                        mol_type = other DNA
                        organism = synthetic construct
SEQUENCE: 263
ggtgcggcgc tacgtgtacc atg                                              23

SEQ ID NO: 264          moltype = DNA   length = 23
FEATURE                 Location/Qualifiers
source                  1..23
                        mol_type = other DNA
                        organism = synthetic construct
SEQUENCE: 264
ggaccagtaa tcagttccaa tag                                              23

SEQ ID NO: 265          moltype = DNA   length = 23
FEATURE                 Location/Qualifiers
source                  1..23
                        mol_type = other DNA
                        organism = synthetic construct
SEQUENCE: 265
gcatgagttg acattagcaa agg                                              23

SEQ ID NO: 266          moltype = DNA   length = 23
FEATURE                 Location/Qualifiers
source                  1..23
                        mol_type = other DNA
                        organism = synthetic construct
SEQUENCE: 266
aaggtctgaa ccggaatttc cta                                              23

SEQ ID NO: 267          moltype = DNA   length = 23
FEATURE                 Location/Qualifiers
source                  1..23
                        mol_type = other DNA
                        organism = synthetic construct
SEQUENCE: 267
acccatccat gttctttctc aaa                                              23

SEQ ID NO: 268          moltype = DNA   length = 23
FEATURE                 Location/Qualifiers
source                  1..23
                        mol_type = other DNA
                        organism = synthetic construct
SEQUENCE: 268
ttgggggagt ctttgatgtt gag                                              23

SEQ ID NO: 269          moltype = DNA   length = 23
FEATURE                 Location/Qualifiers
source                  1..23
                        mol_type = other DNA
                        organism = synthetic construct
SEQUENCE: 269
ctaccggagc caaggtcacc aag                                              23

SEQ ID NO: 270          moltype = DNA   length = 23
FEATURE                 Location/Qualifiers
source                  1..23
                        mol_type = other DNA
                        organism = synthetic construct
SEQUENCE: 270
ttgagtcatt agtggagaaa tta                                              23

SEQ ID NO: 271          moltype = DNA   length = 23
FEATURE                 Location/Qualifiers
```

```
source          1..23
                mol_type = other DNA
                organism = synthetic construct
SEQUENCE: 271
ggagccaagg tcaccaaggc tgc                                           23
```